US012758779B2

(12) United States Patent
Verzal et al.

(10) Patent No.: US 12,758,779 B2
(45) Date of Patent: Oct. 13, 2026

(54) MULTIPLE TARGET STIMULATION THERAPY FOR SLEEP DISORDERED BREATHING

(71) Applicant: INSPIRE MEDICAL SYSTEMS, INC., Golden Valley, MN (US)

(72) Inventors: Kevin Verzal, Lino Lakes, MN (US); Timothy Herbert, Maple Grove, MN (US); Wondimeneh Tesfayesus, New Brighton, MN (US); John Rondoni, Plymouth, MN (US); Quan Ni, Golden Valley, MN (US); Kent Lee, Minneapolis, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 142 days.

(21) Appl. No.: 18/560,886

(22) PCT Filed: May 23, 2022

(86) PCT No.: PCT/US2022/030543
§ 371 (c)(1),
(2) Date: Nov. 14, 2023

(87) PCT Pub. No.: WO2022/246320
PCT Pub. Date: Nov. 24, 2022

(65) Prior Publication Data

US 2024/0252824 A1 Aug. 1, 2024

Related U.S. Application Data

(60) Provisional application No. 63/191,712, filed on May 21, 2021.

(51) Int. Cl.

| | |
|---|---|
| *A61N 1/36* | (2006.01) |
| *A61N 1/04* | (2006.01) |
| *A61N 1/05* | (2006.01) |

(52) U.S. Cl.
CPC ....... *A61N 1/36146* (2013.01); *A61N 1/0452* (2013.01); *A61N 1/0476* (2013.01);
(Continued)

(58) Field of Classification Search
CPC ................ A61N 1/0452; A61N 1/3611; A61N 1/36146; A61N 1/36128; A61B 5/686
See application file for complete search history.

(56) References Cited

U.S. PATENT DOCUMENTS

| | | | |
|---|---|---|---|
| 4,830,008 | A | 5/1989 | Meer |
| 5,190,053 | A | 3/1993 | Meer |

(Continued)

FOREIGN PATENT DOCUMENTS

| | | | |
|---|---|---|---|
| EP | 2358268 | B1 | 3/2019 |
| SU | 1553140 | A1 | 3/1990 |

(Continued)

OTHER PUBLICATIONS

Chhetri et al., "Ansa Cervicalis Nerve: Review of the Topographic Anatomy and Morphology", Laryngoscope 107 (10), (Oct. 1997), pp. 1366-1372.

(Continued)

*Primary Examiner* — Catherine M Voorhees
(74) *Attorney, Agent, or Firm* — Dicke, Billig & Czaja, PLLC

(57) ABSTRACT

Devices and/or methods for treating sleep disordered breathing may include stimulation of a single nerve, multiple nerves, as well as other tissues relating to upper airway patency.

11 Claims, 96 Drawing Sheets

(52) U.S. Cl.
CPC .......... *A61N 1/0504* (2013.01); *A61N 1/3611* (2013.01); *A61N 1/36128* (2013.01); *A61N 1/36139* (2013.01); *A61N 1/36167* (2013.01)

(56) References Cited

U.S. PATENT DOCUMENTS

| | | | |
|---|---|---|---|
| 5,284,161 A | 2/1994 | Karell | |
| 5,540,734 A | 7/1996 | Zabara | |
| 5,591,216 A | 1/1997 | Testerman et al. | |
| 5,792,067 A | 8/1998 | Karell | |
| 6,185,452 B1 | 2/2001 | Schulman et al. | |
| 6,212,435 B1 | 4/2001 | Lattner et al. | |
| 6,240,316 B1 | 5/2001 | Richmond et al. | |
| 6,345,202 B2 | 2/2002 | Richmond et al. | |
| 6,449,512 B1 | 9/2002 | Boveja | |
| 6,587,725 B1 | 7/2003 | Durand et al. | |
| 6,636,767 B1 | 10/2003 | Knudson et al. | |
| 6,650,943 B1 | 11/2003 | Whitehurst et al. | |
| 6,735,474 B1 | 5/2004 | Loeb et al. | |
| 7,167,751 B1 | 1/2007 | Whitehurst | |
| 7,277,749 B2 | 10/2007 | Gordon et al. | |
| 7,367,935 B2 | 5/2008 | Mechlenburg et al. | |
| 7,371,220 B1 | 5/2008 | Koh et al. | |
| 7,481,759 B2 | 1/2009 | Whitehurst | |
| 7,519,424 B2 | 4/2009 | Dennis et al. | |
| 7,565,198 B2 | 7/2009 | Bennett et al. | |
| 7,660,632 B2 | 2/2010 | Kirby et al. | |
| 7,808,447 B1 | 10/2010 | Cook | |
| 7,840,279 B2 | 11/2010 | He | |
| 7,881,783 B2 | 2/2011 | Bonde et al. | |
| 7,882,842 B2 | 2/2011 | Bhat et al. | |
| 8,417,342 B1 | 4/2013 | Abell | |
| 8,424,727 B2 | 4/2013 | Herman | |
| 8,428,727 B2 | 4/2013 | Bolea et al. | |
| 8,478,413 B2 | 7/2013 | Karamanoglu et al. | |
| 8,644,939 B2 | 2/2014 | Wilson et al. | |
| 8,706,232 B2 | 4/2014 | Su et al. | |
| 8,781,587 B2 | 7/2014 | Alt et al. | |
| 8,855,771 B2 | 10/2014 | Tesfayesus et al. | |
| 8,918,181 B2 | 12/2014 | Ackermann et al. | |
| 9,186,511 B2 | 11/2015 | Bolea | |
| 9,205,262 B2 | 12/2015 | Bolea et al. | |
| 9,398,901 B2 | 7/2016 | Tischendorf et al. | |
| 9,457,186 B2 | 10/2016 | Gross | |
| 9,486,628 B2 | 11/2016 | Christopherson et al. | |
| 9,586,048 B2 | 3/2017 | Ternes et al. | |
| 9,821,159 B2 | 11/2017 | Ackermann et al. | |
| 9,821,165 B2 | 11/2017 | Gross | |
| 9,884,191 B2 | 2/2018 | Meadows et al. | |
| 10,052,484 B2 | 8/2018 | Bolea et al. | |
| 10,195,427 B2 | 2/2019 | Kent et al. | |
| 10,195,428 B2 | 2/2019 | Scheiner | |
| 10,213,600 B2 | 2/2019 | Tyler | |
| 10,543,366 B2 | 1/2020 | Christopherson et al. | |
| 10,835,748 B2 | 11/2020 | Ackermann et al. | |
| 10,888,267 B2 | 1/2021 | Christopherson | |
| 11,154,716 B2 | 10/2021 | Libbus et al. | |
| 11,202,908 B2 | 12/2021 | Su et al. | |
| 11,266,837 B2 | 3/2022 | Scheiner et al. | |
| 11,400,293 B2 | 8/2022 | Scheiner | |
| 11,850,424 B2 | 12/2023 | Wagner | |
| 12,194,300 B1 | 1/2025 | Ni | |
| 2001/0018547 A1 | 8/2001 | Mechlenburg et al. | |
| 2002/0049479 A1 | 4/2002 | Pitts | |
| 2003/0153953 A1 | 8/2003 | Park et al. | |
| 2004/0015204 A1 | 1/2004 | Whitehurst et al. | |
| 2004/0153127 A1 | 8/2004 | Gordon et al. | |
| 2005/0267547 A1 | 12/2005 | Knudson et al. | |
| 2006/0020297 A1 | 1/2006 | Gerber et al. | |
| 2006/0041277 A1 | 2/2006 | Deem et al. | |
| 2007/0173893 A1 | 7/2007 | Pitts | |
| 2007/0255333 A1 | 11/2007 | Giftakis et al. | |
| 2007/0288077 A1 | 12/2007 | Bulkes et al. | |
| 2008/0039904 A1 | 2/2008 | Bulkes et al. | |
| 2008/0103545 A1* | 5/2008 | Bolea | A61N 1/0556 607/42 |
| 2008/0147142 A1 | 6/2008 | Testerman et al. | |
| 2009/0014012 A1 | 1/2009 | Sanders | |
| 2010/0204747 A1 | 8/2010 | Lindquist et al. | |
| 2011/0093032 A1 | 4/2011 | Boggs, II et al. | |
| 2011/0202119 A1 | 8/2011 | Ni et al. | |
| 2011/0264164 A1 | 10/2011 | Christopherson et al. | |
| 2012/0022626 A1 | 1/2012 | Bolea et al. | |
| 2012/0109249 A1* | 5/2012 | Tehrani | A61B 5/395 607/42 |
| 2012/0234331 A1 | 9/2012 | Shantha | |
| 2014/0135868 A1 | 5/2014 | Bashyam | |
| 2015/0148860 A1 | 5/2015 | Lima et al. | |
| 2016/0067497 A1 | 3/2016 | Levine et al. | |
| 2016/0303301 A1 | 10/2016 | Bluvshtein et al. | |
| 2017/0120050 A1 | 5/2017 | Meadows et al. | |
| 2017/0128002 A1 | 5/2017 | Christopherson et al. | |
| 2017/0151432 A1 | 6/2017 | Christopherson et al. | |
| 2017/0165101 A1 | 6/2017 | Davidian | |
| 2017/0224987 A1 | 8/2017 | Kent et al. | |
| 2018/0078761 A1 | 3/2018 | Bolea et al. | |
| 2019/0009093 A1* | 1/2019 | Ni | A61N 1/36139 |
| 2019/0117966 A1 | 4/2019 | Kent | |
| 2019/0150772 A1 | 5/2019 | Haraikawa et al. | |
| 2019/0160282 A1 | 5/2019 | Dieken et al. | |
| 2019/0167995 A1 | 6/2019 | Sachs | |
| 2019/0175026 A1 | 6/2019 | Verzal et al. | |
| 2019/0344084 A1 | 11/2019 | Verzal et al. | |
| 2020/0069947 A1 | 3/2020 | Kent | |
| 2020/0121492 A1 | 4/2020 | McCreery | |
| 2020/0147376 A1* | 5/2020 | Dieken | A61N 1/36139 |
| 2020/0254249 A1 | 8/2020 | Rondoni et al. | |
| 2021/0052888 A1 | 2/2021 | Kent | |
| 2021/0106824 A1 | 4/2021 | Caparso et al. | |
| 2021/0308454 A1 | 10/2021 | Wagner et al. | |
| 2022/0032052 A1* | 2/2022 | Kent | A61N 1/0551 |
| 2022/0134101 A1 | 5/2022 | Scheiner et al. | |
| 2022/0134102 A1 | 5/2022 | O'Connor et al. | |
| 2022/0152387 A1 | 5/2022 | Scheiner et al. | |
| 2022/0161031 A1 | 5/2022 | O'Connor et al. | |
| 2022/0339441 A1 | 10/2022 | Elliott et al. | |
| 2022/0346666 A1 | 11/2022 | Elliott et al. | |
| 2022/0370797 A1 | 11/2022 | O'Connor et al. | |
| 2022/0379114 A1 | 12/2022 | Kent | |
| 2022/0409897 A1 | 12/2022 | O'Connor et al. | |
| 2023/0026728 A1 | 1/2023 | Elliott et al. | |
| 2023/0119173 A1 | 4/2023 | Dieken et al. | |
| 2023/0165704 A1 | 6/2023 | Kent | |
| 2023/0172479 A1 | 6/2023 | Verzal et al. | |
| 2023/0338735 A1 | 10/2023 | Masson, Jr. et al. | |
| 2023/0381518 A1 | 11/2023 | Rondoni et al. | |
| 2025/0031993 A1 | 1/2025 | Mazanec et al. | |

FOREIGN PATENT DOCUMENTS

| | | |
|---|---|---|
| WO | 2023028262 A1 | 3/2023 |
| WO | 2023192607 A2 | 10/2023 |
| WO | 2024006529 A1 | 1/2024 |
| WO | 2024064207 A2 | 3/2024 |

OTHER PUBLICATIONS

Eisele et al., "The Effects of Selective Nerve Stimulation on Upper Airway Airflow Mechanics", Arch Otolaryngol Head Neck Surg. 121(12), (Dec. 1995), pp. 1361-1364.

International Search Report and Written Opinion mailed Sep. 15, 2021 for corresponding International Patent Application No. PCT/US2021/033639, pp. 1-11.

International Search Report and Written Opinion mailed Sep. 12, 2022 for International Patent Application No. PCT/US2022/030543, pp. 1-13.

Kezirian et al., "Electrical Stimulation of the Hypoglossal Nerve in the Treatment of Obstructive Sleep Apnea", Sleep Medicine Reviews 14(5), (Oct. 2010), pp. 299-305.

Schwartz et al., "Effect of Electrical Stimulation to the Soft Palate on Snoring and Obstructive Sleep Apnea", Abstract, The Journal of Prosthetic Denistry 76(3), (Sep. 1996), pp. 273-281.

(56) References Cited

OTHER PUBLICATIONS

Heinzer et al., "Lung Volume and Continuous Positive Airway Pressure Requirements in Obstructive Sleep Apnea", American Journal of Respiratory and Critical Care Medicine vol. 175, (Apr. 2005), pp. 1-4.
Heinzer et al., "Effect of increased lung vol. on sleep disordered breathing in patients with sleep apnoea", Thorax 61, (May 2006), pp. 435-439.
Katz et al., "Tracheal hysteresis in sleep apnea", J Appl Physiol 67 (4), (Oct. 1989). pp. 1349-1353.
Mathew, Oommen P., "Upper airway negative-pressure effects on respiratory activity of upper airway muscles", J Appl Physiol 56 (2), (Feb. 1, 1984). pp. 500-505.
Roberts et al., "Pharyngeal airways-stabilizing function of sternohyoid and sternothyroid muscles in the rabbit", J Appl Physiol Respir Environ Exerc Physiol 57 (6), (Dec. 1984) pp. 1790-175.
Schnall et al., "Dilatory effects of upper airway muscle contraction induced by electrical stimulation in awake humans", J Appl Physiol 78 (5), (May 1995) pp. 1950-1956.
Strohl et al., "Assessment of muscle action on upper airway stability in anesthetized dogs", J Lab Clin Med. 110 (2), (Aug. 1987) pp. 221-230.
Van De Graaff, William B., "Thoracic influence on upper airway patency", J Appl Physiol 65 (5), (Nov. 1988) pp. 2124-2131.
Van De Graaff, William B., Thracic traction on the trachea: mechanisms and magnitude, J Appl Physiol 70 (3), (Mar. 1991) pp. 1328-1336.
Van De Graaff et al., "Respiratory function of hyoid muscles and hyoid muscles and hypied arch", J Appl Physiol Respir Environ Exerc Physiol. 57 (1), (Jul. 1984) pp. 197-204.
Van Lunteren, Erik, "Muscles of the pharynx: structural and contractile properties", Ear Nose Throat J. 72 (1), (Jan. 1993) pp. 27-29.
Van Lunteren et al., "Effects of tracheal airway occlusion on hyoid muscle length and upper airway volume", J Appl Physiol 67 (6), (Dec. 1989) pp. 2296-2302.
Van Lunteren et al., "Contractile properties of feline genioglossus, sternohyoid, and sternohyoid muscles", J Appl Physiol 72 (3), (Mar. 1992) pp. 1010-1015.
Van Lunteren et al., "Pharyngeal dilator muscle contractile and endurance properties in neonatal piglets", Respir Physiol 92 (1), (Apr. 1993) pp. 65-75.
Fink, Jennifer, "New developments regarding hypoglossal nerve stimulation for obstructive sleep apnea", ENTtoday, (Feb. 14, 2023) pp. 1-7.
Kent et al., "Ansa Cervicalis and Hypoglossal Nerve Stimulation in a Patient With Obstructive Sleep Apnea", Otolaryngol Head Neck Surg. 165 (4), (Oct. 2021) pp. 1-3.
Kent et al., "Ansa cervicalis stimulation increases pharyngeal patency in patients with obstructive sleep apnea", J Appl Physiol. 131, (Jul. 1, 2021) pp. 487-495.
Yike et al., "Quantitative Effects of Ansa Cervicalis Stimulation in Obstructive Sleep Apnea", AJRCCM Articles in Press., (Jan. 19, 2023) pp. 1-11.
Kent et al., "Ansa Cervicalis Stimulation: A New Direction in Neurostimulation for OSA", Chest. 159 (3), ( Mar. 2021) pp. 1212-1221.
Kent et al., "Ansa Cervicalis Stimulation Increases Pharyngeal Patency in Patients with Obstructive Sleep Apnea", J Appl Physiol. 131 (2), (Aug. 1, 2021) pp. 1-37.
Kent et al., "Ultrasound Localization and Percutaneous Electrical Stimulation of the Hypoglossal Nerve and Ansa Cervicalis", Otolaryngol Head Neck Surg. 164 (1), (Jan. 2021) pp. 1-7.
Kent et al., "Ansa Cervicalis and Hypoglossal Nerve Stimulation in a Patient With Obstructive Sleep Apnea", Otolaryngol Head Neck Surg. 165 (4), (Oct. 2, 2020) pp. 1-3.
Edmonds et al., "The Effects of Transcutaneous Electrical Stimulation during Wakefulness and Sleep in Patients with Obstructive Sleep Apnea", Am Rev Respir Dis. 146 (4), (Oct. 1992) pp. 1030-1036.

* cited by examiner

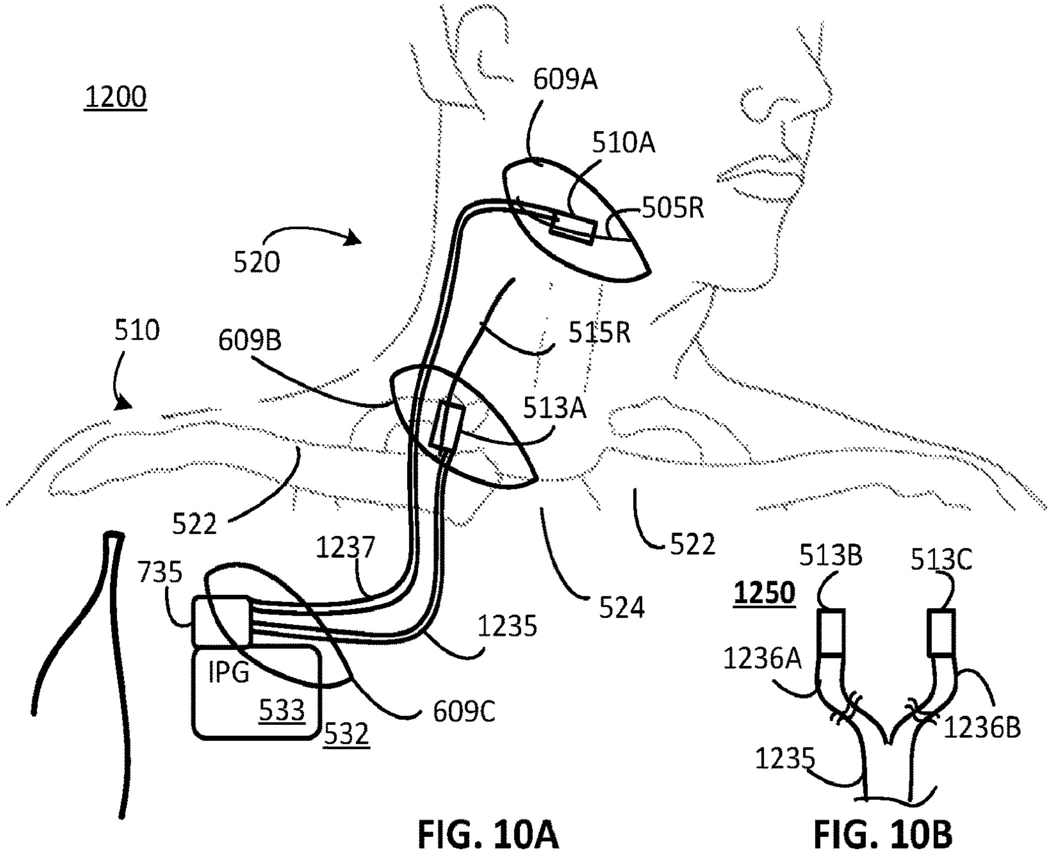
FIG. 10A
FIG. 10B
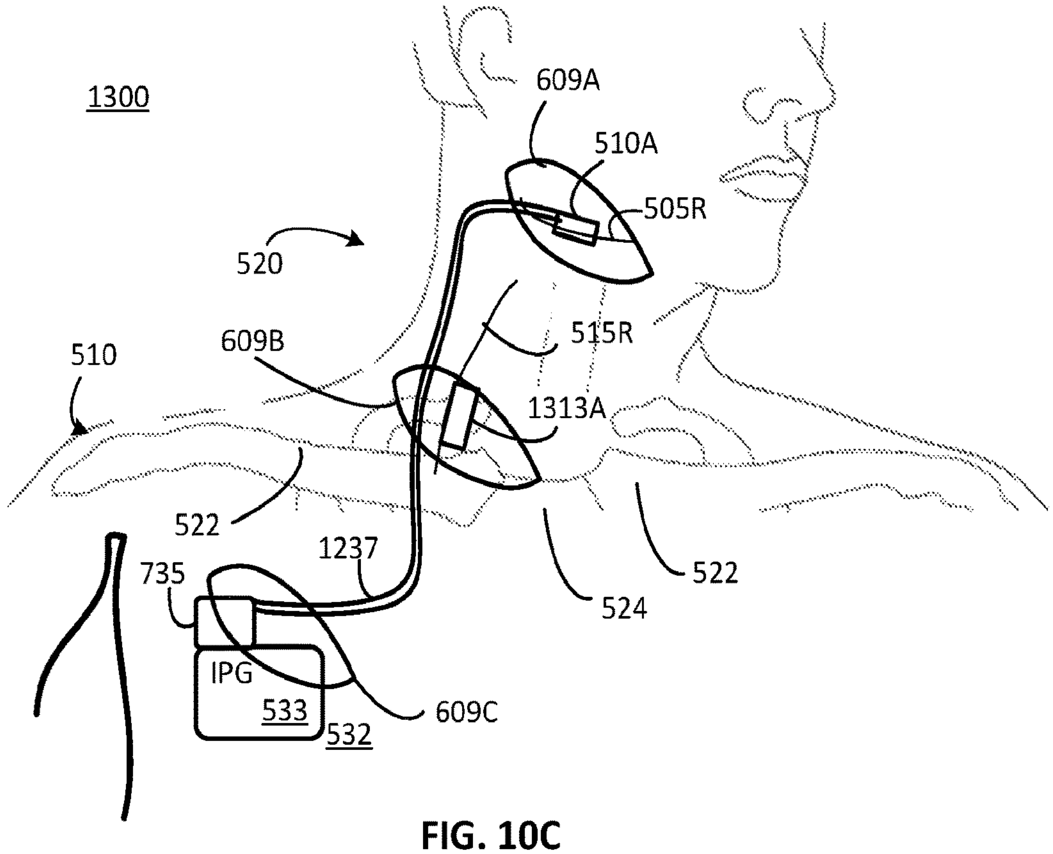
FIG. 10C

8180

ADDING OR SUBTRACTING A NERVE TARGET FROM AMONG MULTIPLE NERVE TARGETS BASED ON A PARAMETER INCLUDING A BODY POSITION/POSTURE AND/OR OTHER PARAMETER(S)

8200

IDENTIFYING FATIGUE OF A TARGET NERVE AND/OR ITS INNERVATED MUSCLE AND ADJUSTING A STIMULATION PARAMETER TO ASSESS POTENTIAL FATIGUE AND/OR TO DECREASE IDENTIFIED FATIGUE

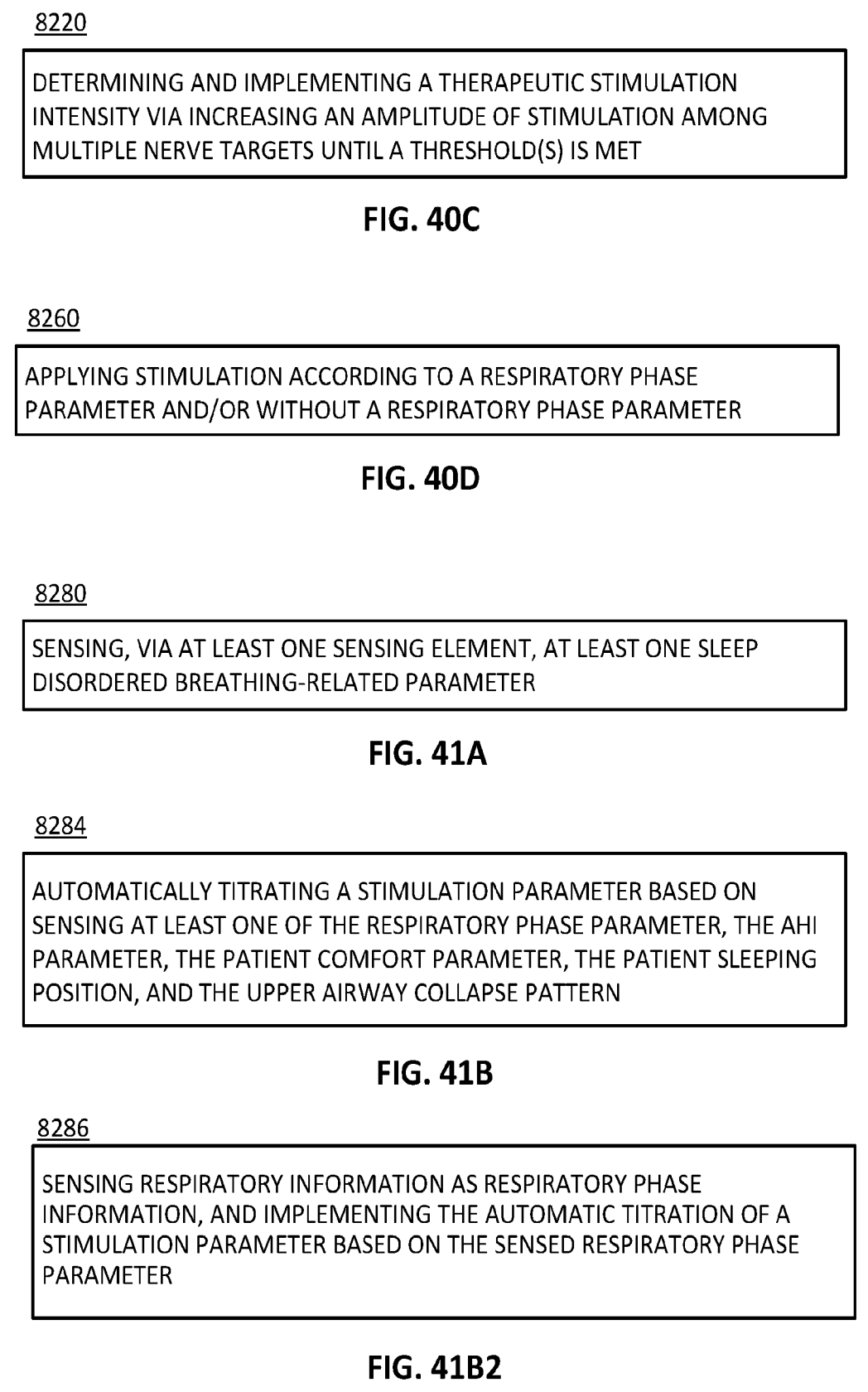

8220

DETERMINING AND IMPLEMENTING A THERAPEUTIC STIMULATION INTENSITY VIA INCREASING AN AMPLITUDE OF STIMULATION AMONG MULTIPLE NERVE TARGETS UNTIL A THRESHOLD(S) IS MET

FIG. 40C

8260

APPLYING STIMULATION ACCORDING TO A RESPIRATORY PHASE PARAMETER AND/OR WITHOUT A RESPIRATORY PHASE PARAMETER

FIG. 40D

8280

SENSING, VIA AT LEAST ONE SENSING ELEMENT, AT LEAST ONE SLEEP DISORDERED BREATHING-RELATED PARAMETER

FIG. 41A

8284

AUTOMATICALLY TITRATING A STIMULATION PARAMETER BASED ON SENSING AT LEAST ONE OF THE RESPIRATORY PHASE PARAMETER, THE AHI PARAMETER, THE PATIENT COMFORT PARAMETER, THE PATIENT SLEEPING POSITION, AND THE UPPER AIRWAY COLLAPSE PATTERN

FIG. 41B

8286

SENSING RESPIRATORY INFORMATION AS RESPIRATORY PHASE INFORMATION, AND IMPLEMENTING THE AUTOMATIC TITRATION OF A STIMULATION PARAMETER BASED ON THE SENSED RESPIRATORY PHASE PARAMETER

FIG. 41B2

8288

TITRATING, WITH THE STIMULATION PARAMETER COMPRISING AT LEAST ONE OF: (1) AT LEAST ONE OF A CHANGE IN AN AMPLITUDE, FREQUENCY, PULSE WIDTH, DUTY CYCLE OF STIMULATION; AND (2) SELECTION OF AT LEAST ONE STIMULATION TARGET AMONG A PLURALITY OF STIMULATION TARGETS, WHICH INCLUDES THE HYPOGLOSSAL NERVE AND THE ANSA CERVICALIS NERVE

FIG. 41B3

8290

TITRATING, WITH THE PLURALITY OF STIMULATION TARGETS COMPRISING A LEFT AND/OR RIGHT HYPOGLOSSAL NERVE, A LEFT AND/OR RIGHT ANSA CERVICALIS-RELATED NERVE, AND/OR OTHER TARGETS INCLUDING A GLOSSOPHARYNGEAL NERVE, A SUPERIOR LARYNGEAL NERVE, A SUPERIOR CERVICAL GANGLION NERVE, AND A CHEMORECEPTOR ASSCOCIATED WITH THE CAROTID BODY

FIG. 41B4

8300

RECEIVING A PATIENT ADJUSTMENT, AS A SINGLE INPUT, TO A STIMULATION PARAMETER, AND IMPLEMENTING THE PATIENT ADJUSTMENT BY AUTOMATICALLY ADJUSTING A STIMULATION ENERGY AMONG A PLURALITY OF STIMULATION SITES INCLUDING AT LEAST ONE OF A HYPOGLOSSAL NERVE SITE, AN ANSA CERVICALIS-RELATED NERVE SITE, AND A SECOND NON-HYPOGLOSSAL NERVE SITE

FIG. 41C

8320

IMPLEMENTING THE AUTOMATIC BALANCING BASED ON SENSING AT LEAST ONE OF A RESPIRATORY PHASE PARAMETER, AHI PARAMETER, A PATIENT COMFORT PARAMETER, A PATIENT SLEEPING POSITION PARAMETER, AND AN UPPER AIRWAY COLLAPSE PATTERN PARAMETER

FIG. 41D

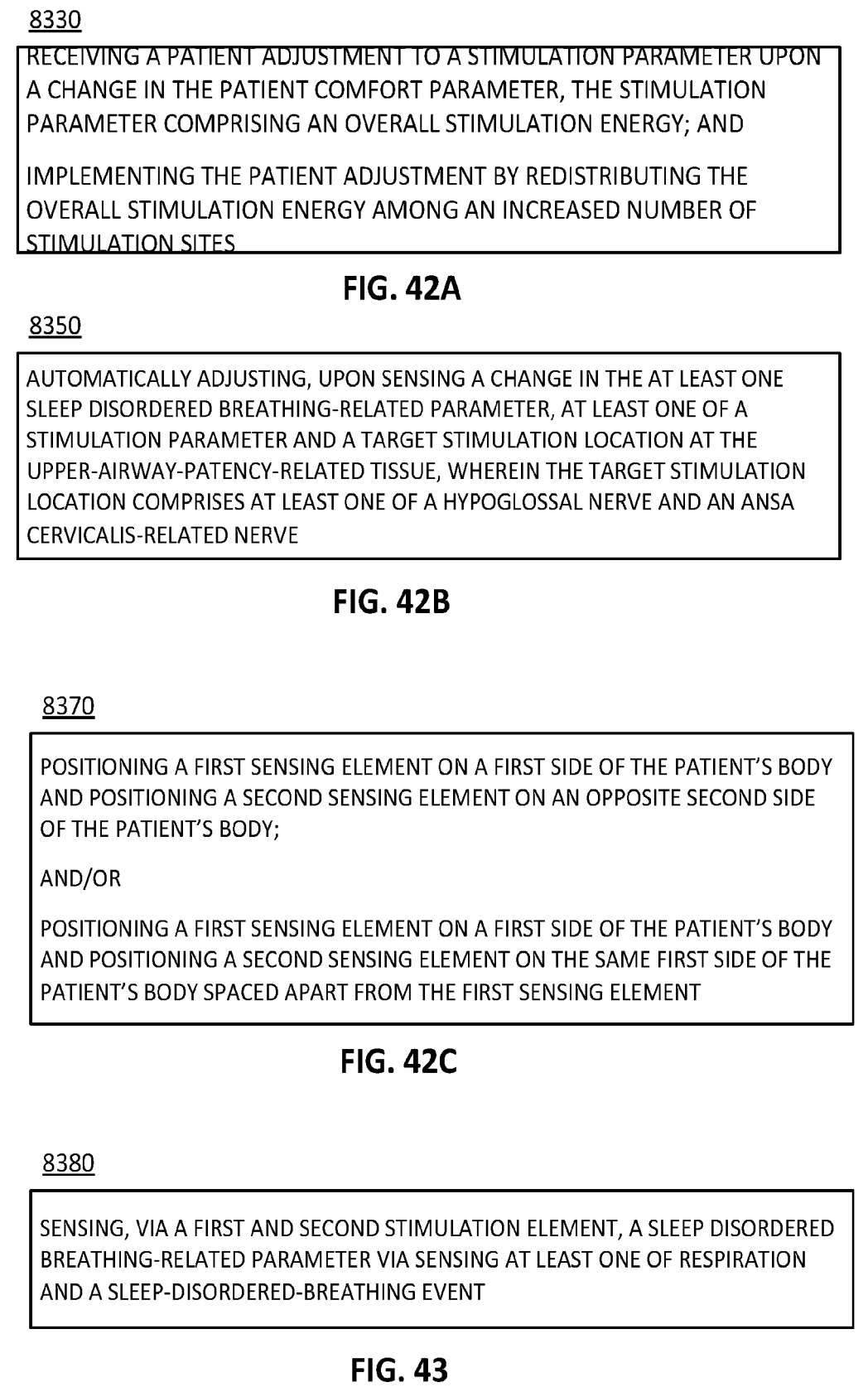

8330

RECEIVING A PATIENT ADJUSTMENT TO A STIMULATION PARAMETER UPON A CHANGE IN THE PATIENT COMFORT PARAMETER, THE STIMULATION PARAMETER COMPRISING AN OVERALL STIMULATION ENERGY; AND

IMPLEMENTING THE PATIENT ADJUSTMENT BY REDISTRIBUTING THE OVERALL STIMULATION ENERGY AMONG AN INCREASED NUMBER OF STIMULATION SITES

FIG. 42A

8350

AUTOMATICALLY ADJUSTING, UPON SENSING A CHANGE IN THE AT LEAST ONE SLEEP DISORDERED BREATHING-RELATED PARAMETER, AT LEAST ONE OF A STIMULATION PARAMETER AND A TARGET STIMULATION LOCATION AT THE UPPER-AIRWAY-PATENCY-RELATED TISSUE, WHEREIN THE TARGET STIMULATION LOCATION COMPRISES AT LEAST ONE OF A HYPOGLOSSAL NERVE AND AN ANSA CERVICALIS-RELATED NERVE

FIG. 42B

8370

POSITIONING A FIRST SENSING ELEMENT ON A FIRST SIDE OF THE PATIENT'S BODY AND POSITIONING A SECOND SENSING ELEMENT ON AN OPPOSITE SECOND SIDE OF THE PATIENT'S BODY;

AND/OR

POSITIONING A FIRST SENSING ELEMENT ON A FIRST SIDE OF THE PATIENT'S BODY AND POSITIONING A SECOND SENSING ELEMENT ON THE SAME FIRST SIDE OF THE PATIENT'S BODY SPACED APART FROM THE FIRST SENSING ELEMENT

FIG. 42C

8380

SENSING, VIA A FIRST AND SECOND STIMULATION ELEMENT, A SLEEP DISORDERED BREATHING-RELATED PARAMETER VIA SENSING AT LEAST ONE OF RESPIRATION AND A SLEEP-DISORDERED-BREATHING EVENT

FIG. 43

8400

SENSING AT LEAST ONE SLEEP DISORDERED BREATHING-RELATED PARAMETER COMPRISES IMPLANTING A FIRST SENSING ELEMENT AND A SECOND SENSING ELEMENT, AND MEASURING A BIOIMPEDANCE BETWEEN THE FIRST SENSING ELEMENT IMPLANTED RELATIVE TO THE AT LEAST ONE UPPER-AIRWAY-PATENCY-RELATED TISSUE AND THE SECOND SENSING ELEMENT IMPLANTED RELATIVE TO AT LEAST ONE OF A PHRENIC NERVE AND A DIAPHRAGM

FIG. 44A

8410

SENSING AT LEAST ONE OF A MOTION OF AN UPPER-AIRWAY-PATENCY-RELATED MUSCLE AND AN ELECTROMYOGRAPH (EMG) OF AN UPPER-AIRWAY-PATENCY-RELATED MUSCLE

FIG. 44B

8420

DETERMINING AT LEAST ONE SLEEP DISORDERED BREATHING-RELATED PARAMETER AS A RESPIRATORY PARAMETER, BY SENSING VIA AT LEAST ONE SENSING ELEMENT AT LEAST ONE OF: (1) A MOTION OF AN UPPER AIRWAY PATENCY RELATED MUSCLE OF THE AT LEAST ONE UPPER AIRWAY PATENCY-RELATED TISSUE; AND (2) A SOUND OF RESPIRATION ASSOCIATED WITH THE AT LEAST ONE UPPER AIRWAY PATENCY-RELATED TISSUE

FIG. 44C

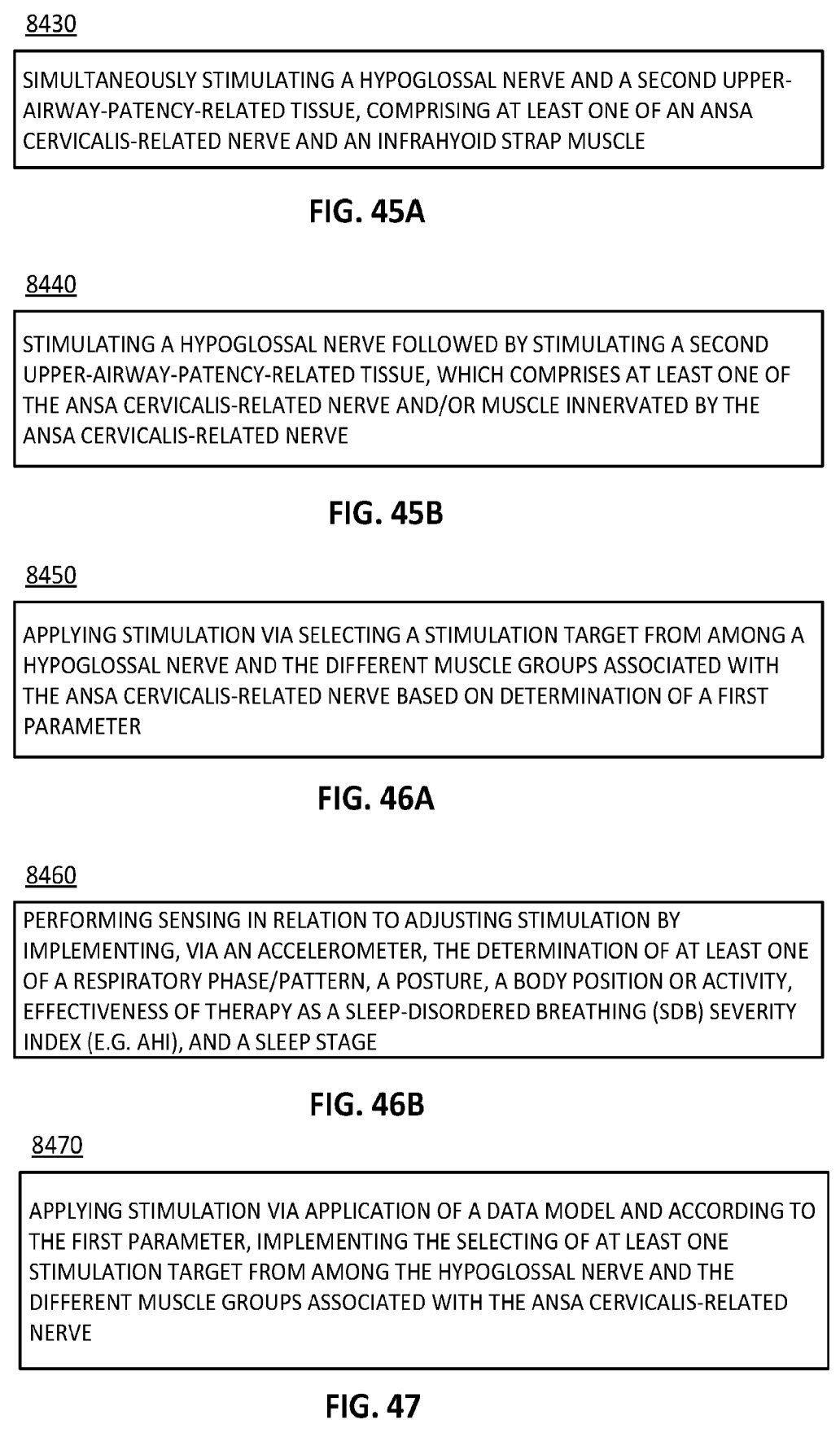

8430

SIMULTANEOUSLY STIMULATING A HYPOGLOSSAL NERVE AND A SECOND UPPER-AIRWAY-PATENCY-RELATED TISSUE, COMPRISING AT LEAST ONE OF AN ANSA CERVICALIS-RELATED NERVE AND AN INFRAHYOID STRAP MUSCLE

FIG. 45A

8440

STIMULATING A HYPOGLOSSAL NERVE FOLLOWED BY STIMULATING A SECOND UPPER-AIRWAY-PATENCY-RELATED TISSUE, WHICH COMPRISES AT LEAST ONE OF THE ANSA CERVICALIS-RELATED NERVE AND/OR MUSCLE INNERVATED BY THE ANSA CERVICALIS-RELATED NERVE

FIG. 45B

8450

APPLYING STIMULATION VIA SELECTING A STIMULATION TARGET FROM AMONG A HYPOGLOSSAL NERVE AND THE DIFFERENT MUSCLE GROUPS ASSOCIATED WITH THE ANSA CERVICALIS-RELATED NERVE BASED ON DETERMINATION OF A FIRST PARAMETER

FIG. 46A

8460

PERFORMING SENSING IN RELATION TO ADJUSTING STIMULATION BY IMPLEMENTING, VIA AN ACCELEROMETER, THE DETERMINATION OF AT LEAST ONE OF A RESPIRATORY PHASE/PATTERN, A POSTURE, A BODY POSITION OR ACTIVITY, EFFECTIVENESS OF THERAPY AS A SLEEP-DISORDERED BREATHING (SDB) SEVERITY INDEX (E.G. AHI), AND A SLEEP STAGE

FIG. 46B

8470

APPLYING STIMULATION VIA APPLICATION OF A DATA MODEL AND ACCORDING TO THE FIRST PARAMETER, IMPLEMENTING THE SELECTING OF AT LEAST ONE STIMULATION TARGET FROM AMONG THE HYPOGLOSSAL NERVE AND THE DIFFERENT MUSCLE GROUPS ASSOCIATED WITH THE ANSA CERVICALIS-RELATED NERVE

FIG. 47

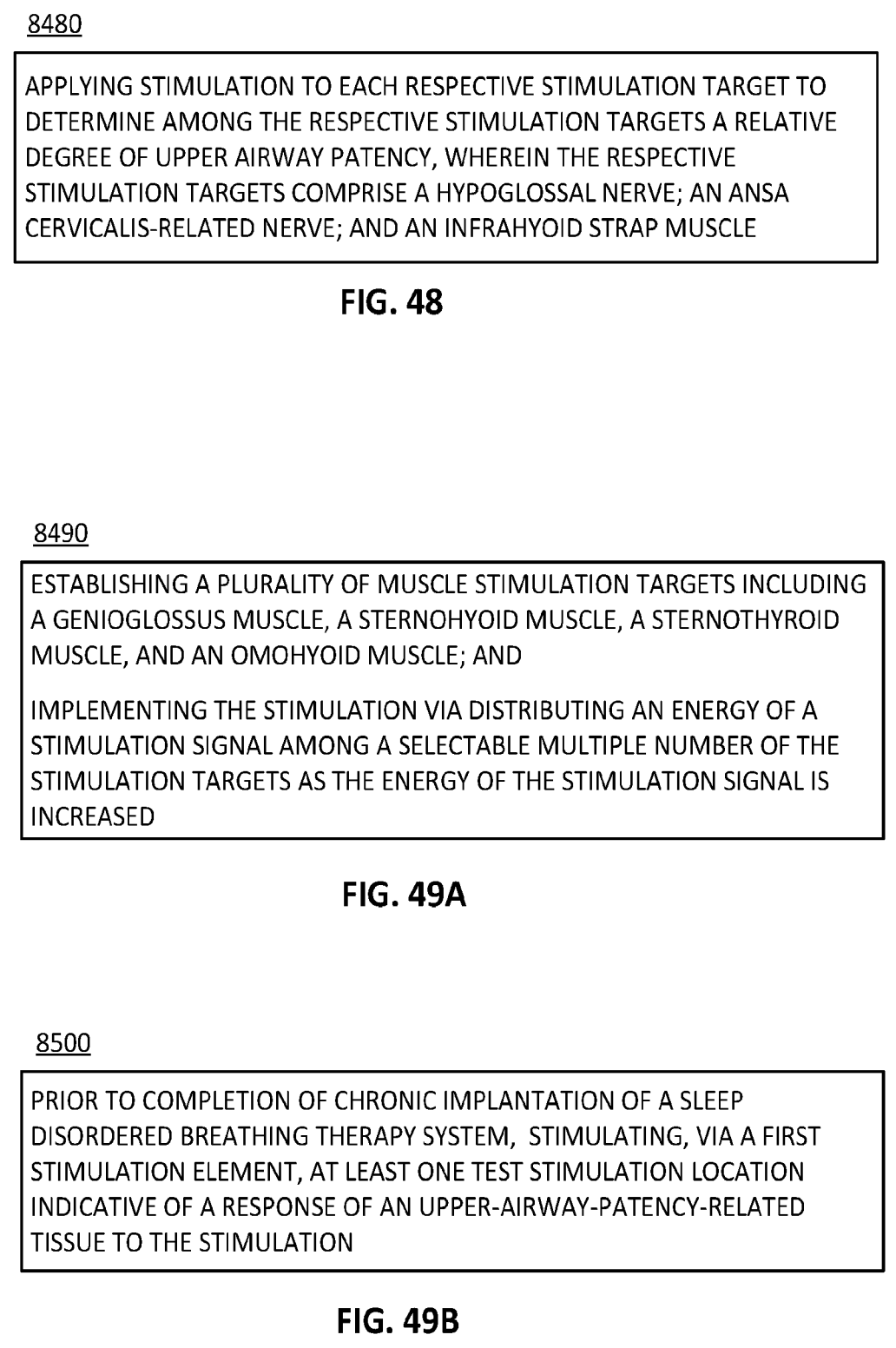

8480

APPLYING STIMULATION TO EACH RESPECTIVE STIMULATION TARGET TO DETERMINE AMONG THE RESPECTIVE STIMULATION TARGETS A RELATIVE DEGREE OF UPPER AIRWAY PATENCY, WHEREIN THE RESPECTIVE STIMULATION TARGETS COMPRISE A HYPOGLOSSAL NERVE; AN ANSA CERVICALIS-RELATED NERVE; AND AN INFRAHYOID STRAP MUSCLE

FIG. 48

8490

ESTABLISHING A PLURALITY OF MUSCLE STIMULATION TARGETS INCLUDING A GENIOGLOSSUS MUSCLE, A STERNOHYOID MUSCLE, A STERNOTHYROID MUSCLE, AND AN OMOHYOID MUSCLE; AND

IMPLEMENTING THE STIMULATION VIA DISTRIBUTING AN ENERGY OF A STIMULATION SIGNAL AMONG A SELECTABLE MULTIPLE NUMBER OF THE STIMULATION TARGETS AS THE ENERGY OF THE STIMULATION SIGNAL IS INCREASED

FIG. 49A

8500

PRIOR TO COMPLETION OF CHRONIC IMPLANTATION OF A SLEEP DISORDERED BREATHING THERAPY SYSTEM, STIMULATING, VIA A FIRST STIMULATION ELEMENT, AT LEAST ONE TEST STIMULATION LOCATION INDICATIVE OF A RESPONSE OF AN UPPER-AIRWAY-PATENCY-RELATED TISSUE TO THE STIMULATION

FIG. 49B

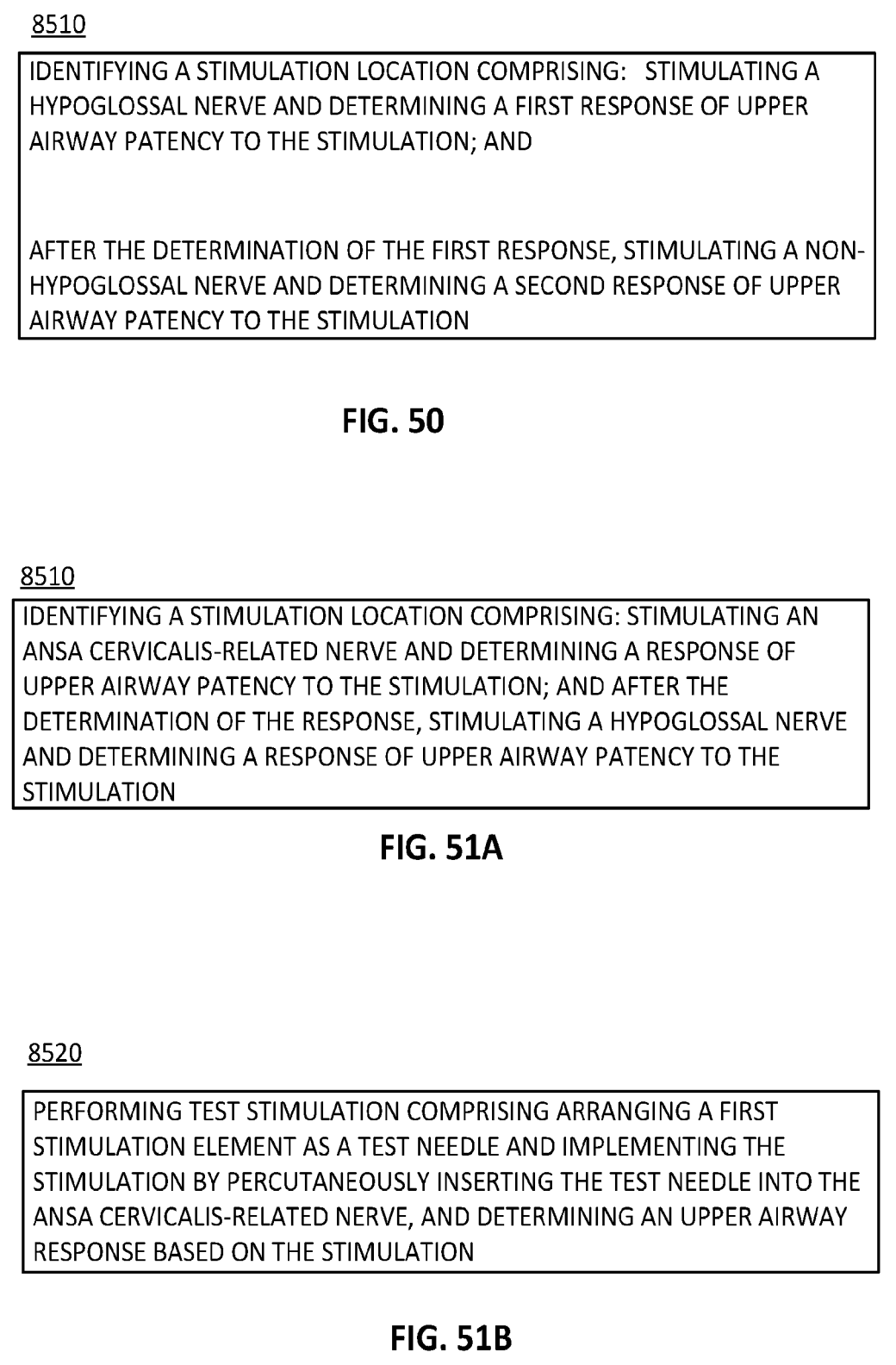

8510

IDENTIFYING A STIMULATION LOCATION COMPRISING: STIMULATING A HYPOGLOSSAL NERVE AND DETERMINING A FIRST RESPONSE OF UPPER AIRWAY PATENCY TO THE STIMULATION; AND

AFTER THE DETERMINATION OF THE FIRST RESPONSE, STIMULATING A NON-HYPOGLOSSAL NERVE AND DETERMINING A SECOND RESPONSE OF UPPER AIRWAY PATENCY TO THE STIMULATION

FIG. 50

8510

IDENTIFYING A STIMULATION LOCATION COMPRISING: STIMULATING AN ANSA CERVICALIS-RELATED NERVE AND DETERMINING A RESPONSE OF UPPER AIRWAY PATENCY TO THE STIMULATION; AND AFTER THE DETERMINATION OF THE RESPONSE, STIMULATING A HYPOGLOSSAL NERVE AND DETERMINING A RESPONSE OF UPPER AIRWAY PATENCY TO THE STIMULATION

FIG. 51A

8520

PERFORMING TEST STIMULATION COMPRISING ARRANGING A FIRST STIMULATION ELEMENT AS A TEST NEEDLE AND IMPLEMENTING THE STIMULATION BY PERCUTANEOUSLY INSERTING THE TEST NEEDLE INTO THE ANSA CERVICALIS-RELATED NERVE, AND DETERMINING AN UPPER AIRWAY RESPONSE BASED ON THE STIMULATION

FIG. 51B

| SITE OF OBSTRUCTION | PATTERN OF OBSTRUCTION | | | DEGREE OF OBSTRUCTION | | |
|---|---|---|---|---|---|---|
| | A-P | LATERAL | CONCENTRIC | NONE | PARTIAL | COMPLETE |
| VELUM(SOFT PALATE) | | | N | | | N |
| ORO-PHARNYX | X | X | X | | | X |
| TONGUE-BASE | X | X | X | | | X |
| EPIGLOTTIS AND LARYNX | | | | | | |

9290A

| SITE OF OBSTRUCTION | PATTERN OF OBSTRUCTION | | | | DEGREE OF OBSTRUCTION | | |
|---|---|---|---|---|---|---|---|
| | A-P | LATERAL | AP + LATERAL | CONCENTRIC | NONE | PARTIAL | COMPLETE |
| VELUM(SOFT PALATE) | | | X | | | | |
| ORO-PHARNYX | X | X | | X | | | X |
| TONGUE-BASE | X | X | | X | | | X |
| EPIGLOTTIS AND LARYNX | | | | | | | |

MULTIPLE TARGET STIMULATION THERAPY FOR SLEEP DISORDERED BREATHING

CROSS-REFERENCE TO RELATED APPLICATIONS

This application is a U.S. National Stage Application under 35 U.S.C. § 371 of International Application No. PCT/US2022/030543, filed May 23, 2022, which claims the benefit of U.S. Provisional Patent Application No. 63/191,712, filed May 21, 2021, each of which are incorporated herein by reference in their entireties.

BACKGROUND

Sleep disordered breathing, such as obstructive sleep apnea, may cause significant health problems and is common among the adult population. Some forms of treatment of sleep disordered breathing may include electrical stimulation of nerves and/or muscles relating to upper airway patency.

BRIEF DESCRIPTION OF THE DRAWINGS

FIGS. 9-11A are diagrams schematically representing an example device and/or method for implanting stimulation elements into stimulating relation to target nerve stimulation locations, such as the hypoglossal nerve and ansa cervicalis-related nerve.

FIGS. 39-51B are block diagrams schematically representing example methods, or portions thereof, of sleep disordered breathing care.

FIGS. 52BB, 52D are diagrams including a side view schematically representing a neck region and an example device and/or example method for sensing impedance and/or relating to delivering stimulation, with the example device/method including a wearable garment.

FIG. 521 is a block diagram including a side view schematically representing a power/control element.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to example devices for, and/or example methods of, therapy for sleep disordered breathing (SDB). In some examples, the sleep disordered breathing may comprise obstructive sleep apnea, while in some examples, the sleep disordered breathing may comprise multiple-type sleep apneas including obstructive sleep apnea and/or central sleep apnea.

Moreover, the general principles associated with the example arrangements of the present disclosure relating to sleep disordered breathing may be applied in other areas of a patient's body to treat conditions other than sleep disordered breathing. For instance, at least some aspects of the example arrangements of the present disclosure may be deployed within a pelvic region to treat urinary and/or fecal incontinence or other disorders, such as via stimulating the pudendal nerve, which may cause contraction of the external urinary sphincter and/or external anal sphincter.

Other body regions and/or disorders also may be suitable candidates for an example arrangements in which multiple nerve targets are available to be stimulated to treat one type or class of physiologic conditions. It will be further understood that example sensing arrangements of the present disclosure (for sensing physiologic data relative to the condition of interest) may be deployed in association with the various example arrangements for stimulating single nerve targets or multiple nerve targets.

Figure 1:
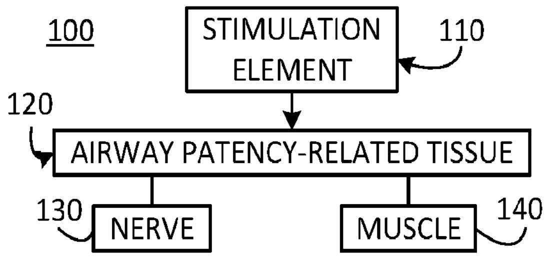
FIG. 1 is a block diagram schematically representing an example device and/or example method for stimulating airway patency-related tissue.

As shown in FIG. 1, some example methods may comprise stimulating, via at least one stimulation element 110, at least one upper airway patency-related tissue 120, which may comprise nerve(s) 130 and/or muscle(s) 140. In some examples, nerve 130 may comprise an ansa cervicalis-related nerve and/or a hypoglossal nerve, as further shown in FIG. 2. Moreover, as further described later throughout various examples, nerve(s) 130 may comprise nerves in addition to, or instead of, the hypoglossal nerve and/or the ansa cervicalis-related nerve. Meanwhile, in some examples the muscle 140 may comprise a genioglossus muscle (innervated by the hypoglossal nerve), while in some examples the muscle 140 may comprise one or more muscle groups (e.g. omohyoid, sternothyroid, sternohyoid) innervated by the ansa cervicalis-related nerve. Moreover, as further described later throughout various examples, muscle 140 may comprise muscles in addition to, or instead of, the genioglossus muscle and/or the muscle groups innervated by the ansa cervicalis-related nerve.

In one aspect, stimulation of one or more of such example nerves and/or muscles may serve to increase or maintain patency of the upper airway of the patient, and hence may sometimes be referred to as upper airway patency-related tissue(s).

Figure 2:
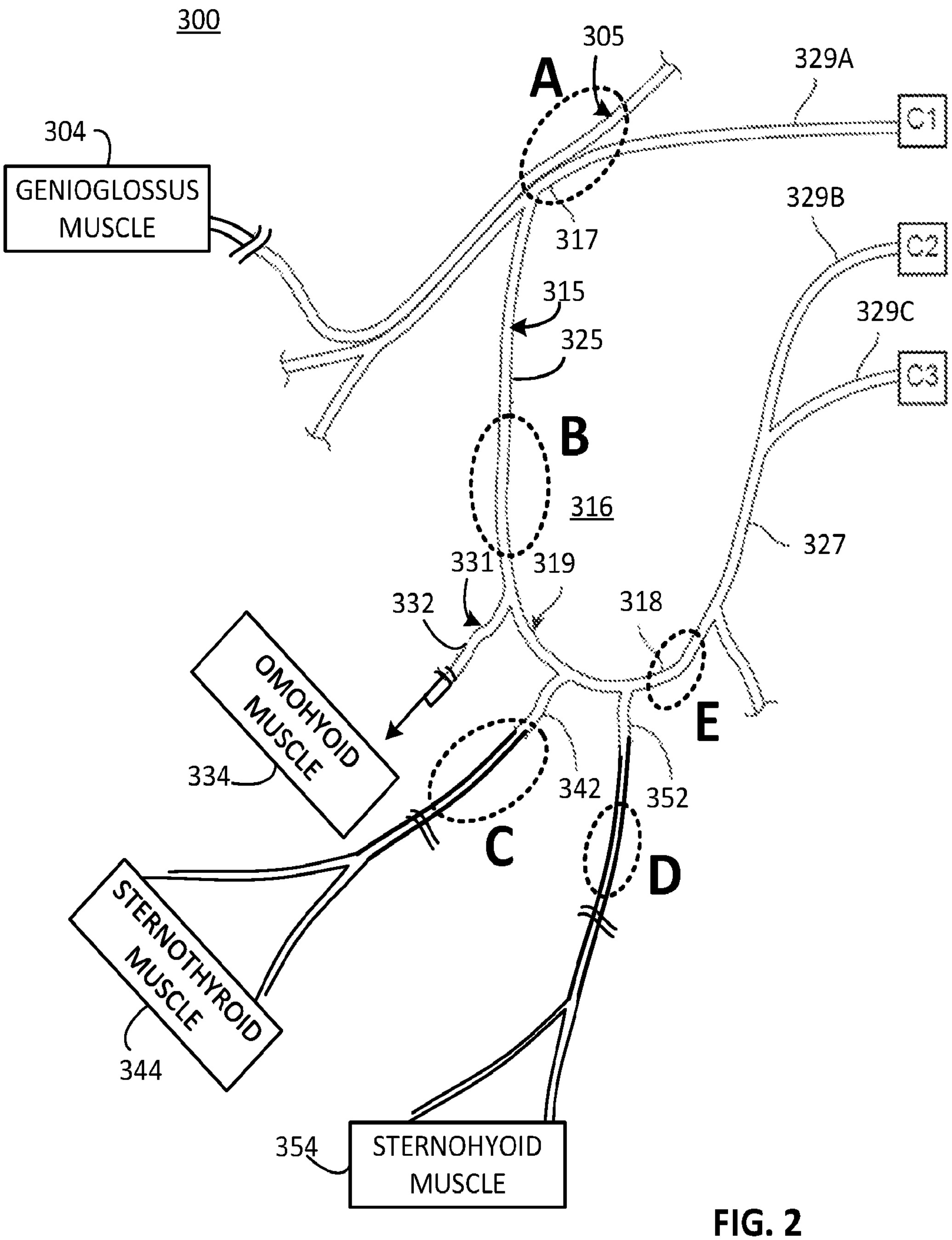
FIG. 2 is a diagram schematically representing patient anatomy and an example device and/or example method for stimulating an ansa cervicalis-related nerve and/or hypoglossal nerve.

FIG. 2 is a diagram 300 including a side view schematically representing an ansa cervicalis nerve 315, in context with a hypoglossal nerve 305 and with cranial nerves C1, C2, C3. As shown in FIG. 2, portion 329A of the ansa cervicalis nerve 315 extends anteriorly from a first cranial nerve C1 with a segment 317 running alongside (e.g. coextensive with) the hypoglossal nerve 305 for a length until the ansa cervicalis nerve 315 diverges from the hypoglossal nerve 305 to form a superior root 325 of the ansa cervicalis nerve 315, which forms part of a loop 319. A portion of the hypoglossal nerve 305 extends distally to innervate the genioglossus muscle 304. As further shown in FIG. 2, the superior root 325 of the ansa cervicalis-related nerve 315 extends inferiorly (i.e. downward) until reaching near bottom portion 318 of the loop 319, from which the loop 319 extends superiorly (i.e. upward) to form an lesser root 327 (i.e. inferior root) which joins to the second and third cranial nerves, C2 and C3, respectively.

As further shown in FIG. 2, several branches 331 extend off the ansa cervicalis loop 319, including branch 332 which innervates the omohyoid muscle group 334, branch 342 which innervates the sternothyroid muscle group 344 and the sternohyoid muscle group 354. Another branch 352, near bottom portion 318 of the ansa cervicalis loop 319, innervates the sternohyoid muscle group 354 and the sternothyroid muscle group. In some examples, the entire ansa cervicalis nerve 315 (including loop 319) and its related branches (e.g. at least 332, 342 352) when considered together may sometimes be referred to as an ansa cervicalis-related nerve 316. It will be further understood that one such ansa cervicalis-related nerve is present on both sides (e.g. right and left) of the patient's body.

In one aspect, stimulation of an ansa cervicalis-related nerve 316 may comprise stimulation of the superior root 325 of the ansa cervicalis nerve 315 (e.g. loop) and/or any one of the branches 331 extending from the loop 319, which may influence upper airway patency. However, in some examples, upper airway patency also may be increased by directly stimulating the above-identified muscle groups, such as the omohyoid, sternothyroid, and/or sternohyoid muscle groups.

Among other effects, stimulation of such nerves and/or muscles act to bring the larynx inferiorly, which may increase upper airway patency.

Various example implementations of stimulating different portions of the ansa cervicalis-related nerve 316 to activate different associated muscle groups are described later in association throughout various examples of the present disclosure. Moreover, some of these FIGURES illustrate various example implementations of stimulating the hypoglossal nerve and/or of stimulating other nerves in addition to, or instead of, the ansa cervicalis-related nerve and the hypoglossal nerve.

While stimulation of just the hypoglossal nerve 305 (or some branches thereof) may be effective in increasing upper airway patency to a sufficient degree to ameliorate obstructive sleep apnea in at least about seventy percent of appropriate patients when using certain types of implantable neurostimulation devices, some patients may benefit from stimulation of an ansa cervicalis-related nerve 316 in addition to, or instead of, stimulation of the hypoglossal nerve 305. Moreover, for a single patient, certain positions of the head-and-neck and/or of their body (e.g. supine, lateral decubitis, etc.) may be treated more effectively by stimulating an ansa cervicalis-related nerve 316, with or without stimulation of the hypoglossal nerve 305. In some such examples, upon detecting that a patient is in a certain body position (e.g. supine), stimulation of the ansa cervicalis-related nerve 316 may be implemented.

In addition, because the ansa cervicalis-related nerve 316 innervates several different muscle groups which may influence upper airway patency, stimulation may be applied at several different locations of the ansa cervicalis-related nerve 316. Such stimulation at the respective different locations may occur simultaneously, sequentially, alternately, etc., depending on which nerves (or muscles) are being stimulated, depending on when the stimulation occurs relative to the respective respiratory phases (or portions of each phase) of a respiratory period of the patient's breathing, and/or based on other factors.

Many different examples of various stimulation locations of an ansa cervicalis-related nerve 316, example timing, patterns, etc. are described below throughout the present disclosure. Of these various potential stimulation locations, FIG. 2 (and FIGS. 16, 32A) generally illustrates three example stimulation locations A, B, and C. In some examples, potential stimulation locations also include stimulation locations D and E. A stimulation element may be placed at all these locations or just some (e.g. one or two) of these example stimulation locations. At each location, a wide variety of types of stimulation elements (e.g. cuff electrode, axial array, paddle electrode) may be implanted depending on the particular delivery path, method, etc. At each example stimulation A, B, C, D, E, a stimulation element may be delivered subcutaneously, intravascularly, etc. At each stimulation location, in some examples the stimulation element may comprise a microstimulator. Various aspects of these example implementations are further described below.

In some example implementations, a stimulation element may be percutaneously delivered to a position to be in stimulating relation to the upper airway patency-related muscle. In some such examples, a percutaneous access point may be formed and located intermediate between a hyoid bone and a sternum and lateral to a midline. As with other implantation methods described herein, the implantation may comprise monitoring nerves during the percutaneous delivery and doing so via a nerve integrity monitor (NIM) in some examples.

Figure 16:
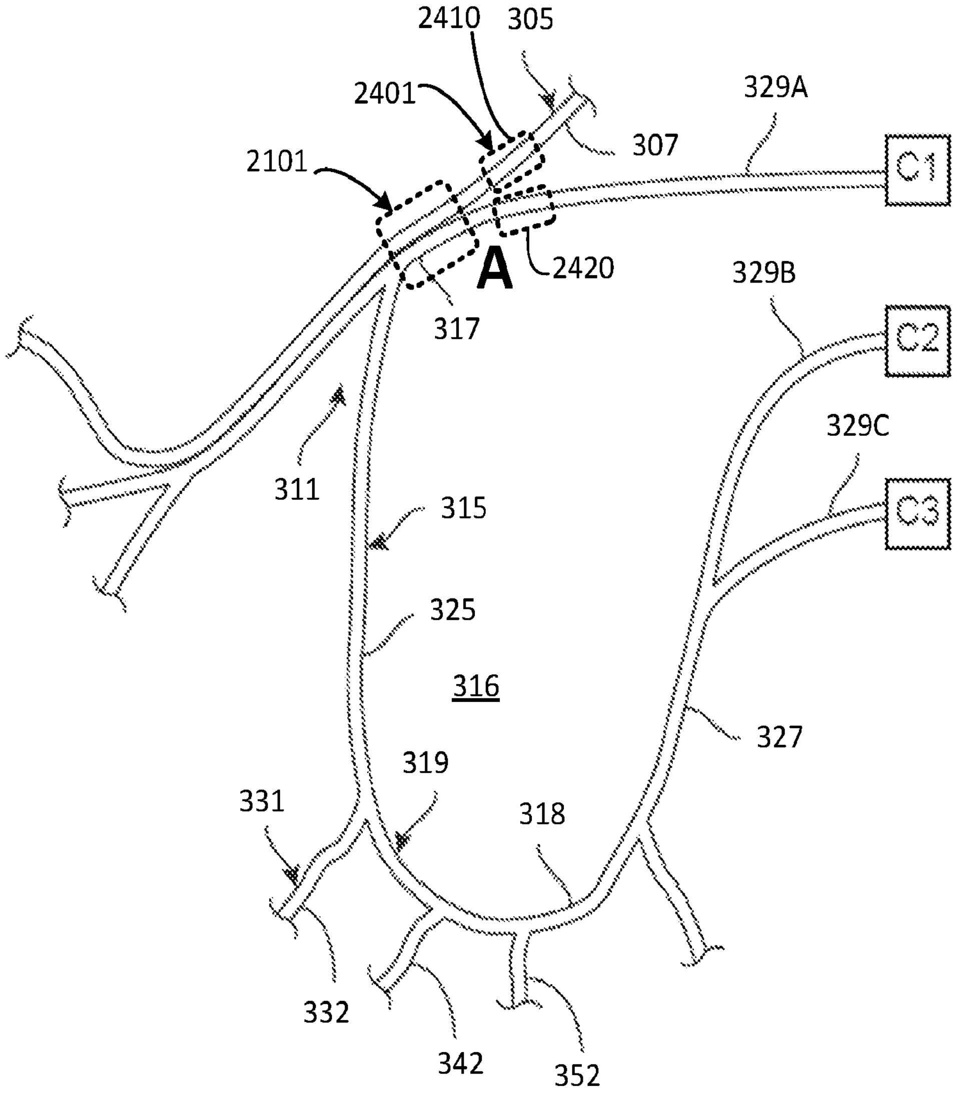
FIG. 16 is a diagram schematically representing an example device and/or example method, relative to patient anatomy, for stimulating an ansa cervicalis-related nerve and/or hypoglossal nerve.
Figure 22B:
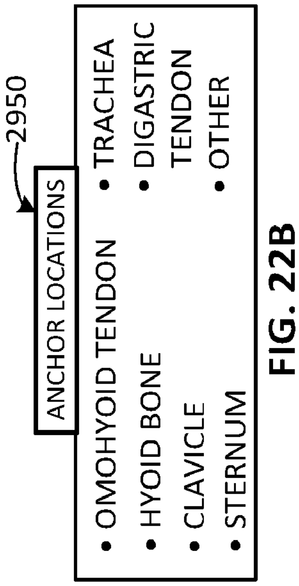
Figure 22A:
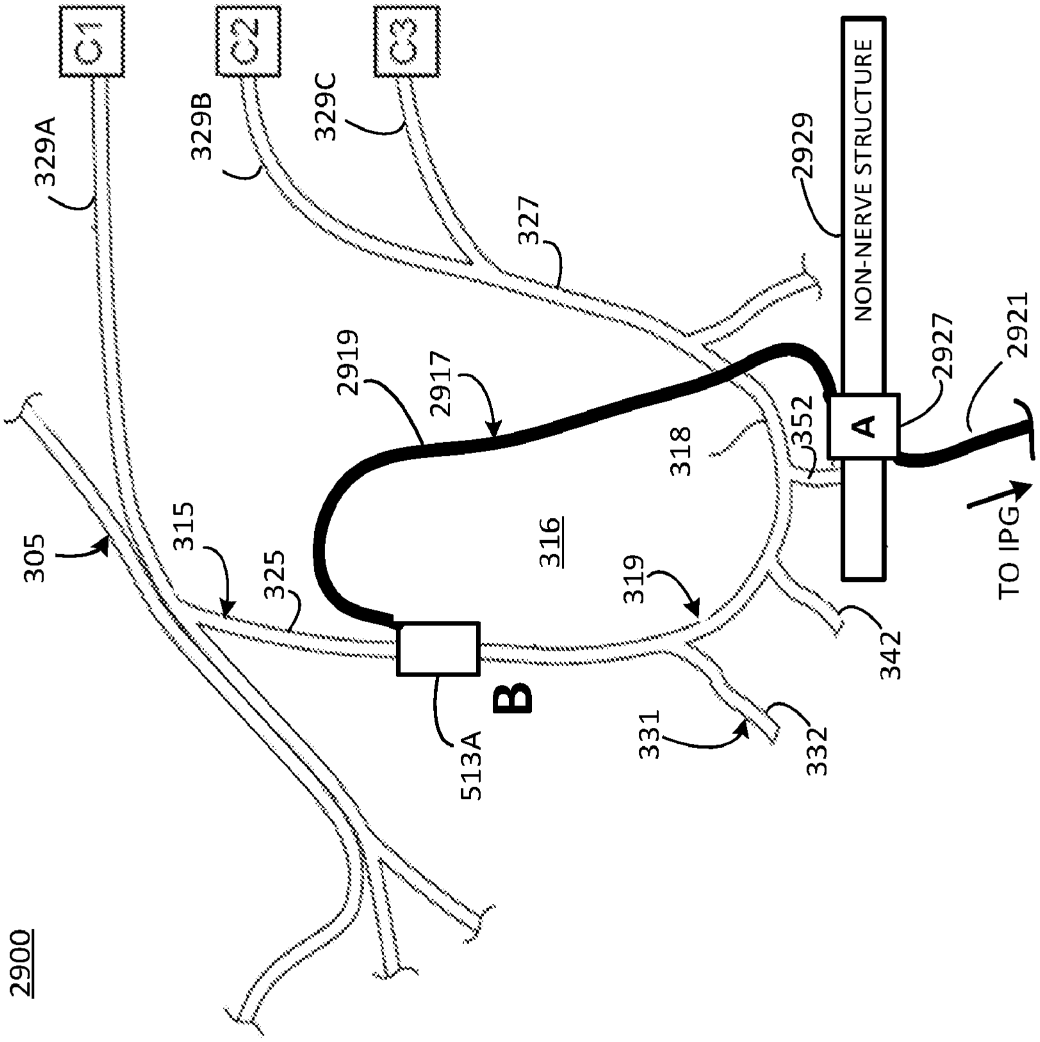
Figure 32A:
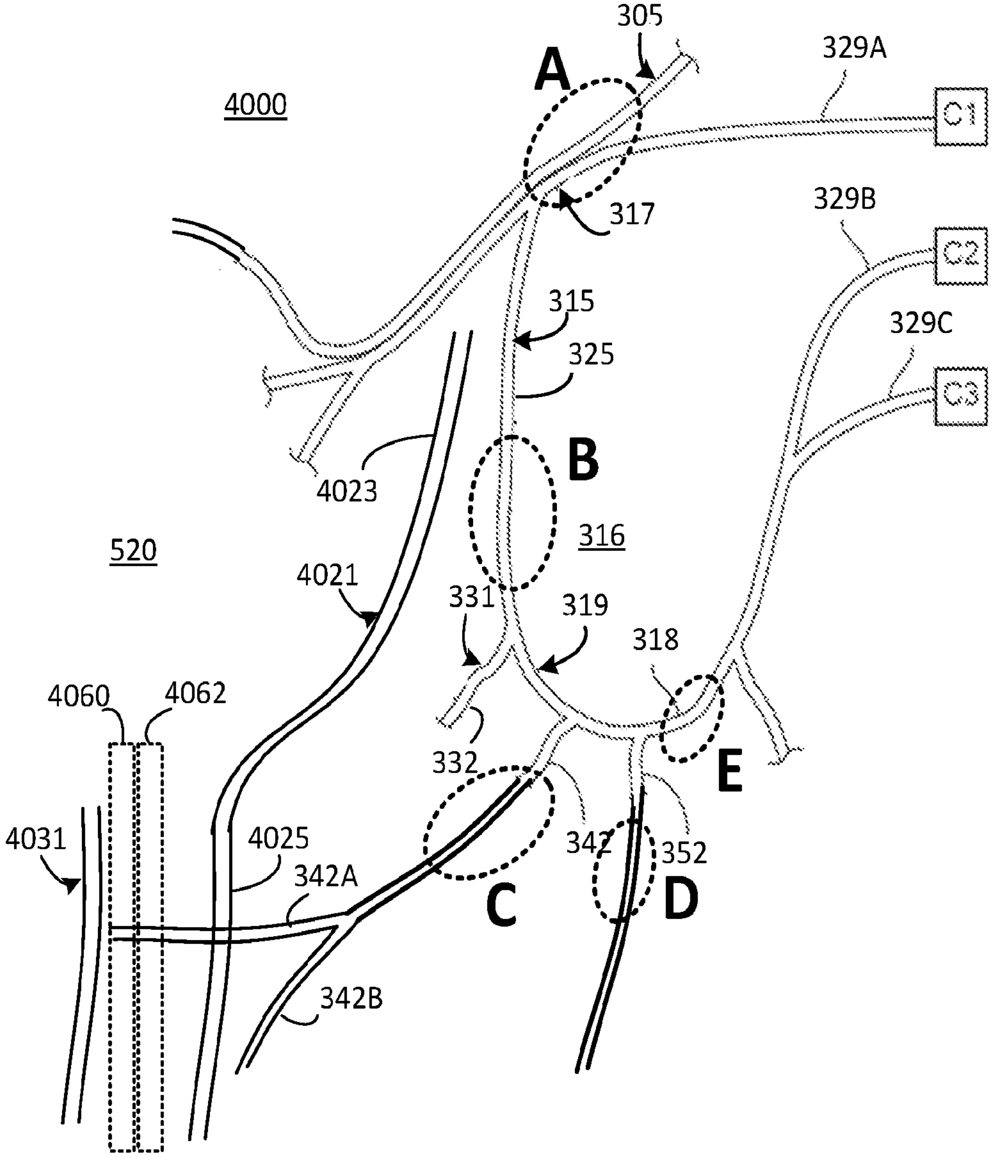
FIGS. 32A-32D are diagrams schematically representing patient anatomy and an example device and/or example method for stimulating various locations of an ansa cervicalis-related nerve, including some intravascular delivery pathways and other delivery pathways.
Figure 32B:
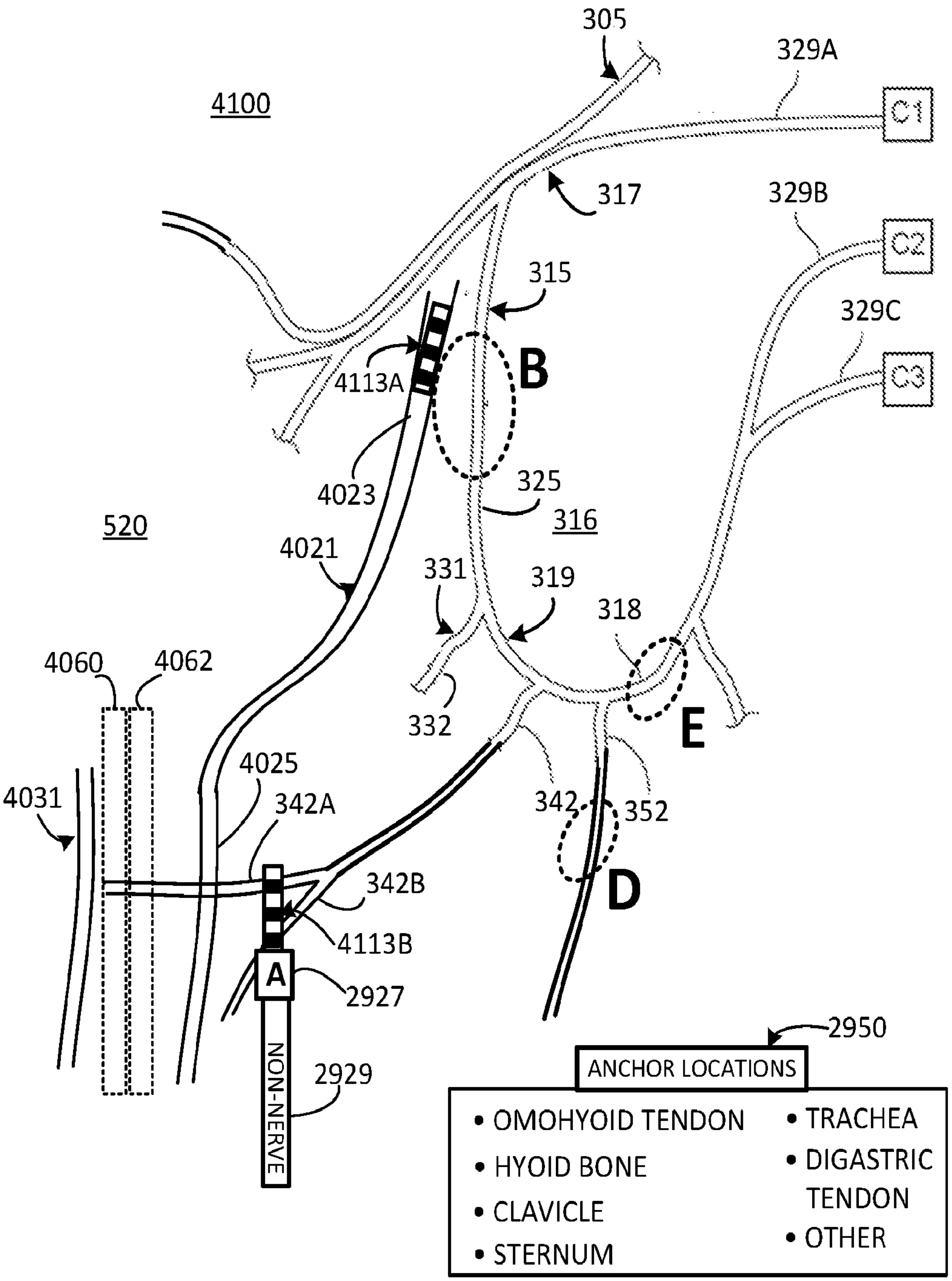

In some examples, further example implementations for these stimulation location are described in association with at least FIG. 16 (at least stimulation location A), FIGS. 22A, 32B (at least stimulation location B), FIG. 32B (stimulation location C). It will be understood that these example stimulation locations A, B, C, D, and E are not limiting and that other portions of the ansa cervicalis-related nerve may comprise suitable stimulation locations, depending on the particular objectives of the stimulation therapy, on the available access/delivery issues, etc.

Among the different physiologic effects resulting from stimulation of the various branches of the ansa cervicalis-related nerve 316, in some examples stimulation of nerve branches which cause contraction of the sternothyroid muscle and/or the sternohyoid muscle may cause the larynx to be pulled inferiorly, which in turn may increase and/or maintain upper airway patency in at least some patients. Such stimulation may be applied without stimulation of the hypoglossal nerve or may be applied in coordination with stimulation of the hypoglossal nerve 305.

Other physiologic effects of stimulating the ansa cervicalis-related nerve 316 and/or other nerves may be described later in the context of particular examples of the present disclosure.

Figure 3B:
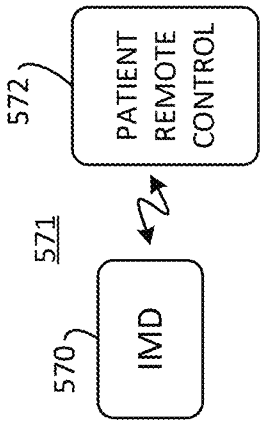
FIG. 3B is a block diagram schematically representing an example device including an IPG and patient remote control.
Figure 3A:
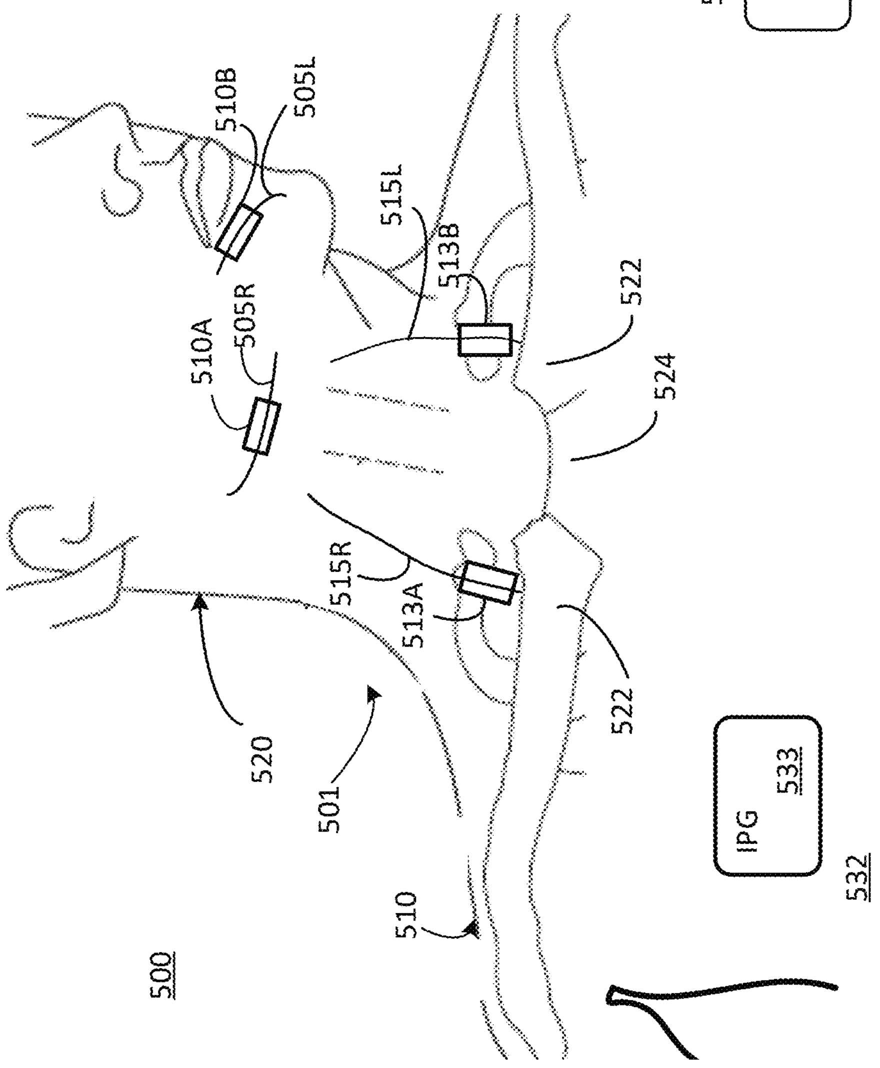
FIG. 3A is a diagram schematically representing patient anatomy and an example device and/or example method for stimulating airway patency-related tissue, including an implantable pulse generator (IPG) and associated stimulation elements.

FIG. 3A is a diagram 500 including a front view schematically representing an example arrangement 501 including one or more stimulation elements forming part of an example device and/or example method for increasing and/or maintaining upper airway patency or other purposes. As shown in FIG. 3A, in some examples, a first stimulation element 510A is positioned at a hypoglossal nerve 505R on a first side (e.g. right side) of a head-and-neck portion 520 of a patient's body and a second stimulation element 510B is positioned at a hypoglossal nerve 505L on an opposite second side (e.g. left side) of the head-and-neck portion 520, and therefore spaced apart from first stimulation element 510A. As further shown in FIG. 3A, in some examples, a third stimulation element 513A is positioned at an ansa cervicalis-related nerve 515R on a first side (e.g. right side) of the head-and-neck portion 520 and a second stimulation element 513B is positioned at an ansa cervicalis-related nerve 515L on an opposite second side (e.g. left side) of the head-and-neck portion, and therefore spaced apart from the third stimulation element 513A. As shown in FIG. 3A, the stimulation elements 513A, 513B are depicted as being in stimulating relation to the first and second ansa cervicalis-related nerve 515L, 515R at a position just superior to the clavicles 522. However, for illustrative simplicity, it will be understood that this depiction is also representative of the stimulation elements 513A, 513B being positioned at any portion of the ansa cervicalis nerve loop and/or related branches, etc. with at least FIGS. 2, 16, 22A, 32A-32D, etc. providing more detailed illustrations of an ansa cervicalis-related nerve 316.

As apparent from FIG. 3A, the stimulation element 510A is also spaced apart from stimulation element 513A, while stimulation element 510B is spaced apart from stimulation element 513B.

While FIG. 3A depicts stimulation elements for both the hypoglossal nerve (e.g. elements 510A, 510B) and for the ansa cervicalis-related nerve (e.g. elements 513A, 513B), it will be understood that in some examples, stimulation of an upper airway patency-related tissue may comprise stimulation of solely of the hypoglossal nerves 505R and/or 505L. In such arrangements, stimulation of the ansa cervicalis-related nerve 515R, 515L does not occur at all or at least does not occur during specified time periods, situations, etc.

Stimulation of just one hypoglossal nerve (e.g. 505R or 505L) may sometimes be referred to as unilateral stimulation, while stimulation of both such hypoglossal nerves (e.g. 505R and 505L) may sometimes be referred to as bilateral stimulation. It will be further understood that in some instances of unilateral stimulation, just one of the respective stimulation elements 510A, 510B has been implanted. However, in other examples of unilateral stimulation, both stimulation elements 510A, 510B may be implanted, but just one of them is stimulated to provide unilateral stimulation.

In some examples of bilateral stimulation of the hypoglossal nerves (e.g. 505R, 505L), the stimulation may be implemented simultaneously, alternately, and/or in other patterns.

Furthermore, in some examples in which one or both of stimulation elements 510A, 510B are implanted (to stimulate hypoglossal nerve(s)), neither of the stimulation elements 513A, 513B (for stimulating an ansa cervicalis-related nerve) are implanted.

However, in some examples in which one or both of stimulation elements 510A, 510B are implanted (to stimulate hypoglossal nerve(s)), one or both of the stimulation elements 513A, 513B (for stimulating an ansa cervicalis-related nerve) may be implanted. In some such examples, even though such stimulation elements 513A, 513B may be implanted, such stimulation elements 513A, 513B may be not activated in some examples in which just stimulation of one or both of the hypoglossal nerve(s) 505R, 505L is to be provided.

While FIG. 3A depicts stimulation elements for both the hypoglossal nerve (e.g. elements 510A, 510B) and for the ansa cervicalis-related nerve (e.g. elements 513A, 513B), it will be understood that in some examples, stimulation of an upper airway patency-related tissue may comprise stimulation of solely one or both of the ansa cervicalis-related nerves 515R, 515L. In such arrangements, stimulation of the hypoglossal nerve 505R, 505L does not occur at all or at least does not occur during specified time periods, situations, etc.

Stimulation of just one ansa cervicalis-related nerve (e.g. 515R or 515L) may sometimes be referred to as unilateral stimulation, while stimulation of both such nerves (e.g. 515R and 515L) may sometimes be referred to as bilateral stimulation. It will be further understood that in some instances of unilateral stimulation, just one of the respective stimulation elements 513A, 513B has been implanted. However, in other examples of unilateral stimulation, both stimulation elements 513A, 513B may be implanted, but just one of them is stimulated to provide unilateral stimulation.

In some examples of bilateral stimulation of ansa cervicalis-related nerves (e.g. 515R, 515L), the stimulation may be implemented simultaneously, alternately, and/or in other patterns.

Furthermore, in some examples in which one or both of stimulation elements 513A, 513B are implanted (to stimulate the ansa cervicalis-related nerve(s)), neither of the stimulation elements 510A, 510B (for stimulating a hypoglossal nerve) are implanted.

However, in some examples in which one or both of stimulation elements 513A, 513B are implanted (to stimulate ansa cervicalis-related nerve(s)), one or both of the stimulation elements 510A, 510B (for stimulating a hypoglossal nerve) may be implanted. In some such examples, even though such stimulation elements 510A, 510B may be implanted, such stimulation elements 510A, 510B may be not activated in some examples in which just stimulation of one or both of the ansa cervicalis-related nerve(s) 515R, 515L is to be provided.

In some examples, stimulation of just the ansa cervicalis-related nerve(s) 515R and/or 515L may be implemented for particular collapse patterns of the upper airway or less than complete collapse behaviors.

With further reference to the example arrangement 501 in FIG. 3A, in some examples just one stimulation element is implanted at a left side of the head-and-neck portion 520 to stimulate a first type of nerve (e.g. hypoglossal, ansa cervicalis-related, or other) and just one stimulation element is implanted at right side of the head-and-neck portion 520 to stimulate a different second type of nerve (e.g. hypoglossal, ansa cervicalis-related, other). For instance, in some examples just stimulation element 510A is implanted to stimulate a right hypoglossal nerve 505R and just stimulation element 513B is implanted to stimulate a left ansa cervicalis-related nerve 515L, or vice versa.

Alternatively, all stimulation elements 510A, 510B, 513A, 513B of example arrangement 501 may be implanted, but stimulation is implemented solely via stimulation element 510A for right hypoglossal nerve 505R and solely via stimulation element 513B for the left ansa cervicalis-related nerve 515L, or vice versa. In some such examples, the stimulation elements (e.g. a combination of 510A and 513B, or a combination of 510B and 513A) may be activated to deliver stimulation simultaneously to the respective hypoglossal and ansa cervicalis-related nerves. However, in some examples, the stimulation elements (e.g. a combination of 510A and 513B, or a combination of 510B and 513A) may be activated to deliver stimulation alternately to the respective hypoglossal and ansa cervicalis-related nerves In yet other examples, various stimulation patterns may be implemented in which one stimulation element (e.g. 510A) is activated multiple times within a selectable period of time and then the other stimulation element (e.g. 513A) is activated one or more times. In further examples, stimulation applied via the respective stimulation elements 510A, 510B, 513A, 513B may be implemented in an interleaving manner.

It will be further understood that the various stimulation elements 510A, 510B, 513A, 513B illustrated in FIG. 3A may be embodied as part of a lead, a microstimulator, etc., and may be anchored to a non-nerve tissue or structure within the patient's body via various anchor elements, as described more fully below in association with at least FIGS. 6A-6B, 22A-23, and/or 27A-30B. For example, with reference to FIG. 3A, in some examples such anchor elements may be secured relative to a non-nerve tissue, such as but not limited to, the illustrated clavicles 522, manubrium 524 of the sternum, etc.

Similarly, the respective stimulation elements 510A, 510B, 513A, 513B may be embodied as one of the various electrode arrays, cuff electrodes, paddle electrodes, etc. as described more fully below in various example arrangements of the present disclosure. The respective stimulation elements may be embodied in a unipolar configuration, a bipolar configuration or multi-polar configuration.

In some examples, the various stimulation arrangements described in association with at least FIG. 3A may be implemented and stimulation performed without any sensing at all or with limited sensing, such as (but not limited to) just sensing to evaluate effectiveness of the stimulation but not using the sensing to time or trigger the stimulation. In either case, in some examples stimulation may be applied simultaneously to both an ansa cervicalis-related nerve and a hypoglossal nerve. Further details are described throughout various examples of the present disclosure.

FIG. 3B is a diagram schematically representing an example arrangement 571 comprising an example device for, and/or example method of, communication between an implantable medical device (IMD) 570 and a patient remote control 572. In some examples, the implantable medical device 570 may comprise an implantable pulse generator (IPG) (e.g. 533 in FIG. 3A, etc.), microstimulator (e.g. 1313A in FIGS. 10A, 10C; 6575 in FIG. 14H). In some examples, the implantable medical device 570 (with the patient remote control 527) may comprise one example implementation of the IPG 533 in FIG. 3A, and is therefore applicable to example implementations throughout the present disclosure.

The patient remote control 572 comprises inputs to change stimulation strength settings, activate or deactivate therapy, etc. The patient remote controls 572 also may receive control data, sensed data, therapy data, and/or other data from the IMD 570. The patient remote control 572 may communicate wirelessly with the IMD 570 via telemetry or other wireless communication protocols. At least some aspects of initiating, terminating, adjusting stimulation settings and/or other settings of the IMD 570 will be further described later in association with various examples throughout the present disclosure.

In some examples, the example arrangement 571 may comprise one example implementation of the care engine 10000 (FIG. 54A), control portions 10500, 10528, 10600 (FIG. 54B, 54C), and/or user interface 10520 (FIG. 54D), as described later. With this in mind, the patient remote control 572 may comprise one example implementation of the patient remote control 10530 in FIG. 54C and/or of the patient remote control 10640 in FIG. 54E.

Figure 3C:
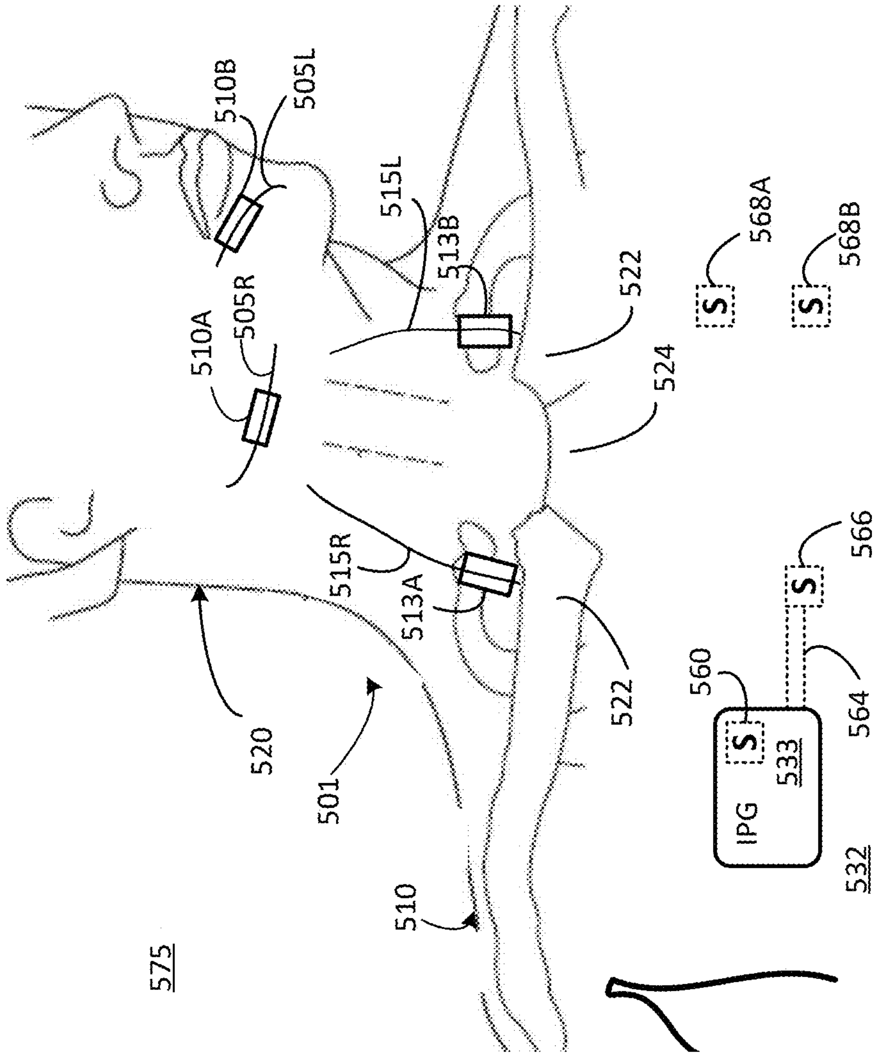
FIG. 3C is a diagram schematically representing patient anatomy and an example device and/or example method like FIG. 3A, while explicitly illustrating sensing elements.

FIG. 3C is a diagram on an example arrangement 575 comprising at least some of substantially the same features and attributes as example arrangement 500 in FIG. 3C, except including various examples of sensors which may form part of the IPG 533 and/or may be independent of the IPG 533. In general terms, the sensors described in association with FIG. 3C may comprise any one or more of the sensing types, modalities, parameters, etc. as later described in association with at least FIGS. 38B-38C, and at least FIGS. 40A-51B, 54A (care engine 10000). In some examples, the example arrangement 575 may comprise one example implementation of the care engine 10000 (FIG. 54A), control portions 10500, 10528, 10600 (FIG. 54B, 54C), and/or user interface 10520 (FIG. 54D), as described later.

In some examples IPG 533 may comprise an on-board sensor 560 which is incorporated within a housing of the IPG 533 and/or exposed on an external surface of the housing of the IPG 533. In some examples, the sensor 560 may comprise an accelerometer (e.g. 8754 in FIG. 38C), which may comprise a single axis accelerometer or a multiple axis (e.g. 3 axis) accelerometer. As noted in association with at least FIGS. 38C-38D, the accelerometer may be used to sense various physiologic information, such as but not limited to body position (e.g. 8722 in FIG. 38B), respiration (e.g. 8274 in FIG. 38B), sleep (e.g. 8728 in FIG. 38B), disease burden (e.g. 8726 in FIG. 38B). In some examples, the sensed respiration may be used for timing application of stimulation to treat sleep disordered breathing, evaluate the severity of the sleep disordered breathing or other disease burdens, the effectiveness of the stimulation therapy, and/or other physiologic information.

In a manner similar to sensing body position, the accelerometer may be used to sense posture and/or activity based on gross body movements. The accelerometer also may be used to sense at least ballistocardiography (8762 in FIG. 38C), seismocardiography (8764 in FIG. 38C), heart rate (HR) (8766 in FIG. 38C), sleep (8728 in FIG. 38C), disease burden (8726 in FIG. 38C), as further described later in association with at least FIG. 38C. In some examples, via at least such accelerometer sensing, the disease burden may comprise a cardiovascular burden and/or be determined via a cardiac output and/or cardiac waveform morphology.

In some examples, the on-board sensor 560 may comprise an electrode formed on the external surface of a housing of the IPG 533, and may be used for sensing impedance (e.g. 8752 in FIG. 38C) in combination with other implanted sensors, such as but not limited to sensors 568A, 568B, which may be located on the torso of the patient. As further described later, sensor 560 also may be used in combination with sensing elements such as electrodes implanted in the head-and-neck region 520. In some examples, a stimulation element (e.g. 510A, 510B, 513A, 513B) may comprise electrodes which may serve in combination with sensor 560 (as an electrode) to sense impedance. In some such examples, the sensed impedance may be used to determine respiration, which may be used for at least some of the above-identified purposes and/or other purposes.

In some examples, sensed impedance may indicate a degree of upper airway patency. For example, a smaller cross-sectional upper airway, which reflects less upper airway patency, may be sensed as a lower impedance. Conversely, a larger cross-sectional upper airway, which reflects more upper airway patency, may be sensed as a higher impedance. Accordingly, maximal patency (measured as a higher impedance) may general correspond to periods of stimulation (HGN and/or ACN) or correspond to peak expiration of a respiratory cycle. Meanwhile, minimal patency (measured as a lower impedance) generally corresponds to inspiration, just prior to inspiration, or the onset of stimulation (e.g. HGN and/or ACN).

Figure 38A:
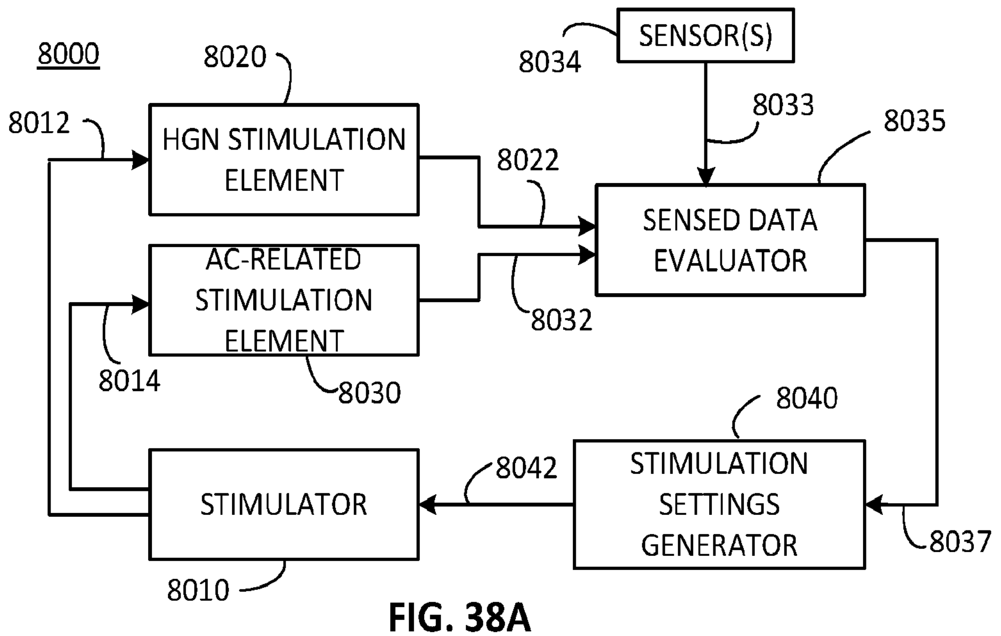
FIG. 38A is a flow diagram schematically representing an example device and/or example method for stimulation therapy.
Figure 38B:
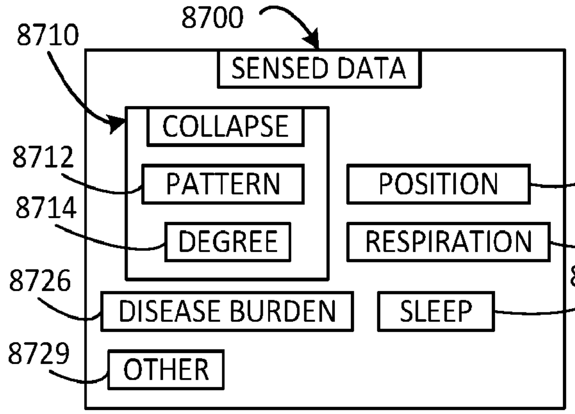
FIGS. 38B, 38C, and 38D are block diagrams schematically representing examples of a sensing engine, sensing tools, and a stimulation engine, respectively.
Figure 38C:
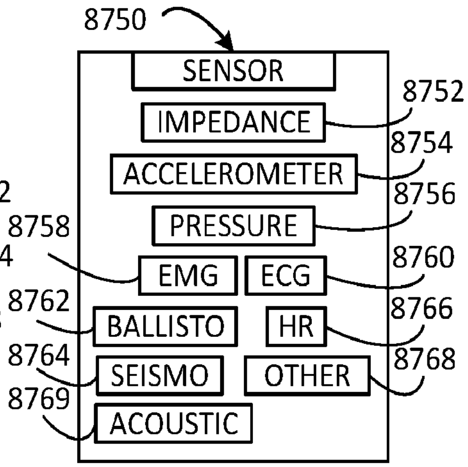

In some examples, the on-board sensor 560 may comprise an ECG sensor or may comprise an electrode, which when used in combination with other electrodes (e.g. 568A, 568B), may be used to sense electrocardiogram (ECG) information, such as per ECG parameter 8760 in FIG. 38C.

As further shown in FIG. 3C, in some example implementations the example arrangement 575 may comprise a sensor lead 564 which supports a sensor 566, which in turn in some examples may comprise a pressure sensor (e.g. differential pressure) (e.g. 8756 in FIG. 38B). Among other physiologic parameters, the pressure sensor may be used to sense respiration, which may be used for at least some of the above-identified purposes and/or other purposes. In some examples, the sensor 566 may sense physiologic parameters other than pressure.

In some examples, the example arrangement 575 may be implemented via at least some external sensors relating to at least some of the sensing types, modalities, physiologic parameters, etc. which were described above as being implemented via implantable sensors.

With the examples of FIGS. 1-3C in mind, in some examples an example method (and/or example device) comprises applying electrical stimulation, via at least one stimulation element, to upper airway patency-related tissue according to at least one stimulation protocol based on an upper airway patency hysteresis parameter. At least some aspects of the example method (and/or example device) are further described later in association with at least FIGS. 37E-37G, FIGS. 38E-38H, and/or FIGS. 52D-52L.

In some examples of the method relating to the patency hysteresis parameter, the upper airway patency-related tissue comprises an ansa cervicalis-related nerve, and in some examples, the ansa cervicalis-related nerve comprises a superior root portion. In some examples, the superior root portion innervates at least one of a sternothyroid muscle, a sternohyoid muscle, and an omohyoid muscle.

In some examples, the upper airway patency-related tissue comprises at least one nerve portion extending distally from the superior root portion and innervating at least one of the sternothyroid muscle, the sternohyoid muscle, and the omohyoid muscle.

In some examples, the upper airway patency-related tissue comprises at least one of a plurality of infrahyoid strap muscles, which comprise at least one of a sternothyroid muscle, a sternohyoid muscle, and an omohyoid muscle. In some such examples, the method comprises applying the electrical stimulation to the at least one infrahyoid strap muscle.

In some of these examples, the method comprises transcutaneously applying the electrical stimulation to the at least one infrahyoid strap muscle. In some such examples, the transcutaneous application may comprise removably securing the stimulation element externally of, and relative to, a neck region.

However, in some examples, applying the electrical stimulation may comprise implanting the stimulation element subcutaneously within a neck region to be in stimulating relation to the at least one infrahyoid strap muscle.

In some examples, the upper airway patency hysteresis parameter represents a degree and a duration of upper airway patency for the upper airway patency-related tissue following at least one stimulation period of the at least one stimulation protocol.

In some examples, the upper airway patency hysteresis parameter comprises an upper airway patency hysteresis reference. In some such examples, the upper airway patency hysteresis reference is based on at least one of: a historical patient-specific average patency hysteresis effect; and a multiple patent average patency hysteresis effect.

In some examples, the upper airway patency-related tissue comprises infrahyoid-based, upper airway patency tissue, and in some such examples, the infrahyoid-based patency tissue comprises at least one of the ansa cervicalis-related nerve and at least one infrahyoid strap muscle innervated by the ansa cervicalis-related nerve.

In some examples, the upper airway patency-related tissue comprises a genioglossus-based patency tissue, and in some such examples, the genioglossus-based patency tissue comprises at least one of a hypoglossal nerve and a genioglossus muscle innervated by the hypoglossal nerve.

In some examples, the upper airway patency-related tissue comprises at least one of an infrahyoid-based, upper airway patency tissue and a genioglossus-based patency tissue. In some such examples, the at least one stimulation element comprises a first stimulation element, and wherein applying the stimulation via the first stimulation protocol comprises performing the stimulation of the infrahyoid-based patency tissue via the first stimulation element without stimulating the genioglossus-based patency tissue.

In some examples the at least one stimulation protocol comprises a first stimulation protocol including a series of stimulation cycles with each stimulation cycle comprising alternating stimulation periods and non-stimulation periods, and applying the electrical stimulation, via the first stimulation protocol and the first stimulation element, to the infrahyoid-based patency tissue via at least one of: a first closed loop mode including timing the stimulation periods relative to sensed respiratory phase information and based on the hysteresis patency parameter; and a first open loop mode including timing the stimulation periods without reference to respiratory phase information and based on the hysteresis patency parameter.

In some examples, the at least one stimulation element comprises a second stimulation element, wherein applying the stimulation via the first stimulation protocol comprises applying the stimulation via the second stimulation element to the genioglossus-based patency tissue via at least one of: a second closed loop mode including timing the stimulation periods of the first stimulation protocol relative to sensed respiratory information and based on the hysteresis patency parameter; and a second open loop mode including timing the stimulation periods without reference to respiratory phase information and based on the hysteresis patency parameter.

In some examples, in the first closed loop mode, based on the hysteresis patency parameter, the method comprises setting a duration of the non-stimulation period between stimulation periods and to comprise: a minimum duration corresponding to at least one respiratory cycle based on sensed respiratory information; or a maximum duration of a selectable number of respiratory cycles based on sensed respiratory information.

In some examples, in the first open loop mode, based on the hysteresis patency parameter, the method comprises setting a duration of the non-stimulation period between stimulation periods and to comprise: a minimum duration corresponding to at least one reference respiratory cycle; or a maximum duration of a selectable number of reference respiratory cycles.

In some examples, in the first open loop mode, the non-stimulation period between stimulation periods has a duration equal to at least one of: at least one reference respiratory cycle; or a sum of a selectable multiple number of reference respiratory cycles.

In some examples, one method of applying electrical stimulation (via at least one stimulation element to upper airway patency-related tissue according to at least one stimulation protocol based on an upper airway patency hysteresis parameter) comprises implementing the timing of stimulation without a sensing element for timing stimulation.

In some examples, one method of applying electrical stimulation (via at least one stimulation element, to upper airway patency-related tissue according to at least one stimulation protocol based on an upper airway patency hysteresis parameter) comprises sensing respiratory information and implementing the timing of stimulation based on the sensed respiratory information. In some such examples, the sensed respiratory information comprises sensed respiratory phase information, which comprises at least one of an inspiratory phase and an expiratory phase.

In some examples, the first stimulation protocol comprises applying a selectable number of consecutive stimulation periods.

In some examples, one method of applying electrical stimulation (via at least one stimulation element to upper airway patency-related tissue according to at least one stimulation protocol based on an upper airway patency hysteresis parameter) comprises at least one of: when a respiration sensing sensitivity parameter is below a threshold, applying the stimulation, via the at least one stimulation protocol, at a first duty cycle which is less than a first selectable percentage of a duration of a reference respiratory cycle or a sensed respiratory cycle; and when the respiration sensing sensitivity parameter is at or above a threshold, applying the stimulation, via the at least one stimulation protocol, at a second duty cycle which is equal to or greater than the first selectable percentage of a duration of a reference respiratory cycle or a sensed respiratory cycle. In some such examples, the first selectable percentage comprises 50 percent.

In some examples, one method of applying electrical stimulation (via at least one stimulation element to upper airway patency-related tissue according to at least one stimulation protocol based on an upper airway patency hysteresis parameter) comprises determining the timing of the application of the stimulation, according to the at least one stimulation protocol, based on the patency hysteresis parameter and according to at least one of: a body position parameter; a time of night parameter; a sleep disordered breathing (SDB) event frequency parameter; a patient stimulation pause parameter; a patient stimulation intensity adjustment parameter; and a swallowing parameter. In some such examples, determining the timing of the application of the stimulation (according to the at least one stimulation protocol) is based on a collapsibility parameter related to at least one of the SDB event frequency parameter and the body position parameter. In some of these examples, the upper airway patency tissue comprises an infrahyoid-based patency tissue, and comprising implementing the timing of stimulation via: starting, or increasing intensity of, stimulation of the infrahyoid-based patency tissue when a value of the collapsibility parameter meets or exceeds a threshold; and terminating, or decreasing intensity of, stimulation of the infrahyoid-based patency tissue when the value of the collapsibility parameter is less than the threshold.

In some examples, an at least one stimulation protocol comprises an open loop stimulation mode, a closed loop stimulation mode, and a selective continuous stimulation mode, and comprising applying the stimulation via selectively switching among the respective modes based on at least one of: a value of the hysteresis patency parameter; and a value of a respiration sensing sensitivity parameter. In some examples, the selective continuous stimulation mode may implement a tone-level stimulation versus a suprathreshold contraction level of stimulation.

Figure 4:
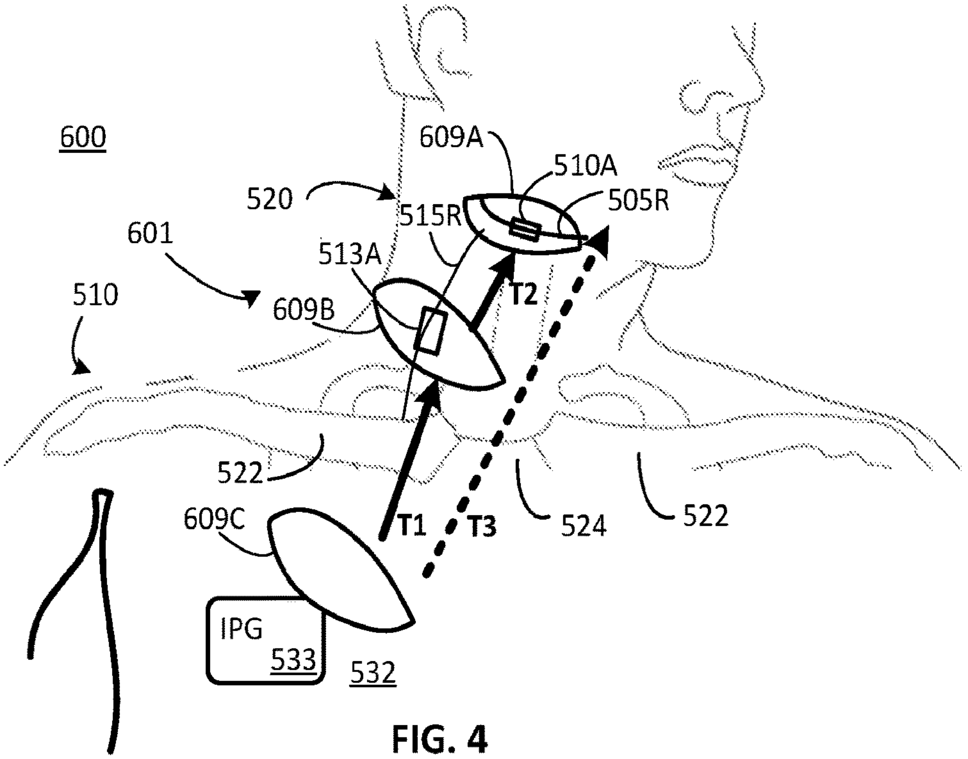
FIG. 4 is a diagram schematically representing an example device and/or method for implanting stimulation elements into stimulating relation to target nerve stimulation locations.

FIG. 4 is a diagram 600 including a front view schematically representing an example arrangement 601 including one or more stimulation elements forming part of an example device and/or example method for increasing and/or maintaining upper airway patency and/or other purposes. In some examples, the example arrangement 601 may comprise at least some of substantially the same features as, or comprise one example implementation of, the examples as previously described in association with at least FIGS. 1-3C.

In some examples, an example method may comprise implanting stimulation element (e.g. 510A and/or 510B) at a hypoglossal nerve (e.g. 505R and/or 505L). As shown in FIG. 4, in some examples this implantation may involve tunneling (T3) between a first incision 609C and a second incision 609A, wherein an implantable pulse generator (IPG) 533 is implanted via first incision 609C and the stimulation element (e.g. 510A) is implanted via second incision 609A. In some examples, this portion of example arrangement 601 may be operated to treat sleep disordered breathing (SDB) without amendment or supplementation, either indefinitely or for at least a period of time during which the treatment is deemed satisfactory.

However, in some examples, the example arrangement 601 may be supplemented to enhance treatment of sleep disordered breathing. In such instances, such as after a time period following the implantation of the first stimulation element (e.g. 510A), a second implant procedure is performed while leaving the first stimulation element (e.g. 510A) implanted relative to the hypoglossal nerve (e.g.

505R). In the separate, second implant procedure, a second stimulation element (e.g. 513A) is implanted to be in stimulating relation to the ansa cervicalis-related nerve (e.g. 515R). In some examples, the method comprises performing the implanting of the second stimulation element (e.g. 513A) upon a determination of a patient exhibiting sleep disordered breathing (SDB) despite treatment via the first stimulation element (e.g. 510A and/or 510B) of the hypoglossal nerve (e.g. 505R and/or 505L). In some such examples, the patient may exhibit symptomatic AHI despite the stimulation of the hypoglossal nerve(s). In some examples, the baseline stimulation therapy involving the hypoglossal nerve may reduce collapsibility of the upper airway as measured in Pcrit by 5 cm of water pressure. However, upon adding stimulation of the ansa cervicalis-related nerve to be concomitant with the stimulation of the hypoglossal nerve, the collapsibility of the upper airway is changed by or to 8 cm of water pressure, in some examples.

There are several example methods by which the first stimulation element 510A and by which the second stimulation element 513A may be implanted to supplement the already implanted stimulation element 510A.

It will be understood that the first stimulation element 510A may be implanted via a first stimulation lead, on which the first stimulation element 510A is supported, in a position to extend between the implanted pulse generator 533 (at or near access incision 609C) and the position of the first stimulation element at the hypoglossal nerve (at or near access incision 609A), as shown in FIG. 4. One example arrangement 700 for doing so is illustrated in FIG. 5A.

Figure 5A:
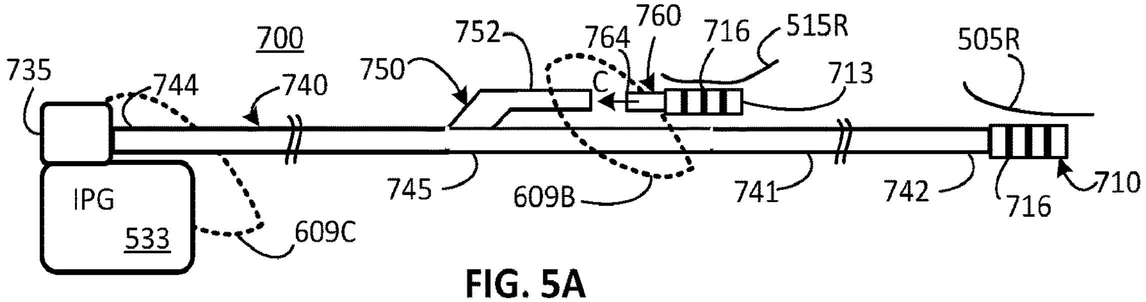
FIGS. 5A-5B are diagrams including a side view schematically representing an example stimulation lead with connection features.

FIG. 5A is a diagram including a side view schematically representing an example device 700 which comprises a stimulation lead 740 comprising a body 741 extending between a proximal portion 744 and an opposite distal portion 742, which supports a first stimulation element 710. In some examples, the first stimulation element 710 may comprise one example implementation of stimulation element 510A in FIG. 4. With further reference to FIG. 5A, the first stimulation element 710 may comprise a linear array of electrodes 716 adapted to stimulate hypoglossal nerve 505R (or 505L). However, it will be understood that the first stimulation element 710 may comprise other types of electrode configurations (e.g. cuff, paddle, etc.). Meanwhile, the proximal portion 744 of lead 740 is connectable to a port in header 735 of implantable pulse generator (IPG) 533. As further represented by the dashed lines in FIG. 5A, the IPG 533 is implanted via implant access-incision 609C, which may be in the pectoral region 532 as shown in FIG. 4.

With this in mind, the first stimulation lead 740 may be implanted subcutaneously via implant access-incisions 609A, 609C, and via appropriate tunneling, stimulation element 710 may be placed in stimulating relation to hypoglossal nerve 505R, with body 741 of lead 740 extending between the hypoglossal nerve 505R and the IPG 533 in the pectoral region 532.

As noted previously, the first stimulation lead 740 may be operated to treat sleep disordered breathing via stimulation of the hypoglossal nerve 505R.

However, upon a determination that the patient exhibits an unsatisfactory level of sleep disordered breathing despite stimulation via stimulation lead 740 at the hypoglossal nerve 505R, an example method schematically represented via FIG. 5A (in context with FIG. 4) comprises implanting a second stimulation lead 760 supporting a second stimulation element 713 to be positioned in stimulating relation to the ansa cervicalis-related nerve 515R. In some examples, the second stimulation element 713 may comprise one example implementation of stimulation element 513A in FIG. 4, and may comprise a linear array of electrodes 716 as shown in FIG. 5A, in some examples.

As further shown in FIG. 5A, the second stimulation lead 760 comprises a proximal portion 764 for connection to an intermediate portion 745 of the first stimulation lead 740. In particular, in some examples, the intermediate portion 745 of lead 740 comprises a port interface 750 including an extension arm 752 including a connection port to receive the proximal portion 764 of second stimulation lead 760 in order to establish electrical connection (and mechanical connection) of the lead 760 to the IPG 533.

As further shown in FIG. 4 (in context with FIG. 5A), in some examples tunneling T1 may be performed between the implant access-incision 609C and a new implant access-incision 609B, via which the second stimulation element 713 (FIG. 5A) is to be positioned, with the tunnel T1 providing a path to implant second stimulation lead 760. As represented via FIG. 5A, the second stimulation lead 760 may be substantially shorter than first stimulation lead 740. While the second stimulation lead 760 is depicted as being relatively short, it will be understood that the second stimulation lead 760 may have a greater relative length than shown in FIG. 5A and that its length may depend on the location of port interface 750 along the stimulation lead 740.

Via this arrangement, once it is determined that stimulation of the ansa cervicalis-related nerve 515R is desirable in view of insufficient treatment of sleep disordered breathing, then at a time period after implantation of the first stimulation lead 740, the second stimulation lead 760 may be implanted for connection to the IPG 533 via releasable connection of second stimulation lead 760 to the port interface 750 of stimulation lead 740.

In some examples, the sequence of implantation described in association with example device 601, 700 in FIGS. 4, 5A may be reversed such that a first stimulation lead is implanted to stimulate the ansa cervicalis-related nerve 515R, and then at a later point in time, a second stimulation lead may be implanted to stimulate the hypoglossal nerve with the second stimulation lead being electrically connectable to the first stimulation lead.

Figure 5B:
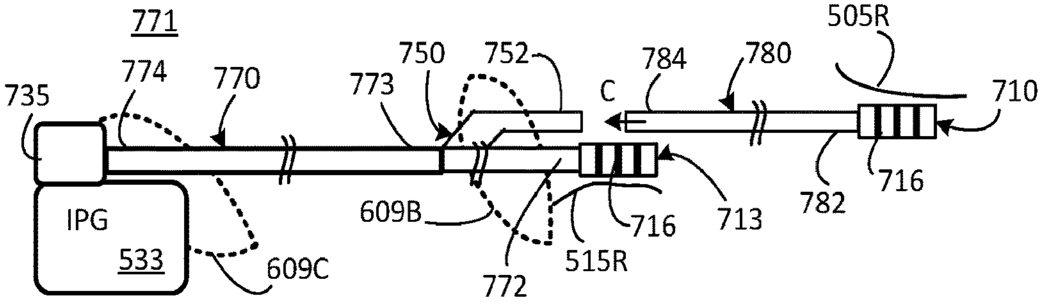

With this in mind, FIG. 5B includes a side view schematically representing an example device 771. In some examples, device 770 may comprise at some of substantially the same features and attributes as device 700 in FIG. 5A, except with device 771 providing a first stimulation lead 770 adapted to be in stimulating relation to the ansa cervicalis-related nerve 515R and to be implanted in an initial implantation procedure instead of first implanting a stimulation lead for the hypoglossal nerve.

As shown in FIG. 5B, the first stimulation lead 770 comprises a distal portion 772 supporting a stimulation element 713 (including a linear array of electrodes 716) and a proximal portion 774 in electrical connection with the IPG 533 via header 735. The first stimulation lead 770 also comprises an intermediate portion 773 which includes port interface 750 (as in FIG. 5A) to receive a proximal portion 784 of a second stimulation lead 780 to be in stimulating relation to a hypoglossal nerve 505R. The second stimulation lead 780 comprises a distal portion 782 supporting stimulation element 710 (including a linear array of electrodes 716). As in other example stimulation leads throughout the present disclosure, the respective stimulation elements 710, 713 in example device 771 of FIG. 5B can comprise a wide variety of types of electrode configurations (e.g. cuff, paddle, axial array, etc.).

In operation, the first stimulation lead 770 is implanted for treating sleep disordered breathing via stimulation of the ansa cervicalis-related nerve 515R. After some period of time elapsing, such as a determination that the neurostimulation therapy is unsatisfactory, a second implant procedure may be performed to implant the second stimulation lead 780 for neurostimulation of the hypoglossal nerve 505R (or 505L). As part of this second implant procedure, the proximal portion 784 of the second stimulation lead 780 is electrically (and mechanically) connected to the port 752 of port interface 750, as represented via directional arrow C in FIG. 5B.

As further represented in FIG. 4 (in context with FIG. 5B), in order to add the second stimulation lead 780, tunneling T2 may be performed from the location of the port interface 750 of lead 770 (at or near implant access-incision 609B in FIGS. 4, 5B) to the intended implant location of the stimulation element 710 on second stimulation lead 780 at implant access-incision 609A (FIG. 4).

Via the example arrangement provided via example device 771 in FIG. 5B, neurostimulation therapy can be conveniently expanded to include additional nerves when desired, such as to address a change in a patient's underlying condition, to enhance therapy, etc.

Additional example implementations of implanting multiple stimulation element(s) for second/type of nerve or a second side of the body are described below in, but not limited to, at least FIGS. 10A-10C.

Figure 6A:
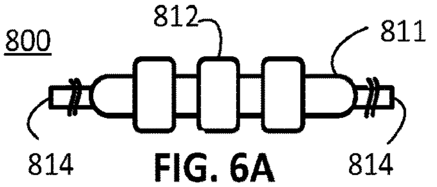
FIGS. 6A-6B are diagrams including a side view schematically representing example anchor elements.
Figure 6B:
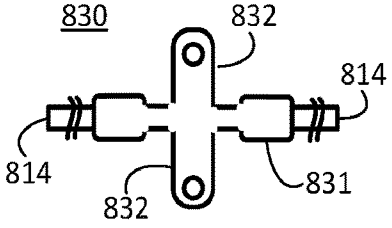

It will be understood that the various leads, stimulation elements, port interfaces, etc. described in association with at least FIGS. 3-5B may be secured with sutures and/or a wide variety of anchors. FIG. 6A-6B provide example implementations of just some such anchors, while other types of anchors are described in association with at least FIGS. 22A-23 and 27A-30B. It will be further understood that the example anchors in FIGS. 6A-6B (e.g. wings, holes for tissue growth, tines, barbs, etc.) may employed on any of the various stimulation elements, leads, etc. as appropriate. Moreover, in some examples, some of the anchor features (e.g. suture-friendly surfaces, wings, holes for sutures, holes for tissue growth, tines, barbs, etc.) may be incorporated into implantable structures, such as a port interface (e.g. 750 in FIGS. 5A-5B, 1070 in FIG. 7, and the like) to facilitate their anchoring relative to non-nerve tissues and structures to stabilize the respective element within the patient's body. In this regard, it also will be understood that such anchoring may occur via at least some of the non-nerve tissues and structures later detailed in association with at least FIGS. 22A-23.

FIG. 6A is side view schematically representing an elongate suture anchor element 800, which comprises a body 811 and a linear array of protrusions 812 to facilitate securing the anchor element, via sutures, relative to a non-nerve tissue. As further shown in FIG. 6A, the anchor element 800 may be fixed on a portion of a lead 814 or slidable movable along the portion of the lead 814 to be secured.

FIG. 6B is a side view schematically representing an anchor element 830, which comprises a body 831 and pair of wings 832 extending perpendicular outward from body 831 to facilitate securing the anchor element 830, via sutures, relative to a non-nerve tissue. As further shown in FIG. 6B, the anchor element 830 may be fixed on a portion of a lead 814 or slidable movable along the portion of the lead 814 to be secured.

Upon securing the anchor element 800 or 830, the lead 814 becomes secured relative to non-nerve tissue within the patient's body. It will be understood that similar types of anchor features may be incorporated into portions of a lead, such as the various example port interfaces (e.g. FIG. 5A, 5B, 7A, etc.) described in several examples of the present disclosure.

Figure 7A:
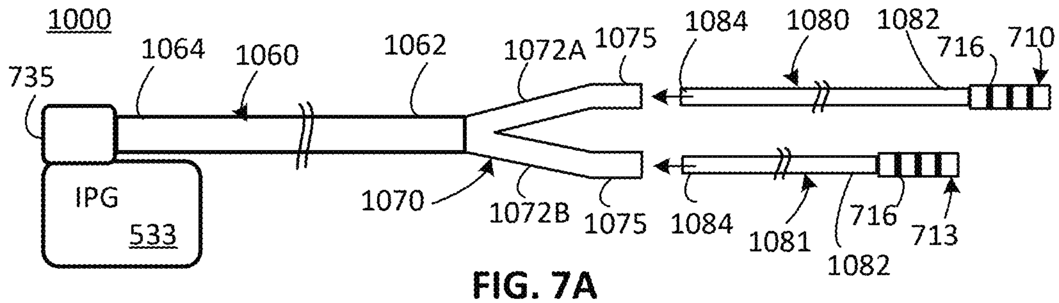
FIGS. 7A-8 are diagrams including a side view schematically representing example stimulation leads with bifurcation features and/or related delivery tools.

FIG. 7A is a diagram including a top view schematically representing an example arrangement 1000 including an IPG 533, bifurcated port interface 1070, and removably insertable stimulation leads 1080, 1081. In some examples, the example arrangement 1000 comprises at least some of substantially the same features and attributes as the example arrangements described in association with at least FIGS. 1-6B, at least with respect to providing for flexibility in a sequence or timing of implanting the respective stimulation leads 1080, 1081 according to patient conditions, anatomy encountered during implantation, changing health over time, etc.

As shown in FIG. 7A, a lead support portion 1060 includes a proximal portion 1064, which is electrically connectable to an IPG 533 via header 735 and a distal portion 1062, which supports a bifurcated port interface 1070. The port interface 1070 comprises two spaced apart prongs 1072A, 1072B which diverge from each other, with each prong 1072A, 1072B comprising a connection port 1075 to removably receive electrical (and mechanical) connection from a proximal portion 1084 of stimulation leads 1080,1081. Each stimulation lead 1080, 1081 comprises a distal portion 1082 supporting a respective stimulation element 710, 713, each of which comprise a linear array of electrodes 716. As in other examples, the stimulation elements 710, 713 can take a wide variety of electrode configurations (e.g. cuff, paddle, etc.) other than the axial array depicted in FIG. 7A. In some examples, the IPG 533 and lead support portion 1060 (including port interface 1070) may be implanted to support the concurrent implantation of both stimulation leads 1080, 1081. However, in some examples, in a manner similar to that previously described in association with at least FIGS. 5A, 5B, in some examples, just one of the stimulation leads 1080, 1081 may be implanted in an initial implantation procedure to be in stimulating relation to a first nerve (e.g. hypoglossal nerve or ansa cervicalis-related nerve). At a later point in time, the other respective one of the stimulation leads 1080, 1081 may be implanted to be in stimulating relation to a second nerve (e.g. hypoglossal nerve or ansa cervicalis-related nerve). In such arrangements, the port interface 1070 conveniently permits selective addition of the second stimulation lead (e.g. 1080 or 1081) during the second implant procedure by insertion of the proximal portion 1084 of the respective stimulation lead.

In some examples, in a manner similar to the port interfaces depicted in FIGS. 5A-5B, the port interface 1070 may be implanted and/or accessed via an implant access-incision, like implant access-incision 609B in a head-and-neck portion 520 in FIGS. 4-5B.

Figure 7B:
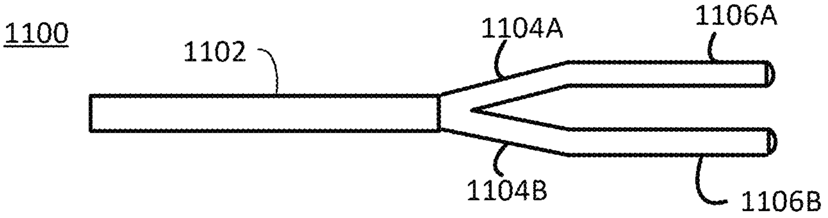

In some examples, implantation of port interface 1070 and/or stimulation leads 1080, 1081 may be facilitated via use of tunneling tool 1100 schematically represented in FIG. 7B. As shown in FIG. 7B, the tunneling tool 1110 comprises a proximal main portion 1102, which supports diverging portions 1104A, 1104B, from which extend spaced apart prongs 1106A, 1106B. The prongs 1106A are insertable into, and may be advanced through, subcutaneous tissue to form tunnels for implantation of stimulation leads and related structures.

In some examples, the tunneling tool 1090 can be employed with example lead arrangements other than shown in FIG. 7A, and in which two different tunnels are to be formed subcutaneously to provide path for implantation of leads, stimulation elements, etc. It will be further understood that prongs 1106A, 1106B may have lengths with differ from each other, and may have tips which are steerable in some examples.

Figure 8:
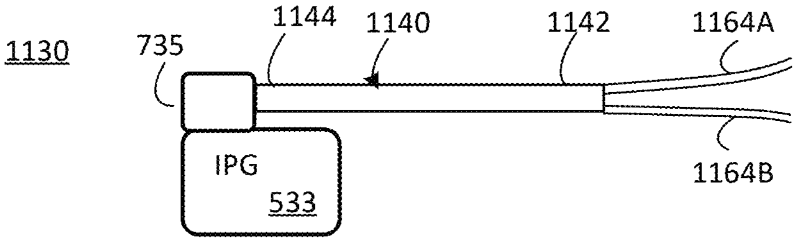

FIG. 8 is a diagram including a top view schematically representing an example arrangement 1130 including a stimulation lead 1140. In some examples, the stimulation lead 1140 may comprise at least some of substantially the same features and attributes as, comprise an example implementation of, and/or be usable with the example arrangements described in association with at least FIGS. 1-7B.

As shown in FIG. 8, in some examples, the stimulation lead 1140 comprises a proximal support portion 1144 electrically (and mechanically) connectable to an IPG 533 via header 735, while a distal portion 1142 comprises a bifurcated pair of distal stimulation portions 1164A, 1164B. While just a portion of the distal stimulation portions 1164A, 1164B are shown for illustrative simplicity, it will be understood that each distal stimulation portion 1164A, 1164B may support a stimulation element, such as stimulation elements 510A, 510B, 513A, 513B, 710, or 713 etc. as described throughout the previously described examples or such as some of the later described stimulation elements.

Figure 9:
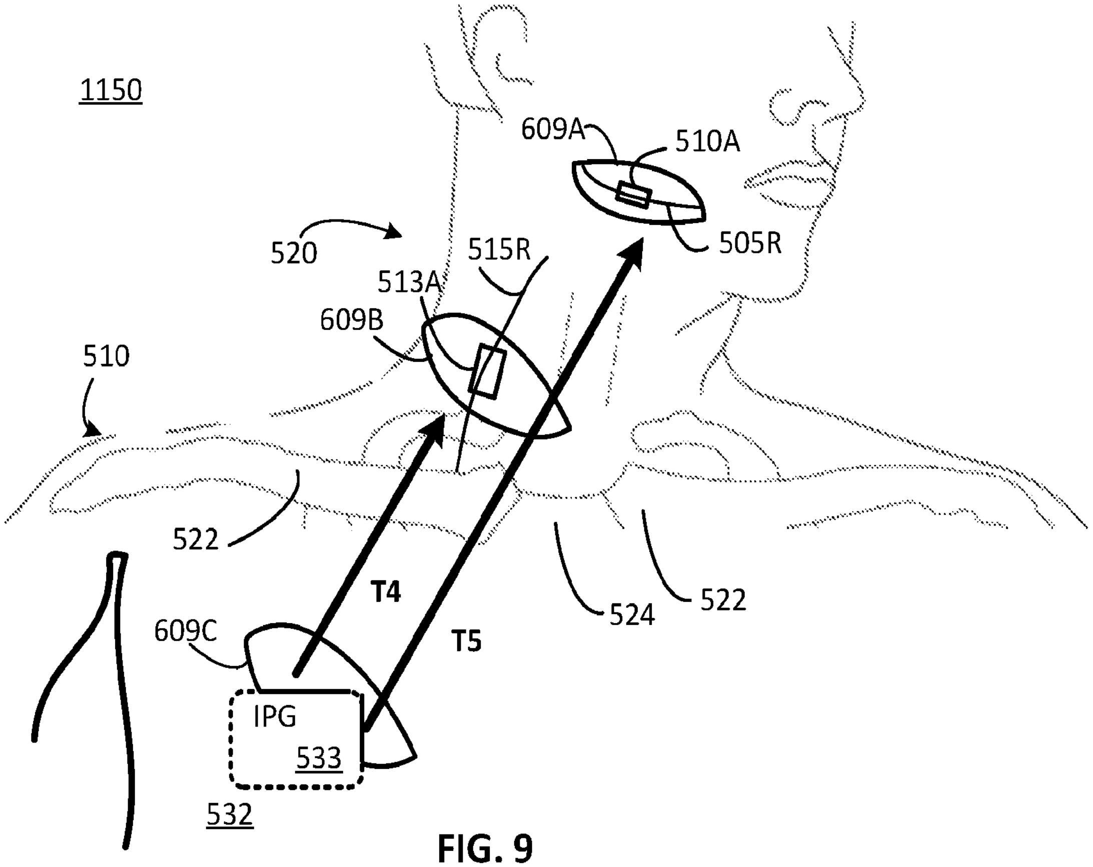

FIG. 9 is diagram including a front view schematically representing an example arrangement 1150 including an example device and/or example method for implantation of stimulation elements 510A and/or 513A. In some examples, the example arrangement 1150 may comprise at least some of substantially the same features and attributes as, comprise an example implementation of, and/or be usable with the example arrangements described in association with at least FIGS. 1-8.

It will be further understood that in some examples the stimulation elements 510A, 513A may be supported by respective separate stimulation leads, which are not shown in FIG. 9 for illustrative simplicity.

As shown in FIG. 9, in order to implant stimulation element 513A a tunnel T4 is formed between implant access-incision 609C and 609B, and in order to implant stimulation element 510A, a tunnel T5 is formed between implant access-incision 609C and 609A. In some examples, both tunnels T4, T5 may be made at the time of an initial implant procedure in which both stimulation elements 510A, 513A (and their respective stimulation leads) are implanted.

However, in some examples, the respective, representative stimulation elements 510A, 513A are implanted at different points in time, with one stimulation element being implanted in an initial implant procedure and the other respective implant procedure being implanted in a separate, later implant procedure. In some such examples, the respective stimulation leads (e.g. supporting stimulation elements 510A, 513A) may be electrically connected relative to the IPG 533 directly as shown in the example arrangement of FIG. 10A, while in some examples, the proximal portion of such stimulation leads may be connected to the IPG 533 indirectly via a port interface (e.g. 750 in FIGS. 5A-5B).

FIG. 10A is a diagram including a front view schematically representing an example arrangement 1200 relative to a patient's body, including an example device and/or example method for implantation of stimulation elements 510A and/or 513A. In some examples, the example arrangement 1200 may comprise at least some of substantially the same features and attributes as, comprise an example implementation of, and/or be usable with the example arrangements described in association with at least FIGS. 1-9.

As shown in FIG. 10A, two separate stimulation leads 1235, 1237 may be implanted to position their respective stimulation elements 513A, 510A for implantation at target nerve locations. In a manner similar to at least some previously described examples, in some examples both of the stimulation leads 1235, 1237 may be implanted as part of the same initial implantation procedure, while in some examples one of the respective stimulation leads (e.g. 1235, 1237) is implanted in a first implantation procedure, while the other respective lead is implanted in a second separate implantation procedure at a later point in time.

As shown in FIG. 10A, in this example a proximal portion of the respective stimulation leads are electrically connected to the IPG 533 directly. However, in some examples, a port interface with bifurcation features (e.g. 1070 in FIG. 7A) near IPG 533 may be employed to connect the proximal ends of the respective leads 1235, 1237 relative the header 735 of the IPG 533.

In some examples, the stimulation lead 1235 may support multiple stimulation elements 513A, as shown in FIG. 10B, in which the distal portion of the stimulation lead 1235 comprises a bifurcation yielding two different distal prongs 1236A, 1236B, each of which support a respective stimulation element 513B, 513C. The respective prongs 1236A, 1236B have a length suitable to place the different respective stimulations elements 513B, 513C at different target nerve locations. For example, one simulation element 513B may be located a first target nerve location of the ansa cervicalis-related nerve (e.g. 316 in FIG. 2) and the other simulation element 513C may be located at different, second target nerve location of the ansa cervicalis-related nerve (e.g. 316 in FIG. 2).

FIG. 10C is a diagram including a front view schematically representing an example arrangement 1300 relative to a patient's body, including an example device and/or example method for implantation of stimulation elements 510A and/or 1313A. In some examples, the example arrangement 1300 may comprise at least some of substantially the same features and attributes as, comprise an example implementation of, and/or be usable with the example arrangements described in association with at least FIGS. 1-9.

As shown in FIG. 10C, the example arrangement 1300 may comprise at least some of substantially the same features and attributes as the example arrangement 1200 in FIGS. 10A and/or 1250 in FIG. 10B, except with the stimulation element 513A being implemented as a microstimulator 1313A such that no stimulation lead extends between the microstimulator 1313A and the IPG 533. However, in some examples, the microstimulator 1313A may be in wireless communication with the IPG 533 to share at least control and/or data signals. In some examples, the microstimulator 1313A may be in wireless communication with the stimulation element 510A (or with a communication element formed as a part of stimulation lead 1237) to share at least control and/or data signals to coordinate the actions of the respective microstimulator 1313A and stimulation element 510A relative to each other or relative to other therapy elements (e.g. IPG 533, sensing, tracking, etc.). In some examples, microstimulator 1313A may be in wireless communication with a control portion, programmer, and/or user interface external to the patient's body, which are in addition to, or instead of, communication with IPG 533.

In a manner similar to that described in association with the example arrangement of FIG. 10A, both the stimulation element 510A (and stimulation lead 1237) and the microstimulator 1313A may both be implanted in the same initial implantation procedure. However, in some examples one of the respective stimulation element 510A (and lead 1237) and the microstimulator 1313A is to be implanted in an initial implantation procedure, and then the other respective element (e.g. element 510A or microstimulator 1313A) may be implanted at a later time in a separate second implantation procedure. The second implanted element may be employed to enhance the neurostimulation therapy already established via the initial implantation procedure. As noted elsewhere, in some examples the example arrangement 1300 may be understood as being representative for the implantation of left and/or right sides of the patient's body and for implantation to provide stimulation in relation to any of the nerves identified within the present disclosure for increasing or maintaining upper airway patency or for other noted purposes.

In some examples, the situation may be reversed in which the microstimulator 1313A is implanted in stimulating relation to the hypoglossal nerve 505R and a stimulation element 513A (FIG. 10A) is implanted in stimulating to the ansa cervicalis-related nerve 515R In general terms, the microstimulator 1313A comprises power and circuitry in a compact package to permit stimulation of an upper airway patency-related tissue (e.g. nerve 515R) via at least one stimulation element located on a housing of the microstimulator or extending from the housing of the microstimulator. The microstimulator 1313A also may comprise a sensing element(s). In some examples, the microstimulator 1313A may comprise at least some of substantially the same features and attributes as described in Rondoni et al, MICROSTIMULATION SLEEP DISORDERED BREATHING (SDB) THERAPY DEVICE, published as WO 2017/087681 on May 26, 2017 and published as US 2020-0254249 on Aug. 13, 2020, and which is hereby incorporated by reference.

Figure 11A:
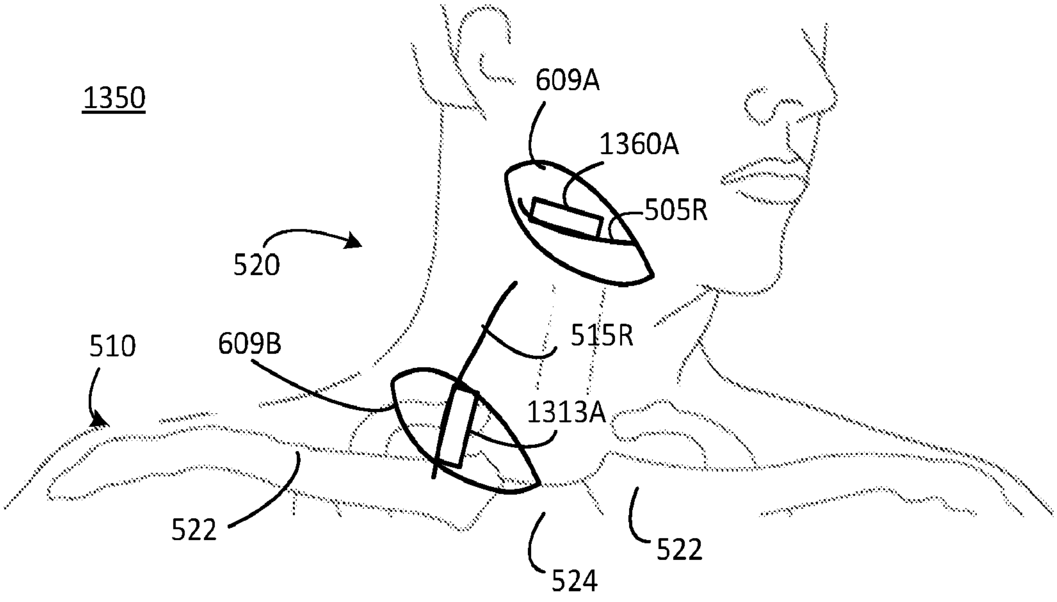

FIG. 11A is a diagram including a front view schematically representing an example arrangement 1350 relative to a patient's body, including an example device and/or example method for implantation of microstimulators 1360A and/or 1313A relative to respective target nerves 505R, 515R. In some examples, the example arrangement 1350 may comprise at least some of substantially the same features and attributes as, an example implementation of, and/or be usable with the example arrangements described in association with at least FIGS. 1-9. Accordingly, in some examples, the target nerves 505R, 515R may comprise a hypoglossal nerve 505R and an ansa cervicalis-related nerve 515R, respectively.

As shown in FIG. 11A, the example arrangement 1350 may comprise at least some of substantially the same features and attributes as the example arrangement 1300 in FIG. 10B, except with the stimulation element 510A being implemented as a microstimulator 1360A such that no IPG is present and no stimulation lead extends between the microstimulator 1360A and an IPG 533. In some examples, the microstimulator 1360A may be in wireless communication with the microstimulator 1313A to share at least control and/or data signals to coordinate the actions of the respective microstimulators 1313A, 1360A relative to each other or relative to other therapy elements (e.g. sensing, tracking, etc.). In some examples, both of the microstimulators 1360A, 1313A may be in wireless communication with a control portion, programmer, and/or user interface external to the patient's body.

In a manner similar to that described in association with the example arrangement of FIG. 10B, both the microstimulator 1360A and the microstimulator 1313A may both be implanted in the same initial implantation procedure, such as via respective implant access-incisions 609A, 609B shown in several previously described examples. However, in some examples one of the respective microstimulators 1360A, 1313A may be implanted in an initial implantation procedure, and then the other respective microstimulator (e.g. 1360A or 1313A) may be implanted at a later time in a separate second implantation procedure. The second implanted element may be employed to enhance the neurostimulation therapy already established via the initial implantation procedure.

Figure 13:
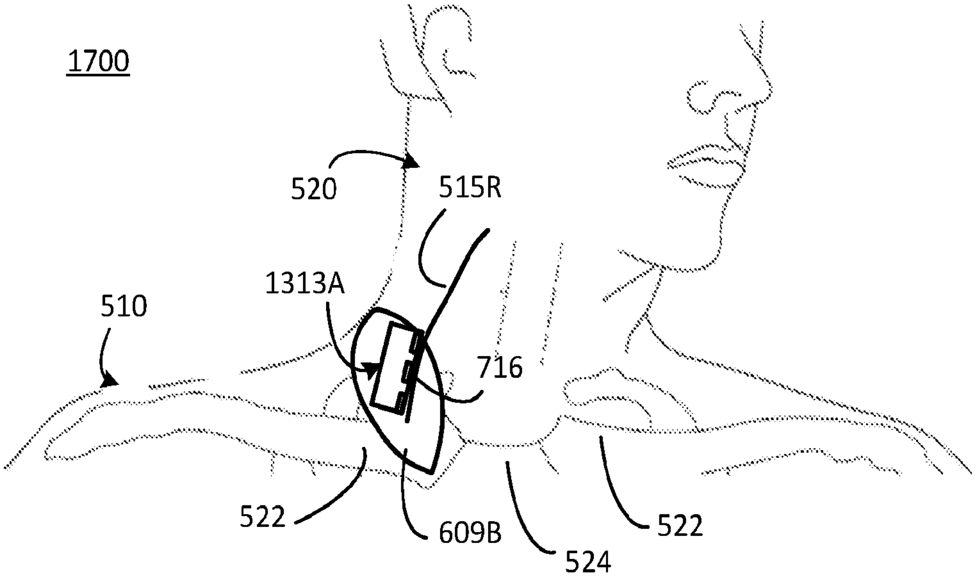

In some examples, the respective microstimulators 1313A, 1360A may be implanted via a single implant access-incision of the type shown in FIG. 13, where some maneuvering may be used (relative to the single access-incision) to place the respective microstimulators 1313A, 1360A adjacent their respective target nerves 515R, 505R.

Figure 11B:
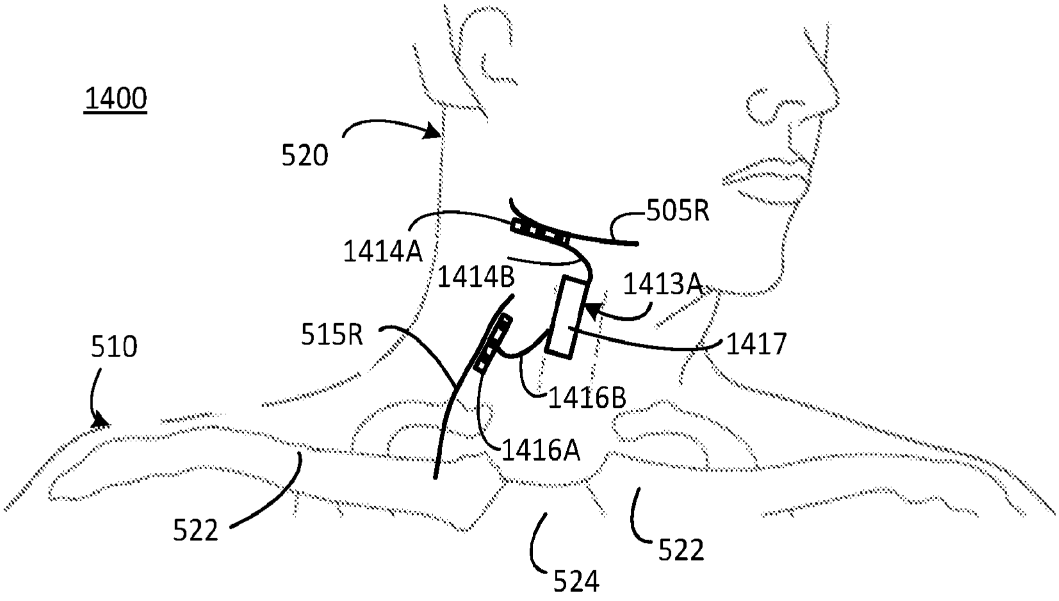
FIG. 11B is a diagram like FIGS. 9-11B including implantation of a microstimulator in the neck region for connected stimulation elements.

FIG. 11B is a diagram including a front view schematically representing an example arrangement 1400 relative to a patient's body 510, including an example device and/or example method for implantation of a single microstimulator 1413A in a head-and-neck region 520. In some examples, the example arrangement 1400 may comprise at least some of substantially the same features and attributes as, comprise an example implementation of, and/or be usable with the example arrangements described in association with at least FIGS. 1-9.

As shown in FIG. 11B, the microstimulator 1413A comprises a power/control element 1417 and a pair of stimulation elements 1414A, 1416A, which are positioned into stimulating relation to the respective nerves 505R, 515R. Each stimulation element 1414A, 1416A extends from the power/control element 1417 via a respective lead 1414B, 1416B. The power/control element 1417 may operate in a manner similar to an IPG 533, but is miniaturized to a smaller scale within a considerably smaller housing.

In some examples, FIG. 11B depicts the respective stimulation elements 1414A, 1416A as an array of electrodes (e.g. 716 in FIGS. 5A, 5B, 7A), which may take the form of a small paddle, axial array of ring electrodes, or other electrode configuration. In some examples, cuff or partial cuff configurations may be employed, as well as pigtail configurations. Each respective stimulation element 1414A, 1416A may comprise its own anchor elements (e.g. tines, barbs, suture hole, and the like) or a separate anchor element may be used to secure the stimulation element 1414A, 1416A relative to the respective nerve 505R, 515R and/or relative to an adjacent non-nerve structure.

In some examples, the microstimulator 1413A (and associated stimulation elements 1414A, 1416A) may be implanted via a single implant access-incision of the type shown in FIG. 13. In some such examples, some minor tunneling and/or maneuvering is used to place the respective stimulation elements 1414A, 1416A adjacent their respective target nerves 505R, 515R.

Figure 17:
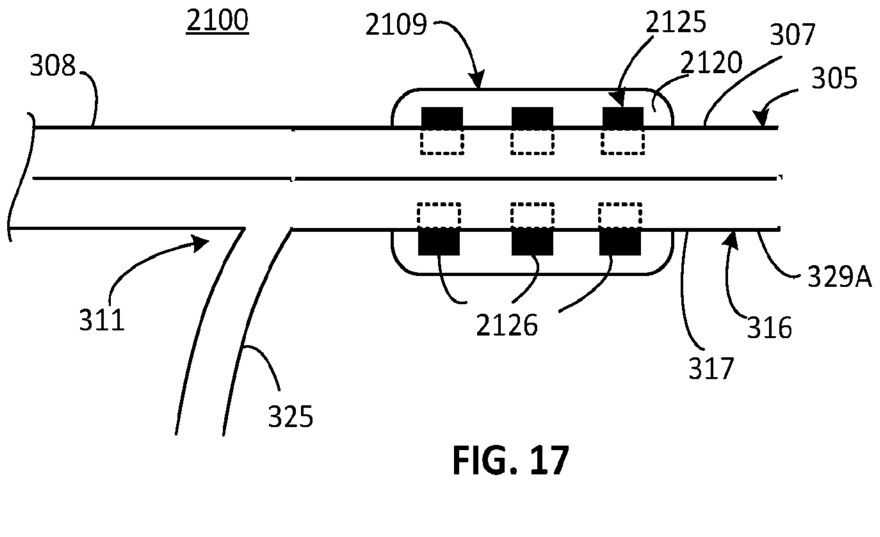
FIG. 17 is a diagram including a top view schematically representing an example stimulation element as paddle electrode in stimulating relation to target nerve stimulation locations.

In some examples, the microstimulator 1413A may be deployed at locations within the head-and-neck region 520 in which the first and second target nerve locations are within close proximity to each other. For instance, the microstimulator 1413A (including stimulation elements 1414A, 1416A) may be implanted as one of the example arrangements 2101 or 2401 in the example method in FIGS. 16-17 (or FIGS. 16, 18-20) such that a single device (e.g. 1413A) in the head-and-neck region 520 may serve to stimulate two different nerves (e.g. 505R, 515R), such as the portion 307 of hypoglossal nerve 305 (FIGS. 16-17) and the portion 329A of the ansa cervicalis-related nerve 315 (FIG. 16-17).

With regard to the various stimulation elements, leads, etc. described in association with at least FIGS. 1-11B, it will be understood that such example arrangements, methods of implantation, etc. may be use to implement sensing elements, where the sensing elements may take the place of the respective stimulation elements and/or where the stimulation elements also may act as or carry sensing elements. At least some additional aspects of sensing are further described later throughout various examples of the present disclosure.

Moreover, with regard to the various example arrangements depicted in at least FIGS. 3-11B, stimulation elements were shown to be in stimulating relation to a right side of the patient's body, such as at hypoglossal nerve 505R and/or the ansa cervicalis-related nerve 515R. However, it will be understood that such examples are intended to be representative of implantation, therapy, etc. for a left side of the patient's body and/or for bilateral implantation of such stimulation elements, leads, etc. Moreover, it will be further understood that the example arrangements in FIGS. 3-11B also may implemented according to the various example implementations represented in association with the example arrangement in FIG. 2.

Moreover, with regard to at least the example arrangements of FIGS. 10A-11B, it will be further understood that the various stimulation elements, lead, and/or microstimulators may be secured within the patient's body relative to a non-nerve structure or tissue via at least some of the various example anchor elements provided throughout the examples of the present disclosure, such as at least FIGS. 6A-6B, 22A-23, and/or 27A-30B.

Figure 12:
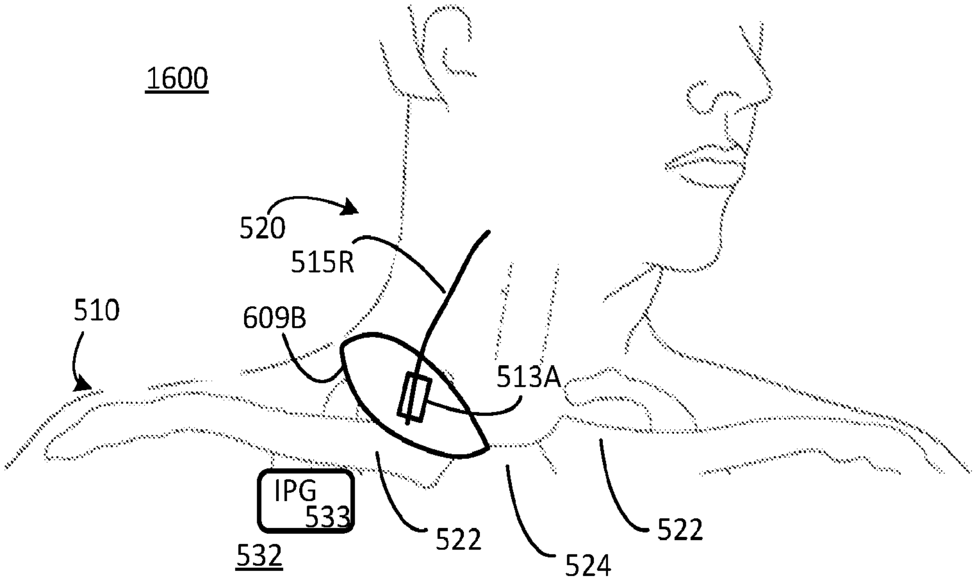
FIGS. 12-13 are diagrams schematically representing an example device and/or method for implanting stimulation elements via an implant-access incision in proximity to ansa cervicalis-related nerve.

FIG. 12 is a diagram including a front view schematically representing an example arrangement 1600 relative to a patient's body 510, including an example device and/or example method for implantation of a stimulation element 513A in stimulating relation to an ansa cervicalis-related nerve 515R. In some examples, the example arrangement 1600 may comprise at least some of substantially the same features and attributes as, comprise an example implementation of, and/or be usable with the example arrangements described in association with at least some of FIGS. 1-11B.

In some examples, the example arrangement 1600 comprises implantation of a stimulation element 513A and IPG 533 via a single implant access-incision 609B. The stimulation element 513A is implanted to be in stimulating relation to ansa cervicalis-related nerve 515R, and is electrically (and mechanically) connected to the IPG 533 via a stimulation lead, which is omitted for illustrative clarity. In some examples, the IPG 533 may be implanted and positioned in a region, such as the upper portion of a pectoral region 532 or the head-and-neck portion 520, in relatively close proximity to the stimulation element 513A. This arrangement may enable the use of shorter stimulation leads, reduce an amount of subcutaneous invasion, etc. By utilizing a single implant access-incision 609B to implant all the elements of the example arrangement 1600, the implantation procedure may be completed faster and in a less invasive manner for the patient.

FIG. 13 is a diagram including a front view schematically representing an example arrangement 1700 relative to a patient's body 510, including an example device and/or example method for implantation of a stimulation element 1313A in stimulating relation to an ansa cervicalis-related nerve 515R. In some examples, the example arrangement 1700 may comprise at least some of substantially the same features and attributes as, comprise an example implementation of, and/or be usable with the example arrangements described in association with at least some of FIGS. 1-11B.

In one particular example, the example arrangement 1700 may comprise at least some of substantially the same features and attributes as the example arrangement 1600 in FIG. 12, except with stimulation element 513A being replaced with a microstimulator 1313A (e.g. 10A) and with the omission of IPG 533. In one aspect, this example arrangement 1700 significantly simplifies the implantation procedure by using a single implant access-incision and a single stimulation element, which includes its own power elements, control circuitry, etc. while embodied as a microstimulator 1313A. In some examples, the microstimulator 1313A may comprise a linear array of electrodes 716 on its exterior housing to provide stimulation element(s) and/or sensing capabilities. However, it will be understood that the microstimulator 1313A may provide other electrode configurations.

With regard to either example arrangement 1600, 1700 in FIGS. 12, 13, it will be understood that such example arrangements may be implemented on just one side or both sides of the patient's body 510. Moreover, it will be understood that such a single implantation procedure via a single implant access-incision 609B may later be supplemented by additional implant access-incisions to implant a second stimulation element (including a stimulation lead) or microstimulator in a second, separate implant procedure, such as in the example implementations described in association with at least some of FIGS. 3-11.

With regard to both of the example arrangements depicted in FIGS. 12-13, it will be understood that at least some aspects of such example arrangements may be applied to implantation of a stimulation element at other nerves such as, but not limited to, the hypoglossal nerve or other nerves.

Figure 14A:
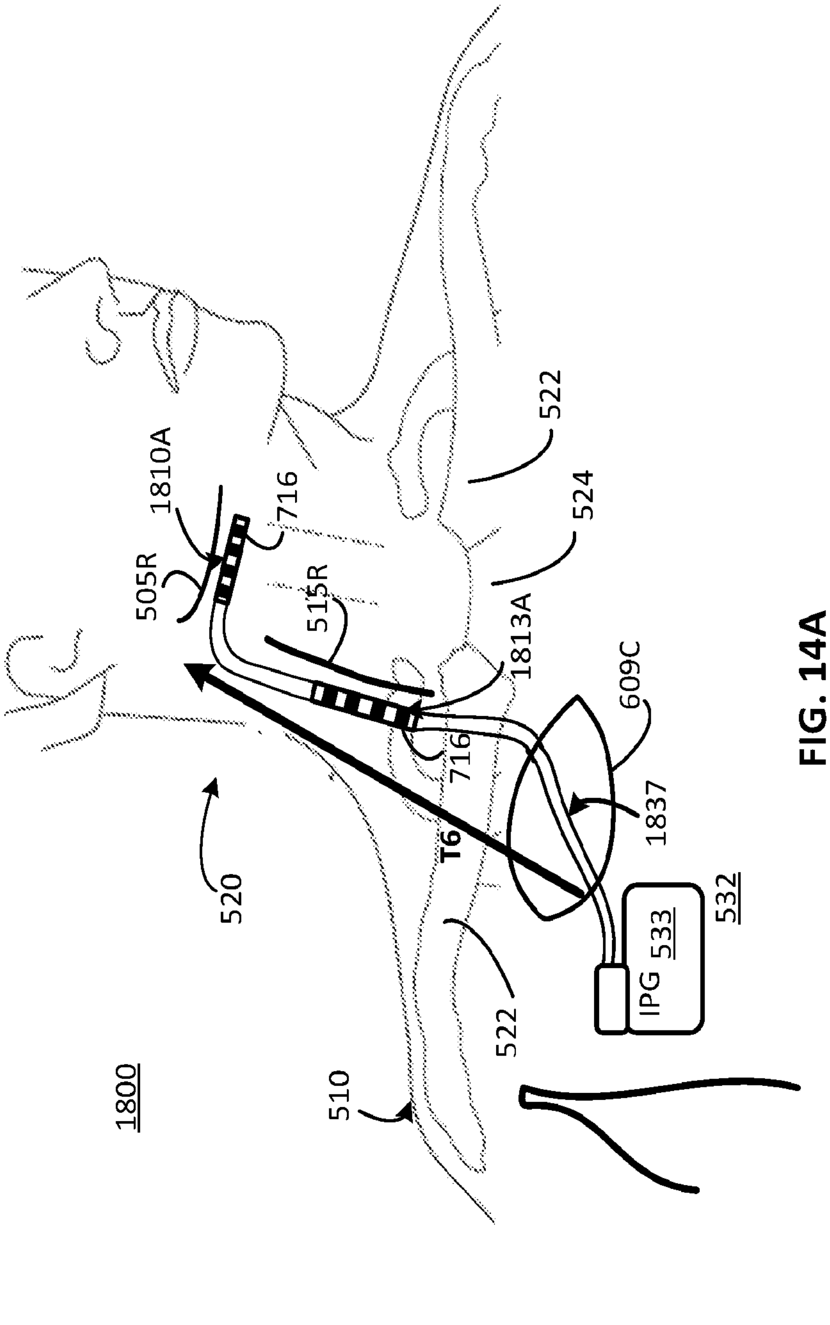
FIGS. 14A-14G are diagrams schematically representing an example device and/or method for implanting stimulation elements and an IPG via implant-access incisions in proximity to ansa cervicalis-related nerve and/or a hypoglossal nerve.

FIG. 14A is a diagram including a front view schematically representing an example arrangement 1800 relative to a patient's body 510, including an example device and/or example method for implantation of a stimulation element 1810A in stimulating relation to a hypoglossal nerve 505R and a stimulation element 1813A in stimulating relation to an ansa cervicalis-related nerve 515R. In some examples, the example arrangement 1800 may comprise at least some of substantially the same features and attributes as, comprise an example implementation of, and/or be usable with the example arrangements described in association with at least some of FIGS. 1-13.

In particular, as shown in FIG. 14A in some examples the example arrangement 1800 may be implanted in a single implantation procedure via a single implant access-incision 609C in a manner similar to that described for example arrangement 1600 in FIG. 12, except including an additional stimulation element 1810A to stimulate the hypoglossal nerve 505R and with both stimulation elements 1810A, 1813A carried on a single stimulation lead 1837. In some examples, the single implant access-incision may be in pectoral region 532 as shown by indicator 609C in FIG. 14 or may be in the head-and-neck portion 520, such as via an implant access-incision 609B shown in some other example FIGS.

As shown in FIG. 14A, via single implant access-incision 609C, tunneling (T6) may performed between the implant access-incision 609C and the target stimulation location of the respective stimulation element 1810A (to be in stimulating relation to the hypoglossal nerve 505R) and/or of the stimulation element 1813A to be in stimulating relation to the ansa cervicalis-related nerve 515R.

As further shown in FIG. 14A, via implant access-incision 609C, IPG 533 is implanted subcutaneously and the stimulation lead 1837 is inserted and advanced through the tunnel T6 until the respective stimulation elements 1810A, 1813A are positioned in stimulating relation to the respective hypoglossal nerve 505R and ansa cervicalis-related nerve 515R, as represented in FIG. 14A.

FIG. 14A also illustrates that the respective stimulation elements 1810A, 1813A may be implemented as a linear array of electrodes 716, which may facilitate appropriate nerve capture by adjusting the linear position of the array relative to the nerve target. In some instances, this example arrangement of electrodes 716 may sometimes be referred to as an axially-arranged electrode array, axial array, axial lead, and the like terminology. However, it will be understood that in some examples, one or both stimulation elements 1810A, 1813A may comprise a different electrode configuration, such as but not limited to some of the example electrode configurations described in association with at least FIGS. 24A-30B.

Figures 14B, 14C:
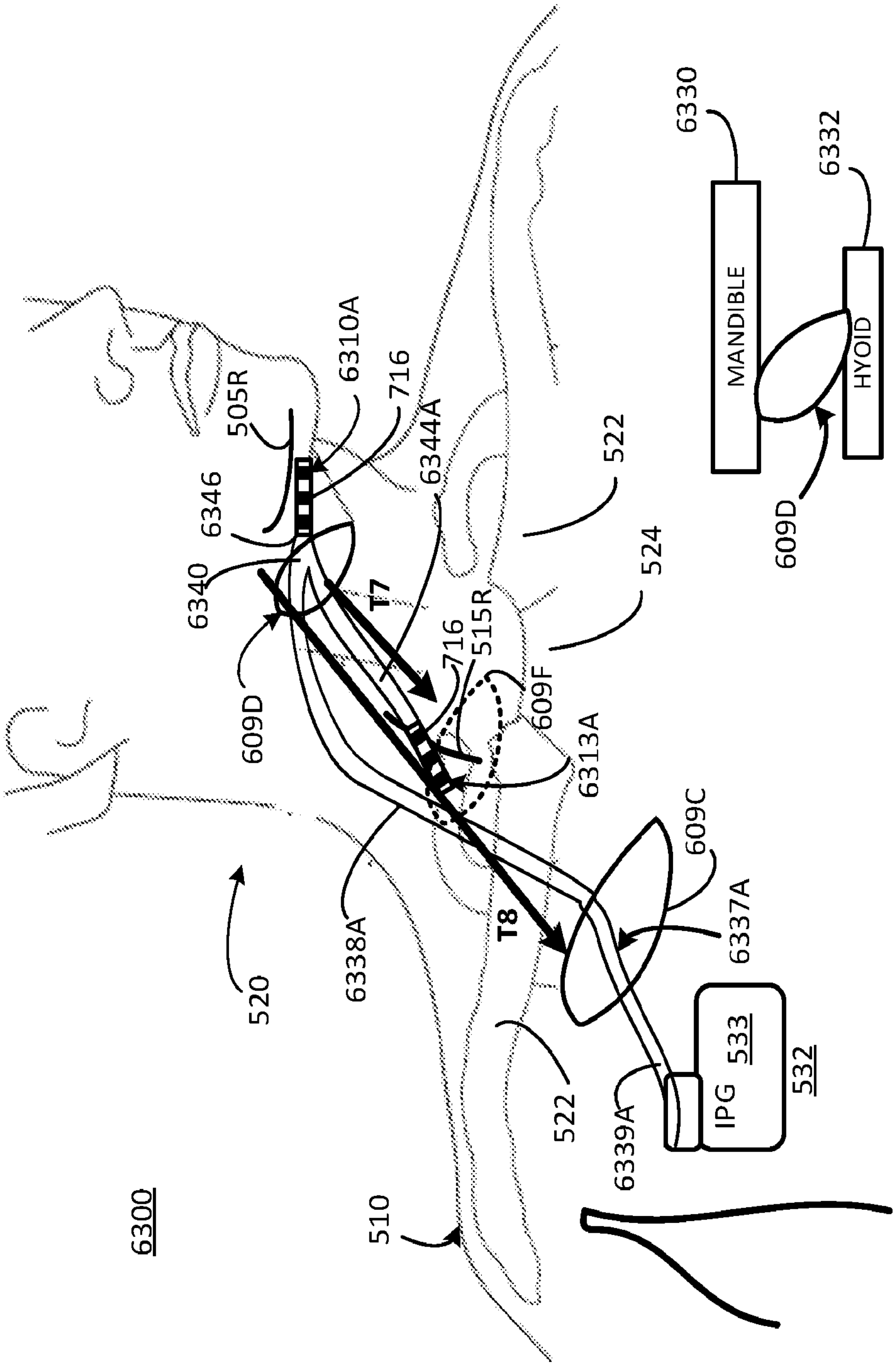
Figure 14B:
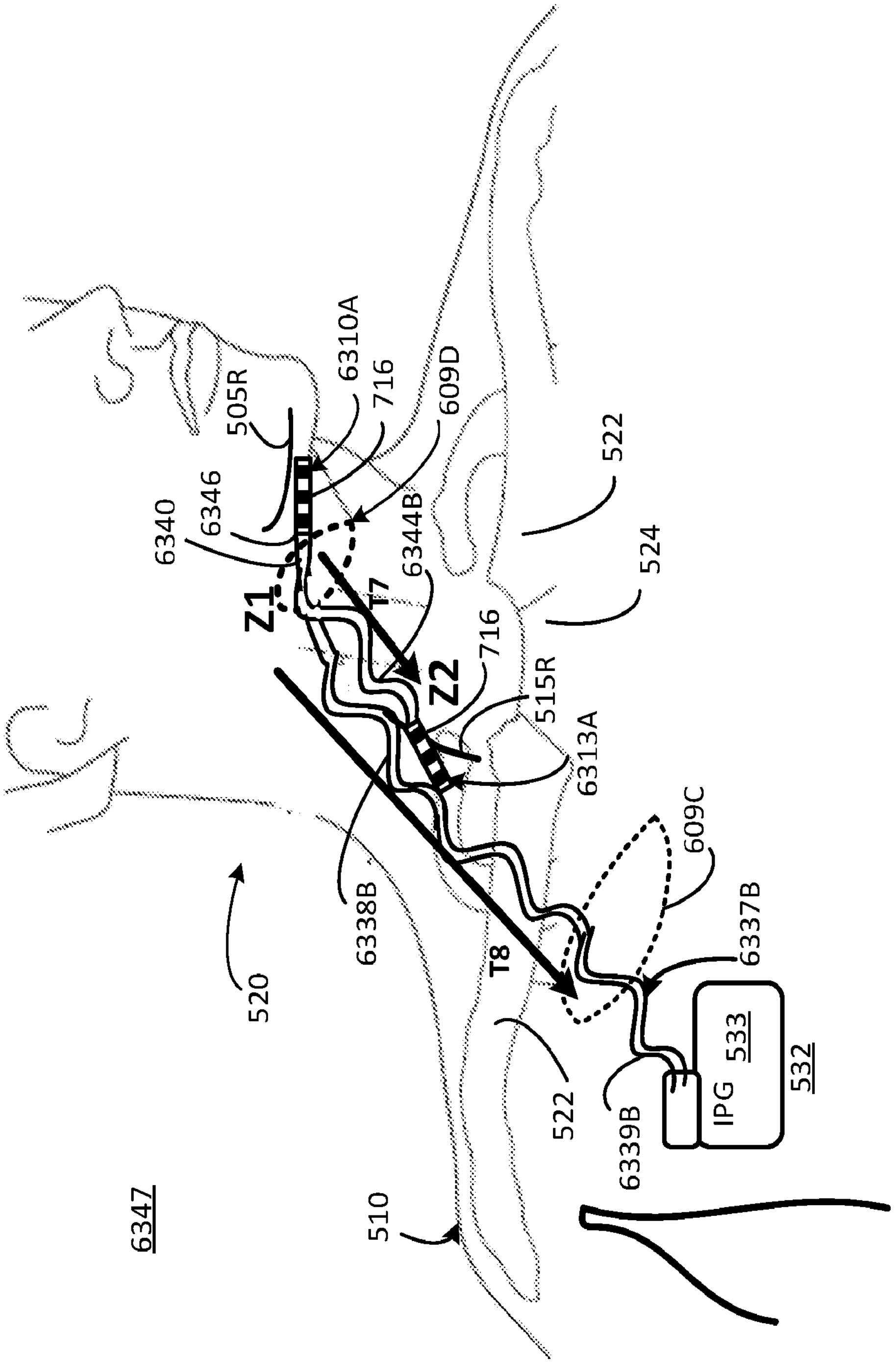

FIG. 14B is a diagram including a front view schematically representing an example arrangement 6300 relative to a patient's body 510, including an example device for, and/or example method of, implantation of a lead 6337A including a stimulation element 6310A in stimulating relation to a hypoglossal nerve 505R and a stimulation element 6313A in stimulating relation to an ansa cervicalis-related nerve 515R. In some examples, the example arrangement 6300 may comprise at least some of substantially the same features and attributes as, comprise an example implementation of, and/or be usable with the example arrangements described in association with at least some of FIGS. 14A and/or 1-13.

As shown in FIG. 14B, the various components of the example arrangement 6300 are implantable via implant-access incision 609C (in a manner similar to the arrangement in FIG. 14A) and via implant-access incision 609D. In some examples upon forming implant-access incision 609C, IPG 533 may be implanted subcutaneously, such as in a subcutaneous pocket within pectoral region 532. In some examples, an implant-access incision 609F is also formed to enable implantation of components of example arrangement 6300 such as, but not limited to, stimulation element 6313A. In some such examples, the stimulation element 6313A may comprise a cuff electrode. It will be further understood that such a third access-incision may be implemented, as desired, in any one of the respective example arrangements of at least FIGS. 14A-14R to facilitate implantation of multiple stimulation elements, lead portions, etc.

Figure 14D:
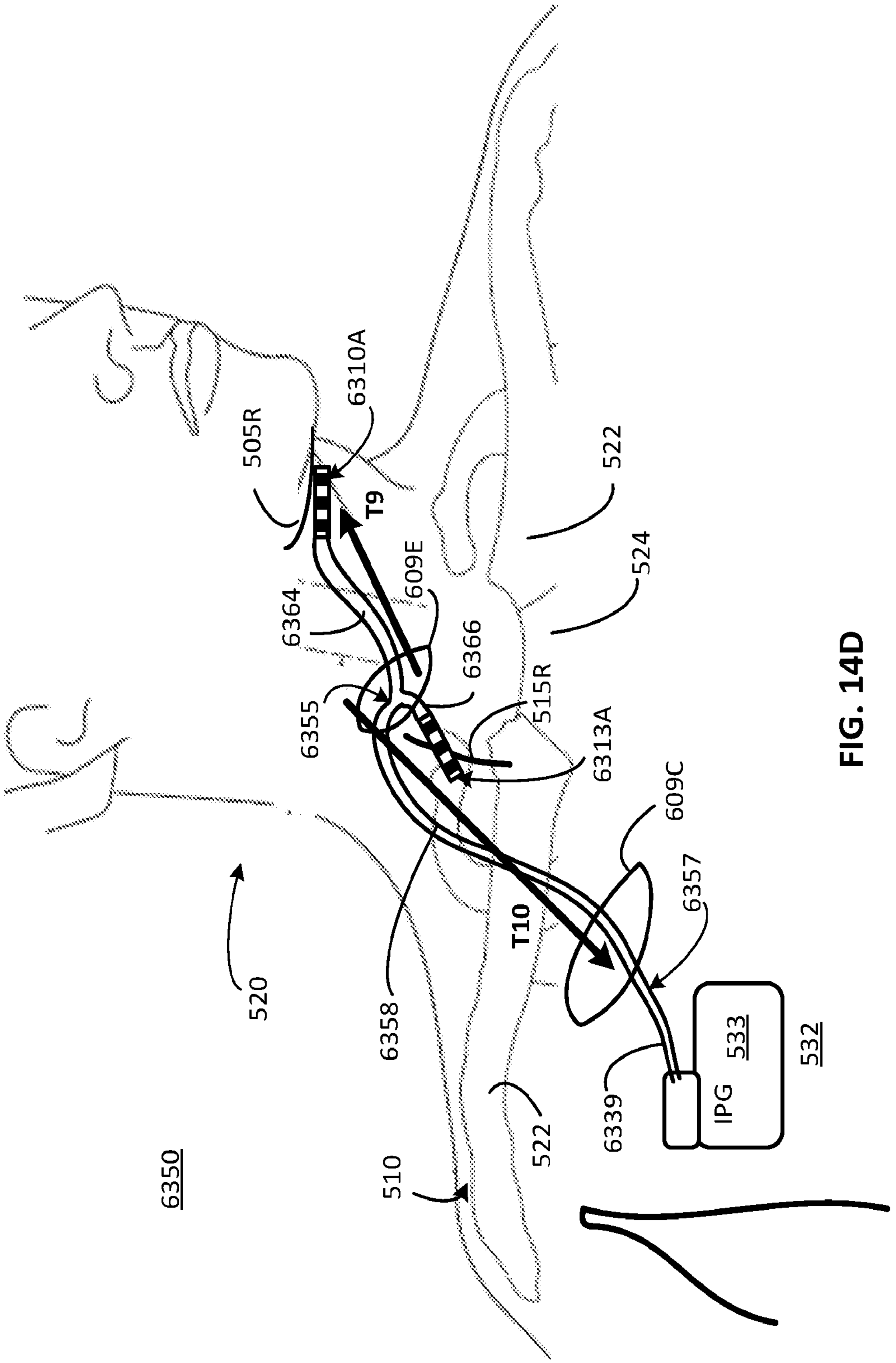
Figure 14E:
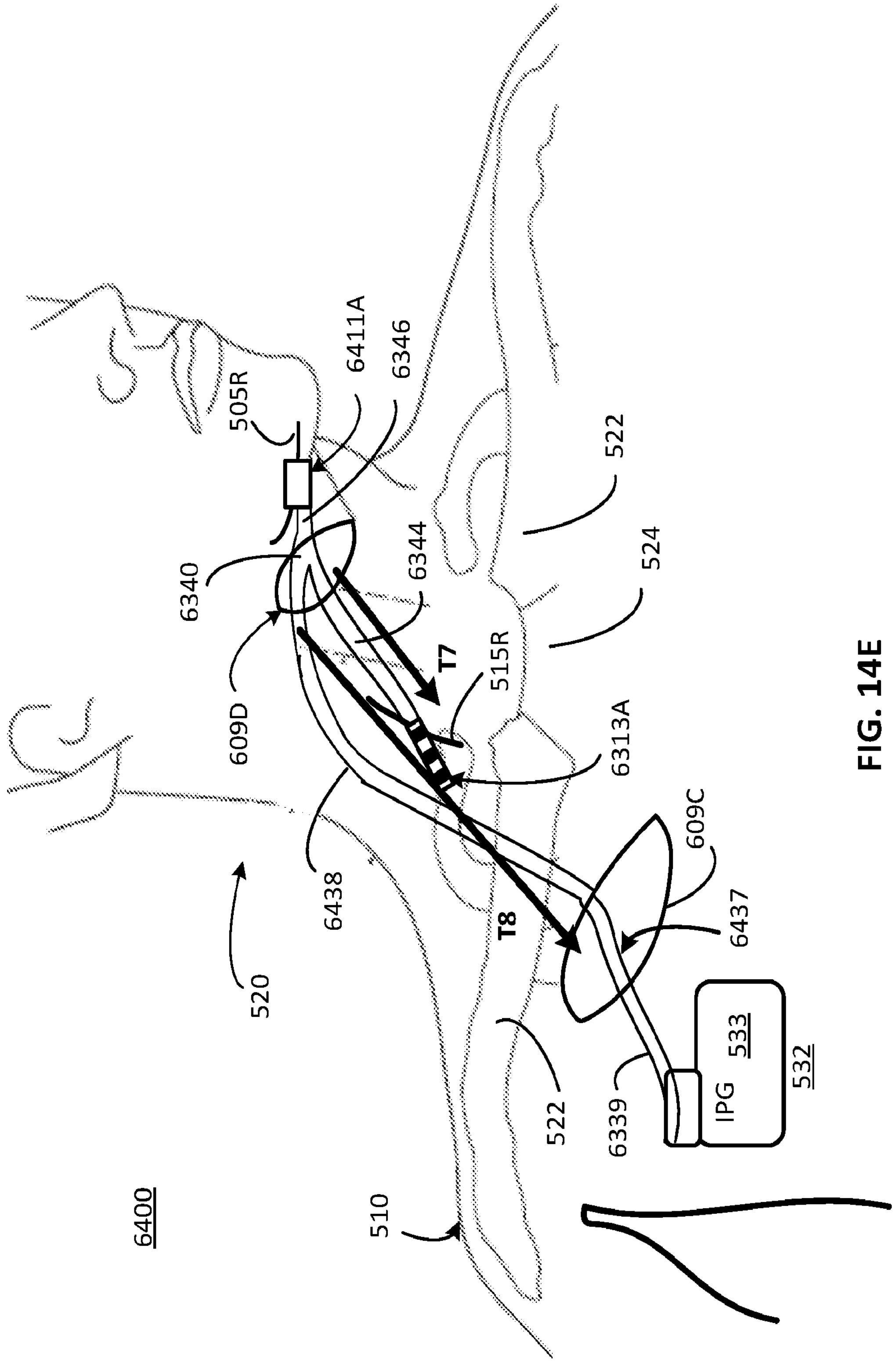
Figure 14F:
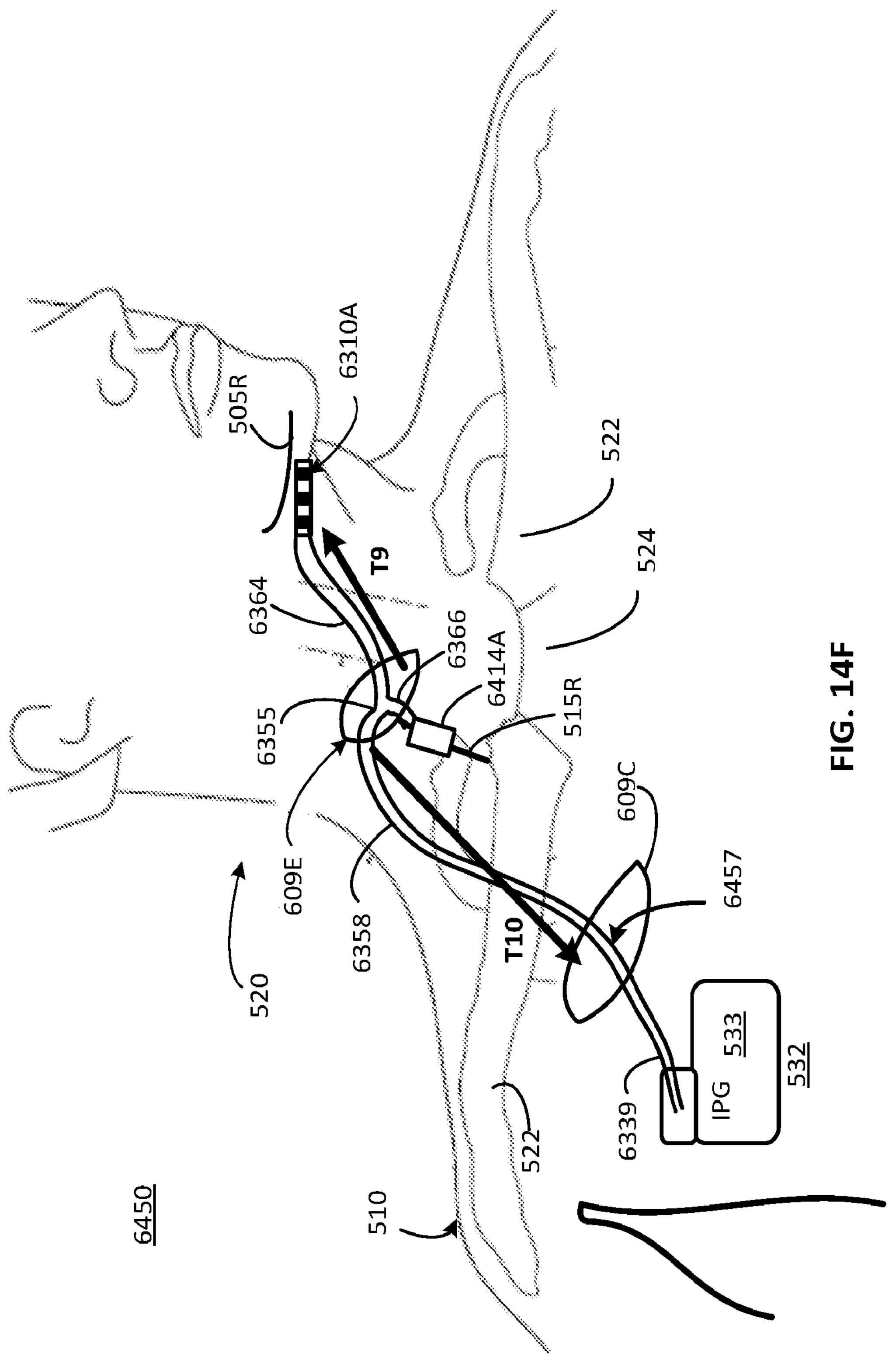
Figure 14G:
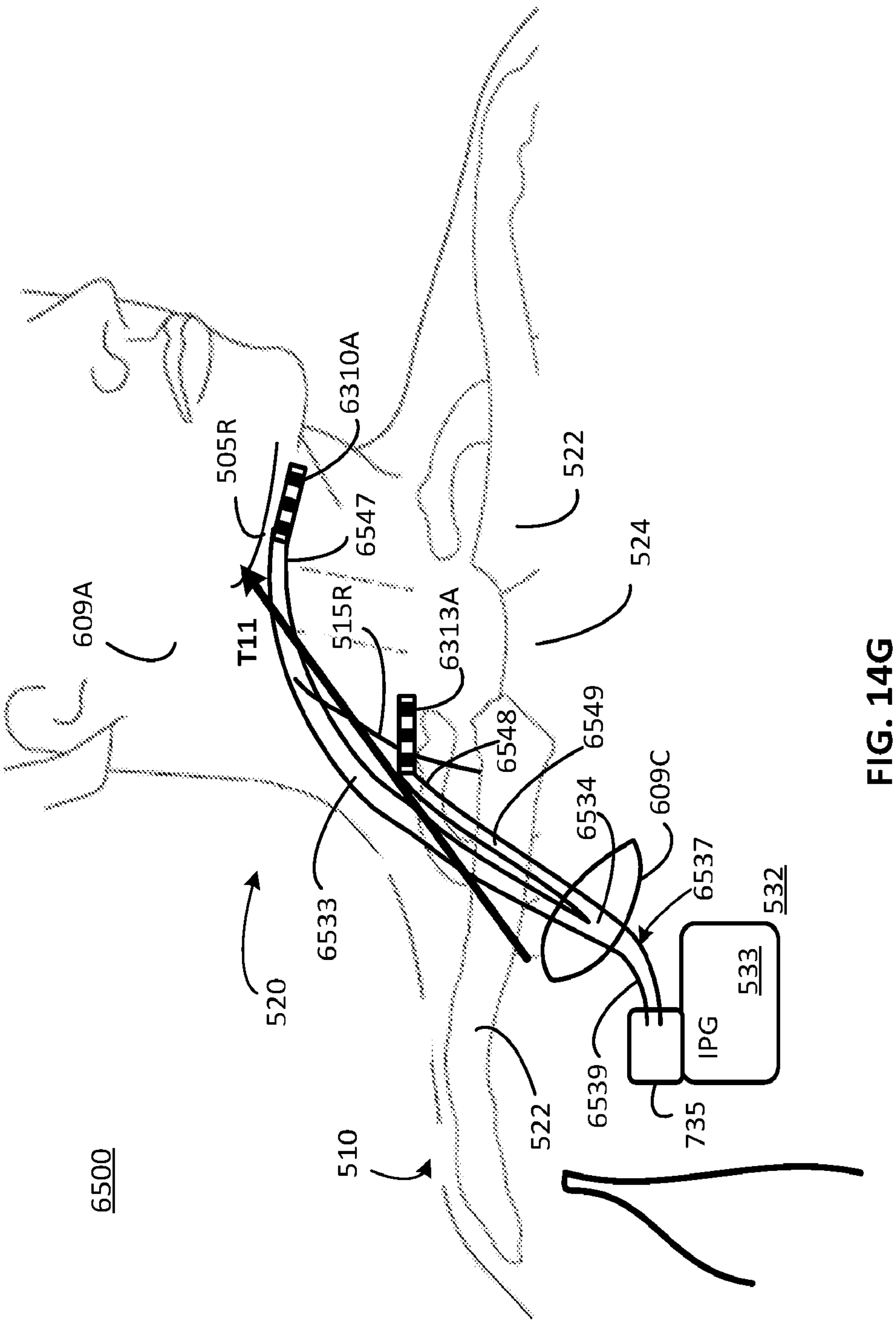
Figure 14H:
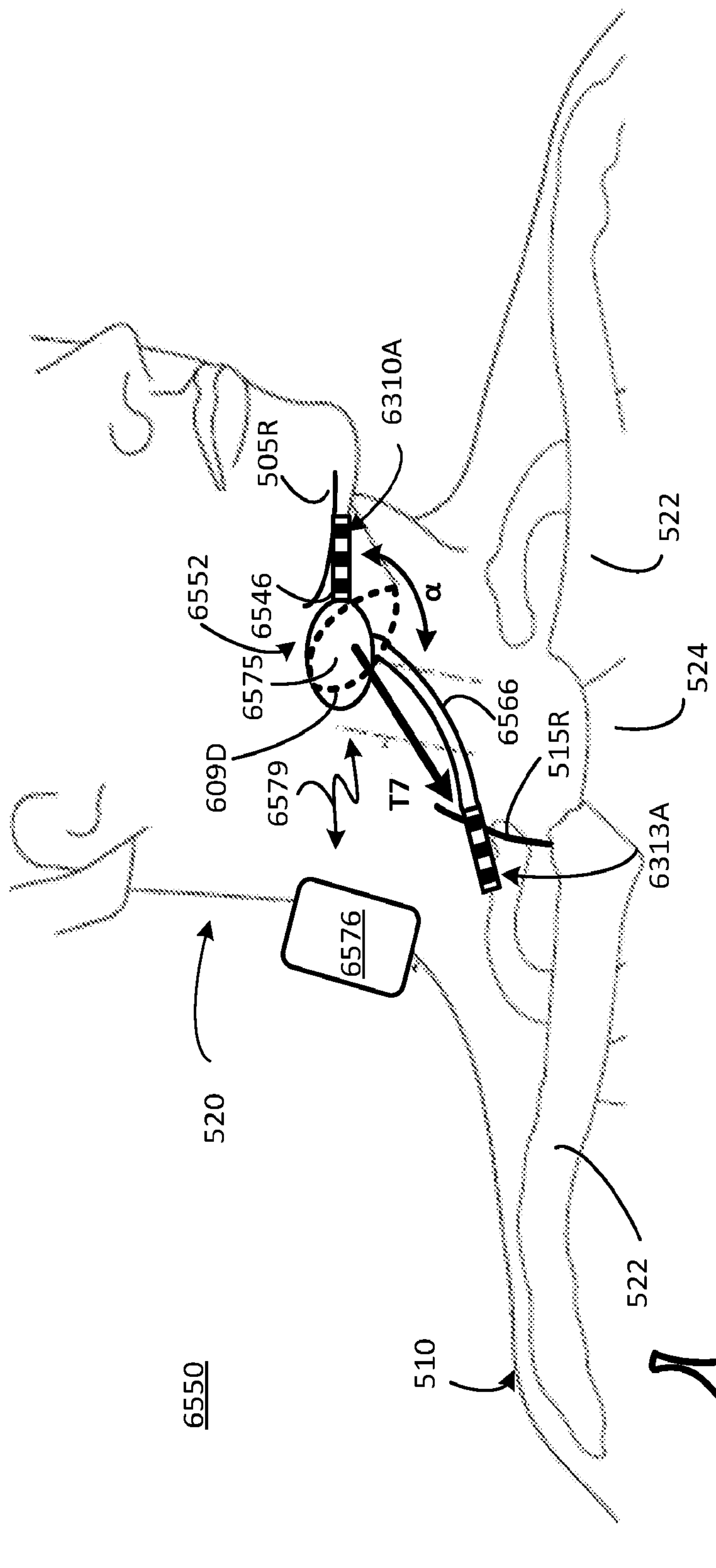
FIGS. 14H-14K are diagrams schematically representing an example device and/or method for implanting stimulation elements and a microstimulator via implant-access incisions in proximity to ansa cervicalis-related nerve and/or a hypoglossal nerve.
Figure 14H:
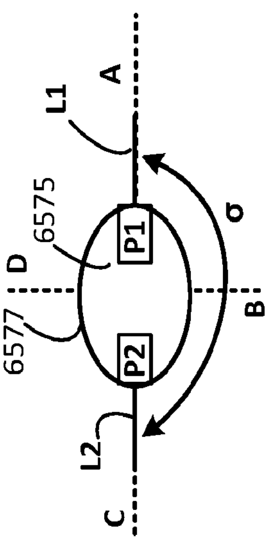
Figure 14I:
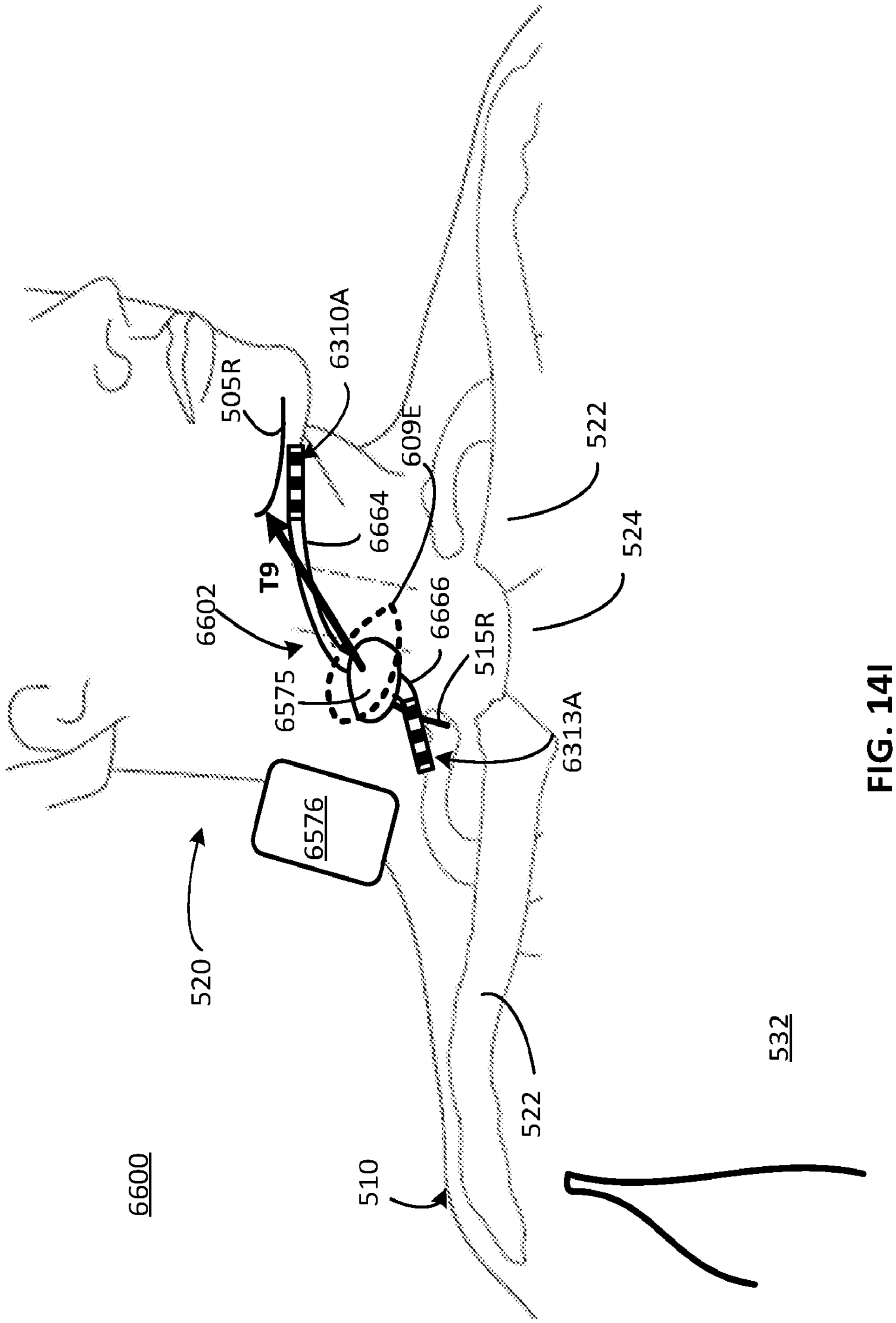
Figure 14J:
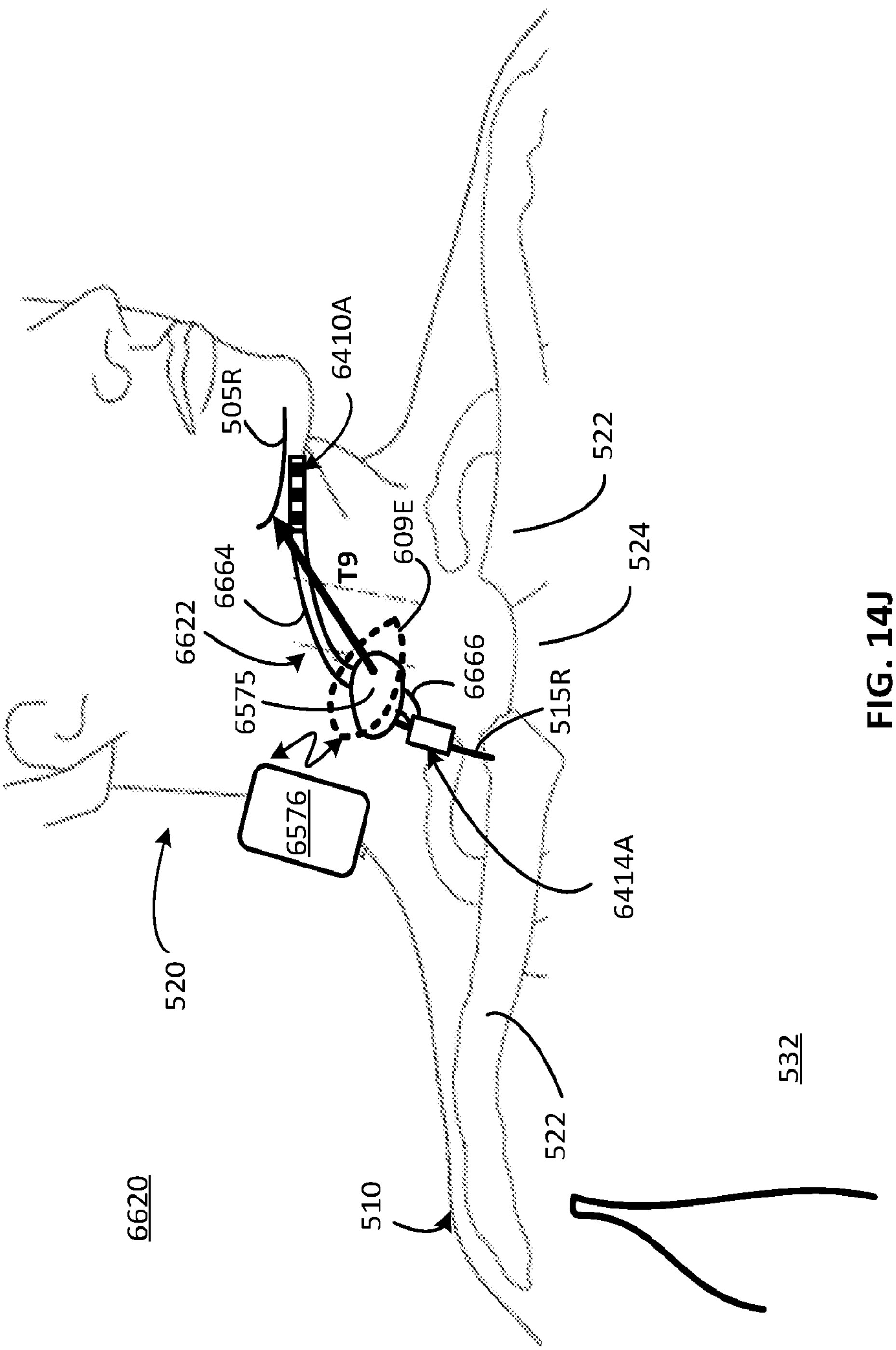
Figure 14K:
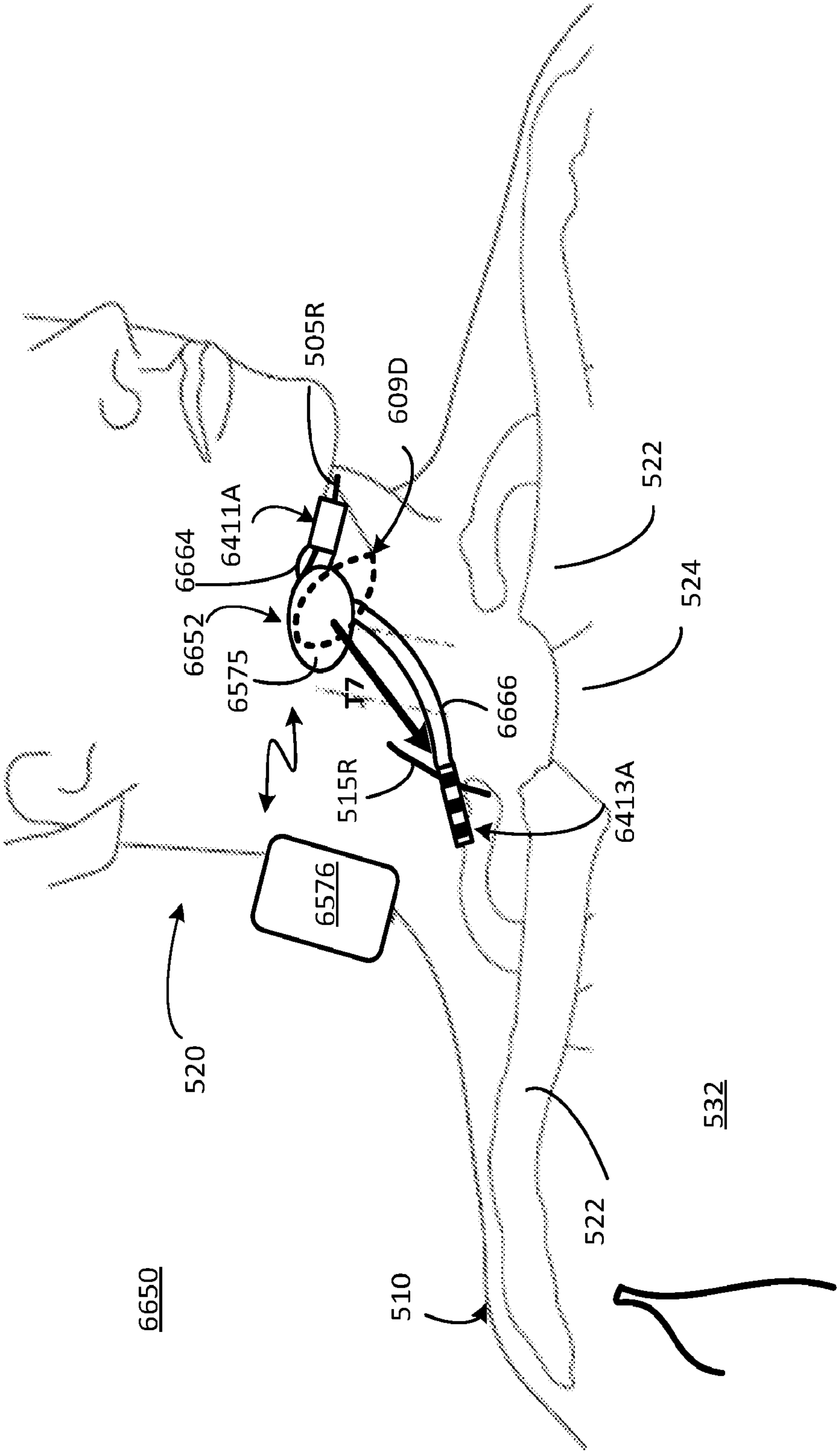
Figure 14L:
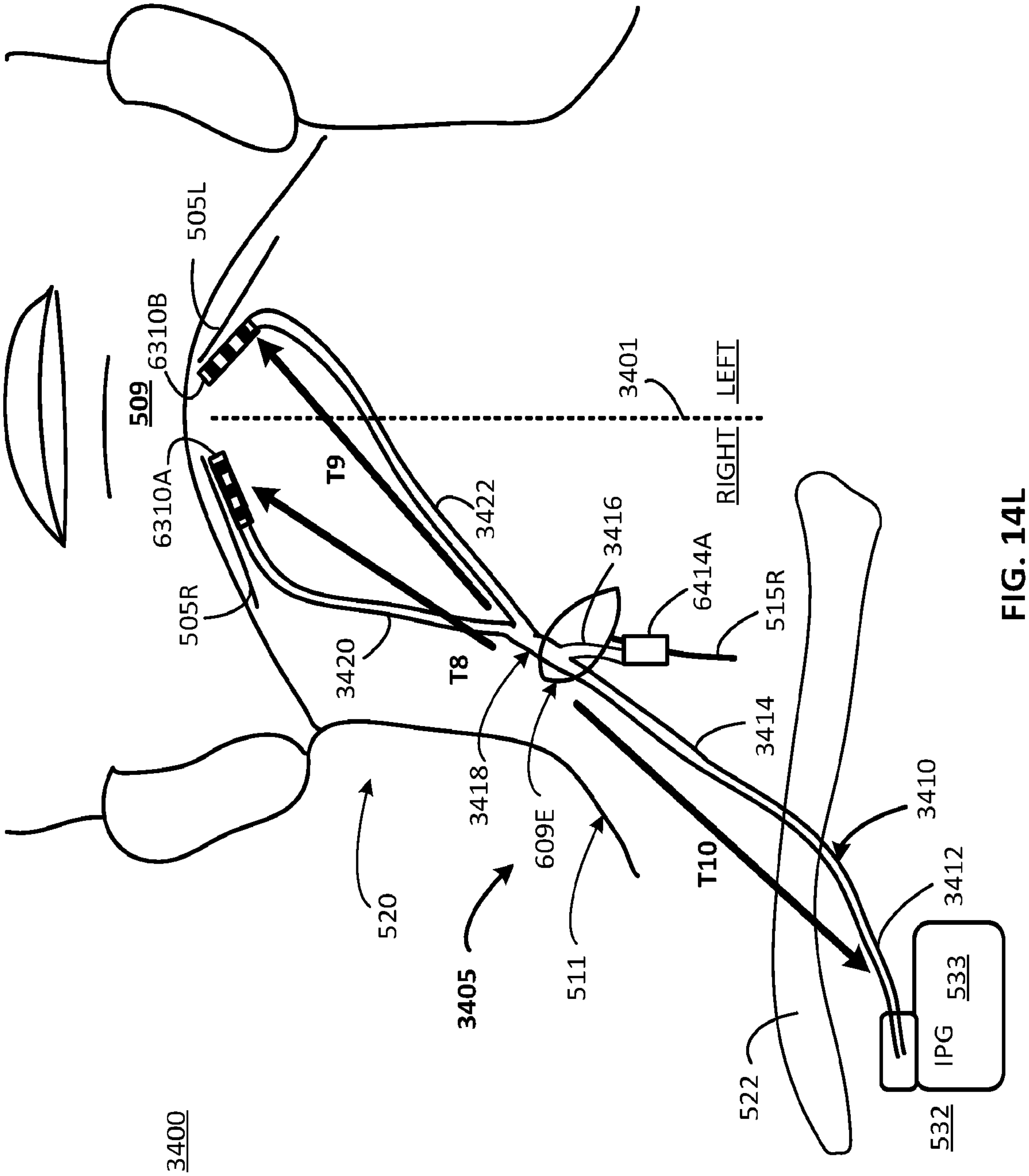
FIGS. 14L-14R are diagrams schematically representing an example device and/or method for implanting stimulation elements and associated leads, IPG or microstimulator via implant-access incision(s) for at least bilateral stimulation locations for the hypoglossal nerve.
Figure 14M:
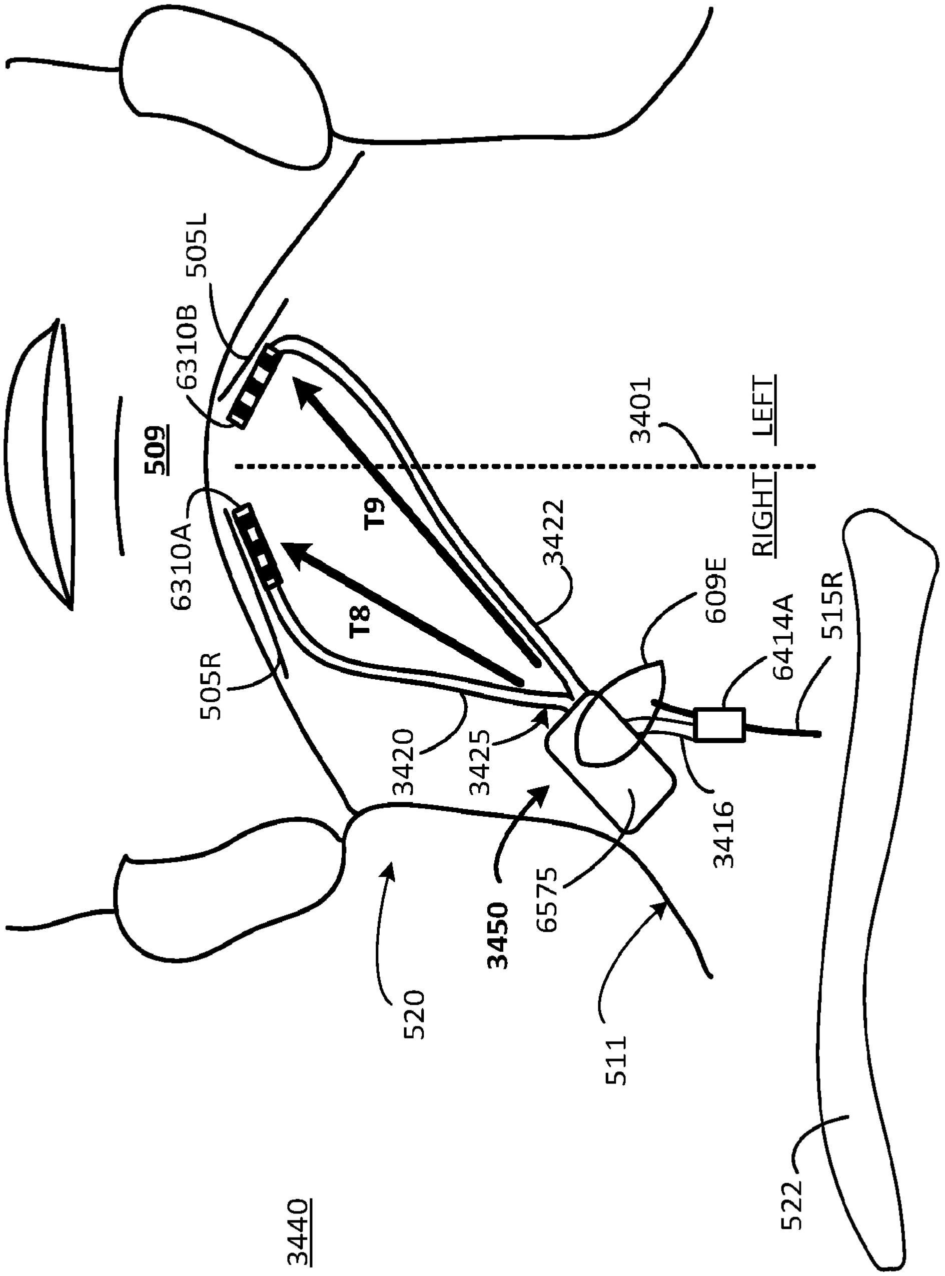
Figure 14N:
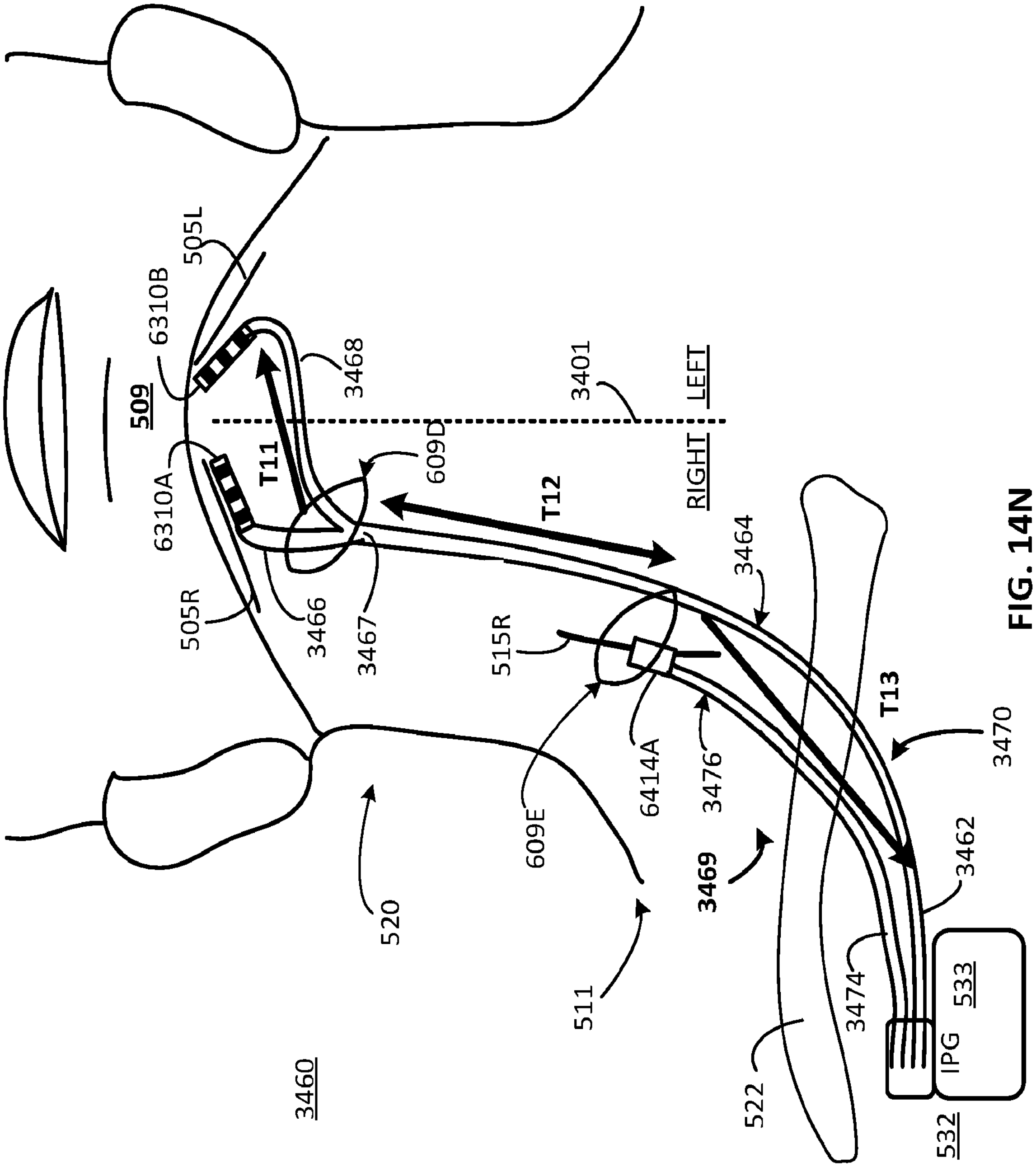
Figure 14O:
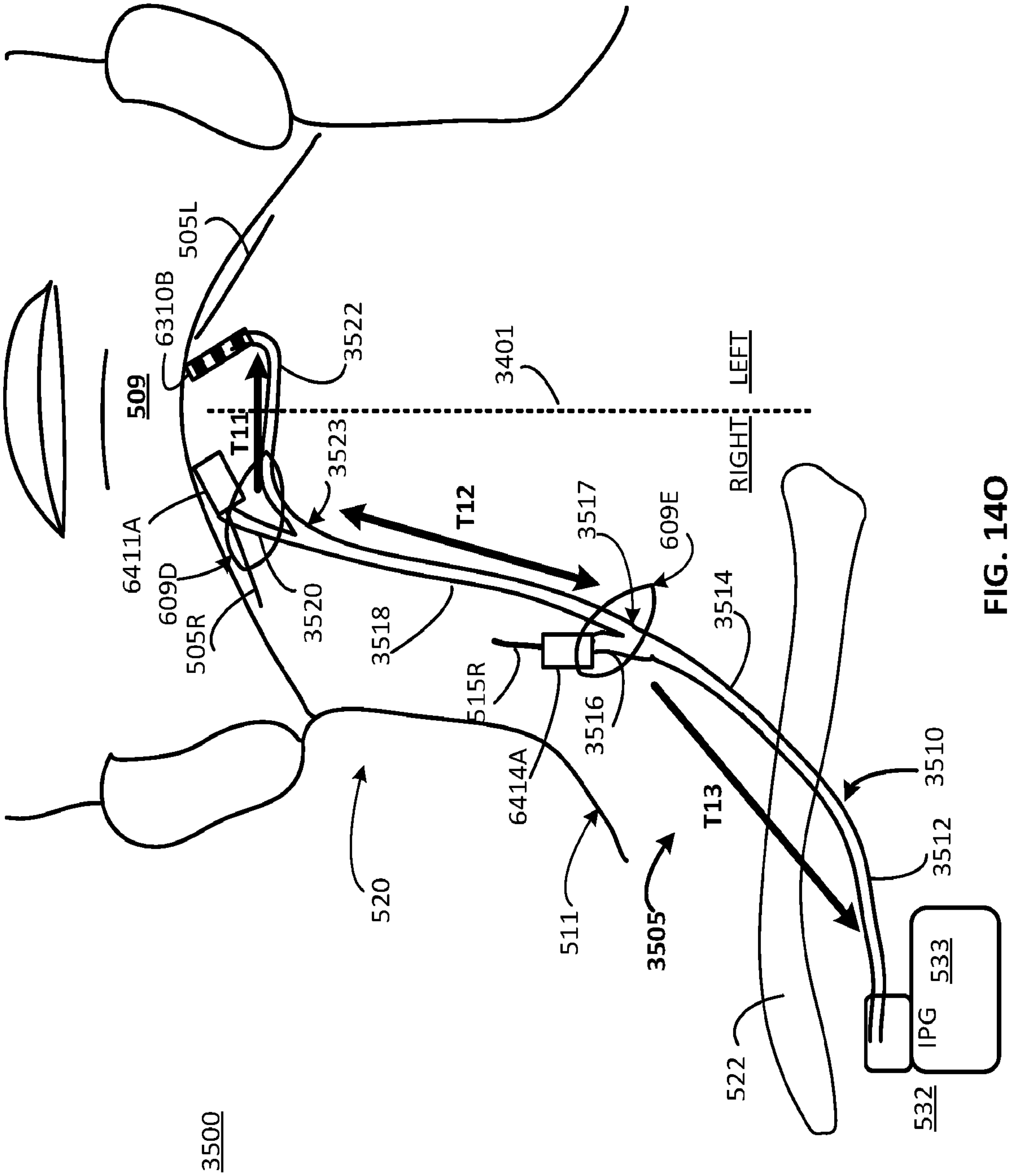
Figure 14P:
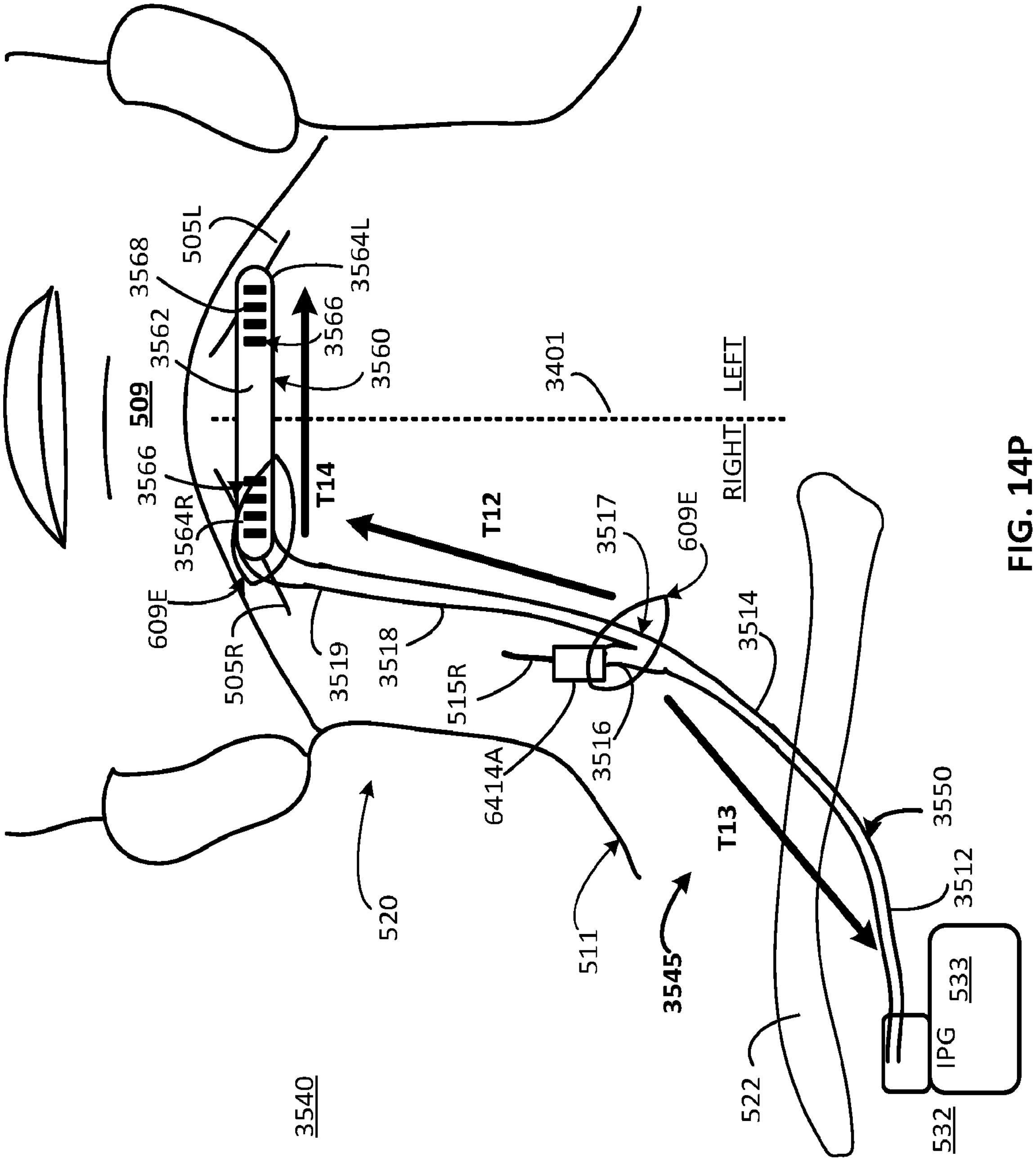
Figure 14Q:
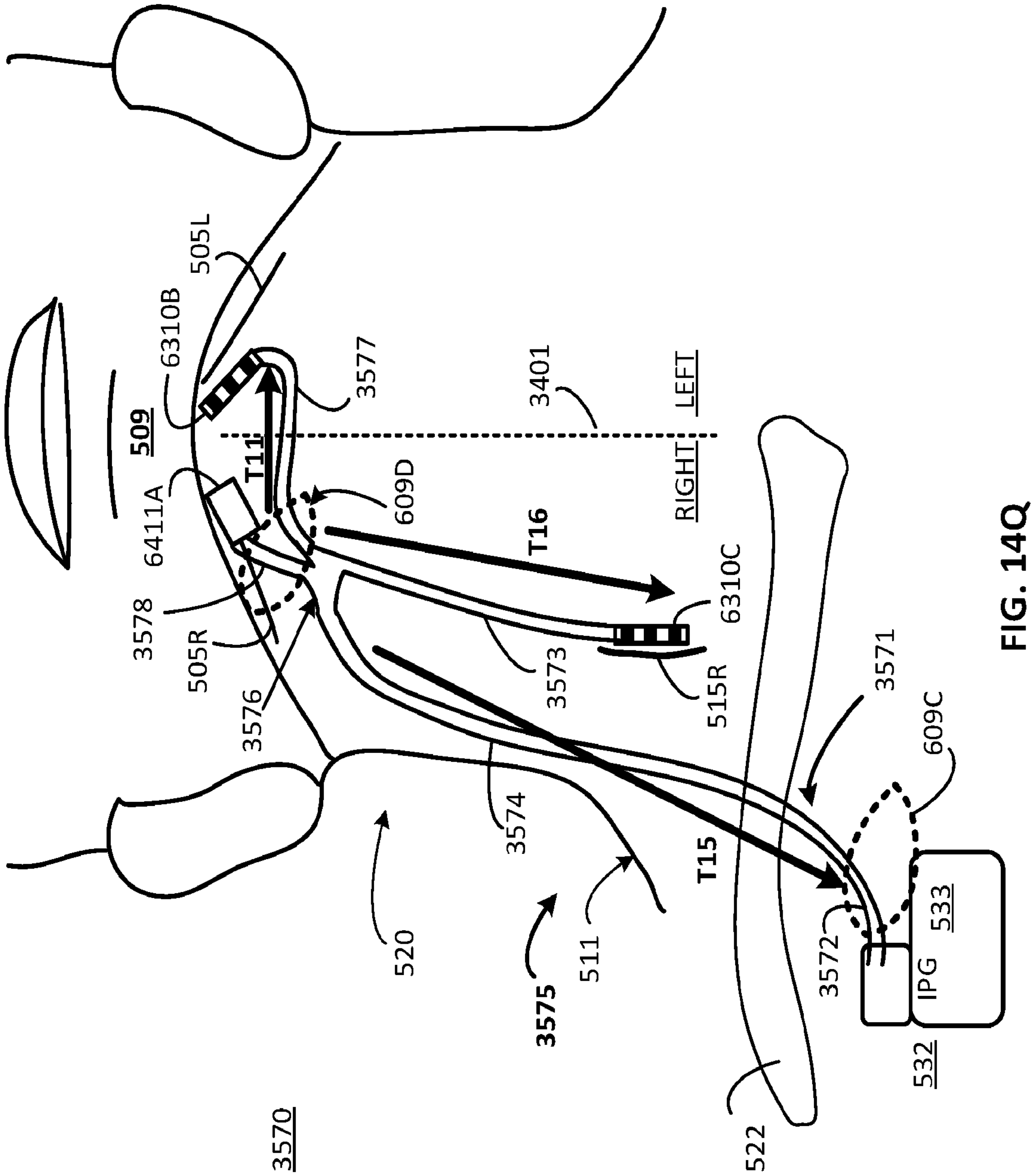
Figure 14R:
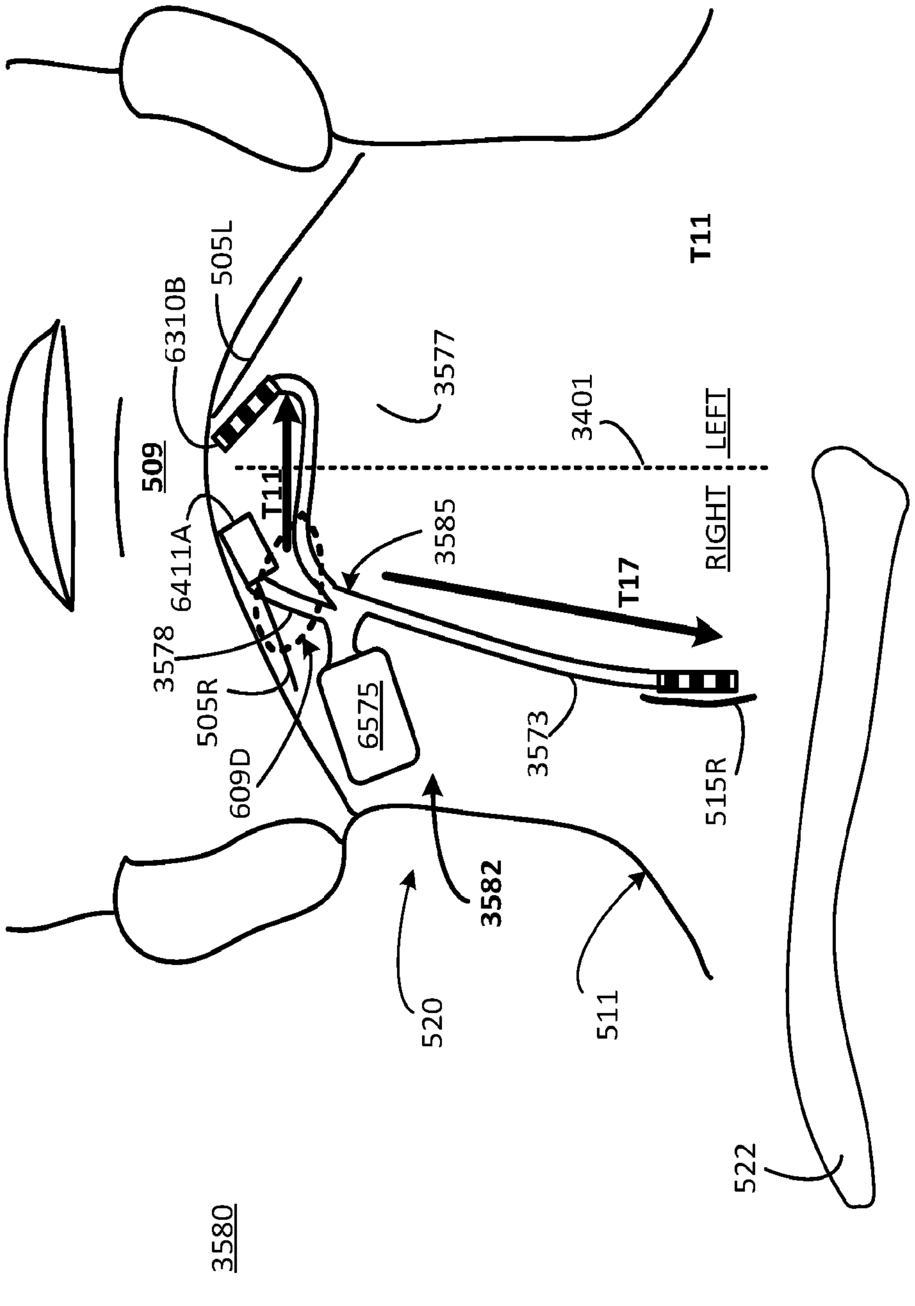

Whereas the example arrangements of at least FIGS. 14A-14R may comprise at least some stimulation elements configured as one or more axial-style electrode array (e.g. series of ring electrodes), it will be understood that in some examples, the example stimulation elements shown in a respective one of FIGS. 14A-14R may comprise a cuff electrode in some examples instead of a depicted axial-style electrode array. At least some such examples are already noted throughout the various examples of the present disclosure.

With regard to the various examples of the present disclosure, an implant-access incision comprises a type, size and/or shape of incision adapted to permit subcutaneous implantation of an implantable medical element, such as a stimulation element, sensing element, etc. An implant-access incision is in contrast to a non-implant-access incision, which may be an incision for purposes other than implanting an implantable medical element, such as a stimulation element and/or sensing element.

Upon forming implant-access incision 609D, a distal portion of lead 6337A can be implanted subcutaneously, which may include several aspects. As further shown in FIG. 14B, the lead 6337A may comprise a proximal portion 6339A, a body portion 6338A, and first and second distal portions 6346, 6344A, which extend from body portion 6338A via a junction 6340. In some instances, the lead 6337A may sometimes be referred to as comprising a bifurcated lead at least to the extent that the junction 6340 extending from lead body portion 6338A is shaped to result in bifurcation of the respective first and second distal portions 6346, 6344A from the lead body portion 6338A.

However, in some examples, the first distal lead portion 6346 of lead 6337A may be considered a continuance of body portion 6338A and second distal lead portion 6344A may be considered as an extension from body portion 6338A via junction 6340. Moreover, in some examples, junction 6340 may be formed to cause the second distal portion 6344A to extend in an opposite orientation from first distal portion 6346 (and stimulation portion 6310A). In some such examples, the junction 6340 and the portions of the first distal portion 6346, and second distal portion 6344A which meet at junction 6340 may be formed as a resilient structure and/or materials so as to bias the second distal portion 6344A to extend in the opposite orientation from first distal portion 6346 (or vice versa). In some examples, the second distal portion 6344A may be considered to extend in generally the same orientation as body portion 6338A of lead 6337A, at least relative to the orientation of first distal portion 6346 (including stimulation portion 6310A). As shown in FIG. 14B, each of stimulation portion 6310A, 6313A comprises a linear array of spaced apart electrodes 716 (e.g. ring electrodes or split-ring electrodes), which may be considered an axial arrangement of electrodes 716. It will be further understood that the electrodes 716 may comprise shapes other than rings, and the stimulation portion 6310A, 6313A may comprise other arrangements, such as paddle electrodes, etc. In some examples, the particular arrangement (e.g. number, shape, spacing, orientation, etc.) of electrodes on stimulation portion 6310A may be different from the particular arrangement of electrodes on stimulation portion 6313A.

In one aspect, the first distal portion 6346 of lead 6337A may be implanted subcutaneously, via implant-access incision 609D, and advanced until stimulation portion 6310A is in stimulating relation to nerve 505R. In particular, first distal portion 6346 (including stimulation portion 6310A) may have a length which is sufficiently short such that first distal portion 6346 (including stimulation portion 6310A) may be implanted with little or no tunneling from implant-access incision 609D. Stated differently, the location of implant-access incision 609D may be selected in sufficiently close proximity to the target stimulation location along nerve 505R such that little or no tunneling (from implant-access incision 609D to the target stimulation site) is performed to implant first distal portion 6346 (including stimulation portion 6310A) in stimulating relation to (a target stimulation location) of nerve 505R. In some examples, the implant-access incision 609D may comprise a different location from implant-access incision 609A (FIGS. 4, 9, etc.) in which implant-access incision 609D is closer to the more distal portions of the nerve 505R. However, in some examples, the implant-access incision 609D may correspond to the location of implant-access incision 609A (e.g. in FIGS. 4, 9, etc.).

In some examples of the first distal portion 6346, the stimulation portion 6310A may have a length which comprises at least about 50 percent, 60 percent, 70 percent, or 80 percent of the length of the entire first distal portion 6346 extending from junction 6340. In some examples, this length relationship may sometimes be expressed as the stimulation portion 6310A having a length comprising a substantial majority of the entire length of the first distal portion 6346.

In another aspect, prior to implanting a second distal portion 6344A of lead 6337A, tunneling (as represented by arrow T7) may be performed from implant-access incision 609D toward nerve 515R. Thereafter, the second distal portion 6344A (including stimulation portion 6313A) may be advanced via the tunnel to place stimulation portion in stimulating relation to nerve 515R. In some examples of the second distal portion 6366, the stimulation portion 6313A may have a length which comprises about 10 percent, 15 percent, 20 percent, 25 percent, or 30 percent of the length of the entire second distal portion 6366 extending from the junction 6340. Stated differently, the length of the entire second distal portion 6366 extending from the junction 6340 may comprise several multiples of a length of the stimulation portion 6313A of the second distal portion.

In one aspect, a proximal end of the body portion 6338 of lead 6337A is to be implanted to extend toward and into connection with IPG 533 . . . . However, in some examples, tunneling is first performed between the implant-access incision 609D and implant-access incision 609C to establish a tunnel (i.e. pathway), as represented by arrow T8). It will be understood that the tunneling may be performed starting at either implant-access incision 609C, 609D. With the tunnel in place, the proximal portion 6339 is inserted and advanced through implant-access incision 609D toward IPG 533 until the body portion 6338 extends from the implant-access incision 609D to implant-access incision 609C, at which the proximal portion 6339 of lead 6337A may be further maneuvered to be electrically and mechanically connected to the IPG 533.

It will be further understood that, in some examples, the particular sequence in which the various aspects of implantation (e.g. first distal portion 6346, second distal branch 6344A, body portion 6338A, IPG 533) are performed may vary depending on the circumstances, preferences, etc.

As shown later in at least FIGS. 14E, 14F, etc. in some examples in which the particular distal portion 6346 or 6344A (including its stimulation portion) of the lead 6337A is relatively short and little or no tunneling is performed, the stimulation portion (e.g. 6310A, 6313A) may comprise a cuff electrode.

In some examples, as shown in FIG. 14C, the implant-access incision 609D (FIG. 14B) is formed between the mandible bone 6330 and the hyoid bone 6332 so as to place the first distal portion 6346 (including stimulation portion 6310A) of lead 6337A in close proximity to at least some portions of the hypoglossal nerve 505R. In some such examples, the particular implant-access incision 609D is selected to place the stimulation 6310A at or near the more distal portions of the hypoglossal nerve 505R, such as those portions unlikely to innervate retrusor muscles (e.g. styloglossus) of the tongue and likely to innervate protrusor muscles (e.g. genioglossus, geniohyoid) of the tongue/airway. In some examples of these more distal locations, the target stimulation location of the hypoglossal nerve 505R may be in close proximity to muscle portions innervated by the hypoglossal nerve 505R, such as being in close proximity to nerve endings of the protrusor-related fibers, fascicles, etc. of the hypoglossal nerve which are more diffusely distributed (vs. well-defined nerve branches) within portions of the genioglossus muscle.

Among other features, the example arrangement 6300 in FIG. 14B may simplify and expedite a surgical implant procedure at least to the extent that the implant-access incision 609D may conveniently enable relatively simple implantation of the stimulation portion 6310A for nerve 505R, while also including a convenient delivery pathway from the implant-access incision 609D to the implant site for the stimulation portion 6313A for nerve 515R.

Figure 36A:
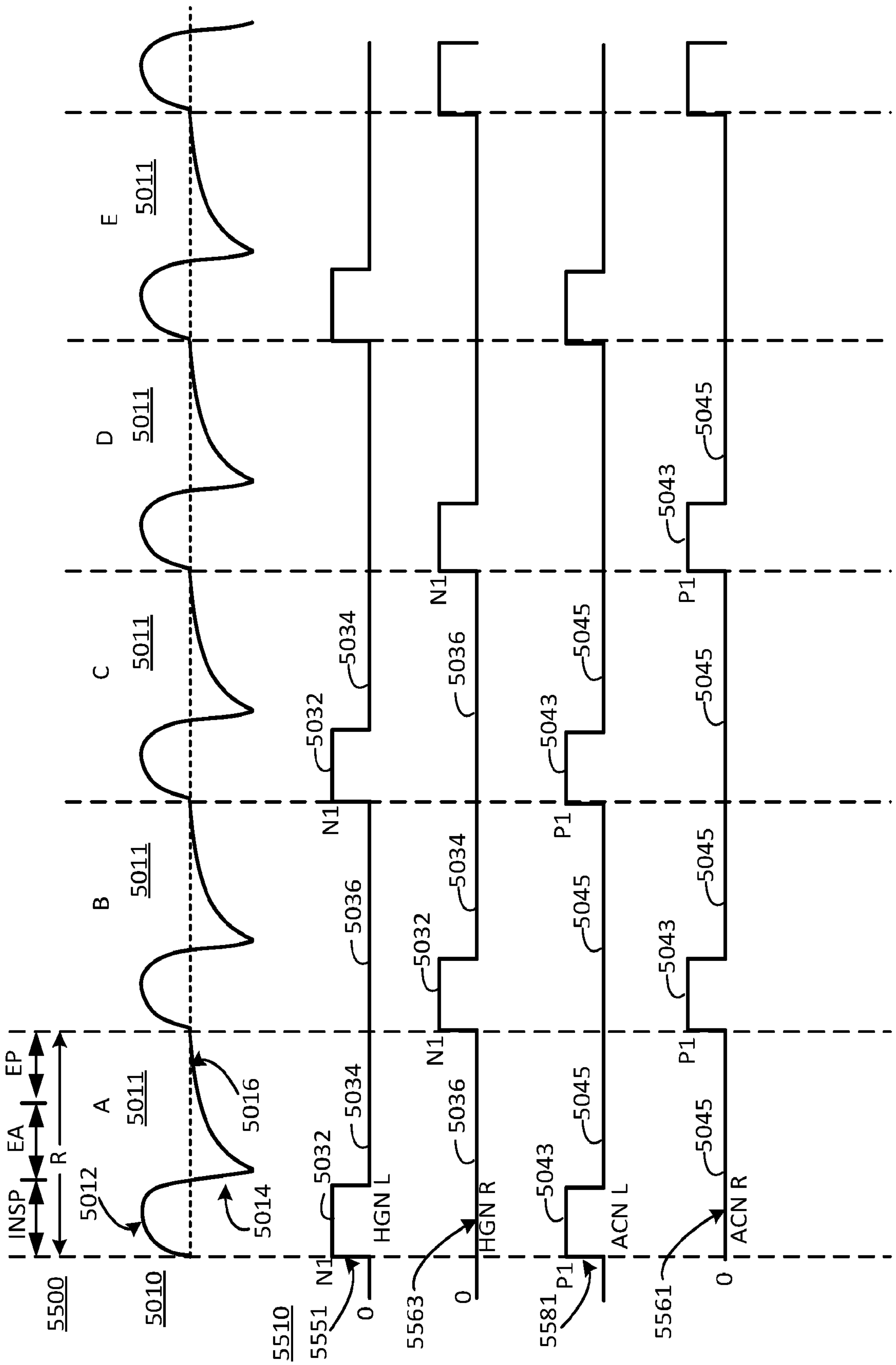

At least some of the example arrangements in FIGS. 14A-14R depict multiple stimulation elements on a single, first side of patient's body (e.g. right side), such as shown in at least FIG. 14B in which both of a first stimulation element for stimulating a hypoglossal nerve and a second stimulation element for stimulating an ansa cervicalis-related nerve are implanted on a same side (e.g. right side or left side) of the patient's body. However, consistent with at least FIG. 3A, in some examples one of the respective stimulation elements (e.g. for the hypoglossal nerve) may be located on one side of the patient's body while another stimulation element (e.g. for the ansa cervicalis-related nerve) may be implanted on an opposite, second side of the patients' body. Moreover, as further consistent with the examples of FIG. 3A, at least some example arrangements of FIGS. 14A-14R may be implemented so that both the left and right hypoglossal nerves and both the left and right ansa cervicalis-related nerves have their own stimulation element (e.g. 4 different locations) such that stimulation may be applied in any desired combination from among a right side hypoglossal nerve, a left side hypoglossal nerve, a right side ansa cervicalis-related nerve, and a left side ansa cervicalis-related nerve. With these examples in mind, FIG. 36A provides one example stimulation protocol 5510 when a stimulation element is implanted at each of the 4 different locations (e.g. FIG. 3A, other). However, of course, the fact that each of the 4 different locations may have an implanted stimulation element does not necessitate that stimulation occurs at any one of the given locations at least because at least some of the various example stimulation protocols, methods, etc. throughout the various examples of the present disclosure may comprise selective stimulation among multiple implanted stimulation elements in order to achieve various goals in treating sleep disordered breathing.

FIG. 14BB is a diagram schematically representing an example arrangement 6347 comprising at least some of substantially the same features and attributes as the example arrangement 6300 in FIG. 14B, except with at least some portions of the body portion 6338B and/or distal lead portion 6344B comprising variable length features (e.g. sigmoid shape, sinusoidal shape, other) which may provide strain relief, among other properties. Accordingly, as shown in FIG. 14BB, the body portion 6338B of lead 6337B extending between the IPG 533 and the junction 6340 (near implant-access incision 609D) comprises at least one segment including variable length features (e.g. a sigmoid shape, sinusoidal shape, etc.) incorporated into the flexible, resilient structure of the body portion 6338B.

As further shown in FIG. 14BB, in some examples a distal portion of the lead body portion 6338B and/or junction 6340 of lead 6337B is anchored relative to a non-nerve tissue, as represented by indicator Z1. In some such examples, this anchoring (Z1) may be implemented via an anchor, such as but not limited to, the example anchors 800, 830 in FIGS.

6A, 6B or other applicable types of anchors disclosed throughout the present disclosure. In some examples, In some examples, the lead body portion 6338B may comprise the sole portion of lead 6337B which comprises variable length features (e.g. sigmoid shape, sinusoidal shape, and the like).

As further shown in FIG. 14BB, the distal lead portion 6344B of lead 6337B extending between the junction 6340 (near implant-access incision 609D) and stimulation portion 6313A comprises at least one segment including variable length features (e.g. a sigmoid shape, sinusoidal shape, etc.) incorporated into the flexible, resilient structure of the distal portion 6344B. In some examples a distal end (near stimulation portion 6313A) or other portion of the distal portion 6344B is anchored relative to a non-nerve tissue, as represented by a second indicator Z2. In some examples, this anchoring (Z2) may be the sole anchoring for lead 6337B or may comprise anchoring in addition to anchoring (Z1) near or at junction 6340, in some examples. The second anchoring (Z2) may implemented via an anchor element comprising at least some of substantially the same features and attributes as the anchor element(s) used to implement the first anchoring (Z2) or may comprise an anchor element(s) having different features.

In some examples, the lead 6337B may be viewed as having a stimulation element (e.g. stimulation portion 6310A, such as an axial electrode array, other) interposed between a distal variable length lead portion (e.g. 6344B) and a proximal variable length lead portion (e.g. 6338B).

In some examples, anchoring (e.g. Z1, Z2) may be implemented at other locations along the length of the lead 6337B in addition to, or instead of, the anchoring shown in FIG. 14BB.

It will be understood that the variable length features (e.g. sigmoid, sinusoidal, etc.) of lead body portion 6338B and distal lead portion 6344B may be implemented in one or more of the lead, lead portions, etc. of any one of the examples of the present disclosure as desired, with or without anchoring Z1, Z2 (e.g. anchor elements 800 in FIG. 6A, 830 in FIG. 6B or other types of anchoring) or at least some of the various example anchoring features disclosed throughout the present disclosure.

FIG. 14D is a diagram including a front view schematically representing an example arrangement 6350 relative to a patient's body 510, including an example device and/or example method for implantation of a lead 6357 including a stimulation element 6310A in stimulating relation to a hypoglossal nerve 505R and a stimulation element 6313A in stimulating relation to an ansa cervicalis-related nerve 515R. In some examples, the example arrangement 6350 may comprise at least some of substantially the same features and attributes as the example arrangement 6300 in association with FIG. 14B-14C, except with a differently located implant-access incision 609E and variation in the configuration of first and second distal portions 6364, 6366 of lead 6357 (relative to the configuration of the first, second distal portions 6346, 6344A of lead 6337A in FIG. 14B).

As shown in FIG. 14D, the various components of the example arrangement are implantable via implant-access incision 609C (in a manner similar to the arrangement in FIG. 14A) and via implant-access incision 609E. In some examples upon forming implant-access incision 609C, IPG 533 may be implanted subcutaneously, such as in a subcutaneous pocket within pectoral region 532. Upon forming implant-access incision 609E, a distal portion of lead 6357 can be implanted subcutaneously, which may include several aspects.

As further shown in FIG. 14D, the lead 6357 may comprise a proximal portion 6339, a body portion 6358, and first and second distal portions 6364, 6366, which extend from body portion 6358 via a junction 6355. In some examples, the junction 6355 and at least the portions of the first distal portion 6364, and second distal portion 6366 which meet at junction 6355 may be formed as a resilient structure and/or materials so as to bias the second distal portion 6366 to generally extend in the opposite orientation from first distal portion 6364 (or vice versa).

In one aspect, a second distal portion 6366 of lead 6357 may be implanted subcutaneously, via implant-access incision 609E, and advanced until stimulation portion 6313A is in stimulating relation to nerve 515R. In particular, like first distal portion 6346 of lead 6337 in FIG. 14B, the second distal portion 6366 (including stimulation portion 6313A) of lead 6357 in FIG. 14D has a length which is sufficiently short such that second distal portion 6366 (including stimulation portion 6313A) may be implanted with little or no tunneling from implant-access incision 609E. Stated differently, the location of implant-access incision 609E may be selected in sufficiently close proximity to the target stimulation location along nerve 515R such that little or no tunneling (from implant-access incision 609E to the target stimulation site) is performed to implant second distal portion 6366 (including stimulation portion 6313A) to be in stimulating relation to (a target stimulation location) of nerve 515R.

In some examples of second distal portion 6366, the stimulation portion 6313A may have a length which comprises at least about 50 percent, 60 percent, 70 percent, or 80 percent of the length of the entire second distal portion 6366 extending from junction 6355. In some examples, this length relationship may sometimes be expressed as the stimulation portion 6313A having a length comprising a substantial majority of the entire length of the second distal portion 6366.

In another aspect, prior to implanting a first distal portion 6364 of lead 6337, tunneling (as represented by arrow T9) may be performed from implant-access incision 609E toward nerve 505R. Thereafter, the first distal portion 6364 (including stimulation portion 6310A) is advanced via the tunnel T9 to place stimulation portion 6310A in stimulating relation to nerve 505R. In some examples of the first distal portion 6364, the stimulation portion 6310A may have a length which comprises about 10 percent, 15 percent, 20 percent, 25 percent, or 30 percent of the length of the entire first distal portion 6364 extending from the junction 6355. Stated differently, the length of the entire first distal portion 6364 extending from the junction 6355 may comprise several multiples of a length of the stimulation portion 6310A of the first distal portion 6364.

In one aspect, the body portion 6358 of lead 6357 is to be implanted to extend toward and into connection with IPG 533. However, in some examples, tunneling is first performed between the implant-access incision 609E and implant-access incision 609C to establish a tunnel (i.e. pathway), as represented by arrow T10. It will be understood that the tunneling may be performed starting at either implant-access incision 609C, 609E. With the tunnel in place, the proximal portion 6339 of lead 6357 is inserted and advanced through implant-access incision 609E toward IPG 533 until the body portion 6358 extends from the implant-access incision 609E to at least implant-access incision 609C, at which the proximal portion 6339 of lead 6357 may be further maneuvered to be electrically and mechanically connected to the IPG 533. It will be further understood that, in some examples, the particular sequence in which the various aspects of implantation (e.g. first distal portion 6364, second distal branch 6366, body portion 6358, IPG 533) are performed may vary in some instances.

In some examples, the particular location of the implant-access incision 609E may correspond to a location within the head-and-neck region by which one can directly access a portion of the ansa cervicalis-related nerve corresponding to a desired stimulation location. In some such examples, the implant-access incision 609E may enable direct access for implantation of a stimulation element (e.g. cuff electrode, stimulation portion, etc.) to place the stimulation element in stimulating relation to one or more of the example stimulation locations A, B, C, D, or E as generally described in association with at least FIGS. 2, 32A, 32C and as described more specifically in association with FIG. 16 (stimulation location A), FIGS. 22A, 32B (stimulation location B), and FIG. 32D (stimulation location C). It will be understood that other stimulation locations (e.g. D, E) of/along the ansa cervicalis-related nerve 316 may be accessed via implant-access incision 609E. Moreover, in some examples, these aspects associated with implant-access incision 609E are applicable to implant-access incision 609B (e.g. FIG. 4) shown in some other example arrangements in the present disclosure.

FIG. 14E is a diagram including a front view schematically representing an example arrangement 6400 relative to a patient's body 510, including an example device for, and/or example method of, implantation of a lead 6437 including a stimulation element 6411A in stimulating relation to a hypoglossal nerve 505R and a stimulation element 6313A in stimulating relation to an ansa cervicalis-related nerve 515R. In some examples, the example arrangement 6400 may comprise at least some of substantially the same features and attributes as the example arrangement 6300 in association with FIG. 14B-14C, except with first distal portion 6346 including a cuff electrode 6411A in FIG. 14E instead of the stimulation portion 6310A (e.g. axial-style array of electrodes 716) in FIG. 14B. In substantially all other respects, example arrangement 6400 comprises substantially the same features and attributes as arrangement 6300 in FIG. 14B. As shown in FIG. 14E, the lead 6437 may comprise a proximal portion 6339, a body portion 6438, and first and second distal portions 6346, 6344, which extend from body portion 6438 via the junction 6340.

In a manner similar to the example arrangement 6300 in FIG. 14B, in the example arrangement 6400 in FIG. 14E, the relatively short length of first distal portion 6346 may be particularly beneficial for implanting a cuff electrode 6411A relative to nerve 505R in close proximity to the implant-access incision 609D at least because such cuff electrodes 6411A are typically not suitable for introduction, advancing, etc. via a tunneled path in the same way that an axial lead (e.g. stimulation portion 6313A) would be. As addressed elsewhere, while FIG. 14A depicts the stimulation element 6411A (for right hypoglossal nerve 505R) and the stimulation element 6313A (for right ansa cervicalis-related nerve 515R) on a same side of the body, it will be understood that example arrangement 6300 may be implemented such that a respective one of the stimulation elements (6411A, 6313A) may be implanted on a first side (e.g. right or left side) of the patient's body and the other respective one of the stimulation elements (6411A, 6313A may be implanted on an opposite, second side (e.g. right or left side) of the patient's body. In some such examples, at least one of the tunnels T7 and/or T8 (or other tunnels) and a lead portion (e.g. 6344 and/or 6438) may extend across a sagittal midline of the patient's body, such along the neck below a patient's chin. This arrangement also may be implemented, as desired among and, via at least some of the other example arrangements of FIGS. 14A-14R.

In a manner similar for the first distal portion 6346 (including stimulation portion 6310A) in FIG. 14B, in some examples the cuff electrode 6411A in FIG. 14E may have a length which comprises at least about 50 percent, 60 percent, 70 percent, or 80 percent of the length of the entire first distal portion 6346 extending from junction 6340. In some examples, this length relationship may sometimes be expressed as the cuff electrode 6411A (e.g. one type of stimulation portion) having a length comprising a substantial majority of the entire length of the first distal portion 6346. Conversely, in some examples of the second distal portion 6344, the stimulation portion 6313A may have a length which comprises about 10 percent, 15 percent, 20 percent, 25 percent, or 30 percent of the length of the entire second distal portion 6344 extending from the junction 6340. Stated differently, the length of the entire second distal portion 6344 extending from the junction 6340 may comprise several multiples of a length of the stimulation portion 6313A of the second distal portion 6344.

FIG. 14F is a diagram including a front view schematically representing an example arrangement 6450 relative to a patient's body 510, including an example device for, and/or example method of, implantation of a lead 6457 including a cuff electrode 6414A in stimulating relation to an ansa cervicalis-related nerve 505R and a stimulation portion 6313A in stimulating relation to a hypoglossal nerve 505R. In some examples, the example arrangement 6450 may comprise at least some of substantially the same features and attributes as the example arrangement 6350 in association with FIG. 14D, except with second distal portion 6366 of lead 6457 in FIG. 14F including a cuff electrode 6414A instead of a stimulation portion 6313A (e.g. including an axial-style array of electrodes 716) as in the example arrangement 6350 of FIG. 14D. In substantially all other respects, example arrangement 6450 comprises substantially the same features and attributes as arrangement 6350 in FIG. 14D. As shown in FIG. 14F, the lead 6457 may comprise a proximal portion 6339, a body portion 6358, and first and second distal portions 6364, 6366, which extend from body portion 6358 via a junction 6355.

In a manner similar to the example arrangement 6350 in FIG. 14D, in the example arrangement 6450 in FIG. 14F, the relatively short length of second distal portion 6366 may be particularly beneficial for implanting a cuff electrode 6414A relative to nerve 515R in close proximity to the implant-access incision 609E at least because such cuff electrodes 6414A are typically not suitable for introduction, advancing, etc. via a tunneled path in the same way that an axial lead (e.g. stimulation portion 6313A) would be. In a manner similar for the second distal portion 6366 (including stimulation portion 6313A) in FIG. 14D, in some examples the cuff electrode 6414A in FIG. 14F may have a length which comprises at least about 50 percent, 60 percent, 70 percent, or 80 percent of the length of the entire second distal portion 6366 extending from junction 6355. In some examples, this length relationship may sometimes be expressed as the cuff electrode 6414A (e.g. one type of stimulation portion) having a length comprising a substantial majority of the entire length of the first distal portion 6346. Conversely, in some examples of the first distal portion 6364, the stimulation portion 6310A may have a length which comprises about 10 percent, 15 percent, 20 percent, 25 percent, or 30 percent of the length of the entire first distal portion 6364 extending from the junction 6355. Stated differently, the length of the entire first distal portion 6364 extending from the junction 6355 may comprise several multiples of a length of the stimulation portion 6310A of the first distal portion 6364.

FIG. 14G is a diagram including a front view schematically representing an example arrangement 6500 relative to a patient's body 510, including an example device for, and/or example method of, implantation of a lead 6537 including a stimulation element 6310A in stimulating relation to a hypoglossal nerve 505R and a stimulation element 6313A in stimulating relation to an ansa cervicalis-related nerve 515R. In some examples, the example arrangement 6500 may comprise at least some of substantially the same features and attributes as, comprise an example implementation of, and/or be usable with the example arrangements described in association with at least some of FIGS. 1-14A.

As shown in FIG. 14G, the various components of the example arrangement are implantable via a single implant-access incision 609C (in a manner similar to the arrangement in FIG. 14A). In some examples upon forming single implant-access incision 609C, IPG 533 may be implanted subcutaneously, such as in a subcutaneous pocket within pectoral region 532. As further shown in FIG. 14G, the lead 6537 may comprise a proximal portion 6539, and first and second lead body portions 6533, 6549, which extend from a junction 6534, which in turn extends distally from proximal portion 6539. In some examples, the respective lead body portions 6533, 6549 may sometimes be referred to as being bifurcated. In some examples, lead body portion 6533 comprises a distal portion 6547 which comprises stimulation portion 6310A while lead body portion 6549 comprises a distal portion 6548, which comprises stimulation portion 6313A.

In another aspect, prior to implanting a lead body portions 6533, 6549 of lead 6537, tunneling may be performed from implant-access incision 609C toward nerve 515R and nerve 505R, as represented by array T11. Thereafter, the first lead body portion 6533 (including stimulation portion 6310A) and second lead body portion 6549 (including stimulation portion 6313A) are advanced via the tunnel (T11) to place the stimulation portion 6310A in stimulating relation to nerve 505R and to place the stimulation portion 6313A in stimulating relation to nerve 515R.

In one aspect, the proximal portion 6539 of lead 6537 is inserted and advanced through implant-access incision 609C toward already-implanted IPG 533 so that proximal portion 6539 may be electrically and mechanically connected to the IPG 533.

It will be further understood that, in some examples, the particular sequence in which the various aspects of implantation (e.g. lead body portions 6533, 6549, 6539, IPG 533) are performed may vary depending on the circumstances, preferences, etc.

Among other features, the example arrangement 6500 provides for single implant-access incision and a single tunnel to thereby simplify and expedite a surgical implantation procedure.

FIG. 14H is a diagram including a front view schematically representing an example arrangement 6550 relative to a patient's body 510, including an example stimulation device (e.g. 6552) for, and/or related example method of, implantation, with the arrangement 6550 including a stimulation portion 6310A in stimulating relation to a hypoglossal nerve 505R and a stimulation portion 6313A in stimulating relation to an ansa cervicalis-related nerve 515R. In some examples, the example arrangement 6550 may comprise at least some of substantially the same features and attributes as lead 6337 in FIG. 14B, except omitting lead body portion 6338 and omitting IPG 533 in pectoral region 532. In particular, instead of IPG 533, in some examples stimulation device 6552 comprises a microstimulator 6575 to which the first lead portion 6546 (including stimulation portion 6310A) and second lead portion 6566 (including stimulation portion 6313A) are directly connected such that no intermediate or body portion (of an implantable medical device) is interposed between the microstimulator 6575 (which provides stimulation circuitry, power, and/or wireless communication to recharge element 6576 for recharging and/or for other control/sensing communications, etc.) and the lead portions 6566, 6564 (each of which include an array of stimulation electrodes). In some examples, the microstimulator 6575 may comprise an example implementation of, or be in wireless communication with, at least a portion of a control portion (e.g. FIGS. 54A-54E), and may be wireless communication with a patient remote (e.g. FIG. 3B), as further described elsewhere in association with the examples of the present disclosure.

As shown in FIG. 14H, in some examples the various components of the example stimulation device 6552 are implantable via a single implant-access incision 609D (in a manner similar to the arrangement in FIG. 14A) and without forming a second implant-access incision, such as incision 609C in FIG. 14B which otherwise would have been used to implant the now omitted IPG 533. As further shown in FIG. 14H, in some examples the stimulation device 6552 may comprise the microstimulator 6575, and first and second lead body portions 6566, 6564, which extend from the microstimulator 6575, and which include stimulation elements 6313A, 6310A, respectively. As noted above, all of these elements may be implanted via the single implant-access incision 609D.

In some examples, and with further reference to previously mentioned FIG. 14C, the implant-access incision 609D in FIG. 14H is formed between the mandible bone 6330 and the hyoid bone 6332 so as to place the first lead portion 6566 (including stimulation portion 6310A) in close proximity to at least some portions of the hypoglossal nerve 505R. In some such examples, the particular implant-access incision 609D is selected to place the stimulation 6310A at or near the more distal portions of the hypoglossal nerve 505R, as previously mentioned.

As further shown in FIG. 14H, in some examples the stimulation device 6552 may be formed, assembled, etc. to cause the respective lead portions 6566 and 6546 to extend outward from a periphery of the housing 6577 of the microstimulator 6575 to be spaced apart from each other by an angle (α). As further shown in FIG. 14HH, the angle (α) at which such lead portions (as represented by solid lines L1, L2) will extend outwardly in their spaced apart configuration may be from 0 to 360 degrees. Moreover, the arrow shown in FIG. 14HH represents just one example in which the two lead portions (L1, L2) would be spaced apart by 180 degrees such that the respective lead portions 6566, 6564 may extend from opposite portions (e.g. ends, sides, etc.) of the periphery of the microstimulator housing 6577. It will be understood that a housing of such an example microstimulator 6575 may comprise a wide variety of shapes, sizes, etc. with the particular obround shape shown in FIG. 14HH being just one example shape.

With further reference to FIG. 14HH, in some examples, the particular angle (α) by which lead portions L1, L2 are spaced apart about a periphery of the microstimulator housing 6577 may be fixed. In some such examples, this fixation may arise from the lead portions (e.g. 6546, 6566 in FIG. 14H) being formed as a unitary member with the microstimulator housing 6577. However, in some examples, the lead portions (e.g. 6564, 6566 in FIG. 14H) are removably attachable (at or near the time of implantation) relative to the microstimulator housing 6577, such as via separate connection ports (e.g. P1, P2 shown in FIG. 14HH) formed in the microstimulator housing 6577 at spaced apart locations which correspond to the angle (α) at which the lead portions 6566, 6564 are intended to extend outwardly from the microstimulator housing 6577.

In some examples, multiple connection ports (e.g. P1, P2) may be adjacent each other on a same side of a microstimulator housing such as (but not limited to) both being in proximity to line A in FIG. 14HH.

Moreover, while FIGS. 14H and 14HH depicts just two lead portions 6566, 6546 (or L1, L2) extending from the microstimulator housing 6577, it will be understood that in some examples, more than two lead portions 6566, 6546 may extend from the microstimulator housing 6577. It will be further understood that some examples, some additional lead portions may comprise a sensing lead portion versus a stimulation lead portion. Moreover, in some examples, at least some of the electrodes of a stimulation lead portion may sometimes be used for sensing.

Among other aspects, with the lead portions (e.g. 6566, 6546) extending outwardly from the microstimulator housing 6577 from different spaced apart locations about a periphery of the housing 6577 (as shown in FIG. 14H, 14HH), this example arrangement may simplify the implantation of a multiple lead stimulation device (e.g. 6552) because each lead portion (e.g. 6566, 6564) will already be biased to extend in an orientation (relative to the microstimulator housing 6577) to align and position the stimulation portions 6313A, 6310A relative to the target nerve 515R, 505R. Moreover, this example arrangement 6550 helps make practical an implantation procedure (FIG. 14H) using a single implant-access incision at least because the single implant-access incision 609D is generally interposed (in at least some examples) between the target nerve locations of the respective target nerve locations (e.g. 515R, 505R). Accordingly, upon formation of the single implant-access incision (e.g. 609D) at an intermediate location between the respective target stimulation locations (at 505R, at 515R), the implantation of the stimulation device 6552 includes positioning the microstimulator 6575 at intermediate location between the two target stimulation locations (at 505R, 515R) such that the lead portions may extend outwardly toward the target stimulation locations in a natural way to simplify advancement of the respective lead portions toward their target stimulation locations. In addition, such arrangements may reduce strain on a lead portion to the extent that maneuvering multiple lead portions extending from a microstimulator 6575 into their desired orientations within the body may induce strain under some circumstances.

In some examples a kit of several different stimulation devices (each including a microstimulator and at least two already connected lead portions L1, L2) may be offered in which each different stimulation device in the kit comprises lead portions (L1, L2) which extend from the microstimulator at a different angle (α in FIG. 14HH) from each other. For example, one stimulation device in the kit may have lead portions (e.g. L1, L2 in FIG. 14HH) which extend from each other by angle (α) of about 130 degrees while a different stimulation device in the kit may have lead portions (e.g. L1, L2) which extend from each other by an angle (α) of about 170 degrees. Accordingly, upon embarking on an implantation procedure for a stimulation device, a surgeon may select a stimulation device from the kit with an angle (α) suited to ease implantation of the stimulation device (including a microstimulator and lead portions) in view of the particular target stimulation locations of the nerves for which a stimulation portion (e.g. electrode array, cuff electrode, etc.) is be implanted.

As previously noted in connection with the example arrangement of at least FIG. 14B, the implant-access incision 609D may be selected such that at least one lead portion (e.g. 6546) may be implanted from the implant-access incision 609D without tunneling.

Conversely, as further shown in FIG. 14H and in a manner similar to that described in connection with at least FIG. 14B, 14E, tunneling (T7) may be formed via the implant-access incision 609D to create a path to advance lead portion 6566 subcutaneously until stimulation portion 6313A becomes aligned and positioned relative to the ansa cervicalis-related nerve 515R, as shown in FIG. 14H.

Moreover, it will be understood that with respect to at least FIGS. 14F, 14H-14K, in some examples tunneling may be performed in two separate orientations, with a first tunnel to be established for a first lead (including a stimulation portion) for stimulating the hypoglossal nerve 505R and with a second tunnel for a second lead (including a stimulation portion).

As further shown in FIG. 14H, in some examples the example arrangement 6550 may comprise a recharge element 6576 for recharging a power supply of the microstimulator 6575. In some such examples, the recharge element 6576 and/or microstimulator 6575 may comprise at least some of substantially the same features and attributes as the example arrangement 2700 as later described in association with at least FIG. 21.

With regard to the example arrangement 6550 in FIG. 14H, in some examples the stimulation portion 6310A in FIG. 14H may have a length which comprises at least about 50 percent, 60 percent, 70 percent, or 80 percent of the length of the entire first lead portion 6546 extending from microstimulator 6575. In some examples, this length relationship may sometimes be expressed as the stimulation portion 6310A having a length comprising a substantial majority of the entire length of the first lead portion 6546. Conversely, in some examples of the second lead portion 6566, the stimulation portion 6313A may have a length which comprises about 10 percent, 15 percent, 20 percent, 25 percent, or 30 percent of the length of the entire second lead portion 6566 extending from the microstimulator 6575. Stated differently, the length of the entire second lead portion 6566 extending from the microstimulator 6575 may comprise several multiples of a length of the stimulation portion 6313A of the second lead portion 6566. It will be understood that these same "relative length" relationships are exhibited in the example arrangements described below in relation to at least FIGS. 14I-14K with regard to analogous lead portions and stimulation portions of each example arrangement.

FIG. 14I is a diagram including a front view schematically representing an example arrangement 6600 relative to a patient's body 510, including an example stimulation device 6602 for, and/or related example method of, implantation, with the arrangement 6600 including a stimulation portion 6310A in stimulating relation to a hypoglossal nerve 505R and a stimulation portion 6313A in stimulating relation to an ansa cervicalis-related nerve 515R. In some examples, the example arrangement 6600 may comprise at least some of substantially the same features and attributes as the example arrangement 6550 in FIG. 14H, 14HH, except with the single implant-access incision 609E having a different location from implant-access incision 609D (FIG. 14H) and the roles of the respective lead portions 6666 and 6664 in FIG. 14I being reversed relative to lead portions 6564 and 6566 in FIG. 14H.

In particular, implant-access incision 609E is formed at a location in reasonably close proximity to the ansa cervicalis-related nerve 515R by which a microstimulator 6575 may be implanted such that lead portion 6666 (including stimulation portion 6313A) becomes suitably aligned and positionable in stimulation relation to the ansa cervicalis-related nerve 515R. Meanwhile, after and via tunneling (like T9 in FIG. 14D), lead portion 6664 may be advanced subcutaneously via the tunnel until stimulation portion 6310A is suitably aligned and positioned in stimulating relation to hypoglossal nerve 505R.

FIG. 14J is a diagram including a front view schematically representing an example arrangement 6620 relative to a patient's body 510, including an example stimulation device 6622 for, and/or related example method of, implantation, with the arrangement 6620 including a stimulation portion 6310A in stimulating relation to a hypoglossal nerve 505R and a stimulation portion provided as a cuff electrode 6414A in stimulating relation to an ansa cervicalis-related nerve 515R. In a manner similar to FIGS. 14H, 14HH, 14I, the stimulation device 6622 comprises at least microstimulator 6575, lead 6666 with stimulation element 6414A, and lead 6664 with stimulation element 6410A.

In some examples, the example arrangement 6620 may comprise at least some of substantially the same features and attributes as the example arrangement 6600 in FIG. 14I, except with the cuff electrode 6414A in FIG. 14J replacing the stimulation portion 6313A in FIG. 14I. For instance, the example arrangement 6620 (including stimulation device 6622) of FIG. 14J comprises a recharge element 6576 and a microstimulator 6575, each of which comprise at least some of substantially the same features and attributes as previously described in association with at least FIGS. 14H, 14HH, 14I and with reference to the features and attributes of FIG. 21.

At least because the single implant-access incision 609E is formed at a location in reasonably close proximity to the ansa cervicalis-related nerve 515R, implanting the cuff electrode 6414A (on lead portion 6666) into stimulating relation to the ansa cervicalis-related nerve 515R may be performed in a relatively simple manner without tunneling. Moreover, this relatively direct access may greatly facilitate implanting a cuff electrode 6414A, which may include more maneuvering in, around, and among tissues in the surgical work field than simply pushably advancing an axial, cylindrically-shaped stimulation portion. Implantation of the cuff electrode 6414A may be favored in some instances, such as but not limited to, reliably establishing stimulating relation of a stimulation element (e.g. carrier with electrodes) relative to a nerve which may be challenging (in some patients) to ensure stable positioning of a non-cuff electrode type of stimulation element. For example, directly visualizing the ansa cervicalis-related nerve 316 may better enable probing for/among different branches of the ansa cervicalis-related nerve 316 to identify the stimulation location (e.g. A, B, C in FIG. 2, or other locations) with the best muscle response to a test stimulation(s). Upon making such identification, the cuff electrode 6414A may be then placed at the identified location and secured in place to establish reliable chronic implantation and robust stimulating relation to the target stimulation location of the nerve. Among other aspects, using a "direct access" implant-access incision may enhance visualization and probing, which in turn may enable greater flexibility and success in performing implantations in view of the anatomical variations among different patients.

FIG. 14K is a diagram including a front view schematically representing an example arrangement 6650 relative to a patient's body 510, including an example stimulation device 6652 for, and/or related example method of, implantation, with the arrangement 6650 including a stimulation portion (provided as a cuff electrode 6411A) in stimulating relation to a hypoglossal nerve 505R and a stimulation portion 6413A in stimulating relation to an ansa cervicalis-related nerve 515R. In some examples, the example arrangement 6650 may comprise at least some of substantially the same features and attributes as the example arrangement 6550 in FIG. 14H, except with the cuff electrode 6411A in FIG. 14K replacing the stimulation portion 6310A in FIG. 14H. For instance, via the example arrangement (and method), the entire stimulation device 6652 (including microstimulator 6575, lead 6666 with stimulation element 6431A, and lead 6664 with stimulation element 6411A) may be implanted via the single implant-access incision 609D.

At least because the single implant-access incision 609D is formed at a location in reasonably close proximity to the hypoglossal nerve (e.g. more distal portions thereof), implanting the cuff electrode 6411A (on lead portion 6666) into stimulating relation to the hypoglossal nerve 515R may be performed in a relatively simple manner without tunneling. Moreover, this relatively direct access may greatly facilitate implanting a cuff electrode 6411A, which may include more maneuvering in, around, and among tissues in the surgical work field than simply pushably advancing an axial, cylindrically-shaped stimulation portion. Implantation of the cuff electrode 6411A may be favored in some instances, such as but not limited to, reliably establishing stimulating relation of a stimulation element (e.g. carrier with electrodes) relative to a nerve which may be challenging (in at least some patients) to ensure stable positioning of a non-cuff electrode type of stimulation element. For example, directly visualizing the hypoglossal nerve 505R may better enable probing for/among different branches (and/or distal nerve endings) of the hypoglossal nerve 505R to identify the stimulation location with the best muscle response to a test stimulation(s). Upon making such identification, the cuff electrode 6411A may be then placed at the identified location and secured in place to establish reliable chronic implantation and robust stimulating relation to the target stimulation location of the nerve. Among other aspects, using a "direct access" implant-access incision may enhance visualization and probing, which in turn may enable greater flexibility and success in performing implantations in view of the anatomical variations among different patients.

Via at least some of these features and attributes such as, but not limited to, the single implant-access incision 609D and the compact stimulation device 6652, a surgeon may implant a stimulation device in a more efficient and effective manner while potentially increasing patient comfort.

FIGS. 14L-14R relate to at least some example methods of implantation and/or methods of stimulation therapy. For instance, various examples methods of stimulation therapy are described in association with at least FIG. 3A which may comprise applying electrical stimulation to a left hypoglossal nerve, a right hypoglossal nerve, a left ansa cervicalis-related nerve, and/or a right ansa cervicalis-related nerve. In some such examples, the therapy may be applied unilaterally or bilaterally for the same type of nerve (e.g. just the hypoglossal nerves or just the ansa cervicalis-related nerves), unilaterally for different types of nerves (e.g. stimulating nerves on just the right side of the body or stimulating nerves on just the left side of the body), or bilaterally for different types of nerve (e.g. stimulating the left hypoglossal nerve and the right ansa cervicalis-related nerve, vice versa). With this in mind, FIGS. 14L-14R comprise some example implementations of the example arrangement in FIG. 3A which are directed to bilateral stimulation of the left and right hypoglossal nerves and unilateral stimulation of a single ansa cervicalis-related nerve (e.g. left or right). In particular, FIGS. 14L-14R relate to at least some examples of methods of implantation and example stimulation devices for implementing the bilateral stimulation of the left and right hypoglossal nerves and unilateral stimulation of a single ansa cervicalis-related nerve (e.g. left or right). Various example methods of stimulation therapy regarding whether (and how) different nerves (e.g. left HGN, right HGN, left AC, and right AC) are stimulated simultaneously, alternately, staggered, sequentially, synchronized, non-synchronized, etc. are provided in at least FIGS. 1-3C, 16, and 32A-50 and/or other various therapy examples throughout the present disclosure. Moreover, the implantation of the various elements of the example stimulation devices in association with at least FIGS. 14L-14R also may be further implemented via at least some of the example arrangements (e.g. devices and methods) described in association with the delivery tools, anchoring elements, lead connectability features, etc. of at least FIGS. 1-32C, 49B-51B, and the like.

While FIGS. 14L-14R illustrate examples in which stimulation may be applied to a right ansa cervicalis-related nerve in combination with bilateral stimulation including the left and right hypoglossal nerves, it will be understood that these examples are equally applicable to example implementations in which stimulation is to be applied a left ansa cervicalis-related nerve in combination with bilateral stimulation including the left and right hypoglossal nerves. Moreover, in some examples, using the similar elements, methods, etc. as described in association with at least FIGS. 14L-14R, some example methods of implantation and/or example stimulation devices comprise bilateral stimulation of a left ansa cervicalis-related nerve (e.g. 515L) and a right ansa cervicalis-related nerve (e.g. 515R).

FIG. 14L is a diagram including a front view schematically representing an example arrangement 3400 including an example device for, and/or example method of, implantation of a stimulation device 3405. The stimulation device 3405 is adapted for providing bilateral stimulation of a left and right hypoglossal nerve 505R, 505L, and unilateral stimulation of an ansa cervicalis-related nerve 515R (e.g. 316 in FIG. 2A) in order to maintain and/or restore upper airway patency, such as to treat obstructive sleep apnea and/or other sleep disordered breathing. Accordingly, FIG. 14L depicts a head-and-neck region 520 of a patient's body 510, while denoting at least some anatomical landmarks such as a chin 509 and providing dashed line 3401 to distinguish between the right (RIGHT) and left (LEFT) sides of the patient's body 510.

As shown in FIG. 14L, the stimulation device 3405 may comprise a stimulation lead 3410 to deliver therapeutic stimulation signals, generated via an implantable pulse generator (IPG) 533 and applied through at least one of a stimulation portion 6310A, stimulation portion 6310B and/or a cuff electrode 6414A. In some examples, the stimulation portions 6310A, 6310B may comprise a linear array of spaced apart electrodes (e.g. ring, split ring, and the like), which may sometimes be referred to an axial lead or axial stimulation portion. In some examples, the stimulation lead 3410 may comprise a proximal portion 3412, body portion 3414, junction 3418, lead portion 3416, and distal lead portions 3420, 3422. The proximal portion 3412 of lead 3410 is connectable to the IPG 533, and the body portion 3414 extends distally from the proximal portion 3412. The junction 3418 connects the distal lead portions 3420, 3422 and lead portion 3416 relative to each other and relative to body portion 3414 of lead 3410. In some examples, the junction 3418 may sometimes be referred to as including or defining a bifurcation point for distal lead portions 3420, 3422 and lead portion 3416 relative to each other and/or relative to body portion 3414 of lead 3410.

In some examples, these elements may be implanted via an implant-access incision 609E, which may comprise the sole implant-access incision via which the elements of the stimulation device 3405 are implanted, in some examples. As noted elsewhere, using a single implant-access incision may reduce surgical complexity, increase patient comfort, reduce procedure time, etc. in at least some examples. As shown in FIG. 14L, the implant-access incision 609E is located in close proximity to the ansa cervicalis-related nerve 515R.

It will be understood that in some examples, more than one implant-access incision may be used.

In one aspect, a method of implantation may comprise forming the implant-access incision 609E and then introducing and advancing the lead portion 3416 to place the cuff electrode 6414A into stimulating relation to the ansa cervicalis-related nerve 515R, such as on one side (e.g. right side) of the body. From the single implant-access incision 609E, a tunnel T8 may be formed subcutaneously toward a pertinent portion of the right hypoglossal nerve 505R, followed by introducing and advancing distal lead portion 3420 to place stimulation portion 6310A in stimulating relation to a target stimulation portion on the right hypoglossal nerve 505R. Similarly, also via implant-access incision 609E, a tunnel T9 may be formed relative to the left hypoglossal nerve 505L, followed by introducing and advancing distal lead portion 3422 to place stimulation portion 6310B in stimulating relation to a target stimulation portion on the left hypoglossal nerve 505R. Via this arrangement, the respective distal lead portions 3420, 3422 provide a mechanism by which bilateral stimulation of the left and right hypoglossal nerves may be delivered. As previously noted elsewhere, in some examples the stimulation portions 6310A, 6310B may comprise an axial lead-type of stimulation portion including a linear array of spaced apart electrodes (e.g. ring electrodes, split-ring electrodes, and the like). As further noted elsewhere, each stimulation portion 6310A, 6310B and supporting distal lead portion 3420, 3422 (respectively) may comprise anchor element(s) as described in various examples of the present disclosure, such as but not limited to those in FIGS. 30B-32B.

Among other aspects, a cuff-style electrode 6414A secured at the ansa cervicalis-related nerve 515R may help ensure robust engagement of the stimulation electrodes in stimulating relation of the stimulation electrodes relative to nerve 515R in view of the smaller size of the nerve, in view of the type and location of the nerve 515, and/or in view of the type, size, etc. of surrounding non-nerve tissues. In other aspects, the axial type stimulation portions 6310A, 6310B are more conducive to introduction and advancement through a tunnel (e.g. T8, T9) than a cuff electrode, and also may help avoid having to make a separate implant-access incision near nerves 505R, 505L, thereby helping to implement an implantation procedure with fewer implant-access incisions. By doing so, surgical time and complexity may be reduced, patient comfort increased, etc.

In a further aspect of a method of implantation, from the single implant-access incision 609E, a tunnel T10 may be subcutaneously formed to a suitable location at which the IPG 533 may be implanted, such as in the pectoral region 532 of the patient's body. In some examples, an additional implant-access incision may formed in close proximity to the location at which the IPG 533 is to be implanted. With tunnel T10 formed, via implant-access incision 609E a body portion 3414 of lead 3410 is introduced and advanced to the implant location of IPG 533 to enable proximal portion 3412 of stimulation lead 3410 to be connected (electrically and mechanically) to the IPG 533.

While the example arrangement shown in FIG. 14L provides a bifurcation point near the implant-access incision 609E, in some examples the stimulation lead may comprise a bifurcation point near the IPG 533 such as (but not limited to) the example implementation in later described FIG. 14N.

FIG. 14M is a diagram including a front view schematically representing an example arrangement 3440 including an example device for, and/or example method of, implantation of a stimulation device 3450. In some examples, the stimulation device 3450 may comprise at least some of substantially the same features and attributes as the stimulation devices, methods, etc. as previously described in association with at least FIG. 14L, except with the stimulation device 3450 in FIG. 14M including a microstimulator 6575 (e.g. FIG. 14H) instead of the IPG 533 in FIG. 14L (and omitting the body portion 3414 of lead 3410 associated with the IPG 533).

As shown in FIG. 14M, in some examples the microstimulator 6575 is implanted at or in close proximity to the target stimulation location of the ansa cervicalis-related nerve 515R.

Accordingly, with further reference to FIG. 14M in comparison to FIG. 14L, the stimulation device 3450 in FIG. 14M comprises the same distal lead portions 3420, 3422 and their respective stimulation portions 6310A, 6310B for delivering bilateral stimulation to the respective right and left hypoglossal nerves 505R, 505L. Moreover, the stimulation device 3450 in FIG. 14M also comprises the same lead portion 3416 and cuff electrode 6414A in stimulating relation to the ansa cervicalis-related nerve 515R.

As further shown in FIG. 14M, the microstimulator 6575 is directly connected to the respective lead portions 3420, 3422, 3416 with distal lead portions 3420, 3422 having a bifurcation point 3425 at or near a housing of the microstimulator 6575. In some examples, the lead portion 3416 may extend directly from the microstimulator 6575 as shown in FIG. 14M or in some examples, may extend from the same bifurcation point 3425 (or junction) as the distal lead portions 3420, 3422. As noted elsewhere in relation to some examples of the present disclosure, the microstimulator 6575 may comprise stimulation/control circuitry, a power source (e.g. rechargeable), and may be in communication with an external power recharging device, element, and the like.

It will be further understood that in some examples, at least some of the stimulation portions (e.g. 6310A, 6310B), cuff electrodes (e.g. 6414A) may be in wireless communication with the microstimulator 6575 such that one or more of the associated lead portions (e.g. supporting a respective stimulation portion or cuff electrode) may be omitted in some examples.

FIG. 14N is a diagram including a front view schematically representing an example arrangement 3460 including an example device for, and/or example method of, implantation of a stimulation device 3469. In some examples, the stimulation device 3469 may comprise at least some of substantially the same features and attributes as the stimulation devices, methods, etc. as previously described in association with at least FIG. 14L, except with the stimulation device 3469 including a stimulation lead array 3470 having bifurcated leads 3464, 3476 extending from the IPG 533 and distal lead portions 3466, 3468 of lead 3464 originating from a bifurcation point 3467 much closer to the target stimulation locations at the hypoglossal nerves 505R, 505L. As further shown in FIG. 14N, the stimulation device 3469 comprises a cuff electrode 6414A supported on a distal portion of lead 3476 for stimulating the ansa cervicalis-related nerve 515R. The stimulation device 3469 also comprises stimulation portions 6310A, 6310B (e.g. axial/linear electrode array) on respective distal lead portions 3466, 3468 for respectively stimulating the hypoglossal nerves 505R, 505L on opposite sides (RIGHT, LEFT) of the patient's neck.

With this framework in mind and as shown in FIG. 14N, one aspect of an example method of implantation may comprise forming the implant-access incision 609E, and implanting (via the incision 609E) the cuff electrode 6414A to be in stimulating relation to the ansa cervicalis-related neve 515R. Via the implant-access incision 690E, a tunnel (T13) may be formed to an implant location for IPG 533 and lead 3476 may be introduced and advanced via tunnel T13 to enable proximal portion 3474 of lead 3476 to be connected (electrically and mechanically) to an IPG 533.

In some examples, an additional implant-access incision may be formed near IPG 533 to facilitate implantation of the IPG 533, lead 3476, and/or lead 3464.

In another aspect of the method of implantation, in some examples, an implant-access incision 609D may be formed in close proximity to expected target stimulation locations of the hypoglossal nerve 505R on the same side (RIGHT) of the neck as the implant-access incision 609E. From the implant-access incision 609D, a tunnel T11 is formed to the target stimulation location of the left hypoglossal nerve 505L. Via implant-access incision 609D, distal lead portion 3466 (including stimulation portion 6310A) and distal lead portion 3468 (including stimulation portion 6310B) are introduced and advanced subcutaneously to the target stimulation locations of the respective right and left hypoglossal nerves 505R, 505L to yield the chronically implanted configuration of stimulation portions 6310A, 6310B shown in FIG. 14N.

In some examples, the implant-access incision 609D is in close proximity to the target stimulation location of the right hypoglossal nerve 505R such that little or no tunneling may be used to place distal lead portion 3466 in stimulating relation to the right hypoglossal nerve 505R.

Via implant-access incisions 609D and/or 609E, a tunnel T12 is formed to enable introduction and advancement of lead 3464 between implant-access incision 606D and implant-access incision 6009E. Previously formed tunnel T13 may be used to further subcutaneously advance the lead 3464 to, and for electrical and mechanical connection of proximal portion 3462 with, the IPG 533 in the pectoral region 532.

FIG. 14O is a diagram including a front view schematically representing an example arrangement 3500 including an example device for, and/or example method of, implantation of a stimulation device 3505. In some examples, the stimulation device 3505 may comprise at least some of substantially the same features and attributes as the stimulation devices, methods, etc., as previously described in association with at least FIGS. 14L-14N, except with the stimulation device 3500 comprising a single stimulation lead 3510 extending from the IPG 533 and bifurcated distal lead portions 3520, 3522 originating from a junction 3523 (i.e., a bifurcation point) which may be positioned in close proximity to the target stimulation locations at the hypoglossal nerves 505R, 505L. In some examples, a stimulation portion 6310B (e.g. axial/linear electrode array) is supported on (and by) distal lead portion 3522 for stimulating the left hypoglossal nerve 505L, while a cuff electrode 6411A is supported on and by distal lead portion 3520 for stimulating the right hypoglossal nerve 505R. As further shown in FIG. 14O, the stimulation device 3550 comprises a cuff electrode 6414A supported on a lead portion 3516 extending, via a junction 3517 (i.e. bifurcation point), from main portion 3514 of lead 3510 and configured for stimulating the ansa cervicalis-related nerve 515R.

With this framework in mind and as shown in FIG. 14O, one aspect of an example method of implantation may comprise forming the implant-access incision 609E, and implanting (via the incision 609E) the cuff electrode 6414A (supported on lead portion 3516) to be in stimulating relation to the ansa cervicalis-related neve 515R. Via the implant-access incision 690E, a tunnel (T13) may be formed to an implant location for IPG 533 and lead portion 3514 of lead 3510 may be introduced and advanced via tunnel T13 to enable proximal portion 3512 of lead 3510 to be connected (electrically and mechanically) to IPG 533, such as in pectoral region 532. In some examples, an additional implant-access incision may be formed near IPG 533 to facilitate implantation of the IPG 533, lead 3476, and/or lead 3464.

In another aspect of the method of implantation, in some examples, an implant-access incision 609D may be formed in close proximity to expected target stimulation locations of the hypoglossal nerve 505R on the same side (RIGHT) of the neck as the implant-access incision 609E. From the implant-access incision 609D, a tunnel T11 is formed to the target stimulation location of the left hypoglossal nerve 505L. Via implant-access incision 609D, distal lead portion 3520 (including cuff electrode 6411A) and distal lead portion 3522 (including stimulation portion 6310B) are introduced and advanced subcutaneously to the target stimulation locations of the respective right and left hypoglossal nerves 505R, 505L to yield the chronically implanted configuration of stimulation portions 6411A, 6310B shown in FIG. 14O.

In some examples, the implant-access incision 609D is in close proximity to the target stimulation location of the right hypoglossal nerve 505R such that little or no tunneling would be used to place distal lead portion 3520. Via this arrangement, sufficient space is available to implant cuff electrode 6411A on nerve 505R. However, as noted above, a non-cuff stimulation portion 6310B is provided for left hypoglossal nerve 505L so that the distal lead portion 3522 (including stimulation portion 6310B) may be delivered to the target stimulation location via tunneling (T11) without making an addition implant-access incision on the left side of the patient's neck.

Via implant-access incisions 609D, 609E, a tunnel T12 is formed to enable introduction and advancement of lead portion 3518 between implant-access incision 606D and implant-access incision 609E.

Via the example arrangement, a cuff electrode 6414A is secured relative to the ansa cervicalis-related nerve 515R and a cuff electrode 6411A is secured relative to the right hypoglossal nerve 505R via pertinent implant-access incisions 609E, 609D, while capability for bilateral stimulation of left and right hypoglossal nerves 505L, 505R is achieved via tunneling (T11) from the implant-access incision 609D. In this way, robust secure implantation of stimulation elements for multi-target therapy may be implemented with generally reduced surgical complexity.

In some examples, the IPG 533 may be omitted and instead a microstimulator (e.g. 6575 in FIG. 14M) may be implanted, via implant-access incision 609D, in close proximity to the target stimulation location of the right hypoglossal nerve 505R such as, but not limited to, the location of junction 3523 of lead 3550. Similarly, instead of implanting the IPG 533, a microstimulator (e.g. 6575 in FIG. 14M) may be implanted, via implant-access incision 609E, in close proximity to the target stimulation location of the ansa cervicalis-related nerve 515R such as, but not limited to, the location of junction 3517 of lead 3550. It will be understood, of course, in these examples that appropriate modifications would be made for connecting the various lead portions relative to the microstimulator. As noted elsewhere, in some examples the implanted microstimulator may be in wireless communication with at least some of the stimulation portions, cuff electrodes, etc.

FIG. 14P is a diagram including a front view schematically representing an example arrangement 3540 including an example device for, and/or example method of, implantation of a stimulation device 3545. In some examples, the stimulation device 3545 may comprise at least some of substantially the same features and attributes as the stimulation devices, methods, etc. as previously described in association with at least FIG. 14O, except with the stimulation device 3545 in FIG. 14P comprising a single distal portion 3519 of lead 3510 comprising a paddle electrode 3560 in FIG. 14P (to achieve bilateral hypoglossal nerve stimulation) instead of the bifurcated distal lead portions 3520, 3522 in FIG. 14O.

With this framework in mind and as shown in FIG. 14P, one aspect of an example method of implantation may comprise forming a tunnel T14 from the previously described implant-access incision 609D, and via the tunnel T14, introducing and advancing a paddle electrode 3560 subcutaneously to establish the paddle electrode 3560 in a position extending between, and overlapping with, both the target stimulation locations of the left and right hypoglossal nerves 505L, 505R as shown in FIG. 14P. In some examples, the paddle electrode 3560 may comprise a carrier (e.g. body) 3562 supporting a linear array 3566 of electrodes 3568 on a first portion 3564R of the carrier 3562 and supporting a linear array 3566 of electrodes 3568 on a second portion 3564L of the carrier 3562. By providing these linear arrays, one can be assured that at least some electrodes 3568 will become juxtaposed in stimulating relation to target stimulation locations of the respective left and right hypoglossal nerves 505L, 505R. As a related aspect, by establishing multiple electrodes 3568 in a juxtaposed position of being in potential stimulating relation to each respective nerve 505L, 505R, some example methods of stimulation therapy may include selective stimulation of different multiple fascicles within a nerve, nerve branch, etc. to optimize the intended therapeutic effect, manage fatigue, etc.

In some examples, the arrays 3566 on the left and right portions 3564L, 3564R of the paddle electrode 3560 may be sized so that they join to form a single array of electrodes 3568 extending along/across substantially the entire length of the carrier 3562 of the paddle electrode 3560.

In some examples, the array(s) 3566 of electrodes 3568 may comprise electrodes 3568 which are sized, shaped, and/or arranged to comprise a two dimensional array of electrodes 3568 having rows/columns of spaced apart electrodes 3568.

In some examples, the particular features of paddle electrode 3560 and associated methods of implantation, methods of therapy, etc. may comprise at least some of substantially the same features and attributes as described in PCT Application PCT/US21/17754, entitled STIMULATION ELECTRODE ASSEMBLIES, SYSTEMS AND METHODS FOR TREATING SLEEP DISORDERED BREATHING, filed Feb. 12, 2021, and filed on Feb. 1, 2022 as a U.S. Section 371 National Stage Application having Ser. No. 17/631,982, and published as US20220280788 on Sep. 8, 2022, all of which are hereby incorporated by reference in their entirety.

FIG. 14Q is a diagram including a front view schematically representing an example arrangement 3570 including an example device for, and/or example method of, implantation of a stimulation device 3575. In some examples, the stimulation device 3575 may comprise at least some of substantially the same features and attributes as the stimulation devices, methods, etc. as previously described in association with at least FIG. 14O, except with the stimulation device 3575 in FIG. 14Q comprising an axial stimulation portion 6310C for stimulation of the ansa cervicalis-related nerve 515R instead of the cuff electrode 6414A in FIG. 14O and with the axial stimulation portion 6310C in FIG. 14Q being supported by a different lead portion 3573, among other differences. However, similar to the example arrangement in FIG. 14), the stimulation device 3575 in FIG. 14Q comprises a stimulation portion 6310B (e.g. axial/linear electrode array) supported on and by distal lead portion 3577 for stimulating the left hypoglossal nerve 505L, while a cuff electrode 6411A is supported on and by distal lead portion 3578 for stimulating the right hypoglossal nerve 505R. As further shown in FIG. 14Q, the stimulation device 3550 comprises a lead portion 3573 extending from a main portion 3574 of lead 3571, via a junction 3576 (i.e. bifurcation point) of lead 3571 near implant-access incision 690D, to a nerve stimulation location of the ansa cervicalis-related nerve 515R to support the axial stimulation portion 6310C in stimulating relation to the ansa cervicalis-related nerve 515R.

With this framework in mind and as shown in FIG. 14Q, one aspect of an example method of implantation may comprise forming the implant-access incision 609D, and implanting (via the incision 609D) the cuff electrode 6411A and stimulation portion 6310B in a manner similar to that described in association with at least FIG. 14O. In addition, via the implant-access incision 690D, a tunnel T16 may be formed toward the ansa cervicalis-related nerve 515R and lead portion 3573 of lead 3571 may be introduced and advanced via tunnel T16 to extend toward a target stimulation location of ansa cervicalis-related nerve 515R to place stimulation portion 6310C (similar to 6310B) in stimulating relation to the ansa cervicalis-related nerve 515R.

As further shown in FIG. 14Q, a main lead portion 3574 of lead 3571 extends proximally from junction 3576. Via the implant-access incision 609D, a tunnel (T15) may be formed to an implant location for IPG 533, at which an additional implant-access incision 609C may be formed near IPG 533 to facilitate implantation of the IPG 533 and lead portion 3574. With this framework, in some examples, lead portion 3574 of lead 3571 may be introduced and advanced via tunnel T15 to enable proximal portion 3572 of lead 3571 to be connected (electrically and mechanically) to IPG 533, such as in pectoral region 532.

In some examples, the junction 3576 may be configured to permit releasable connectability of the various lead portions 3573, 3577, 3578 relative to main lead portion 3574 and/or relative to each other. Moreover, in some examples, junction 3576 may be configured to permit releasable connection of main lead portion 3574 relative to the junction 3576.

Among other aspects, in association with implant-access incision 609D, the example arrangement 3570 may reduce surgical complexity while providing a way to establish a cuff electrode 6411A at a right hypoglossal nerve 505R, an axial stimulation portion 6310B at a left hypoglossal nerve, and an axial stimulation portion 6310C at an ansa cervicalis-related nerve 515R.

FIG. 14R is a diagram including a front view schematically representing an example arrangement 3580 including an example device for, and/or example method of, implantation of a stimulation device 3582. In some examples, the stimulation device 3582 may comprise at least some of substantially the same features and attributes as the stimulation devices, methods, etc. as previously described in association with at least FIG. 14Q, except with the stimulation device 3580 in FIG. 14R including a microstimulator 6575 instead of an IPG 533 in FIG. 14Q with the main lead portion 3574 being omitted in addition to IPG 533.

Accordingly, with further reference to FIG. 14R in comparison to FIG. 14Q, the stimulation device 3582 in FIG. 14R comprises the same distal lead portions 3578, 3577 and their respective stimulation elements (e.g. cuff electrode 6411A, stimulation portion 6310B) for delivering bilateral stimulation to the respective right and left hypoglossal nerves 505R, 505L. Moreover, like the stimulation device in FIG. 14Q, the stimulation device 3582 in FIG. 14R also retains the same lead portion 3573 and axial stimulation portion 6310C in stimulating relation to the ansa cervicalis-related nerve 515R.

As further shown in FIG. 14R, the microstimulator 6575 is directly connected to the respective lead portions 3578, 3577, 3573 with distal lead portions 3578, 3577 having a bifurcation point (formed by junction 3585) at or near a housing of the microstimulator 6575. In some examples, the lead portion 3573 (of stimulation portion 6310C) may extend directly from the microstimulator 6575 as shown in FIG. 14R or in some examples, may extend from the same junction 3585 as the distal lead portions 3578, 3577. As noted elsewhere in relation to some examples of the present disclosure, the microstimulator 6575 may comprise stimulation/control circuitry, a power source (e.g. rechargeable), and may be in communication with an external power recharging device, element, and the like.

Among other aspects, the example arrangement 3580 may comprise an example method of implantation which significantly reduces surgical complexity, reduces the time for performing the implantation, increases patient comfort, etc. In some such examples, these features may be achieved, at least in part, because of the single (i.e. sole) implant-access incision 609D made at or near the target stimulation location of the right hypoglossal nerve 505R, which simultaneously enables convenient implantation of the cuff electrode 6411A on the right side of the patient's neck, implantation of the axial stimulation portion 6310B on the left side of the patient's neck, implantation of the axial stimulation portion 6310C on the right side of the patient's neck, and implantation of the microstimulator 6575 to support the respective cuff electrodes and stimulation portions of stimulation device 3582. In a manner similar to that described in association with FIG. 14Q, the junction 3585 may permit various forms of permanent connection or releasable connection among the various lead portions 3578, 3577, 3573 relative to the microstimulator 6575 and/or relative to each other. This aspect also may enhance reduced surgical complexity, shortened procedure time, etc.

Figure 15A:
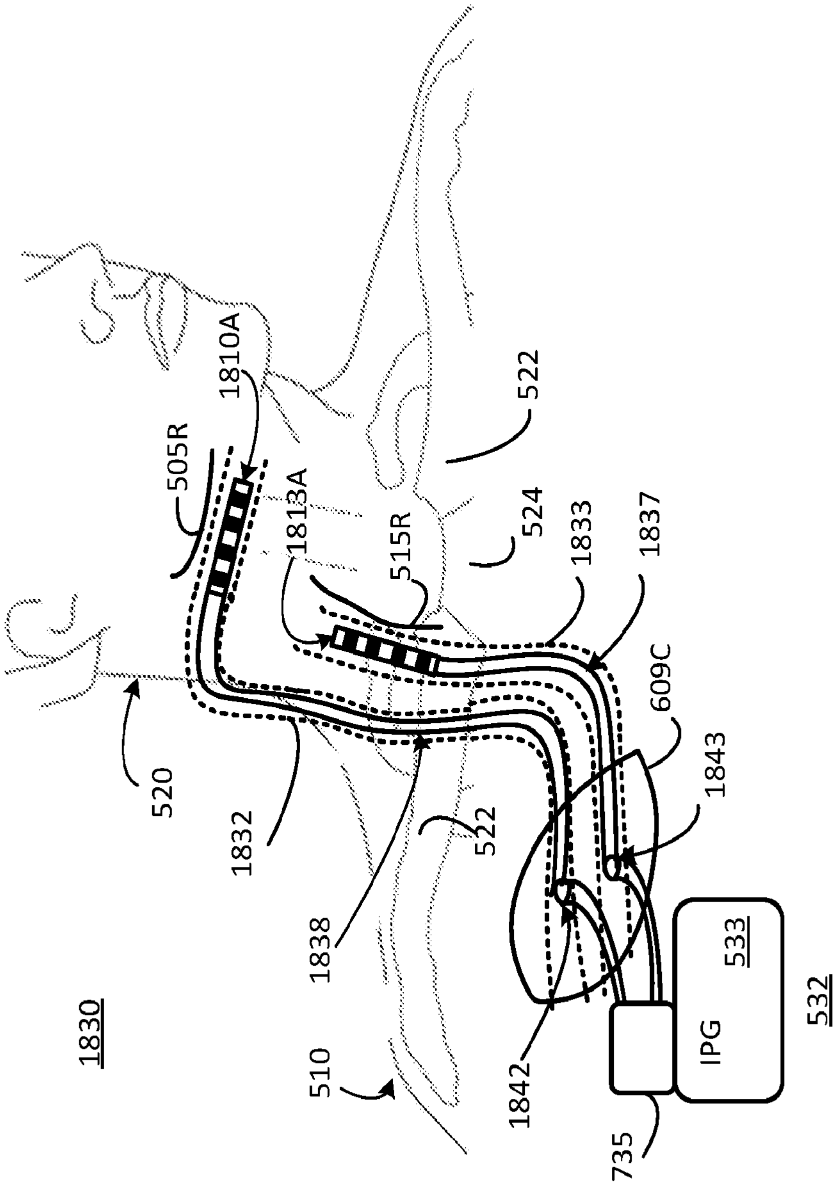
FIGS. 15A-15C are diagrams schematically representing an example device and/or method for implanting stimulation elements via intravascular access and delivery.

FIG. 15A is a diagram including a front view schematically representing an example arrangement 1830 relative to a patient's body 510, including an example device and/or example method for implantation of a stimulation element 1810A in stimulating relation to a hypoglossal nerve 505R and a stimulation element 1813A in stimulating relation to an ansa cervicalis-related nerve 515R. In some examples, the example arrangement 1850 may comprise at least some of substantially the same features and attributes as, comprise an example implementation of, and/or be usable with the example arrangements described in association with at least some of FIGS. 1-13.

In particular, as shown in FIG. 15A in some examples the arrangement 1830 may be implanted in a single implantation procedure via a single implant access-incision 609C in a manner similar to that described for example arrangement 1800 in FIG. 14A. However, instead of tunneling as in the example of FIG. 14A, in the example of FIG. 15A a stimulation lead 1838 is delivered via access point 1842, and implanted within, the vasculature to position the stimulation element 1810A within vein 1832 shown in dashed lines (to be in stimulating relation to the hypoglossal nerve 505R).

Similarly, a stimulation lead 1837 is delivered via access point 1843, and implanted within, the vasculature to positon the stimulation element 1813A within vein 1833 (shown in dashed lines) to be in stimulating relation to the ansa cervicalis-related nerve 515R. As further described later in association with at least FIGS. 32A-32B, in some examples the applicable vasculature 1855 may comprise veins such as the anterior jugular vein, inferior thyroid vein, superior thyroid vein, external jugular vein, etc.

In some examples, both stimulation elements 1810A, 1813A may comprise an axial array of electrodes 716, which facilitates linear positioning and adjustment to ensure a desired co-extensive location of the electrodes 716 relative to a desired portion of the respective nerves to be stimulated. In some examples, the respective stimulation elements 1810A, 1813A may comprise one of the electrode configurations, such as one of the stimulation elements as later described in association with at least FIGS. 25-26 and 29-30B, which may comprise anchor elements in some examples. In addition, one example implementation of the stimulation leads 1838 and/or 1837 is described in association with FIG. 15C.

As further shown in FIG. 15A, IPG 533 may also implanted subcutaneously via the implant access-incision 609C and electrically connected to a proximal portion of the respective stimulation leads 1838, 1837.

Figure 15B:
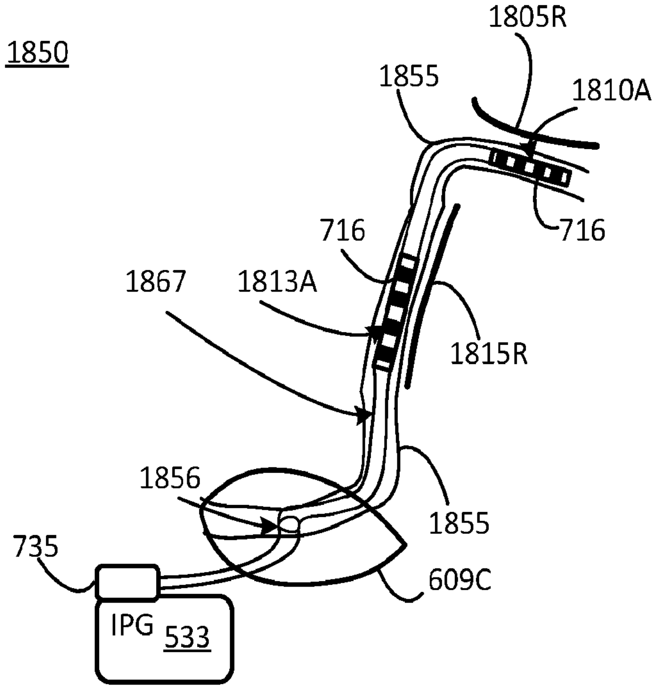

FIG. 15B is a diagram schematically representing an example arrangement 1850, which may comprise at least some of substantially the same features and attributes as the example arrangement 1800 in FIG. 15A, except with the two stimulation elements 1810A, 1813A are arranged on a single stimulation lead 1867 instead of separate stimulation leads 1838, 1837 as in FIG. 15A. As further shown in FIG. 15B, via single implant access-incision 609C, a portion of the stimulation lead 1867 is inserted into the vasculature 1855 at access point 1856 and advanced through the vasculature 1855 until the stimulation element 1810A at the distal portion of the stimulation lead 1867 is positioned adjacent a first target nerve 505R. In some examples, the first target nerve 1805R may comprise a hypoglossal nerve (e.g. 505R), while in some examples the first target nerve 1805R may comprise some portion of the ansa cervicalis-related nerve 315 (FIG. 2) or yet another nerve. Upon such positioning, the second stimulation element 1813A, which is located more proximally on the same stimulation lead 1867 will become positioned within the vasculature 1855 adjacent to, and in stimulating relation to, a second nerve target 1815R. In some examples, the second target nerve may comprise some portion of the ansa-cervicalis related nerve 515R or other nerve.

Figure 15C:
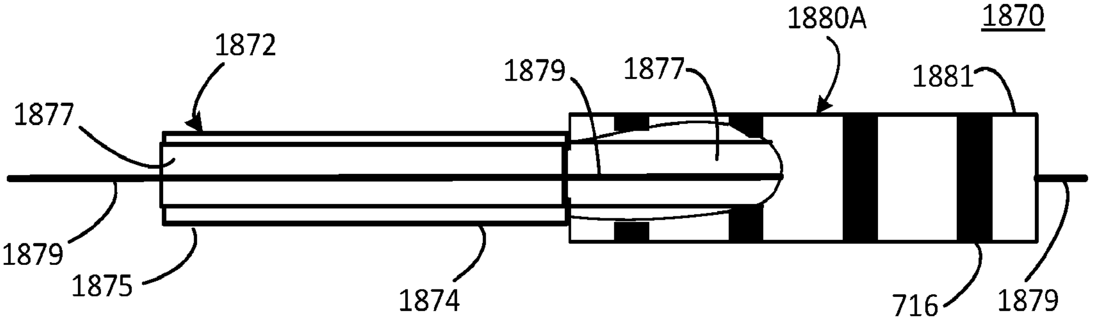

FIG. 15C is a side view schematically representing an example arrangement 1870 including example stimulation lead 1872, which may comprise one example implementation of the stimulation leads 1837, 1838 in FIG. 15A or of the stimulation lead 1867 in FIG. 15B. As shown in FIG. 15C, the stimulation lead 1872 comprises a stimulation element 1880A including an array (e.g. axial) of electrodes 716 and supported by a distal portion 1874 of a lead body 1875, with a proximal portion (not shown) of the lead body 1875 adapted for electrical and mechanical connection to IPG 533 (e.g. via a header 735).

As further shown in FIG. 15C, the lead body 1875 defines an interior lumen 1877, which extends through a length of the lead body 1875 and of the stimulation element 1880A. The lumen 1877 is sized and shaped to enable the stimulation lead body 1875 and stimulation element 1880A to be slidably advanced and maneuverable over a guide wire 1879, or stylet or other guiding element. Via this arrangement, in order to implant the stimulation lead 1872 in a manner shown like that in FIG. 15A or 15B, the guide wire 1879 may first be inserted into, and advanced through, the vasculature (e.g. 1832, 1833 in FIG. 15A) until a distal portion of the guide wire 1879 is positioned just beyond the most distal target stimulation location, such as the hypoglossal nerve 505R in FIG. 15A. Next, an open end of the lumen 1877 at the distal portion 1881 of the stimulation lead 1872 (including the stimulation element 1880A) is slidably mounted onto a proximal end of the guide wire 1879 in the region of the implant access-incision 609C (e.g. FIG. 15A, 15B). The stimulation lead 1872 is then slidably advanced through the vasculature (e.g. 1832, 1833 in FIG. 15A or 1855 in FIG. 15B) until the distal portion 1881 of the stimulation lead 1872 is positioned such that the stimulation element 1880A (e.g. an example implementation of element 1810A in FIG. 15A) is in stimulating relation to the target nerve, such as hypoglossal nerve 505R for stimulation lead 1838 in FIG. 15A. It will be understood that the example arrangement 1870 is likewise applicable to the stimulation lead 1837 in FIG. 15A and/or stimulation lead 1867 in FIG. 15B.

Moreover, in some examples more than one transvascular (e.g. transvenous) stimulation lead and/or more than one branches of such transvascular stimulation leads may be implanted to provide stimulation of multiple stimulation targets of the ansa cervicalis-related nerve and/or other upper airway patency-related tissues.

FIG. 16 is a diagram including a side view schematically representing an example arrangement 2000 including example devices and/or example methods for stimulating a portion of the ansa cervicalis-related nerve 316 (FIG. 2) and/or a portion of the hypoglossal nerve 305. In one example implementation, an example stimulation arrangement 2101 is deployed as further described in association with at least FIGS. 17-19. In one example implementation, a stimulation arrangement 2401 includes separate stimulation elements 2410, 2420 as further described in association with at least FIG. 20.

FIG. 17 is a diagram including a side view schematically representing an example arrangement 2100, which may comprise one example implementation of the example stimulation element 2101 in FIG. 16. In some examples, the example arrangement 2100 in FIG. 17 comprises a stimulation element 2109 in stimulating relation to both a hypoglossal nerve 305 and portion 317 of the ansa cervicalis-related nerve 316 to implement an example method for treating sleep disordered breathing, such as via increasing and/or maintaining upper airway patency. In some examples, the example arrangement 2100 may comprise at least some of substantially the same features and attributes as, comprise an example implementation of, and/or be usable with the example arrangements described in association with at least some of FIGS. 1-16.

As shown in FIG. 17, the stimulation element 2101 represented in FIG. 16 may comprise a paddle electrode 2109 including an array 2125 of spaced apart electrodes 2126, which are disposed on body 2120. While not shown for illustrative clarity, it will be understood that in some examples the paddle electrode 2109 may be supported on a distal portion of a stimulation lead or in some examples may form part of a microstimulator which omits a stimulation lead of the type connected to an IPG (e.g. 533). With this in mind, one microstimulator which may comprise one example implementation of stimulation element 2101 may comprise at least some of substantially the same features and attributes as the microstimulator 1413A, as previously described in association with at least FIG. 11B.

With further reference to the paddle electrode 2109, the body 2120 and array 2125 of electrodes 2126 are sized and shaped such that when the paddle electrode 2109 is juxtaposed with a pair of nerves, one or both of the respective nerves may be stimulated as desired. In some such examples, the nerves may comprise a hypoglossal nerve 305 and portion 317 of an ansa cervicalis-related nerve 316. In particular, in the example implementation shown in FIG. 17, the stimulation element 2109 is positioned proximal to a junction 311 (FIG. 16) at which superior root 325 of the ansa cervicalis-related nerve 315 diverges from a proximal portion 307 of the hypoglossal nerve 305. It will be understood that in this context, the term "proximal portion" of the hypoglossal nerve 305 is with specific regard to the junction 311.

Via this example arrangement 2100 in FIG. 17, an example method of treating sleep disordered breathing may comprise stimulating one or both of the respective hypoglossal nerve 305 and the ansa cervicalis-related nerve 316 to increase and/or maintain upper airway patency. In one aspect, this arrangement may comprise use of selective steering of the stimulation signals to capture particular fascicles (e.g. motor) within each respective bundles of nerves 305, 316 at least because, at this particular location, both the hypoglossal nerve 305 and portion 329A of the ansa cervicalis-related nerve 316 include some non-targeted fibers (e.g. innervating retractor muscles of the tongue for the HGN) among the targeted nerve fibers, such as those nerve fibers (of the HGN) innervating protrusor muscles of the tongue and/or those nerve fibers (of the ACN) innervating the sternothyroid muscles and/or sternohyoid muscles (as an example).

At the particular stimulation location in the example arrangement 2000 in FIG. 16 (including example arrangement 2101 or 2401), stimulation is to be applied to a main trunk of the hypoglossal nerve 305 and portion 329A of the ansa cervicalis-related nerve 316. In some examples, this stimulation location may provide sufficient space and an anatomical environment to enable placement of a paddle electrode (FIG. 17) or cuff electrode(s) (FIGS. 18-20), such as but not limited to a single implant-access incision adjacent the hypoglossal nerve 305 (e.g. main trunk). Via such arrangements, a single electrode arrangement as in FIGS. 17, 18-19, and/or 20 is able to provide stimulation to both the hypoglossal nerve 305 and the ansa cervicalis-related nerve 316 (via portion 329A). Moreover, this stimulation location may enable use of a larger size (e.g. diameter) cuff electrodes or larger paddle electrodes, which are easier to handle and may provide for more robust chronic implantation than if such cuff electrodes or paddle electrodes are implanted in relation to small diameter nerves.

Figure 18:
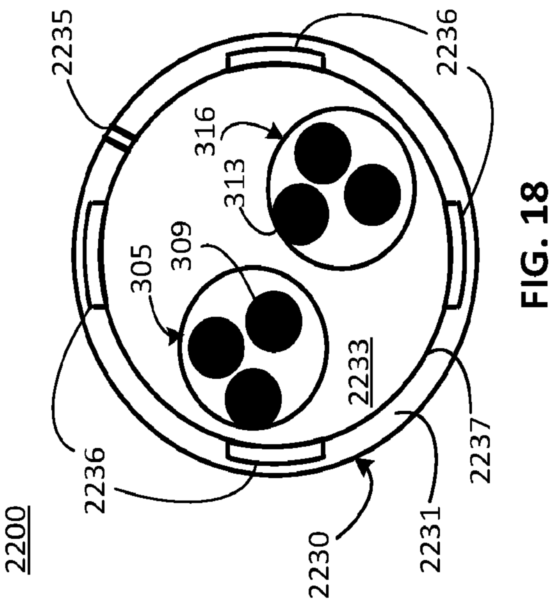
FIGS. 18, 20 are diagrams including a sectional view schematically representing example cuff electrodes.

FIG. 18 is a diagram including a sectional view schematically representing an example arrangement 2200 including an example device and/or example method of providing stimulation to two different types of nerves for increasing and/or maintaining upper airway patency. In some examples, the example arrangement 2200 comprises one example implementation of the example arrangement 2101 in FIG. 16 to provide stimulation to one of, or both, the hypoglossal nerve 305 and the ansa cervicalis-related nerve 316 (FIG. 16). As shown in FIG. 18, in some examples the example arrangement 2200 may comprise cuff electrode 2230, which comprises a cylindrically shaped body 2231 defining a lumen 2233 to at least partially enclose or encircle the respective nerves 305, 316. As shown in FIG. 18, the body 2231 may comprise a slit or re-closable opening 2235 to permit placing the cuff electrode 2230 about the nerve(s) 305, 315 and re-closure of the wall of the body 2231 about the nerves. While not shown for illustrative simplicity, in some examples the cuff electrode 2230 may comprise overlapping flange members to enhance releasably securing the cuff electrode about the nerves 305, 316. Moreover, in some examples, the cuff electrode 2230 comprises an array of circumferentially spaced apart electrodes 2236 exposed on an interior surface 2237 to be in stimulating relation to the respective nerves 305, 316. Via various combinations of the electrodes 2236 and selectable parameters (e.g. amplitude, pulse width, current, frequency, duty cycle, sequence of activation, etc.) of stimulation signal, various fascicles 309 within the hypoglossal nerve 305 and/or various fascicles 313 within the ansa cervicalis-related nerve 316 may be targeted to effect desired stimulation of at least motor fibers to increase and/or maintain upper airway patency. In some such examples, the various nerves 305, 316 (and their various fascicles) may be stimulated according to at least some of the stimulation patterns as described in association with at least FIGS. 33A-37D.

Figure 19:
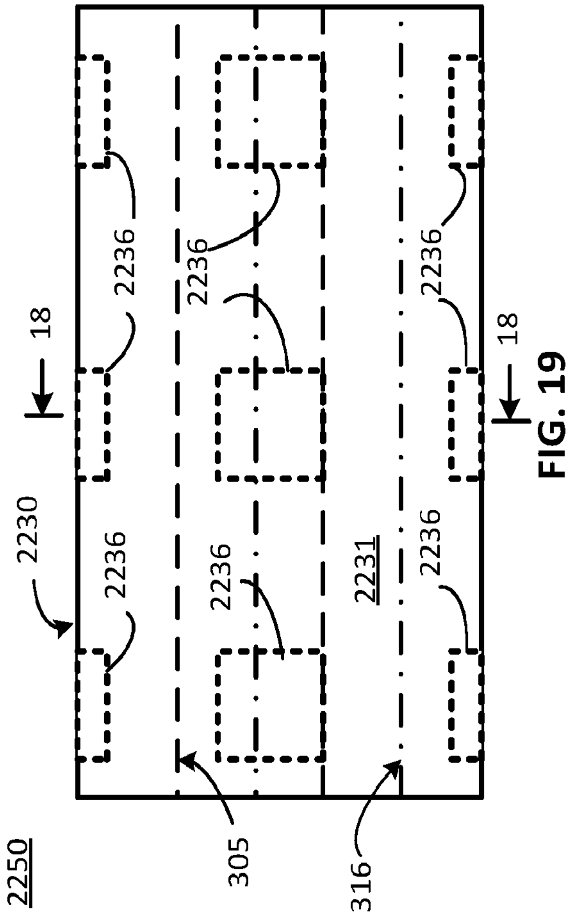
FIG. 19 is a diagram including a side view schematically representing the example cuff electrodes of FIG. 18.

FIG. 19 is a side view schematically representing the cuff electrode 2230 in FIG. 18, which further illustrates various features and attributes of the cuff electrode 2230. For instance, FIG. 19 illustrates one example configuration of the electrodes 2236 when arranged in an array in which the electrodes 2236 extend in a spaced apart manner axially along a length of the body 2231 of cuff electrode 2230 and extend in a spaced apart manner circumferentially about the interior surface 2237 (FIG. 18) of the body 2231 of cuff electrode 2230.

Figure 20:
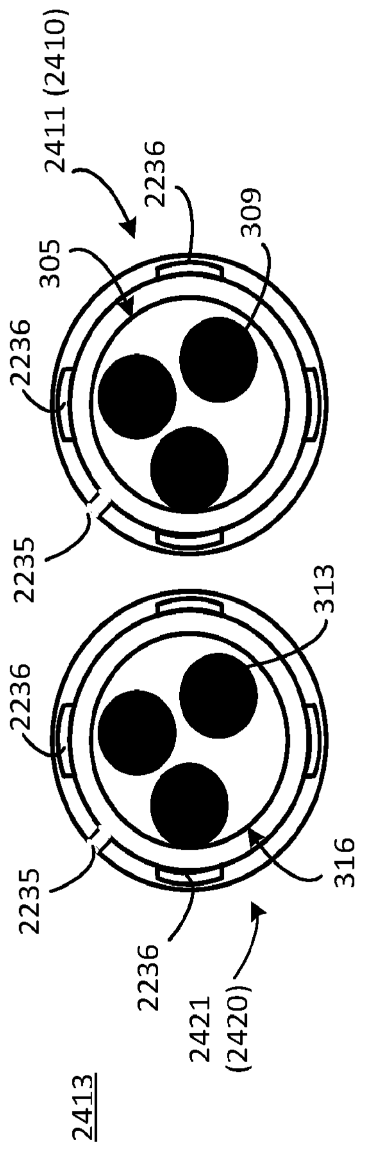

FIG. 20 is a sectional view schematically representing an example arrangement 2413 which comprises one example implementation of the example arrangement 2401 in FIG. 16. As shown in FIG. 20, in some examples the example arrangement 2413 comprises a first cuff electrode 2411, which may comprise one example implementation of stimulation element 2410 in FIG. 16 and may comprise a second cuff electrode 2421, which may comprise one example implementation of stimulation element 2420 in FIG. 16. As shown in FIG. 20, each cuff electrode 2411, 2421 comprises at least some of substantially the same features and attributes as the cuff electrode 2230 in FIG. 18, except being sized to at least partially encircle and enclose just one nerve, such as nerves 305, 316 respectively instead of two nerves as in FIG. 18. Accordingly, the features of cuff electrodes 2411, 2421 are identified via similar reference elements as in FIG. 18.

Via this example arrangement 2411, stimulation of each nerve 305, 316 is applied via separate cuff electrodes 2411, 2421 in a side-by-side arrangement, which may simplify at least some aspects of selectively stimulating certain fascicles within each respective nerve 305, 316 relating to controlling upper airway patency and related physiologic functions.

In some example implementations, the cuff electrodes 2230, 2411, and/or 2421 may comprise at least some of substantially the same features and attributes as described in Bonde et al, SELF EXPANDING ELECTRODE CUFF, issued as U.S. Pat. No. 9,227,053 on Jan. 5, 2016, in Bonde et al, SELF EXPANDING ELECTRODE CUFF, issued as U.S. Pat. No. 8,340,785 on Dec. 25, 2012, in Johnson et al, NERVE CUFF, issued as U.S. Pat. No. 8,934,992 on Jan. 13, 2015, and in Rondoni et al, CUFF ELECTRODE, published as WO 2019/032890, on Feb. 14, 2019, and later published as U.S. 2020/0230412 on Jul. 23, 2020, and which are all hereby incorporated by reference in their entirety.

In some examples, the cuff electrodes of FIGS. 18-20 may be employed in other example arrangements of the present disclosure and are not limited to use solely in the anatomical and physiologic context presented in relation to FIGS. 18-20. Accordingly, in any example of the present disclosure calling for a stimulation element in which a cuff electrode may be a suitable example implementation, such stimulation elements may comprise one of the cuff electrodes in FIGS. 18-20 or in later described FIGS. 26A-26B.

In some examples, the stimulation location for example stimulation electrode arrangements 2101, 2401 in FIG. 16 may correspond to the stimulation location “A” in the example arrangements later described in association with at least FIG. 32C, in which stimulation at location “A” may be implemented via an intravascular approach (e.g. transvenous) through the interior jugular vein 4250, in some examples.

Figure 21:
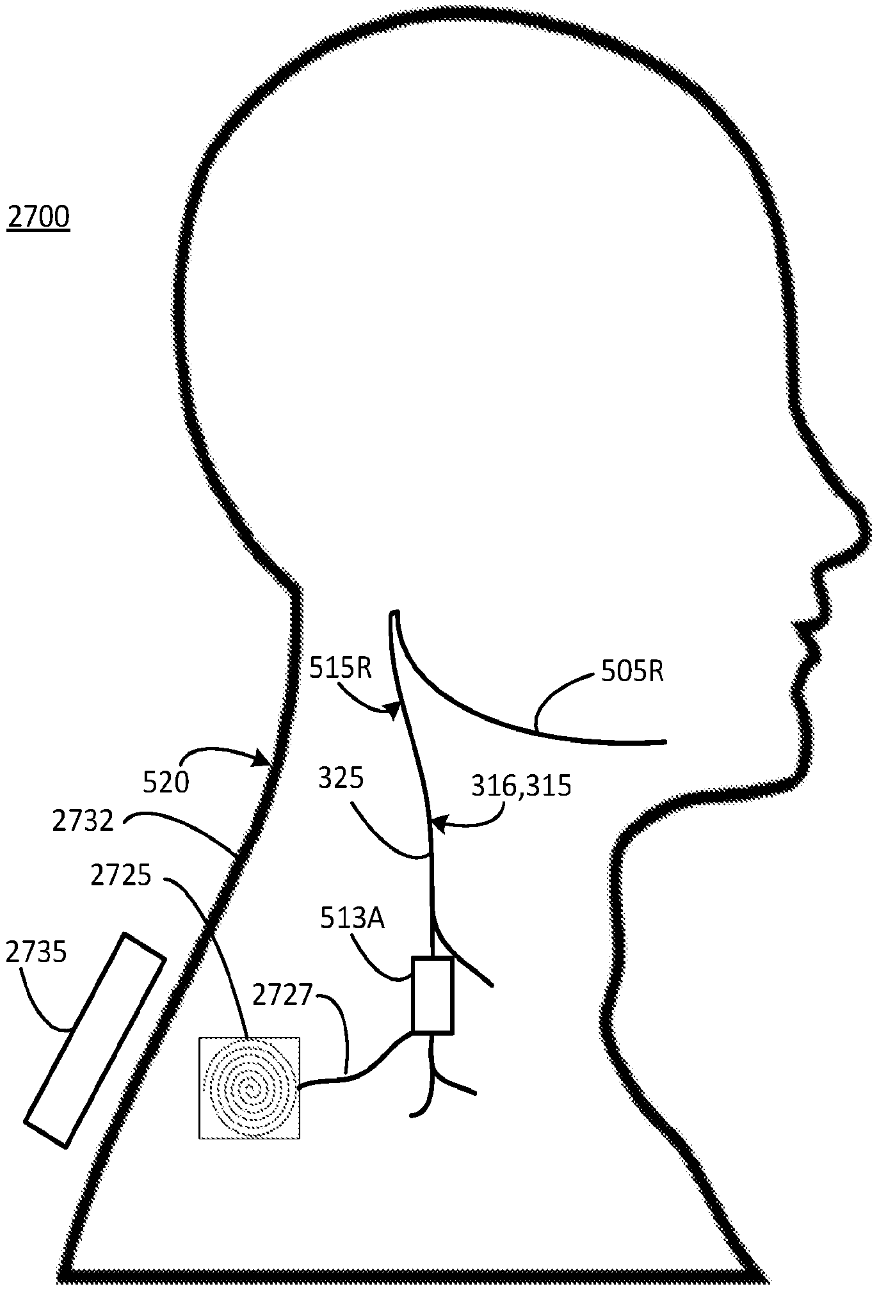
FIG. 21 is a diagram including a side view schematically representing an example device and/or example method for implanting a microstimulator within a neck region, along with wireless power delivery to an external power element.

FIG. 21 is a side view schematically representing an example arrangement 2700 including a stimulation element 513A and a passive receiver 2725 to obtain and provide power and control signals to the stimulation element 513A. In this arrangement, the stimulation element 513A is a standalone element without a stimulation lead (such as connected to an IPG 533) and is positioned in stimulating relation to the ansa cervicalis-related nerve 316. However, in other respects, the stimulation element 513A may comprise at least some of substantially the same features and attributes as stimulation elements (and related arrangements) described in association with various example stimulation elements described throughout the present disclosure. It will be further understood that the same example arrangement also may be implemented relative to the hypoglossal nerve 505R in addition to, or instead of, being implemented relative to the ansa cervicalis-related nerve 316.

As further shown in FIG. 21, the passive receiver 2725 may be connected (e.g. via wires 2727) to the stimulation element 513A and positioned adjacent an external surface 2732 of the patient’s body, such as in the head-and-neck region 520. In some such examples, the example arrangement 2700 may comprise an externally located power-control element 2735 to provide power and/or control signals to the stimulation element 513A, via wireless communication with the passive receiver 2725. In some examples, whether also embodied as a sensing element or not so embodied, the power-control element 2735 can receive sensed data from the stimulation element 513A via the passive receiver 2725.

FIG. 22A is a diagram including a side view schematically representing an example arrangement 2900 including a stimulation element 513A in stimulating relation to the ansa cervicalis-related nerve 316 (e.g. at superior root 325) and a supporting stimulation lead 2917 anchored relative to non-nerve structure 2929 (e.g. tissue). In some examples, the stimulation element 513A and/or stimulation lead 2917 may comprise at least some of substantially the same features and attributes as stimulation elements (and related arrangements) described in association with various examples described in association with at least FIGS. 1-21.

It will be understood that the particular location of the stimulation element 513A in FIG. 22A is merely representative of many different positions of the ansa cervicalis-related nerve 316 at which the stimulation element(s) 513A may be located.

As shown in FIG. 22A, the stimulation lead 2917 includes a distal portion 2919 which may be formed into a strain relief loop or portion extending between the stimulation element 513A and the anchor element 2927, with the anchor element 2927 secured to the non-nerve structure 2929 in order to secure the stimulation lead 2917 thereto. A lead body 2921 of the stimulation lead 2917 extends proximally from the anchor element 2927.

As further shown in FIG. 22B, box 2950 schematically represents at least some of the non-nerve structures 2929 (in FIG. 22A) to which the anchor element 2927 may anchor a portion of the stimulation lead 2917. In some examples, such non-nerve structures may comprise an omohyoid tendon, a hyoid bone, a clavicle, a sternum (including the manubrium), a trachea, a digastric tendon, and/or other non-nerve structures. Moreover, such non-nerve structures may be used for anchoring a stimulation lead, port interface (e.g. FIGS. 5A, 5B, 7A, and the like), stimulation element, etc. relative to an upper airway patency-related tissue, whether in relation to the example of FIG. 22A, 23 and/or other examples throughout the present disclosure.

Figure 23:
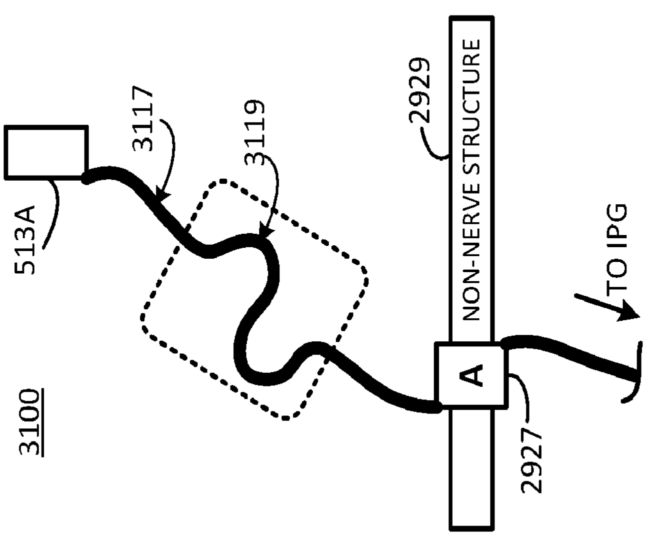
FIGS. 22A-23 are diagrams schematically representing patient anatomy and an example device and/or example method for stimulating to an ansa cervicalis-related nerve, including anchor elements.

FIG. 23 is a diagram including a side view schematically representing an example arrangement 3100 which comprises at least some of substantially the same features and attributes as the example arrangement 2900 in FIG. 22A-22B, except with a distal portion of a stimulation lead 3117 including a pre-formed strain relief segment 3119 between the anchor element 2927 and the stimulation element 513A. The pre-formed strain relief segment 3119, shown within the dashed lines, may comprise any flexible, resilient shape (e.g. sigmoid, other) which helps to relieve strain on the stimulation element 513A in its fixed position relative to a nerve or muscle to be stimulated, such as strain occurring during movement of the neck and/or other body movements.

It will be understood that the anchoring arrangements (e.g. anchor element, non-nerve structures, strain relief segments, etc.) described in association with at least FIGS. 22A-23 may be implemented in various forms with any of the stimulation elements, stimulation leads, port interfaces, sensing leads, etc. as described throughout the various examples of the present disclosure.

FIG. 24A-26B provide a series of illustrations of various example stimulation elements. In some examples, the various stimulation elements described in FIGS. 24-26B may comprise at least some of substantially the same features and attributes as, may be example implementations of, and/or may be consistent with the stimulation elements (and related arrangements) described in association with various example stimulation elements described throughout the present disclosure.

Figure 24A:
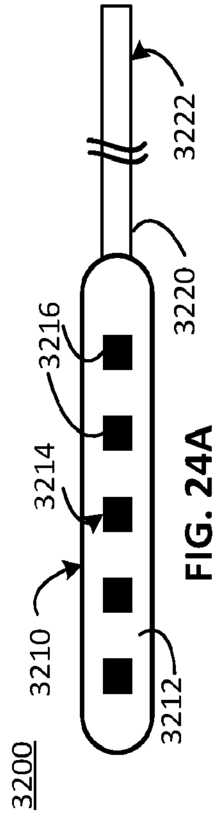
FIGS. 24A-25B are diagrams including top and side views schematically representing example stimulation elements including a linear electrode array.

FIG. 24A is top plan view schematically representing example stimulation element 3200. As shown in FIG. 24A, example stimulation element 3200 comprises a paddle electrode 3210 comprising a paddle-style body 3212 on which a linear array 3214 of electrodes 3216 are located. In some examples, the array 3214 may comprise a two-dimension array of electrodes 3216. The paddle electrode 3210 is supported by, and extends from, a distal portion 3220 of a stimulation lead 3222.

Figure 24B:
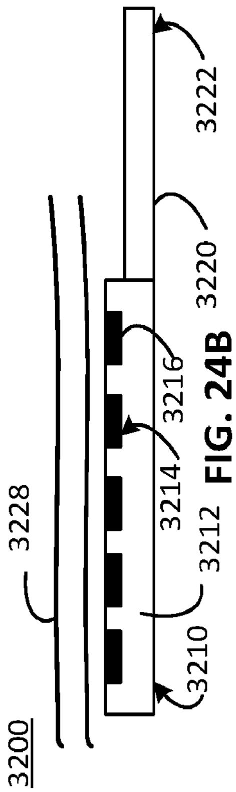

As further shown in the side view of FIG. 24B, the paddle electrode 3210 may be positioned in stimulating relation to a nerve 3228, such as a hypoglossal nerve (e.g. 505R) or ansa cervicalis-related nerve (e.g. 513R) or other nerve related to increasing and/or maintaining upper airway patency. The paddle electrode 3210 may be secured in pressing contact with the nerve 3228 or may be secured in close proximity to, but spaced apart from, the nerve 3228.

Figure 25A:
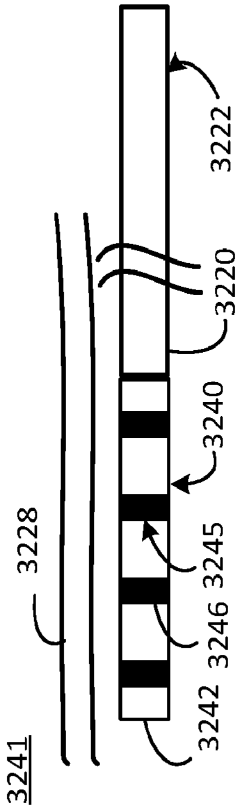

FIG. 25A is a side plan view schematically representing an example arrangement 3241 in which stimulation element 3240 is in stimulating relation to a nerve 3228 (like in FIG. 24B). In some examples, the stimulation element 3240 may comprise at least some of substantially the same features and attributes as stimulation element 3210, except with electrodes 3216 being arranged in a linear array 3245 of spaced apart ring electrodes 3246.

Figure 25B:
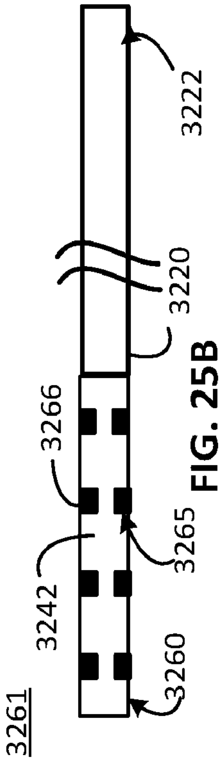

FIG. 25B is a side plan view schematically representing an example arrangement 3261 in which stimulation element 3260 is adapted to be in stimulating relation to a nerve (like nerve 3228 in FIGS. 24B, 25A). In some examples, the stimulation element 3260 may comprise at least some of substantially the same features and attributes as stimulation element 3240 in FIG. 25A, except comprising a linear array 3265 of spaced apart split ring electrodes 3266 instead of ring electrodes 3246 in FIG. 25A and with body 3242 comprising a generally cylindrical shape.

Figure 26A:
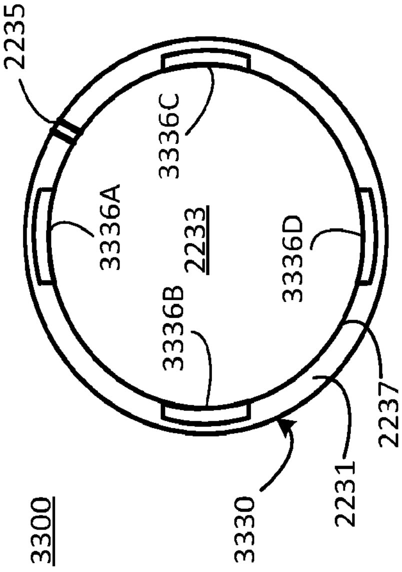
FIG. 26A is a sectional view as taken along lines 26B-26B of FIG. 26B of an example cuff electrode.
Figure 26B:
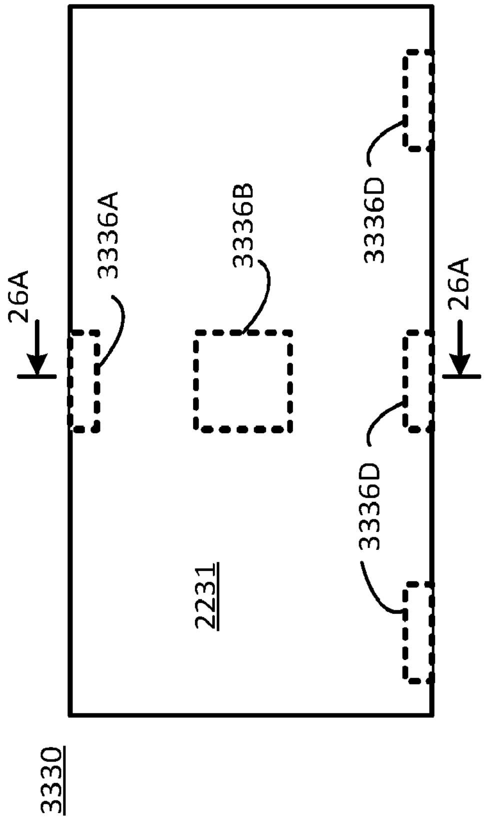
FIG. 26B is a side view schematically representing an example cuff electrode.

FIG. 26A is a side view, and FIG. 26 B is a side view, schematically representing an example arrangement 3300 including a cuff electrode 3330. In some examples, the cuff electrode 3330 in FIGS. 26A-26B may comprise at least some of substantially the same features and attributes as the cuff electrode 2230 in FIGS. 18-19, except with the cuff electrode 3330 comprising fewer electrodes as shown in FIGS. 26A, 26B. In particular, cuff electrode 3330 comprises a bottom row of axially spaced apart electrodes 3336D and a middle row of circumferentially spaced apart electrodes 3336A, 3336B, 3336D, 3336C. By employing various combinations of the respective electrodes 3336A, 3336B, 3336C, 3336D, as well as variations in the stimulation signal as previously described, this electrode configuration may be used to provide selective stimulation and/or stimulation steering of a stimulation signal relative to different fascicles, nerve fibers, etc. within a nerve about which the cuff electrode 3310 is secured.

FIG. 27A-31G are a series of diagrams of various example arrangements of stimulation elements, each of which are equipped with some form of anchoring elements to provide example devices and/or example methods for anchoring a stimulation element within a patient's body relative to a non-nerve tissue. Via such anchoring, the stimulation element may be secured in stimulating relation to a target nerve associated with controlling upper airway patency. In some examples, the various stimulation elements described in FIGS. 27A-31G may comprise at least some of substantially the same features and attributes as, may be example implementations of, and/or may be consistent with the stimulation elements (and related arrangements) described in association with various example stimulation elements described throughout the present disclosure. Moreover, the various anchor elements described in association with FIGS. 27A-31G may be used with at least some of the various previously described (and some later described) example stimulation elements, as appropriate to the context in which they are being implanted.

Figure 27A:
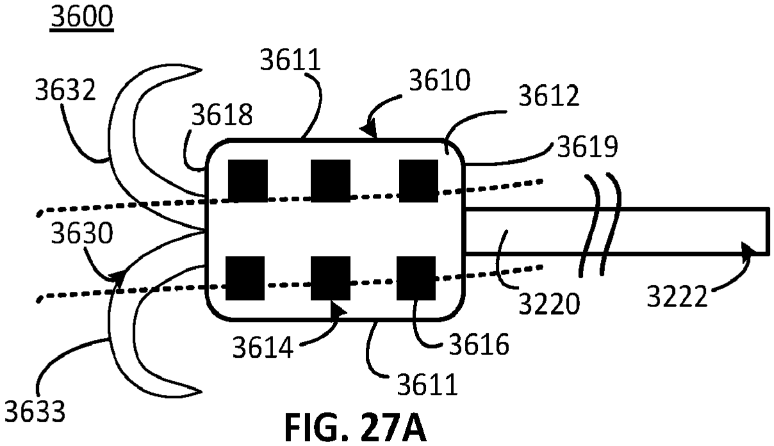
FIGS. 27A-28 are diagrams including top views schematically representing an example paddle electrode including anchor elements.

FIG. 27A is a top plan view schematically representing an example arrangement 3600 including a paddle electrode 3610 supported on a distal portion 3220 of a stimulation lead 3222. The paddle electrode 3610 comprises an array 3614 of electrodes 3616 disposed on a body 3612, with a proximal portion 3619 connected to the stimulation lead 3222. A distal portion 3618 of the paddle electrode 3610 supports an anchor element 3630 comprising a pair of curved, pointed fingers 3632, 3633 which diverge from each other and outwardly relative to sides 3611 of the body 3612 of the paddle electrode 3610. In some examples, the curved fingers 3632, 3633 are formed of a resilient, flexible material. As shown in FIG. 27A, the curved pointed fingers 3632, 3633 are configured to engage non-nerve tissues adjacent to a position at which the paddle electrode 3610 would be positioned in stimulating relation to a nerve (shown in dashed lines), thereby anchoring the paddle electrode 3610 in a desired, therapeutic position.

Figure 27B:
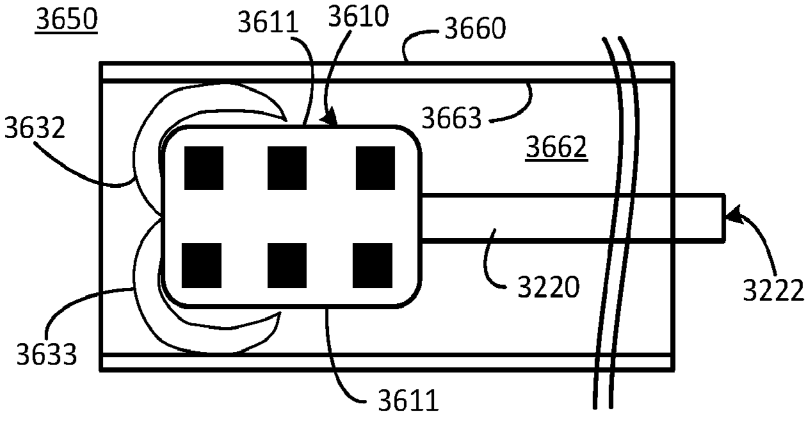

As further shown in FIG. 27B, in some example arrangements 3650, an introducer 3660 (or guide catheter) defining an internal lumen 3662 is provided to facilitate advancement and positioning of the paddle electrode 3610 with curved fingers 3632, 3633. The lumen 3662 of the introducer 3660 may maintain the curved fingers 3632, 3633 in a folded position against opposite sides 3611 of the paddle electrode 3610 until the paddle electrode 3610 is in its desired position. Then, the introducer 3660 may be slidably withdrawn to permit the curved fingers 3632, 3633 to expand outwardly into the deployment position and deployment shape shown in FIG. 27A, thereby causing the fingers 3632, 3633 to engage the surrounding non-nerve tissue.

As shown in FIG. 27B, the introducer 3660 may comprise a wall 3663 defining a lumen 3662 in which the paddle electrode 3610 may be slidably, releasably inserted in the manner previously described.

Figure 28:
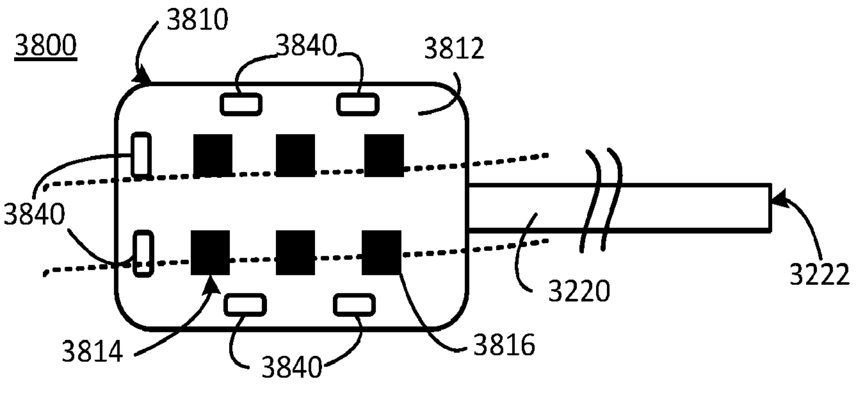

FIG. 28 is a top plan view schematically representing an example arrangement 3800 including a paddle electrode 3810 like paddle electrode 3610 in FIG. 27A, except omitting fingers 3633, 3632 and instead including holes 3840 about a periphery of a body 3812 of the paddle electrode 3810 to facilitate tissue growth to help anchor the body 3812 of the paddle electrode 3810 relative to non-nerve tissues/structures. However, in some examples, the holes 3840 may be used to secure the paddle electrode 3810, via sutures, relative to surrounding non-nerve structures/tissues. As shown in FIG. 28, the paddle electrode 3810 comprises a two-dimensional array 3814 of electrodes 3816, and may be mounted on a stimulation lead 3222 similar to the arrangement in FIG. 27A.

Figure 29A:
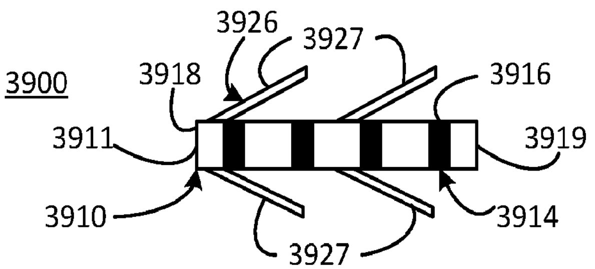
FIGS. 29A-29C are diagrams including top views schematically representing an example axial stimulation portion including a linear electrode array and anchor elements.

FIG. 29A is a side view schematically representing an example stimulation element 3910 comprising a linear array 3914 of spaced apart ring electrodes 3916 and an anchor element comprising an array 3926 of flexible, resilient tines 3927 extending outward from opposite sides of body 3911 of the stimulation element 3910. In one aspect, the stimulation element 3910 comprises distal portion 3918 and opposite proximal portion 3919, which may be supported via a distal portion 3220 of a stimulation lead 3222, as further shown in FIG. 29B. When deployed in a desired location, the tines 3927 engage non-nerve tissue to secure the stimulation element in a position to be in stimulating relation to a target nerve, such as for increasing and/or maintaining upper airway patency.

Figure 29B:
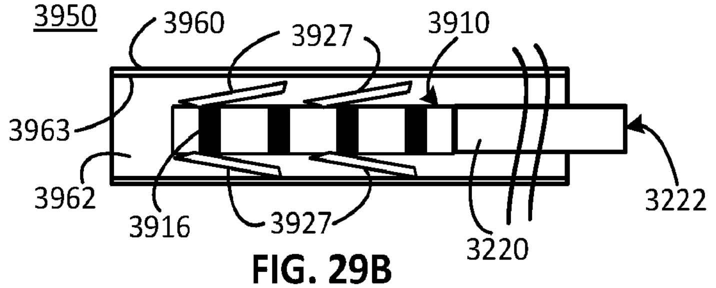

FIG. 29B is a diagram including a side view schematically representing an example arrangement 3950 including the example stimulation element 3910 of FIG. 29A in association with an example introducer 3960 (or guide catheter) for delivering the stimulation element 3910 to a target location. In some examples, the introducer 3960 comprises a wall 3963 defining a lumen 3962 within which the stimulation element 3910 is slidably inserted to cause tines 3927 to fold against sides of the body 3911 of the stimulation element 3910 to prevent their engagement with surrounding non-nerve tissues during delivery of the stimulation element 3910 to a target nerve location. Upon arrival of the stimulation element 3910 at the target nerve location, the introducer 3960 is slidably withdrawn, which releases the tines 3927 to fold outward into their deployment position and shape, such as shown in FIG. 29A, to engage the surrounding non-nerve tissue to thereby anchor the stimulation element 3910 in stimulating relation to the target nerve location.

Figure 29C:
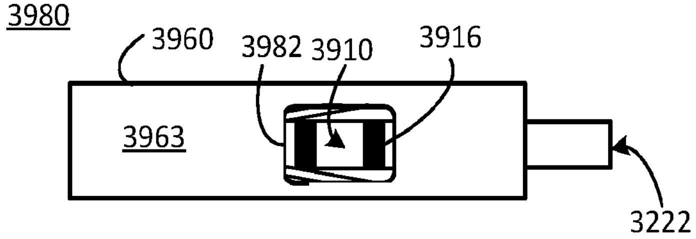

FIG. 29C is a diagram including a side view schematically representing an example arrangement 3980 in which the introducer 3960 comprises a window 3982 formed in wall 3963. In some examples, the window 3982 may permit at least some electrodes 3916 of the stimulation element 3910 to be exposed to potential target nerve locations so that test stimulation signals may applied while maneuvering the stimulation element 3910, with tines 3927 in their non-deployed position, during such test maneuvering. In this way, the introducer 3960 allows selective deployment of the anchor tines 3927, while also permitting application of test stimulation signals via window 3982.

It will be further understood that a similar style introducer 3960 including window(s) 3982 may be employed as or with at least some other example arrangements (e.g. introducer 3660 in FIG. 27B) associated with a stimulation element in other examples of the present disclosure in order to facilitate application of test stimulation signals when identifying a target nerve location.

At least the example implementations of FIGS. 30A-31G relate to delivery tools, anchors, and related elements, which may be used as part of an example method of implantation and/or example device for implantation, treatment, etc. Among other attributes, the use of delivery tools as part of an example method of implantation for multi-target therapy may minimize the amount of dissection of tissues (e.g. on a path to and/or near the intended target stimulation site), may minimize a size of an incision in the patient's skin, tissues, etc. while also providing access to multiple target stimulation sites. In some examples, at least some of these features may be implemented or achieved via a single implant-access incision (i.e. sole implant-access incision in the patient's body, in some examples) such as but not limited to at least some of the previously described examples of single implant-access incisions. As a related aspect, these features may reduce surgical implantation time.

Figure 30A:
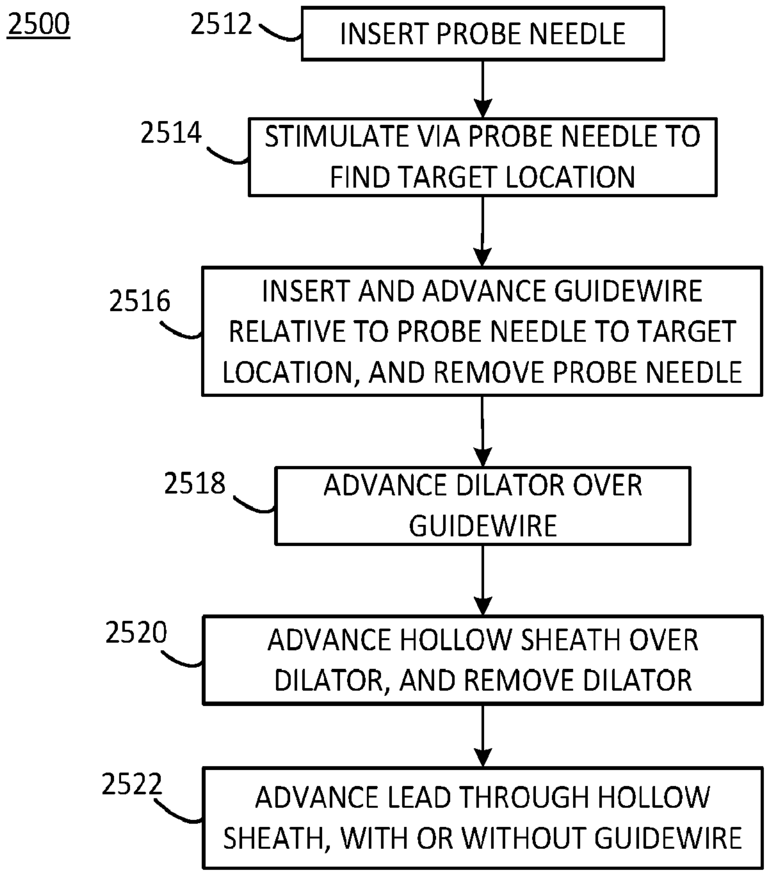
FIG. 30A is a flow diagram schematically representing an example method of implantation.

FIG. 30A is a flow diagram schematically representing an example method 2500 of implantation. In some examples, the method 2500 may comprise an example implementation of at least some methods of implantation of the various stimulation leads in at least some of the examples of the present disclosure. For example, at least some aspects of method 2500 may comprise one example implementation of the various examples of implanting a stimulation element (e.g. device, lead, stimulation device, stimulation portion, etc.) as described in association with at least FIGS. 3-29C and 30B-32C and/or one example implementation of the various examples of identifying a target stimulation site in association with at least FIGS. 51A-51B.

As shown at 2512 in FIG. 30A, method 2500 comprises inserting a probe needle into a patient's body in a region at which at target stimulation location (e.g. nerve) is generally located: The probe needle may comprise at least some conductive elements supported by stimulation-control circuitry for applying a test stimulation signal via the probe needle to the tissue in which the probe needle has been inserted. As further shown at 2514 in FIG. 30A, via application of the test stimulation signal, one can determine a location at which a stimulation portion of a lead is to be delivered within the pertinent tissue of the patient's body.

During application of the test stimulation signal via the probe needle, a clinician may observe a muscle response, such as a response of upper airway patency-related muscle(s) to the test stimulation signal. In some examples, the response to be observed may comprise a tongue protrusion (e.g. contraction of the genioglossus muscle innervated by the hypoglossal nerve) and/or contraction of muscles (e.g. sternohyoid, sternothyroid) innervated by an ansa cervicalis-related nerve 316 (e.g. at least FIGS. 2A, 32A, other). Accordingly, to the extent that a muscle response is not observed upon application of a test stimulation signal, the user may continue to advance and maneuver the probe needle until a suitable response is observed.

It will be understood that the probe needle may be inserted into more than one location and/or maneuvered carefully within a given area in order to determine the desired target stimulation location with a test stimulation signal being applied at the various locations at which the probe needle is maneuvered. Moreover, in some examples, the probe needle may comprise an elongate flexible needle capable of being flexed in a desired orientation relative to pertinent anatomical structures, tissues, etc. in order to reach the desired target locations.

Figure 30B:
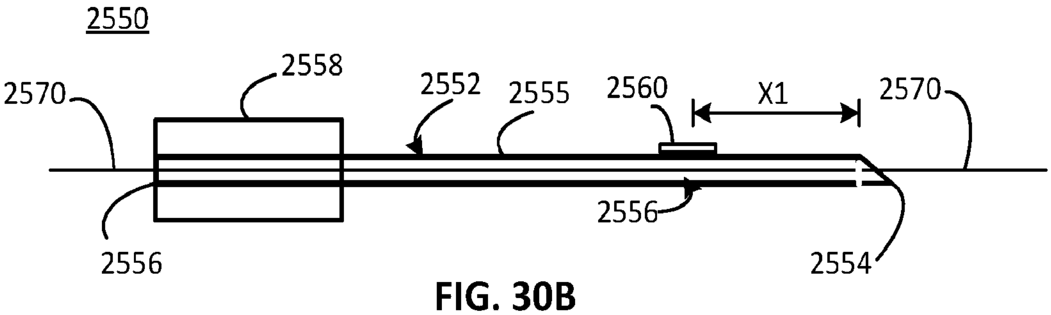
FIGS. 30B-30U are diagrams including a side view schematically representing example devices and/or example methods of implantation, including access and delivery tools for stimulation elements, some of which include anchor elements.

FIG. 30B is a side view schematically representing an example probe needle 2550 which may comprise one example implementation of a probe needle used in the example method of FIG. 30A. As shown in FIG. 30B, in some examples the probe needle comprises an elongate tubular member 2552 (i.e. sleeve) defining a lumen 2556 via side wall 2555. The tubular member 2552 may comprise a semi-rigid or flexible, resilient material and extend between a distal end 2554 and a proximal end 2556. In some examples, a handle portion 2558 may be formed or mounted at or near the proximal end 2556 of the probe needle 2550 to facilitate handling, maneuverability, etc. of the probe needle 2550.

In some examples, the probe needle 2550 may comprise at least one stimulation test electrode 2560 for applying the test stimulation signal. In some examples, the test electrode 2560 may be in a position spaced apart proximally from the distal end 2554 of the probe needle 2550 by a distance X1 such that the test electrode 2560 may sometimes be referred to as being set back from the distal tip 2554 of the probe needle 2550. In some such examples, the setback distance X1 may generally correspond to a setback distance on a stimulation lead, i.e. a distance between a distal tip of a stimulation lead and a distal end of an electrode array of a stimulation portion on the stimulation lead. In one aspect, the setback position of the test electrode 2560 on the probe needle 2550 may increase a likelihood that, upon full implantation of a stimulation lead based on a method of implantation including the use of the probe needle (e.g. at 2512, 2514, 2516 in FIG. 30A; 2550 in FIG. 30B), all or most of the electrodes of a stimulation electrode array will coincide positionally with (or be in close proximity to) the target stimulation location identified via the probe needle (e.g. 2550) from or during the application of test stimulation signals via the probe needle at various potential stimulation locations. In some such examples, the coincidental position may sometimes be referred to as the stimulation electrode array being generally centered on, or generally co-located with, the target stimulation site of the target nerve.

In some examples, the test electrode 2560 of probe needle 2550 may be positioned at the distal end 2554 of probe needle 2550, e.g. a distal tip of the probe needle 2550 and not setback from the distal end 2554 as shown in FIG. 30B.

In some examples, in one example implementation of a method of implantation, a determination where and how to insert and advance of a probe needle (e.g. 2550) may be performed via a visualization method including palpation, such as with respect to known, observable anatomical landmarks and/or user experience. In some examples, in addition to or instead of such palpation, example methods may comprise using visualization provided external image-based monitoring, such as via ultrasound, fluoroscopy, x-ray, etc. In some examples, one example implementation of visualization and/or other forms of guiding a probe needle and other delivery tools, stimulation lead, etc.) within a patient's body during a method of implantation may comprise at least some of substantially the same features and attributes as described in U.S. Pat. No. 9,888,864, issued Feb. 13, 2018, entitled METHOD AND SYSTEM FOR IDENTIFYING A LOCATION FOR NERVE STIMULATION, and which is hereby incorporated by reference in its entirety.

In some examples, instead of using a probe needle (e.g. 2512, 2514 in FIG. 30A, 2550 in FIG. 30B) to identify a target stimulation site along a nerve, some example implementations of method 2500 in FIG. 30A may comprise use of the stimulation electrodes on the to-be-implanted stimulation lead to provide the role or function of a probe needle, such as but not limited to aspects 2512, 2514 in method 2500 (FIG. 30A). In some such examples, application of a test stimulation signal may be applied via a stimulation portion of a stimulation lead while the stimulation lead is present within a delivery tool (e.g. cannula, hollow insertion needle, etc.) and during insertion and advancement of the delivery tool within or near the pertinent tissue at which the target stimulation location is expected to be identified. In some such examples, instead of using the stimulation electrodes of the stimulation lead, a dedicated test electrode may be present on the stimulation lead in addition to the stimulation electrodes. In some examples, another alternative to use of the probe needle may comprise a delivery tool (e.g. cannula, hollow insertion needle, and the like) which carries one or more test stimulation electrodes to enable application of a test stimulation signal to identify and/or confirm a location of a target stimulation site prior to withdrawal of the delivery tool (which may complete implantation of the stimulation lead).

Once the target location has been identified per 2512, 2514 of method 2500, then at 2516 as shown in FIG. 30A, the method 2500 comprises inserting a guidewire into the patient's body and into and through the probe needle, which is already located at the target stimulation location. With the guide wire in its desired position at the target stimulation location, the probe needle is withdrawn (via the guidewire) from the body.

With this in mind, FIG. 30B provides a schematic representation of an example guide wire 2570 extending through a lumen 2556 of the probe needle 2550. It will be understood that the guidewire 2570 may comprise an elongate flexible, resilient element, which may comprise a metal material in some examples, and may comprise a biocompatible outer coating, etc.

As further shown at 2518 in FIG. 30A, a dilator is advanced over the guidewire to the target stimulation location and at 2520, a hollow sheath (e.g. introducer, etc.) is advanced over the dilator to the target stimulation location with the dilator being removed thereafter, thereby leaving the hollow sheath in place at the target stimulation location. At 2522, a stimulation lead (or other type of lead) is inserted into and advanced through the hollow sheath (with or without the guidewire) until the stimulation portion of the lead arrives at the target stimulation location.

In some examples, after the stimulation portion of the lead has been delivered to its location for chronic implantation, the hollow sheath may be removed from the patient's body, which may comprise peeling or breaking the hollow sheath in order to free the hollow sheath from the stimulation lead and from the implantation location within the patient's body.

In some examples, removal of the hollow sheath from the stimulation lead may result in the automatic activation of any anchor elements (e.g. tines, threads, coils, filaments) on the stimulation lead which were being retained in a non-deployed state (e.g. collapsed, covered, etc.) within the delivery tool(s) (e.g. hollow sheath, sleeve, etc.) during delivery of the stimulation element (e.g. electrode array, etc.) of the stimulation lead to the target stimulation location, such as in accordance with method 2500 of FIG. 30A. With this in mind, various example implementations of delivering a stimulation lead while retaining an anchor element in a non-deployed state and later deploying the anchor element upon withdrawal of a delivery tool are described in association with at least FIGS. 30B-31G.

While some details of example methods of implantation may vary depending on a size, length, shape of an element (e.g. stimulation lead) to be implanted, it will be understood that the example method 2500 of FIG. 30A provides one example implementation by which at least some of the example leads, example stimulation devices, etc. of the present disclosure may be implanted, including but not limited to at least some of the leads, stimulation devices of the examples described in association with at least FIGS. 1-29C, FIGS. 30C-30W, and/or FIGS. 31A-32D.

Figure 30C:
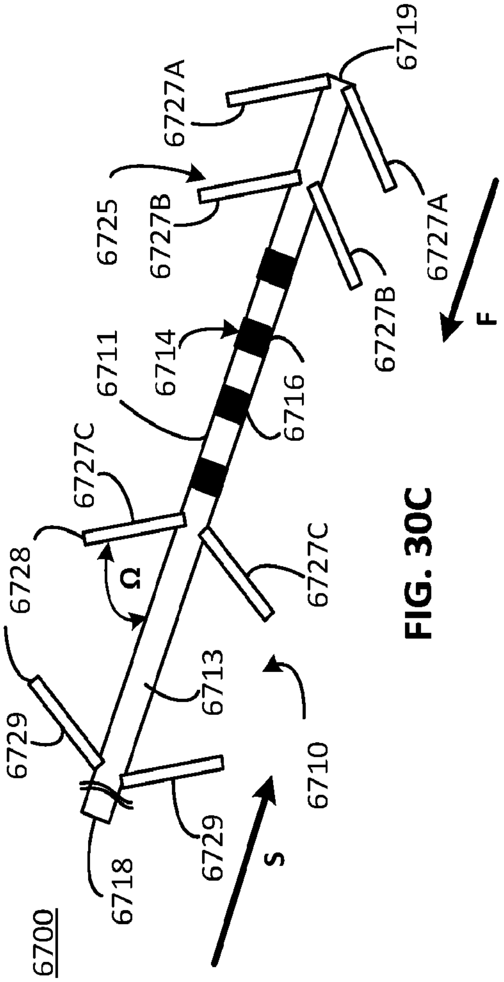
FIGS. 30V-30W are diagrams including a top view and a side view, respectively, schematically representing example anchor structures.

FIG. 30C is a diagram including a front view schematically representing an example arrangement 6700 comprising an example stimulation device 6710 which may be used in example methods of implantation, with or without additional tools. In some examples, the stimulation device 6710 may comprise at least some of substantially the same features and attributes of at least some of the example arrangements described in association with at least FIGS. 1-29C and later described in association with at least FIGS. 30D-32C. As shown in FIG. 30C, the stimulation device 6710 may comprise a body 6713 which extends between a distal end 6719 and a proximal end 6718. In some such examples, the proximal end 6718 may be connected to, or extend from, a lead body connectable to a pulse generator or microstimulator, in a manner similar to various example stimulation portions, leads, etc. of the present disclosure.

As further shown in FIG. 30C, stimulation device 6710 comprises an array 6714 of electrodes 6716, such as ring electrodes or split-ring electrodes spaced apart from each other axially along a portion of a length of the body 6713 of device 6710. In some examples, the stimulation device 6710 also comprises an anchoring structure 6725, which in some examples may comprise an array of tines (or similar elements) 6727A, 6727B, 6727C, 6729.

While shown in a two-dimensional format in FIG. 30C, it will be understood that a plurality of tines (e.g. 6727A, etc.) at a particular location along the body 6713 of stimulation device 6710 may be arranged about a circumference of the body (e.g. cylindrical).

With further reference to FIG. 30C, tines 6727A and tines 6727B are positioned distal to the array 6714 of electrodes 6716, being between the array 6714 and the distal end 6719 of the body 6713 of the stimulation device 6710. Meanwhile, in some examples, tines 6727C and 6729 are positioned proximal to the array 6714 of electrodes 716, being between the array 6714 and the proximal end 6718 of the body 6713 of stimulation device 6710. Each of the respective tines (6727A, 6727B, 6727C, 6729) are connected to (and extend from) the side(s) 6711 of the body 6713 and extend outwardly at an angle (Ω) from the side(s) 6711. As further shown in FIG. 30C, an end 6728 of the tines 6727A, 6727B, 6727C extend in a first orientation (F), with their ends 6728 pointed rearwardly toward the proximal end 6718 of the body 6713 of device 6710. In contrast, tines 6279 extend in an opposite second orientation (arrow S), with their ends 6728 pointed toward the distal end 6719 of the body 6713 of device 6710. Accordingly, the tines 6729 have an orientation which are opposite to the orientation of tines 6727A, 6727B, 6727C. As further described later below, this orientation may facilitate robust, stable anchoring of the stimulation device 6710 within a patient's body via the respective tines 6727A, 6727B, 6727C, 6729 engaging non-nerve structures.

In some examples, the tines 6727A, 6727B, 6727C, 6729 are made of a flexible, resilient material and formed relative to the side(s) 6711 of body 6713 such that the tines are biased to extend outward (at an angle Ω) from the side(s) 6711 in the manner shown in FIG. 30C. From this outwardly extending angle, the tines (e.g. 6727A, 6727B, 6727C, 6729) also are collapsible (e.g. flexibly bending, folding) toward and/or against the side(s) 6711 of body 6713, as later shown in at least FIGS. 30E-30G, upon some external force or structure causing such collapse (i.e. bending toward side(s) 6711). In some examples, at least some of the tines may comprise an elongate, cylindrical member having a cross-sectional shape which is circular or similar. Of course, while still bearing a generally elongate shape, in some examples the tines may comprise different/other cross-sectional shapes such as rectangular, triangular, etc.

In some examples, the stimulation device 6710 may be implanted using a wide variety of tools for delivery, implantation, etc. With this in mind, FIGS. 30D-30G schematically represent example methods to prepare for implantation, and/or execute implantation of, stimulation device 6710.

Figure 30D:
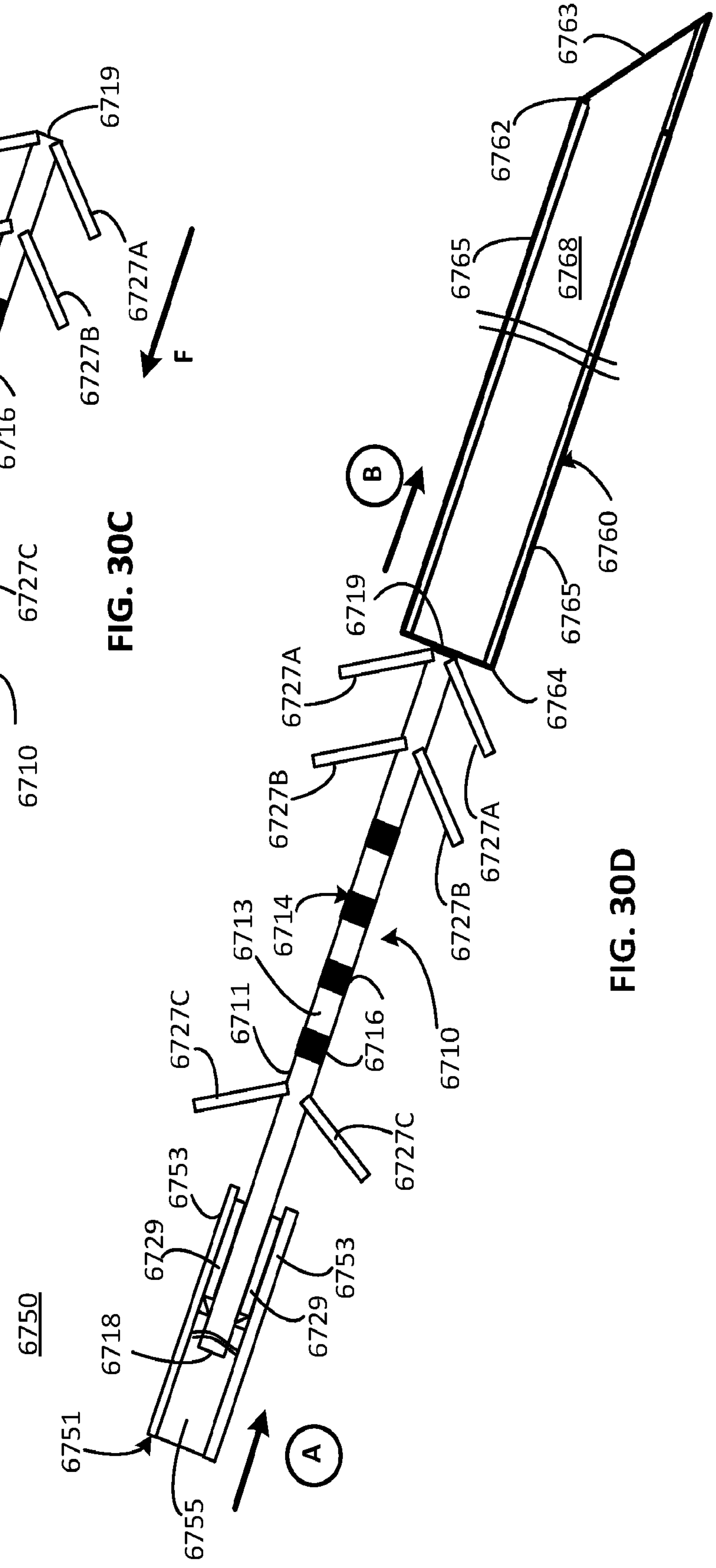

FIG. 30D is diagram including a side view schematically representing an example arrangement 6750 including example stimulation device 6710 in use with a hollow insertion needle 6760 and sleeve 6751 as part of a method of implanting stimulation device 6710. In some examples, the stimulation device 6710 may comprise at least some of substantially the same features and attributes as the stimulation device 6710 of FIG. 30C. As further shown in FIG. 30D, sleeve 6751 may comprise a body defined by sidewall(s) 6753, which are spaced apart by a distance to slidably fit over and cause temporary collapse (i.e. bending, folding, flexing, etc.) of tines 6729 against side 6711 of body 6713 of stimulation device 6710, as shown in FIG. 30D. In some examples, the sleeve 6751 may comprise a slit along its side or other mechanism to enable removably mounting the sleeve 6751 onto the stimulation device 6710 in the region of the "reverse orientation" tines 6729 into the collapsed configuration shown in FIG. 30D. In some such examples, this removably mounting may comprise a sliding motion as represented via the directional arrow at identifier A to facilitate collapse of tines 6729.

As further shown in FIG. 30D, in one aspect the preparation to implant the stimulation device 6710 further comprises slidably inserting the stimulation device 6710 into and within the hollow insertion needle 6760, beginning with insertion of the distal end 6719 of stimulation device 6710 into the proximal end 6764 of the hollow insertion needle 6760, as represented by directional arrow B. In some examples, the hollow insertion needle 6760 comprises a lumen 6768 defined by side wall 6765, with the lumen 6768 extending between the proximal end 6764 and opposite distal end 6762. The needle 6760 also may include a beveled portion 6763 at distal end 6762 to facilitate penetration of the needle 6760 into pertinent tissues at, and through, which the stimulation device 6710 is to be implanted. At least some example pertinent tissues may comprise tissues such as (but not limited to) subcutaneous tissues including but not limited to muscles like the sternocleidomastoid platysma, omohyoid, sternohyoid, sternothyroid, etc.

Figure 30E:
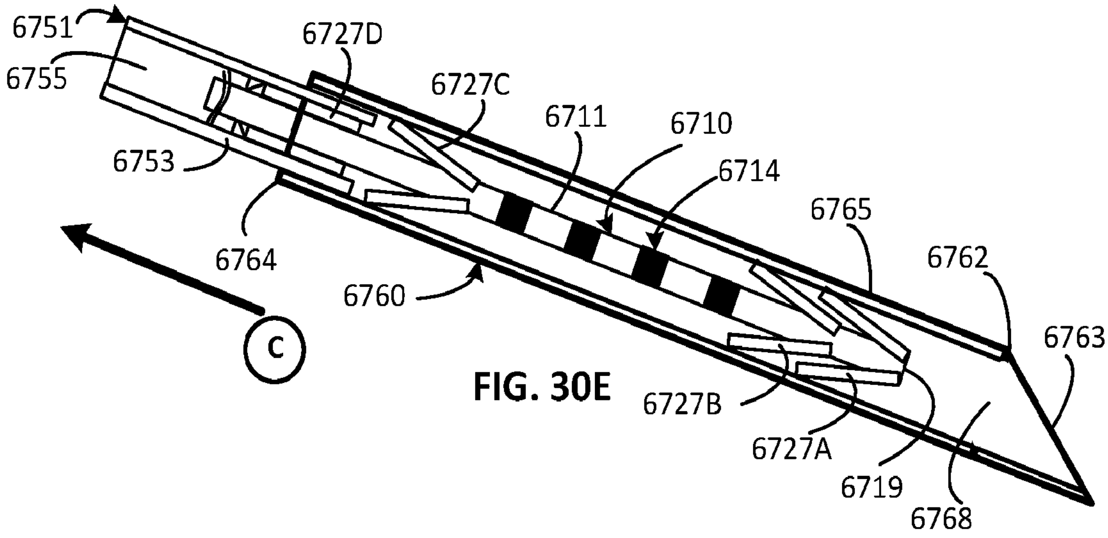
Figure 30F:
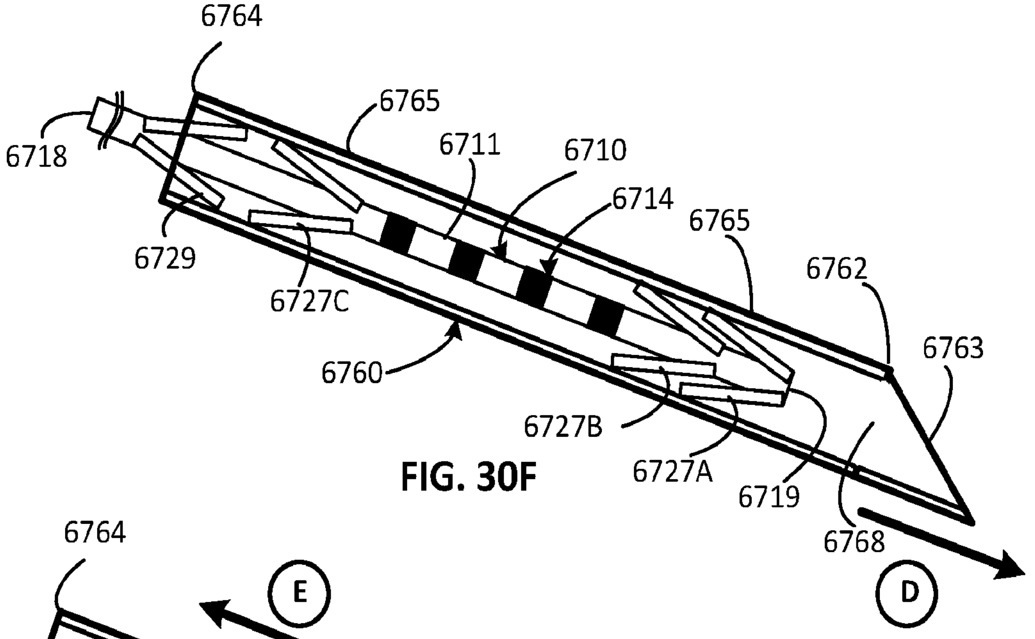

FIG. 30E is a diagram including a side view schematically representing the example arrangement 6750 of FIG. 30C, 30D including example stimulation device 6710 being fully inserted within the hollow insertion needle 6760 to result in collapse (e.g. bending) of the tines 6727A, 6727B, 6727C relative to (e.g. toward, against, etc.) side 6711 of stimulation device 6710. Moreover, as shown in FIG. 30E, the lumen 6768 of the needle 6710 is sized to slidably receive the sleeve 6751, in its already mounted state over tines 6729 of stimulation device 6710, within the hollow insertion needle 6760. Finally, as represented by directional arrow C in FIG. 30E, sleeve 6751 may be slidably removed out of the proximal end 6764 of needle 6760 and off the "reverse orientation" tines 6729 of the stimulation device 6710 to yield the configuration shown in FIG. 30F in which the tines 6729 expand outward slightly to be in contact against the sidewall 6765 of needle 6760.

Accordingly, in this ready-to-be-implanted configuration, hollow insertion needle 6760 is inserted into and through pertinent tissues, as represented via directional arrow D.

Figure 30G:
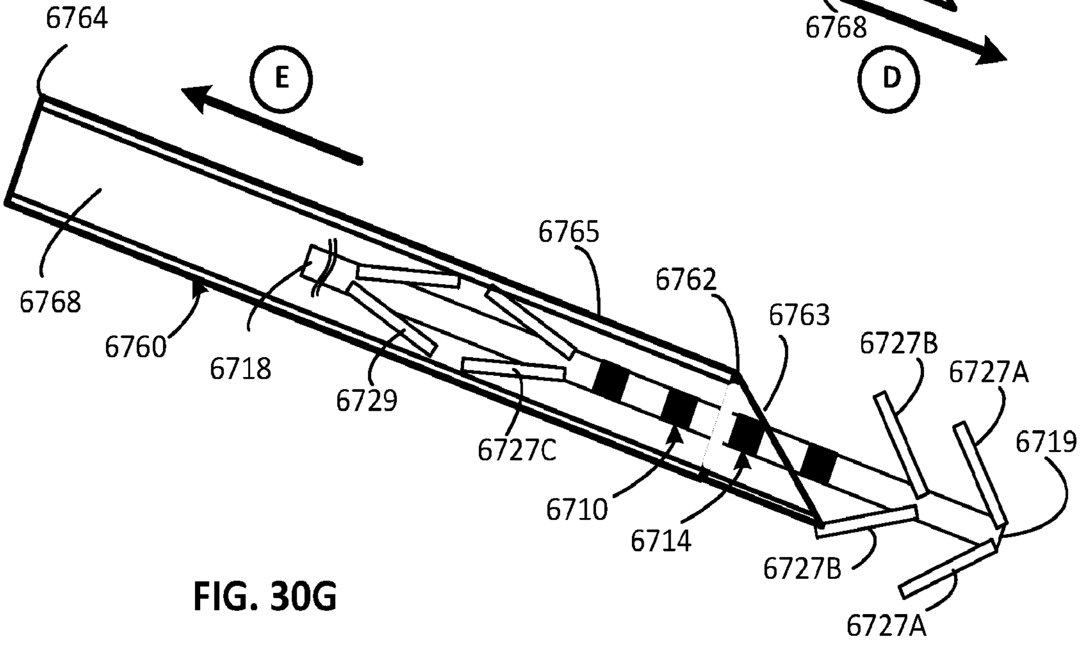

As further shown in FIG. 30G, once the distal end 6719 of stimulation device 6710 has been positioned in its desired location relative to a target stimulation site (e.g. in stimulating relation to a target location along a nerve), then the needle 6760 may be slidably removed from the stimulation device 6710 as represented via directional arrow E. This maneuver causes release of tines 6727A, 6727B (from their collapsed position as in FIGS. 30E, 30F) into their extended position for engaging surrounding non-nerve tissues to secure the stimulation device 6710 (including the array 6714 of electrodes 6716) to be in stimulating relation to a target nerve or tissue (e.g. muscle). Further proximal sliding movement of needle 6760 relative to stimulation device 6710 will result in the release of tines 6727C and of the "reverse orientation" tines 6729 to also engage surrounding tissues so that the stimulation device 6170 will be present in the configuration shown in FIG. 30C will all tines 6727A, 6727B, 6727C, 6729 engaging surrounding tissues. In one aspect, by including at least one set of "reverse orientation" tines 6729 spaced apart from, and juxtaposed axially, relative to the tines 6727A, 6727B, 6727C, the combination of tines 6727A, 6727B, 6727C and "reverse orientation" tines 6729 may act to prevent or minimize "ratcheting" which may sometimes occur with some implanted medical elements. In some instances, ratcheting may arise in areas of high motion, such as for implanted medical elements in the neck region at which repeated turning, tilting, flexion, etc. of the head repeated flexes the neck in various orientations. To the extent that an implanted medical element may have tines or other protrusions engaging surrounding non-nerve tissue, these repeated motions of the neck may result in the implanted medical element moving or migrating from its originally implanted position because the tines (or other protrusions) may move or "walk" slightly during or upon such repeated neck motion, thereby resulting in movement of the implanted medical element.

However, the juxtaposition of tines 6729 with tines 6727A, 6727B, 6727C may prevent or minimize such "ratcheting" because such repeated neck motion, with the presence of the "reverse orientation" tines 6729 would tend to cause potential movement of the stimulation device 6170 in a direction or orientation opposite of the movement that might otherwise result from the orientation of tines 6727A, 6727B, 6727C.

Figure 30H:
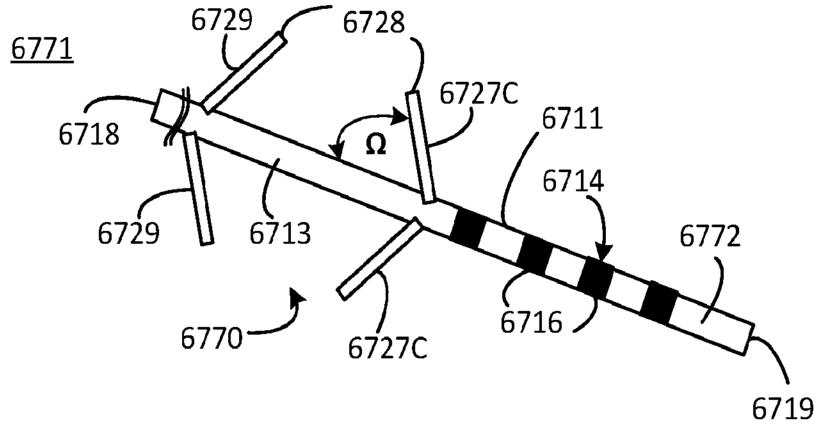

FIG. 30H is a diagram including a front view schematically representing an example arrangement 6771 comprising an example stimulation device 6770 which may be used in example methods of implantation with or without additional tools. In some examples, the stimulation device 6770 may comprise at least some of substantially the same features and attributes as the stimulation device 6710 as described in association with at least FIG. 30C, except with all tines being positioned proximal to the electrode array 6714 and a lower quantity of tines (e.g. 6727C) which have a first orientation. However, as in the stimulation device 6710, the stimulation device 6770 of FIGS. 30H-30J comprises at least one set of opposite second orientation (i.e. "reverse orientation") tines 6729, which when juxtaposed with first orientation tines 6727C, may prevent or minimize ratcheting-type migration of stimulation device 6770 from its original or intended implant location.

As shown in FIG. 30H, in addition to the features common with stimulation device 6710, in some examples the stimulation device 6770 may comprise no tines distal to the electrode array 6714, comprise at least one set of first orientation tines 6727C adjacent electrode array 6714, and at least one set of opposite, second orientation (i.e. "reverse orientation") tines 6729 interposed between the first orientation tines 6727C and proximal end 6718 of stimulation device 6770. In examples in which the least one set of first orientation tines 6727C may comprise more than one set of tines, the tines may be configured similar to the configuration shown in FIG. 30C in which at least two sets of tines 6727A, 6727B are present but are spaced from each other along a portion of a length of the body 6713. Moreover, in some examples, to the extent at no tines are present distal to the electrode array 6714, a distal portion 6722 of body 6713 may be reduced in length as shown in FIG. 30H, as compared to such a distal portion 6722 having a greater length when tines (e.g. 6727A, 6727B) are present.

With further reference to FIG. 30H, like the stimulation device 6710 in FIGS. 30C-30G, a method of implanting stimulation device 6770 may comprise initially collapsing (e.g. bending) the "reverse orientation" tines 6829 against the side 6711 of body 6713 of stimulation device 6770 in order to permit loading of the stimulation device 6770 into and within a hollow insertion needle 6760. Accordingly, in some examples the example arrangement 6771 may utilize a sleeve like sleeve 6751 in FIG. 30D to engage and causes collapse (e.g. bending) of "reverse orientation" tines 6729 into a collapsed configuration. In a manner similar to that shown in FIGS. 30E-30F, upon proximal slidable removal of such a sleeve, the resulting configuration of just the stimulation device 6770 within the lumen 6768 of the needle 6760 is shown in FIG. 30I and in which the "reverse orientation" tines 6729 are in a partially collapsed state as constrained by sidewall 6765 of hollow insertion needle 6760.

Figure 30I:
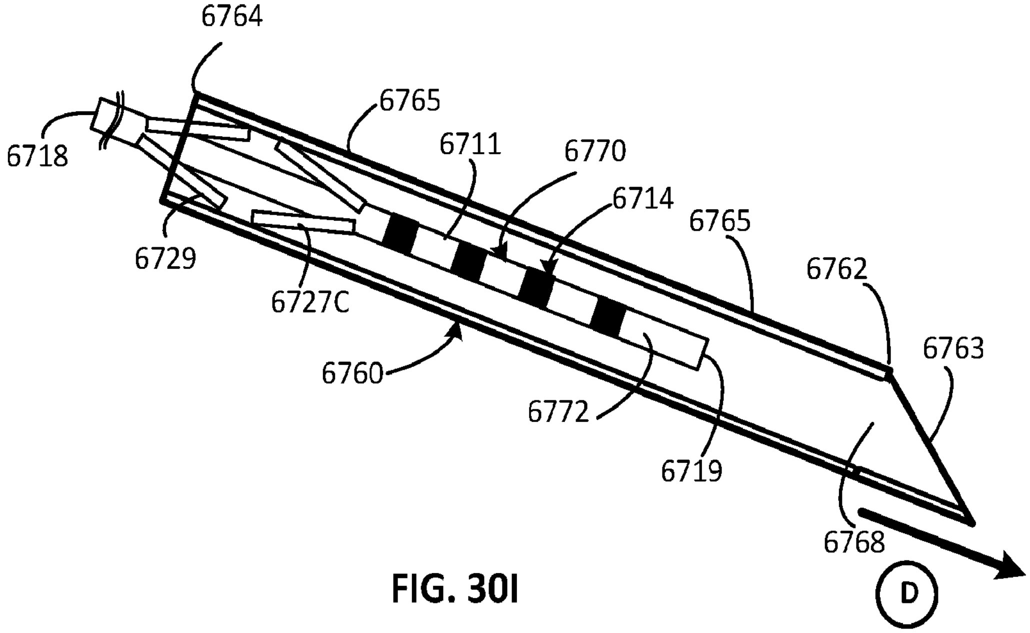

In the configuration shown in FIG. 30I, with the stimulation device 6770 releasably retained within the hollow insertion needle 6760, the needle 6760 is inserted into and through pertinent tissues to deliver the stimulation device 6770 (which may comprise a stimulation portion of a longer lead (not shown for illustrative simplicity)) into stimulating relation to target tissue, such as a target location along a nerve, as represented by directional arrow D.

Figure 30J:
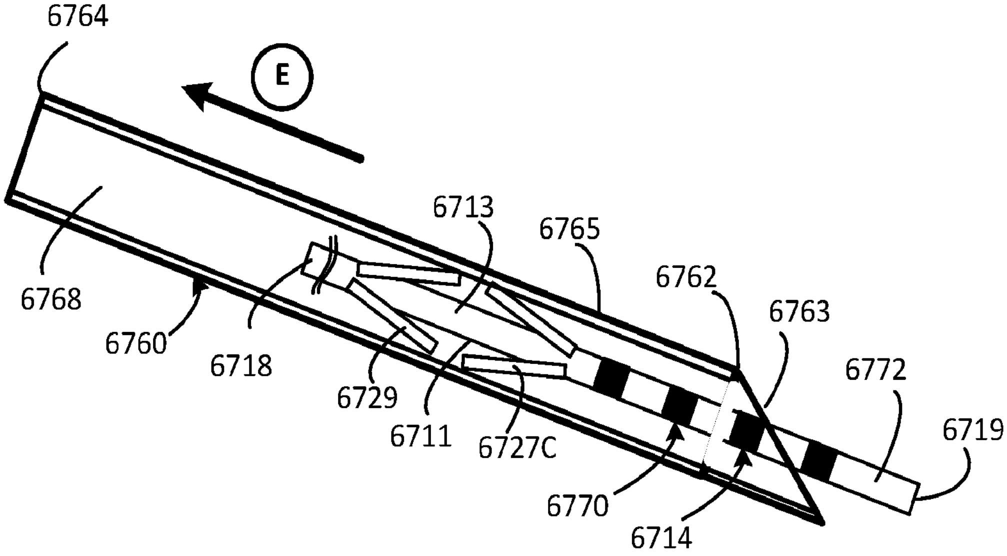

Once the stimulation device 6770 has been delivered and positioned as desired relative to a target tissue, the needle 6760 is slidably withdrawn from the stimulation device 6770, as represented by directional arrow E in FIG. 30J. This maneuver results in the release of tines 6727C, 6729 from their collapsed state (FIG. 30I) into an expanded state (FIG. 30K) so that the tines 6727C, 6829 may engage surrounding non-nerve tissues to secure the stimulation device 6770 in a robust, stable position in stimulating relation to a target tissue (e.g. nerve).

However, with further reference to FIG. 30J, when the hollow insertion needle 6760 is in a position just prior to the tines 6727C, 6729 being released, in some examples the electrode array 6714 may significantly protrude from the distal end 6762 of the hollow needle 6760 such that further maneuvering of the combination of the needle 6760 and stimulation device 6770 may be performed while applying test stimulation signals via the electrode array 6714 to further identify or confirm a location of a desired target stimulation site. In one aspect, the absence of tines distal to the electrode array 6714 and the absence of tines among the electrodes 6716 of array 6714 may facilitate further positioning of the stimulation device 6770 (with support of needle 6760) without the interference of more distal tines (as in FIGS. 30C, 30D, etc.) relative to a target stimulation location.

Accordingly, after any further refinement of identifying or confirming a target stimulation location and upon further slidable removal of needle 6760 from the now implanted stimulation device 6770 (and from the pertinent portion of the patient's body), the tines 6727C, 6729 of stimulation device 6770 may fully expand to their unrestrained state like that shown in FIG. 30H, and which in turn engage surrounding non-nerve tissues to secure the stimulation device 6770 in the patient's body at the desired stimulation site.

Figure 30K:
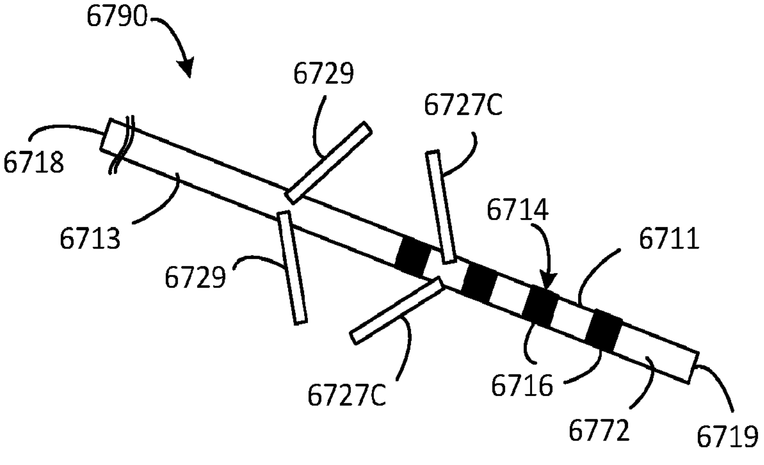

FIG. 30K is a diagram including a front view schematically representing an example arrangement comprising an example stimulation device 6790 which may be used in example methods of implantation with or without additional tools. In some examples, the stimulation device 6790 may comprise at least some of substantially the same features and attributes as the stimulation device 6770 as described in association with at least FIG. 30H-30J, except with at least one set of first orientation tines 6727C being positioned among the electrodes 6716 of electrode array 6714, such as being interposed between adjacent electrodes 6716. Via this arrangement, the generally more proximal location of the tines 6727C, 6729 relative to the electrode array 6714 (e.g. no tines distal to the electrode array) may still permit some maneuverability of the stimulation device 6790 (in a manner similar to that described for stimulation device 6770) while further identifying and/or confirming a target stimulation site just prior to finalizing a chronic implantation location. Moreover, as in the stimulation device 6770, the stimulation device 6790 of FIG. 30K comprises at least one set of opposite second orientation (i.e. "reverse orientation") tines 6729, which when juxtaposed with first orientation tines 6727C, may prevent or minimize ratcheting-type migration of stimulation device 6810 from its original or intended implant location as a result of flexion and motion of the neck and upper body. Finally, as also noted elsewhere regarding some other example implementations, by interposing some tines 6727C between some electrodes 6716 of array 6716 may enhance robust securing of the electrode array 6714 in close proximity to and stimulating relation to a target stimulation site.

Figure 30L:
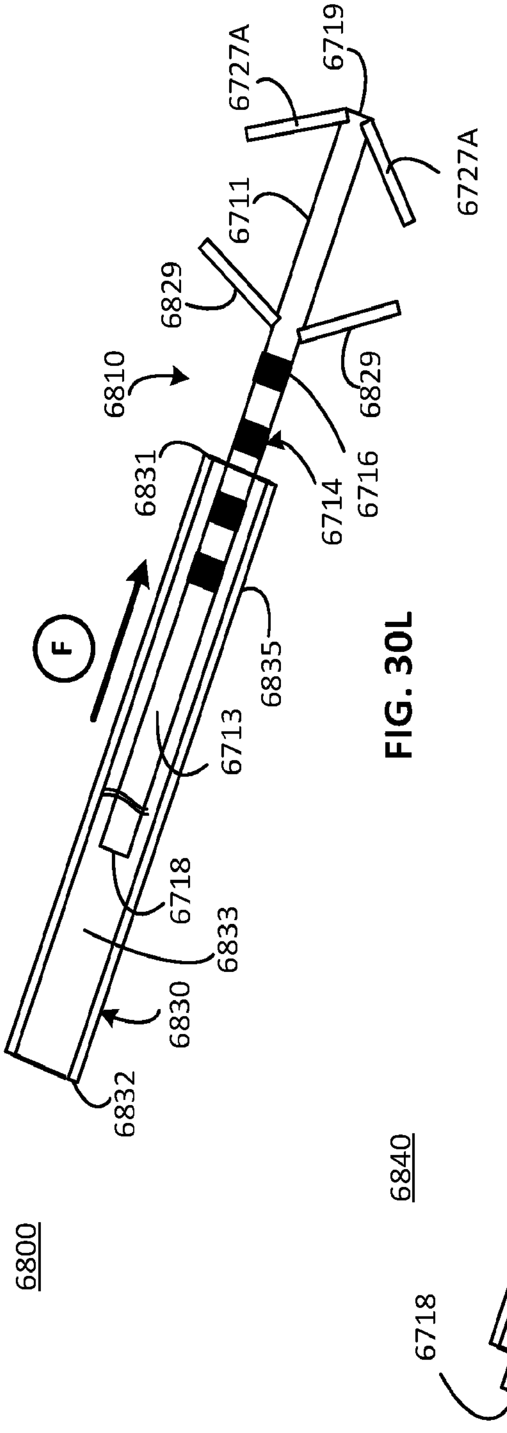

FIG. 30L is a diagram including a front view schematically representing an example arrangement 6800 comprising an example stimulation device 6810 which may be used in example methods of implantation with or without additional tools. In some examples, the stimulation device 6810 may comprise at least some of substantially the same features and attributes as the stimulation device 6710 as described in association with at least FIG. 30C, except with all tines being positioned distal to the electrode array 6714 and a lower quantity of tines 6727A which have a first orientation. However, as in the stimulation device 6710, the stimulation device 6810 of FIGS. 30L-30R comprises at least one set of opposite second orientation (i.e. "reverse orientation") tines 6829, which when juxtaposed with first orientation tines 6727A, may prevent or minimize ratcheting-type migration of stimulation device 6810 from its original or intended implant location. However, in some examples, all tines present distal to the electrode array 6714 may have the same orientation.

As shown in FIG. 30L, in addition to the features common with stimulation device 6710, in some examples the stimulation device 6810 may comprise no tines proximal to the electrode array 6714, at least one set of first orientation tines 6727A adjacent distal end 6719, and at least one set of opposite, second orientation (i.e. "reverse orientation") tines 6829 interposed between the electrode array 6714 and the first orientation tines 6727A. In examples in which the least one set of first orientation tines 6727A may comprise more than one set of tines, the tines may be configured similar to the configuration shown in FIG. 30C in which at least two sets of tines 6727A, 6727B are present but spaced from each other along a portion of a length of the body 6713.

With further reference to FIG. 30L, like the stimulation device 6710 in FIGS. 30C-30G, a method of implanting stimulation device 6810 may comprise initially collapsing (e.g. bending) the "reverse orientation" tines 6829 against the side 6711 of body 6713 of stimulation device 6810 in order to permit loading of the stimulation device 6810 into and within a hollow insertion needle 6760. Accordingly, in some examples the example arrangement 6800 may comprise a sleeve 6830 which is removably mounted relative to the body 6713 of stimulation device 6810 near proximal end 6718 (which may be connected to or extend distally from a lead body) and then slidably advanced, as represented via directional arrow F, over and along the body 6713 of stimulation device 6810 until a distal end 6831 of sleeve 6830 engages and causes collapse (e.g. bending) of "reverse orientation" tines 6829 into a collapsed configuration within lumen 6833 of sleeve 6830, as shown in FIG. 30M.

Figure 30M:
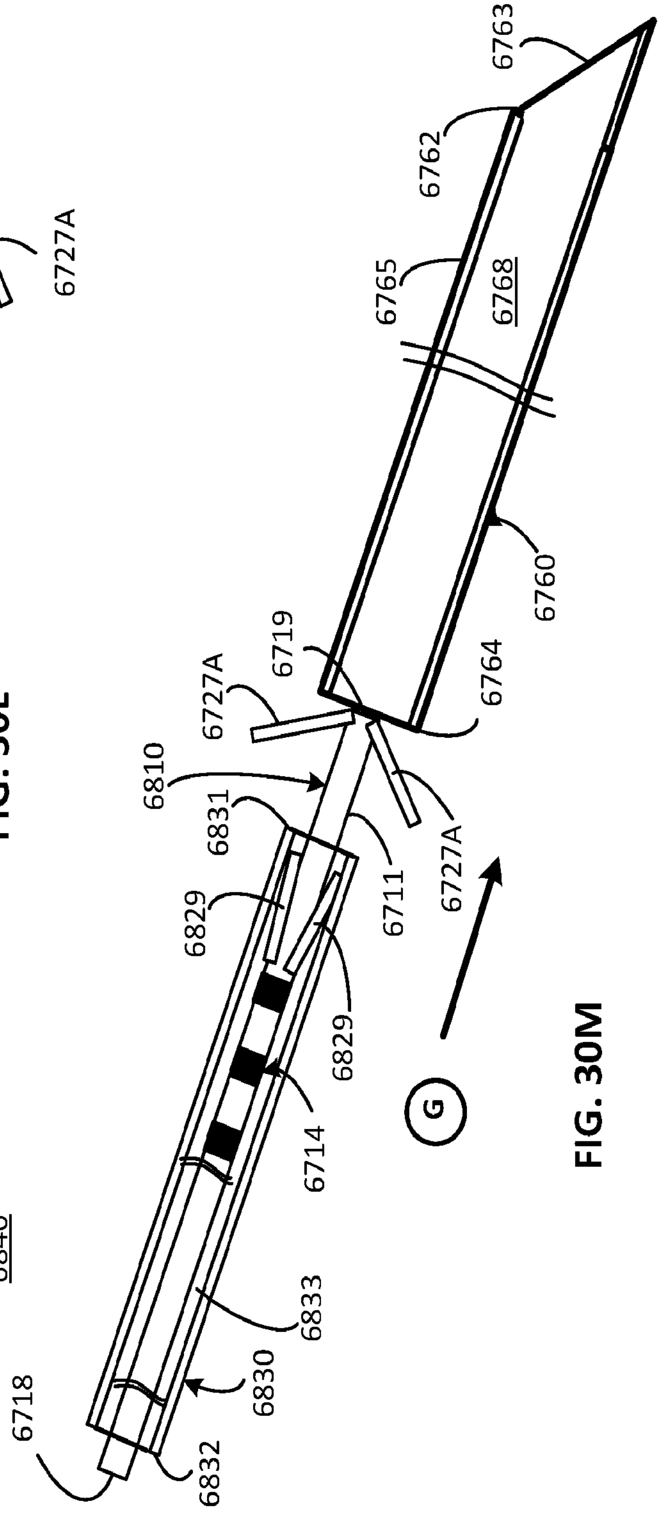
Figure 30N:
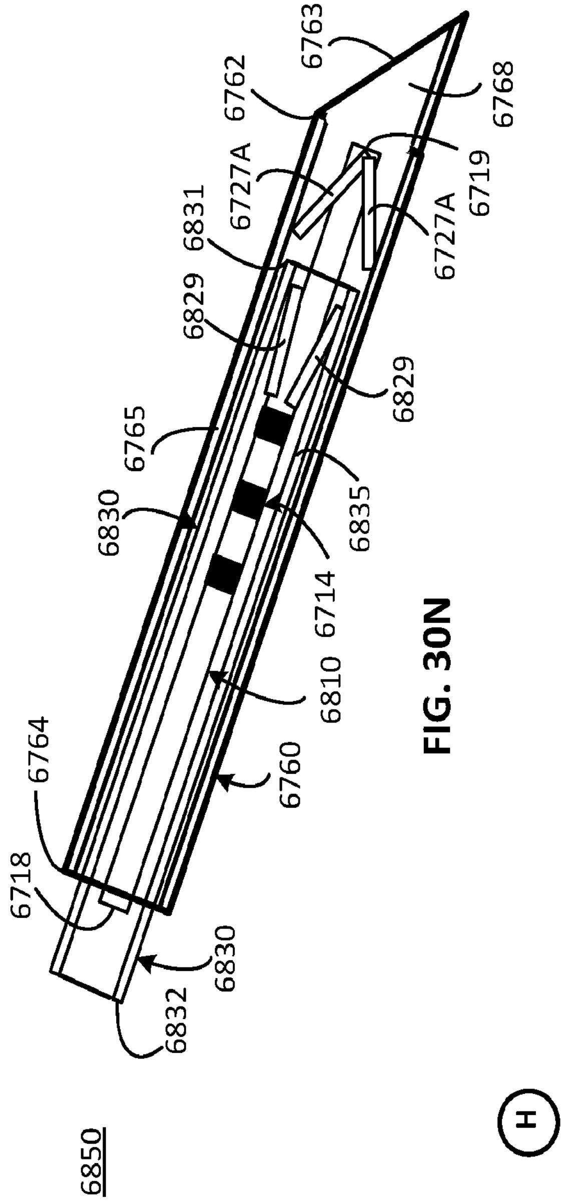

With the stimulation device 6810 and sleeve 6830 in the configuration shown in FIG. 30M, this combination of elements is slidably inserted, via a proximal end 6764 of the hollow insertion needle 6760, into and within lumen 6768 of needle 6760, as represented via directional arrow G (FIG. 30M) to cause collapse (e.g. bending, rotation, etc.) of the first orientation tines 6727A relative to the sides 6711 of body 6713 of stimulation device 6810 and insertion and advancement of the already removably-mounted sleeve 6830 within lumen 6768 of needle 6760. The resulting configuration is shown as example arrangement 6850 in FIG. 30N.

Figure 30O:
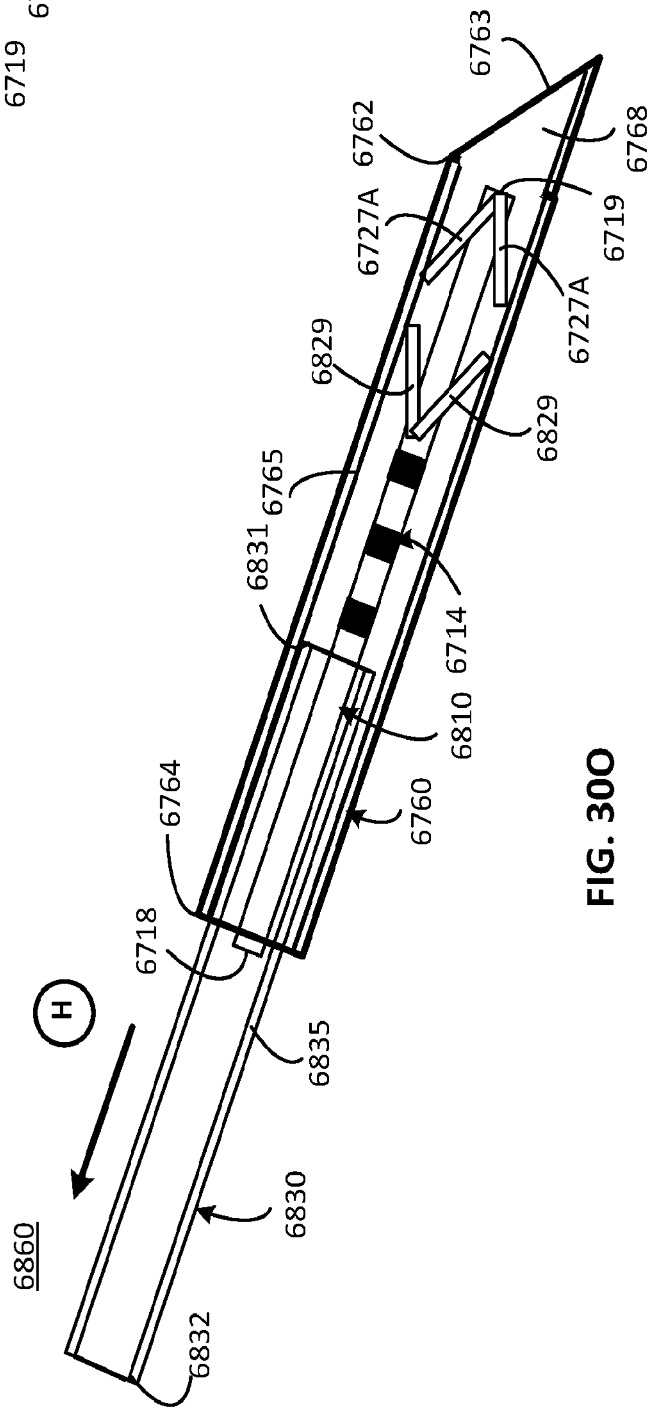

Thereafter, as represented by directional arrow H in FIG. 30O, the sleeve 6830 is slidably withdrawn proximally out of needle 6760 via the proximal end 6764 of needle 6760 while stimulation device 6810 is retained within lumen 6768 of needle 6810. Among other factors, the releasable engagement of tines 6727A against the sidewall 6765 of needle 6760 help to retain stimulation device 6810 within the lumen 6768 of needle 6760 both during and after slidable removal of sleeve 6830 from stimulation device 6810 and needle 6760. As the sleeve 6830 is being slidably removed proximally just past the opposite second orientation (i.e. "reverse orientation") tines 6829, those tines 6829 are released to extend slightly outward while still being constrained by the sidewall 6765 of the needle 6760, as shown in FIG. 30O. Upon complete withdrawal of the sleeve 6830 from the stimulation device 6810 and needle 6760, the resulting configuration of just the stimulation device 6810 within the lumen 6768 of the needle 6760 is shown in FIG. 30P.

Figure 30P:
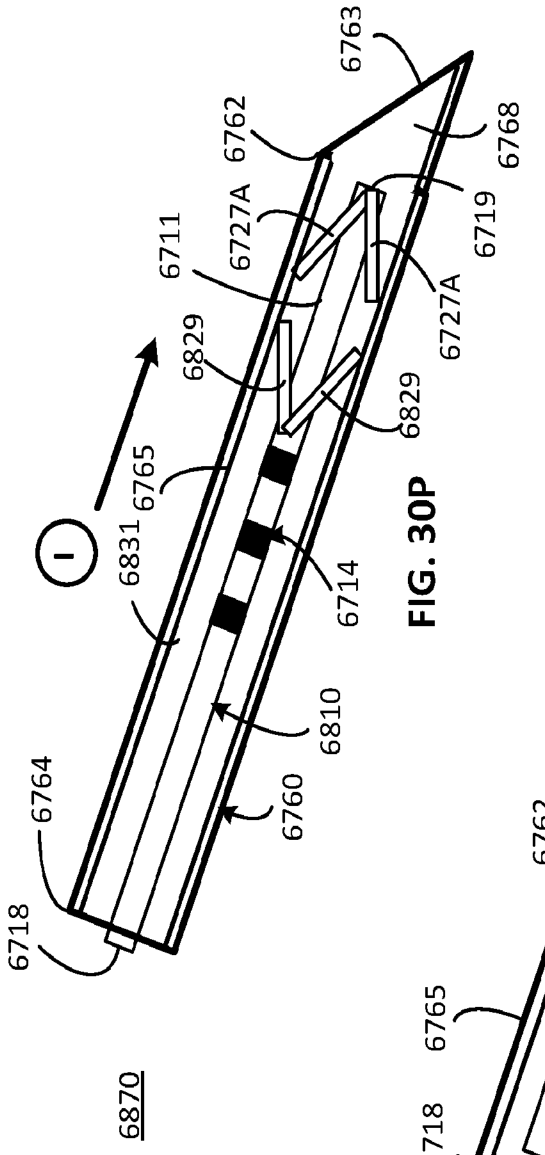

In the configuration shown in FIG. 30P, with the stimulation device 6810 releasably retained within the needle 6760, the needle 6760 is inserted into and through pertinent tissues to deliver the stimulation device 6810 (which may comprise a stimulation portion of a longer lead (not shown for illustrative simplicity)) into stimulating relation to target tissue, such as a target location along a nerve, as represented by directional arrow I.

Figure 30Q:
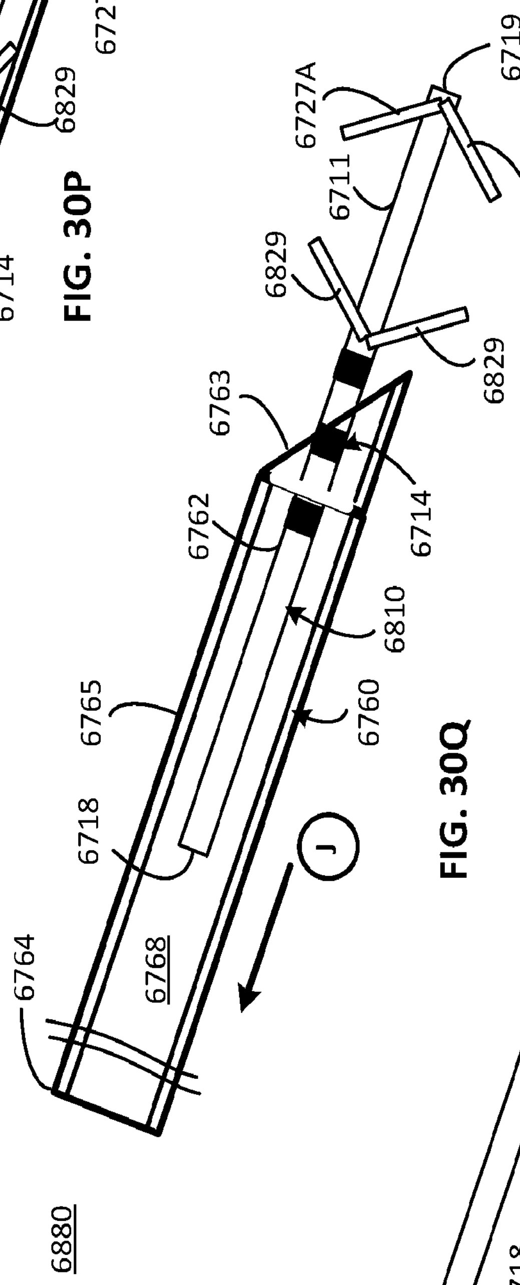
Figure 30R:
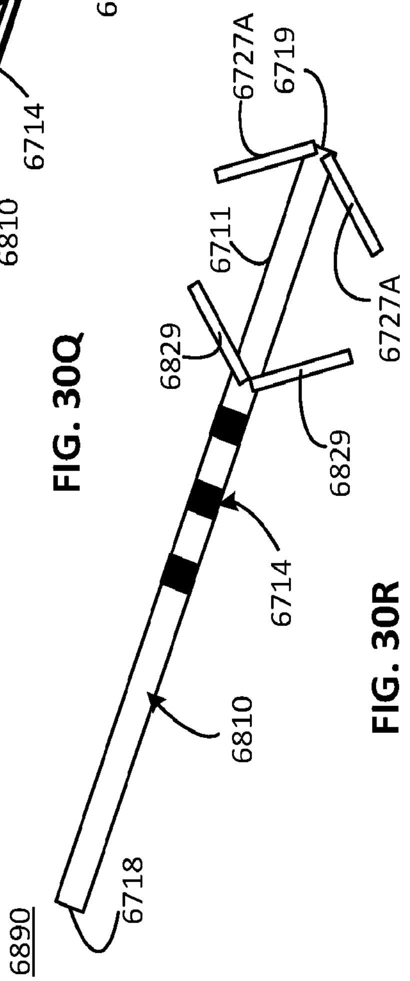

Once the stimulation device 6810 has been delivered and positioned as desired relative to a target tissue, the needle 6760 is slidably withdrawn from the stimulation device 6810, as represented by directional arrow J in FIG. 30Q. This maneuver results in the release of tines 6727A, 6829 from their collapsed state (FIG. 30P) into an expanded state (FIG. 30Q) so that the tines 6727A, 6829 may engage surrounding non-nerve tissues to secure the stimulation device 6810 relative in a robust, stable position in stimulating relation to a target tissue (e.g. nerve).

Upon further slidable removal of needle 6760 (FIG. 30Q) from the now implanted stimulation device 6810 (and from the pertinent portion of the patient's body), the stimulation device 6810 remains chronically implanted (in the configuration shown in FIG. 30R) in the patient's body at the desired stimulation site.

Figure 30S:
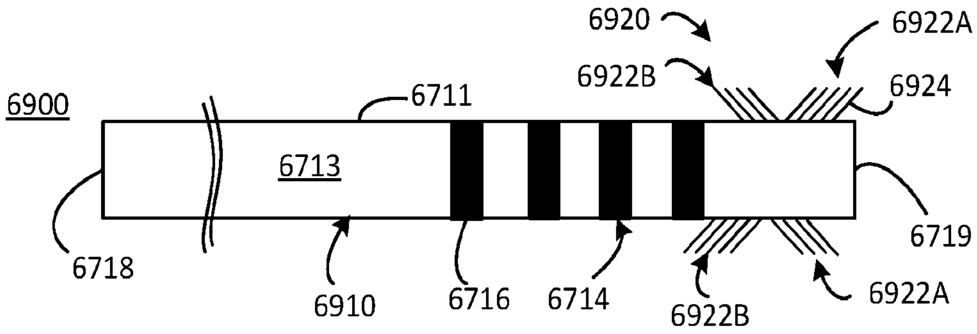

FIG. 30S is a diagram 6900 including a side view schematically representing an example stimulation device 6910. In some examples, the stimulation device 6910 comprises at least some of substantially the same features and attributes as the stimulation device 6810 described in association with at least FIGS. 30L-30R, except with stimulation device 6910 comprising anchoring structure 6920 instead of the anchoring arrangement of tines 6727A, 6829 in the stimulation device 6810 of FIGS. 30L-30R. As in the examples of stimulation devices 6710, 6810, the stimulation device 6910 may comprise a distal portion of a stimulation lead body which extends proximally from the proximal end 6718 of the stimulation device 6910.

As shown in FIG. 30S, in some examples the anchoring structure 6920 comprises a plurality of anchor elements 6924 which protrude from the sides 6711 of the body 6713 of the stimulation device 6910. In some examples, the anchor elements 6924 may be grouped into different arrays 6922A, 6922B while in some examples, the anchor structure 6920 may comprise a single cluster of elements 6924.

It will be understood that in some examples, the elements 6924 may extend about an entire periphery (e.g. circumference of body 6713).

As shown in FIG. 30S, the anchor structure 6920 is positioned distal to the electrode array 6716, being between the electrode array 6714 and the distal end 6719 of the body 6713 of the stimulation device 6910.

In this configuration, the position of the anchor structure 6920 on just one end (e.g. the distal end) of the electrode array 6714 may prevent or minimize "lead elongation", i.e. elongation of the lead body 6713 which may potentially be caused by muscle movement when anchoring elements (e.g. tines) are present on opposite ends of the electrode array 6714.

In some examples, the elements 6924 may comprise a filament (e.g. fine thread) which is flexible and resilient, and biased to extend outward from the side 6711 of body 6713. The filament may be formed of a polymer material, such as but not limited to, nylon, propylene, silk, polyester, trimethylene carbonate, and the like. In some examples, such filaments may be resorbable or may be non-resorbable.

In some examples, each element 6924 may comprise a diameter (or greatest cross-sectional dimension) of about 0.05 to about 0.40 millimeters. In some examples, each element 6924 may comprise a length of about 0.2 to about 2 millimeters. In some examples, each element 6924 may comprise a length about 0.5 percent to about 50 percent of a diameter of the lead body 6710 in the region of the electrode array 6714 and/or at distal end 6719. In some examples, the anchor structure 6920 may be embodied as a matrix of heterogeneous elements via filaments having pseudo-random sizes, shapes, orientations and/or positions exhibiting more variation than a plurality of identical discrete elements (e.g. 6927 in FIG. 30T), which may be visually recognizable. Meanwhile, all of the various features of the matrix of heterogeneous elements may not be readily visually recognizable. Among other features, this heterogeneous matrix may enable fixation in both (e.g. opposite) orientations (along length of stimulation portion/lead) and ease deliverability of the lead, lead portions. At least some example implementations of anchor structures 7000, 7100 comprising a matrix of heterogeneous elements are described later in association with at least FIGS. 30V-30W. In some examples, the heterogeneous elements may sometimes be referred to as heterogeneous fixation elements.

In some examples, the anchor structure 6920 may comprise a plurality of well-defined, discrete elements but with at least some of the discrete elements comprising a size, shape, orientation, and/or position different from a size, shape, orientation, and/or position of other respective discrete elements of the anchor structure 6920.

In some examples, the anchor structure 6920 may enhance some example methods of implantation of a stimulation device at least because the respective elements 6924 exhibit a low profile relative to an outer diameter of the body 6713 of the stimulation device 6910 such that the stimulation device 6910 (FIG. 30S-30) can be delivered via hollow insertion needle 6760 without a sleeve (e.g. 6751 in FIG. 30D, 6830 in FIG. 30O, etc.) or similar elements while still robustly securing the stimulation device 6910.

Figure 30T:
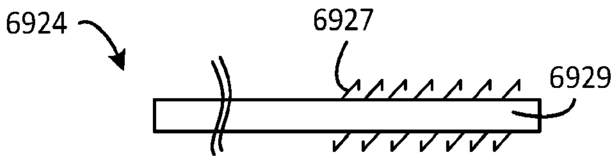

As further shown in the greatly enlarged side view of just one element 6924 in FIG. 30T, in some examples, at least some (or all) of the elements 6924 may comprise protrusions 6927 on their surfaces, which in some examples may comprise barbs, hooks, or other sharp tipped structures. In some examples, the protrusions 6927 may be present on just a portion of the element 6925, such as but not limited to a distal portion 6929 of the element 6924. However, in some examples, the protrusions 6927 may be present on the entire or substantially entire surface of the element 6924. In yet other examples, groups of protrusions 6927 may be positioned in spaced apart clusters, which are spaced apart from each other along and around the surface of the element 6924.

It will be further understood that the protrusions 6927 are not strictly limited to structures having a sharp-tip or hook but may comprise structures comprising a rounded edge while including a sticky surface coating or formed as a non-sharp tipped member which can securely engage a surrounding non-nerve tissue in close proximity to a target stimulation site.

With regard to the example stimulation device 6910 in FIGS. 30S-30W, it will be understood that in some examples the anchoring structure 6920 may be located solely proximally of the electrode array 6714 such that no similar anchoring structure 6920 is located distal to the electrode array 6714.

However, in some examples, a first anchoring structure 6920 may be present distal to the electrode array 6714 as shown in FIGS. 30O-30Q and a second anchoring structure, similar to anchoring structure 6920, may be present proximal to the electrode array 6714 so that the stimulation device 6910 bears resemblance to the stimulation device 6710 of FIG. 30C, at least to the extent that some anchoring structure or elements are present on opposite sides of the electrode array 6714.

Figure 30U:
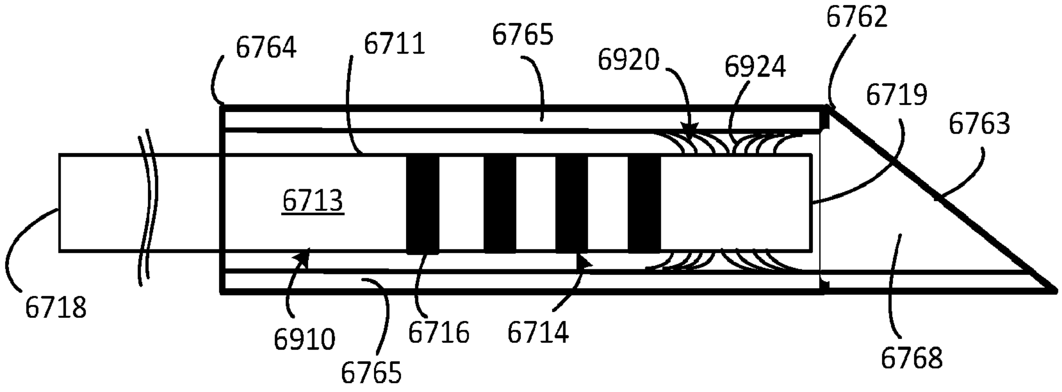

FIG. 30U is a diagram including a side view schematically representing an example arrangement 6950 of an example device and/or example method of implantation including the stimulation device 6910 slidably, removably inserted within the hollow insertion needle 6760. In some examples, the needle 6760 may comprise at least some of substantially the same features and attributes of the needle 6760 and associated example methods as previously described in association with at least FIGS. 30C-30N.

As shown in FIG. 30U, upon insertion of stimulation device 6910 within lumen 6768 of hollow insertion needle 6760, the elements 6924 of anchor structure 6920 become at least partially collapsed against side 6711 of stimulation device 6910. In a manner similar to previously-described examples, with the stimulation device 6910 carried within the hollow insertion needle 6760, the combination of these elements are finally positioned within the vicinity of a target stimulation location. Needle 6760 is then withdrawn (represented by directional arrow Q) to leave the stimulation device 6910 in stimulation relation to the target stimulation location and to enable the elements 6924 of anchor structure 6924 to engage surrounding non-nerve tissues to robustly secure the stimulation portion (e.g. electrode array 7614) in the stimulating relation position.

Figure 30V:
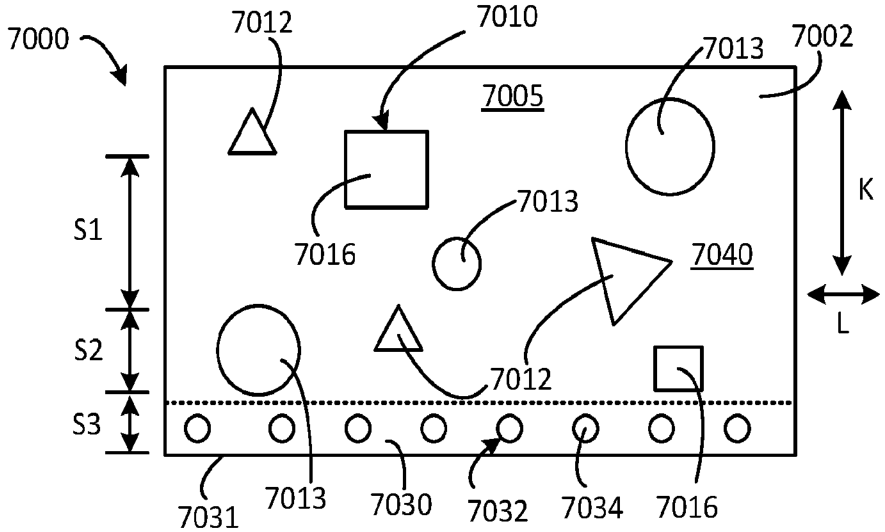

FIG. 30V is a diagram including an enlarged top view schematically representing an example anchor structure 7000 formed on, and including as part of the anchor structure, a base 7002. In some examples, the anchor structure 7000 may comprise an analogous example implementation of the anchor structure 6920 in FIGS. 30S-30U and may comprise at least substantially the same features and attributes as the anchor structure 6920, particularly with respect to providing a matrix of heterogeneous elements. However, in some examples, the anchor structure 7000 may have wide applicability to act as an anchor or position-influencing element.

As shown in FIG. 30V, the anchor structure 7000 may comprise an array 7010 of example heterogeneous elements 7012, 7013, 7016 which together may form a matrix, network, or the like which may overlap or otherwise be juxtaposed relative to each other to create a generally traction-favoring surface profile. It will be understood that in some examples, the various heterogeneous elements of array 7010 may be positioned much closer to each other than shown in FIG. 30V in order to touch, overlap, partially interlock or interfere with each other, etc. so as to increase the frictional properties (e.g. slide-resistance) of the anchor structure or to reduce the frictional properties (e.g. slidability) of the anchor structure, depending on the type, size, orientation, coating, etc. of the particular arrangement of elements of the array 7010.

In general terms, the various elements of the array 7010 may comprise a flexible, resilient material. However, depending on the goals re slidability or slide-resistance, some elements may be firmer or softer.

In some examples, the particular types, spacing between, orientation, position, relative flexibility, etc. of the heterogeneous elements of the array 7010 may be selected and formed to correspond to a selectable coefficient of kinetic friction to enable a desired bias for controlled slidable movement relative to tissues within a patient's body and/or relative to lumen within a patient's body and/or to correspond to a selectable coefficient of static friction to enable a desired bias to remain statically positioned at a chose location relative to tissues or within a lumen.

In some examples, whether or not expressed formally as a coefficient of kinetic or static friction, the various heterogeneous elements of the array 7010 are selected and formed according to their shape, position, spacing, orientation relative to each other, relative flexibility, etc. to create a desired anchoring effect while still permitting some degree of slidable advancement.

As shown in FIG. 30V, at least some example shapes (as seen in cross-section from a top view) may comprise elements with shapes which are triangular 7012, circular 7013, rectangular 7016, and the like. The elements also may have different sizes (e.g. S2), and spacing (e.g. S1) between each other or relative to an edge 7031 (e.g. S2) of the base 7002. In some examples, at least some of the elements of array 7010 may comprise hook-shapes, J-shapes, U-shapes, etc. In some examples, at least some of the elements or the juxtaposed pattern of such elements, may promote tissue in-growth and long term fixation, such as but not limited to, apertures formed in such elements or by the juxtaposition of some of the respective elements.

The various elements also may be organized in directional patterns, such as being in rows aligned in a first orientation (K) or second orientation (L) which are orthogonal to each other, or in other non-orthogonal orientations. Such orientations may be used to effect selectable bias to permit or prevent slidable movement in various directions, which may enhance positioning and/or anchoring of the medical element on which the anchor structure 7000 is located.

In some examples, at least some elements of the array 7010 may be arranged along a periphery 7030 of the base 7002 in a row or other organizational pattern. The elements 7034 may have the same size, shape, positions, etc. or may have sizes, shapes, positions different from each other. By providing this configuration along one or more edges 7031 of the base 7002, the anchor structure 7010 may influence slidability or slide-resistance in particular directions. In a related aspect, the presence or absence of elements of array 7010 in an interior portion 7040 also may provide analogous influences, with or without the edge-type rows, etc. of such elements.

In some examples, the surface 7040 of the base 7002 and/or the elements of array 7010 also may comprise a coating with desired lubricous and/or frictional qualities, which may be selected to work synergistically with the various shapes, sizes, positions, spacing, orientation, etc. of the elements of array 7010.

Figure 30W:
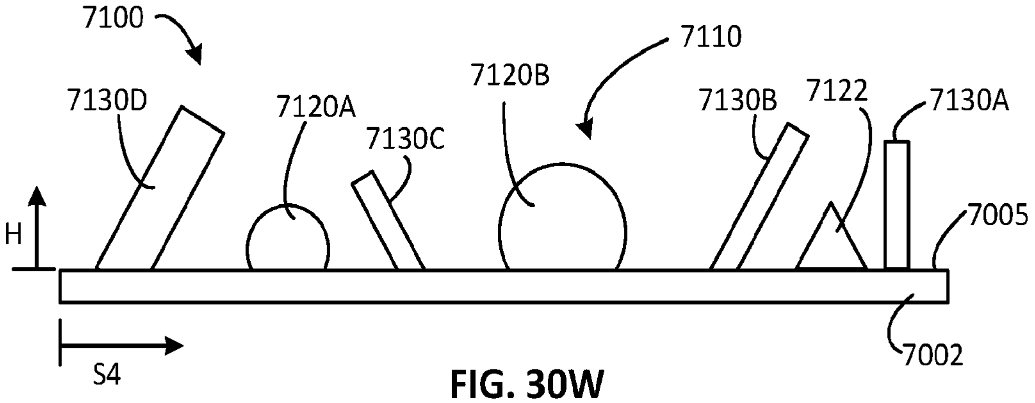

FIG. 30W is a diagram including an enlarged side view schematically representing an example anchor structure 7100 formed on, and including as part of the anchor structure, a base 7002. In some examples, the anchor structure 7100 may comprise an analogous example implementation of the anchor structure 6920 FIGS. 30S-30U and may comprise at least substantially the same features and attributes as the anchor structure 6920, particularly with respect to providing a matrix or network of heterogeneous elements. However, in some examples, the anchor structure 7100 may have wide applicability to act as an anchor or position-influencing element.

In some examples, the anchor structure 7100 in FIG. 30W may comprise at least some of substantially the same features and attributes as anchor structure 7000 in FIG. 30V.

As shown in FIG. 30V, the array 7110 of elements comprise different shapes, sizes, positions, spacing, orientations, etc. For example, rectangular elements 7130A, 7130B, 7130C, 7130D exhibit differing angular orientations (e.g. relative to a horizontal plane through which base 7002 extends), which may sometimes be referred to as being bi-directional or multi-directional. Other elements may comprise spherical shaped elements 7120A, 7120B, pyramid-shaped elements 7122, etc. The respective elements of array 7110 may be formed according to a selectable height (per height arrow H), which may vary from each other as part of a desired effect to promote slidability or slide-resistance, depending on the intended use of the anchor structure and medical element to which is formed/attached. It will be further understood that some shapes, such as the spherical elements 7120A, 7120B may be more likely to enhance slidability because of their smooth convex surface while some shapes, such as the pyramid element 7122 or rectangular elements (7130A-7130D), may enhance slide-resistance, depending on their orientation. In some examples, directional arrow S4 may represent relative horizontal spacing between elements of array 7010.

In some examples, the base 7002 may formed in a two-dimensional plate shape such that the anchor structure 7000 or 7100 may be readily formed or attached to a back side of a carrier opposite to an electrode side of a stimulation portion, such as a paddle electrode. However, in some examples, the base may comprise a cylindrical shape such that the elements of array 7010 (FIG. 30V) and/or array 7110 (FIG. 30W) may extend circumferentially outward from a cylindrically shaped lead on which the array 7010 or 7110 is formed or attached.

Figure 31A:
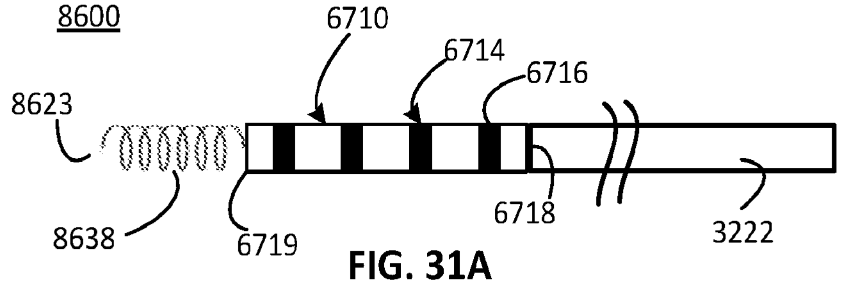
FIGS. 31A-31G are diagrams including a side view schematically representing example axial stimulation elements including examples anchor elements.

FIG. 31A is a diagram including a side view schematically representing an example arrangement 8600 including a stimulation element 6710 comprising a linear array 6714 of spaced apart electrodes 6716 (e.g. ring electrodes, split ring electrodes, or other electrodes). The stimulation device 6710 may comprise a distal end 6719 and an opposite proximal end 6718, which is supportable on (or which extends from) a stimulation lead body 3222. In some examples, the example arrangement 8600 (including stimulation element 6710) comprises at least some of substantially the same features and attributes as at least some of the stimulation devices in examples of the present disclosure, as described in association with at least FIGS. 1-30W.

In addition, the example arrangement 8600 comprises an anchor element 8638 in the shape of a spiral or helix, which may be used to anchor a distal end 6719 of stimulation device 6710 relative to non-nerve tissue to thereby secure the stimulation element in stimulating relation to a target nerve location. In some examples, the anchor element 8638 may be formed as a flexible, resilient member to at least partially wrap around a non-nerve structure (e.g. tendon) and/or have its tip 8623 configured to puncture or penetrate a non-nerve structure near the target nerve location.

Figure 31B:
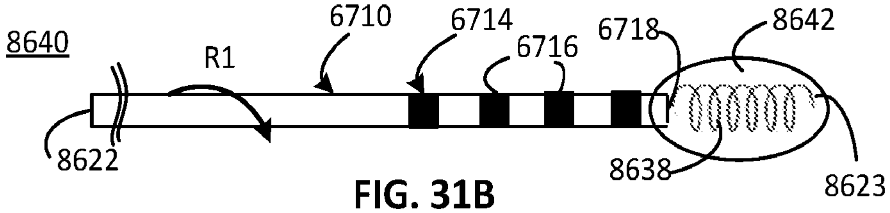

FIG. 31B is a diagram including a side view schematically representing an example arrangement 8640 including a stimulation device 6710 and comprising at least some of substantially the same features and attributes as the example arrangement 8600 in FIG. 31A, except further comprising a dissolvable capsule 8642. In some examples, the dissolvable capsule 8642 encapsulates the anchor element 8638 prior to and during delivery (e.g. via an implant-access incision, via delivery tools, etc.) of the stimulation device 6710 to its target stimulation location. In one aspect, the capsule 8642 comprises a dissolvable material, which when exposed to fluids and/or the temperature within a patient's body during implantation, will dissolve within a suitable time frame during which the capsule 8642 remains intact at least until the stimulation lead is delivered to its target stimulation location and a relatively short time thereafter. Via this arrangement, the capsule 8642 may prevent the anchor element 8638 (including tip 8623) from engaging tissues prior to the stimulation portion (e.g. electrode array 6714) reaching its target stimulation location. However, after the stimulation device 6710 has been delivered to the intended location, after a short period of time the capsule 8642 dissolves to expose the anchor element 8638 at which time a clinician may rotate the stimulation device 6710 (as represented by directional arrow R1) to cause the exposed anchor element 8638 to rotatably engage the surrounding non-nerve tissue to robustly secure the electrode array 6714 in stimulating relation to the target nerve stimulation location.

In some examples, the material forming the dissolvable capsule 8642 may comprise a sugar-based material or other material which dissolves reasonably quickly (but not instantly) when exposed to body fluids, body temperature, etc. within a patient's body. The particular composition of the material may be selected to control or influence the time duration before the capsule 8642 starts and/or completes dissolving within the patient's body.

Figure 31C:
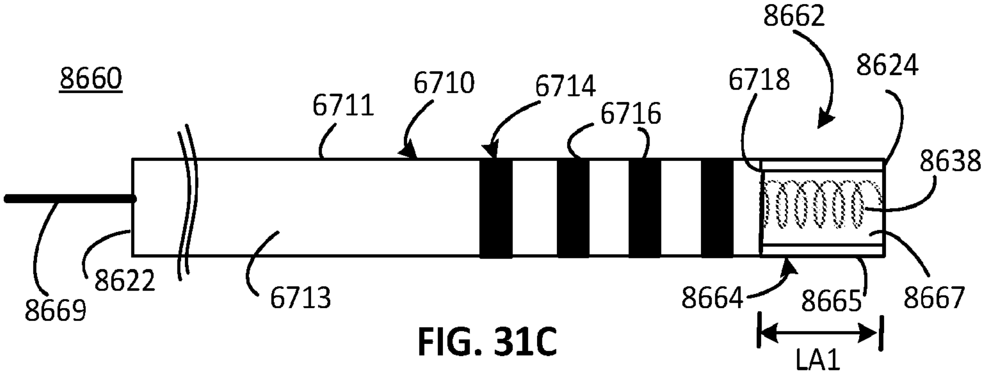
Figure 31D:
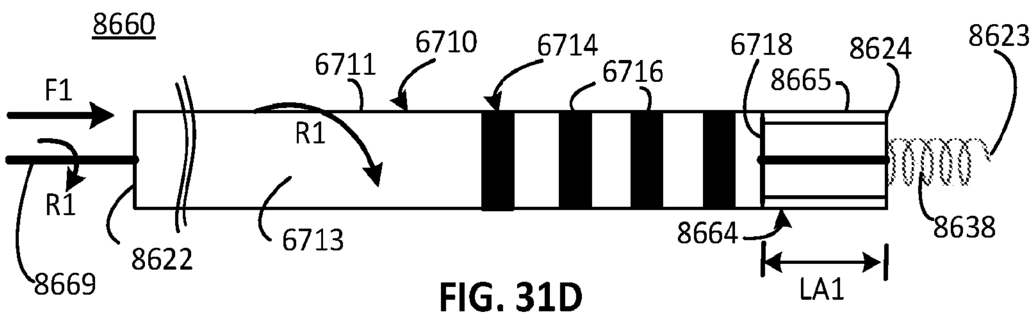

FIGS. 31C-31D are diagrams including a side view schematically representing an example arrangement 8660 including a stimulation device 6710 and comprising at least some of substantially the same features and attributes as the example arrangement 8600 in FIG. 31A, except with the anchor element 8638 being selectively moveable from a retracted position shown in FIG. 31C to an extended position shown in FIG. 31D.

As shown in FIG. 31C, the stimulation device 6710 may comprise an array 6714 of spaced apart electrodes 6716 and an anchor structure 8662 positioned distal to the electrode array 6714 and defining a distal portion of the stimulation device 6710. In some examples, the anchor structure 8662 may comprise a hollow tubular frame portion 8664 including a sidewall 8665 to define a lumen 8667. The anchor structure 8662 also comprises an anchor element 8638 (e.g. helix, coil, and the like) releasably retained (e.g. temporarily housed) within the lumen 8667 of the tubular frame portion 8664. In this configuration, the stimulation device 6710 is adapted for insertion into and within delivery tools and/or for advancement within and among tissues of a patient's body while preventing anchor element 8638 from engaging such tissues at least until a stimulation portion (e.g. electrode array 6714) of the stimulation device 6710 (of a stimulation lead) has been delivered to its target stimulation location at which it will become chronically implanted. Once in that chronic implant location, the anchor element 8638 is released to extend outwardly (e.g. protrude relative to) from the distal end 8624 of the stimulation device 6710 so that the anchor element 8638 may engage surrounding non-nerve tissues and thereby robustly and reliably secure at least the stimulation portion (e.g. electrode array 6714) in stimulating relation to the identified target stimulation location. In some examples, as shown in FIGS. 31C-31D, the anchor element 8638 may be supported by a rod 8669 or other element such that translational movement (as represented by directional arrow F1) and/or rotational movement (as represented by directional arrow R1) of rod 8669 (or other element) will cause the extension of the anchor element 8638 into the position shown in FIG. 31D. In some examples, the rod 8669 may extend through and within a lumen within the body 6713 of the stimulation device 6710 (and supporting lead). In some examples, mechanisms other than rod 8669 may be used to activate and/or otherwise cause movement of the anchor element 8638 from its retracted position (FIG. 31C) to its extended position (FIG. 31D). In some such examples, the rod 8669 and/or other mechanisms may be detachable from the anchor element 8638.

With the anchor element 8638 in its extended position, the user may rotate (e.g. twist) the body 6713 of the stimulation device 6710 (as part of twisting the entire lead supporting the body of the stimulation device 6710) to cause the anchor element 8638 to securely engage surrounding non-nerve tissue, as mentioned above, which in turn secures the electrode array 6714 in stimulating relation to the identified target stimulation location of a nerve.

In some examples, the tubular frame portion 8662 may comprise a length (LA1) which is generally the same as or slightly longer than a length of the anchor element 8638 so that when the anchor element 8638 is in its retracted position (FIG. 31C), the anchor element 8638 is prevented from engaging surrounding non-nerve tissues until the anchor element 8638 is moved into its extended position as noted above.

Figure 31E:
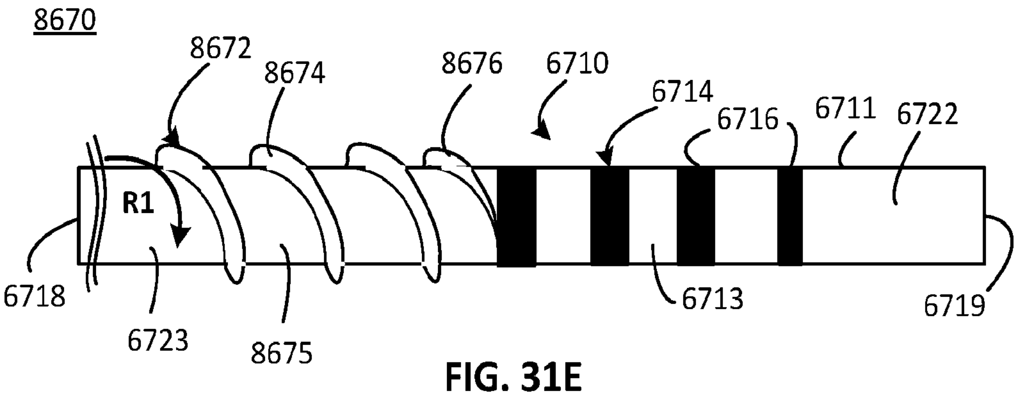

FIG. 31E is a diagram including a side view schematically representing an example arrangement 8670 comprising an example device for, and/or example method of, implantation of stimulation device 6710. In some examples, the stimulation device 6710 may comprise at least some of substantially the same features and attributes as the stimulation device in the example arrangement 8600 of at least FIG. 31A, except including a helical-type anchor element 8672 formed or mounted on a body 6713 of the stimulation device 6710 (FIG. 31E) instead of an end-mounted anchor element 8638 in FIG. 31A. In some examples, the anchor element 8672 comprises a helical screw thread extending outward from side 6711 of body 6713 of the stimulation device 6710 with gaps 8675 extending between successive threads 8674 of the anchor element 8672. In some examples, an utmost distal thread 8676 of the screw thread 8672 terminates proximal to the electrode array 6714. In some such examples, the utmost distal thread 8676 may terminate in close proximity to the electrode array 6714, which may in some examples further ensure that the electrode array 6714 remains robustly in stimulating relation to a target stimulation location. The screw thread 8672 is sized and shaped to engage surrounding non-nerve tissues upon a clinician exerting, during implantation, rotation (e.g. twisting) of the body 6713 of the stimulation device 6710 (and its supporting stimulation lead body), as represented by directional arrow R1.

In a manner similar to that described with respect to at least some of the previously described examples tines, in some examples the electrodes 6716 of array 6714 may be spaced apart by a distance large enough such at least some threads 8676 may be interposed between adjacent electrodes 6716 of the array 6714. This arrangement may help further co-locate the anchoring forces (created by the gripping action of the threads 8676 relative to surrounding non-nerve tissue) with the elements (e.g. electrodes 6716) which are desired to be secured robustly in stimulating relation to a target stimulation location. While not shown in explicitly in FIG. 31E, at least some threads 8674 also may be located distal to the electrode array 6714, whether or not some threads 8674 are present proximal to electrode array 6714 and/or interposed among electrodes 6716 of the electrode array 6714.

Figure 31F:
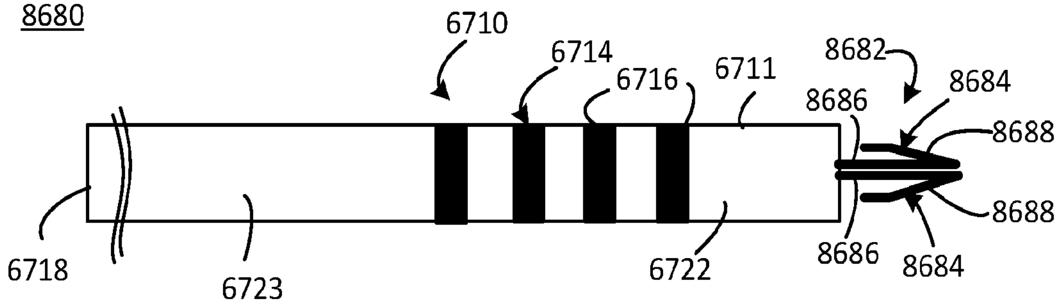
Figure 31G:
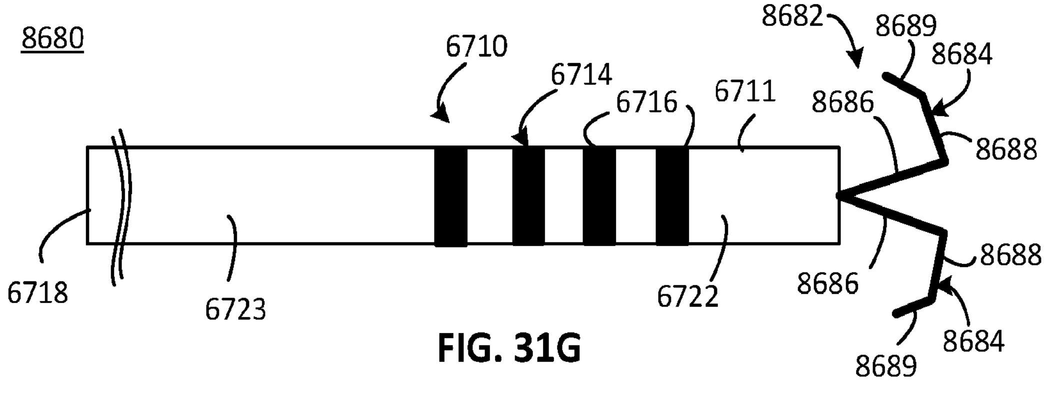

FIGS. 31F-31G are diagrams including a side view schematically representing an example arrangement 8680 comprising an example device for, and/or example method of, implantation of stimulation device 6710. In some examples, the stimulation device 6710 may comprise at least some of substantially the same features and attributes as the stimulation device of at least FIG. 31A, except with the end-mounted anchor structure 8682 taking the form of a non-helical structure. FIG. 31F shows the anchor structure 8682 in a collapsed, first state prior to deployment while FIG. 31G shows the same anchor structure 8682 in an expanded, second state upon deployment within the patient's body in proximity to a target stimulation location for electrode array 6714.

As further shown in both FIGS. 31F-31G, in some examples the anchor element structure 8682 may comprise multiple elements 8684, each of which may comprise a base portion 8686, arm 8688, and extension 8689. The base portion 8686 of each element 8684 is mounted to the distal portion 6722 of the stimulation device 6710 and in some examples, the base portion 8686 of the multiple elements 8684 may be connected together or form a common element. In some examples, arm 8688 extends in a generally opposite orientation from base portion 8686 and extension 8689 may extend at some angle relative to the arm 8688. In general terms, the size, shape, and relative orientations of the base portion 8686, arm 8688, and extension 8689 are arranged together so that in a retracted/collapsed state as shown in FIG. 31F, each element 8682 exhibits a compressed volume which is capable of expanding to a much larger volume as shown in FIG. 31G. In some examples, each element 8684 may comprise a shape-memory material (e.g. Nitinol, other) such that the anchor structure 8682 can remain in its collapsed/reduced volume state (FIG. 31F) until the anchor structure 8682 is placed within another tool (e.g. cannula, hollow sheath, sleeve, other) and/or desired environment (e.g. within the patient's body at desired location) in which expansion of the anchor structure 8682 into its expanded volume (FIG. 31G) will be appropriate. In particular, once placed within the patient's body, the shape memory material will respond to the increased temperature and transition from the collapsed state (FIG. 31F) to the expanded state (FIG. 31G). However, using a delivery tool such as, but not limited to, at least some of the example delivery tools in the various examples of the present disclosure, the anchor structure 8682 may be prevented from fully expanding by the walls (or other elements) of the delivery tool until the delivery tool is within the patient's body at a desired location and the delivery tool is withdrawn, thereby permitting the elements 8684 of anchor structure 8682 to fully expand via a slight divergence of the base portions 8686 (relative to each other), unfolding of the arms 8688 relative to the base portions 8686, and unfolding of the extensions 8689 relative to the arms 8688 due to the automatic, natural activation of the shape memory features of the respective elements 8684 of anchor structure 8682.

Among other aspects, in its expanded state (FIG. 31G), the arms 8688 and extensions 8689 of each element 8684 have an opposite, second orientation (i.e. a rearward orientation) relative to a first orientation (i.e. forward) of the base portion 8686, such that the arms/extensions 8688/8689 effectively form a hook or catch which may further facilitate robust securement of the stimulation device 6710 relative to the surrounding non-nerve tissues.

It will be understood that the shape, size, number, etc. of the elements 8684 of anchor structure 8682 may take a wide variety of forms and that the particular arrangement of the base portion 8686, arm 8688, and extension 8689 of elements 8684 as shown in FIGS. 31F-31G is just one example implementation.

Among other aspects, the use of shape memory material to form elements 8684 may enable the anchor structure 8682 to achieve a significantly smaller collapsed volume and a significantly larger, expanded volume than might otherwise be achieved in the absence of the shape memory material, which eases both delivery and deployment, respectively, of the anchor structure 8682. As shown in FIG. 31G, in its fully expanded state the anchor structure 8682 may extend significantly further outward from the sides 6711 of the stimulation device 6710 than may otherwise be achievable via at least some other anchors present on a body of a stimulation device, which in turn, may enhance a robust securing of the electrode array 6714 to be in stimulating relation to a target stimulation location.

However, in some examples, anchor structure 8682 may be formed of materials other than a shape memory material with a delivery tool being relied upon to retain the expandable anchor structure 8682 in a primarily collapsed stated within a delivery tool until the stimulation device 6710 is in a location suitable for deployment of the anchor structure 8682 to its fully expanded state within and relative to surrounding non-nerve tissues.

With regard to the various example arrangements (e.g. devices, methods, etc.) throughout the present disclosure which may comprise implanting more than one lead, such as but not limited to, bifurcated leads, it will be understood that at least some of the various example anchors (e.g. tines, filaments, elements, etc.) for securing a stimulation lead may be included on each lead of a bifurcated lead. In one aspect, doing so will secure each lead independently relative to the other lead(s). Among other features, this independent anchoring of multiple leads (e.g. bifurcated leads, other) may permit relative motion of the leads relative to each other while still maintaining robust securement of the stimulation portion of each respective lead at the respective target stimulation location. This arrangement, in turn, may enhance patient comfort.

It will be understood that the various anchors, delivery tools, elements and associated delivery methods as described throughout various examples of the present disclosure with regard to stimulation devices, etc. may be used to deliver, implant, etc. sensing leads and/or other types of leads, appropriately shaped/sized implantable medical elements, etc.

FIG. 32A is a diagram including a side view schematically representing an example arrangement 4000 including intravascular pathways and/or other access for delivering a stimulation element to target stimulation locations at the ansa cervicalis-related nerve 316 and/or hypoglossal nerve 305. In some examples, the example arrangement 4000 may comprise stimulation elements (and associated methods) comprising at least some of substantially the same features and attributes, or an example implementation of, the previously described example arrangements of the present disclosure.

FIG. 32A depicts the ansa cervicalis-related neve 316 in the same general manner as in at least FIG. 2, and further depicts the anterior jugular vein 4031, thyroid vein 4021 (inferior 4025 and superior 4023), and the sternohyoid muscle 4060, which overlies (e.g. anterior to) the sternothyroid muscle 4062. It will be understood that just portions of the above-identified anatomical features as shown in FIG. 32A for illustrative simplicity and clarity.

As shown in FIG. 32A, in at least some patients, one or both of the anterior jugular vein 4031 and the inferior thyroid vein 4025 pass near at least some of the portions of the sternothyroid branches (e.g. 342) of the ansa cervicalis nerve loop 319. Accordingly, via an example device and/or example method, a stimulation element may be delivered intravascularly via one or both such veins 4031, 4025 to be in transvascular stimulating relation to a portion of the ansa cervicalis-related nerve 316 in order to increase and/or maintain upper airway patency by causing contraction of the sternothyroid muscle 4062 and/or sternohyoid muscle 4060.

As further shown in FIG. 32A, the superior thyroid vein 4023 may pass near a superior root 325 or other portions of the ansa cervicalis-related nerve 316. Accordingly, in an example device and/or example method, a stimulation element may be delivered intravascularly via the superior thyroid vein 4023 to be positioned adjacent to, and in transvascular stimulating relation to, the superior root 325 of the ansa cervicalis-related nerve 316 in order to increase and/or maintain upper airway patency by causing contraction of at least some muscles (e.g. sternothyroid, sternohyoid, etc.) innervated by the superior root 4023 of the ansa cervicalis-related nerve 316. As previously noted, among other effects, contraction of such muscles may cause inferior movement of the larynx, which may increase and/or maintain upper airway patency to thereby prevent or ameliorate sleep disordered breathing, such as obstructive sleep apnea.

In some examples, such intravascular delivery (for transvenous stimulation) via the anterior jugular vein 4031 and/or the thyroid vein 4021 may be implemented via at least some of substantially the same features and attributes of the example stimulation elements as previously described in association with at least FIGS. 1-31, and in particular with respect to at least some of substantially the same features and attributes of the intravascular delivery examples in association with at least FIGS. 15A-15C. For instance, just one or both of stimulation elements 1810A, 1813A may be provided for such intravascular delivery and transvenous stimulation via veins 4031, 4021 in the example arrangement 4000 of FIG. 32A. Moreover, more than one transvascular (e.g. transvenous) stimulation lead and/or more than one branch of such transvascular stimulation leads may be implanted to provide stimulation of multiple stimulation targets of the ansa cervicalis-related nerve and/or other upper airway patency-related tissues.

In some examples, other portions of the vasculature may be used to intravascularly deliver a stimulation element to be in stimulating relation to a target nerve location, including but not limited to, the ansa cervicalis-related nerve 316 and/or other upper airway patency-related tissues.

FIG. 32B is a diagram like the diagram in FIG. 32A, except further schematically representing an example arrangement 4100 in which at least two microstimulators 4113A, 4113B are implanted within a head-and-neck region 520 (e.g. also FIG. 11A). In some examples, the example arrangement 4100 may comprise stimulation elements (and associated methods) comprising at least some of substantially the same features and attributes and/or comprising an example implementation of, the previously described example arrangements of the present disclosure.

As shown in FIG. 32B, a first microstimulator 4113A is delivered within and through the vasculature (i.e. intravascularly) to be adjacent to, and in transvascular stimulating relation to, a target nerve. In one example shown in FIG. 32B, the blood vessel comprises a superior thyroid vein 4023 and the target nerve comprises a superior root 325 of the ansa cervicalis-related nerve 316. However, it will be understood that this depiction is merely representative and that the microstimulator 4113A may be delivered intravascularly within and through other vessels such as, but not limited to, the anterior jugular vein 4031, external jugular vein, and/or other blood vessels (e.g. superior laryngeal vein). With this in mind, the microstimulator 4113A may be placed in transvascular (e.g. transvenous) stimulating relation to nerve branches of the ansa cervicalis-related nerve 316 other than the superior root 325.

Meanwhile, as further shown in FIG. 32B, a second microstimulator 4113B is implanted subcutaneously (or percutaneously) to be in stimulating relation to a target nerve location and secured in place relative to a non-nerve tissue 2929 via an anchor element 2927. In one example depicted in FIG. 32B, the second microstimulator 4113B is placed in stimulating relation to nerve branches 342A, 342B (of the ansa cervicalis-related nerve 316) associated with at least the sternothyroid and sternohyoid muscles. However, it will be understood that this depiction is merely representative and that the microstimulator 4113B may be implanted relative to other nerve branches, roots, etc. of the ansa cervicalis-related nerve 316. With this in mind, the microstimulator 4113A may be placed in stimulating relation to nerve branches of the ansa cervicalis-related nerve 316 other than the branches 342A, 342B.

Moreover, in some examples, in general terms the microstimulator 4113B may be secured relative to a non-nerve tissue 2929 and relative to its target nerve locations via at least some of the anchoring elements described in association with at least FIGS. 6A-6B, 22A-22B, and/or 27A-31. As further shown in FIG. 32B, depending on the particular nerve branch to be stimulated, the anchor element 2927 may comprise at least one the anchor elements (or analogous elements) identified in legend 2950 "Anchor Locations" in FIG. 32B.

Via the example arrangement 4100, multiple different nerve locations of the ansa cervicalis-related nerve 316 may be stimulated in a coordinated manner to more fully leverage the physiologic processes associated with a particular goal, such as increasing and/or maintaining upper airway patency.

In some such examples, and as noted relative to other examples of the present disclosure, the respective microstimulators 4113A, 4113B may communicate (e.g. wirelessly) with each other and/or with a third device which is implanted or external in order to facilitate control, therapy, etc.

Of course, depending on particular patient anatomy or other purposes/goals, just one of several implanted stimulation elements (e.g. microstimulators 4113A, 4113B) may be activated to apply stimulation, sensing, etc.

In some examples, one or both of the stimulation elements 4113A, 4113B may comprise a cuff electrode, paddle electrode, axial array, etc. (supported by a IPG 533) may be implanted instead of one or both of the stimulation elements 4113, 4113B comprising a microstimulator. Accordingly, one variation example arrangement may comprise the microstimulator 4113A being intravascularly delivered and implanted relative to some portion of the ansa cervicalis-related nerve 316 (whether at the superior root 325 or elsewhere) and the other stimulation element 4113B comprising something other than a microstimulator.

As noted elsewhere, it will further understood that in some examples, the general principles associated with the example arrangement 4100 (and other example stimulation arrangements of the present disclosure) may be used to implement the example arrangement in other areas of a patient's body to treat conditions other than sleep disordered breathing. For example, the arrangement 4100 of stimulation elements (e.g. microstimulators 4113A, 4113B), anchors, etc. may be deployed within a pelvic region to treat urinary and/or fecal incontinence or other disorders, such as via stimulating the pudendal nerve, which may cause contraction of the external urinary sphincter and/or external anal sphincter. While not shown explicitly in association with FIG. 32B, it will be understood that associated sensing elements described within the present disclosure (for sensing physiologic data relative to the condition of interest) may be deployed in association with the various example arrangements for stimulating multiple nerve targets. However, other body regions and/or disorders may be suitable candidates for an example arrangement (e.g. 4100) in which multiple nerve targets (of a single nerve or of wholly different nerves) are available to be stimulated to treat one type of physiologic behavior.

Figure 32D:
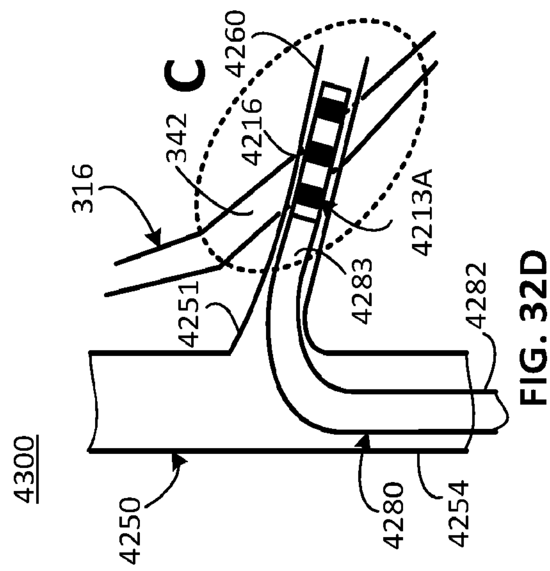
Figure 32C:
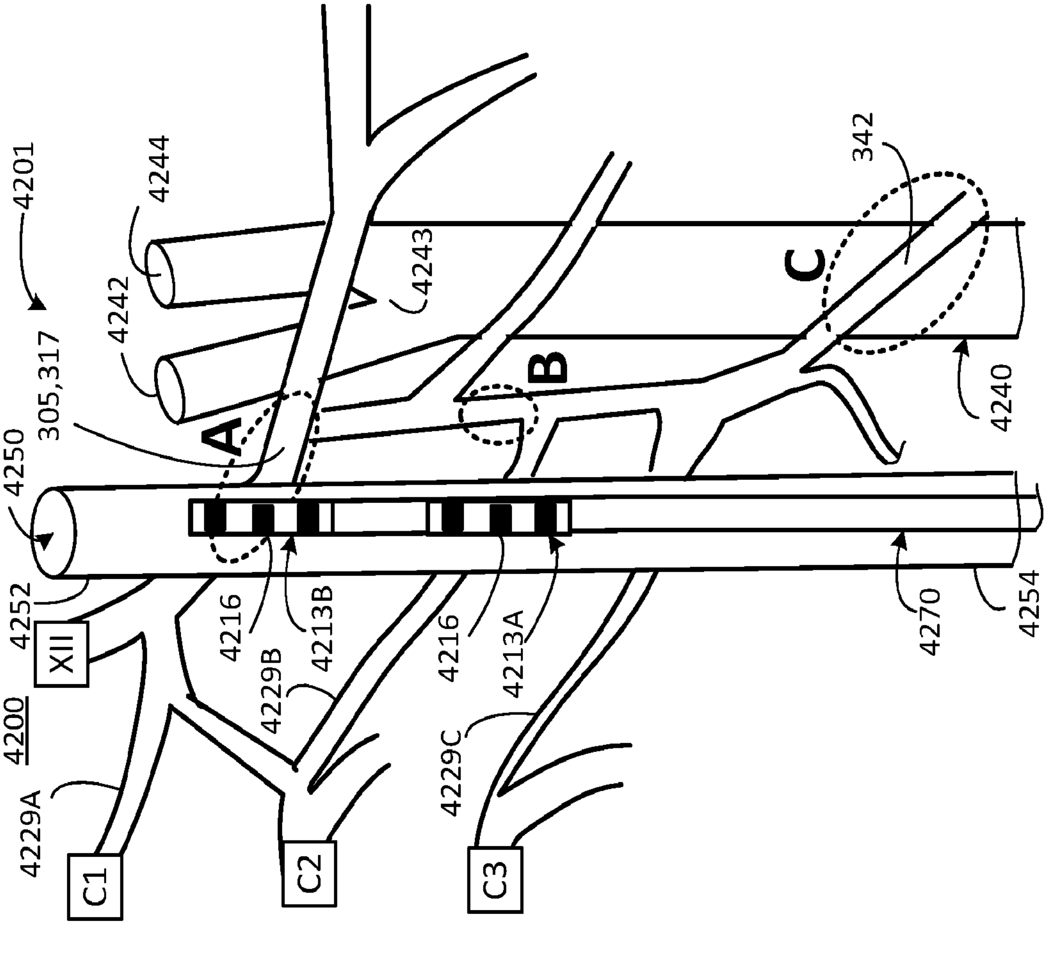

FIG. 32C is a diagram including a front view of a patient's anatomy 4201 relating to a hypoglossal nerve 305 and ansa cervicalis-related nerve 316 and schematically representing an example arrangement 4200 of various potential stimulation locations (e.g. at least A, B, C, D, or E in FIG. 2) and example intravascular delivery of stimulation elements for transvascular (e.g. transvenous) stimulation. As shown in FIG. 32C, the pertinent patient anatomy comprises the ansa cervicalis-related nerve 316, in context with the hypoglossal nerve 305 and with cranial nerves C1, C2, C3. At least because of the well-documented variances in patient anatomy (among different patients) regarding the ansa cervicalis-related nerve and/or challenges in graphically depicting such structures and their relationship, the schematic representation of the patient anatomy 4201 in FIG. 32C (and FIG. 32D) exhibits some differences relative to the schematic representation of the ansa cervicalis-related nerve 316 in FIGS. 2, 16, 32A, 32B. Nevertheless, as shown in FIG. 32C, the general position of the example stimulation locations A, B, and C (and D, E in FIG. 2) remain consistent at least in terms of the particular muscle groups which are innervated by the portion(s) of the nerve 316 at the example stimulation locations A, B, C as reproduced in FIG. 32C-32D (relative to their depiction in FIGS. 2, 16, 32A-32B).

As shown in FIG. 32C, portion 4229A of the ansa cervicalis-relate nerve 316 extends anteriorly from a first cranial nerve C1 with a segment 317 running alongside (e.g. coextensive with) the hypoglossal nerve 305 (indicated via "305, 317") for a length until the ansa cervicalis-related nerve 3165 diverges from the hypoglossal nerve 305 to form a superior root (e.g. 325 in FIG. 2A) of the ansa cervicalis-related nerve 316.

As further shown in FIG. 32C, patient anatomy 4201 comprises an interior jugular vein 4250, which extends along a superior-inferior orientation and within the context of the ansa cervicalis-related nerve 316, may comprise a superior portion 4252 and an opposite inferior portion 4254. Generally parallel to this portion of the interior jugular vein 4250, the common carotid artery 4240 extends superiorly toward junction 4243, from which the interior carotid artery 4242 and exterior carotid artery 4244 bifurcate from each other. As shown, an example first stimulation location (dashed lines A, and indicator "305, 317") generally corresponds to the target stimulation location A previously shown in at least FIG. 2A, 16, 32A, 32B. Moreover, in some examples, the stimulation at location A may be implemented via example stimulation arrangements 2101, 2401, which in turn correspond (in some examples) to example stimulation arrangements in FIGS. 17-20. Various aspects relating to this stimulation location (A, "305, 317") were previously described in association with at least FIGS. 16-20, at least some of which are equally applicable in relation to the example arrangement 4200 in FIG. 32C.

Portions 4229B, 4229C in FIG. 32C generally correspond to portions 329B, 329C in FIGS. 2A, 16, 32A, etc.

As further shown in FIG. 32C, in some examples example arrangement 4200 may comprise a stimulation lead 4270 which may be advanced within and through the interior jugular vein 4250 to position a stimulation portion 4213B in stimulating relation, at location "A" ("305, 317"), to the hypoglossal nerve 304 and portion 317 of the ansa cervicalis-related nerve 316. In some examples, the stimulation lead 4270 and its delivery, anchoring, etc. may comprise at least some of substantially the same features and attributes as described in association with at least FIGS. 15A-15C, 25A-25B, 29A-29B, 30A-31G, and/or 30A, 32A-32B. In just one example, the stimulation portion 4213B may comprise a linear array of spaced apart electrodes 4216 (e.g. ring electrodes, split ring electrodes, etc.) sized, shaped, and/or distributed to enable applying stimulation selectively to the various fibers, fascicles, etc. of the respective hypoglossal nerve 305 (e.g. main trunk portion) and portion 317 of the ansa cervicalis-related nerve 316 in order to treat sleep disordered breathing (e.g. at least OSA). As noted elsewhere, applying stimulation at this location A activates at least some nerve fibers of the ansa cervicalis-related nerve which innervate the sternothyroid muscles to increase upper airway patency and activates at least some nerve fibers of the hypoglossal nerve which innervate at least protrusor muscles of the tongue to maintain or increase upper airway patency.

In some examples, the stimulation portion 4213B may be supported on a lead body 4271. While FIG. 32C depicts two stimulation portions (e.g. 4213A, 4213B) on lead body 4271, it will be understood that in some examples, the lead 4270 comprises just one stimulation portion 4213B for stimulating at location A or just one stimulation portion for stimulating at location B, as further described below. In some examples, the stimulation lead 4271 may comprise both stimulation portions 4213A, 4213B on lead 4271, whether just one or both stimulation locations A and B are to be stimulated.

In some examples, prior to chronic intravascular implantation of at least the stimulation portion 4213B, the position of lead body 4271 and stimulation portion 4213B may be optimized for desired effective selective stimulation and/or various combinations of electrodes may be selected to determine which combination of electrodes, stimulation protocol (e.g. timing, sequence, etc.), etc. provides the desired effective selective stimulation of the hypoglossal nerve 305 and/or ansa cervicalis-related nerve 316 at portion 317.

As further shown in FIG. 32C, example arrangement 4200 may comprise an example second target stimulation location (dashed lines "B") along the ansa cervicalis-related nerve 316, as was similarly illustrated in FIG. 2, 16, etc. In some examples, a cuff electrode or paddle electrode may be implanted at stimulation location B, in accordance with the many examples throughout the present disclosure of implanting such electrodes to be in stimulating relation to the ansa cervicalis-related nerve 316. As shown in FIG. 32C, in some examples the stimulation lead 4270 may be delivered intravascularly within and through the interior jugular vein 4250, as similarly described above, to position stimulation portion 4213A in close proximity to stimulation location B.

In some examples, when both stimulation portions 4213B and 4213A are provided on lead 4270, then stimulation may be provided solely at stimulation location A, solely at stimulation location B, or at both stimulation locations A and B. As also further described elsewhere, when both stimulation locations A and B may be stimulated, such stimulation may be simultaneous, alternating, staggered, etc., or the stimulation of the respective locations may depend on other parameters such as a collapse pattern, body position, etc., as well as whether or not the hypoglossal nerve is also being stimulated.

In some examples, stimulation lead 4270 may be constructed to comprise just one stimulation portion (either 4213B or 4213A) with such single stimulation portion being positioned within the interior jugular vein 4250 in stimulating relation, at location B, to pertinent portions of the ansa cervicalis-related nerve 316.

With further reference to stimulation location B in FIG. 32C, this portion of the ansa cervicalis-related nerve 316 may comprise a significantly large number (e.g., most or all) of the motor nerve fibers which innervate the sternothyroid muscles, such that delivering stimulation at location B may yield a robust response and contraction of the sternothyroid muscle(s), which contributes to upper airway patency. Accordingly, in some such examples, non-selective stimulation may be applied, at least with respect to the nerve fibers at location B innervating the sternothyroid muscles.

As further shown in FIG. 32C, example arrangement 4200 may comprise an example third target stimulation location (dashed lines "C") at portion 324 along the ansa cervicalis-related nerve 316. In some examples, a cuff electrode or paddle electrode may be implanted at stimulation location C, in accordance with the many examples throughout the present disclosure of implanting such electrodes to be in stimulating relation to the ansa cervicalis-related nerve 316, such as at portion 324.

As further shown in FIG. 32D, an example arrangement 4300 may comprise a stimulation lead 4280 to delivered intravascularly within and through the interior jugular vein 4250, and then within and through a middle thyroid vein 4260, which branches (at 4251) off from the interior jugular vein 425. Via such intravascular delivery, the example arrangement results in positioning a stimulation portion 4213A of stimulation lead 4280 in close proximity to, and in stimulating relation to, stimulation location C along the portion 324 of the ansa cervicalis-related nerve 316. As further shown in FIG. 32D, a main body portion 4282 of lead 4280 may extend within and through the interior jugular vein 4250 while a distal portion 4283 of lead 4280 extends within and through the middle thyroid vein 4260.

At this stimulation location C, portion 324 of the ansa cervicalis-related nerve 316 may comprise a significantly large number (e.g., most or all) of the motor nerve fibers which innervate the sternothyroid muscles, such that delivering stimulation at location C may yield a robust response and contraction of the sternothyroid muscle(s), which may contributes to upper airway patency. Accordingly, in some such examples, non-selective stimulation may be applied, at least with respect to the nerve fibers at location C innervating the sternothyroid muscles.

In some examples, a single/same type of electrode arrangement (e.g. cuff electrode, etc.) may be implanted at each of the respective stimulation locations A, B, and C or just one or two of such locations. However, in some examples, different types of electrode arrangements may be implanted among the respective stimulation locations A, B, and C. In one non-limiting example, a cuff electrode may be implanted at location A while an axial-style stimulation portion may be intravascularly delivered for applying stimulation at location B. Other combinations will be apparent.

In a manner consistent with several examples throughout the present disclosure, any one of electrode arrangements (e.g. cuff electrode, paddle electrode, axial electrode array, etc.) in FIGS. 32A-32D may be embodied as part of a microstimulator instead of being connected to, supported by, etc. a lead in connection with an IPG (e.g. 533). In some such examples, the microstimulator may be implanted subcutaneously or intravascularly, such as but not limited to example methods and devices described throughout various examples of the present disclosure.

FIGS. 33A-37D are a series of diagrams including views which schematically represent various stimulation protocols, including closed loop stimulation patterns and/or open loop stimulation patterns, including stimulation of at least the hypoglossal nerve and/or the ansa cervicalis-related nerve 316. In some examples, the stimulation implemented via the various stimulation protocols may be implemented via at least some of substantially the same features and attributes of the various example stimulation arrangements as previously described in association with at least FIGS. 1-32D and/or as of the various later described example arrangements involving sensing, control, etc. Accordingly, unless specifically noted otherwise the various example stimulation protocols may be applicable for unilateral stimulation or bilateral stimulation of the respective targeted nerves. Moreover, in some examples, the stimulation pattern of one of the example stimulation protocols (as described in FIGS. 33A-37D) for a given nerve (e.g. HGN) may be switched and applied to another nerve (e.g. ACN), or vice versa.

Figure 33A:
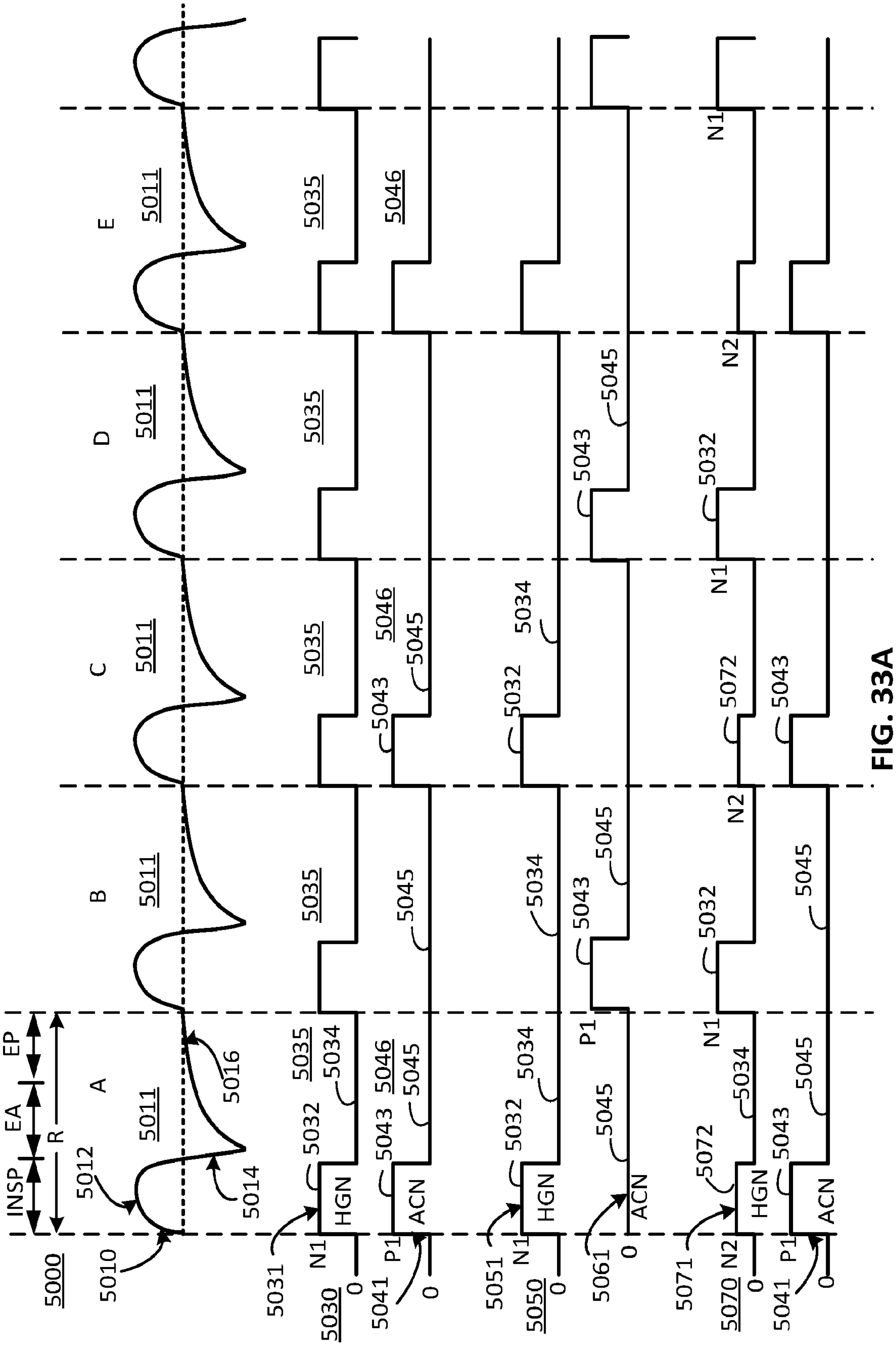
FIGS. 33A-37D are diagrams including graphs schematically representing example respiratory cycles and example methods of stimulation for upper airway patency-related nerves.

FIG. 33A is a diagram 5000 schematically representing an example respiratory waveform 5010 and a series of stimulation protocols 5030, 5050, 5070, each of which include a stimulation pattern for a hypoglossal nerve (HGN) and an ansa cervicalis-related nerve (ACN) 316. Among other things, FIG. 33A provides an example respiratory waveform 5010, including an inspiratory phase 5012 having duration INP, active expiratory phase 5014 having duration EA, and expiratory pause 5016 having duration EP. Together, these phases comprise an entire respiratory cycle 5011 having a duration (e.g. respiratory period) of R. This respiratory cycle 5011 is repeated, as represented in successive frames A, B, C, D, E, and so on. It will be understood that the respiratory cycles 5011 depicted in each frame A-E of FIG. 33A are depicted as being identical, but in reality there may be variations in the respiratory cycle from breath-to-breath, and each patient may exhibit some variances in their respiratory waveform from other patients. Moreover, for illustrative simplicity, the respiratory waveforms shown in FIGS. 33A-37D do not purport to depict disruptions to the respiratory waveform, which correspond to sleep disordered breathing, signal imperfections, etc.

As shown in FIG. 33A, one example stimulation protocol 5030 comprises an example first stimulation pattern 5031 for stimulating a hypoglossal nerve (HGN) and an example second stimulation pattern 5041 for stimulating an ansa cervicalis-related nerve (ACN).

The first stimulation pattern 5031 to stimulate the hypoglossal nerve (HGN) comprises a stimulation cycle 5035 including a stimulation period 5032 and a non-stimulation period 5034, with the stimulation cycle 5035 being repeated through successive frames A, B, C, D, E and so on. As shown for the first stimulation cycle 5035, the stimulation pattern 5031 includes the stimulation period 5032 comprising an amplitude of N1 during the inspiratory phase 5012 and the subsequent non-stimulation period 5034 having an amplitude of zero during the expiratory phases 5014, 5016. In one aspect, this stimulation pattern 5031 may sometimes be referred to as being synchronous with the inspiratory phase (5012) of the patient's respiratory cycles (e.g. breathing pattern). In another aspect, this stimulation pattern 5031 may sometimes be referred to as being a closed loop stimulation pattern in that sensed respiratory information (i.e. sensed feedback) is used to time the stimulation period 5032 to coincide with the inspiratory phase (5012) of the patient's respiratory cycles (e.g. breathing pattern).

As further shown in FIG. 33A, the second stimulation pattern 5041 comprises a stimulation cycle 5046 including a stimulation period 5043 and a non-stimulation period 5045 which lasts through two respiratory cycles 5011 (e.g. two frames). This stimulation cycle 5046 is repeated through pairs of frames A and B, C and D, and so on.

As shown for the first stimulation cycle 5046, the second stimulation pattern 5041 (for the ACN) includes the stimulation period 5043 comprising an amplitude of P1 during the inspiratory phase 5012 and the subsequent non-stimulation period 5045 having an amplitude of zero during the expiratory phases 5014, 5016, and the entire subsequent respiratory cycle (e.g. frame B). It will be noted that the amplitude P1 for stimulation of the ACN 315 may comprise a value different than the amplitude N1 for stimulation of the hypoglossal nerve. In one aspect, this stimulation pattern 5046 may sometimes be referred to as being periodically synchronous with the inspiratory phase (5012) of the patient's respiratory cycles (e.g. breathing pattern) to the extent that when stimulation is applied in some respiratory cycles (e.g. periodically in frames A, C, E), the stimulation coincides with the inspiratory phase 5012 of the patient's respiratory cycle 5011. It may be further observed that when stimulation is applied to the ACN 316 per stimulation pattern 5041, it is applied synchronous with stimulation of the hypoglossal nerve.

By providing stimulation to the ansa cervicalis-related nerve (e.g. 316 in FIG. 2) according to the second stimulation pattern 5041, the action of the stimulation of the hypoglossal nerve (per first stimulation pattern 5031) to increase and/or maintain upper airway patency is supplemented while also looking to prevent or minimize fatigue to the ansa cervicalis-relate nerve (ACN) 316 and/or its associated targeted muscles by providing stimulation to the ACN 316 every other breath (i.e. respiratory cycle). As previously noted, for at least some patients, some patient positions, etc., providing stimulation to the ansa cervicalis-related nerve 316 (in addition to stimulating the hypoglossal nerve) may help increase and/or maintain upper airway patency because certain patients may have a particular anatomical features, certain co-morbidities, etc.

FIG. 33A also depicts an example stimulation protocol 5050 in which the second stimulation pattern 5061 of the ACN 316 is substantially the same as in the example stimulation pattern 5041 of protocol 5030, but a first stimulation pattern 5051 of the hypoglossal nerve provides for stimulation every other respiratory cycle, illustrated as occurring in frames A, C, E, and so on. In one aspect, this stimulation pattern may act to prevent or minimize fatigue of the hypoglossal nerve and/or genioglossus muscle. In some examples, the alternating stimulation periods in pattern 5051 (for the HGN) are offset from the stimulation periods in pattern 5061 (for the ACN 316). However, in some examples, the alternating HGN stimulation periods (e.g. frames A, C, E) in pattern 5051 may be shifted so that they are applied to coincide with (i.e. be synchronous with) the alternating stimulation periods (e.g. frames B, D, etc.) in stimulation pattern 5061 for the ACN 316.

FIG. 33A also depicts an example stimulation protocol 5070 in which the second stimulation pattern 5041 of the ACN 316 is substantially the same as in the example stimulation pattern 5041 of protocol 5030, but in a first stimulation pattern 5071 (for the hypoglossal nerve), an amplitude of stimulation varies every other respiratory cycle. As shown in FIG. 33A, in the first stimulation pattern 5071 of the stimulation protocol 5070, the amplitude of the stimulation period 5032 in frames B, D, etc. for the hypoglossal nerve comprises N1 while the amplitude of the stimulation period 5072 in frames A, C, E, etc. for the hypoglossal nerve comprises N2, which is less than the amplitude N1. In some examples, N2 may be substantially less (e.g. 50% less, 25% less, etc.) than amplitude N1. In one aspect, this stimulation pattern may act to prevent or minimize fatigue of the hypoglossal nerve and/or genioglossus muscle.

Moreover, as further shown in FIG. 33A, in this example stimulation protocol 5070 the respiratory cycles (e.g. frames A, C, E) for which a lower amplitude N2 of stimulation is applied to the hypoglossal nerve is timed to coincide with stimulation periods 5043 by which stimulation is applied to the ansa cervicalis-related nerve. In one aspect, this arrangement times the stimulation of the ACN 316 to supplement the stimulation of the hypoglossal nerve when the amplitude of the HGN stimulation is lower, such that the stimulation of the ACN 316 may help increase and/or maintain upper airway patency during such respiratory cycles. Moreover, this stimulation protocol 5070 still provides for alternating stimulation periods for the ACN 316 to also help minimize or manage potential fatigue of the ACN 316 and/or associated targeted muscles. Moreover, while not shown in FIG. 33A, it will be understood that in some examples, the amplitude P1 of the stimulation periods 5043 for stimulating the ACN 316 also may be reduced to a lower amplitude in at least some respiratory cycles to further minimize or manage potential fatigue issues.

It will be further noted that the examples shown in FIG. 33A in which a stimulation period is applied every other respiratory cycle (e.g. 5041, 5051, 5061), whether for the hypoglossal nerve or the ansa cervicalis-related nerve, are also representative for some further examples in which a stimulation period may be applied every third respiratory cycle or every fourth respiratory cycle, and so on. Similarly, the examples in which a reduced amplitude of stimulation is applied every other respiratory cycle (e.g. 5071) are also representative for some further examples in which a reduced amplitude, stimulation period may be applied every third respiratory cycle or every fourth respiratory cycle, and so on, whether for the hypoglossal nerve or for the ansa cervicalis-related nerve.

With regard to the reduced stimulation amplitude (e.g. N2) in the stimulation pattern 5071, in some examples an intensity of the applied stimulation also can be reduced via adjusting other stimulation parameters (i.e. other than amplitude) such that the reduced stimulation amplitude in the pattern 5071 in FIG. 33A (or in the pattern 5211 in FIG. 34) also may be generally representative of reducing or adjusting other stimulation parameters to reduce an intensity of stimulation to a particular nerve and/or at a particular stimulation location.

Figure 33B:
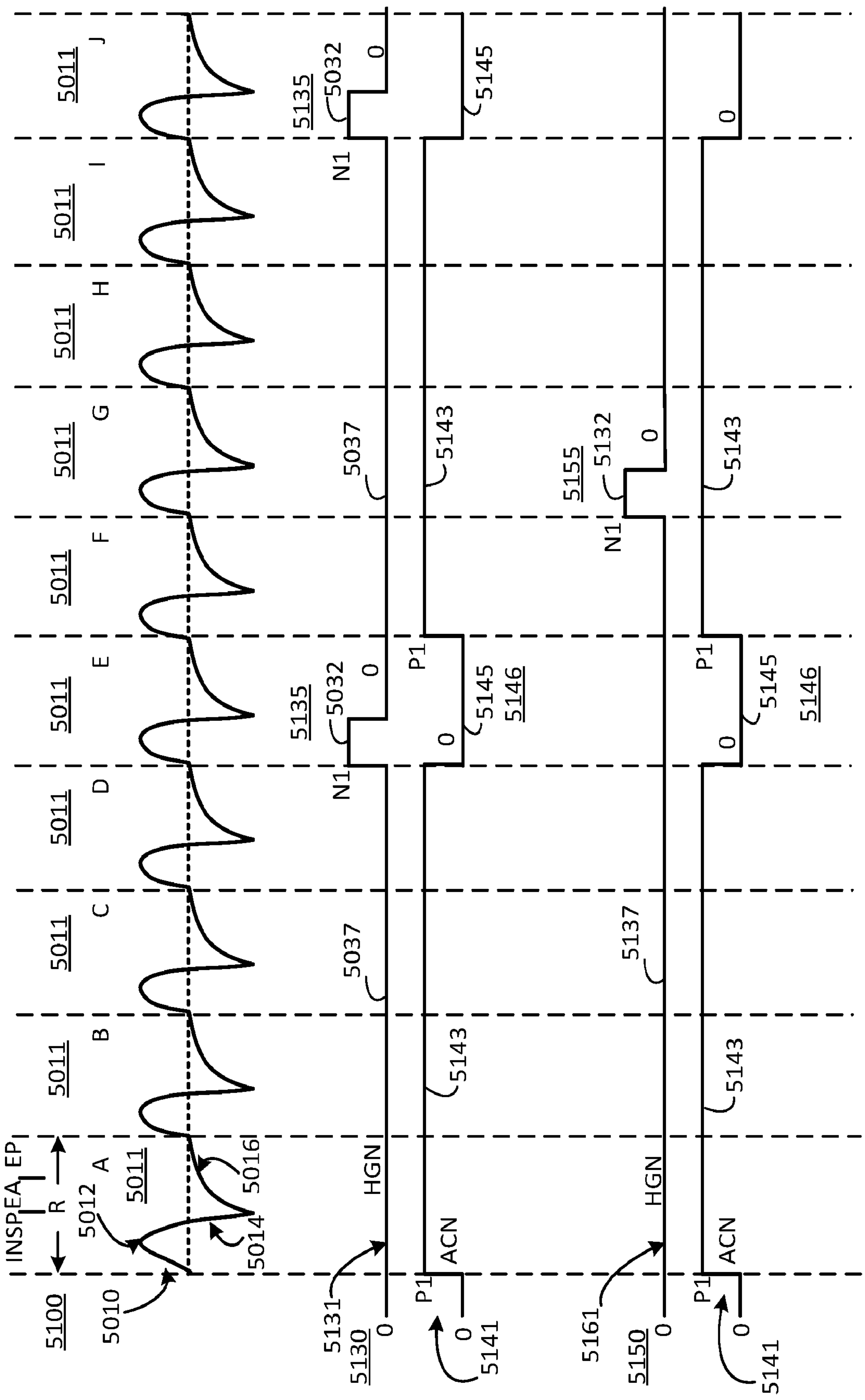

FIG. 33B is a diagram schematically representing further example stimulation protocols 5130, 5150. FIG. 33B illustrates a respiratory waveform 5010, which has the substantially the same features and attributes as the respiratory waveform 5010 as in FIG. 33A, except with FIG. 33B depicting a greater number of respiratory cycles 5011 than in FIG. 33A.

As shown in FIG. 33B, one example stimulation protocol 5130 comprises an example first stimulation pattern 5131 for stimulating a hypoglossal nerve (HGN) and an example second stimulation pattern 5141 for stimulating an ansa cervicalis-related nerve (ACN).

The example second stimulation pattern 5141 to stimulate the ansa cervicalis-related nerve (ACN) comprises an example stimulation cycle 5135 which extends over five successive frames (e.g. A, B, C, D, E) including a stimulation period 5143 (e.g. 4 frames) and a non-stimulation period 5145 (e.g. 1 frame), with the stimulation cycle 5146 being repeated. As shown for the first stimulation cycle 5146, the stimulation pattern 5141 includes the stimulation period 5143 comprising an amplitude of P1 and the subsequent non-stimulation period 5145 having an amplitude of zero during the entire respiratory cycle 5011 in frame E. In one aspect, this stimulation pattern 5141 may sometimes be referred to as being synchronous relative to at least the inspiratory phase (5012) of the patient's respiratory cycles (e.g. breathing pattern), at least to the extent that when the stimulation period 5143 begins, it coincides with a beginning of an inspiratory period of a respiratory cycle. On the other hand, in some respects the stimulation pattern 5141 may be considered as being asynchronous solely relative to an inspiratory phase 5012 of the respiratory cycles 5011, at least to the extent that the stimulation is maintained through the entire respiratory cycle (e.g. 5011) of several consecutive respiratory cycles, such that stimulation is not discontinued at the conclusion of each inspiratory phase in each respective respiratory cycle 5011 during which stimulation is being applied.

In another aspect, this stimulation pattern 5141 may sometimes be referred to as being a closed loop stimulation pattern in that sensed respiratory information (i.e. sensed feedback) is used to time the beginning of the stimulation period 5143 to coincide with the beginning of the inspiratory phase (5012) of the patient's respiratory cycles (e.g. breathing pattern) and the sensed respiratory information is used to time the termination of the stimulation period 5134 to coincide with an end of the expiratory phase of the last respiratory cycle 5011 (e.g. frame E) in the stimulation cycle 5035.

As further shown in FIG. 33B, the first stimulation pattern 5131 comprises a stimulation cycle 5135 which generally corresponds to the number of respiratory cycles (5011) of the stimulation cycle 5146 for the second stimulation pattern 5141. Each stimulation cycle 5135 of the first stimulation pattern 5131 includes a stimulation period 5032 and a non-stimulation period 5037. In general terms, the non-stimulation period 5037 of the first stimulation pattern 5131 has a duration generally matching the duration of the stimulation period 5143 of the second stimulation pattern 5141. Via this arrangement, stimulation is withheld (i.e. does not occur) from the hypoglossal nerve (HGN) during periods (e.g. such as several respiratory cycles) (e.g. 5037 in FIG. 33B) in which stimulation is being applied to the ansa cervicalis-related nerve (ACN) (e.g. 5143 in FIG. 33B). Conversely, in the same example, as noted below stimulation is applied (i.e. does occur) to the hypoglossal nerve (HGN) (e.g. 5032 in FIG. 33B) during at least a portion of the period(s) in which stimulation is withheld (i.e. is not being applied to) from the ansa cervicalis-related nerve (ACN) (e.g. 5145 in FIG. 33B).

In some examples, the stimulation period 5032 has a duration corresponding to a duration of an inspiratory phase 5012 as shown in FIG. 33B. In some examples, the stimulation period 5032 can be shorter or longer than the inspiratory phase 5012. Accordingly, in some such examples, the stimulation period 5032 may have a duration corresponding to the duration R of the respiratory cycle 5011 (e.g. single frame E). However, in some examples, the stimulation period 5032 in first stimulation pattern 5131 may have longer durations.

For at least the example in FIG. 33B, this stimulation cycle 5135 of the first stimulation pattern 5131 is repeated, along with the stimulation cycle 5146 of the second stimulation pattern 5141, for five respiratory cycles at a time, and repeated.

As shown for the first stimulation cycle 5146, the second stimulation pattern 5141 (for the ACN) includes the stimulation period 5143 comprising an amplitude of P1 during the inspiratory phase 5012 and the subsequent non-stimulation period 5145 having an amplitude of zero during the entire respiratory cycle 5011 (e.g. frame E). It will be noted that in some examples the amplitude P1 for stimulation of the ACN 316 may comprise a value different than the amplitude N1 for stimulation of the hypoglossal nerve (HGN).

In some examples, a duration of the stimulation cycle 5146 of the second stimulation pattern 5141 may be longer or shorter than shown in FIG. 33B. In some such examples, a duration of the stimulation period (e.g. 5143) of a stimulation cycle 5146 in the second stimulation pattern 5141 may be significantly longer such as up to a dozen respiratory cycles (e.g. 1 minute), or even two dozen respiratory cycles (e.g. 2 minutes). Meanwhile, the non-stimulation period 5145 may be some multiple of respiratory cycles.

In general terms, in some examples of the stimulation protocol 5130 in FIG. 33B, a duty cycle (e.g. percentage of stimulation to non-stimulation) for stimulation may comprise between about 60 to about 90 percent. In some examples, the duty cycle may comprise between about 65 to about 85 percent, while in some examples, the duty cycle may comprise between about 70 percent and about 80 percent. In the particular example shown in FIG. 33B, the duty cycle is about 80 percent per a ratio of a stimulation period 5143 of four respiratory cycles 5011 to one non-stimulation period 5145 of one respiratory cycle 5011. While in the example of FIG. 33B, the stimulation period 5143 comprises a discrete multiple of respiratory cycles (5011), in some examples, the stimulation period 5143 may have a duration not corresponding to a discrete multiple of respiratory cycles 5011.

In some examples, the HGN stimulation period 5032 may have a duration in which the HGN stimulation is applied continuously for a period which is at least as long as, or longer than, a non-stimulation period 5145 (e.g. rest period) of the second stimulation pattern 5141 of the ansa cervicalis-related nerve. In some such examples, in which the ACN non-stimulation period 5143 has a duration no more than 10 seconds, the HGN stimulation period 5032 may be applied continuously during the ACN rest period 5145.

In some examples, by providing stimulation to the ansa cervicalis-related nerve (e.g. 316 in FIG. 2) according to the longer duty cycles per the second stimulation pattern 5141, reasonable patient comfort may be achieved while generally maintaining or increasing upper airway patency while stimulating the hypoglossal nerve (HGN) just periodically when the ansa cervicalis-related nerve (ACN) is resting. In some examples, stimulating the ansa cervicalis-related nerve as a primary target for longer periods of time may result in generally maintaining a stiffer upper airway in a more open position. This effect may be achieved via stimulating portions innervating the sternothyroid and/or sternohyoid muscles, which pull the larynx inferiorly. This arrangement may enhance patient comfort (while maintaining upper airway patency) at least because the contraction of the upper airway muscles innervated by the ansa cervicalis-related nerve may result in more a diffuse sensation than the more discrete, recognizable protrusion of the tongue. This arrangement also may yield a more effective therapy (in at least some patients) because, with the upper airway already being in a more open configuration due to the stimulation of the ansa cervicalis-related nerve, then the tongue need not be moved as far in order to restore or maintain upper airway patency, and therefore less stimulation of the hypoglossal nerve may be applied, which in turn may enhance patient comfort.

For at least some patients, some patient positions, etc., providing stimulation to the ansa cervicalis-related nerve 316 as a primary target (with periodic supplemental stimulation of the hypoglossal nerve) may help increase and/or maintain upper airway patency generally and/or because certain patients may have particular anatomical features, certain co-morbidities, etc. more therapeutically responsive to the ansa cervicalis-related nerve as a primary target.

FIG. 33B also schematically represents an example stimulation protocol 5150 comprising stimulation of both the ansa cervicalis-related nerve (ACN) and the hypoglossal nerve (HGN). In some examples, the stimulation protocol 5150 may comprise at least some of substantially the same features and attributes as stimulation protocol 5130 in FIG. 33B, except with stimulation protocol 5150 in FIG. 33B comprising HGN stimulation which may occur during ACN stimulation instead of occurring during an ACN rest period. Accordingly, as shown in FIG. 33B, the stimulation protocol 5150 may comprise a second stimulation pattern 5141 for the ansa cervicalis-related nerve as described for stimulation protocol 5130, including the variations thereof. Meanwhile, the stimulation protocol 5150 may comprise a first stimulation pattern 5161 for the hypoglossal nerve (HGN) comprising HGN stimulation periods 5132 and HGN non-stimulation periods 5137. In some examples, the stimulation protocol 5150 may comprise a series of repeating stimulation cycles in which the HGN stimulation period 5132 occurs at regular intervals, and is timed to occur during an ACN stimulation period 5143 as shown in FIG. 33B. For instance, the HGN stimulation period 5132 may occur every other ACN stimulation period 5143, may occur every third ACN stimulation period 5143, and so on.

However, in some examples, the HGN stimulation period 5132 may not occur at regular intervals, but may still be implemented during ACN stimulation periods 5143. In other words, the HGN stimulation does not occur during an ACN rest period 5145. In some such examples, the occurrence of the HGN stimulation period 5132 may be pseudo-random (e.g. one type of open loop stimulation). In some example implementations, the pseudo-random HGN stimulation may be implemented without sensing respiration or without using sensed respiration information, In some such examples, a frequency, duration, etc. of the HGN stimulation period 5132 may be selected to ensure a high likelihood that at least some of the pseudo-random HGN stimulation periods 5132 will overlap with at least some of the inspiratory phases of the respiratory cycles 5011.

In some examples, the occurrence of the HGN stimulation period 5132 (in stimulation protocol 5150) may occur upon detection that more upper airway patency is warranted, and therefore some HGN stimulation is desirable and will be implemented. In some such examples, the HGN stimulation is timed to be applied simultaneous with an ACN stimulation period 5143 and the HGN stimulation may be applied during and/or overlapping with an inspiratory phase of the respiratory cycle, in some examples.

Figure 34:
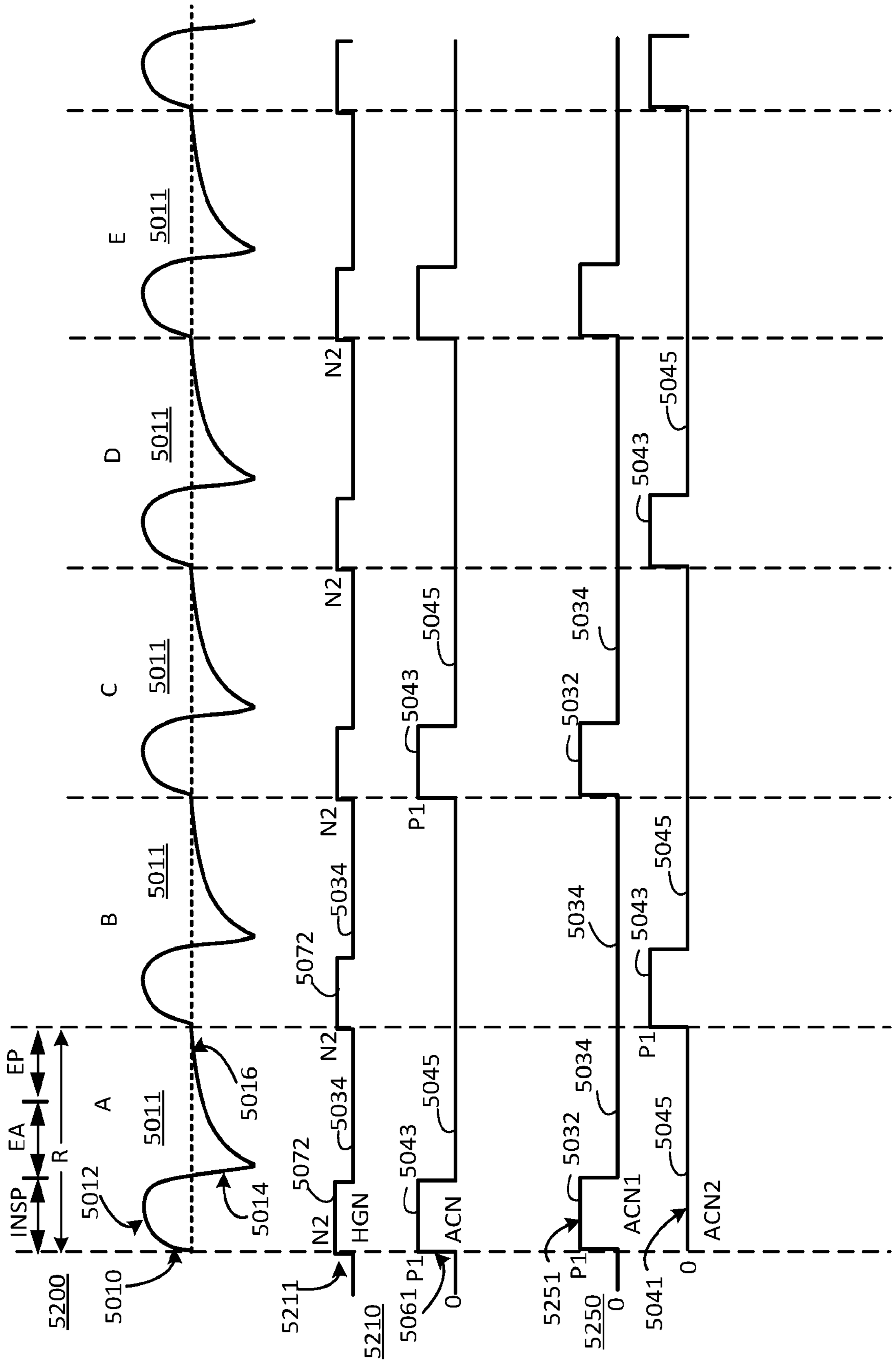

FIG. 34 is diagram schematically representing the same respiratory waveform 5010 as in FIG. 33A and two different example stimulation protocols 5210, 5250.

As shown in FIG. 34, the example stimulation protocol 5210 comprises a second stimulation pattern 5061 (to stimulate the ansa cervicalis-related nerve) having substantially the same features as stimulation pattern 5041 as in FIG. 33A and a first stimulation pattern 5211 (to stimulate the hypoglossal nerve) comprising features and attributes like stimulation pattern 5031 in FIG. 33A, except with each stimulation period 5072 having a reduced amplitude N2 (of some selectable value). In one aspect, this example stimulation protocol also may help reduce fatigue for the hypoglossal nerve (and/or associate genioglossus muscle) while the stimulation of the ansa cervicalis-related nerve (ACN) 316 can compensate for the reduced amplitude of the hypoglossal nerve stimulation signal, such that the concomitant stimulation patterns 5211, 5061 helps to increase and/or maintain upper airway patency.

As further shown in FIG. 34, an example stimulation protocol 5250 comprises a second stimulation pattern 5061 having substantially the same features as stimulation pattern 5061 as in FIG. 33A for application to a portion (e.g. ACN2) of the ansa cervicalis-related nerve 316, and a first stimulation pattern 5251 comprising features and attributes like stimulation pattern 5051 in FIG. 33A, except with that the stimulation pattern 5251 is applied to a portion (e.g. ACN1) of the ansa cervicalis-related nerve 316 instead of the hypoglossal nerve. Accordingly, in the example stimulation protocol 5250, one stimulation pattern 5251 is applied to a first portion ACN1 (i.e. target stimulation location) of the ansa cervicalis-related nerve 316 and the other stimulation pattern 5061 is applied to a different, second portion ACN2 of the ansa cervicalis-related nerve 316. By applying the stimulation in an alternating pattern to different portions (e.g. ACN1, ACN2) of the ansa cervicalis-related nerve 316, the example stimulation protocol may enhance upper airway patency by leveraging different mechanisms of action to increase and/or maintain upper airway patency, while also helping to manage potential fatigue of the ansa cervicalis-related nerve 316 that could possibly be associated with a single target stimulation location.

In some examples, the example stimulation protocol 5250 may comprise three or more different stimulation patterns corresponding to three or more different portions of the ansa cervicalis-related nerve 316.

In some examples, the example stimulation protocol 5250 also may be enhanced via also applying stimulation to the hypoglossal nerve in addition to the two (or more) different portions of the ansa cervicalis-related nerve. Such hypoglossal nerve stimulation may be applied via any one of the example stimulation patterns described in association with at least FIGS. 33A-37D and/or other suitable stimulation patterns.

Figure 35:
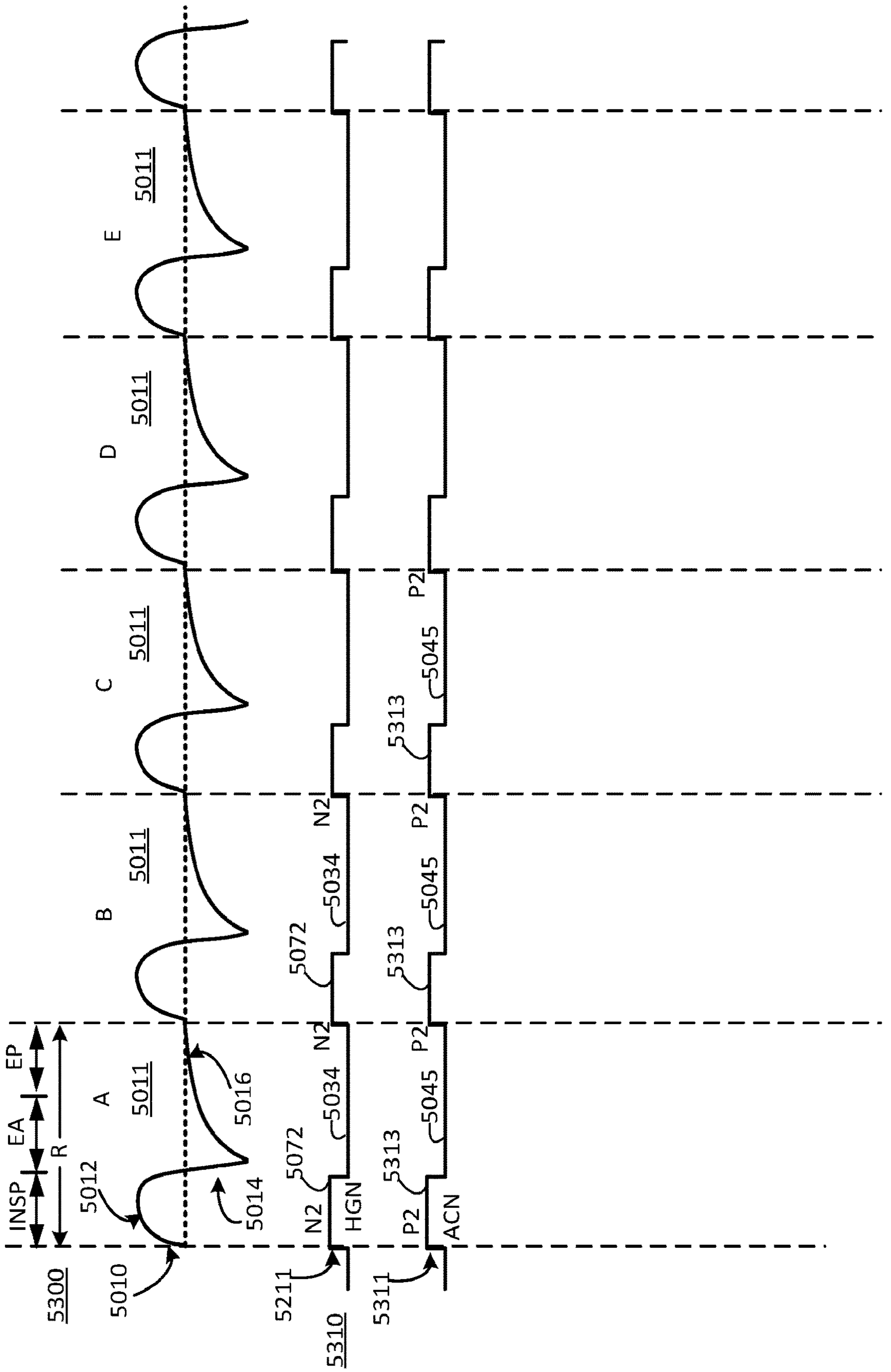

FIG. 35 is a diagram schematically representing the same respiratory waveform 5010 as in FIG. 34 and an example stimulation protocol 5310. As shown in FIG. 35, the stimulation protocol 5310 comprises a first stimulation protocol 5211 comprising substantially the same features and attributes as stimulation protocol 5211 in FIG. 34 in which the stimulation applied to the hypoglossal nerve comprises a reduced amplitude N2 applied in a stimulation period 5072 of each stimulation cycle (e.g. each frame A, B, C, etc.). The stimulation protocol 5310 of FIG. 35 also comprises a second stimulation protocol 5311 which also comprises a reduced stimulation amplitude (P2) for each stimulation period 5313, except with the stimulation being applied to the ansa cervicalis-related nerve ACN. In some examples, the amplitude N2 comprises a value different than a value of the reduced amplitude P2.

In a manner analogous to other example stimulation protocols, it is believed that the example stimulation protocol 5310 in FIG. 35 may enhance increasing and/or maintaining upper airway patency and/or may enhance fatigue management of target stimulation locations of the nerves, muscles, etc.

FIG. 36A is a diagram 5500 schematically representing the same respiratory waveform 5010 as in FIG. 34 and an example stimulation protocol 5510, which comprises a plurality of stimulation patterns 5551, 5563, 5581, 5561 involving both the left and right hypoglossal nerves and both the left and right ansa cervicalis-related nerves. While FIG. 36A depicts a particular stimulation pattern for each particular nerve (L and R), it will be understood that the example stimulation protocol 5510 in FIG. 36A is also generally representative of applying different stimulation patterns to the left patient side and right patient side of a particular nerve. Moreover, in some examples, one, two or three of the stimulation patterns (e.g. 5551, 5563, 5581, 5561) may be omitted entirely or for just a selectable period of time.

As shown in FIG. 36A, the example stimulation pattern 5551 is to be applied to a first hypoglossal nerve (e.g. patient left side, HGN L) and may comprise substantially the same features and attributes as stimulation pattern 5051 in FIG. 33A in which stimulation period 5032 occurs in frames A, C, E (e.g. every other respiratory cycle). Meanwhile, the example stimulation pattern 5563 in FIG. 36A is to be applied to a second hypoglossal nerve (e.g. patient right side, HGN R) and may comprise substantially the same features and attributes as the stimulation pattern 5051 in FIG. 33A, except with the stimulation periods 5032 being applied in respiratory cycles (e.g. frames B, D) in which no stimulation is applied to the respiratory cycle such that stimulation is alternated between the left and right hypoglossal nerves.

As further shown in FIG. 36A, the example stimulation pattern 5581 is to be applied to a first ansa cervicalis-related nerve (e.g. patient left side, ACN L) and may comprise substantially the same features and attributes as stimulation pattern 5041 of stimulation protocol 5070 in FIG. 33A in which stimulation is applied in frames A, C, E (e.g. every other respiratory cycle). Meanwhile, the example stimulation pattern 5561 in FIG. 36A is to be applied to a second ansa cervicalis-related nerve (e.g. patient right side, ACN R) and may comprise substantially the same features and attributes as the stimulation pattern 5061 in FIG. 33A, i.e. with the stimulation periods 5032 being applied in respiratory cycles (e.g. frames B, D), so as to be alternating with respect to stimulation of the left ACN.

As apparent from the foregoing example stimulation protocols and the example stimulation devices and methods as previously described in various examples throughout the present disclosure, adjustments to the stimulation patterns 5551, 5563, 5581, 5561 may be made regarding applying the stimulation to various nerves and left and right sides as desired to achieve the desired increase or maintenance of upper airway patency.

Figure 36B:
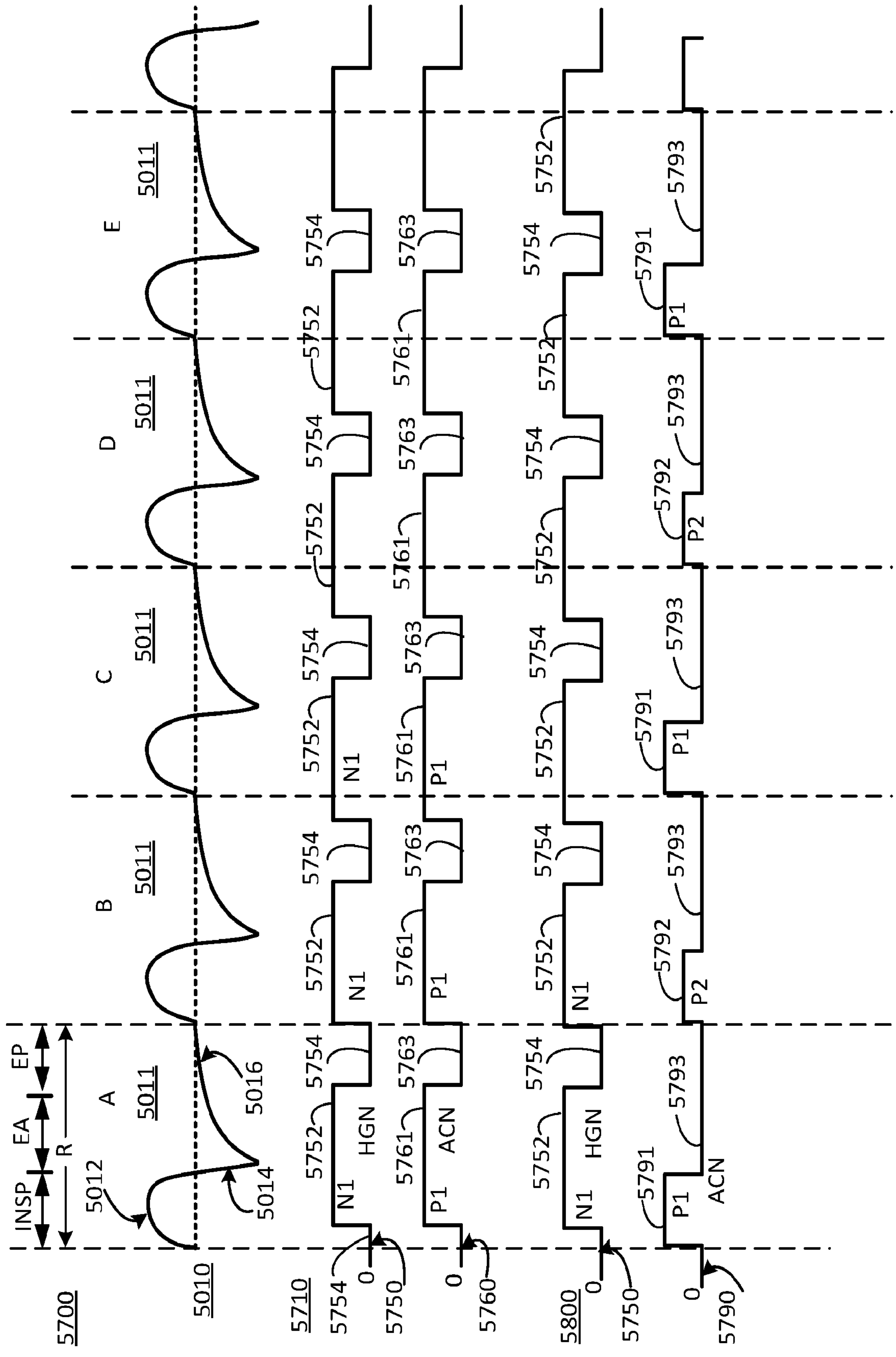

FIG. 36B is a diagram 5700 schematically representing the same respiratory waveform 5010 as in FIG. 34, and example stimulation protocols 5710, 5800.

As shown in FIG. 36B, the example stimulation protocol 5710 comprises a first stimulation pattern 5750 to stimulate a hypoglossal nerve (HGN) and a second stimulation pattern 5760 to stimulate the ansa cervicalis-related nerve (ACN). The first stimulation pattern 5750 comprises a stimulation cycle, including a stimulation period 5752 and subsequent non-stimulation period 5754, with the stimulation cycle repeating itself. In some examples, the stimulation period 5752 comprises a duration greater than a duration of the non-stimulation period 5754. In some examples, the stimulation period 5752 comprises a duration greater than a duration (INSP) of the inspiratory phase 5012 of the respiratory cycle 5011. Moreover, in some examples, the stimulation period 5752 is not synchronized relative to a sensed inspiratory phase 5012 of the patient's respiratory cycle 5011, and therefore the first stimulation pattern 5750 may sometimes be referred to as an open loop stimulation pattern. Via such example stimulation pattern 5750, the stimulation period 5752 may regularly overlap with at least a portion of the inspiratory phase 5012, despite the lack of synchronization relative to the inspiratory phase 5012. In the example shown in FIG. 36B, the stimulation cycle (including the stimulation period 5752 and non-stimulation period 5754) has a duration less than a duration (R) of the respiratory cycle 5011.

However, in some examples, the stimulation period 5752 has a duration greater than the duration of the non-stimulation period 5754, and the stimulation cycle (including the stimulation period 5752 and non-stimulation period 5754) has a duration greater than a duration (R) of the respiratory cycle 5011, which also may act to cause the stimulation period 5752 to regularly overlap with an inspiratory phase of the patient's respiratory cycle 5011.

In some examples, such open loop stimulation may comprise at least some of substantially the same features and attributes as described in Wagner et al, STIMULATION FOR TREATING SLEEP DISORDERED BREATHING, published as U.S. Patent Publication 2018/01176316 on May 3, 2018, issued as U.S. Pat. No. 10,898,709 on Jan. 26, 2021, and hereby incorporated by reference.

With further reference to FIG. 36B, the second stimulation pattern 5760 of the example stimulation protocol 5710 comprises substantially the same features and attributes as the first stimulation pattern 5750, except being applied to an ansa cervicalis-related nerve (ACN) instead of to the hypoglossal nerve (HGN). As shown in FIG. 36B, the second stimulation pattern 5760 comprises stimulation cycles, each including a stimulation period 5761 and non-stimulation period 5763, which comprise the same durations, relationships, etc. as the stimulation period 5752 and non-stimulation period 5754 of stimulation pattern 5750, in some examples. Accordingly, as shown in FIG. 36B, in some examples the stimulation period 5761 of the second stimulation pattern 5760 is synchronized with the stimulation period 5752 of the first stimulation pattern 5750, and the non-stimulation period 5763 of the second stimulation pattern 5760 is synchronized with the non-stimulation period 5754 of the first stimulation pattern 5750.

However, in some examples, the second stimulation pattern 5760 is not synchronized with the first stimulation pattern 5750 and may be implemented such that the stimulation period 5671 of the second stimulation pattern 5670 is initiated at a point time different than initiation of the stimulation period 5752 of the first stimulation pattern 5750. Moreover, in some examples, the respective durations of the stimulation and/or non-stimulation periods (e.g. 5761, 5763) of the second stimulation pattern 5760 may be different than the respective durations of the stimulation and/or non-stimulation periods (e.g. 5752, 5754) of the first stimulation pattern 5750.

FIG. 36B also schematically represents an example stimulation protocol 5800 including first stimulation pattern 5750 to stimulate a hypoglossal nerve (HGN) and a second stimulation pattern 5790 to stimulate an ansa cervicalis-related nerve (ACN). In some examples, the first stimulation pattern 5750 of example stimulation protocol 5800 comprises substantially the same features and attributes as the first stimulation pattern 5750 of example stimulation protocol 5710 in FIG. 36B.

In some examples, the second stimulation pattern 5790 comprises stimulation cycles with a stimulation period 5791 and non-stimulation period 5793, with the stimulation period 5791 being synchronized relative to a sensed inspiratory phase 5012 of the patient's respiratory cycle, and in some examples, having a duration generally corresponding to the duration (INSP) of the inspiratory phase. However, in some examples, the stimulation period 5791 is not synchronized relative to a sensed inspiratory phase 5012. Accordingly, the hypoglossal nerve is stimulated in an open loop (non-synchronized) manner while the ansa cervicalis-related nerve is stimulated in a closed loop (synchronized) manner.

As further shown in FIG. 36B, regarding stimulation pattern 5790, the amplitude of the stimulation period alternates between stimulation periods 5791 having a first amplitude P1 and a second stimulation period 5792 having a second amplitude P2 less than first amplitude P1, which may minimize potential fatigue of the ansa cervicalis-related nerve and/or associated innervated muscles. However, in some examples, the amplitude of the stimulation periods 5791, 5792 may be the same. In yet other examples, the stimulation period 5791 having amplitude P1 may be applied in every other stimulation cycle (e.g. frames A, C, E) with no stimulation therebetween (e.g. no stimulation in frames B, D, etc.), in a manner similar to that shown for stimulation pattern 5041 in FIG. 33A.

Figure 37A:
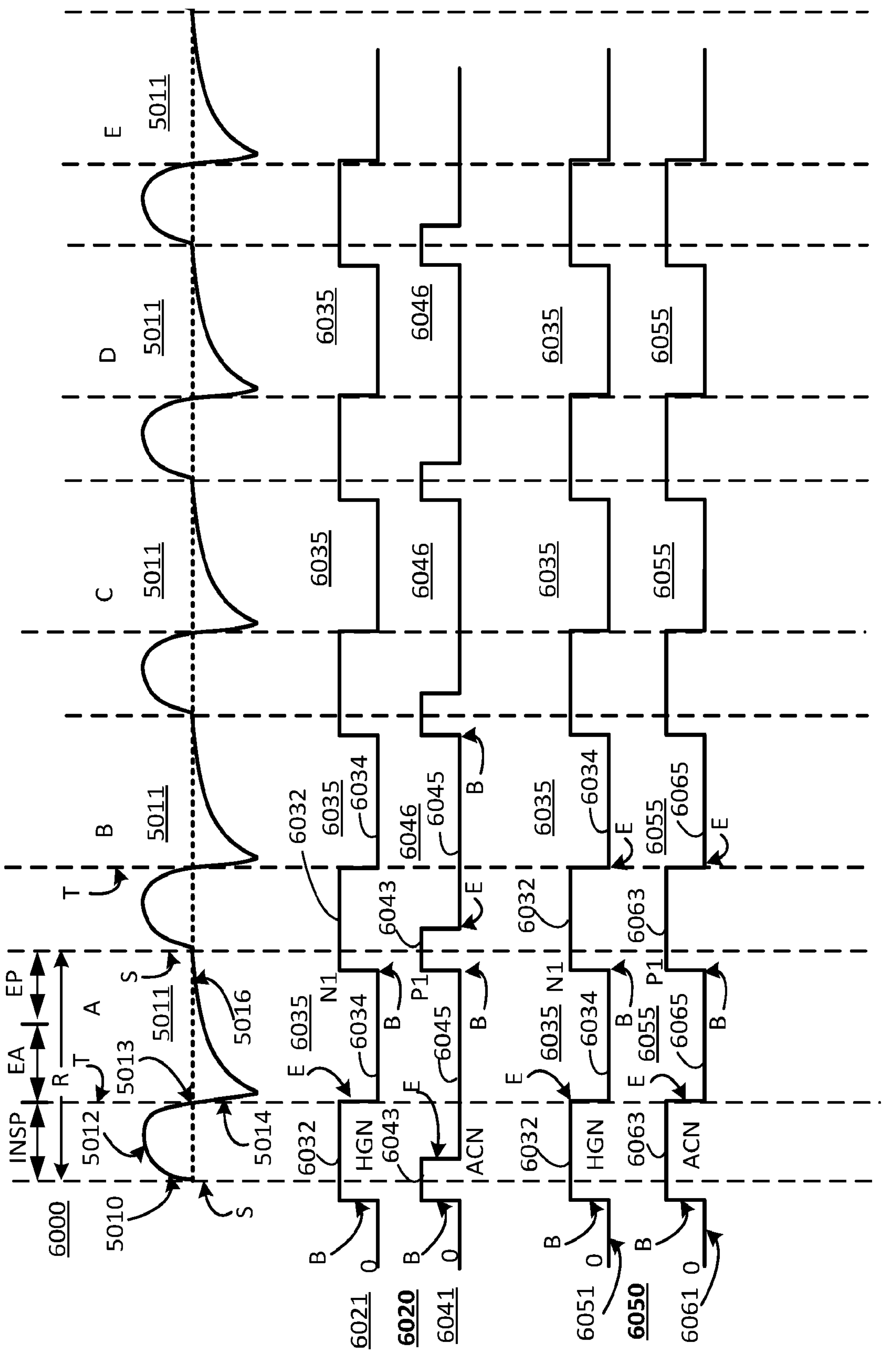
FIGS. 37E-37G are diagrams including graphs schematically representing example respiratory cycles and example methods of stimulation for upper airway patency-related tissues including at least some stimulation methods and devices relating to a patency hysteresis parameter.
Figure 37B:
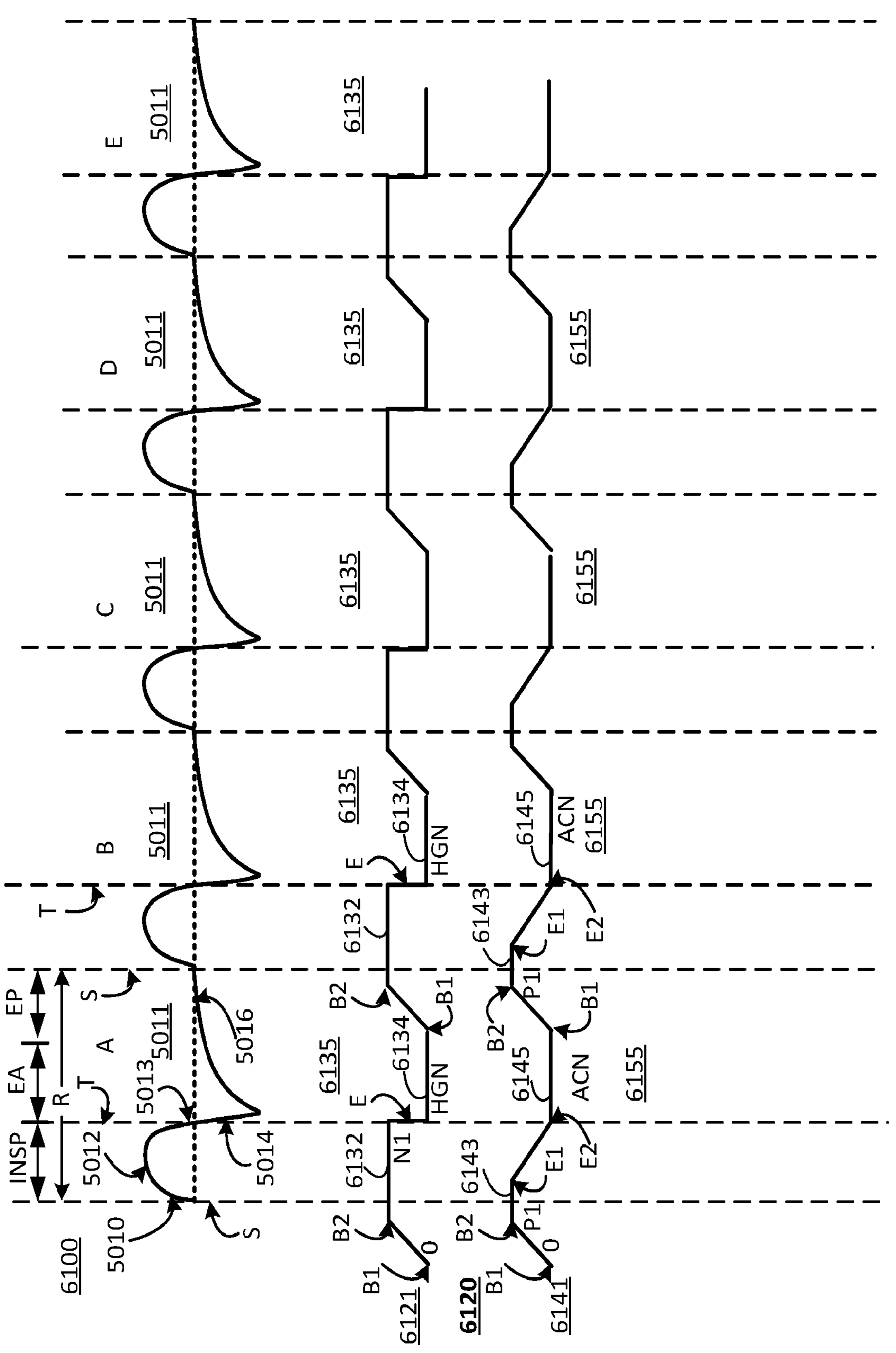

In some examples, any of the stimulation patterns of the example stimulation protocols described in association with FIGS. 33A-36B may be modified such that the beginning portion of the stimulation period of the respective stimulation cycles is to slightly precede the start(S) of the inspiratory phase (INSP) to provide at least some pre-inspiratory stimulation, in a manner similar to that shown and described in the example stimulation protocols in at least FIGS. 37A-37B. In some examples, at least some of the features and attributes (e.g. reduced amplitude, applying stimulation every other respiratory cycle, alternating stimulation between different nerves, etc.) described and illustrated in association with FIGS. 33A-36B may be implemented in at least some of the example stimulation patterns of the example stimulation protocols described and illustrated in FIGS. 37A-37D.

FIG. 37A is a diagram 6000 schematically representing the same respiratory waveform 5010 as in FIG. 34, and example stimulation protocols 6020, 6050. As shown in FIG. 37A, example stimulation protocol 6020 comprises a first stimulation pattern 6021 to stimulate a hypoglossal nerve (HGN) and a second stimulation pattern 6041 to stimulate an ansa cervicalis-related nerve (ACN). In some examples, the first stimulation pattern 6021 of example stimulation protocol 6020 comprises substantially the same features and attributes as the first stimulation pattern 5031 of example stimulation protocol 5030 in FIG. 33A, except with the stimulation period 6032 having a longer duration such that a beginning (B) of the stimulation period 6032 precedes the start(S) of the inspiratory phase (INSP) of the patient's respiratory cycle 5010, while the end (E) of the stimulation period 6021 coincides with the end of the inspiratory phase (INSP), corresponding to the transition (T) between the inspiratory phase (INSP) and expiratory phase (EA, EP). By beginning (B) the stimulation just prior to the start(S) of the inspiratory phase (INSP), the stimulation may ensure upper airway patency prior to the patient starting(S) inspiration.

Consequently, as further shown in FIG. 37A, the non-stimulation period 6034 of stimulation pattern 6021 has a shorter duration than in the non-stimulation period 5034 of stimulation pattern 5030 in FIG. 33A so that the subsequent stimulation period 6034 in FIG. 37A may begin (B) prior to the start(S) of the next inspiratory phase (INSP) of the patient's next breath (i.e. subsequent respiratory cycle 5011).

As shown in FIG. 37A, this stimulation cycle 6035 is repeated throughout the first stimulation pattern 6021 such that the stimulation of the hypoglossal nerve is synchronized in a closed-loop manner relative to the inspiratory phase (INSP) of the patient's respiratory cycles 5011.

As further shown in FIG. 37A, the second stimulation pattern 6041 (to stimulate an ansa cervicalis-related nerve) comprises a stimulation period 6043 which begins (B) prior to, and overlaps with, the start(S) of the inspiratory phase (INSP), with the stimulation period 6043 ending (E) during the inspiratory phase (INSP) and prior to the end of the inspiratory phase (INSP) at transition (T). The non-stimulation period 6034 of the stimulation cycle 6035 lasts until just prior to the start(S) of the next inspiratory phase (INSP) at which the next stimulation period 6043 begins (B).

As shown in FIG. 37A, this stimulation cycle 6046 for the ansa cervicalis-related nerve is repeated throughout the first stimulation pattern 6041 such that the stimulation of the ansa cervicalis-related nerve is synchronized in a closed-loop manner relative to a portion of the inspiratory phase (INSP) of each of the patient's respiratory cycles 5011.

By providing stimulation period 6043 of the ansa cervicalis-related nerve (ACN) to coincide with just the start(S) of the inspiratory phase (INSP) (but not the entire inspiratory phase), the stimulation periods 6043 enhance increasing and/or maintaining upper airway patency in a complementary, additive manner to the stimulation of the hypoglossal nerve (via stimulation period 6032) to increase and/or maintain upper airway patency.

For some patients, once upper airway patency has been established prior to, and during, the start(S) of inspiration, further stimulation of the ansa cervicalis-related nerve may be unnecessary. Accordingly, by ending (E) the stimulation period 6043 shortly after the start(S) of the inspiratory phase (INSP), fatigue of the nerve and/or innervated muscles may be minimized or avoided.

In some examples, the example stimulation protocol 6020 may be modified so that the stimulation period 6032 of the stimulation pattern 6021 (to stimulate the hypoglossal nerve) and/or so that the stimulation period 6043 of the stimulation pattern 6041 (to stimulate the ansa cervicalis-related nerve) begins (B) at the start(S) of the inspiratory phase (INSP) instead of beginning (B) prior to the start(S) of the inspiratory phase (INSP), which may be prudent for at least some patients at least some of the time.

As further shown in FIG. 37A, an example stimulation protocol 6050 comprises a first stimulation pattern 6051 to stimulate a hypoglossal nerve (HGN) and a second stimulation pattern 6061 to stimulate an ansa cervicalis-related nerve (ACN). In some examples, the first stimulation pattern 6051 of example stimulation protocol 6050 comprises substantially the same features and attributes as the first stimulation pattern 6021 of example stimulation protocol 6020 in FIG. 37A. Moreover, in some examples, the second stimulation pattern 6061 of example stimulation protocol 6050 comprises substantially the same features and attributes as the second stimulation pattern 6041 of example stimulation protocol 6020 in FIG. 37A, except with the stimulation period 6063 having a longer duration such that the end (E) of the stimulation period 6063 coincides with the end of the inspiratory phase (INSP), corresponding to the transition (T) between the inspiratory phase (INSP) and expiratory phase (EA, EP). By timing the stimulation period 6063 of the ansa cervicalis-related nerve to coincide with the entire inspiratory phase (INSP) (including some stimulation just prior to the start(S) of the inspiratory phase (INSP)), the stimulation may ensure upper airway patency throughout the entire inspiratory phase for at least some patients where such stimulation is prudent.

Consequently, as further shown in FIG. 37A, the non-stimulation period 6065 of stimulation pattern 6061 has a shorter duration than the non-stimulation period 6045 in the stimulation pattern 6041 in FIG. 37A so that the subsequent stimulation period 6063 may begin (B) prior to the start(S) of the next inspiratory phase (INSP) of the patient's next breath (i.e. subsequent respiratory cycle 5011).

As shown in FIG. 37A, this stimulation cycle 6055 (including stimulation period 6063 and non-stimulation period 6065) is repeated throughout the second stimulation pattern 6061 such that the stimulation of the ansa cervicalis-related nerve is synchronized in a closed-loop manner relative to the inspiratory phase (INSP) of the patient's respiratory cycles 5011.

FIG. 37B is a diagram 6100 schematically representing the same respiratory waveform 5010 as in FIG. 34, and example stimulation protocol 6120. As shown in FIG. 37B, example stimulation protocol 6120 comprises a first stimulation pattern 6121 to stimulate a hypoglossal nerve (HGN) and a second stimulation pattern 6141 to stimulate an ansa cervicalis-related nerve (ACN). In some examples, the first stimulation pattern 6121 of example stimulation protocol 6120 comprises substantially the same features and attributes as the first stimulation pattern 6021 of example stimulation protocol 6020 in FIG. 37A, except with the stimulation period 6132 additionally including an increasing ramped portion from a beginning (B1) of the stimulation period 6132 (preceding the start(S) of the inspiratory phase (INSP)) in which the amplitude (or intensity) of the HGN stimulation increases from zero (at B1) to an amplitude N1 at B2, wherein the amplitude N1 is maintained through the start(S) of the inspiratory phase (INSP) and thereafter to point (E), at which the stimulation period 6132 terminates, which coincides with the end of the inspiratory phase (INSP), corresponding to the transition (T) between the inspiratory phase (INSP) and expiratory phase (EA, EP). Non-stimulation period 6134 follows the termination of the stimulation period 6132 and extends through a portion of the expiratory phase (including active expiration (EA) and a portion of the expiratory pause EP), until the next stimulation period 6132 begins (B1) with the ramped increase in stimulation to point (B2) and brief leveling of stimulation amplitude N1, prior to the start(S) of inspiration (INSP), as previously described. In one aspect, the ramped beginning portion (B1 to B2) provides a more gradual initiation of HGN stimulation (of the stimulation period), which may be less noticeable to a patient and/or which may be easier on the respective nerves and muscles. Even with this ramped beginning of stimulation, a full (selectable) amplitude of stimulation is achieved (at B2) prior to the start(S) of the inspiratory phase (INSP), which may be desirable or prudent for at least reasons described in association with FIG. 37A.

As shown in FIG. 37B, this stimulation cycle 6135 for the hypoglossal nerve is repeated throughout the first stimulation pattern 6121 such that the stimulation of the hypoglossal nerve is synchronized in a closed-loop manner relative to a portion of the inspiratory phase (INSP) of each of the patient's respiratory cycles 5011, while including a ramped beginning portion (B1 to B2).

As further shown in FIG. 37B, the second stimulation pattern 6141 of example stimulation protocol 6120 comprises substantially the same features and attributes as the second stimulation pattern 6041 of example stimulation protocol 6020 in FIG. 37A, except with the stimulation period 6143 (in FIG. 37B) additionally including an increasing ramped portion from a beginning (B1) of the stimulation period 6143 (preceding the start(S) of the inspiratory phase (INSP)) in which the amplitude (or intensity) of the ACN stimulation increases from zero (at B1) to an amplitude P1 at B2, wherein the amplitude P1 is maintained through the start(S) of the inspiratory phase (INSP) and beyond to point (E1) at which the amplitude (or intensity) of stimulation decreases in a downwardly ramping manner to point (E2). At point E2 the stimulation period 6143 terminates, which coincides with the end of the inspiratory phase (INSP), corresponding to the transition (T) between the inspiratory phase (INSP) and expiratory phase (EA, EP).

In one aspect, the ramped ending portion (E1 to E2) of the stimulation period 6143 provides a more gradual termination of ACN stimulation (in the stimulation period 6143), which may help to prolong or maintain the patency-inducing effect achieved by the portion of the stimulation period 6143 which precedes, and coincides with the start(S) of the inspiratory phase (INSP). This gradual termination (in each stimulation cycle) also may be less noticeable to a patient and/or which may be easier on the respective nerves and muscles.

Non-stimulation period 6145 of the second stimulation pattern 6141 follows the termination (at E2) of the stimulation period 6143 and extends through a portion of the expiratory phase (including active expiration (EA) and a portion of the expiratory pause EP), until the next stimulation period 6143 begins (B1) with the ramped increase in stimulation to point (B2) and brief constant stimulation amplitude P1, prior to the start(S) of inspiration (INSP), as previously described. In one aspect, the ramped beginning portion (B1 to B2) provides a more gradual initiation of stimulation (of the stimulation period), which may be less noticeable to a patient and/or which may be easier on the respective nerves and muscles. Even with this ramped beginning of stimulation, a full (selectable) amplitude of ACN stimulation is achieved (at B2) prior to the start(S) of the inspiratory phase (INSP), which may be desirable or prudent for at least reasons described in association with FIG. 37A.

In one aspect, the non-stimulation period 6145 of stimulation pattern 6141 in FIG. 37B has a shorter duration than the non-stimulation period 6045 in the stimulation pattern 6041 in FIG. 37A such that the subsequent stimulation period 6143 (of stimulation pattern 6141 in FIG. 37B) may begin (B1, B2) prior to the start(S) of the next inspiratory phase (INSP) of the patient's next breath (i.e. subsequent respiratory cycle 5011).

Similarly, as noted above, the more gradual ramped termination of stimulation (E1 to E2) in each stimulation period 6143 in the second stimulation pattern of protocol 6120 in FIG. 37B may, in some examples: (1) act to prolong the upper airway patency effect of the portion of stimulation (of the ansa cervicalis-related nerve) coinciding with the start(S) of the inspiratory phase (INSP); (2) be less noticeable to a patient; and/or (3) be easier on the respective nerves and muscles.

As shown in FIG. 37B, this stimulation cycle 6155 for the ansa cervicalis-related nerve (ACN) is repeated throughout the second stimulation pattern 6141 such that the stimulation of the ansa cervicalis-related nerve is synchronized in a closed-loop manner relative to a portion of the inspiratory phase (INSP) of each of the patient's respiratory cycles 5011, while including a ramped beginning portion (B1 to B2) and a ramped ending portion (E1 to E2).

Figure 37C:
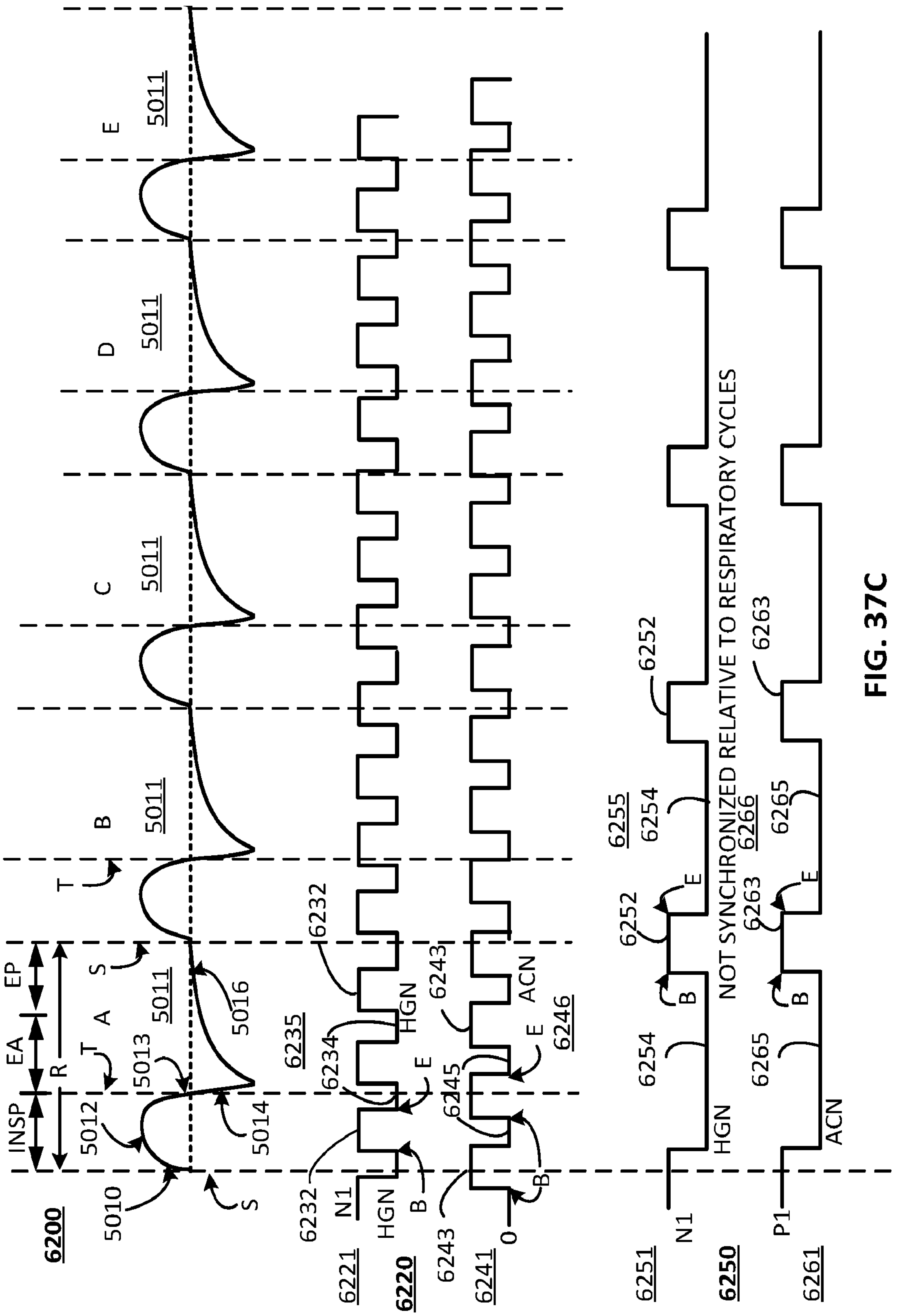
Figure 37C:
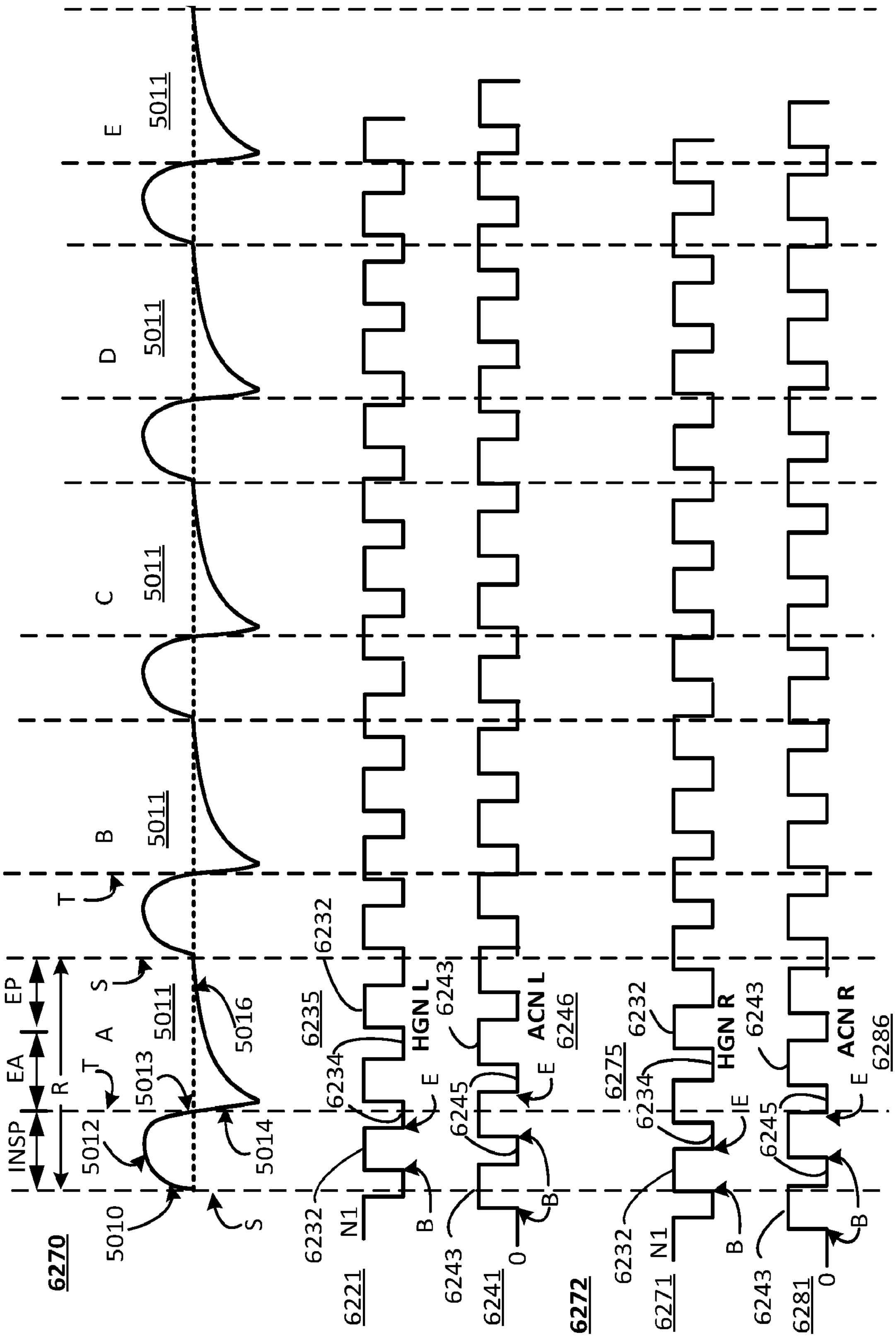

FIG. 37C is a diagram 6200 schematically representing the same respiratory waveform 5010 as in FIG. 34, and example stimulation protocols 6220, 6250. Unlike the closed-loop example stimulation protocols in at least FIGS. 37A-37B and 37D, the example stimulation protocols 6220, 6250 in FIG. 37C comprise open-loop stimulation protocols in which the stimulation periods are not synchronized relative to a feature of the respiratory cycle 5011 such as, but not limited to, a feature of the inspiratory phase (INSP) and/or the expiratory phase (EA, EP).

It will be understood that the presence of the respiratory waveform 5010 in FIG. 37C is merely to provide some context regarding the duration and/or other aspects of the respective stimulation and non-stimulation periods of the respective example stimulation patterns. Accordingly, any seemingly regular correspondence between certain aspects of the respiratory cycles and the respective stimulation periods (and non-stimulation periods) in FIG. 37C is merely coincidental and present to facilitate illustrative simplicity and clarity, and not intended to convey synchronization of the stimulation patterns relative to the respiratory cycles.

As shown in FIG. 37C regarding the first stimulation protocol 6220, the first stimulation pattern 6221 is provided to stimulate the hypoglossal nerve (HGN) while the second stimulation pattern 6241 is provided to stimulate the ansa cervicalis-related nerve (ACN). The first stimulation pattern 6221 comprises a series of stimulation cycles 6235, with each stimulation cycle 6235 comprising a stimulation period 6232 and a non-stimulation period 6234. Meanwhile, the second stimulation pattern 6241 of the first stimulation protocol 6220 in FIG. 37C comprises a series of stimulation cycles 6246, with each stimulation cycle 6246 comprising a stimulation period 6243 and a non-stimulation period 6245. For both patterns 6221, 6241, the labels B and E identify a beginning and an end, respectively, of the stimulation periods 6232 and 6243, respectively.

As shown in FIG. 37C, the stimulation periods 6232 of the first stimulation pattern 6221 (to stimulate the hypoglossal nerve) are offset relative to the stimulation periods 6243 of the second stimulation pattern 6241 (to stimulate the ansa cervicalis-related nerve). In some examples of this arrangement, the stimulation periods 6232 of the first stimulation pattern 6221 (to stimulate the hypoglossal nerve) generally overlap with the non-stimulation periods 6245 of the second stimulation pattern 6241 (to stimulate the ansa cervicalis-related nerve). Via this arrangement, stimulation is always being applied to increase and/or maintain upper airway patency with the hypoglossal nerve being rested while the ansa cervicalis-related nerve is being stimulated, and vice versa. In other words, at any given time, a stimulation period (e.g. 6232, 6243) of one of the stimulation patterns 6221, 6241 (of the HGN and of the ACN) is being delivered. While the stimulation periods of the different stimulation patterns 6221, 6241 may slightly overlap each other, when the stimulation is "ON" for a first nerve (e.g. HGN), the stimulation is "OFF" for the second nerve (e.g. ACN) such that the second nerve (e.g. ACN) is resting while the first nerve (e.g. HGN) is being stimulated. In some examples, this arrangement may be applied between a left HGN (first nerve) and a right HGN (second nerve) or between a left ACN (first nerve) and a right ACN (second nerve).

Accordingly, in some such examples stimulation is being applied continuously, although being split between ACN stimulation and HGN stimulation with the ACN stimulation being "ON" one-half of the treatment period and the HGN stimulation being "ON" one-half of the treatment period. In some examples as later described in association with FIG. 37CC, this paradigm may be extended to additional targets, such that stimulation is applied per a protocol in which stimulation is "ON" continuously yet distributed among two, three, or four targets, such as the left HGN, left ACN, right HGN, right ACN. It will be understood that stimulation being "ON" continuously presumes that the stimulation signal(s) comprise a series of stimulation pulses applied at a high enough frequency for stimulation to be considered relatively continuous. Moreover, it will be further understood that continuous stimulation may correspond to stimulation being "ON" 100 percent of the time. In some such examples, the stimulation may be applied substantially continuously, such as 95, 96, 97, 98, 99 percent of the duration of the treatment period.

Among other effects, this example stimulation protocol 6220 in FIG. 37C may help minimize or avoid fatigue of a single type of nerve (e.g. the hypoglossal or the ansa cervicalis-related) while providing consistency in neurostimulation to increase and/or maintain upper airway patency. Moreover, because stimulation of one type of nerve may be beneficial under certain conditions (e.g. body position, head-and-neck position, etc.) and another type of nerve may be more beneficial under certain conditions, alternating stimulation between both types of nerves may provide consistent therapy.

In one aspect, the example stimulation protocol may promote consistency in increasing and/or maintaining upper airway patency because of the relative fast duty cycle (e.g. short duration of the stimulation periods and non-stimulation periods) by which each type of nerve is frequently stimulated. For instance, as shown in FIG. 37C, in some examples multiple stimulation cycles 6235 may occur within a duration of a typical respiratory cycle 5011. However, in some examples, the duration of the stimulation period 6232 and/or non-stimulation period 6234 may be longer such that one stimulation cycle 6235 may be longer than the duration of a typical respiratory cycle 5011.

In one aspect, the open loop nature of the example stimulation protocol 6220 enables stimulation therapy without using a sensor or sensed information that might otherwise be used to synchronize the stimulation cycles (e.g. 6235, 6246) relative to at least one feature of the patient's respiratory cycles 5011. Among other effects, this arrangement may simplify implantation and/or other aspects of providing stimulation therapy for sleep disordered breathing or other physiologic conditions.

As further shown in FIG. 37C, an example open-loop, stimulation protocol 6250 comprises a first stimulation pattern 6251 for stimulating the hypoglossal nerve (HGN) and a second stimulation pattern 6261 for stimulating the ansa cervicalis-related nerve (ACN). The first stimulation pattern 6251 comprises a series of stimulation cycles 6255, with each stimulation cycle 6255 comprising a stimulation period 6252 and a non-stimulation period 6254. Meanwhile, the second stimulation pattern 6261 comprises a series of stimulation cycles 6266, with each stimulation cycle 6266 comprising a stimulation period 6263 and a non-stimulation period 6265. For both patterns 6251, 6261, the labels B and E identify a beginning and an end, respectively, of the stimulation periods 6252 and 6263, respectively.

As shown in FIG. 37C, the stimulation periods 6252 of the first stimulation pattern 6251 (to stimulate the hypoglossal nerve) coincide with the stimulation periods 6263 of the second stimulation pattern 6261 (to stimulate the ansa cervicalis-related nerve).

In a manner similar to example stimulation protocol 6220, the open loop nature of the example stimulation protocol 6250 enables stimulation therapy without using a sensor or sensed information that would otherwise be used to synchronize the stimulation cycles (e.g. 6255, 6266) relative to at least one feature of the patient's respiratory cycles 5011. Among other effects, this arrangement may simplify implantation and/or other aspects of providing stimulation therapy for sleep disordered breathing or other physiologic conditions.

In some examples, a duration of the respective stimulation periods 6252, 6263 may be longer than shown in FIG. 37C to generally increase the overall amount of stimulation delivered to the respective hypoglossal and ansa cervicalis-related nerves.

FIG. 37CC is a diagram 6270 schematically representing the same respiratory waveform 5010 as in FIG. 34, and example stimulation protocol 6272 comprising at least some of substantially the same features and attributes as example stimulation protocol 6220 of FIG. 37C (e.g. comprising open-loop stimulation patterns) except with stimulation protocol 6272 explicitly comprising stimulation patterns for up to four targets including the left HGN, left ACN, right HGN, and right ACN. In a manner similar to the stimulation protocol 6220 in FIG. 37C, the stimulation protocol 6272 comprises a stimulation pattern 6221 (like 6221 in FIG. 37C) applied to a first nerve (e.g. left HGN "L HGN") and a stimulation pattern 6241 (like 6241 in FIG. 37C) applied to a second nerve (e.g. left ACN "L ACN"). Meanwhile, stimulation protocol 6272 comprises a stimulation pattern 6271 for application to a third nerve such as a right HGN (R HGN) and comprising stimulation cycles 6275 like stimulation cycles 6235 (or 6246) of stimulation patterns 6221, 6241. However, the stimulation pattern 6271 is offset from both of the stimulation patterns 6221, 6241 such that the stimulation periods 6232 of stimulation pattern 6271 for the right HGN (R HGN) are offset relative to the occurrence of the stimulation periods 6232 of both the stimulation patterns 6221 (L HGN) and 6241 (L ACN). Finally, stimulation protocol 6272 comprises a stimulation pattern 6281 for application to a fourth nerve such as a right ACN (R ACN) and comprising stimulation cycles 6286 like stimulation cycles 6235 (or 6246) of stimulation patterns 6221, 6241. However, the stimulation pattern 6281 is offset from all three of the stimulation patterns 6221, 6241, 6271 such that the stimulation periods 6232 of stimulation pattern 6281 for the right ACN (R ACN) are offset relative to the occurrence of the stimulation periods 6232 of all three stimulation patterns 6221 (L HGN), 6241 (L ACN), and 6271 (R HGN).

Via this arrangement, stimulation may be applied to all four target nerves to apply stimulation with the stimulation being apportioned roughly into fourths among the four nerves such that about one-fourth of the stimulation over a treatment period is applied to a first nerve (e.g. L HGN or other), one-fourth applied to a second nerve (e.g. L ACN or other), one-fourth applied to a third nerve (e.g. R HGN or other), and one-fourth applied to a fourth nerve (e.g. R ACN).

In some examples in which just three nerves are stimulated (instead of all four), then with stimulation being applied continuously the stimulation is apportioned roughly into thirds such that about one-third of the stimulation over a treatment period is applied to a first nerve (e.g. L HGN or other), one-third applied to a second nerve (e.g. L ACN or other), and one-third applied to a third nerve (e.g. R HGN or R CACN as an example).

Via such example implementations, it is believed that a robust, stable arrangement of promoting upper airway patency may be achieved while enhancing patient comfort, managing nerve/muscle fatigue, etc.

It will be understood that in some such examples where just two target nerves are being stimulated, the two target nerves may comprise both hypoglossal nerves (left and right) or may comprise both ansa cervicalis-related nerves (left and right). Moreover, in some examples where just two target nerves are being stimulated, the two target nerves may comprise both just nerves on one side of the body (e.g. left HGN and left CAN OR right HGN and right ACN).

In some examples, one instance of stimulation protocol 6272 may comprise applying offsetting stimulation patterns for both hypoglossal nerves (L HGN and R HGN) and just one of the ansa cervicalis-related nerves (L CAN OR R ACN). It is believed that stimulation of just one of the ansa cervicalis-related nerves may be adequate or sufficient to open the upper airway generally at least because even just one sided (e.g. left or right) ACN stimulation will sufficiently pull the larynx inferiorly to yield the desired opened/stiffened upper airway. In a complementary manner, both hypoglossal nerves may be stimulated bilaterally (e.g. alternately, other) in a way to enhance patient comfort, adapt to different collapse patterns (e.g. type, degree) per different body positions, etc. Accordingly, in one aspect, the stimulation of just one ansa cervicalis-relate nerve may sometimes be referred to as providing a baseline therapy to open/stiffen the upper airway, while the stimulation of the hypoglossal nerves (left and/or right) may sometimes be referred to as providing a more dynamic aspect to the overall stimulation therapy.

In view of these features, in some examples, in general terms not specific to FIG. 37CC, the particular arrangement of stimulating both the left and right hypoglossal nerves and just one ansa cervicalis-related nerve may be employed using other specific stimulation patterns which also may be open loop and/or closed loop.

It will be understood that nerves other than the hypoglossal nerve and ansa cervicalis-related nerve which relate to promoting upper airway patency or otherwise treating sleep disordered breathing can be included in a complementary manner as part of the example stimulation protocols of FIG. 37C or 37CC.

Figure 37D:
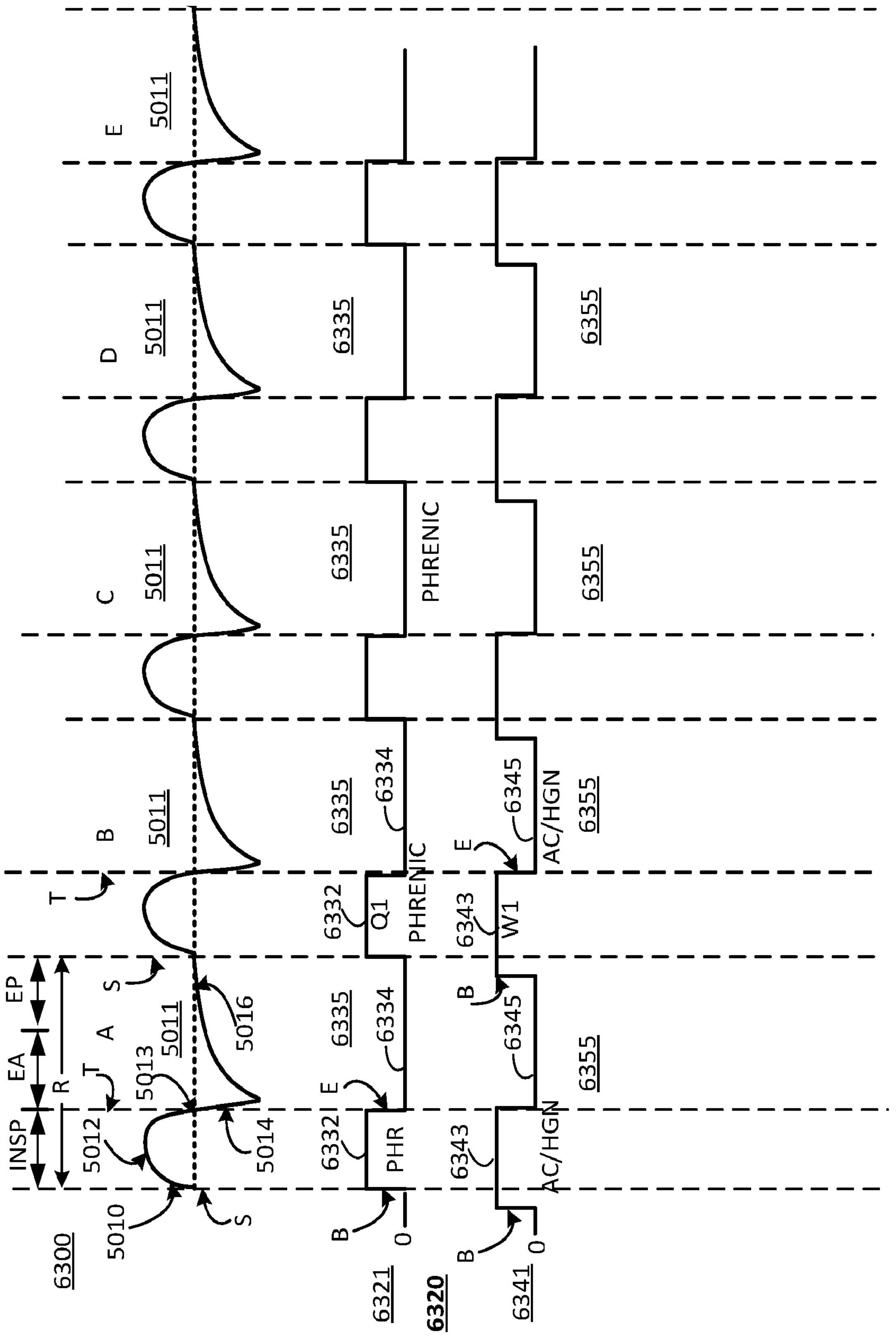

FIG. 37D is a diagram 6300 schematically representing the same respiratory waveform 5010 as in FIG. 34, and example stimulation protocol 6320. As shown in FIG. 37D, example stimulation protocol 6320 comprises a first stimulation pattern 6321 to stimulate a phrenic nerve (PHR) and a second stimulation pattern 6341 to stimulate both an ansa cervicalis-related nerve and a hypoglossal nerve (AC/HGN). In some examples, the first stimulation pattern 6321 of example stimulation protocol 6320 comprises substantially the same features and attributes as the first stimulation pattern 5021 of example stimulation protocol 5030 in FIG. 33A, except with the stimulation signal being applied to a phrenic nerve (PHR) instead of a hypoglossal nerve (HGN). As shown in FIG. 37D, the first stimulation pattern 6321 comprises a series of stimulation cycles 6335, with each stimulation cycle 6335 comprising a stimulation period 6332 (like 5032 in FIG. 33A) and a non-stimulation period 6334 (like 5034 in FIG. 33A).

In some examples, the second stimulation pattern 6341 of example stimulation protocol 6320 in FIG. 37D comprises substantially the same features and attributes as the first stimulation pattern 6021 of example stimulation protocol 6020 in FIG. 37A, except with the stimulation signal being applied to both an ansa cervicalis-related nerve and a hypoglossal nerve (AC/HGN) instead of being applied to solely a hypoglossal nerve (HGN). As shown in FIG. 37D, the second stimulation pattern 6341 comprises a series of stimulation cycles 6355, with each stimulation cycle 6355 comprising a stimulation period 6343 (like 6032 in FIG. 37A) and a non-stimulation period 6345 (like 6034 in FIG. 37A). As further shown in FIG. 37D, the stimulation period 6343 in the stimulation cycles 6355 of stimulation pattern 6341 (to stimulate both the respective ansa cervicalis-related and hypoglossal nerves) is generally synchronous with, and coincides with the inspiratory phase (INSP) while also including a brief pre-inspiratory stimulation component, as identified via the stimulation beginning (B) just prior to the start(S) of the inspiratory phase (INSP) of the patient's respiratory cycle 5011 in a manner similar to stimulation pattern 6021 in FIG. 37A.

With this in mind, the example stimulation protocol 6320 in FIG. 37D may be implemented to treat instances of multiple-type sleep apnea and/or more complex sleep disordered breathing behaviors. For example, in a multiple-type sleep apnea involving both central and obstructive sleep apnea behaviors, the stimulation pattern 6341 may be applied to prevent or minimize obstructive sleep apneas while the stimulation pattern 6321 may be applied to prevent or minimize central sleep apneas. In some such examples, by applying the stimulation pattern 6341 including the pre-inspiratory stimulation component, the stimulation protocol 6320 may help ensure patency of the upper airway prior to the inspiratory phase (INSP) and the stimulation of phrenic nerve (via stimulation pattern 6321) may ensure appropriately timed contraction of the diaphragm as part of the target respiratory cycle.

In some examples, the example stimulation protocol 6320 in FIG. 37D may be employed in association with at least the example stimulation arrangements described later in association with at least FIG. 55—regarding stimulation elements, anchors, delivery methods for stimulating a phrenic nerve and/or for stimulating an ansa cervicalis-related nerve. Moreover, it will be understood that such example stimulation arrangements in association with at least FIGS. 55-59B may be employed in a complementary manner, or separately from, the various example stimulation arrangements for stimulating the hypoglossal nerve.

With regard to the various example stimulation elements, sensing elements, target nerve locations, stimulation element/lead delivery arrangements, etc. described throughout various examples of the present disclosure, it will be understood that in some examples, stimulation protocols other than those described and illustrated in association with FIGS. 33A-37D may be employed.

Figure 37E:
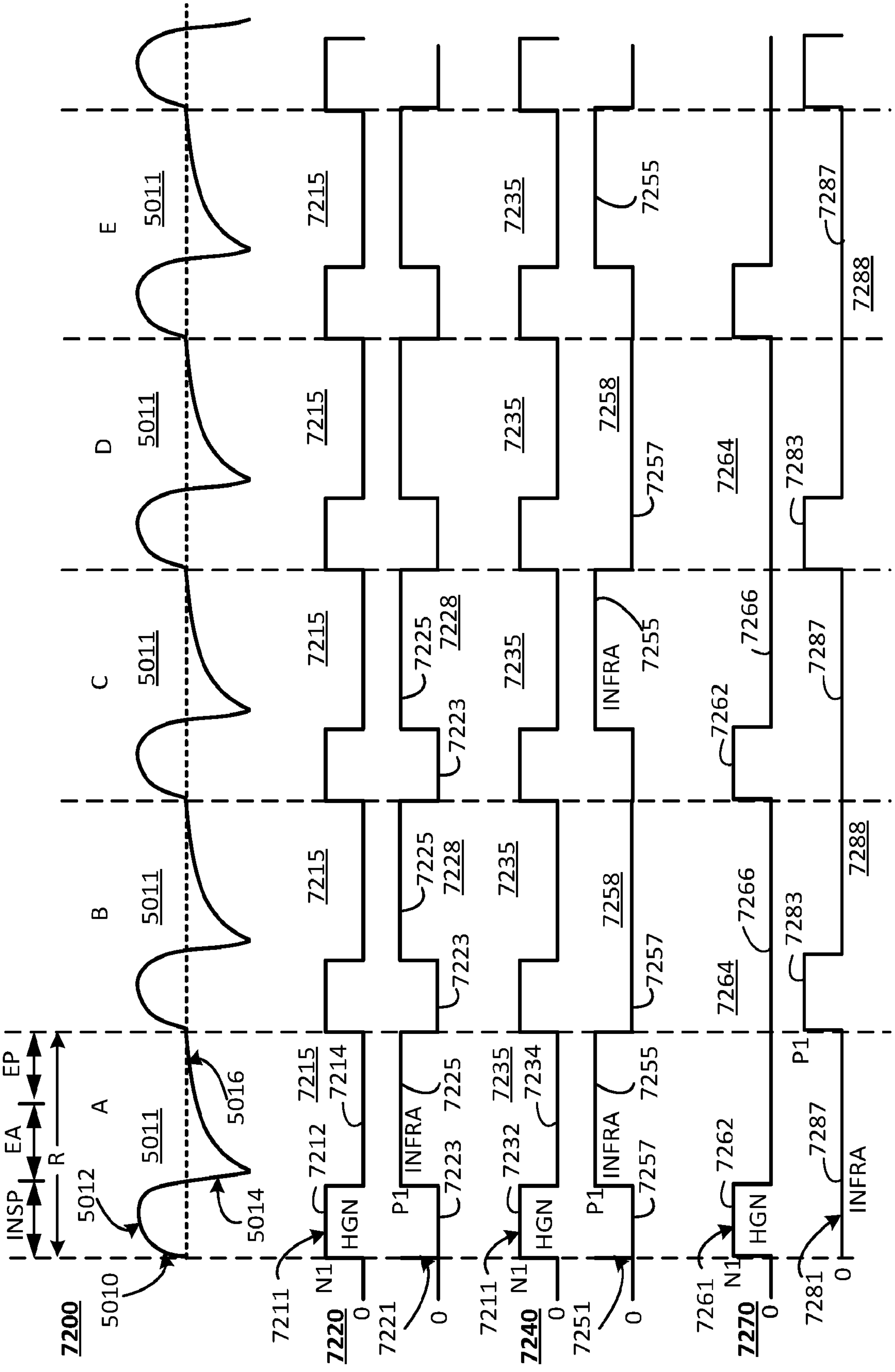
Figure 37F:
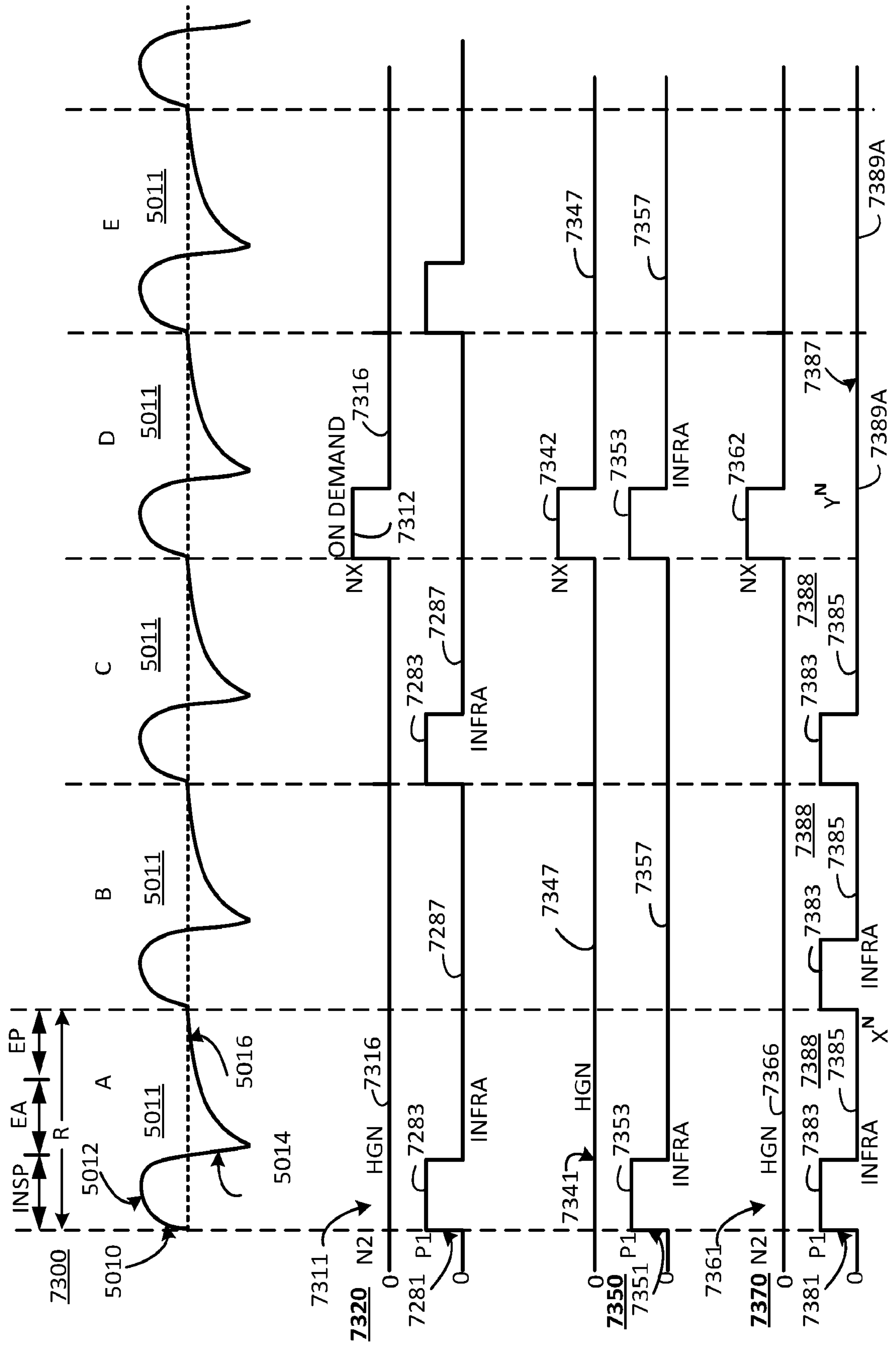
Figure 37G:
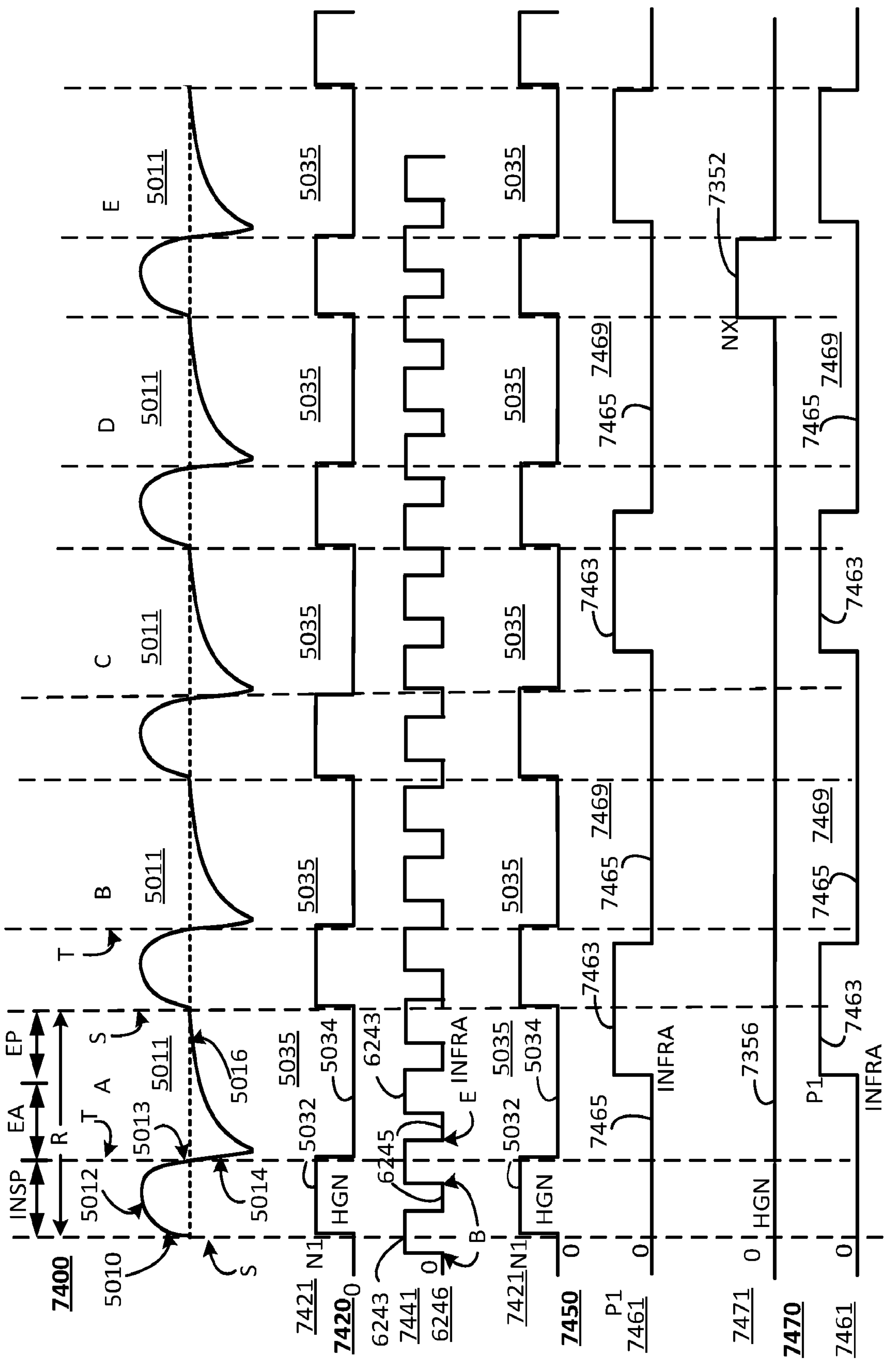

FIGS. 37E-37G are a series of diagrams including views which schematically represent various stimulation protocols, including closed loop stimulation patterns and/or open loop stimulation patterns, including stimulation of upper airway patency tissues. The upper airway patency tissues may comprise a genioglossus-based patency tissue and/or infrahyoid-based patency tissue. In some examples, the genioglossus-based patency tissue may comprise a hypoglossal nerve and/or genioglossus muscles innervated by the hypoglossal nerve. While the examples may generally refer more specifically to hypoglossal nerve (HGN) stimulation, it will be understood that in some such examples, stimulation may be applied to the genioglossus muscle with (or instead of) stimulating the hypoglossal nerve. Meanwhile, in some examples, the infrahyoid-based patency issue may comprise an ansa cervicalis-related nerve and/or infrahyoid strap muscles innervated by the ansa cervicalis-related nerve.

In some examples, the stimulation implemented via the various stimulation protocols may be implemented via at least some of substantially the same features and attributes of the various example stimulation arrangements as previously described in association with at least FIGS. 1-32D, 33A-37D, and/or as of the various later described example arrangements involving sensing, control, etc. Accordingly, unless specifically otherwise noted, the various example stimulation protocols of FIGS. 37E-37G may be applicable for unilateral stimulation or bilateral stimulation of the respective targeted nerves. Moreover, in some examples, the stimulation pattern of one of the example stimulation protocols (as described in FIGS. 37E-37G) for a given nerve (e.g. HGN) may be switched and applied to another upper airway patency tissue (e.g. INFRA), or vice versa.

In some example, at least some of the example stimulation protocols of FIGS. 37E-37G may have particular applicability to the examples of at least FIGS. 38E-38H which address an upper airway patency hysteresis effect exhibited upon electrical stimulation of at least some upper airway patency tissues, such as infrahyoid-based patency tissue, in some examples. However, to achieve at least some purposes, in some examples at least some of the stimulation protocols in the examples of FIGS. 37E-37G may be implemented independent of (i.e. without regard to) a patency hysteresis effect (if present) or implemented even in the absence of a patency hysteresis effect if the particular stimulation protocol, in combination with other factors, may achieve a particular SDB care objective.

In some examples, at least some of the example stimulation protocols of FIGS. 33A-37D may be used in association with a patency hysteresis parameter. For instance, as previously described in association with FIG. 36B, in some stimulation protocols such as (but not limited to) the example stimulation pattern 5790 (of stimulation protocol 5800), the "second" stimulation periods 5792 have a lesser intensity P2, or even may be omitted completely such that no stimulation is provided. In some of these previously described ACN stimulation patterns, at least one stimulation period already has been skipped. In some such examples, these stimulation patterns for the ansa cervicalis-related nerve may be used in association with the patency hysteresis parameter in which some stimulation periods (which might otherwise be applied) are skipped because of the positive prolonged effect of maintained upper airway patency following stimulation of an infrahyoid-based patency tissue.

As previously noted in association with FIGS. 33A-37D, it will be understood that the respiratory cycles 5011 depicted in each frame A-E of FIGS. 37E-37G are depicted as being identical, but in reality there may be variations in the respiratory cycle from breath-to-breath, and each patient may exhibit some variances in their respiratory waveform from other patients. Moreover, for illustrative simplicity, the respiratory waveforms shown in FIGS. 37E-37G do not purport to depict disruptions to the respiratory waveform, which correspond to sleep disordered breathing, signal imperfections, etc. unless otherwise noted or depicted for a particular Figure.

In some examples, the example stimulation patterns in FIGS. 37E-37G depict electrical stimulation of an infrahyoid-based patency tissue (as represented by identifier INFRA), which may comprise an ansa cervicalis-related nerve and/or an infrahyoid strap muscle innervated by the ansa cervicalis-related nerve.

It will be further understood that in examples in which just an upper airway patency-related muscle is stimulated (without stimulating the associated innervating nerve), the amplitude of the stimulation depicted by the example stimulation patterns in FIGS. 37E-37G may represent a different quantitative scale than the quantitative scale of an amplitude of the stimulation of the associated nerve, and vice versa. Moreover, as a general matter, it will be understood that an amplitude of a stimulation pattern for stimulation of one upper airway patency-related tissue (whether nerve or muscle) may be on a quantitative scale (or range) which is different from a quantitative scale (or range) for stimulating a different type of upper airway patency-related tissue (e.g. nerve or muscle).

As shown in FIG. 37E, a stimulation protocol 7220 comprises a stimulation pattern 7211 of a series of stimulation cycles 7215 for electrically stimulating a hypoglossal nerve (HGN) in a closed loop manner in which stimulation periods 7212 of the respective cycles 7215 are synchronized with an inspiratory phase of respiration and each stimulation period 7212 is followed by a non-stimulation period 7214.

The stimulation protocol 7220 also may comprise a stimulation pattern 7221 of a series of stimulation cycles 7228 for electrically stimulating an infrahyoid-based patency tissue (INFRA) in a closed loop manner in which stimulation periods 7223 of the respective cycles 7228 are synchronized with at least a portion of an expiratory phase 5016 of respiration and each stimulation period 7223 is followed by a non-stimulation period 7225.

In this particular example, a duration of the respective stimulation cycles 7215, 7228 are generally equal to a duration (R) of the respective respiratory cycles 5011, at least due to the above-noted synchronization relative to sensed respiratory phase information.

In some examples, the stimulation of the infrahyoid-based patency tissue may be applied independent of (i.e. without regard to a patency hysteresis parameter).

However, in some examples, by timing the stimulation of the infrahyoid-based patency tissue to be synchronized with at least a portion of the expiratory phase, then a patency hysteresis effect may occur during a following inspiratory phase 5012 to increase or maintain upper airway patency prior to the stimulation period 7212 of the hypoglossal nerve, which in turn may facilitate a more successful result from stimulating the hypoglossal nerve for some patients.

In some examples, the proportion of the stimulation period 7225 and the non-stimulation period 7223 of the INFRA stimulation pattern 7221 can be modified so that the duration of the stimulation period 7225 can be less than the entire expiratory phase (5016) or even slightly greater than an entire expiratory phase (5016).

With regard to at least the example stimulation protocols 7220, 7240 in FIG. 37E, in some examples of the present disclosure in which stimulation of infrahyoid-based patency tissue induces a patency hysteresis effect, the stimulation of the hypoglossal nerve may be omitted completely or for at least certain portions of a treatment period (e.g. nightly therapy regimen). As further shown later, in some examples the hypoglossal nerve (HGN) stimulation may be applied on an on-demand basis, as further described in association with at least FIGS. 37F-37G. Moreover, as illustrated in other examples, the hypoglossal nerve stimulation also may be implemented in an open loop manner.

As further shown in FIG. 37E, in some examples an example stimulation protocol 7240 comprises a stimulation pattern 7211 for a hypoglossal nerve as in stimulation protocol 7220 and a stimulation pattern 7251 for an infrahyoid-base patency tissue like previously described stimulation pattern 7221, except with the INFRA stimulation pattern 7251 configured to skip stimulation in every other breath (e.g. every other respiratory cycle 5011). In this arrangement, non-stimulation periods 7257 between consecutive stimulation periods 7255 have a duration greater than a single respiratory cycle 5011 (e.g. a duration of an entire respiratory cycle) plus a duration an inspiratory phase of a respiratory cycle, in some examples.

In some such examples, despite the absence of stimulation (in the skipped respiratory cycles), the inventors have observed a patency hysteresis effect (e.g. prolonged upper airway patency effect) from the preceding stimulation period 7255 of the infrahyoid-based patency tissue helps to maintain upper airway patency during the INFRA non-stimulation period 7257. As previously mentioned, in some examples the prolonged effect (i.e. hysteresis effect) of infrahyoid-based upper airway patency may begin a first time period after initiating stimulation of the infrahyoid-base patency tissue and extend up to an entire respiratory cycle after the termination of such stimulation, in some examples. In some examples, the first time period may be about 80 to about 120 milliseconds, about 90 to about 110 milliseconds, or about 100 milliseconds.

In one aspect, the stimulation protocol 7240 may enhance therapeutic efficacy for at least some patients who may not respond as beneficially from hypoglossal nerve stimulation alone while simultaneously accomplishing a positive therapeutic effect with overall less stimulation than if stimulation of infrahyoid-based patency tissue were applied in every respiratory cycle (5011) as in stimulation pattern 7221 of protocol 7220.

With respect to stimulation pattern 7251 (of stimulation protocol 7240 in FIG. 37E), it will be understood that the non-stimulation period 7257 may have a duration greater than one respiratory cycle. It also will be understood that in some closed loop stimulation patterns and/or open loop stimulation patterns for the infrahyoid-based patency tissue, the non-stimulation periods 7257 may comprise a duration less than a duration of a respiratory cycle 5011 (e.g. a breath). As previously noted, in some examples a maximum duration of such non-stimulation periods 7257 may comprise up to ten respiratory cycles (e.g. ten breaths). In some such examples, the maximum duration of the non-stimulation periods 7257 may depend on other factors such as implementing a selectable number of consecutive stimulation periods applied before implementing the skipping of a selectable number of stimulation periods 7255 (which lengthens a duration of the non-stimulation period 7257 between consecutive stimulation periods 7255) for some number of respiratory cycles, as later described below in association with at least stimulation protocol 7370 of FIG. 37F.

In some examples, some example INFRA stimulation patterns may comprise different proportions of a selectable number of stimulation periods followed by a selectable number of non-stimulation periods. For instance, one example pattern may comprise 3 stimulation periods (of 3 stimulation cycles) following by a single interrupted non-stimulation period including 2 consecutive non-stimulation period portions. Other example proportions may comprise 3:1, 4:2, and the like.

As further shown in FIG. 37E, one example stimulation protocol 7270 may comprise a HGN stimulation pattern 7261 (e.g. for stimulating a hypoglossal nerve (HGN)) and an INFRA stimulation pattern 7281 (e.g. for stimulating an infrahyoid-based patency tissue (INFRA)). The HGN stimulation pattern 7261 may comprise a series of stimulation cycles 7264, which comprise at least substantially the same features as stimulation pattern 7211, except with the stimulation periods 7262 being applied every other respiratory cycle 5011 instead of being applied in each and every respiratory cycle 5011. In this arrangement, a non-stimulation period 7266 extends between consecutive stimulation periods 7262 of HGN stimulation pattern 7261. Meanwhile, the INFRA stimulation pattern 7281 may comprise a series of stimulation cycles 7288 with each cycle 7288 including a stimulation period 7283 and a non-stimulation period 7287. The stimulation periods 7283 are applied in a closed loop manner with a stimulation period 7283 applied in synchronization with an inspiratory phase 5012 of every other respiratory cycle 5011 and with such stimulation periods 7283 being offset (e.g. by one respiratory cycle) from the stimulation periods 7262 of the HGN stimulation pattern 7261. Non-stimulation periods 7287 occur between consecutive stimulation periods 7283 of INFRA stimulation pattern 7281.

Via this example stimulation protocol 7270 (FIG. 37E), a stimulation period (7262 or 7287) is applied during an inspiratory phase of every respiratory cycle 5011 of the patient's breathing but with such stimulation alternating between the hypoglossal nerve (HGN) and an infrahyoid-based patency tissue (INFRA) as shown in FIG. 37E. As in the other example stimulation protocols of at least FIG. 37E, a patency hysteresis effect induced via application of the INFRA stimulation periods 7283 may help to increase or maintain upper airway patency during a time period just prior to and/or during an inspiratory phase 5012 in which stimulation of a hypoglossal nerve (e.g. stimulation period 7262) may be applied. In this example arrangement, while stimulation is being applied during a portion of every respiratory cycle, the overall stimulation applied to each respective upper airway patency tissue (e.g. hypoglossal nerve, infrahyoid-based patency tissue) is significantly reduced (e.g. 50% less) and much less than might otherwise occur than if stimulation were applied to both respective upper airway patency tissues (the hypoglossal nerve and the infrahyoid-based patency tissue) in every respiratory cycle. In some examples, this type of arrangement also may be applied including both left and right sides of the patient's body in accordance with the various examples in association with at least FIGS. 3A-3C, FIG. 36A, and the like.

FIG. 37F is a diagram of example arrangements 7300, including an example stimulation protocol 7320 comprising a closed loop stimulation pattern 7281 (like that in FIG. 37E) of infrahyoid-based patency tissue (INFRA) and an on-demand HGN stimulation pattern 7311. In the particular illustrated example, the on-demand HGN pattern 7311 comprises an on-going non-stimulation period 7316 that extends (e.g. continues) until an on-demand HGN stimulation period 7312 is implemented, and then the HGN stimulation pattern 7311 reverts to the next on-going non-stimulation period 7316. The particular example on-demand stimulation period 7312 is shown in FIG. 37F as being synchronized with an inspiratory phase 5012 in a closed loop manner with the aim of maximizing a probability that the on-demand HGN stimulation may be the most beneficial manner of increasing or maintaining upper airway patency for the particular circumstances triggering the on-demand stimulation.

However, in some examples the on-demand stimulation period 7312 may be applied in an open loop manner which is not synchronized to, and/or triggered by, a particular respiratory phase (e.g. inspiratory, expiratory), portion of a respiratory phase and/or a particular respiratory morphological feature.

Moreover, in some examples, the on-demand HGN stimulation period 7312 of stimulation protocol 7320 may comprise a duration which is less than or greater than the duration shown in FIG. 37F. In some examples, to the extent that the duration of the on-demand stimulation period 7312 is greater than a duration of an inspiratory phase 5012, in some examples the duration of the on-demand stimulation period 7312 may correspond to a duration of a fixed time, such as 3 second, 5 seconds, etc. In some examples, the duration of the on-demand stimulation period 7312 may comprise some multiple (e.g. 2x, 3x, and so on) of a respiratory cycle or a designated portion of a respiratory cycle. In some examples, the duration of the on-demand stimulation period 7312 may comprise a multiple of a duration of a reference respiratory cycle, which may comprise a duration of a patient-specific average respiratory cycle or a duration of a multiple patient average respiratory cycle.

In considering the above-noted different ways of determining and implementing a duration of the on-demand stimulation period 7312, it will be understood that the duration also may depend on, and/or be associated with, some parameter of the stimulation pattern 7281 (or other example INFRA stimulation pattern) such as, but not limited to, a duration of a stimulation period 7283, a duration of a non-stimulation period 7287, duty cycle, patency hysteresis parameter, etc. in association with the INFRA stimulation pattern 7281. In some examples, the application timing of the on-demand HGN stimulation period 7312 also may intentionally coincide with a stimulation period 7283 of the INFRA stimulation pattern 7281, with a non-stimulation period 7287 of the INFRA stimulation pattern 7281, or even straddle a portion of both a stimulation period 7283 and non-stimulation period 7287 of the INFRA stimulation pattern 7281.

In addition, whether implemented in a closed loop manner or an open loop manner (to relative respiratory information) a starting point and/or an ending point for such on-demand HGN stimulation period 7312 is not limited to the particular example starting and/or ending points depicted in example stimulation pattern 7311 of stimulation protocol 7320 in FIG. 37F.

Furthermore, it will be understood that the use of the on-demand HGN stimulation pattern 7311 is not limited to use with the particular INFRA stimulation pattern 7281 but may be implemented via a wide variety of other INFRA stimulation patterns, at least some of which are provided as example stimulation patterns within the examples of the present disclosure.

In this stimulation protocol 7320 of FIG. 37F, in some examples the on-demand HGN stimulation period 7312 is not applied at all until or unless a determination is made, in view of the already occurring INFRA stimulation pattern 7281, that further intervention is desired to increase or maintain upper airway patency. In some examples, any one or more of a plurality of parameters (e.g. inputs) affecting patency may be part of such determination. As noted elsewhere, a degree and/or type of patency also may be expressed in terms of a degree and/or type of collapsibility which reduces patency. At least some example implementations of such patency parameters and/or patency determination is described later in association with at least FIGS. 38A-38H, and in particular, FIGS. 38E-38H. In some examples, a change in such patency parameters may be a reason to modify a stimulation protocol such as, but not limited to, implementing an on-demand HGN stimulation period 7312 among other modifications, as described in association with at least FIGS. 38E-38H. As just two examples, one such change in patient parameters affecting patency (e.g. patency parameters) may relate to body position, such as a patient moving from a side-lying position to a supine position (or vice versa), and/or sleep disordered breathing (SDB) event frequency.

In one aspect, the example stimulation protocol 7320 may produce efficacious therapy with a lower overall volume of stimulation for at least a couple reasons. First, the INFRA stimulation pattern 7281 may produce generally stable and sufficient upper airway patency by leveraging the patency hysteresis effect from stimulating (via pattern 7281) infrahyoid-based patency tissue such that the stimulation periods 7283 may occur every other respiratory cycle or at even greater intervals, as further described below. Moreover, to the extent that a given patient may periodically benefit from a boost in stimulation in certain temporary situations (e.g. supine body position, other) and it is desirable to not disrupt the otherwise effective INFRA stimulation pattern 7281. In such situations, the on-demand HGN stimulation may be sufficient to increase or maintain upper airway patency, where the HGN stimulation may be more effective than solely delivering INFRA stimulation for that circumstance. Of course, whether with or without on-demand HGN stimulation, the INFRA stimulation pattern 7281 also may be adjusted temporarily to deal with such situations.

In some examples, a stimulation protocol which is the converse of the stimulation protocol 7320 may be implemented in which a regular HGN stimulation pattern is implemented and an INFRA stimulation pattern is applied in an on-demand manner. In some examples, the HGN stimulation pattern may be a closed loop pattern in which stimulation periods are synchronized relative to the inspiratory phase (or other phase, morphology) of a sensed respiratory cycle or may be an open loop pattern, in some examples. At least some such example implementations are further illustrated in association with at least FIG. 38H.

As further shown in FIG. 37F, another example stimulation protocol 7350 also provides HGN on-demand stimulation. In this example, the stimulation protocol 7350 comprises at least some of substantially the same features and attributes as the example stimulation protocol 7320 (FIG. 37F), except with non-stimulation periods 7357 of an INFRA stimulation pattern 7351 comprising a duration (e.g. at least two respiratory cycles 5011) greater than a duration of the non-stimulation periods 7287 of stimulation pattern 7281 (FIG. 37F, 37E). It will be further understood that the INFRA stimulation pattern 7351 may be considered also representative of further examples in which the duration of the non-stimulation periods 7357 (between consecutive stimulation periods 7353) may be even longer, such as 3, 4, 5, or more respiratory cycles up to a selectable limit of the number of respiratory cycles between consecutive stimulation periods 7353.

However, it will be understood that in at least some examples, the duration of the non-stimulation periods 7357 corresponds to, and/or bears a relationship with, a duration of the patency hysteresis effect, which may be monitored and at least partially controlled, etc. via a patency hysteresis parameter as part of a stimulation protocol. In other words, in at least some examples the duration of the non-stimulation periods 7357 is not arbitrary but rather reflects a duration of an expected patency hysteresis effect as selectively controllable via a patency hysteresis parameter. At least some such example implementations are further described later in association with at least FIGS. 38E-38H. Among other types and ways of at least partially controlling the patency hysteresis effect, a timing of INFRA stimulation periods (e.g. duration, frequency, open loop or closed loop, amplitude, etc.) may be used to at least partially control the duration and amplitude of the patency hysteresis effect.

In some examples, the various example implementations of delivering stimulation via a patency hysteresis parameter/effect may be applied to at least some of the example stimulation protocols of FIGS. 33A-37D, such as via skipping at least some stimulation periods in some of the ACN stimulation patterns (e.g. INFRA stimulation patterns) by which a patency hysteresis effect may be implemented.

With this in mind, in some examples, a longer duration of patency hysteresis effect may be implemented by applying stimulation periods, each of which may have a relatively longer duration than shown in protocol 7350 and/or by applying a series of INFRA stimulation periods (with a relatively shorter non-stimulation period therebetween) before implementing a longer duration non-stimulation period because the series of INFRA stimulation periods may produce a cumulative hysteresis effect in at least some patients. In the cumulative hysteresis effect, following a series of INFRA stimulation periods a duration of the patency hysteresis effect is greater than when just a single INFRA stimulation period (of the same duration as the stimulation periods in the series) is applied before a longer non-stimulation period.

As shown in FIG. 37F, a stimulation protocol 7370 provides one example implementation which may be used to achieve at least some aspects of the above-noted cumulative hysteresis effect. In particular, an example stimulation pattern 7370 comprises an example INFRA stimulation pattern 7381 comprising a series of stimulation cycles 7388, each of which comprise a stimulation period 7383 and a first non-stimulation period 7385. After some selectable number ($X^N$) of such consecutive stimulation cycles 7388 (including consecutive stimulation periods), then the stimulation pattern 7381 comprises a second non-stimulation period 7387 In some examples, a respective first non-stimulation period 7385 occurring after the last stimulation period 7383 (of a series of stimulation cycles) may be considered part of the second non-stimulation period 7387. However, in some examples, this respective first non-stimulation period 7385 of a last stimulation cycle 7388 may be considered separate from the second non-stimulation period 7387.

The duration of the second non-stimulation period 7387 of the INFRA stimulation pattern 7381 may correspond to a sum of a selectable number (YN) of respiratory cycles 5011 (or other unit of measure) resulting in a single, uninterrupted period of non-stimulation during which the patency hysteresis effect is permitted to occur, which in turn may increase or maintain upper airway patency even in the absence of stimulation of infrahyoid-based patency tissue (such as via stimulation period 7383).

In some examples, an alternate arrangement may be used to specify the duration of the non-stimulation period 7387 during which the patency hysteresis effect is to be applied (e.g. occur). For instance, the single uninterrupted non-stimulation period 7387 (e.g. intended period of patency hysteresis effect) may be viewed as a selectable number (Y) of non-stimulation period portions 7389A, 7389B, etc. In some examples, these non-stimulation period portions 7389A, 7389B, etc. comprise a duration generally equal to an average duration of a sensed respiratory cycle for the patient. However, in some examples, these non-stimulation period portions 7389A, 7389B, etc. may comprise a duration generally equal to an average duration of a reference respiratory cycle, which is not based on actively-sensed respiration but which is based on a historical patient-specific average respiratory cycle or a multiple patient average duration respiratory cycle.

In example arrangements in which the single uninterrupted non-stimulation period 7387 is determined as a selectable number of non-stimulation period portions 7389A, 7389B (or as a selectable number of respiratory cycles). In some examples this selectable number may match the selectable number of stimulation periods 7383 of the series of stimulation cycles 7388 preceding the single uninterrupted patency non-stimulation period 7387, However, the selectable number of non-stimulation portions 7389A, 7389B, etc. or number of respiratory cycles (to comprise the intended non-stimulation period 7387 during which non-stimulation is to occur to permit the patency hysteresis effect) may be selected to be greater than or fewer than the selectable number of stimulation periods 7383 (of stimulation cycles 7388) applied to produce the intended patency hysteresis effect. In some examples, the selectable number may depend on the patient parameters (including patency parameters) for a particular patient, as well as the particular patient's patency hysteresis response to different patterns of stimulations.

In the example stimulation pattern 7381 of protocol 7370, it will be understood that, after the non-stimulation period 7387, another series of stimulation cycles 7388 (including a selectable number of stimulation periods 7383 (e.g. 3) will be implemented before the next non-stimulation period 7387 for patency hysteresis effect.

It will be further understood that within a treatment period (e.g. nightly treatment period, such as 10 pm to 6 am), the selectable number of consecutive stimulation periods (in a series of stimulation cycles) or the selectable number of non-stimulation period portions comprising a single uninterrupted non-stimulation period (e.g. 7387) may remain the same or may be modified based on a patency hysteresis parameter (e.g. time of night, position, etc.) with such timing and the selectable number being pre-programmed or being responsive to sensed information during the treatment period.

In some examples, the duration of the non-stimulation period 7387 may be determined as a number of time units (e.g. number of seconds), as a percentage of an overall duty cycle during an entire treatment period or portion of a treatment period.

With further reference to the example stimulation protocol 7370 in FIG. 37F, the HGN stimulation pattern 7361 is an on-demand pattern like the on-demand stimulation patterns in stimulation protocols 7320, 7350. In some examples, one goal of providing such on-demand stimulation is to respond to particular circumstances such that HGN stimulation may be omitted relatively long periods of time, such as minutes, hours, etc. By providing the HGN stimulation on an on-demand basis, this example arrangement may reduce nerve/muscle fatigue, conserve power, etc.

It will be understood that in some examples, the INFRA stimulation periods 7383 may have a longer duration than shown in FIG. 37F, may be synchronized relative to a different portion of a respiratory cycle, or even be applied in an open loop manner (e.g. not synchronized relative to a particular portion of a sensed respiratory cycle). Even with these variations, by providing some selectable multiple number ($X^N$) of consecutive stimulation periods 7383 (of regular stimulation cycles) of infrahyoid-based patency tissue, a cumulative hysteresis effect may be achieved for some multiple number of respiratory cycles.

FIG. 37G is a diagram of example arrangements 7400, including a schematically representation of an example stimulation protocol 7420 which comprises an HGN stimulation pattern 7421 and an INFRA stimulation pattern 7441. In some examples, the HGN stimulation pattern 7421 of FIG. 37G may comprise at least some of substantially the same features and attributes of stimulation pattern 5031 (of stimulation protocol 5030) of FIG. 33A, and in some examples the stimulation pattern 7441 of FIG. 37G may comprise at least some of substantially the same features and attributes of stimulation pattern 6241 (of stimulation protocol 6220) of FIG. 37C.

In some examples of the stimulation protocol 7420, the HGN stimulation pattern 7421 provides closed loop stimulation to the hypoglossal nerve (e.g. genioglossus-based patency tissue). In some such examples, the stimulation periods 5032 may be synchronized relative to the inspiratory phase 5012 of sensed respiratory cycles 5011. However, this closed loop stimulation pattern can take other forms such as some of the example HGN stimulation patterns throughout the examples of at least FIGS. 33A-37F.

In some examples of this stimulation protocol 7420 of FIG. 37G, the INFRA stimulation pattern 7441 provides open loop stimulation of infrahyoid-based patency tissue (e.g. an ansa cervicalis-related nerve and/or an infrahyoid muscle innervated by the ansa cervicalis-related nerve) in which the stimulation periods 6243 are not synchronized relative to a particular respiratory phase (e.g. inspiratory phase, expiratory phase, etc.). As later noted for stimulation protocol 7450, in other examples the stimulation periods 6243 (and associated non-stimulation periods 6245) may comprise other durations, frequencies, etc. such as (but not limited to) the example stimulation patterns 7461 in FIG. 37G.

As further shown in FIG. 37G, one example stimulation protocol 7450 comprises an HGN stimulation pattern 7421 (like that of stimulation protocol 7420 in FIG. 37G) and an INFRA stimulation pattern 7461 which provides for open loop stimulation of infrahyoid-based patency tissue comprising a different duration and frequency of stimulation periods 7463 (and non-stimulation periods 7465) than in INFRA stimulation pattern 7441. In the INFRA stimulation pattern 7461, each stimulation cycle 7469 comprises a stimulation period 7463 and a non-stimulation period 7465. As shown for the example INFRA stimulation pattern 7461, in some examples, the non-stimulation portions 7465 have a duration greater than a duration (R) of a respiratory cycle 5011 in order to take advantage of the patency hysteresis effect immediately following each respective INFRA stimulation period 7463.

As shown in at least some other example stimulation patterns in the present disclosure, the duration of the non-stimulation periods 7465 of stimulation pattern 7461 may be shorter than shown in FIG. 37G. However, in some such examples, the duration of the non-stimulation periods 7465 is still long enough to benefit from at least a portion of the patency hysteresis effect following the termination of the preceding stimulation period 7463.

In some examples, a duration of each stimulation period 7463 may be greater than shown in FIG. 37G while still preserving the same duration of the non-stimulation periods 7465. In some examples, the duration of each INFRA stimulation period 7463 may be greater than a duration of an inspiratory phase 5012, greater than a duration of an expiratory phase 5016, and/or greater than a duration of an entire respiratory cycle 5011. In some such examples, the duration of each stimulation period 7463 may be the same throughout the stimulation pattern 7461 or may intentionally be varied throughout a treatment period or segments within a treatment period.

As further shown in FIG. 37G, an example stimulation protocol 7470 comprises at least some substantially the same features and attributes as example stimulation protocol 7450, except with the HGN stimulation pattern 7471 comprising an on-demand stimulation period(s) 7352. In some examples, the on-demand HGN stimulation pattern 7471 may comprise at least some of substantially the same features and attributes as the example HGN on-demand stimulation pattern 7341, 7361 as previously described in association with at least FIG. 37F. Accordingly, the duration, amplitude, and timing (open or closed loop) of the on-demand stimulation period 7352 is not strictly limited to the example shown in stimulation pattern 7471 in FIG. 37G.

With regard to at least the examples of stimulation protocols including an on-demand HGN stimulation pattern, it will be understood that in some examples the HGN stimulation pattern may be completely omitted either by not implanting a stimulation element relative to a hypoglossal nerve or by not making a HGN stimulation pattern available for clinician programming and/or for patient use, even when an HGN stimulation element already may be implanted.

In some examples, the example implementations of FIGS. 37E-37F may be implemented as part of a control portion such as, but not limited to, the control portion(s) described in association with at least FIGS. 54A-54E.

FIG. 38A is a flow diagram schematically representing an example arrangement 8000 including an example device for, and/or example method of, using sensed data as feedback to adjust an intensity (e.g. strength) of, or other parameters, aspects, etc. regarding, stimulation of a hypoglossal nerve and/or ansa cervicalis-related nerve. In some examples, the example arrangement 8000 may comprise at least some of substantially the same features and attributes as the example stimulation devices and/or methods previously described examples of the present disclosure, including stimulation protocols, stimulation arrangements, etc. In some examples, the sensing may comprise at least some of the same features and attributes as at least the later described sensing/control examples, such as but not limited to FIGS. 38B-38H.

As shown in FIG. 38A, example arrangement 8000 comprises a stimulator 8010 to generate stimulation signals 8012, 8014 to deliver stimulation via a hypoglossal (HGN) stimulation element 8020 and via an ansa cervicalis-related nerve (ACN) stimulation element 8030, respectively. During and/or after such stimulation, data 8022, 8032 can be sensed from the stimulation elements 8020, 8030, such as but not limited to, an impedance between the respective elements 8020, 8030. In some examples, a sensor(s) 8034 may supply other or additional data as input 8033, as further described later.

At 8035, the sensed data is evaluated (e.g. checked) such as a sensed data evaluator and the value 8037 of the measured parameter(s) (e.g. impedance) is fed to the stimulation settings generator (at 8040), which in turn generates updated (or maintained) settings 8042, which are fed to the stimulator 8010. In some examples, the impedance may indicate a degree of upper airway patency. For example, a smaller cross-sectional upper airway, which reflects less upper airway patency, may be sensed as a lower impedance. Conversely, a larger cross-sectional upper airway, which reflects more upper airway patency, may be sensed as a higher impedance. Accordingly, maximal patency (measured as a higher impedance) may general correspond to periods of stimulation (HGN and/or ACN) or correspond to peak expiration of a respiratory cycle. Meanwhile, minimal patency (measured as a lower impedance) generally corresponds to inspiration, just prior to inspiration, or the onset of stimulation (e.g. HGN and/or ACN).

Among other adjustments, the determination made at 8035 may be used to balance a relative amount of stimulation to be applied via the HGN stimulation element 8020 and/or the ACN stimulation element 8030. For example, per some example determinations at 8035, balancing the stimulation comprise applying stimulation solely via the HGN stimulation element 8020, while per some example determinations at 8035, balancing the stimulation may comprise applying stimulation solely via the ACN stimulation element 8030. Moreover, per some example determinations at 8035, balancing the stimulation may comprise applying the stimulation as some stimulation via the HGN stimulation element 8020 and some stimulation via the ACN stimulation element 8030 while controlling a relative proportion of the stimulation between the respective HGN and ACN nerves. In addition to the extent that bilateral stimulation may be applied among a left HGN nerve, a right HGN nerve, a left ACN nerve, and/or a right ACN nerve, the above-described adjustments may be made among those four nerves.

In some examples, generating the stimulation settings at 8040 (e.g. stimulation setting generator) may comprise other parameters in addition to, or other than, adjusting which nerves are stimulation (and by how much). Such other parameters may comprise adjusting an intensity or strength of the stimulation at any given nerve (HGN and/or ACN), whereby the strength adjustment may comprise adjustments in amplitude, pulse width, pulse frequency, duty cycle, pulse duration, and the like, at least some of which are described in association with and/or implemented via the stimulation engine 8800 in FIG. 38D. In some examples, additional adjustments may comprise whether stimulation of the nerves (left HGN, right HGN, left ACN, and/or right ACN) are implemented simultaneously, alternately, in a particular sequence, randomly, and the like.

In some examples, in addition to or instead of using the inputs 8022, 8032 from the stimulation elements 8020, 8030 to perform a check of sensed data, an example method/device may comprise a sensed data input 8031 from at least one sensing source 8034, which may comprise a dedicated sensing element or an element not dedicated to sensing. The sensing source(s) 8034 may comprise at least one of a plurality of sensing modalities, types, etc.

FIG. 38B is a block diagram schematically representing an example sensed data engine 8700 including a plurality of different physiologic parameters determinable from sensed data which may be used in at least the sensed data check 8035 as part of the example method in FIG. 38A. As shown in FIG. 38B, in some example physiologic parameters determinable from sensed data may comprise parameters regarding collapse 8710, position 8722, respiration 8724, disease burden 8726, sleep 8728, and other 8729.

In some examples, the collapse parameter 8710 (e.g. collapsibility parameter) may comprise further parameters regarding a pattern 8712 and/or a degree 8714 of collapse of the upper airway in the patient's body. In some such examples, the sensing of data regarding a collapse pattern parameter 8712 and/or a degree parameter 8714 may be implemented via at least some of substantially the same features and attributes as later described in association with at least FIGS. 53A-53F by which a pattern, location, and degree of collapse may be determined and characterized so as to use this information as part of the sensed data check.

In some examples, per collapse parameter 8710, if an antero-posterior collapse is detected (of a sufficient degree), then in some examples the stimulation settings are generated (e.g. 8040 in FIG. 38A) to implement stimulation therapy via applying stimulation to the hypoglossal nerve solely, initially, or primarily (but not solely). In some examples, applying the stimulation initially may sometimes be referred to as applying stimulation first, i.e. prior to applying stimulation to the ansa cervicalis-related nerve.

In some examples, per collapse parameter 8710, if a lateral and/or concentric collapse pattern (of a sufficient degree) is detected, then in some examples the stimulation settings are generated (e.g. 8040 in FIG. 38A) to implement stimulation therapy via applying stimulation solely, initially, or primarily (i.e. not solely) to the ansa cervicalis-related nerve. In some examples, applying the stimulation initially may sometimes be referred to as applying stimulation first, i.e. prior to applying stimulation to the hypoglossal nerve.

In some examples, via the collapse parameter 8710 in FIG. 38B, one example implementation of the example arrangement 8000 in FIG. 38A may comprise generating stimulation settings (e.g. 8040 in FIG. 38A) using the sense data check (e.g. 8035 in FIG. 38A) based on sensor inputs 8022, 8032 (e.g. impedance) or sensor input 8033 to automatically assess the pattern, location, and/or degree of collapse and then select which nerves (e.g. HGN, ACN) are applied, and if both types of nerves are to be stimulated, then select a sequence of stimulation, simultaneous application, proportion, etc. In some examples, such selection may be implemented in cooperation with the relationship parameter 8813 of the stimulation engine 8100 (e.g. FIG. 38B), as further described below.

In some examples, collapse information may be determined via sensing impedance (8752 in FIG. 38C), such as via sensor inputs 8022, 8032 (via the stimulation elements 8020, 8030 or other electrodes) or other sensor input 8033. In some examples, one or more of the other sensor tools (array 8750 in FIG. 38C) may be used to determine collapse, such as but not limited to sensed accelerometer data (per 8754 in FIG. 38C), which may be used alone or with sensed impedance. Similarly, sensed acoustic data (8769 in FIG. 38C) from an accelerometer or other sources may reveal collapse information, with one non-limiting example including sensing snoring information (e.g. via snoring partner, other).

In some examples, a typical collapse pattern for a given patient may be known prior to implanting a nerve stimulation system such that the sensed data engine 8700 (as supported by memory of the control portion 10500) may retrieve stored data regarding such collapse pattern(s) for use in initial or ongoing programming of stimulation therapy, adapting the stimulation therapy and/or use in confirming sensing of such collapse patterns. In some such examples, a clinician/other may enter such known collapse information as part of the programming, whether initially or later. This information may be entered via user interface 10520 (FIG. 54D), clinician programmer 10650 (FIG. 54E), and/or a patient management tool 10660 (FIG. 54E) such as (but not limited to) a cloud portal resource 10662 (FIG. 54E).

Moreover, to the extent that the stimulation therapy may be effective in lessening or preventing the known collapse pattern, then example devices/methods may compare a degree, type, etc. of the stored, known collapse pattern with the currently sensed collapse pattern (or lack thereof) as one way to evaluate the stimulation therapy and potentially determine what, if any, adjustments to stimulation therapy may be warranted. For example, one may evaluate the sensed collapse (e.g. pattern, degree) and adjust how each nerve (e.g. left HGN, right HGN, left ACN, right ACN, and combinations thereof) is to be stimulated such as via various aspects of the relationship parameter 8813 and/or other parameters of the stimulation engine 8800 (FIG. 38D, relative to available stimulation protocols (e.g. FIGS. 33-37D) as well as in cooperation with other sensed data (8700 in FIG. 38B), sensor tools (array 8750 in FIG. 38C) or other parameters, factors, engines, methods, as described throughout various examples of the present disclosure.

In some examples, the position parameter 8722 of sensed data engine 8700 in FIG. 38B for a wide variety of purposes. In some examples, sensed data regarding body position (or posture) may be used to initiate, terminate, and/or adjust therapy stimulation settings, patterns, etc. For instance, in some examples, upon sensing the patient being in a supine position, such as when one may expect a highest likelihood of obstructive sleep apnea for at least some patients, then an example method may comprise delivering stimulation to both a hypoglossal nerve (e.g. left and/or right) and an ansa cervicalis-related nerve (e.g. left and/or right), such as via elements 8020, 8030 in FIG. 38A. As previously mentioned, posture and/or activity sensed via an accelerometer may be used with sensed body position for making the preceding determination.

In some examples, upon sensing the patient is lying on their side (e.g. a lateral decubitis position), then an example method may comprise delivering stimulation solely to an ansa cervicalis-related nerve (e.g. left and/or right), such as solely via element 8030 in FIG. 38A.

In some examples, upon sensing the patient is lying prone, then an example method may comprise delivering stimulation to neither the hypoglossal nerve nor the ansa cervicalis-related nerve per 8020, 8030 in FIG. 38A.

At least because some patients may exhibit atypical position-dependent sleep disordered breathing, it will be understood that other stimulation settings may be generated (8040 in FIG. 38A) than described above.

In some examples, a sensed position (e.g. 8722 in FIG. 38A for 8035 in FIG. 38A) may be used to determine or adjust timing of when stimulation is to be applied and/or to adjust which nerve targets (left HGN, right HGN, left ACN, right ACN) are to be stimulated.

With further reference to FIG. 38B and FIG. 38A, in some examples, a respiration parameter (8728 in FIG. 38B) may comprise the sensed data which is evaluated (8035 in FIG. 38A) and on which stimulation settings may be generated (8040 in FIG. 38A) to determine which nerves (and at which strength settings, etc.) are to be stimulated (8020, 8030 in FIG. 38A). In some such examples, the sleep parameter 8728 may comprise a sleep state, such as whether the patient is awake or asleep and/or such as the sleep stage of the patient.

With further reference to FIG. 38B and FIG. 38A, in some examples, a respiration parameter (8724 in FIG. 38B) may comprise the sensed data which is evaluated (8035 in FIG. 38A) and on which stimulation settings may be generated (8040 in FIG. 38A) to determine which nerves (and at which strength settings, etc.) are to be stimulated (8020, 8030 in FIG. 38A). At least some example implementations of the respiration parameter 8724 as sensed data (8035) and/or for other uses were previously described in association with at least FIG. 3C and/or are later described in association with at least FIGS. 38C-38D, as well in association with at least FIGS. 40A-51B.

With further reference to FIG. 38B and FIG. 38A, in some examples, a disease burden parameter (8726 in FIG. 38B) may comprise the sensed data which is evaluated (8035 in FIG. 38A) and on which stimulation settings may be generated (8040 in FIG. 38A) to determine which nerves (and at which strength settings, etc.) are to be stimulated (8020, 8030 in FIG. 38A). In some such examples, the disease burden parameter 8726 may comprise an indication of a severity (e.g. apnea-hypopnea index-AHI) (e.g. burden) on the patient imposed by the disease (e.g. sleep disordered breathing, such as but not limited to obstructive sleep apnea). It will be understood that in some examples, the disease burden parameter 8726 may comprise burden indications of other diseases, such as cardiac disorders, etc. which may be related to the disease burden imposed by sleep disordered breathing. At least some example implementations of the disease burden parameter 8726 as sensed data (8035) and/or for other uses were previously described in association with at least FIG. 3C and/or are later described in association with at least FIGS. 38C-38D, as well in association with at least FIGS. 40A-51B.

It will be understood that at least some of the various parameters in the sensed data engine 8700 may be used in a complementary manner in various combinations in methods of stimulation therapy for treating sleep disordered breathing according to examples of the present disclosure.

FIG. 38C is a block diagram schematically representing example sensor tools array 8750, which may comprise one or more types of sensors which may comprise example implementations of one or more of the various sensors described as part of one or more of the example arrangements throughout the present disclosure, such as but not limited to the sensors (e.g. 560, 566, 568A, 568B, other) described in association with at least FIG. 3C. In some examples, the example sensor tools in array 8750 may comprise sensors to sense impedance 8752, acceleration (e.g. accelerometer) 8754, pressure 8756, EMG 8758, ECG 8760, ballistocardiograph (BALLISTO) 8762, seismocardiograph (SEISMO) 8764, heart rate (HR) 8766, and other 8768.

In some examples, the impedance sensor 8752 in sensor tools array of FIG. 38C may not be a separate standalone sensor but represent that impedance sensing may be performed via multiple spaced apart electrodes and further represent any associated hardware or aspects of a control portion for performing such impedance sensing.

Like the sensing types, physiologic parameters etc. described in association with FIG. 3C, sensing parameters regarding ballistocardiograph 8762 or a seismocardiograph sensor may determine respiration, among other physiologic parameters. In some examples, sensing an EMG (parameter 8758) may be used to determine upper airway patency, tongue protrusion, responsiveness to stimulation therapy, and the like, and thereby be used for timing in applying stimulation, determining effectiveness in the delivered stimulation therapy. As related aspects, the sensed EMG information may provide respiratory phase information, stimulation response information, and the like. In some examples, methods of sensing an EMG (parameter 8758) or using sensed EMG information may further comprise at least the example implementations of method 8250 in FIG. 51B, method 8400 in FIG. 44A, and/or other examples of the present disclosure including EMG sensing or sensed EMG information.

With regard to sensing various parameters such as (but not limited to) respiration (8724 in FIG. 38B), sleep (8728 in FIG. 38B), and/or position/posture (8722 in FIG. 38B) via an accelerometer 8754 (FIG. 38C), in some examples such sensing may comprise at least some of substantially the same features and attributes as described in: (1) U.S. 2019/0160282, published May 30, 2019, and titled ACCELEROMETER-BASED SENSING FOR SLEEP DISORDERED BREATHING (SDB) CARE; (2) WO/2021/016558, published Jan. 28, 2021, titled SLEEP DETECTION FOR SLEEP DISORDERED BREATHING (SDB) CARE, and filed on Sep. 4, 2020 as a 371 National Stage Application, published as US20230095780 on Mar. 30, 2023; (3) WO/2021/016562 published on Jan. 28, 2021, titled RESPIRATION DETECTION, and filed on Sep. 2, 2020 as a 371 National Stage Application, published as US20230119173 on Apr. 20, 2023; and/or (4) WO/2021/016536 published Jan. 28, 2021, titled SYSTEMS AND METHODS FOR OPERATING AN IMPLANTABLE MEDICAL DEVICE BASED ON POSTURE DETECTION, and filed on Sep. 4, 2020, as a 371 National Stage Application, published as U.S. 21210268279 on Sep. 21, 2012, each of which are hereby incorporated by reference in their entirety.

Figure 38D:
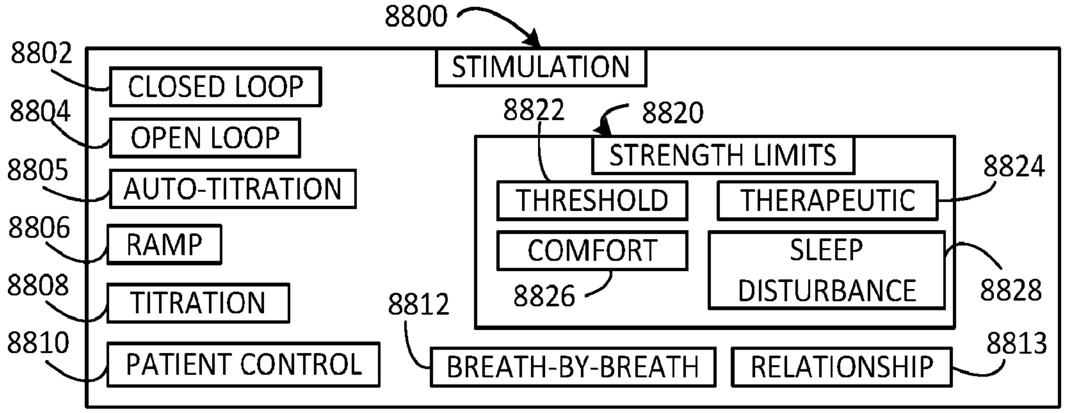

FIG. 38D is a block diagram schematically representing an example stimulation engine 8800. In some examples, the stimulation engine 8800 may comprise one example implementation of control portion 10000 in FIG. 54B as a whole, and/or of instructions 10511 of control portion 10000 In some examples, the stimulation engine 8800 may comprise a treatment period parameter 8801, closed loop parameter 8802, an open loop parameter 8804, an auto-titration parameter 8805, a ramp parameter 8806, a titration parameter 8808, a patient control parameter 8810, a breath-by-breath parameter 8812, a relationship (e.g. nerve stimulation relationship) parameter 8813, and/or a strength limits parameter 8820. In some examples, the strength limits parameter 8820 may further comprise a threshold parameter 8822, a therapeutic parameter 8824, a comfort parameter 8826, and a sleep disturbance parameter 8828.

In some examples, stimulation may be delivered according to a treatment period, which may comprise a period of time beginning with the patient turning on the therapy device and ending with the patient turning off the device. In some examples, the treatment period may comprise a selectable, predetermined start time (e.g. 10 p.m.) and selectable, predetermined stop time (e.g. 6 a.m.). In some examples, the treatment period may comprise a period of time between an auto-detected initiation of sleep and auto-detected awake-from-sleep time. With this in mind, the treatment period corresponds to a period during which a patient is sleeping such that the stimulation of the upper airway patency-related nerve and/or central sleep apnea-related nerve is generally not perceived by the patient and so that the stimulation coincides with the patient behavior (e.g. sleeping) during which the sleep disordered breathing behavior (e.g. central or obstructive sleep apnea) would be expected to occur.

To avoid enabling stimulation prior to the patient falling asleep, in some examples stimulation can be enabled after expiration of a timer started by the patient (to enable therapy with a remote control), or enabled automatically via sleep stage detection. To avoid continuing stimulation after the patient wakes, stimulation can be disabled by the patient using a remote control, or automatically via sleep stage detection. Accordingly, in at least some examples, these periods may be considered to be outside of the treatment period or may be considered as a startup portion and wind down portion, respectively, of a treatment period.

In some examples, stimulation of an upper airway patency-related nerve may be performed via open loop stimulation, such as per open loop parameter 8804 of stimulation engine 8800 in FIG. 38D. In some examples, the open loop stimulation may refer to performing stimulation without use of any sensory feedback of any kind relative to the stimulation.

In some examples, the open loop stimulation may refer to stimulation performed without use of sensory feedback by which timing of the stimulation (e.g. synchronization) would otherwise be determined relative to respiratory information (e.g. respiratory cycles). However, in some such examples, some sensory feedback may be utilized to determine, in general, whether the patient should receive stimulation based on a severity of sleep apnea behavior.

Conversely, in some examples and as previously described in relation to at least several examples, stimulation of an upper airway patency-related nerve may be performed via closed loop stimulation, such as per closed loop parameter 8802 of stimulation engine 8800 in FIG. 38D. In some examples, the closed loop stimulation may refer to performing stimulation at least partially based on sensory feedback regarding parameters of the stimulation and/or effects of the stimulation.

In some examples, stimulation of one nerve (left or right) may be performed via open loop stimulation (e.g. without use of sensed physiologic data for timing application of the stimulation) while stimulation of another nerve (left or right) may be performed via closed loop stimulation, which may use sensed physiologic data for timing application of the stimulation.

In some examples, stimulation of one nerve (ACN or HGN) may be performed via open loop stimulation (e.g. without use of sensed physiologic data for timing application of the stimulation) while stimulation of another nerve (ACN or HGN) may be performed via closed loop stimulation, which may use sensed physiologic data for timing application of the stimulation.

In some examples, the closed loop stimulation (per parameter 8802) may comprise stimulation performed via use of sensory feedback by which timing of the stimulation (e.g. synchronization) is determined relative to respiratory information, such as but not limited to respiratory cycle information, which may comprise onset, offset, duration, morphology, etc. of the respiratory cycles. In some examples, the respiration information excludes (i.e. is without) tracking a respiratory volume and/or respiratory rate. In some examples, stimulation based on such synchronization may be delivered throughout a treatment period or throughout substantially the entire treatment period. In some examples, such stimulation may be delivered just during a portion or portions of a treatment period.

In some examples of "synchronization", the stimulation relative to the inspiratory phase may extend to a pre-inspiratory period and/or a post-inspiratory phase. For instance, in some such examples, a beginning of the synchronization may occur at a point in each respiratory cycle which is just prior to an onset of the inspiratory phase. In some examples, this point may be about 200 milliseconds, or 300 milliseconds prior to an onset of the inspiratory phase.

In some examples in which the stimulation is synchronous with at least a portion of the inspiratory phase, the upper airway muscles are contracted via the stimulation to ensure they are open at the time the respiratory drive controlled by the central nervous system initiates an inspiration (inhalation). In some such examples, in combination with the stimulation occurring during the inspiratory phase, example implementation of the above-noted pre-inspiratory stimulation helps to ensure that the upper airway is open before the negative pressure of inspiration within the respiratory system is applied via the diaphragm of the patient's body. In one aspect, this example arrangement may minimize the chance of constriction or collapse of the upper airway, which might otherwise occur if flow of the upper airway flow were too limited prior to the full force of inspiration occurring. In some examples, such stimulation may relate to stimulation of the hypoglossal nerve, the ansa cervicalis-related nerve, other nerves relating to upper airway patency, and/or stimulating various combinations of such nerves including left and/right options.

In some such examples, the stimulation of the upper airway patency-related nerve may be synchronized to occur with at least a portion of the expiratory period.

With regard to at least some of the example methods of treating sleep apnea as previously described throughout the present disclosure, at least some such methods may comprise performing the delivery of stimulation to the upper airway patency-related first nerve without synchronizing such stimulation relative to a portion of a respiratory cycle. In some instances, such methods may sometimes be referred to as the previously described open loop stimulation.

In some examples, the term "without synchronizing" may refer to performing the stimulation independently of timing of a respiratory cycle. In some examples, the term "without synchronizing" may refer to performing the stimulation being aware of respiratory information but without necessarily triggering the initiation of stimulation relative to a specific portion of a respiratory cycle or without causing the stimulation to coincide with a specific portion (e.g. inspiratory phase) of respiratory cycle.

In some examples, in this context the term "without synchronizing" may refer to performing stimulation upon the detection of sleep disordered breathing behavior (e.g. obstructive sleep apnea events) but without necessarily triggering the initiation of stimulation relative to a specific portion of a respiratory cycle or without causing the stimulation to coincide with the inspiratory phase. At least some such examples may be described in Wagner et al., STIMULATION FOR TREATING SLEEP DISORDERED BREATHING, issued as U.S. Pat. No. 10,898,709 on Jan. 26, 2021, and which is incorporated by reference herein in its entirety.

In some examples, while open loop stimulation may be performed continuously without regarding to timing of respiratory information (e.g. inspiratory phase, expiratory phase, etc.) such an example method and/or device may still comprise sensing information for diagnostic data and/or to determine whether (and by how much) the continuous stimulation should be adjusted. For instance, via such sensing, it may be determined that the number of sleep disordered breathing (SDB) events are too numerous (e.g. an elevated AHI) and therefore the intensity (e.g. amplitude, frequency, pulse width, etc.) of the continuous stimulation should be increased or that the number of SDB events are relatively low such that the intensity of the continuous stimulation can be decreased while still providing therapeutic stimulation. It will be understood that via such sensing, other SDB-related information may be determined which may be used for diagnostic purposes and/or used to determine adjustments to an intensity (e.g. strength) of stimulation, initiating stimulation, and/or terminating stimulation to treat sleep disordered breathing.

Some non-limiting examples of such devices and methods to recognize and detect the various features and patterns associated with respiratory effort and flow limitations include, but are not limited to Christopherson, U.S. Pat. No. 8,938,299 Issued on Jan. 30, 2015, titled SYSTEM FOR TREATING SLEEP DISORDERED BREATHING (SDB) (formerly published as PCT Publication WO/2010/059839, titled A METHOD OF TREATING SLEEP APNEA, published on May 27, 2010); Christopherson U.S. Pat. No. 5,944,680, titled RESPIRATORY EFFORT DETECTION METHOD AND APPARATUS; and Testerman U.S. Pat. No. 5,522,862, titled METHOD AND APPARATUS FOR TREATING OBSTRUCTIVE SLEEP APNEA, each of which is hereby incorporated by reference herein in their entirety.

Moreover, in some examples various stimulation methods may be applied to treat obstructive sleep apnea, which include but are not limited to: Ni et al. U.S. 2019/0009093, published on Jan. 10, 2019, titled METHOD AND SYSTEM FOR SELECTING A STIMULATION PROTOCOL BASED ON SENSED RESPIRATORY EFFORT (previously published as WO 2013/023218, SYSTEM FOR SELECTING A STIMULATION PROTOCOL BASED ON SENSED RESPIRATORY EFFORT); Christopherson et al. U.S. Pat. No. 8,938,299, SYSTEM FOR TREATING SLEEP DISORDERED BREATHING, issued Jan. 20, 2015; and Wagner et al., U.S. 2018/0117316, STIMULATION FOR TREATING SLEEP DISORDERED BREATHING, published on May 3, 2018, issued as U.S. Pat. No. 10,898,709 on Jan. 26, 2021, and previously published as WO 2016/149344, on Sep. 22, 2016), each of which is hereby incorporated by reference herein in its entirety.

Figure 38E:
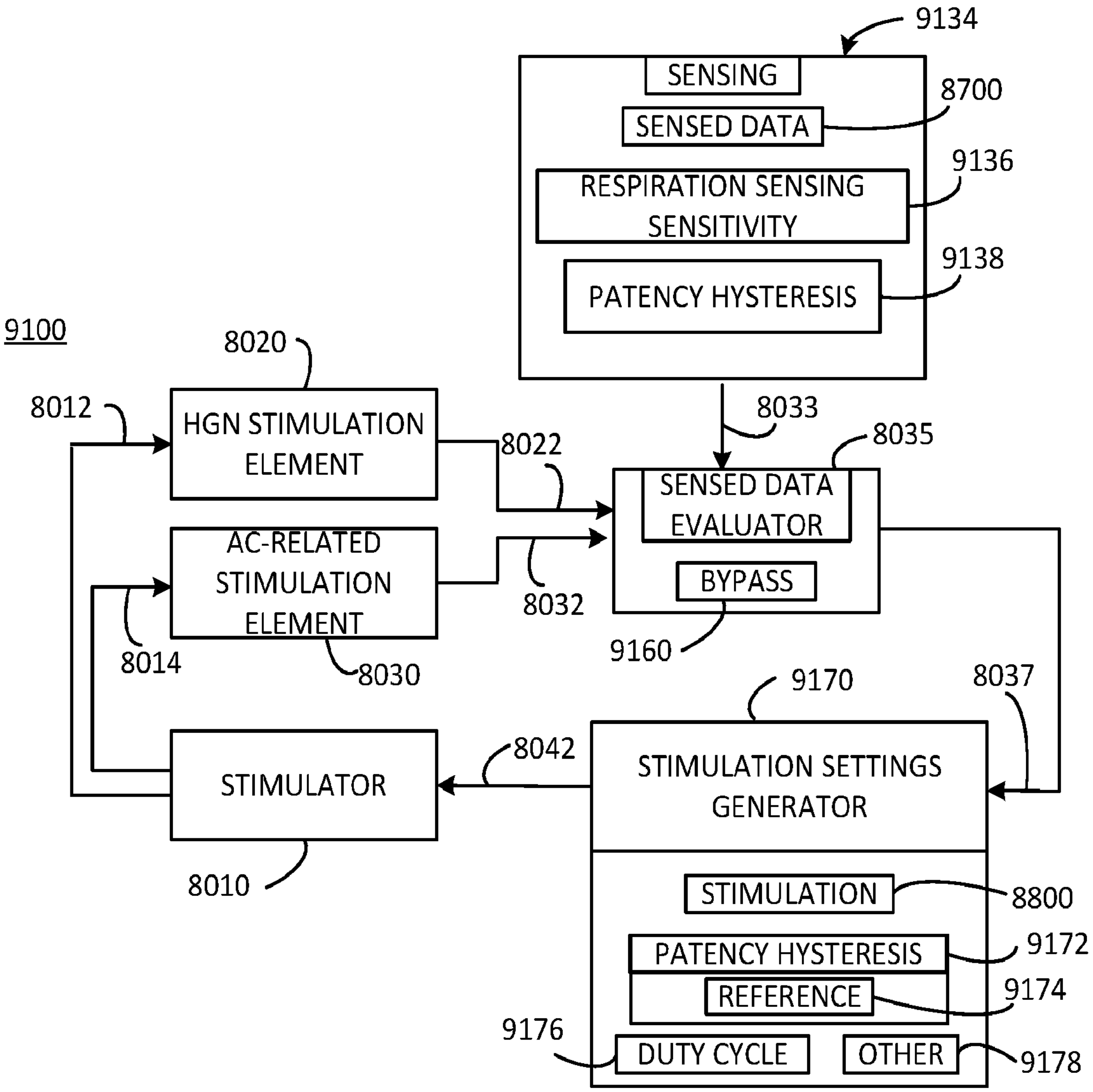
FIGS. 38E-38F are flow diagrams schematically representing an example device and/or example method for stimulation therapy relating to at least a patency hysteresis parameter, among other parameters, functions, engines, etc.
Figure 38F:
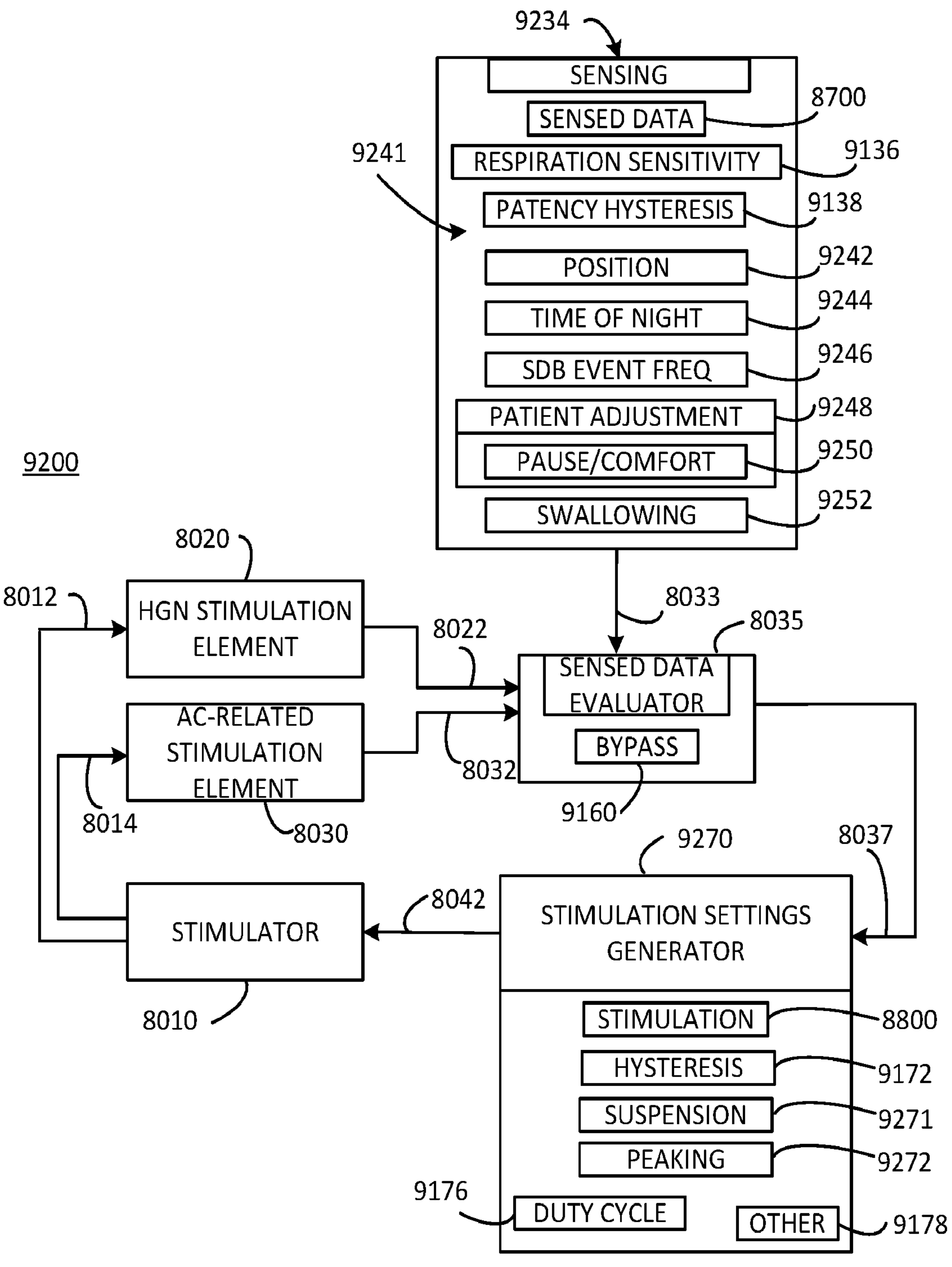
Figure 38G:
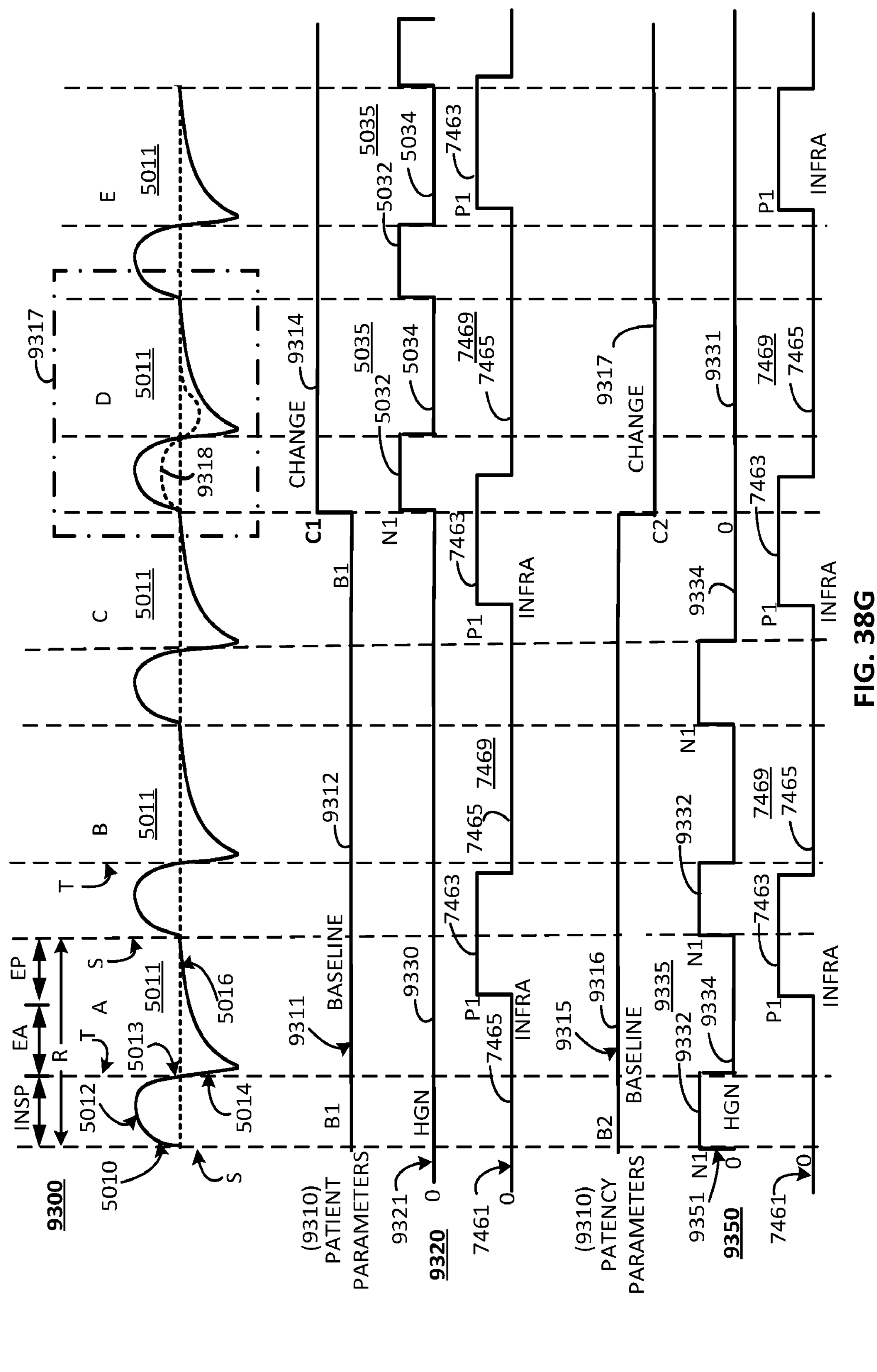
FIGS. 38G-38H are diagrams including graphs schematically representing example respiratory cycles and example methods of stimulation for upper airway patency-related tissues including at least some stimulation methods relating to a patency hysteresis parameter.
Figure 38H:
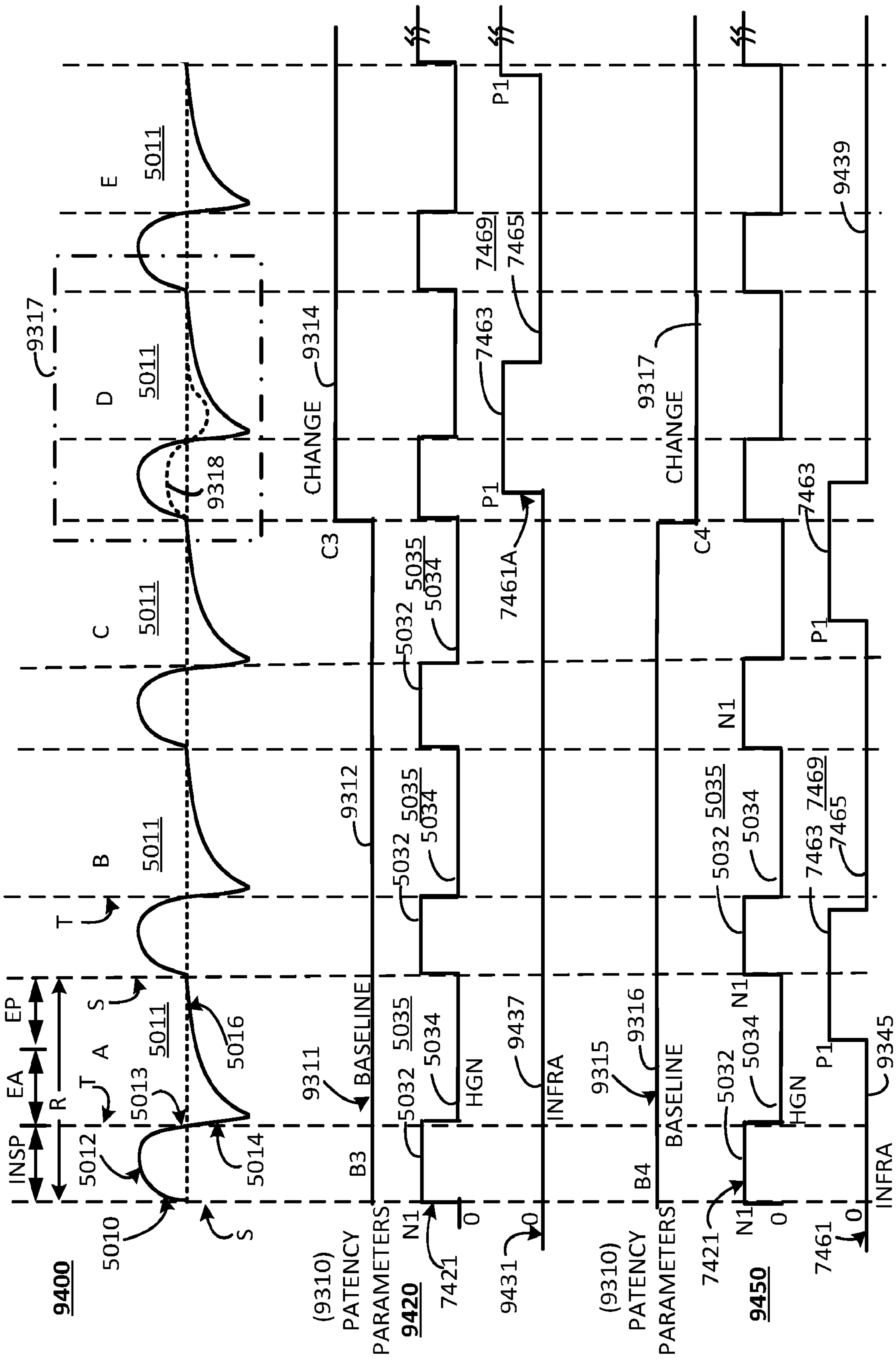
Figures 39, 40A, 40B:
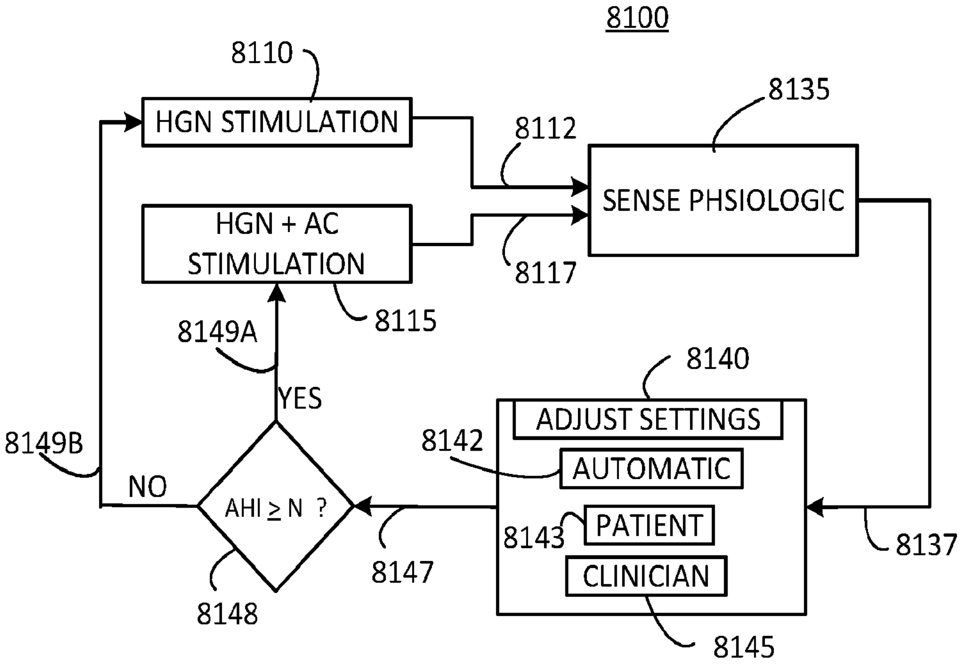

In some examples, at least the respective closed loop and open loop parameters 8802, 8804 of the stimulation engine 8800 in FIG. 38D may be implemented via, and/or comprise an example implementation of, the example method 8260 of FIG. 40D, the example stimulation protocols of FIGS. 33A-37D, and at least some of the example methods, protocols, etc. described in association with at least FIGS. 38A-39, and/or 40B-51B. In some examples, one example implementation of the closed loop parameter 8802 is later described as example arrangement 8100 in association with at least FIG. 39.

In some examples, the stimulation engine 8000 may comprise an auto-titration parameter 8805 by which stimulation settings may be automatically adjusted based on some sensed information and other criteria, such patient parameters, clinician parameters, and/or other parameters. One example implementation of the auto-titration parameter 8805 is later described as example arrangement 8100 in association with at least FIG. 39, and at least some of the substantially the same features and attributes of the example methods, protocols, etc. described in association with at least FIGS. 40B-51B.

In some examples, per patient control parameter 8810 of the stimulation engine 8800 and a patient remote control (e.g. 572 in FIG. 3B) in communication with an implantable medical device (e.g. IMD 570 in FIG. 3B, such as IPG 533 (e.g. FIG. 3A) or microstimulator 6575), a patient may disable or enable stimulation of either the hypoglossal nerve (e.g. 505R or 505L) and/or the ansa cervicalis-related nerve 316 (e.g. 515R, 515L). Similarly, per patient control parameter 8810, the patient may control stimulation strength (e.g. amplitude, other) via inputs on the patient remote control for each nerve independently of the other respective nerves. Stated differently, the patient remote control 572 (FIG. 3B), as supported by patient control parameter 8810 of stimulation engine 8800, enables a patient to have full independent control over stimulation of different nerves, such as the hypoglossal nerve (left and/or right) and the ansa cervicalis-related nerve (left and/or right). In some examples, a patient app (10630 in FIG. 54E) may cooperate with the remote control (572 in FIG. 3B; 10530 in FIG. 54C; 10640 in FIG. 54E) to implement the patient's control over stimulation.

In some examples, the patient remote control 572 (FIG. 3B), per patient control parameter 8810 of stimulation engine 8800 (FIG. 38D) may enable a patient to have some limited control (e.g. amplitude, other) over stimulation of a first nerve but not a second nerve, except to turn off stimulation for both nerves. In some such examples, a clinician may adjust which nerves the patient has control over (and the degree of control for each nerve), such as via clinician programmer, clinician portal, etc. as described in FIGS. 54A-54E.

For instance, in some examples, the patient control parameter 8810 may be used to permit the patient to control stimulation parameters (e.g. amplitude) for the hypoglossal nerve but not for the ansa cervicalis-related nerve. In this arrangement, the patient control parameter 8810 is used to permit some patient control (within manufacturer or clinician limits) over a nerve for which the patient may be more sensitive to different stimulation strengths in relation to patient comfort. Conversely, the patient control parameter 8810 then does not offer such patient adjustments to stimulation strength of a second nerve (e.g. ansa cervicalis-related nerve) because the patient generally experiences more overall comfort with such stimulation such that patient adjustability of stimulation strength for that second nerve may be unnecessary in most instances.

In some examples, in association with at least titration parameter 8808, stimulation may be applied by a breath-by-breath parameter 8812, by which stimulation is delivered on an alternating basis to a first nerve (e.g. one of hypoglossal nerve and ansa cervicalis-related nerve) and then a second nerve (e.g. the other one of the hypoglossal nerve and the ansa cervicalis-related nerve), the first nerve, the second nerve, and so on. By doing so, one can evaluate the effect of each instance of stimulation and adjust stimulation strength, targets along a particular nerve, whether to favor stimulation of one nerve more than another etc. At least some example implementations of switching stimulation between two different respective nerves on a breath-by-breath basis (via parameter 8812) are provided in association with at least FIGS. 33A-36A, including alternating patterns, every third breath patterns, etc.

In some examples, the stimulation engine 8800 comprises a ramp parameter 8806 by which increases in stimulation strength (e.g. amplitude, other) during titration of stimulation settings and/or as inputs of patient remote control adjustments of stimulation therapy (within limits set by clinician and/or manufacturer) are implemented as a ramped increase (versus a step change increase) and/or ramped decrease.

In some examples of implementing ramp parameter 8806, such as when stimulation is applied to both an ansa cervicalis-related nerve and a hypoglossal nerve simultaneously, increases in stimulation strength (e.g. amplitude, other) may be implemented simultaneously by a ramped increase in a first stimulation signal for the ansa cervicalis-related nerve (e.g. left and/or right) and a ramped increase in a second stimulation signal for the hypoglossal nerve (e.g. left and/or right). However, because of the different nerves, potentially different stimulation thresholds, etc. the ramped increase for one nerve (e.g. HGN or ACN) may not necessarily comprise the same slope, etc. as the ramped increase for the other nerve.

In some example implementations of ramp parameter 8806, whether for titration and/or patient control inputs, increases in stimulation strength may be implemented as ramped increases among different nerves on an alternating basis, such as a partial ramped increase of a first nerve (e.g. ansa cervicalis-related), followed by a partial ramped increase of a second nerve (e.g. hypoglossal nerve), followed by a further partial ramped increase of the first nerve, and so on. In some such examples, these gradual increases may be implemented as incremental changes in strength (e.g. amplitude, other) or conversely, if stimulation strength is to be decreased, then such changes may be made in decrements. Via these arrangements, stimulation strength can be increased gradually among all the different nerves to be stimulated, thereby providing time to observe the effects of the respective ramped increase for the different nerves, which in turn may help prevent too quickly increasing overall stimulation strength for multiple nerves.

In some examples, the ramp parameter 8806 may be implemented in a complementary manner with method 8220 in FIG. 40C.

In some examples, per titration parameter 8808, stimulation settings (e.g. amplitude, pulse width, duty cycle, frequency, etc.) may be determined, adjusted, etc. for each nerve to be stimulated and/or in a comprehensive manner for the multiple nerves. In some examples, per the titration parameter 8808, the stimulation settings of the ansa cervicalis-related nerve (e.g. left and/or right) may be titrated to reach a functional threshold (parameter 8822 in FIG. 38D) corresponding to a minimum level at which stimulation causes contraction (versus subcontraction) of the muscle(s) innervated by the particular targeted portion of the ansa cervicalis-related nerve. In particular, in some examples, delivering stimulation to an upper airway patency related nerve is to cause contraction of upper airway patency-related muscles. In some such examples, the contraction comprises a suprathreshold stimulation, which is in contrast to a subthreshold stimulation (e.g. mere tone) of such muscles. In one aspect, a suprathreshold intensity level corresponds to a stimulation energy greater than the nerve excitation threshold, such that the suprathreshold stimulation may provide for upper-airway clearance (i.e. patency) and obstructive sleep apnea therapy efficacy.

Meanwhile, the stimulation settings of the hypoglossal nerve may be titrated to a level greater than a functional contraction threshold (for the hypoglossal nerve) to an optimal therapeutic level (parameter 8824 in FIG. 38D) and/or to a comfort level (parameter 8826 in FIG. 38D). In some such examples, this arrangement may enhance selection of appropriate stimulation settings at least because the tongue (innervated by the hypoglossal nerve) may exhibit more sensitivity regarding selection and adjustment of a comfort level than muscles associated with the ansa cervicalis-related nerve. In some such examples, at least some of the foregoing aspects of the titration parameter 8808 may be implemented in a complementary manner with the ramp parameter 8806 of stimulation engine 8800 of FIG. 38D.

In some examples, per the titration parameter 8808 of stimulation engine 8800 in FIG. 38D, different stimulation settings may be established relative to a comfort limit (per parameter 8826 in FIG. 38D) and/or a sleep disturbance limit (per parameter 8828 in FIG. 38D), which may be in addition to the previously described threshold limit (per parameter 8822) and/or therapeutic parameter 8824.

In some examples, titrating for appropriate settings per the titration parameter may comprise determining at least the comfort limit (8826 in FIG. 38D) and/or sleep disturbance limit (8828 in FIG. 38D) by starting the titration process below a functional threshold (8822 in FIG. 38D) or at the functional threshold (8822 in FIG. 38D). Titrating toward and up to the respective limits (e.g. comfort, sleep disturbance, etc.) may comprise incrementing stimulation strength in steps or a ramped manner as described above with respect to at least the previously described ramp parameter 8806 in FIG. 38D.

In some examples, the threshold parameter 8822 in the stimulation engine 8800 of FIG. 38D and impedance sensor 8752 in sensor tools array 8570 in FIG. 38C may be used to implement an automatic threshold detection function by which a functional threshold (e.g. an amplitude at which muscle contraction occurs) for electrical stimulation of an upper airway patency-related nerve may be automatically determined. Such determination may replace and/or supplement more cumbersome clinician-intensive titration techniques, which may include a protocol such as a clinician programming an IPG with a stimulation setting (e.g. amplitude), the clinician applying a test stimulation, observing a patient response, the clinician further increasing the stimulating setting and the clinician programming the IPG with the updated settings, testing stimulation, and so on.

In some examples, in general terms and per threshold parameter 8822, the automatic threshold detection function may automatically determine a functional threshold based on sensed impedance information (e.g. per sensor 8752 in FIG. 38C) in response to test stimulations automatically applied at different stimulation strengths (e.g. amplitude expressed as voltage). In one aspect, sensing impedance in relation to the upper airway may be implemented via a plurality of electrodes spaced apart from each other and at least some of which are in proximity to the upper airway, including upper airway muscles and related tissue including (but not limited to) the genioglossus muscle (e.g. tongue). The spaced apart electrodes may comprise sensing electrodes (i.e. dedicated to sensing) and/or stimulation electrodes, which also may be used for sensing in some instances. The electrodes may be supported on a non-electrically conductive carrier to form a stimulation element, such as a cuff body to form a cuff electrode, such as a paddle to form a paddle electrode, such as an axial lead body to form an axial electrode lead/array, and the like. In some examples, at least one or more of the spaced apart electrodes may be present on a housing (e.g. case) of an IPG (533 in FIG. 2) or of a microstimulator. Several examples of each of these electrode arrangements of stimulation elements are described and illustrated throughout many examples of the present disclosure.

In another aspect, upon implantation of such example stimulation elements (and supporting IPG or microstimulator), then multiple spaced apart electrodes become positioned relative to pertinent tissues which move in response to electrical stimulation of an upper airway patency-related nerve (e.g. the hypoglossal nerve, ansa cervicalis-related nerve, and the like), which may then be sensed as a changed impedance. Among the implanted multiple spaced apart electrodes, at least some of the electrodes may be used for applying stimulation while at least some of the electrodes may be used for sensing the changes in impedance. In some examples, some of the electrodes may be used for both stimulation and sensing.

In some examples, some of the implanted multiple spaced apart electrodes may comprise an array of electrodes on a first implanted stimulation element and some of the multiple spaced apart electrodes may comprise an array of electrodes on a second implanted stimulation element. In some examples, the first and second stimulation elements may be implanted in spaced apart locations on the same side of the body or in some examples may be implanted on opposite sides (e.g. left and right) of the body to assume a spaced apart relationship. Moreover, in some examples even the electrodes of an array of electrodes of a stimulation element (such as an axial lead array of electrodes, array of electrodes on a cuff electrode or on a paddle electrode, etc.) are spaced apart from each other and maybe used to sense a change in impedance. In each instance, implanting the stimulation elements in stimulating relation to an upper airway patency-related nerve necessarily places the electrodes of such implanted stimulation elements in sufficient proximity to potentially responsive muscles/tissues (e.g. those muscles/tissues which will move in response to electrical stimulation of the target upper airway patency-related nerve) such that various combinations of the spaced apart electrodes of the implanted stimulation elements may effectively form an array of impedance sensing electrodes, i.e. an effective impedance sensing array.

In some examples, sensing a change in impedance (via the effective array of impedance sensing electrodes) may be representative of opening/stiffening of the upper airway generally in response to ACN stimulation while in some examples, sensing a change in impedance (via the effective array) may be representative of protrusion of the tongue in response to hypoglossal nerve stimulation. In some examples, sensing a change in impedance (via the effective array) may be representative of both a general change in the opening of the upper airway and movement of the tongue relative to the opening in the upper airway, which may both occur in response to a combination of ACN stimulation and HGN stimulation.

In some examples, a change in the sensed impedance may result from contraction of pertinent muscles and/or result from directional movement of the pertinent muscles, such as protrusion of the tongue which causes movement of the electrodes used for sensing.

With this framework in mind and per the impedance sensor 8752 (FIG. 38C) and the threshold parameter 8822 (FIG. 38D), an IPG or microstimulator may automatically apply test stimulation signals to a target nerve and then automatically sense an impedance via the effective array of impedance sensing electrodes. If no change in impedance is sensed upon application of the test stimulation signal, the functional threshold has not been met. Accordingly, the IPG (or microstimulator) automatically makes an incremental increase in a strength setting (e.g. amplitude identified as a voltage setting) and again delivers electrical stimulation to the target nerve, and further senses the impedance via the effective array. This process is automatically repeated iteratively until one of the automatic, incremental increases in the stimulation strength setting results in a changed impedance (which is automatically sensed) of a magnitude indicative of muscular contraction associated with tongue protrusion and/or opening/stiffening of the upper airway tissues. At this point, it may be concluded that a functional threshold for electrical stimulation of an upper airway patency-related nerve has been established.

In some examples, the stimulation and impedance sensing may be occur simultaneously or on an interleaved basis. In some examples, stimulation may be applied on a first side of the body and impedance sensing may be performed on an opposite second side of the body. In some examples, both the stimulation and the impedance sensing may be performed on a single/same side of the body.

In some examples, per at least the threshold parameter 8822, the automatic threshold detection function may comprise monitoring the functional threshold over time as a diagnostic on system performance.

It will be understood that, in some examples and per at least parameter 8822, the automatic threshold detection function may be applied via a plurality of different stimulation electrode configurations which may be used to apply the test stimulation signal, with at least some of the different stimulation electrode configurations corresponding to different target nerve locations, such as but not limited to a left HGN, right HGN, left ACN, right ACN, etc.

In some examples, per threshold parameter 8822, in addition to or instead of sensing impedance, the automatic threshold detection function may be implemented via a signal from an accelerometer, such as but not limited to, a signal from an implanted accelerometer where the accelerometer is used to detect the change resulting from muscle contraction or movement of the tongue or other physiologic effects exhibited from the functional threshold being met. In some examples, the implanted accelerometer may be incorporated within a microstimulator implanted within the neck region or as the on-board sensor 560 of the IPG in FIG. 3C.

In some examples, the stimulation engine 8800 comprises a relationship parameter 8813 (e.g. nerve stimulation relationship) which may facilitate a relationship by which multiple different nerves are stimulated relative to each other. In some examples, multiple different nerves may comprise two different types of nerves, such as the hypoglossal nerve, the ansa cervicalis-related nerve, the phrenic nerve, etc. In some examples, multiple different nerves also can comprise a left nerve (e.g. left HGN, left ACN, right phrenic, etc.) and a right nerve (e.g. right HGN, right ACN, right phrenic, etc.).

In some examples, per the relationship parameter 8813, the stimulation engine 8800 may track and/or control a sequence of stimulation, i.e. within a time frame or cycle (e.g. stimulation cycle), which nerve (e.g. hypoglossal, ansa cervicalis-related, phrenic, other) is stimulated first, which stimulated second, etc. Similarly, the relationship parameter 8813 may track and/or control that multiple different nerves be stimulated simultaneously, alternately, or in a staggered manner. In some examples, the relationship parameter 8813 may track and/or control which nerve(s) of an array of nerves are being stimulated, such as whether stimulation is to be applied solely to one type of nerve, applied to at least two types of nerves, applied to the full array of nerves, applied to both left and right nerves of a type of nerve, etc. Of course, specifying which nerve is to be stimulated (or not stimulated) may further depend on a timing of the stimulation of one nerve relative to another.

In some example implementations of the relationship parameter 8813, a stimulation protocol may be implemented in which, for a given stimulation cycle, an ansa cervicalis-related nerve (ACN) stimulation is started first or prior to starting stimulation of the hypoglossal nerve (HGN) and the ACN stimulation continues as HGN stimulation commences such that stimulation of both the hypoglossal and ansa cervicalis-related nerves continues (within the stimulation cycle) simultaneously once stimulation has started for both. For instance, as mentioned elsewhere herein, stimulating the ansa cervicalis-related nerve tends to stiffen the upper airway and increase the size of the opening of the upper airway by action, at least, of the sternothyroid muscles and/or sternohyoid muscles pulling down on the thyroid/larynx. Among other aspects, in the absence of such stimulation of the ansa cervicalis-related nerve, some OSA patients may exhibit a collapse of the lateral walls of the upper airway, which may contribute to antero-posterior collapse of the upper airway. Meanwhile, stimulation of the hypoglossal nerve may cause protrusion of the tongue to move the tongue out of the upper airway opening, but such protrusion does not otherwise generally contribute to stiffening/opening of the upper airway in the manner noted above in relation to stimulation of the ansa cervicalis-related nerve. Accordingly, in some example implementations of the present disclosure, such as per the relationship parameter 8813 of the stimulation engine 8800 (FIG. 38D), stimulating the ansa cervicalis-related nerve prior to the hypoglossal nerve (within a stimulation cycle of a stimulation pattern of repeating stimulation cycles) may increase and/or generally maintain a size of the opening of the upper airway such that a desired patency can be achieved with less stimulation (e.g. degree of stimulation, duration of stimulation, etc.) of the hypoglossal nerve because the tongue need not be moved as much to achieve the desired degree of patency.

In some examples, this particular sequence of stimulating the ansa cervicalis-related nerve prior to the hypoglossal nerve may be implemented via the relationship parameter 8813 in cooperation with (at least) the ramp parameter 8806 of the stimulation engine 8800 by which stimulation of the ansa cervicalis-related nerve may be ramped up to about 60 to about 70 percent of a therapeutic stimulation strength for that nerve prior to stimulating the hypoglossal nerve. This arrangement may significantly establish opening/stiffening of the upper airway prior to causing a portion of the tongue to move out of the opening of the upper airway via tongue protrusion form stimulation of the hypoglossal nerve.

In some such examples, as the stimulation period of a stimulation cycle is to be terminated, the stimulation pattern may comprise terminating stimulation of the hypoglossal nerve prior to terminating (such as but not limited to a ramped decrease) stimulation of the ansa cervicalis-related nerve. This arrangement may help to prolong patency because the stimulation of the ansa cervicalis-related nerve produces a more significant overall effect on patency than merely moving the tongue out of the way via hypoglossal nerve stimulation.

At least some example implementations of the nerve relationship parameter 8813 are described in association with at least some of the examples of the present disclosure such as, but not limited to, the examples associated with at least FIGS. 1-3C, 16-20, 32A-32C, 33-51B, etc. In some such example implementations, the relationship parameter 8813 may be implemented in cooperation with the any one or more of the parameters of the sensed data engine 8700, any one or more of the types, modalities, etc. of sensor tools array 8750, and/or any one or more of the parameters, engines, etc. of the stimulation engine 8800. In just one example, a particular expression of the relationship parameter 8813 (e.g. which nerves are stimulated, their sequence or simultaneous, etc.) may depend on sensed data, such as a sensed type or degree of collapse (e.g. 8710 in FIG. 38B), may depend on sensed body position (e.g. 8722 in FIG. 38B), may depend on sensed respiration (e.g. 8724 in FIG. 38B), may depend on sensed disease burden (e.g. 8726 in FIG. 38B), etc.

In one example implementation of the nerve relationship parameter 8813 (and/or breath-to-breath parameter 8812), stimulation of other nerves such as the hypoglossal nerve (HGN) may be supplemental to stimulation of an ansa cervicalis-related nerve (ACN) or muscles innervated by the ACN, in view of a patency hysteresis by which one stimulation period may produce a prolonged upper airway patency beyond the stimulation period of the ansa cervicalis-related nerve (ACN) or muscles innervated by the ACN. Various aspects of such example stimulation methods (and associated devices) are further described below.

FIG. 38E is a flow diagram schematically representing an example arrangement 9100 including an example device for, and/or example method of, using sensed data as feedback to adjust an intensity (e.g. strength) of, or other parameters, aspects, etc. regarding, stimulation of upper airway patency-related tissue. As previously noted such tissues may comprise a genioglossus-based patency tissue, which may comprise a hypoglossal nerve and/or a genioglossus-related muscle innervated by the hypoglossal nerve. In some examples, the upper airway patency-related tissue comprises infrahyoid-based patency tissue, which comprises an ansa cervicalis-related nerve and/or an infrahyoid strap muscle innervated by the ansa cervicalis-related nerve.

In some examples, the example arrangement 9100 may comprise at least some of substantially the same features and attributes of, or an example implementation of, example arrangement 8000 of FIG. 38A, and further comprising additional aspects as described below.

As shown in FIG. 38E, the example arrangement 9100 comprises a sensing portion 9134 which includes a sensed data portion 8700, which comprises at least some of substantially the same features and attributes of sensed data portion 8700 of FIG. 38B. Among other aspects of sensed data portion 8700, a previously described collapse parameter 8710 of sensed data portion 8700 in FIG. 38B provides one example mechanism to express or represent upper airway patency. In addition, the sensing portion 9134 comprises respiration sensing sensitivity parameter 9136, and/or a patency hysteresis sensing parameter 9138.

In general terms, the sensing portion 9134 receives, obtains, and/or determines information related to sensing physiologic information (or other information) of the patient which may facilitate sleep disordered breathing (SDB) care such as (but not limited to) treating obstructive sleep apnea and/or other forms of sleep disordered breathing.

In some examples, via the respiration sensing sensitivity parameter 9136, the sensing portion 9134 receives, tracks, and/or determines a degree of sensitivity of a respiratory sensing signal. In some such examples, the respiratory sensing signal may be based on any one of the sensor types in sensor tools array 8750 (FIG. 38C). For a variety of reasons, the sensitivity of the sensing signal to respiration may vary during a treatment period due to various factors such as movement, body position, etc.

With this in mind, in some examples via the respiration sensing sensitivity parameter 9136, stimulation may be applied at a greater, selectable first duty cycle percentage when the sensing sensitivity is less than a selectable threshold and stimulation may be applied at a lower, selectable second duty cycle percentage when the sensing sensitivity is greater than the selectable threshold. The sensing sensitivity threshold may vary depend on the type of respiratory sensing. In some examples, the lower, selectable first duty cycle percentage is lower than 50 percent and the selectable second duty cycle percentage is greater than 50 percent. In other words, when the sensing sensitivity is relatively low (e.g. lower than the threshold), then the stimulation is to be applied at higher duty cycle percentage because it may be more difficult to ensure stimulation is being applied at a desired portion of a respiratory cycle (e.g. during inspiration, other portion). Similarly, when the sensing sensitivity is relatively high (e.g. higher than the threshold), then the stimulation is to applied a lower duty cycle percentage because it may be easier to ensure stimulation is being applied at a desired portion of a respiratory cycle (e.g. during inspiration, other portion).

In some examples, the respiration sensitivity parameter 9136 may be employed whether or not the patency hysteresis sensing parameter 9138 is being implemented.

In some examples, via the patency hysteresis sensing parameter 9138, the sensing portion 9134 is to receive, track, and/or determine a duration, amplitude, morphology, etc. of upper airway patency which continues (e.g. is prolonged) after stimulation of an upper airway patency-related tissue has ceased, such as at the end of a stimulation period. In some such examples, the parameter 9138 is based on (or relates to) a patency hysteresis effect occurring from stimulation an infrahyoid-based patency tissue, such as stimulation of an infrahyoid strap muscle and/or an infrahyoid strap muscle innervated by an ansa cervicalis-related nerve.

In some examples, via at least the patency hysteresis parameter 9138 (and/or later described parameter 9172), one may track and/or determine the particular parameters of stimulation which produce a particular duration, amplitude, etc. of patency hysteresis effect.

In some examples, the prolonged hysteresis effect may be sensed via one of sensing modalities of the sensor tools array 8750 and may or may not be the same sensing modality used to sense respiration for use in closed loop stimulation and/or to track a frequency of sleep disordered breathing (SDB) events. Among other modalities, airflow sensing may comprise one such modality by which the upper airway patency is determined.

In some examples, the patency hysteresis parameter 9138 receives or obtains information determined in a sleep study or other format regarding the patency hysteresis effect exhibited by a particular patient, which may result in a historical patient-specific average patency hysteresis effect, which may in turn be used as a reference, such as reference parameter 9174, for determining stimulation settings as later described in association with stimulation settings generator 9170.

As shown in FIG. 38E, sensed data evaluator 8035 comprises at least some of the substantially the same features and attributes as sensed data evaluator 8035 in FIG. 38A, while further comprising a bypass parameter 9160.

In some examples, the bypass parameter 9160 enables bypassing the use of at least some types or forms of sensed data via the sensed data evaluator 8035 in at least some examples, such as an implementation of open loop stimulation. In some such examples, a method of open loop stimulation may bypass use of some sensed data in determining stimulation settings, such as ignoring sensed respiratory phase information which might otherwise be used for synchronizing the stimulation periods with a particular respiratory phase of the patient's respiratory cycles. However, in some examples other forms or types of sensed data, including other respiratory information, may be used to inform or determine at least some stimulation settings, even for open loop stimulation (which is not synchronized to actively sensed respiratory information).

In some examples, the bypass parameter 9160 may be implemented in the sensed data evaluator 8035 of the example arrangement 8000 in FIG. 38A.

As further shown in FIG. 38E, in some examples, the stimulation settings generator 9170 may comprise at least some of substantially the same features and attributes as stimulation setting generator 8040 of the example arrangement 8000 of FIG. 38A. As shown in FIG. 38E, the stimulation settings generator 9170 may comprise or access a stimulation engine 8800, which may comprise at least some of substantially the same features as stimulation portion 8800 of stimulation engine 8800 in FIG. 38D.

As further shown in FIG. 38E, in some examples the stimulation settings generator 9170 comprises a patency hysteresis stimulation parameter 9172, a duty cycle parameter 9176, and an other parameter 9178. In some examples, the patency hysteresis parameter 9172 further comprises a reference parameter 9174.

In some examples, the patency hysteresis stimulation parameter 9172 is to implement a stimulation pattern by which an intended patency hysteresis effect for upper airway patency may be achieved. In some such examples, the parameter 9172 may be implemented based on a reference 9174 such as a reference patency hysteresis effect which has already been determined for a particular patient, such as a historical patient-specific average patency hysteresis effect for an array of know stimulation settings. In some examples, the reference 9174 may be determined according to a multiple patient average patency hysteresis effect for an array of known stimulation settings.

However, in other examples, determining stimulation settings according to a patency hysteresis parameter 9172 may be implemented according to ongoing or recently sensed patency hysteresis information per patency hysteresis parameter 9138 of sensing portion 9134.

The example stimulation protocols as previously described in association with at least FIGS. 37E-37G provide example implementations of employing stimulation settings, per generator 9170 of FIG. 38E, including the patency hysteresis parameter 9172. As apparent from at least FIGS. 37E-37G, the patency hysteresis parameters 9138, 9172 may be used to determine different proportions, timing, etc. of stimulating upper airway patency-related tissues via stimulation elements 8020, 8030 (FIG. 38E). It will be further understood that, in at least some examples, the AC-related stimulation element 8030 may encompass stimulation components, placement, etc. which may be used to stimulate infrahyoid-based patency tissue, which may comprise an ansa cervicalis-related nerve and/or infrahyoid strap muscle(s) innervated by an ansa cervicalis-related nerve.

It will be understood that in some examples, the generator 9170 may generate stimulation settings for stimulation elements 8020, 8030 without employing the patency hysteresis parameter 9172 even if the patency hysteresis may be occurring in response to certain types or forms of stimulation.

In some examples, the stimulation settings generator 9170 comprises a duty cycle parameter 9176 which may complement, and/or be an example implementation of, the parameters and functions of stimulation engine 8800 (FIGS. 38D, 38E). In some examples, the duty cycle parameter 9176 may track and/or control a duty cycle in delivering stimulation to upper airway patency-related tissue. In some such examples, the duty cycle parameter 9176 may comprise one example arrangement to implement stimulation settings according to the above-described, respiration sensing sensitivity parameter 9138. In some examples of delivering open loop stimulation (e.g. fixed duty cycle to implement a patency hysteresis effect, in some examples, the duty cycle may comprise about 25 percent to about 75 percent.

With further reference to FIG. 38E, upon the stimulation settings generator 9170 providing stimulation settings (such as but not limited to patency hysteresis stimulation parameter 9172) via stimulator 8010 to stimulation elements 8020, 8030 for stimulating genioglossus-based patency tissue and/or for stimulating infrahyoid-based patency tissue, such as via the example stimulation protocols of at least FIGS. 37E-37G and/or at least FIGS. 33A-37D.

FIG. 38F is a flow diagram schematically representing an example arrangement 9200 which comprises at least some of substantially the same features and attributes as, or an example implementation of, example arrangement 9100 of FIG. 38E, and further comprising additional aspects as described below.

As shown in FIG. 38F, the example arrangement 9200 comprises a sensing portion 9234 which comprises at least some of substantially the same features and attributes of sensing portion 9134 of FIG. 38E, while further comprising additional aspects. For example, the sensing portion 9234 of FIG. 38F may additionally comprise various parameters, and which may sometimes be referred to as input parameters or patency parameters 9241, by which sensing information is received, obtained, and/or determined. In addition to, or as a complement to, the patency hysteresis parameter 9138 and/or the respiration sensing sensitivity parameter 9136, these patency parameters 9241 may be used to assess, determine, and/or implement stimulation via sensed data evaluator 8035 and/or stimulation settings generator 9270 (including patency hysteresis parameter 9172). In some such examples, at least some of the patency parameters 9241 may be associated with a change in upper airway patency (e.g. collapsibility) at which a change in stimulation settings may be implemented per the patency hysteresis parameters 9138, 9172. In some examples, the stimulation patterns later illustrated in FIGS. 38G-38H may schematically represent such changes and corresponding modifications of a stimulation pattern, which accounts for a patency hysteresis parameter (e.g. 9138, 9172) among other factors.

As shown in FIG. 38F, in some examples the patency parameters 9241 comprises position parameter 9242, a time of night parameter 9244, a sleep disordered breathing (SDB) event frequency parameter 9246, a patient adjustment parameter 9248, and a swallowing parameter 9252. The patient adjustment parameter 9248 may comprise a pause/comfort parameter 9250.

In some examples, via the position parameter 9242, the sensing portion 9234 may obtain, track, and/or determines a body position, posture, and the like, wherein a change in the body position (e.g. lateral side-sleeping to supine, vice versa or another body position change) may result in a change in upper airway patency. In some such examples, a change in a stimulation protocol according to a HGN stimulation pattern and/or INFRA stimulation pattern may be used to increase or maintain upper airway patency despite the change identified via the position parameter 9242.

In some examples, via the time of night parameter 9244, the sensing portion 9234 may obtain, track, and/or determine a time of night within a patient treatment period (e.g. 10 pm to 6 am, in some examples) at which a particular patient or class of patients may be more susceptible or less susceptible to a change in upper airway patency.

In some examples, via the SDB event frequency parameter 9246, the sensing portion 9234 may obtain, track, and/or determine a SDB event frequency at which a particular patient or class of patients may be more susceptible or less susceptible to a change in upper airway patency.

In some examples, via the patient adjustment parameter 9248, the sensing portion 9234 may obtain and/or track patient adjustments to stimulation (within a clinician permitted range) during a treatment period, such as a pause, off, or increase or decrease in stimulation amplitude. In some instances, such patient adjustments may be indicative of discomfort (9250) or other patient perception, which in some examples may relate to a degree of collapsibility (e.g. patency).

In some examples, via the swallowing parameter 9252, the sensing portion 9234 may obtain, track, and/or determine a swallowing behavior which may result from stimulation of infrahyoid-based patency tissue or other causes. If a swallowing behavior was determined (e.g. identified), then such information may be communicated via the sensed data evaluator 8035 to the stimulation settings generator 9270.

As further shown in FIG. 38F, in some examples the stimulation settings generator 9270 comprises at least some of substantially the same features and attributes as the stimulation setting generator 9170 in FIG. 38E, while further comprising a suspension parameter 9271 and a peaking parameter 9272.

In some examples, via the suspension parameter 9271, stimulation may be suspended for a particular type of stimulation (e.g. hypoglossal nerve or infrahyoid-based patency tissue). In such examples, the stimulation may be suspended upon identifying particular sensed physiologic information such as, but not limited to, swallowing behavior per swallowing parameter 9252.

In some examples, via the peaking parameter 9272, the stimulation settings generator 9270 may be used to evaluate whether addition (or subtraction) of a particular type of stimulation (e.g. infrahyoid-based patency tissue) to another type of stimulation (e.g. hypoglossal nerve) may increase upper airway patency, or vice versa.

As just one example, one evaluation method may comprise performing ongoing HGN stimulation via stimulation element 8020 and then adding bursts of stimulation via the stimulation element 8030 to infrahyoid-based patency tissue of stimulation so that combined stimulation occurs. Using sensed data from sensing portion 9234, the stimulation settings generator 9270 may evaluate whether upper airway patency increased, decreased, or stayed the same upon adding the second type of stimulation. In some such examples, the sensed data may comprise airflow (e.g. airflow amplitude), SDB event frequency (9246), surrogates thereof, and/or other parameters indicative of patency (e.g. collapse). The evaluation may rely upon current or recently sensed data and/or historical averages (e.g. patient-specific or multiple patient).

Via peaking parameter 9272, a similar test and evaluation may be performed for removing one of the types of stimulation from combined stimulation to determine a patient's upper airway patency response.

In some examples, via peaking parameter 9272, a patient's tolerance (e.g. comfort/discomfort) to combined stimulation (e.g. two different types of stimulation) may be evaluated using sensed data such as the pause/comfort parameter 9250 of the patient adjustment parameter 9248.

In some examples, it will be understood that such testing and evaluating per a peaking framework can be performed prior to chronic implantation of both an HGN stimulation element 8020 and an infrahyoid-based patency stimulation element 8030 to facilitate evaluating combined stimulation of both targets as compared to stimulation of just one of the targets. In some such examples, percutaneously insertable stimulation test tools, stimulation elements 8020, 8030, or other techniques may be used to implement the test stimulation for peaking.

With at least the above-described aspects in mind, the example arrangement 9200 of FIG. 38F may operate in a manner consistent with the example arrangements of FIGS. 38A-38E to implement sleep disordered breathing stimulation therapy while selectively leveraging a patency hysteresis effect associated with at least stimulation of infrahyoid-based patency tissues.

With this in mind, FIGS. 38G, 38H provide at least two example arrangements by which example methods of stimulation according to a patency hysteresis parameter may be implemented.

FIG. 38G is a diagram schematically representing an example stimulation protocol 9320 including an HGN stimulation pattern 9321 and an INFRA stimulation pattern 7461. While many different INFRA stimulation patterns may be used, for illustrative simplicity the example INFRA stimulation pattern 7461 comprises at least some of substantially the same features and attributes as the stimulation pattern 7461 in FIG. 37G. In some examples, the HGN stimulation pattern 9321 comprises at least some of substantially the same features as stimulation pattern 7241 of FIG. 37G, except comprising an extended non-stimulation period 9330 preceding the initiation of, at change C1, the series of stimulation cycles 5035, which include stimulation periods 5032 and non-stimulation periods 5034.

As further shown adjacent stimulation protocol 9320 in FIG. 38G, a patient parameters pattern 9311 represents at least one of the parameters of the patients, such as one or more of the parameters from sensing portion 9134, 9234 (FIGS. 38E, 38F). In some such examples, such sensed parameters may comprise patency parameters (e.g. 9241 in FIG. 38F), with or without other sensed parameters from sensing portion 9134, 9234. The patient parameters pattern 9311 comprises a baseline portion 9312 and a changed portion 9314. In some examples, the baseline portion 9312 comprises one segment within a treatment period (e.g. 10 pm to 6 am, in some examples) at which the INFRA stimulation pattern 7461 is being applied and during which an extended HGN non-stimulation period 9330 is being applied prior to a change occurring (at C1) in one of the patient parameters, such as but not limited to patency parameters 9241 (FIG. 38F). Upon the change at C1, an upper airway patency may have decreased as represented by dashed line 9318 in an inspiratory phase 5012. As previously noted, just one example change may be determined via position parameter (e.g. 9242 in FIG. 38F) in which a patient has been sleeping on their side (e.g. lateral decubitus) as represented via the baseline portion 9312 in FIG. 38G, and then the patient moving (during sleep) into a supine position (e.g. on their back) which is represented as a change at C1. Via this change, the patient may be more susceptible to a reduction in upper airway patency (e.g. a collapse) and accordingly, the stimulation protocol 9320 reacts by adding HGN stimulation per pattern 9321 in an effort to increase or maintain upper airway patency despite the change in body position.

In some examples, the added HGN stimulation periods 5032 of stimulation pattern 9321 may apply HGN stimulation in a combined upper airway patency effect resulting from INFRA stimulation periods 7463 at least partially concurrent (at least partially overlapping) with HGN stimulation periods and/or a patency hysteresis effect of the INFRA stimulation pattern 7461 at least partially concurrent with (at least partially overlapping with) HGN stimulation periods 5032.

It will be understood that upon such a change (e.g. at C1), the initiation of the first stimulation period 5032 of the HGN stimulation pattern 9321 may not occur immediately as a transition period may occur before such first stimulation period 5032. However, for illustrative purposes FIG. 38G depicts the first stimulation period 5032 as occurring concurrent with the change C1. Alternatively, one can view FIG. 38G as representing the initiation of first stimulation period 5032 as occurring at C1 upon the change in patient parameters occurring some small period of time prior to the moment represented at C1.

FIG. 38G also further provides a diagram of an example arrangement including a patient parameters pattern 9315 and an example stimulation protocol 9350 comprising an HGN stimulation pattern 9351 and an INFRA stimulation pattern 7461, which is the same as in stimulation protocol 9320. The HGN stimulation pattern 9321 may comprise at least some of substantially the same features as stimulation pattern 7421 of FIG. 37G (including a series stimulation cycles 5035), except comprising an extended non-stimulation period 9331 starting at change C2 in the patient parameters pattern 9315.

The patient parameters pattern 9315 comprises at least some of substantially the same features and attributes as patient parameters pattern 9311 (FIG. 38G) except that a baseline portion 9316 represents a portion of a treatment period during which a patient is receiving both HGN stimulation (e.g. closed loop stimulation periods 9332, in some examples) and INFRA stimulation (e.g. open loop stimulation periods 7463, in some examples) to increase or maintain upper airway patency when the patient would otherwise be experiencing decreased upper airway patency but for the combined HGN and INFRA stimulation. However, at C2, the diagram shows a changed portion 9317 in the patient parameters pattern 9315, which represents the patient having a change in their patient parameters (e.g. changed body position, other) such that the patient can experience adequate upper airway patency with just INFRA stimulation pattern 7461 (per stimulation periods 7463) and cessation of the HGN stimulation pattern 9351 as represented by extended HGN non-stimulation period 9330.

With regard to the example stimulation protocols 9320, 9350 of FIG. 38G, it will be understood that in some examples just one type of stimulation of upper airway patency tissue is performed, such as infrahyoid based patency tissue, and upon a change (e.g. C1 or C2) a greater intensity or less intensity of such stimulation may be applied depending on the type of change (e.g. sensed data, patency parameters 9241) and/or in view of the patency hysteresis parameters (e.g. 9138, 9172 in FIG. 38F). Similarly, with regard to the example stimulation protocols 9420, 9450 of FIG. 38H, it will be understood that in some examples just one type of stimulation of upper airway patency tissue is performed, such as HGN stimulation, and upon a change (e.g. C3 or C4) a greater intensity or less intensity of such stimulation may be applied depending on the type of change (e.g. sensed data, patency parameters) and/or in view of the patency hysteresis parameters (e.g. 9138, 9172 in FIG. 38F).

FIG. 38H is a diagram schematically representing an example arrangement 9400 including a patient parameters pattern 9311 (as in FIG. 38G) in association with a stimulation protocol 9420, which comprises an HGN stimulation pattern 7241 (as in FIG. 37G) and an INFRA stimulation pattern 9431.

In this example implementation, an on-going HGN stimulation is delivered to the patient such as (but not limited to) stimulation pattern 7241, in some examples. During a baseline portion 9312 of patient parameters pattern 9311, no INFRA stimulation is delivered as represented by INFRA non-stimulation period 9437 at least because the on-going HGN stimulation pattern 7461 may adequately increase or maintain upper airway patency for the particular patient parameters, as represented by baseline portion 9312 of patient parameters pattern 9311. However, in a manner similar to patient parameters pattern 9311 in FIG. 38G, at C3 a change in the patient parameters such as a change in body position and/or other changes, inputs, etc. may otherwise cause a decrease in upper airway patency but for the added INFRA stimulation provided INFRA stimulation pattern 7461 which is initiated at or near change C3. While the INFRA stimulation pattern can take a variety of forms, in some examples the INFRA stimulation pattern leverages a patency hysteresis effect such that less overall INFRA stimulation may be delivered while still increasing or maintaining upper airway patency in combination with the on-going delivery of HGN stimulation pattern 7461. As noted elsewhere, the INFRA stimulation pattern 9431 may comprise an open loop stimulation pattern as shown in FIG. 38H or a closed loop stimulation pattern (as shown in other examples), and in some examples, the INFRA stimulation pattern of stimulation protocol 9420 also may comprise stimulation periods having a different duration, frequency, amplitude, etc. than shown in FIG. 38H.

As further shown in FIG. 38H, an example stimulation protocol 9450 comprises an on-going HGN stimulation pattern 7421 (like for stimulation protocol 9250) and an on-going INFRA stimulation pattern 7461 (as in FIG. 38G), which is delivered in combination with the HGN stimulation pattern 7421 at least during a baseline portion 9316 of the patient parameters pattern 9315. In a manner similar to FIG. 38G, the baseline portion 9316 represents the patient having a set of patient parameters 9310 which would be expected to otherwise cause decreased upper airway patency (e.g. a high degree of collapsibility but for the combined HGN and INFRA stimulation. As further shown in FIG. 38H, a change (at C4) in the patient parameters 9310 corresponds to patient parameters 9310 likely to increase or maintain an upper airway patency with just the on-going HGN stimulation pattern 7421, such that the stimulation protocol 9450 terminates the INFRA stimulation cycles 7469 (including stimulation period 7463 and non-stimulation period 7465) as represented by the extended non-stimulation period 9439.

With regard to the various stimulation protocols described in association with at least FIGS. 33A-37G, it will be understood that in some examples when there may be a lower probability of collapse, such as when a patient is sleeping on their side or other situations, the INFRA stimulation patterns and/or HGN stimulation patterns may be provided in a continuous stimulation pattern at a lower amplitude (e.g. tone level instead of suprathreshold contraction level) for at least a portion of a treatment period. In some such examples, the tone-level stimulation may be delivered for stimulation periods such as about 5 to about 30 seconds, with suitable non-stimulation periods between the tone-level stimulation periods.

FIG. 39 is a flow diagram schematically representing an example arrangement 8100 including an example device and/or example method to automatically select between stimulation of only the hypoglossal nerve (at 8110) or both the hypoglossal nerve and the ansa cervicalis-related nerve (at 8115). In some examples, the example arrangement 8100 may comprise at least some of substantially the same features and attributes as the example stimulation devices and/or methods in the previously described examples of the present disclosure, including stimulation protocols, stimulation arrangements, etc. In some examples, the sensing in example arrangement 8100 may comprise at least some of the same features and attributes as the later described sensing/control examples.

As shown at 8110 in FIG. 39, stimulation may be applied to the hypoglossal nerve (e.g. left and/or right) or stimulation may be applied to both the hypoglossal nerve (HGN) and the ansa cervicalis-related nerve (ACN) (e.g. left and/or right), as shown at 8115. Upon such stimulation of these tissues to increase and/or maintain upper airway patency, a resulting effect 8112, 8117 on the patient's physiology and breathing behavior may be sensed at 8135. This sensed information is fed (at 8137) to a control portion or other element (at 8140) to adjust the therapy settings (at 8140), which may be implemented automatically (at 8142) or manually via a patient resource (8143) and/or clinician resource (8145). These respective resources 8143, 8145 may be dedicated programmers or non-dedicated programmers (e.g. smart phone, web portal, etc.). When implemented automatically, the adjustment may occur within an implantable pulse generator or other resource by which the stimulation settings and signal are implemented.

Upon any adjustment (or lack thereof) to the settings, and as further shown in FIG. 39, an output 1847 is fed to a determination or query (at 1848) whether a sensed severity index (e.g. an Apnea-Hypopnea Index AHI) is greater than a selectable quantity N (e.g. threshold). If the answer is YES, then via path 8149A, the example arrangement 8100 implements stimulation of both the hypoglossal nerve (HGN) and the ansa cervicalis-related nerve (ACN) (at 8115) in order to provide more aggressive therapy for treating sleep disordered breathing. However, if the answer to the query at 1848 is NO, then via path 8149B, the example arrangement 8100 implements stimulation of solely the hypoglossal nerve (at 8110) to maintain, increase, or decrease the therapy within a range which can be met by the hypoglossal nerve (HGN) without stimulation of the ansa cervicalis-related nerve (ACN).

Via this example arrangement 8100, efficacious therapy can be achieved while balancing stimulation of multiple different nerves.

In some examples, multiple stimulation locations of the ansa cervicalis-related nerve may be included in such determinations, at least with regard to their effectiveness in promoting therapy.

While not shown in FIG. 39, it will be understood that in some examples, the element 8110 may comprise solely stimulation of the ansa cervicalis-related nerve instead of solely stimulating the hypoglossal nerve such that activation of block 8115 provides supplemental stimulation via the hypoglossal nerve (instead of via the ansa cervicalis-related nerve) so that both the ansa cervicalis-related nerve and the hypoglossal nerve would be stimulated in block 8115 in this example.

The example arrangement in FIG. 39 provides just one example within the present disclosure of using multiple stimulation elements, which are already implanted within the patient's body and positioned among multiple nerve targets (e.g. multiple targets on the ansa cervicalis-related nerve, the hypoglossal nerve, other nerves) in a method of therapy in which one or more such stimulation elements are selectively included (e.g. added) in the stimulation therapy or one or more such stimulation elements are selectively excluded (e.g. removed) from the stimulation therapy. The selective inclusion or selective exclusion of the respective nerve targets (via a corresponding already implanted stimulation element) may be based on one parameter or a plurality of parameters. In some examples, the parameter(s) may be selectable for their inclusion or exclusion as affecting the stimulation therapy and/or a value, criteria, threshold associated with those parameters may be selectable as well. In some examples, these features can be implemented with at least some externally located stimulation elements.

With these general principles of at least some examples of the present disclosure in mind, FIG. 40A schematically represents an example implementation of the example arrangement 8100 (FIG. 39) including a method 8180 (or aspect of an example device) of adding or subtracting a nerve target from among multiple nerve targets based on a body position/posture and/or other parameters. For example, the method may comprise sensing (e.g. at 8135 in FIG. 39) the body position or posture, and if it were sensed that a patient moved to a supine position, then an additional nerve target may be included in the stimulation therapy to enhance increasing or maintaining upper airway patency. Similarly, if the patient moved out of a supine position into a different body position (lateral decubitis), then at least one nerve target may be excluded (e.g. temporarily, selectively, etc.) from the stimulation therapy if/when such stimulation of the extra nerve target is no longer prudent or helpful. It will be understood that, in some examples, this example arrangement is applicable to changes in other body position/postures and/or applicable to changes in parameters other than body position/posture.

Per the foregoing description regarding the example arrangement in FIG. 39, in some examples this method (or aspect of an example device) at 8180 may comprise adding stimulation (via an already implanted stimulation element) of the ansa cervicalis-related nerve where stimulation of the hypoglossal nerve was already being implemented. It will be understood that a similar method may comprise removing stimulation (via an already implanted stimulation element) of the ansa cervicalis-related nerve, where stimulation of the hypoglossal nerve was already included or implemented as part of the stimulation therapy.

In some examples, this method (at 8180 in FIG. 40A) may comprise adding stimulation (via an already implanted stimulation element) of the hypoglossal nerve, where stimulation of the ansa cervicalis-related nerve was implemented as part of the therapy. It will be understood that a similar method may comprise removing stimulation (via an already implanted stimulation element) of the hypoglossal nerve, where stimulation of the ansa cervicalis-related nerve was already included or implemented as part of the stimulation therapy.

In some examples, this method (at 8180 in FIG. 40A) may comprise adding stimulation (via an already implanted stimulation element) of a different, second nerve target of the ansa cervicalis-related nerve, where stimulation of a first nerve target of the ansa cervicalis-related nerve was already included or implemented as part of the stimulation therapy. It will be understood that a similar method may comprise removing stimulation (via an already implanted stimulation element) of a different, second nerve target of the ansa cervicalis-related nerve, where stimulation of a first nerve target of the ansa cervicalis-related nerve was already included or implemented as part of the stimulation therapy.

In some examples, this method (at 8180 in FIG. 40A) may comprise adding stimulation (via an already implanted stimulation element) of a different, second nerve target (other than the ansa cervicalis-related nerve or hypoglossal nerve), where stimulation of the ansa cervicalis-related nerve and/or the hypoglossal nerve was already included or implemented as part of the stimulation therapy. It will be understood that a similar method may comprise removing stimulation (via an already implanted stimulation element) of the different, second nerve target (other than the ansa cervicalis-related nerve or hypoglossal nerve), where stimulation of the ansa cervicalis-related nerve and/or hypoglossal nerve was already included or implemented as part of the stimulation therapy.

In some examples, this method (at 8180 in FIG. 40A) may comprise adding stimulation (via an already implanted stimulation element) of a different, second nerve target (other than the ansa cervicalis-related nerve and/or hypoglossal nerve), where stimulation of the ansa cervicalis-related nerve and/or the hypoglossal nerve was already included or implemented as part of the stimulation therapy. It will be understood that a similar method may comprise removing stimulation (via an already implanted stimulation element) of the different, second nerve target (other than the ansa cervicalis-related nerve and/or hypoglossal nerve), where stimulation of the ansa cervicalis-related nerve and/or hypoglossal nerve was already included or implemented as part of the stimulation therapy.

In some examples, this method (at 8180 in FIG. 40A) may comprise adding stimulation (via an already implanted stimulation element) of the ansa cervicalis-related nerve and/or hypoglossal nerve, where stimulation of another nerve target (e.g. other than the ansa cervicalis-related nerve and/or hypoglossal nerve) was already included or implemented as part of the stimulation therapy. It will be understood that a similar method may comprise removing stimulation (via an already implanted stimulation element) of the ansa cervicalis-related nerve or hypoglossal nerve), where stimulation of another nerve target (e.g. other than the ansa cervicalis-related nerve and/or hypoglossal nerve) was already included or implemented as part of the stimulation therapy.

In some examples, the inclusion or exclusion of a nerve target to stimulation therapy may be based on parameters (or physiologic conditions) other than body position or posture, with such parameters generally affecting upper airway patency and/or sleep disordered breathing.

It will further understood that these principles associated with examples of the present disclosure, including but not limited to the example arrangements in FIGS. 39, 40A, may be applicable to other nerve targets for other physiologic conditions, which may in the head-and-neck region or may be in areas of the body other than the head-and-neck region. For example, as noted elsewhere herein, these principles may be applied to stimulation of multiple nerve targets in the pelvic region including, but not limited to, the pudendal nerve for treating pelvic disorders such as (but not limited to) urinary and/or fecal incontinence issues, which may involve (but is not limited to) the external urinary sphincter and/or external anal sphincter.

Moreover, while the foregoing principles of the example arrangements associated with at least FIGS. 39-40A relate to at least some examples comprising multiple, available nerve targets associated with already implanted stimulation elements, it will be understood that these principles may be extended to the addition of a not currently available nerve target by implanting a stimulation element in a second, separate implant procedure to make a desired nerve target available for stimulation therapy in order to implement the example arrangements associated with at least FIGS. 39-40A. At least the example arrangements associated with at least FIGS. 5A-5B provide some examples by which a nerve target may be made available (for selective inclusion or selective exclusion per the example arrangements in association with at least FIGS. 39-40A) via implanting a stimulation element via a second, separate implant procedure which occurs some period of time after an initial/original implant procedure for one or more original nerve targets.

In some examples, the preceding example methods and/or example devices associated with at least FIGS. 38-40A and/or the following example methods and/or example devices described in association with at least FIGS. 40B-60 may be implemented via at least some of the features and attributes (such as, but not limited to, the stimulation arrangements, stimulation elements, leads, stimulation protocols, etc.) of the example arrangements described in association with at least FIGS. 1-37D.

FIG. 40B is a block diagram schematically representing an example arrangement at 8200 including an example method and/or example device for sensing and/or managing fatigue. In some examples, the example arrangement 8200 in association with FIG. 40B may be implemented in coordination with, and/or as part of the example arrangements previously described in association with at least FIGS. 39-40A. As shown at 8200 in FIG. 40B, in some examples the method comprises identifying fatigue of a target nerve and/or its innervated muscle and adjusting a stimulation parameter to assess potential fatigue and/or to decrease identified fatigue.

In some examples, identifying the fatigue may be performed as part of a closed loop sensing system to determine when stimulation is becoming less effective. In some examples, an accelerometer or EMG may be used to directly measure motion, which may be indicative of reduced therapy effectiveness. In some examples, the accelerometer may already be implanted in the patient. In some examples, a respiratory sensor may be used to detect increasing instances of obstruction, which may be indicative of reduced therapy effectiveness. For patients for which the stimulation was previously effective in increasing or maintaining upper airway patency, sensing the change in motion or increasing obstruction may be indicative of fatigue (of nerves and/or muscles) from stimulation therapy.

In some examples, an intensity (e.g. a duty cycle or other parameter) of stimulation therapy may be decreased or stimulation therapy may be temporarily paused, and then it may be observed if the stimulation becomes more effective, which then may be indicative of fatigue (of the stimulated nerves and/or associated muscles).

In some examples, adjusting the stimulation parameter may comprise switching nerve targets for implementing the stimulation therapy and/or adding (or removing) a nerve target from among multiple nerve targets for implementing the stimulation therapy. In some examples, such switching, adding, or removing may be implemented via at least some aspects of the example arrangements described in association with at least FIGS. 39-40A.

FIG. 40C is a block diagram schematically representing an example arrangement at 8220 including an example method and/or example device for increasing amplitudes of stimulation therapy to therapeutically effectively levels when multiple nerve targets are included as part of the stimulation therapy. In some examples, the example arrangement 8220 in association with FIG. 40C may be implemented in coordination with, and/or as part of the example arrangements previously described in association with at least FIGS. 39-40A and/or other example arrangements of the present disclosure.

As shown at 8220 in FIG. 40C, in some examples the method comprises determining and implementing a therapeutic stimulation intensity via increasing an amplitude of stimulation among multiple nerve targets until a threshold(s) is met. In some examples, this method (at 8220) may comprise a first determination/implementation protocol including increasing a stimulation amplitude applied to a first nerve target until a first threshold is met, and then increasing a stimulation amplitude applied to a second nerve target until a second threshold is met. In some examples, the first protocol is repeated.

In some examples, this method (at 8220) may comprise a second determination/implementation protocol including increasing stimulation amplitude at first and second nerve targets by equal amounts until a first threshold is met, and then thereafter increasing stimulation amplitude solely at just one of the respective first and second nerve targets.

In some examples, this method (at 8220) may comprise a third determination/implementation protocol including increasing stimulation amplitude solely at a first nerve target while maintaining the same amplitude at a second nerve target.

In some examples, this method (at 8220) may comprise a fourth determination/implementation protocol including increasing stimulation amplitude alternately at a first nerve target and a second nerve target.

In some examples, this method (at 8220) may comprise a fifth determination/implementation protocol includes combining at least some aspects of the respective first, second, third, and fourth determination/implementation protocols.

It will be understood that the general principles associated with the example arrangement at 8220 in FIG. 40C may be applied to more than two nerve targets.

FIG. 40D is a block diagram schematically representing an example arrangement at 8260 including an example method and/or example device for applying stimulation according to a respiratory phase parameter and/or without a respiratory phase parameter, with such stimulation providing therapy to increase or maintain upper airway patency to treat sleep disordered breathing. In some examples, this method may comprise applying stimulation based on detecting a fiducial of an expiratory phase of a respiratory cycle, while in some examples, applying stimulation is based on detecting a fiducial of an inspiratory phase of a respiratory cycle. Such fiducials may comprise an onset, offset, peak, etc., In some examples, the method may comprise applying stimulation based on detecting both of a fiducial of an inspiratory phase of a respiratory cycle and a fiducial of an expiratory phase of a respiratory cycle.

In some examples, basing the application of stimulation with regard to a respiratory phase parameter may comprise triggering the application of stimulation based on such sensed respiratory phase parameter.

In some examples, basing the application of stimulation with regard to a respiratory phase parameter may comprise causing a stimulation period of the stimulation signal to coincide with at least a portion of a respiratory phase, such as the inspiratory phase and/or expiratory phase. In some such examples, this type of stimulation may sometimes be referred to as the stimulation being synchronous with at least a portion of a respiratory phase. Moreover, in some of these examples, causing the stimulation period to coincide with at least a portion of a respiratory phase may comprise making the stimulation coincide solely with a single type of respiratory phase, e.g. the inspiratory phase. In some examples, such arrangements may comprise the stimulation coinciding with a brief pre-inspiratory phase of the respiratory cycle, which corresponds to a latter portion of an expiratory pause (e.g. respiratory pause).

At least some examples of these arrangements are illustrated in association with at least some of the stimulation protocols in FIGS. 37A, 37B, and 37D.

In some examples, the method at 8260 in FIG. 40D comprises applying stimulation without regard to any sensed respiratory phase parameter, and may be referred to as open loop-based stimulation in some instances. However, in some such open loop examples, while sensed respiratory phase information is not used to trigger stimulation and/or is not used to make stimulation synchronous with some portion of a respiratory phase, the method(s) do permit sensed respiratory information to be used generally regarding therapy. For examples, some example arrangements may comprise sensing respiratory information to determine whether the open loop stimulation is effective, e.g. is the patient experiencing fewer sleep disordered breathing events. If the stimulation is not as effective as desired, this sensed information may be used to determine how to adjust the stimulation therapy. Accordingly, a distinction may be drawn between using sensed respiratory information for triggering or synchronizing stimulation relative to each respiratory cycle versus using sensed respiratory information more generally to determine the effectiveness of the stimulation therapy and adjustments thereto.

In some examples, the method at 8260 in FIG. 40 may comprise applying stimulation using a combination of both closed loop (e.g. sensing respiratory phase parameter) and open loop (e.g. not using sensed respiratory phase parameter) arrangements.

FIG. 41A is a flow diagram schematically representing an example arrangement including an example method 8280 (and/or example device) for sensing, via at least one sensing element, at least one sleep disordered breathing-related parameter. In some examples, the at least one sleep disordered breathing-related parameter comprises at least one of a respiratory phase parameter, an apnea-hypopnea index, a patient comfort parameter, an arousal index, and an upper airway collapse pattern. In some examples, stimulation can be modulated based on at least one of the respiratory phase parameter, an apnea-hypopnea index, a patient comfort parameter, a patient sleeping position, and an upper airway collapse pattern. In some examples, the patient comfort parameter may comprise an arousal index.

In some examples, the stimulation may be synchronized relative to the sensed respiratory phase parameter such as, but not limited to being synchronized relative to a sensed inspiratory phase of the patient's respiratory cycle. At least some example implementations of such synchronization are illustrated in association with the example stimulation patterns in association with at least FIGS. 32A-37D and FIG. 40D.

In some examples, as shown at 8284 in FIG. 41B an example method may comprise automatically titrating a stimulation parameter based on sensing at least one of the respiratory phase parameter, the AHI parameter, the patient comfort parameter, the patient sleeping position, and the upper airway collapse pattern. In some such examples, sensing the upper airway collapse pattern may comprises determining the upper airway collapse pattern via sensing a bioimpedance in relation to the neck region of the patient's body.

In relation to at least method 8284 in FIG. 41B, some example methods may comprise identifying a type of the upper airway collapse pattern via: (1) identifying at least one of a value of, a change in value of, and a location of the sensed bioimpedance along the upper airway; and (2) implementing the automatically titration of the stimulation parameter based on the identified value, identified change in value or identified location. In some examples, the type of upper airway collapse pattern may comprise at least one of anterior-posterior collapse, concentric collapse, lateral collapse, or composite collapse, which are illustrated schematically in FIGS. 53A-53C, while FIG. 53D also schematically illustrates collapse locations along the upper airway.

In some examples, this sensed information about a type, degree, and/or location of collapse pattern may be used as feedback (sensed data) to determine (e.g. initiate, terminate, select, adjust) stimulating settings to stimulate a hypoglossal nerve (e.g. left and/or right) and/or an ansa cervicalis-related nerve (e.g. left and/or right), as further described in association with at least FIGS. 38A-38D.

It will be understood that sensing information about a collapse pattern may comprise identifying which muscles (and their associated nerves) of the upper airway are involved in a particular collapse pattern according to its type, location, degree, such that stimulation of such identified muscles and nerves (including which multiple potential nerve targets) may be used to prevent or minimize such collapse patterns.

In further relation to at least the example method 8284 in FIG. 41B, in some examples the sensing a collapse pattern (e.g. type, location, degree) may be implemented via an implantable, removably insertable array of spaced apart electrodes. In some such examples, the removably insertable array may be inserted into and through a nose or mouth of the patient, with one example implementation illustrated in FIG. 52C. However, in some examples, the sensing of collapse patterns (e.g. their type, location, and degree) may be implemented via an externally mountable array of spaced apart electrodes conformable to an exterior portion of the neck overlying the region of upper airway collapse, with on example implementation illustrated in FIGS. 52A-52B.

As shown at 8286 in FIG. 41B2, some example methods may comprise sensing respiratory information as respiratory phase information, and implementing the automatic titration of a stimulation parameter (per method 8284 in FIG. 41B) based on the sensed respiratory phase parameter. As shown at 8288 in FIG. 41B3, in some examples the stimulation parameter may comprise at least one of: (1) at least one of a change in an amplitude, frequency, pulse width, duty cycle of stimulation; and (2) selection of at least one stimulation target among a plurality of stimulation targets, which includes the hypoglossal nerve and the ansa cervicalis nerve. As shown at 8290 in FIG. 41B4, in some examples, the method comprises titrating, with the plurality of stimulation targets comprising a left and/or right hypoglossal nerve, a left and/or right ansa cervicalis-related nerve (including different target stimulation branches), other nerve targets, and/or muscle targets. In some examples, the muscle targets may comprise a genioglossus muscle (innervated by the hypoglossal nerve) and/or infrahyoid strap muscles innervated by the ansa cervicalis-related nerve.

In some examples, the other stimulation nerve targets may further comprise a glossopharyngeal nerve, a superior laryngeal nerve, a superior cervical ganglion nerve, and a chemoreceptor (e.g. in close proximity to the carotid body). In some such examples, the combination of the glossopharyngeal nerve and the superior laryngeal nerve comprises a stimulation target. One example implementation of this example combination is described and illustrated in association with FIG. 60.

As shown at in FIG. 41C, one example method comprises receiving a patient adjustment, as a single input, to a stimulation parameter, and implementing the patient adjustment by automatically adjusting a stimulation energy among a plurality of stimulation sites including at least one of a hypoglossal nerve site, an ansa cervicalis-related nerve site, and a second non-hypoglossal nerve site. In some such examples, the single input may sometimes be referred to as a single control element, such as a single button on a patient remote control app, whether embodied in a dedicated device or non-dedicated device (e.g. smart phone, tablet, watch, etc.)

In some such examples, the method at 8300 may comprise implementing the automatically balancing of the stimulation among the different stimulation sites.

In some such examples methods, the automatically balancing comprises: (1) initiating and maintaining the stimulation via stimulation of a first one of the respective stimulation sites; and (2) adding, at a later point in time, stimulation of at least one respective second stimulation sites of the plurality of stimulation sites.

As shown at 8320 in FIG. 41D, one example method comprises implementing the automatic balancing based on sensing at least one of a respiratory phase parameter, an AHI parameter, a patient comfort parameter, a patient sleeping position parameter, and an upper airway collapse pattern parameter.

In some examples, the first one of the respective stimulation sites comprises a hypoglossal nerve and the second respective stimulation site comprises an ansa cervicalis-related nerve.

In some examples, the automatic balancing may comprise a relative percentage among two stimulation sites, such as among the hypoglossal nerve and the ansa cervicalis-related nerve or among two different stimulation locations of the ansa cervicalis nerve. The relative percentage between the multiple stimulation sites may vary over time, and may be periodically adjusted or continually adjusted. In some examples, the relative percentage may be a 50/50 relative percentage, which may be implemented via alternating the stimulation between the two different sites or by applying the stimulation in a non-alternating manner such as applying each stimulation at 50 percent of full stimulation to achieve the 50/50 relative percentage.

In some examples, during the automatic balancing, the first one of the respective stimulation site comprises an ansa cervicalis-related nerve and the second respective stimulation site comprises a hypoglossal nerve.

In some examples, in performing the adjustment according to a patient comfort parameter, the patient comfort parameter may comprise an arousal index.

As shown at 8330 in FIG. 42A, in some examples a method may comprise: (1) receiving a patient adjustment to a stimulation parameter upon a change in the patient comfort parameter, the stimulation parameter comprising an overall stimulation energy; and (2) implementing the patient adjustment by redistributing the overall stimulation energy among an increased number of stimulation sites. In some such examples, the redistribution may be implemented while maintaining the same overall energy as before the patient adjustment. In some such examples, the patient adjustment may comprise a single input parameter, such as the previously described "single knob" patient input on a patient remote control, patient app, and the like.

With further reference to the method 8330 in FIG. 42A, in some examples, the patient adjustment may comprise a request to decrease stimulation. In some such examples, the patient adjustment may implemented by decreasing some aspect(s) of stimulation while maintaining the overall stimulation energy as before the patient request to decrease the stimulation. Via this arrangement, the patient has some control over patient comfort and may experience increased patient comfort, while the example device may still provide efficacious stimulation therapy via a modified stimulation protocol/settings.

As shown at 8350 in FIG. 42B, in some examples a method may comprise automatically adjusting, upon sensing a change in the at least one sleep disordered breathing-related parameter, at least one of a stimulation parameter and a target stimulation location at the upper-airway-patency-related tissue, wherein the target stimulation location comprises at least one of a hypoglossal nerve and an ansa cervicalis-related nerve. In some examples, the at least one sleep disordered breathing-related parameter comprises an AHI parameter. In some examples, the stimulation location of a non-hypoglossal nerve target may comprise, in addition to or instead of, the ansa cervicalis-related nerve, at least one of: glossopharyngeal nerve; a superior laryngeal nerve; a superior cervical ganglion; and a chemoreceptor (e.g. in close proximity to the carotid body). In some such examples, this may comprise implementing the sensing of the increase in the AHI parameter.

In some such examples, the method may comprise, upon determining that the sensed change in the AHI parameter is associated with a change in patient sleeping position, adjusting the stimulation parameter relating to the ansa cervicalis-related nerve.

In some such examples, the method may comprise adjusting of the change in the stimulation parameter via increasing the stimulation parameter when the sensed change in the AHI parameter comprises a sensed increase in the AHI parameter. However, in some examples, a further adjustment may comprise decreasing a stimulation parameter regarding the hypoglossal nerve to increase or maintain patient comfort while adjusting or increasing stimulation parameters of other nerve stimulation targets to achieve the desired increase in stimulation intensity to respond to the sensed increase in the AHI parameter.

In some examples, the increase in the stimulation parameter may comprise a change from a first value to a higher second value. In some examples, the first value may comprise zero, while in some examples, the first value comprises a non-zero value corresponding to tonic stimulation or contraction-type stimulation.

Some example methods and/or example devices comprise sensing. It will be understood that such sensing may be performed even if no stimulation is occurring, even if no stimulation elements are implanted or present externally, etc. However, in some examples, such sensing may be performed in relation to some aspect affecting stimulation.

In some examples, sensing of various physiologic parameters may be implemented via a first sensing element and a second sensing element. Accordingly, as shown at 8370 in FIG. 42C, in some examples a method may comprise positioning the first sensing element on a first side of the patient's body and positioning the second sensing element on an opposite second side of the patient's body. However, as further illustrated in FIG. 42C, in some examples a method may comprise positioning the first sensing element on a first side of the patient's body and positioning the second sensing element on the same first side of the patient's body spaced apart from the first sensing element.

In some such examples, the sensing comprises sensing an impedance between the respective first and second sensing elements. Among other example implementations, such impedance sensing may be performed in association with at least the example arrangement 8000 of FIG. 38A, the impedance sensor 8752 of FIG. 38C, the collapse parameter 8710 of FIG. 38B, etc.

As shown at 8380 in FIG. 43, in some examples a method comprises sensing, via a first stimulation element and a second stimulation element, a sleep disordered breathing-related parameter comprises sensing at least one of respiration and a sleep-disordered-breathing event. In some example implementations, this sensing method may comprise locating the first stimulation element at a first hypoglossal nerve on the first side of the patient's body and the second stimulation element at a second hypoglossal nerve on the second side of the patient's body. However, in some example implementations, such sensing methods may comprise locating the first stimulation element at a first ansa cervicalis-related nerve on the first side of the patient's body and the second stimulation element at a second ansa cervicalis-related nerve on the second side of the patient's body.

In some examples, such sensing methods may comprise: (1) locating the first stimulation element, on the first side of the patient's body, at at least one of the first hypoglossal nerve and a first ansa cervicalis-related nerve; and (2) locating the second stimulation element, on the second side of the patient's body, at at least one of the second hypoglossal nerve and a second ansa cervicalis-related nerve.

In some such examples, the method comprises locating the first stimulation element, on the first side of the patient's body, at the first hypoglossal nerve and locating the second stimulation element on the first side of the patient's body at the first ansa cervicalis-related nerve.

In some such examples, the method comprises locating the second stimulation element, on the second side of the patient's body, at the second hypoglossal nerve and locating the second stimulation element on the second side of the patient's body at the second ansa cervicalis-related nerve.

With further reference to at least the example method 8370 in FIG. 42C, in some examples the first sensing element comprises a first stimulation element and the second sensing element comprises an electrode on a housing of a pulse generator. In some such examples, the method may comprise positioning the first stimulation element at at least one of: (1) at least one of a first hypoglossal nerve on a first side of the patient's body and a second hypoglossal nerve on an opposite second side of the patient's body; and (2) at least one of a first ansa cervicalis nerve on the first side of the patient's body and a second ansa cervicalis nerve on the second side of the patient's body.

As shown at 8400 in FIG. 44A, in some examples a method of sensing at least one sleep disordered breathing-related parameter comprises providing (e.g. via implanting within a patient's body) a first sensing element and a second sensing element, and measuring a bioimpedance between the first sensing element implanted relative to the at least one upper-airway-patency-related tissue and the second sensing element implanted relative to at least one of a phrenic nerve and a diaphragm. In some such examples, the first sensing element comprises a first stimulation element and the second sensing element comprises a second stimulation element.

In relation to a method of sensing at least one sleep disordered breathing-related parameter (e.g. 8280 in FIG. 41A), an upper airway patency-related tissue may comprise an upper-airway-patency-related muscle, and a method of sensing as shown at 8410 in FIG. 44B may comprise sensing at least one of a motion of the upper-airway-patency-related muscle and an electromyograph (EMG) of the upper-airway-patency-related muscle. In some such examples, the method of sensing comprises performing, via at least one of the sensed motion and the sensed EMG, at least one of: (1) titration of an amplitude of a stimulation signal to be applied via the at least one stimulation element; and (2) determination of a sufficiency of capture of the upper airway patency-related tissue to be stimulated via the stimulation element.

In relation to a method of sensing at least one sleep disordered breathing-related parameter (e.g. 8280 in FIG. 41A), as shown at 8420 in FIG. 44C, in some examples a method of sensing comprises determining at least one sleep disordered breathing-related parameter as a respiratory parameter, by sensing via the at least one sensing element at least one of: (1) a motion of an upper airway patency related muscle of the at least one upper airway patency-related tissue; and (2) a sound of respiration associated with the at least one upper airway patency-related tissue.

In some examples of stimulation, an example method comprises applying a first duty cycle of stimulation to the hypoglossal nerve to be different from a second duty cycle of stimulation for application to the ansa cervicalis-related nerve. In some examples, the first duty cycle is longer than the second duty cycle, while in some examples, the first duty cycle is shorter than the second duty cycle. At least some example implementations of different duty cycles are described in association with the stimulation protocols in at least FIGS. 33A-37D.

With further respect to some stimulation parameters, in some examples, a method of stimulation comprises applying stimulation to the hypoglossal nerve as a phasic stimulation; and applying stimulation to the ansa cervicalis-related nerve as a tonic stimulation. In some such examples, the tonic stimulation comprises a stimulation cycle comprising a stimulation period greater than a non-stimulation period.

As shown at 8430 in FIG. 45B, in some examples a method of stimulation comprises simultaneously stimulating a hypoglossal nerve and a second upper-airway-patency-related tissue, which may comprise at least one of an ansa cervicalis-related nerve and an infrahyoid strap muscle. In some such examples, the stimulation may be implemented via interleaving a first stimulation signal to stimulate the hypoglossal nerve and a second stimulation signal to stimulate the second upper-airway-patency-related tissue. In some such examples, the method comprises implementing both of the respective first and second stimulation signals via a single pulse generator.

In some such examples, the method comprises implementing the interleaving via applying the stimulation via a first frequency for the hypoglossal nerve and a different second frequency for the second upper-airway-patency-related tissue.

In some such examples, the method may comprise implementing the simultaneous stimulation via time-shifting or may comprise implementing the simultaneous stimulation synchronously.

As shown at 8440 in FIG. 45B, in some examples, a method comprises stimulating the hypoglossal nerve followed by stimulating the second upper-airway-patency-related tissue, which comprises at least one of the ansa cervicalis-related nerve and/or muscle innervated by the ansa cervicalis-related nerve. In some such examples, the method comprises maintaining the stimulation of the hypoglossal nerve during stimulation of the second upper-airway-patency-related tissue.

In some examples, the method of stimulation may comprise applying a continuous stimulation at a low frequency. In some examples, the method of stimulation comprises applying a non-continuous stimulation including an on period (e.g. stimulation period) and an off period (e.g. non-stimulation period), in which the intensity of stimulation is sufficient to cause muscular contraction.

As shown at 8450 in FIG. 46A, in some examples a method of stimulation comprises selecting a stimulation target from among a hypoglossal nerve and the different muscle groups associated with the ansa cervicalis-related nerve based on determination of a first parameter. In some examples, the first parameter comprises at least one of a respiratory parameter including respiratory phase information, a patient comfort, a posture, an effectiveness of therapy, device usage, a sleep stage, an upper airway collapse pattern, and AHI. In some such examples, an effectiveness of stimulation therapy may change over the short term or the long term, and therefore selecting among different muscle groups may help maintain effectiveness despite such changes in effectiveness.

As shown at 8460 in FIG. 46B, in some examples a method of sensing in relation to adjusting stimulation may comprise implementing, via an accelerometer, the determination of at least one of a respiratory phase/pattern, a posture, a body position or activity, effectiveness of therapy as a sleep-disordered breathing (SDB) severity index (e.g. AHI), and a sleep stage. In some such examples, the method may comprise implementing determination of the sleep stage via sensing via at least one of modalities of: accelerometer; bioimpedance; pressure; pneumotach; and thermistor.

In further relation to method 8460, in some examples the method comprises implementing the sensing of sleep stage via employing at least some of the modalities to sense at least one of: respiration; posture; body position; body activity; and cardiac information. In further relation to method 8460, in some examples, a determination of patient comfort may be implemented via at least one of patient feedback and clinician feedback.

In further relation to method 8460, in some examples the method comprises implementing the selectivity of a stimulation target, from among the hypoglossal nerve and the different muscle groups associated with the ansa cervicalis-related nerve loop, according to the first parameter via clinician titration.

In further relation to method 8450, and as shown at 8470 in FIG. 47, in some examples a method of stimulation comprises via application of a data model and according to the first parameter, implementing the selecting of at least one stimulation target from among the hypoglossal nerve and the different muscle groups associated with the ansa cervicalis-related nerve. In some such examples, the method comprises at a first time period prior to the implementing the selecting of at least one stimulation target, constructing the data model via known inputs corresponding to all of the stimulation targets relative to known outputs corresponding to the first parameter. In some examples, the constructed data model comprises a trained data model, which optionally comprises a trained machine learning model. In some examples, the trained machine learning model comprises at least one of an artificial neural network, deep learning model, and a support vector machine. In some examples, the first time period comprises a non-treatment period of the patient.

As shown at 8480 in FIG. 48, in some examples, a method comprises applying stimulation to each respective stimulation target to determine among the respective stimulation targets a relative degree of upper airway patency, wherein the respective stimulation targets comprise a hypoglossal nerve; an ansa cervicalis-related nerve; and an infrahyoid strap muscle. In some such examples, the stimulation signal may comprise an increasing ramp signal. In some such examples, the method comprises applying the stimulation simultaneously to at least two of the respective stimulation targets.

In some such examples regarding method 8480, the method may comprise selecting which of the respective stimulation targets to stimulate based on an upper airway collapse pattern. In some such examples, the method comprises classifying a type and a severity of the upper airway collapse pattern based on at least one of: snoring; a plurality of polysomnongraphy (PSG) parameters; a body position; a head-and-neck position; and a sleep stage.

In further relation to at least the method 8480, in some examples the method comprises implementing the selection of stimulation targets based on the type and the severity of the upper airway collapse pattern.

In further relation to method 8480 and/or the above-described associated methods, one example method comprises at least one of: (1) selecting the stimulation target as a first portion of the ansa cervicalis-related nerve upon the upper airway collapse pattern being predominantly a lateral wall collapse pattern; (2) selecting the stimulation target as a hypoglossal nerve upon the upper airway collapse pattern being predominantly a genioglossal (tongue) collapse pattern; and (3) selecting the stimulation target of an ansa cervicalis-related nerve as a first stimulation target prior to other stimulation targets upon the upper airway collapse pattern being predominantly a palate collapse pattern. In some such examples, the method comprises titrating at least one stimulation parameter of the stimulation for at least one of: each different collapse pattern; and each sleeping position. In such example methods, at least some stimulation parameters comprise an amplitude, a pulse width, a frequency, a duty cycle, and/or a number, a type, and a location of stimulation elements.

As shown at 8490 in FIG. 49A, in some examples a method comprises (1) establishing (e.g. implanting stimulation elements within a patient's body at) a plurality of muscle stimulation targets including a genioglossus muscle, a sternohyoid muscle, a sternothyroid muscle, and an omohyoid muscle; and (2) implementing the stimulation via distributing an energy of a stimulation signal among a selectable multiple number of the stimulation targets as the energy of the stimulation signal is increased. In some such examples, the method comprises implementing the stimulation of the muscle targets via at least one of: (1) directly stimulating the respective muscle stimulation target; and (2) stimulating a nerve by which the respective muscle stimulation targets are innervated.

As shown at 8500 in FIG. 49B, in some examples a method comprises, prior to completion of chronic implantation of a sleep disordered breathing therapy system, stimulating, via a first stimulation element, at least one test stimulation location indicative of a response of an upper-airway-patency-related tissue to the stimulation. In some such examples, the phrase "prior to completion" comprises at least one of pre-operatively and intra-operatively.

In some such examples, the first stimulation element comprises a test stimulation element, while in some examples, the first stimulation element comprises a chronically implantable stimulation element. In some examples, the chronically implantable stimulation element may comprise a stimulation electrode on a lead or a microstimulator.

In some such examples, the test stimulation location corresponds to a target stimulation location for implantation of a chronically implantable stimulation element.

In some such examples, the method comprises implementing the stimulation, via the first stimulation element, with the at least one test stimulation location comprising at least one of a hypoglossal nerve and a non-hypoglossal nerve.

As shown at 8510 in FIG. 50, in some examples, a method of stimulation to identify a stimulation location comprises: (1) stimulating a hypoglossal nerve and determining a first response of upper airway patency to the stimulation; and (2) after the determination of the first response, stimulating a non-hypoglossal nerve and determining a second response of upper airway patency to the stimulation. In some such examples, the method comprises maintaining the stimulation of the hypoglossal nerve during stimulation of the non-hypoglossal nerve.

As shown at 8520 in FIG. 51A, in some examples a method comprises identifying a stimulation location by: first stimulating an ansa cervicalis-related nerve and determining a response of upper airway patency to the stimulation; and after the determination of the response, stimulating a hypoglossal nerve and determining a response of upper airway patency to the stimulation. In some such examples, comprising maintaining the stimulation of the ansa cervicalis-related nerve during stimulation of the hypoglossal nerve.

In some examples, the test stimulation location corresponds to a first location not intended for implantation of a chronically implantable stimulation element. In some examples, the first location corresponds to an external location under the tongue.

In some examples, the method comprises determining the response of the upper-airway-patency-related tissue to the stimulation. In some such examples, the method comprises implementing the determining via observing the response. Moreover, in some examples, the method comprises observing the response via imaging at least one of a patency of the upper airway and a response of the upper airway patency-related muscle, and then evaluating the relative patency and/or the response of the upper airway patency-related muscle. In some examples, such imaging may comprise fluoroscopy, such as biplane modalities.

As shown at method 8520 in FIG. 51B, in some examples, a method of performing test stimulation comprises the first stimulation element comprising a test needle and implementing the stimulation by percutaneously inserting the test needle into the ansa cervicalis nerve, and determining an upper airway response based on the stimulation. In some such examples of the method, determining the response comprises identifying inferior movement of the larynx and implementing the identifying, during the stimulation, via at least one of measuring an EMG response of the larynx and imaging of the larynx.

Figure 52A:
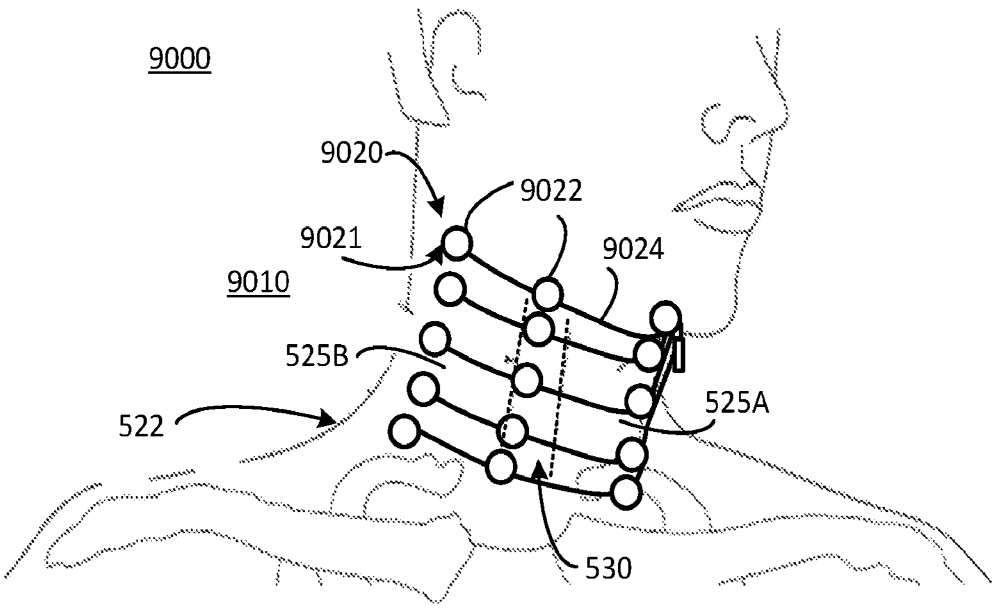
FIGS. 52A-52C are diagrams including front and side views schematically representing a neck region and an example device and/or example method for sensing impedance.
Figure 52B:
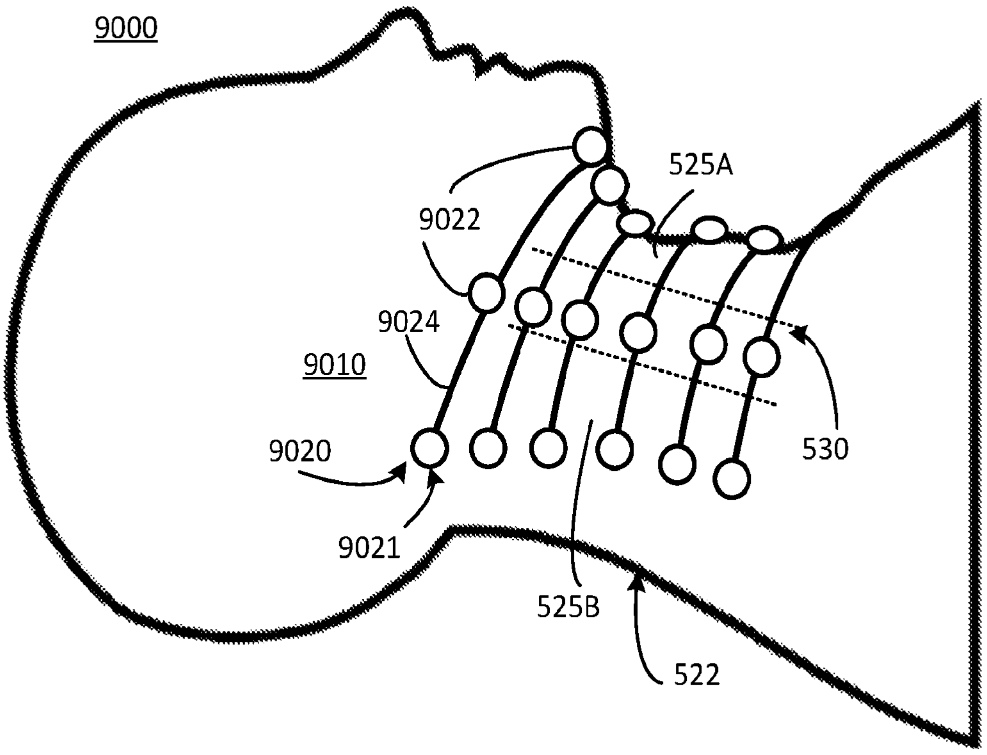
Figure 52B:
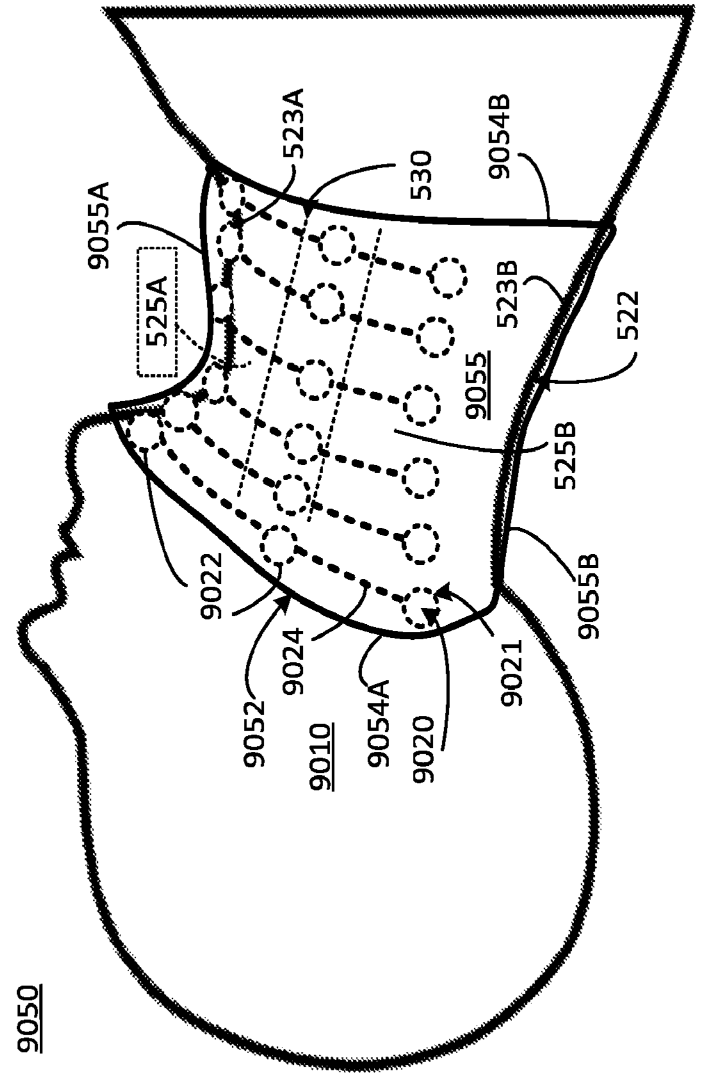

FIGS. 52A and 52B are diagrams including a front view and side view, respectively, schematically representing an example arrangement 9000 including an example device and/or example method to identify an upper airway collapse pattern. In one aspect, the example arrangement 9000 comprises a device which is externally, releasably mountable to a neck region 522 of a patient's body. As shown in FIGS. 52A, 52B, the example arrangement 9000 comprises an array 9020 of spaced apart electrodes 9022 to be located across and around the external surface of a front 525A and sides 525B of the patient's neck 522. In some examples, the electrodes 9022 are arranged in rows 9021, such that the array 9020 may form a grid (e.g. 4×4, 3×6, 4×5, and so on) via the spaced apart electrodes 9022. The electrodes 9022 of the array 9020 are spaced apart by a distance suitable to provide the desired level of detail regarding the function, structure, collapse, opening, etc. of the patient's upper airway.

Figure 52C:
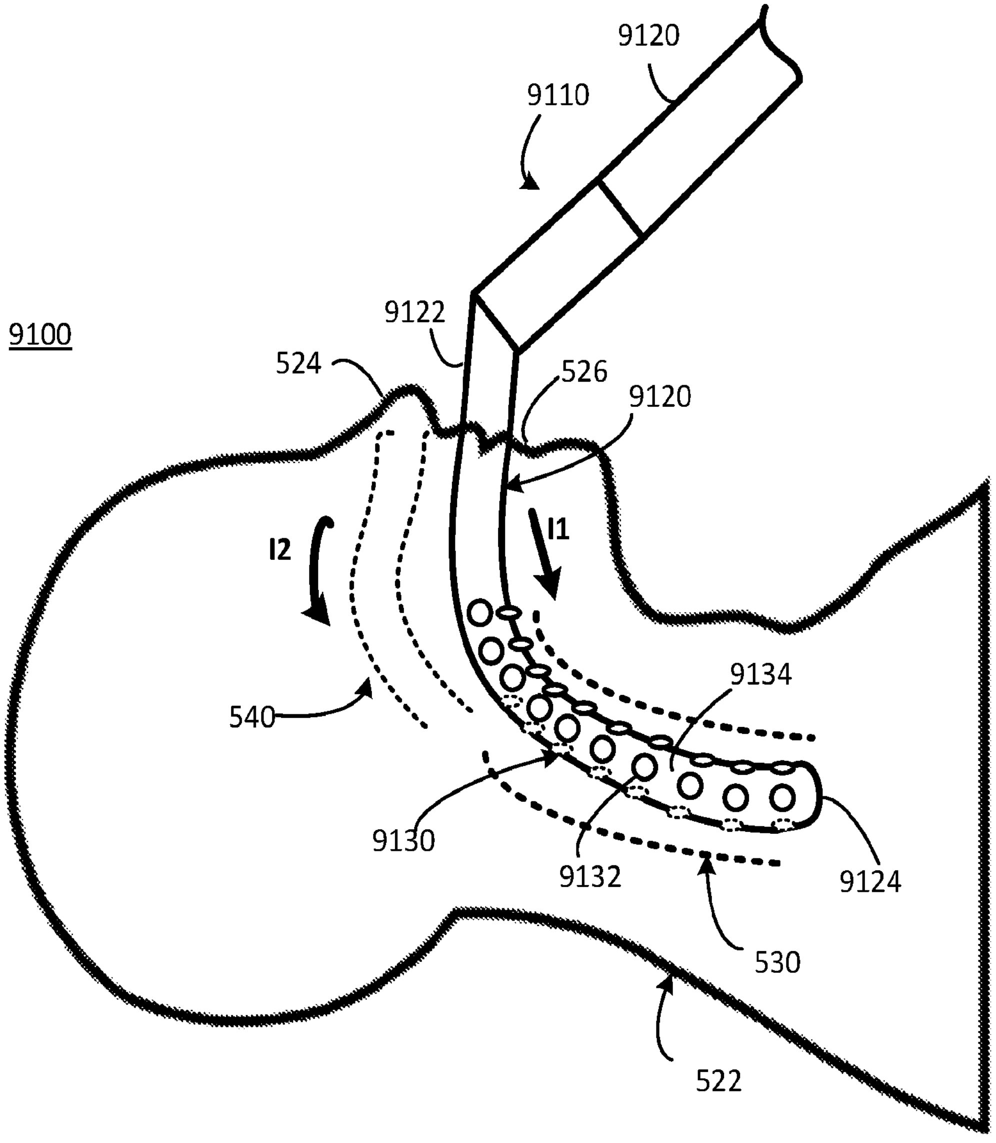

As shown in FIG. 52A-52C, a patient's body comprises a head-and-neck including neck region 522. The neck region 522 comprises an upper airway 530 (FIGS. 52A-52C) and a nasal airway passage 540 (FIG. 52C). In some examples, the upper airway 530 comprises at least some of the detailed anatomical features illustrated in association with FIGS. 53A-53F and 53EE-53FF.

As further shown in FIG. 52A, the electrodes 9022 may be interconnected via wires 9024 or other electrically conductive elements. While not shown for illustrative simplicity, in some examples the example arrangement 9000 may comprise a material, such as a fabric, mesh, etc. which acts as a body to provide stability and ease of handling of the array 9020 of electrodes 9022. In some examples, the electrodes 9020, wires 9024, and/or fabric comprises or carries a releasable adhesive for releasably securing the example arrangement 9000 to an external skin surface of the patient's neck 522. In addition, or alternatively, straps or other wrapping/securing features may be provided to secure the device relative to the patient's neck 522.

In some examples, the array 9020 of electrodes 9022 is sized and shaped to cover an external portion of the patient's neck and a portion of the surrounding regions in order to provide sensing information regarding anatomical structures, such as muscles, bones, connective tissues, etc. which define the upper airway of the patient. In some examples, one method may comprise sensing an impedance between at least some of the example electrodes 9022, which may be indicative of the opening, closing, collapse patterns, etc. of the patient's upper airway. In some such examples, this sensing may be performed while the patient is sleeping to identify their particular collapse pattern when the patient experiences sleep disordered breathing (SDB) events, such as obstructive sleep apnea events. In some such examples, the sensed impedance information may provide a type of collapse, a site of collapse, and/or a degree of collapse with details regarding the type, site and/or degree of collapse shown and described in association with at least FIGS. 53A-53F and 53EE-53FF.

In some examples, sensing the impedance (and/or delivering stimulation in response thereto) regarding the collapse pattern may be performed in association with at least the example arrangements within FIGS. 38A-38D, 38E-38G, including impedance sensor 8752 (FIG. 38C), collapse parameter 8710 (FIG. 38B), disease burden parameter 8726 (FIG. 38C), etc.

In some examples, the device and/or method comprises performing such impedance sensing during application of a stimulation signal to the hypoglossal nerve and/or the ansa cervicalis-related nerve in order to determine how, when, and/or where the patient may respond to such stimulation in terms of the upper airway collapse pattern being affected by the stimulation. In some examples, such determinations may be used to identify which single portion or which multiple portions (and a pattern of stimulation among those portions) of the ansa cervicalis-related nerve should be stimulated for a particular patient, or some patients in general, in order to increase and/or maintain upper airway patency. Moreover, some examples methods also comprise performing the stimulation of the ansa cervicalis-related nerve without or with stimulation of the hypoglossal nerve, and vice versa, in order to better understand how combinations of stimulating different types of nerves (or different nerve branches) affect increasing and/or maintaining upper airway patency during sleep to thereby treat sleep disordered breathing. One example arrangement for delivering stimulation in relation to determining a collapse pattern in relation to sensed impedance is described in association with at least FIGS. 38A-38D, 38E-38H.

With regard to the example arrangement 9000 in at least FIG. 52B, an example arrangement 9050 in FIG. 52BB schematically represents one example implementation of a garment 9052 or wearable structure (e.g. material, fabric, body) supporting the array 9020 of electrodes 9022 in the manner described with respect to FIG. 52B. In some example, the electrodes 9022 may be embedded between adjacent layers of the garment 9052, and the electrodes 9022 may be exposed on a surface of the garment 9052 facing the skin surface of the neck region 522. As shown in FIG. 52BB, the garment 9052 may comprise a sleeve-like body 9055 which conformably fits about a neck region 522. The sleeve-like body 9055 may comprise an upper edge portion 9054A and opposite lower edge portion 9054B, as well as a front portion 9055A and opposite rear portion 9055B. The rear portion 9055B (or a side portion) may comprise a re-closable opening defined by a zipper, buttons, hook-and-loop fasteners, and/or the like to facilitate removable securing about the neck region 522. The type, size, and/or shape of material, fabric, etc. facilitates comfort while ensuring a snug enough fit to place and maintain the electrodes 9022 coupled relative to the skin surface and tissues of the neck region 522 to facilitate accurate impedance or other measurements during movement (or in a rest state) of specific tissue portions (e.g. underlying muscles, muscle groups, airway, etc.) within the neck region 522 relating to upper airway patency, which may relate to infrahyoid-based patency and/or genioglossus-based patency. In some examples, the snug fit may sometimes be referred to as conformably fitting to the particular topography of the neck region 522 for each patient.

In some examples, via the array 9020 of electrodes 9022 in example arrangements 9000, 9050, impedance measurement may be indicative of motion of a pharynx (and/or other tissues) upward upon application of electrical stimulation to infrahyoid-based patency tissue, such as an ansa cervicalis-related nerve or infrahyoid strap muscle innervated by the ansa cervicalis-related nerve. Among other purposes, identifying this upward motion during stimulation may confirm capture of the target upper airway patency tissue (e.g. nerve and/or muscle) to which a stimulation element(s) is placed into stimulating relation.

FIG. 52C is a diagram including a side view schematically representing an example arrangement 9100 comprising an example device and/or example method for at least identifying an upper airway collapse pattern. In some examples, the example arrangement 9100 may be used to determine at least some of substantially the same information described above in association with at least FIGS. 52A-52B regarding upper airway collapse patterns, causes, stimulation responses thereto, etc.

As shown in FIG. 52C, in some examples an example sensing device 9110 comprises a handle 9120 which supports an insertable, elongate member 9120, which comprises a proximal portion 9122 and opposite distal portion 9122. In some examples, the elongate member 9120 is sized and shaped, and is resiliently, flexible to facilitate some maneuverability and ease of insertion and passage, while exhibiting some rigidity to facilitate advancing the elongate member, which may comprise structural features analogous to tools used in intubation procedures.

In some examples, the insertable elongate member 9120 comprises an array 9130 of spaced apart electrodes 9132 arranged on external surface of body 9134 of the member 9120, with the array comprising a size and shape suitable to perform impedance sensing of the type, manner, and/or purposes described above with respect to at least FIGS. 52A-52B.

In some examples, the electrodes 9132 may be exposed at or mounted on the external surface of the body 9134 of elongate member 9120. However, in some examples, the electrodes 9132 may be located below the external surface of the body 9134 but with the type, thickness, etc. of the external surface and/or electrodes 9132 suited to perform the desired impedance sensing.

In some examples, the device 9110 may sometimes be referred to as an internally insertable, electrode impedance sensing array (or variations thereof).

In some examples, the size, shape, and configuration of the device 9110 may be adapted for insertion (11) into and through the mouth 526 of the patient, as shown in FIG. 52C, to be advanced into the upper airway 530. However, in some examples, the size, shape, and configuration of the device 9110 may be adapted to perform such sensing via insertion (12) of the device into and through the nose 524 of the patient for passage through the nasal airway/passage 540 and into pertinent portions of the upper airway 530. With regard to either a nasal entry approach or a mouth entry approach, at least some example devices and/or methods include placing at least some sensing electrodes in close proximity to the velopharnyx or at least within a distance by which the velopharnyx may be sensed, along with other anatomical features of the upper airway.

In some examples, the example devices and/or example methods in FIGS. 52A, 52B, and 52C may be utilized to identify an upper airway collapse pattern at a time prior to completing implantation of a chronically implantable stimulation element in stimulating relation to an upper airway patency-related tissue such as, but not limited to, a hypoglossal nerve and a non-hypoglossal nerve, which comprises the ansa cervicalis-related nerve and/or other nerves, muscles, etc.

Figure 52D:
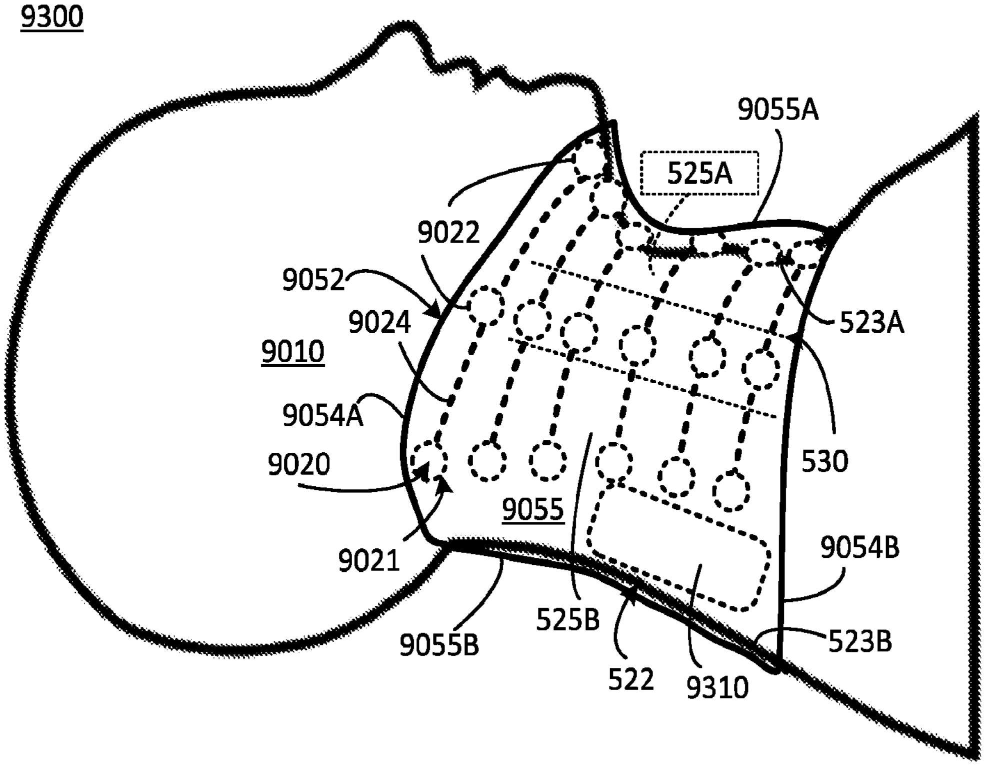
FIG. 52E is a block diagram schematically representing an external power/control element in wireless communication with an implantable neural interface.
FIG. 52F is diagram including a side view schematically representing a neck region and an example device and/or example method, including a wearable garment to support sleep disordered breathing (SDB) care including multi-target stimulation.
FIGS. 52G, 52H are block diagrams including a plan view and side view, respectively, schematically representing an electrode array of a stimulation element.
FIG. 52J is a block diagram including a side view schematically representing a power/control element in combination with a stimulation portion in stimulating relation to a muscle.
FIG. 52K is a diagram including a side view schematically representing a stimulation element externally attachable to a neck region for providing power/control and/or stimulating an upper airway patency-related tissue.
FIG. 52L is a diagram including a side view schematically representing an externally attachable stimulation element and an implantable combination microstimulator-cuff arrangement.

FIG. 52D is a diagram schematically representing an example arrangement 9300 comprises a garment 9052 and impedance sensing arrangement like that in FIG. 52A-52BB, except further comprising a power/control element 9310 which may be removably carried within, and/or otherwise supported by, removably attachable garment 9052. The power/control element 9310 may take a wide variety of forms and may comprise an on-board power source, which may or may not be wirelessly chargeable from an external source. In some examples, the power/control element 9310 also may comprise control circuitry, communication circuitry, and/or wireless communication circuitry (e.g. transceiver, antenna, etc.). In some examples, the control circuitry may comprise stimulation circuitry to generate stimulation signals. The power/control element 9310 may wirelessly communicate with an implanted stimulation element, such as any one of the implanted stimulation elements (e.g. a microstimulator or other) as previously described in association with at least FIGS. 14H-K, 14M, 14R, and/or 21 for stimulation an hypoglossal nerve, an ansa cervicalis-related nerve, and/or an infrahyoid strap muscle innervated by the ansa cervicalis-related nerve, as described in association with at least FIG. 52F, in some examples.

In some examples, the power/control element 9310 may comprise at least some of substantially the same features and attributes as, and/or an example implementation of, the recharge element 6576 in FIG. 14H and/or the power/control element 2735 in FIG. 21.

Figure 52E:
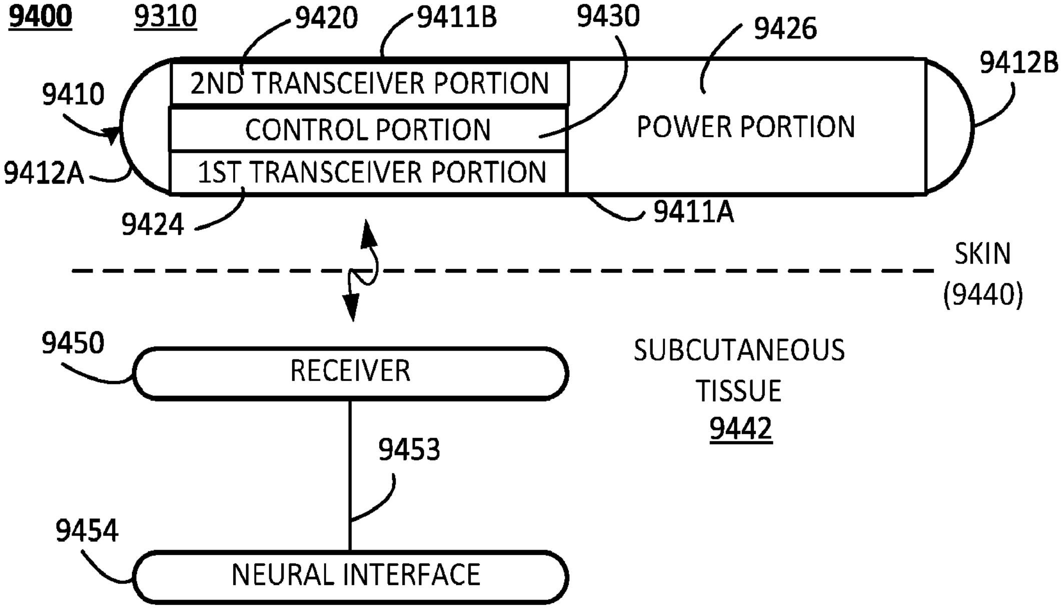

FIG. 52E is a block diagram schematically representing an example arrangement 9400 which may comprise one example implementation of the power/control element 9310 of FIG. 52D as well as comprising an implantable neural interface 9454 and passive receiver 9450 for wireless communicating (e.g. via inductive telemetry or other wireless protocols) with the externally located power/control element 9310. The neural interface 9454 may be implanted to be in stimulating relation to nerves, muscles, or combinations thereof of upper airway patency tissue, which may comprise infrahyoid-based patency tissue and/or genioglossus-based patency tissue.

In some examples, the power/control element 9310 may comprise a power portion 9426, a control portion 9430, a first transceiver portion 9424 and a second transceiver portion. In some examples, the control portion 9430 may comprise at least some of substantially the same features and attributes as (or an example implementation of) the control portion in FIGS. 54A-54E.

In some examples, the power portion 9426 may comprise a rechargeable power source or other type of power source. The first transceiver portion 9424 is configured to wirelessly communicate through skin 9440 and tissue 9442 with implanted receiver 9450 to send/receive data, commands, etc. to and from the neural interface 9454 (e.g. stimulation element) via connection 9453. In some examples, the first transceiver portion 9424 may comprise inductive telemetry (e.g. magnetic induction) antenna/elements or electronic components for other types of wireless communication. In some examples, the second transceiver portion 9420 may communicate with a patient remote control, external recharging station, or other externally located device. The second transceiver portion 9420 may comprise an antenna and circuitry to wireless communicate with the external devices via any one of many wireless communication protocols (e.g. Bluetooth® or any one of several short range RF-based protocols).

The power/control element 9310 may comprise a housing 9410 (e.g. can) to contain the control portion 9430, power portion 9426 (which may be removable), and the first and second transceiver portions 9424, 9420. The housing 9410 may comprise opposite ends 9412A, 9412B, and opposite first and second surfaces 9411A, 9411B.

With regard to at least the example arrangements in FIGS. 52BB, 52D, 52E, and the below-described example of FIG. 52F, in some examples the impedance-sensing electrode array may be omitted from the garment 9052. However, with regard to FIG. 52F below, it will be understood that the electrode array 9020 may be included and supported by garment 9052 (as in FIG. 52BB) in some examples, but is merely omitted from FIG. 52F for illustrative clarity.

Figure 52F:
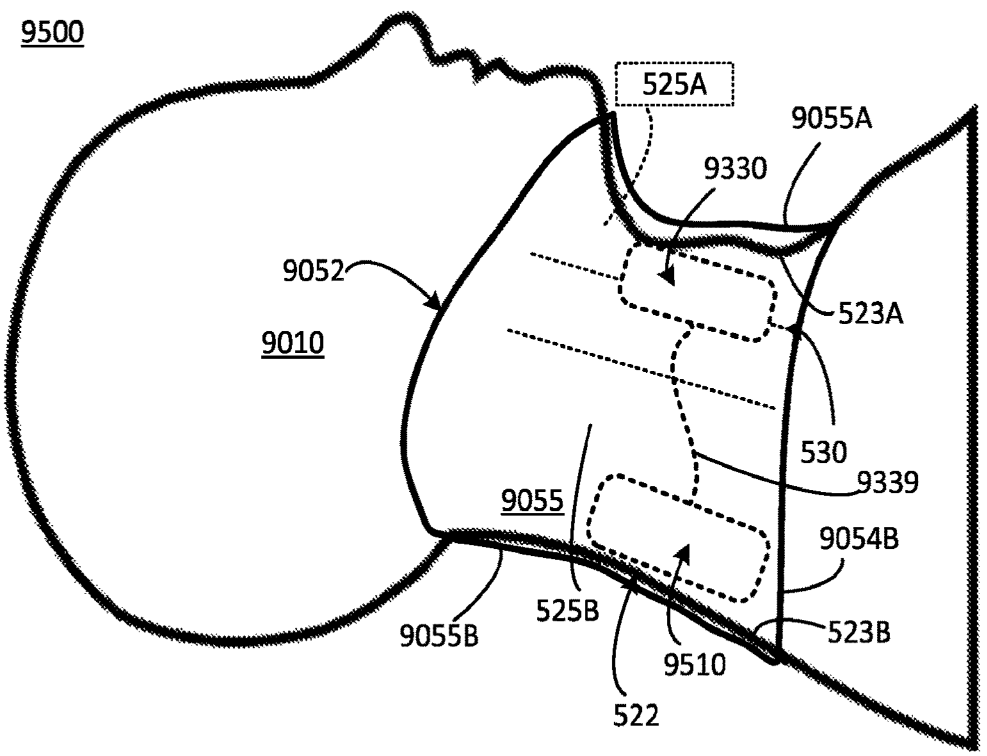

FIG. 52F is a diagram schematically representing an example arrangement like that in FIG. 52D, except further comprising a removably insertable stimulation element 9330 and/or removably insertable power/control element 9510, both of which may be removably received by a portion of garment 9052. The stimulation element 9330 may communicate with element 9510 via wired connection 9339 or wirelessly. In some examples, the stimulation element 9330 is sized, shaped, positionable, and securable via garment 9052 to be in stimulating relation to an infrahyoid strap muscle for stimulation to increase and/or maintain upper airway patency, which in some examples may further comprise leveraging a patency hysteresis effect, as previously described. In such examples, the stimulation element 9330 may comprise one example implementation of stimulation element 8030 in FIGS. 38A-38F.

Figure 52G:
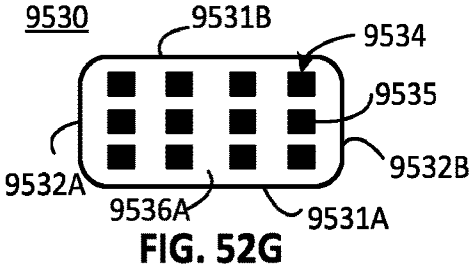
Figure 52H:
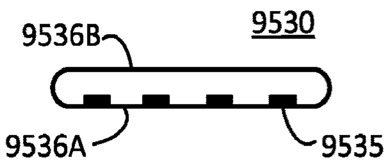
Figure 52I:
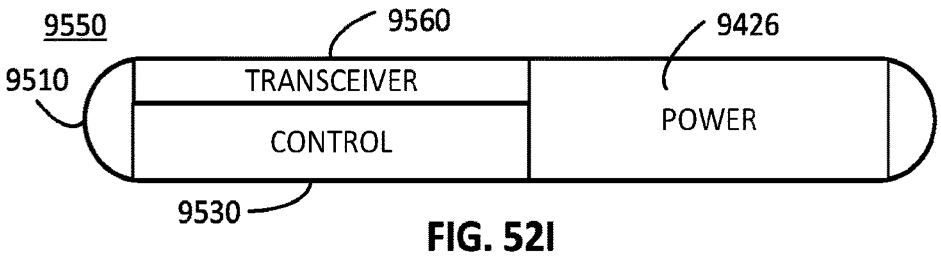

As further shown in FIGS. 52G, 52H, one example implementation of the stimulation element 9330 comprises an carrier 9530 comprising opposite ends 9532A, 9532B, opposite sides 9531A, 9531B, and opposite faces 9536A, 9536B with an array 9534 of electrodes 9535 on face 9536A for presentation to a tissue to be stimulated and/or a skin surface/tissue through which a stimulation signal will be delivered to a target tissue (e.g. muscle) such as an infrahyoid strap muscle.

In some examples, the stimulation element 9330 may be supported by a power/control element or recharge element 9510, as shown in FIG. 52F. In some examples, the element 9510 may comprise a power/control element as shown in the diagram 9550 of FIG. 52I, and which may comprise a power portion 9426, a control portion 9530, and/or a transceiver portion 9560. These power, control, and transceiver portions may comprise at least some of substantially the same features and attributes as previously described for corresponding portions in FIG. 52D-52E.

Figure 52J:
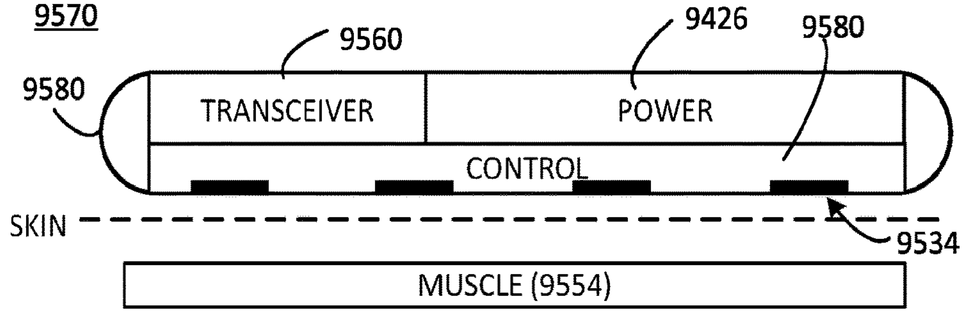

However, in some examples, the stimulation element 9330 may incorporate the components of the element 9510 as shown in FIG. 52J as schematically represented in diagram 9570 as stimulation element 9580. As shown in FIG. 52J, in this example, the stimulation element 9580 comprises a power portion 9426, a transceiver 9560, and a control portion 9582 which incorporates with (or is co-located with) array 9534 of electrodes 9535.

Figure 52K:
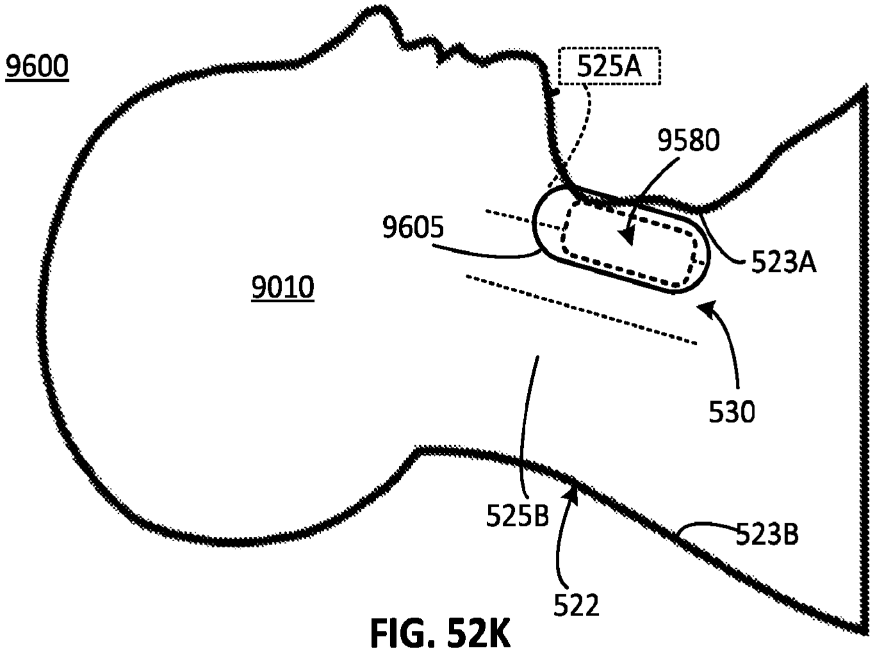

As further shown in FIG. 52J, the stimulation element 9580 may be externally mounted relative to a skin surface, such as via garment in FIG. 52F or via an adhesive patch 9605 in the example arrangement 9600 of FIG. 52K, to be in stimulating relation to a target muscle 9554, which may comprise an upper airway patency-related tissue such as (but not limited to) an infrahyoid strap muscle.

It will be understood that in some examples, a portion of or the entire control portion or a portion of (or the entire) power portion of the example power/control element 9510 (e.g. FIG. 52F, 52I) can be incorporated into the stimulation element 9330 (e.g. FIGS. 52F, 52G, 52H).

Figure 52L:
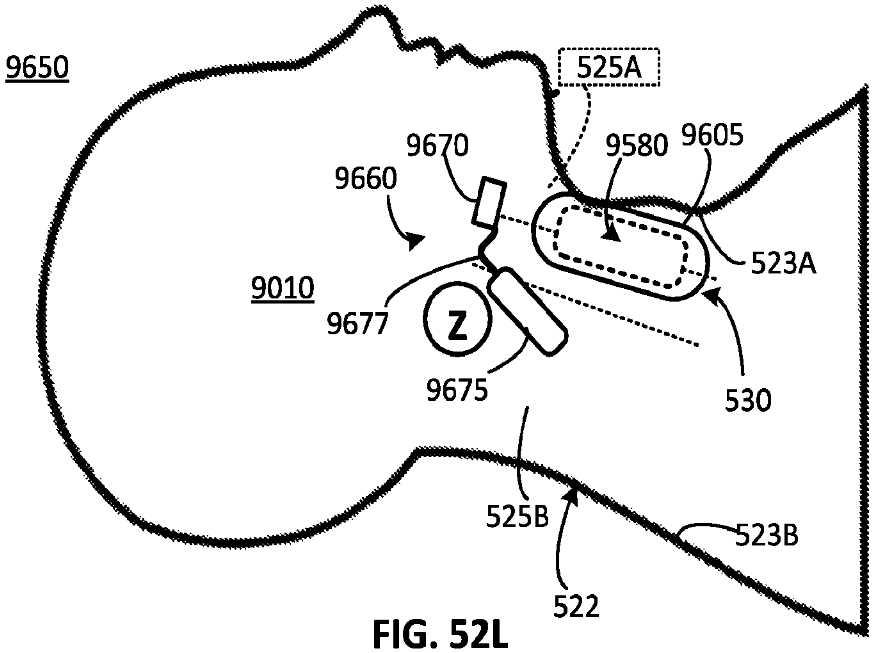

FIG. 52L is a diagram schematically representing an example arrangement 9650 comprising the stimulation element 9580 (FIGS. 52J, 52K) externally mounted to neck region via adhesive patch 9605 for stimulating an upper airway patency-related tissue such as (but not limited to) an infrahyoid strap muscle. In addition, the example arrangement May 9650 may comprise an implantable stimulation portion 9660 including a cuff electrode 9670 (or other carrier-based electrode array) and a microstimulator 9675 (including stimulation circuitry, communication elements, power element, etc.) comprising at least some of substantially the same features and attributes as other microstimulators (including support elements such as recharging, etc.) described in examples of the present disclosure, in some examples. A flexible lead 9677 may connect, and extend between, the cuff electrode 9670 and the microstimulator 9675. The stimulation portion 9660 may comprise one example of stimulation element 8020 in FIGS. 38A-38F for stimulating upper airway patency-related tissue such as a hypoglossal nerve. The identifier Z simply indicates a general designator of implantation within the neck region, and that the stimulation portion 9660 may not necessarily be implanted exactly at the location, orientation, etc. as shown in FIG. 52L.

Figure 53A:
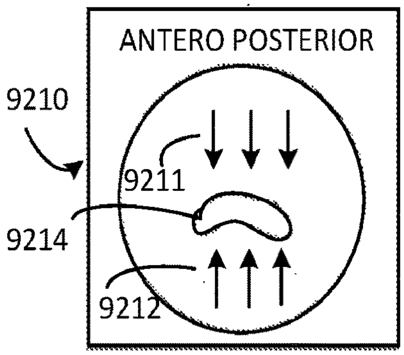
FIGS. 53A-53D are diagrams including front and side views schematically representing patient anatomy and example methods relating to collapse patterns associated with upper airway patency.
Figure 53B:
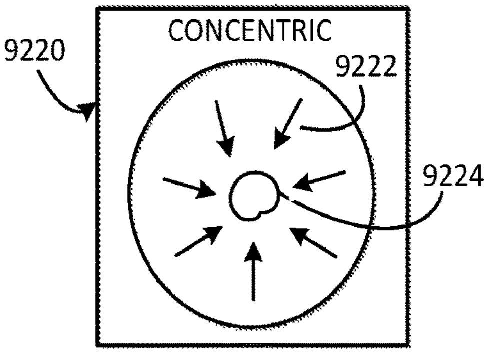
Figure 53C:
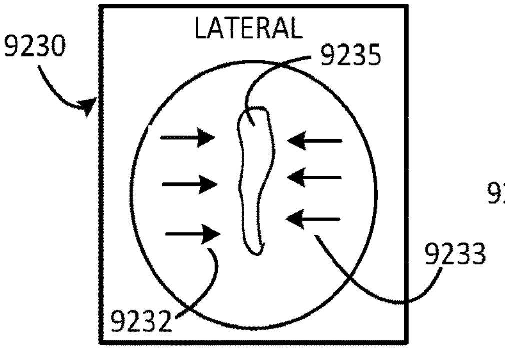
Figure 53C:
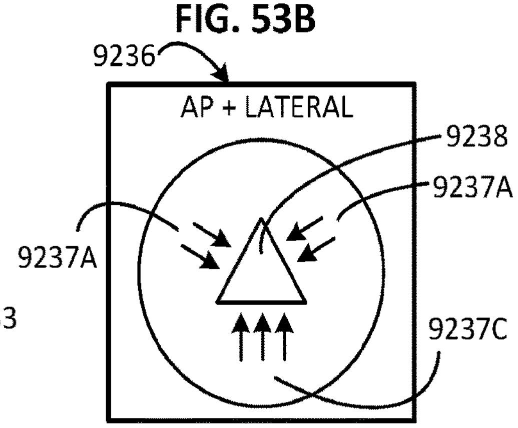

FIGS. 53A-53CC are a series of diagrams schematically representing at least some different upper airway collapse patterns, including an anterior-posterior (AP) collapse pattern (FIG. 53A), a concentric collapse pattern (FIG. 53B), a lateral collapse pattern (FIG. 53C), and an anterior-posterior (AP)—lateral collapse pattern (FIG. 53CC). In addition to observing such collapse patterns and/or other collapse patterns, at least some aspects of such collapse patterns may be measured, such as via impedance sensing using implanted electrodes (e.g. sensing elements and/or stimulation elements), using externally applied arrays of electrodes, etc. such as described and illustrated in association with at least FIGS. 53A-53CC. By determining an upper airway collapse pattern, some example arrangements may determine whether to apply stimulation via a hypoglossal nerve, via an ansa cervicalis-related nerve (including which single or multiple portions thereof to stimulate), via other non-hypoglossal nerve related to upper airway patency, and/or combinations of these nerves including unilateral and bilateral options.

Figure 53D:
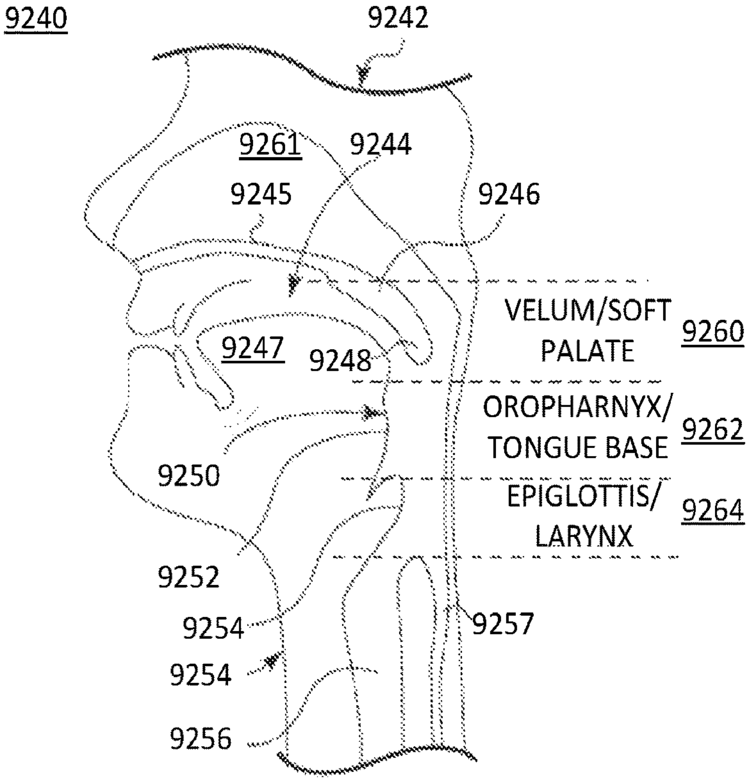

At least some more specific details regarding FIGS. 53A-53D are further described below in relation to at least FIGS. 53D-53FF.

Figures 53E, 53F:
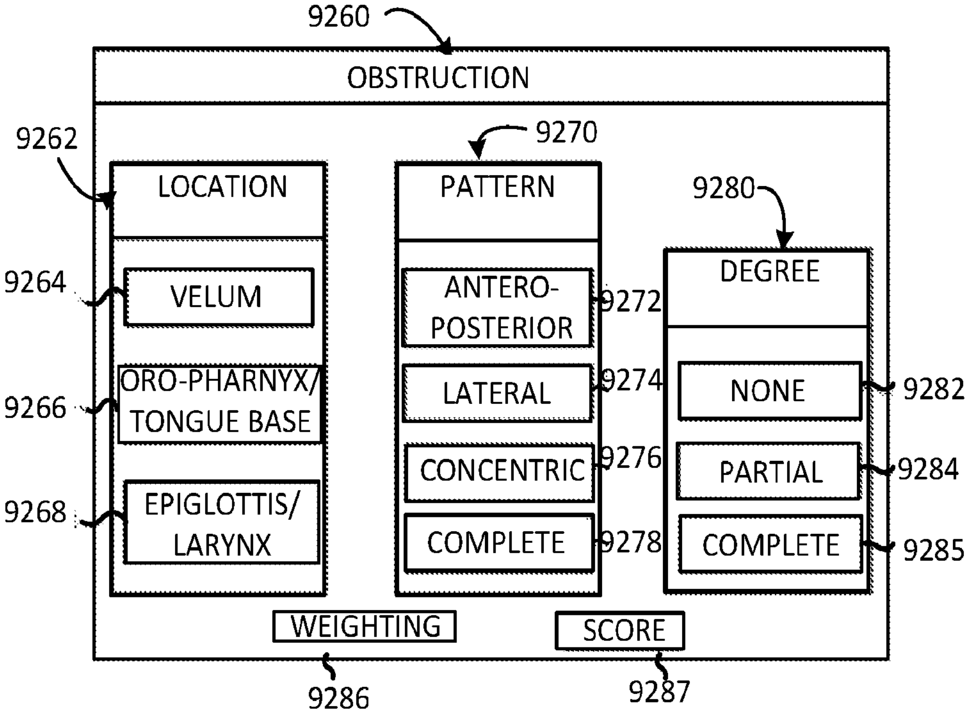
FIGS. 53E-53FF are block diagrams schematically representing example devices and/or example methods relating to collapse patterns associated with upper airway patency.
Figures 53E, 53F:
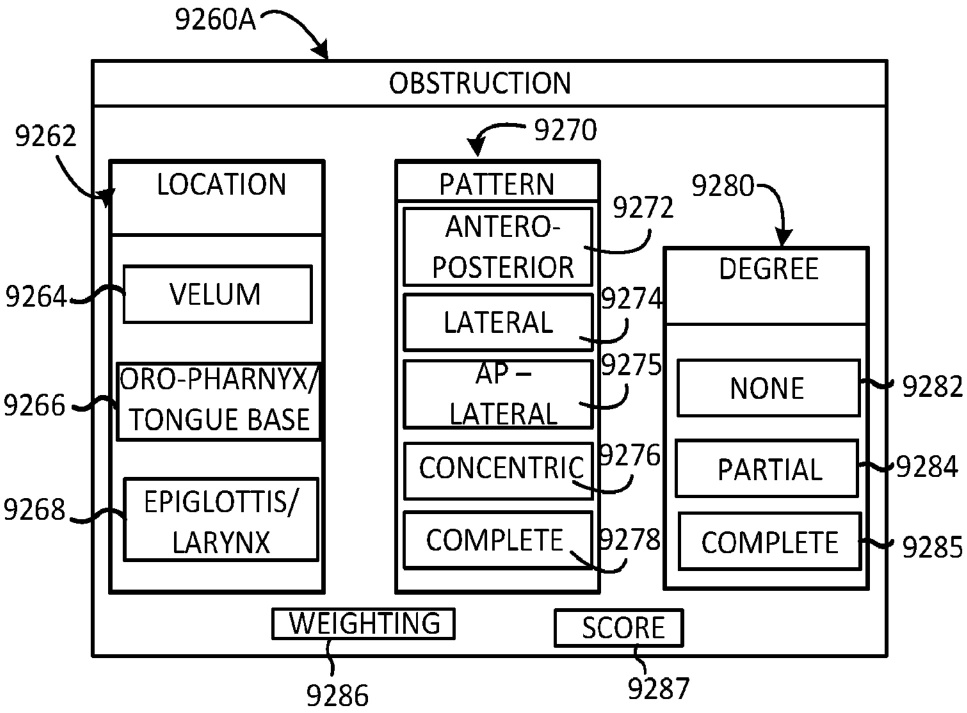

FIG. 53E is a block diagram schematically representing an example sorting tool 9260 by which to sort and weigh a location, pattern, and degree of obstruction or patency. As shown in FIG. 53E, obstruction sorting tool 400 includes functions for location detection 9262, pattern detection 9270, and degree detection 9280. In general terms, the location detection function 9262 operates to identify a site along the upper airway at which an obstruction occurs and which is believed to cause sleep disordered breathing. In one example, the location detection function 9262 includes a velum (soft palate) parameter 9264, an oropharynx-tongue base parameter 9266, and an epiglottis/larynx parameter 9268. Each respective parameter denotes an obstruction identified in the respective physiologic territories of the velum (soft palate), oropharnyx-tongue base, and epiglottis which are generally illustrated for an example patient in FIG. 53D. In one aspect, these distinct physiologic territories define an array of vertical strata within the upper airway. Moreover, each separate physiologic territory (e.g. vertical portion along the upper airway) exhibits a distinct characteristic behavior regarding obstructions and associated impact on breathing during sleep. Accordingly, each physiologic territory responds differently to implantable upper airway stimulation.

With this in mind, the velum (soft palate parameter 9264 denotes obstructions taking place in the level of the region of the velum (soft palate), as illustrated in association with FIG. 53D. FIG. 53D is a diagram including a side view schematically representing at least some anatomical features of the upper airway, as well as different sites or levels at which obstruction may occur. By determining a site or location of upper airway collapse, some example arrangements may determine whether to apply stimulation via a hypoglossal nerve, via an ansa cervicalis-related nerve (including which portions thereof to stimulate), via other non-hypoglossal nerve related to upper airway patency, and/or combinations of these nerves including unilateral and bilateral options.

As shown in FIG. 53D, a diagram 9240 provides a side sectional view (cross hatching omitted for illustrative clarity) of a head and neck region 9242 of a patient. In particular, an upper airway portion 9250 extends from the mouth region 9244 to a neck portion 9254. The upper airway portion 9250 includes a velum (soft palate) region 9260, an oropharnyx-tongue base region 9262, and an epiglottis region 9264. The velum (soft palate) region 9260 includes an area extending below sinus 9261, and including the soft palate 9260, approximately to the point at which tip 9248 of the soft palate 9246 meets a portion of tongue 9247 at the back of the mouth 9244. The oropharnyx-tongue base region 9262 extends approximately from the tip of the soft palate 9246 (when in a closed position) along the base 9252 of the tongue 9247 until reaching approximately the tip region of the epiglottis 9254. The epiglottis-larynx region 9262 extends approximately from the tip of the epiglottis 9254 downwardly to a point above the esophagus 9257.

As will be understood from FIG. 53D, each of these respective regions 9260, 9262, 9264 within the upper airway correspond the respective velum parameter 9264, oropharnyx-tongue base parameter 9266, and epiglottis parameter 9268, respectively of FIG. 53E.

With further reference to FIG. 53E, in general terms the pattern detection function 9270 enables detecting and determining a particular pattern of an obstruction of the upper airway portion 9244. In one example, the pattern detection function 9270 includes an antero-posterior parameter 9272, a lateral parameter 9274, a concentric parameter 9276, and composite parameter 9278.

The antero-posterior parameter 9272 of pattern detection function 9270 (FIG. 53E) denotes a collapse of the upper airway that occurs in the antero-posterior orientation, as further illustrated in the diagram 9210 of FIG. 53A. In FIG. 53A, arrows 9211 and 9212 indicate one example direction in which the tissue of the upper airway collapses, resulting in the narrowed air passage 9214. FIG. 53A is also illustrative of a collapse of the upper airway in the soft palate region 9260, whether or not the collapse occurs in an antero-posterior orientation. For example, in some instances, the velum (soft palate) region 9260 exhibits a concentric (i.e. circular) pattern of collapse, as shown in diagram 9220 of FIG. 53B.

The concentric parameter 9276 of pattern detection function 9270 (FIG. 53E) denotes a collapse of the upper airway that occurs in a concentric orientation, as further illustrated in the diagram 9220 of FIG. 53B. In FIG. 53B, arrows 9222 indicate the direction in which the tissue of the upper airway collapses, resulting in the narrowed air passage 9224.

The lateral parameter 9230 of pattern detection function 9270 (FIG. 53E) denotes a collapse of the upper airway that occurs in a lateral orientation, as further illustrated in the diagram 9230 of FIG. 53C. In FIG. 53C, arrows 9232 and 9233 indicate the direction in which the tissue of the upper airway collapses, resulting in the narrowed air passage 9235.

The composite parameter 9278 of pattern detection function 9270 (FIG. 53E) denotes a collapse of the upper airway portion that occurs via a combination of the other mechanisms (lateral, concentric, antero-posterior) or that is otherwise ill-defined from a geometric viewpoint but that results in a functional obstruction of the upper airway portion.

With further reference to obstruction sorting tool of FIG. 53E, in general terms the degree detector module 9280 indicates a relative degree of collapse or obstruction of the upper airway portion. In one embodiment, degree detection function 9280 includes a none parameter 9282 a partial parameter 9284, and a complete parameter 9285. In some examples, the none parameter 9282 may correspond to a collapse of 25 percent or less, while the partial collapse parameter 9284 may correspond to a collapse of between about 25 to 75%, and the complete collapse parameter 9285 may correspond to a collapse of greater than 75 percent.

It will be understood that various patterns of collapse occur at different levels of the upper airway portion and that the level of the upper airway in which a particular pattern of collapse appears can vary from patient-to-patient.

In some embodiments, obstruction sorting tool 9260 comprises a weighting function 9286 and score function 9287. In general terms, the weighting function 9286 assigns a weight to each of the location, pattern, and/or degree parameters (FIG. 53E) as one or more those respective parameters can contribute more heavily to the patient exhibiting sleep disordered breathing or to being more responsive to implantable upper airway stimulation. More particularly, each respective parameter (e.g. antero-posterior 9272, lateral 9274, concentric 9276, composite 9278) of each respective detection modules (e.g. pattern detection function 9270) is assigned a weight corresponding to whether or not the patient is eligible for receiving implantable upper airway stimulation. Accordingly, the presence of or lack of a particular pattern of obstruction (or location or degree) will be become part of an overall score (according to score parameter 9287) for an obstruction vector indicative how likely the patient will respond to therapy via an implantable upper airway stimulation system.

FIG. 53F is diagram (e.g. chart) 9290 schematically representing an index or scoring tool to sort and weigh a location, pattern, and degree of obstruction or patency for a particular patient. Chart 9290 combines information regarding location (9262 in FIG. 53E), pattern (9270 in FIG. 53E), and degree (9280 in FIG. 53E) into a single informational grid or tool by which the obstruction is documented for a particular patient and by which appropriate stimulation settings may be determined and applied according to the various examples of the present disclosure, such as but not limited to those in association with at least FIG. 41B, FIGS. 38A-38C, etc.

FIGS. 53EE, 53FF are diagrams 9260A, 9290A like the diagrams 9260, 9290 of FIGS. 53E, 53F, respectively, except with FIGS. 53EE, 53FF further addressing an anterior-posterior (AP) lateral collapse pattern, which is depicted in diagram 9236 of FIG. 53CC, provided as a parameter 9275 of a pattern detection function 9270 of FIG. 53EE, and incorporated into the index of FIG. 53FF.

As shown in FIG. 53CC, this pattern comprises a combination of the anterior-posterior pattern (FIG. 53A) and the lateral pattern (FIG. 53C) with arrows 9237A, 9237B, 9237C indicating example directions in which the tissue of the upper airway collapses, resulting in the narrowed air passage 9238. The narrowed air passage 9238 may comprise a triangular shape in some examples. In some examples, the AP-lateral collapse pattern at a velum/soft palate (9260 in FIG. 53D, 9264 in FIG. 53EE, FIG. 53FF) may respond better (e.g. increase patency) to stimulation of an infrahyoid-based patency tissue than a concentric collapse pattern having a similar severity/completeness as the AP-lateral collapse pattern at the soft palate.

Accordingly, in some examples, the information sensed and collected via at least FIGS. 53E-53F may be used to determine whether to apply stimulation via a hypoglossal nerve, via an ansa cervicalis-related nerve (including which single portion or multiple portions thereof to stimulate), via other non-hypoglossal nerves related to upper airway patency, and/or combinations of these nerves including unilateral and bilateral options.

Figure 54A:
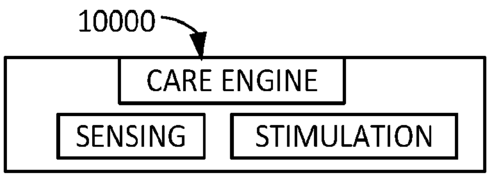
FIG. 54A is a block diagram schematically representing an example care engine.

FIG. 54A is a block diagram schematically representing an example care engine 10000. In some examples, the SDB care engine 10000 may form part of a control portion 10500, as later described in association with at least FIG. 54B, such as but not limited to comprising at least part of the instructions 10511. In some examples, the SDB care engine 10000 may be used to implement at least some of the various example devices and/or example methods of the present disclosure as previously described in association with FIGS. 1-53F and/or in later described examples devices and/or methods. In some such examples, the SDB care engine 10000 may comprise a sensing engine 10020 and/or a stimulation engine 10030. In some examples, the sensing engine 10020 may be implemented via at least some of the sensing elements, sensor types/modalities, etc. as described in association with at least FIG. 3C, FIGS. 38A-39, and throughout FIGS. 40A-53F. In some examples, the stimulation engine 10030 may be implemented via at least some of the stimulation elements (e.g. stimulation portions, electrode arrays, cuff electrodes, paddle electrodes, axial leads/electrodes, IPG 533, microstimulators, etc.), example methods, example engines (e.g. 8800 in FIG. 38D) described throughout the various examples of the present disclosure In some examples, the SDB care engine 10000 (FIG. 54A) and/or control portion 10500 (FIG. 54B) may form part of, and/or be in communication with, the example arrangements, stimulation elements, sensing elements, microstimulators, pulse generators, etc. such as a portion of the devices and methods described in association with at least FIGS. 1-53F and/or the later described examples, such as FIGS. 54B-60.

It will be understood that various functions and parameters of SDB care engine 10000 may be operated interdependently and/or in coordination with each other, in at least some examples.

Figure 54B:
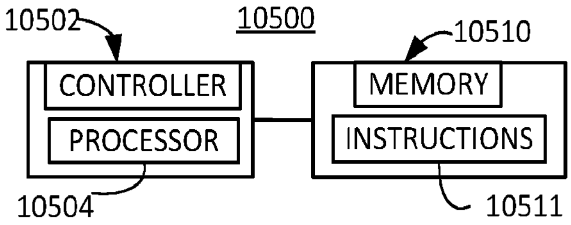
FIGS. 54B-54E are block diagrams schematically representing example control portions, a user interface, and associated devices.

FIG. 54B is a block diagram schematically representing an example control portion 10500. In some examples, control portion 10500 provides one example implementation of a control portion forming a part of, implementing, and/or generally managing the example arrangements, the stimulation elements, sensing elements, microstimulators, pulse generators, control portion, instructions, engines, functions, parameters, and/or methods, as described throughout examples of the present disclosure in association with FIGS. 1-53F and later FIGS. In some examples, control portion 10500 includes a controller 10502 and a memory 10510. In general terms, controller 10502 of control portion 10500 comprises at least one processor 10504 and associated memories. The controller 10502 is electrically couplable to, and in communication with, memory 10510 to generate control signals to direct operation of at least some of the example arrangements, stimulation elements, sensing elements, microstimulators, pulse generators, control portion, instructions, engines, functions, parameters, and/or methods, as described throughout examples of the present disclosure. In some examples, these generated control signals include, but are not limited to, employing instructions 10511 stored in memory 10510 to at least direct and manage sleep disordered breathing (SDB) care (e.g. sensing, stimulation, etc.) in the manner described in at least some examples of the present disclosure. In some instances, the controller 10502 or control portion 10500 may sometimes be referred to as being programmed to perform the above-identified actions, functions, etc.

In response to or based upon commands received via a user interface (e.g. user interface 10520 in FIG. 54C) and/or via machine readable instructions, controller 10502 generates control signals as described above in accordance with at least some of the examples of the present disclosure. In some examples, controller 10502 is embodied in a general purpose computing device while in some examples, controller 10502 is incorporated into or associated with at least some of the example arrangements, stimulation elements, sensing elements, microstimulators, pulse generators, control portion, instructions, engines, functions, parameters, and/or methods, etc. as described throughout examples of the present disclosure.

For purposes of this application, in reference to the controller 10502, the term "processor" shall mean a presently developed or future developed processor (or processing resources) that executes machine readable instructions contained in a memory or that includes circuitry to perform computations. In some examples, execution of the machine readable instructions, such as those provided via memory 10510 of control portion 10500 cause the processor to perform the above-identified actions, such as operating controller 10502 to implement sleep disordered breathing (SDB) care (e.g. stimulation, sensing, etc.) via the various example implementations as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 10510. The machine readable instructions may include a sequence of instructions, a processor-executable machine learning model, or the like. In some examples, memory 10510 comprises a computer readable tangible medium providing non-volatile storage of the machine readable instructions executable by a process of controller 10502. In some examples, the computer readable tangible medium may sometimes be referred to as, and/or comprise at least a portion of, a computer program product. In other examples, hard wired circuitry may be used in place of or in combination with machine readable instructions to implement the functions described. For example, controller 10502 may be embodied as part of at least one application-specific integrated circuit (ASIC), at least one field-programmable gate array (FPGA), and/or the like. In at least some examples, the controller 10502 is not limited to any specific combination of hardware circuitry and machine readable instructions, nor limited to any particular source for the machine readable instructions executed by the controller 10502.

In some examples, control portion 10500 may be entirely implemented within or by a stand-alone device.

In some examples, the control portion 10500 may be partially implemented in one of the example arrangements, stimulation elements, sensing elements, microstimulators, pulse generators, etc. and partially implemented in a computing resource separate from, and independent of, the example arrangements, stimulation elements, sensing elements, microstimulators, pulse generators, etc. but in communication with such example arrangements, etc. For instance, in some examples control portion 10500 may be implemented via a server accessible via the cloud and/or other network pathways. In some examples, the control portion 10500 may be distributed or apportioned among multiple devices or resources such as among a server, an example arrangement, and/or a user interface.

Figure 54C:
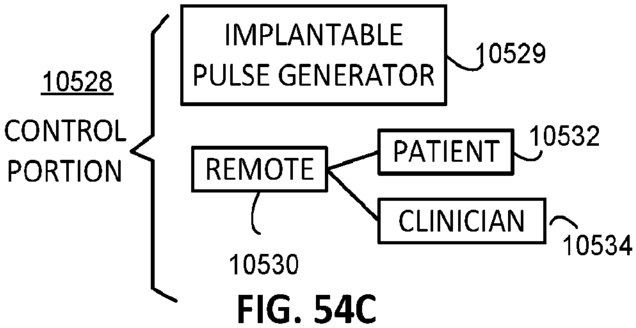

FIG. 54C is a diagram schematically illustrating at least some example arrangements of a control portion 10528 by which the control portion 10500 (FIG. 54B) can be implemented, according to one example of the present disclosure. In some examples, control portion 10528 is entirely implemented within or by an IPG assembly 10529, which has at least some of substantially the same features and attributes as a pulse generator (e.g. IPG 533, microstimulator, etc.) as previously described throughout the present disclosure. In some examples, control portion 10528 is entirely implemented within or by a remote control 10530 (e.g. a programmer) external to the patient's body, such as a patient control 10532 and/or a physician control 10534. Patient control 572 in FIG. 3C may comprise one example implementation of the remote control 10532. In some examples, the control portion 10500 is partially implemented in the IPG assembly 10529 and partially implemented in the remote control 1530 (at least one of patient control 10532 and physician control 10534).

Figure 54D:
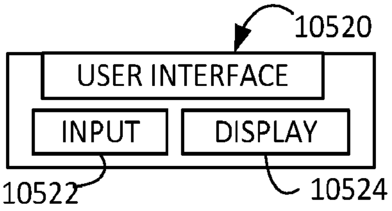
Figure 54E:
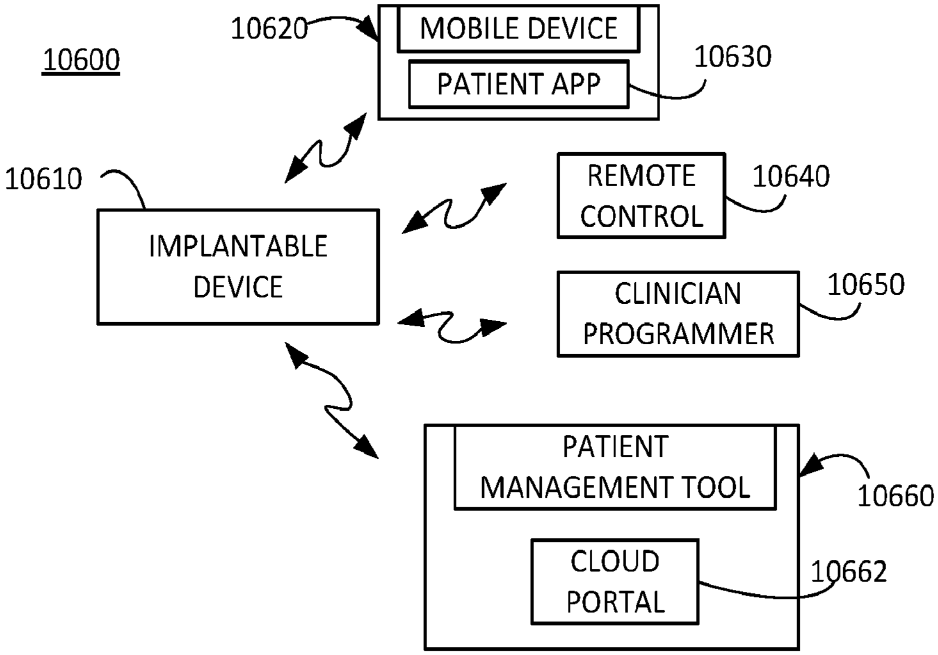

In some examples, control portion 10500 includes, and/or is in communication with, a user interface 10520 as shown in FIG. 54D. In some examples, user interface 10520 forms part or and/or is accessible via a device external to the patient and by which the therapy system may be at least partially controlled and/or monitored. The external device which hosts user interface 10520 may be a patient remote (e.g. 10532 in FIG. 54C), a physician remote (e.g. 10534 in FIG. 54C) and/or a clinician portal. In some examples, user interface 10520 comprises a user interface or other display that provides for the simultaneous display, activation, and/or operation of at least some of the example arrangements, stimulation elements, sensing elements, microstimulators, pulse generators, control portion, instructions, engines, functions, parameters, and/or methods, etc., as described in association with FIGS. 1-53F and/or later described FIGS. In some examples, at least some portions or aspects of the user interface 10520 are provided via a graphical user interface (GUI), and may comprise a display 10524 and input 10522.

FIG. 54E is a block diagram 10600 which schematically represents some example implementations by which an implantable device (IMD) 10610 (e.g. IPG 533, sensors, microstimulators, etc.) may communicate wirelessly with external devices outside the patient. As shown in FIG. 54E, in some examples, the IMD 10610 may communicate with at least one of patient app 10630 on a mobile device 10620, a patient remote control 10640, a clinician programmer 10650, and a patient management tool 10660. Patient control 572 in FIG. 3C may comprise one example implementation of the patient remote control 10640. The patient management tool 10660 may be implemented via a cloud-based portal 10662, the patient app 10630, and/or the patient remote control 10640. Among other types of data, these communication arrangements enable the IMD 10610 to communicate, display, manage, etc. patient therapy information as well as to allow for adjustment to the various elements, portions, etc. of the example devices and methods if and where needed.

FIGS. 55-59B are a series of diagrams including views which schematically represent several ways in which stimulation elements may be implanted to enable stimulation of the ansa cervicalis-related nerve and/or a phrenic nerve, such as in situations in which a patient may experience multiple type sleep apnea, including obstructive and central sleep aspects.

Moreover, stimulation via such example arrangements involving the phrenic nerve and/or ansa cervicalis-related nerve may be implemented without stimulation of the hypoglossal nerve in some examples. However, in some examples, the hypoglossal nerve may be stimulated in coordination with stimulation of the phrenic nerve and/or ansa cervicalis-related nerve in order to provide therapy for multiple-type sleep apnea. By providing the option of stimulating the hypoglossal nerve, the ansa cervicalis-related nerve, and/or the phrenic nerve, a greater range of therapeutic stimulation protocols are available to better tailor the stimulation therapy to the particular anatomical features and/or other physiologic traits of a particular patient.

Among other aspects, pacing stimulation of the phrenic nerve also may be used to prevent hyperventilation, which may be implemented as a standalone method or implemented in a complementary manner in association with other example arrangements of the present disclosure to treat sleep disordered breathing (e.g. OSA, CSA, multiple type sleep apnea).

In some example implementations, stimulation of the phrenic nerve, with or without stimulation of the ansa cervicalis-related nerve, may be implemented via at least some of substantially the same features and attributes as described in U.S. Patent Publication 2020/0147376, published on May 14, 2020, and entitled Multiple Type Sleep Apnea, and which is hereby incorporated by reference in its entirety.

Figure 55:
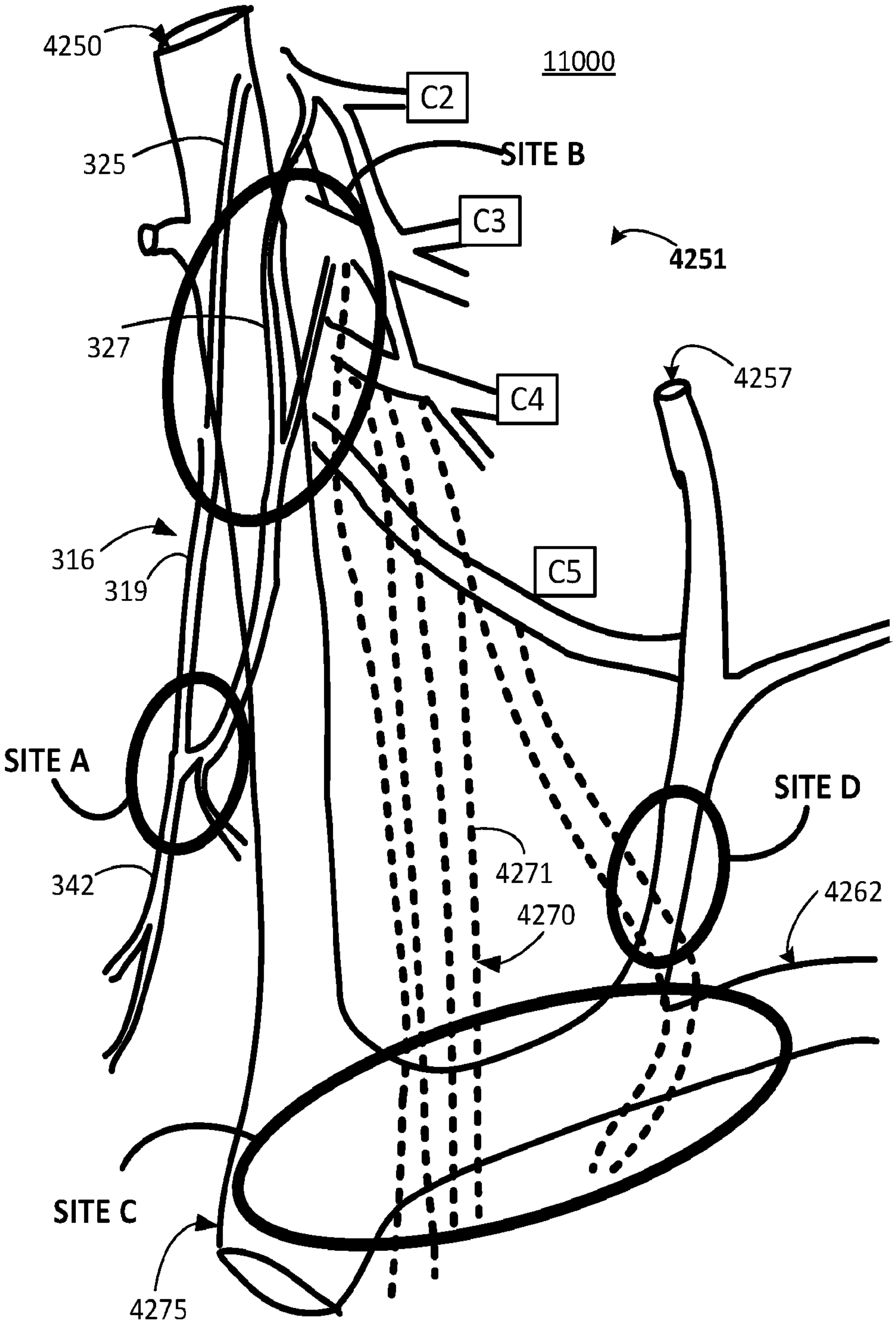
FIGS. 55-59B are diagrams schematically representing patient anatomy and example devices and/or example methods for implanting stimulation elements and applying stimulation therapy for a phrenic nerve and/or ansa cervicalis-related nerve.

With the foregoing in mind, among other potential stimulation sites, FIG. 55 is a diagram including a front view schematically representing patient anatomy 4251 and example arrangement 11000, which illustrates at least three different general stimulation sites A, B, C, D, by which the phrenic nerve may be stimulated with at least sites A and B providing locations at which a single stimulation arrangement may be used to stimulate the phrenic nerve and/or the ansa cervicalis-related nerve.

Moreover, in some examples in which the phrenic nerve and/or ansa cervicalis-related nerve are to be stimulated, stimulation also may be applied in a complementary manner to the hypoglossal nerve according to at least some of the various examples throughout the present disclosure. In some examples, applying stimulation to the phrenic nerve, ansa cervicalis-related nerve, and hypoglossal nerve may be implemented via the stimulation protocol 6320 in FIG. 37D. Moreover, at least some of the example arrangement in FIGS. 55-59B may be used to implement the example method 8400 in FIG. 43 regarding sensing and/or stimulation including the phrenic nerve, to implement at least some features and attributes of the example arrangements in FIGS. 38A-51B regarding sensing and/or stimulation in relation to a phrenic nerve, ansa cervicalis-related nerve, and/or hypoglossal nerve.

As shown in FIG. 55, the patient anatomy 4251 may comprise an internal jugular vein 4250 and a subclavian vein 4262, which branch off an innominate vein 4275, as well as an external jugular vein 4257. Patient anatomy 4251 further comprises an ansa cervicalis-related nerve 316 (e.g. FIG. 2, 16, etc.), with just some portions identified for illustrative simplicity, such as loop 319, portion 327, and portion 342 which innervates at least the sternothyroid muscle(s). As shown in FIG. 55, at least a portion of loop 319 of the ansa cervicalis-related nerve 316 is draped along/across the internal jugular vein 4250. Potential stimulation site B is located at the upper portion (e.g. superior) of the loop of the ansa cervicalis-related nerve 316, which includes portions which innervate the sternothyroid muscles and/or sternohyoid muscles, among other muscles. Meanwhile, potential stimulation site A may be located a lower portion (e.g. inferior) of the loop 319 of the ansa cervicalis-related nerve 316, which includes the portion 342 innervating at least the sternothyroid muscles.

FIG. 55 also shows cranial nerves C2, C3, C4, C5, with at least C2, C3 being nerves from which the ansa cervicalis-related nerve 316 originates.

Moreover, the patient anatomy 4251 depicted in FIG. 55 comprises an array 4270 (i.e. phrenic array) of phrenic nerve portions 4271 (shown in multiple dashed lines), at least some of which correspond to accessory phrenic nerve portions and/or secondary phrenic nerve portions joined to a principal phrenic nerve (not shown). As noted above, electrical stimulation of the phrenic nerve (including phrenic nerve portions) may cause contraction of the diaphragm, which may be used to treat central sleep apnea and/or treat multiple type apnea (including aspects of central sleep apnea).

Figure 56:
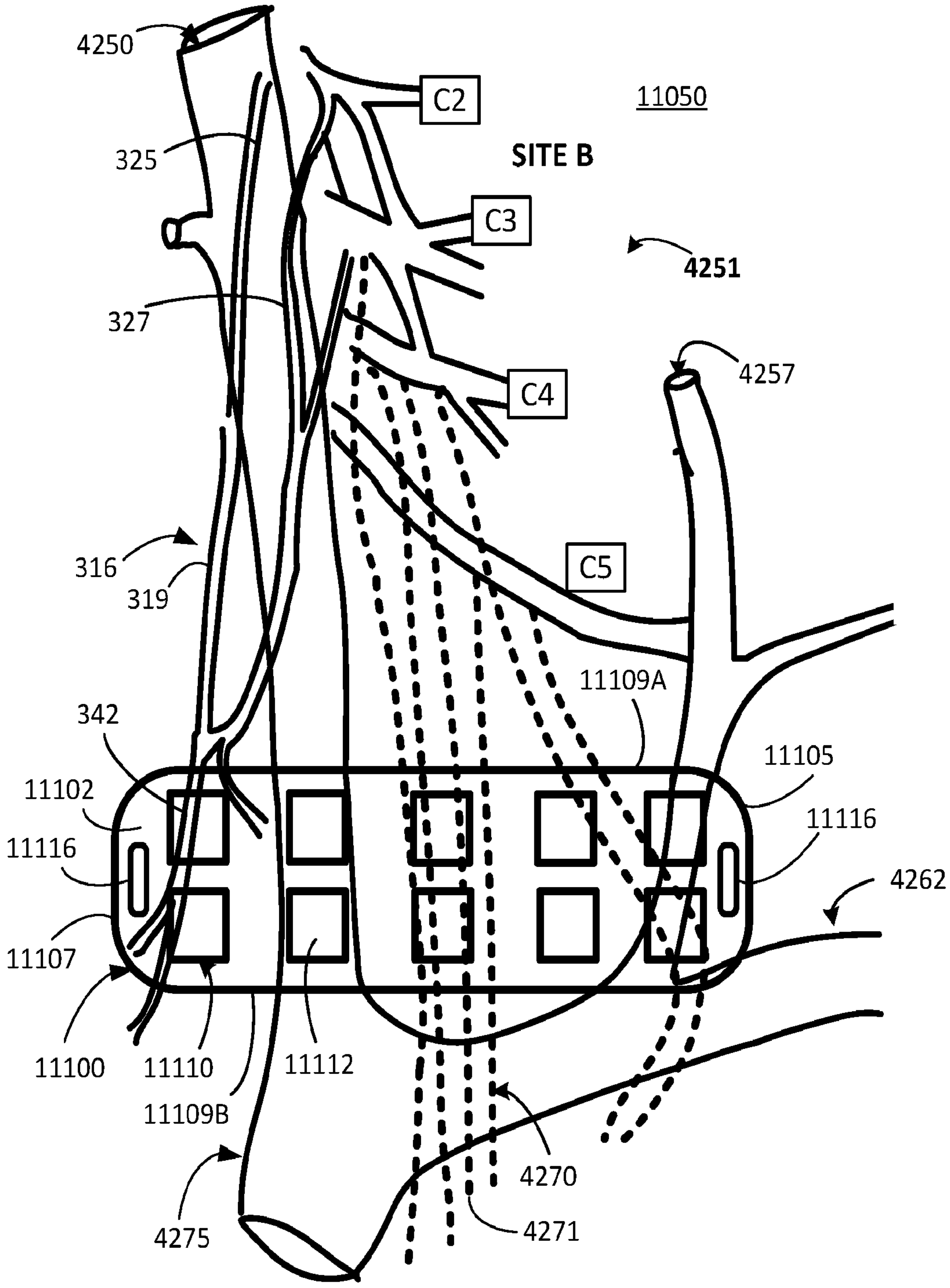

FIG. 56 is a diagram like FIG. 55 while further schematically representing an example arrangement 11050 including a paddle electrode 11100 implanted in a position juxtaposed relative to, and in stimulating relation to, portions of the ansa cervicalis-related nerve 316 and phrenic nerve portions 4271 (shown as dashed lines). As shown in FIG. 56, the paddle electrode 11100 comprises a carrier body 11102 which supports an array 11110 of spaced apart electrode contacts 11112. The array 11110 may comprise a two-dimensional array (e.g. multiple rows and columns) as shown, may comprise a single row of electrode contacts. The electrode array 11110 extends between first and second opposite ends 11105, 11107 of the carrier body 11102, and between opposite sides 11109A, 11109B.

In some examples, the carrier body 11102 may comprise at least some holes 11116 at the ends 11105, 11107 and/or sides 11109A, 11109B to enable tissue growth and/or suturing to secure the carrier body 11102 relative to surrounding non-nerve tissues to anchor the paddle electrode 11100 securely in stimulating relation to the respective target nerves. In some examples, various tines, barbs, and/or similar elements may be provided on the carrier body 11100 to anchor it in place.

In some examples, the carrier body and electrode array 11110 are sized and shaped to be co-located with multiple nerves, such as portions (e.g. 342) of the ansa cervicalis-related nerve 316, phrenic nerve portions 4271, etc., while accommodating anatomy variation among different patients. Via the electrode array 11110 of paddle electrode 11100, stimulation may be applied to solely to the ansa cervicalis-relate nerve 316, solely to the phrenic nerve (e.g. 4271), or to both of these respective nerves. When applied to both nerves, the stimulation may be applied simultaneously, alternately, in a staggered manner, etc.

Figure 57:
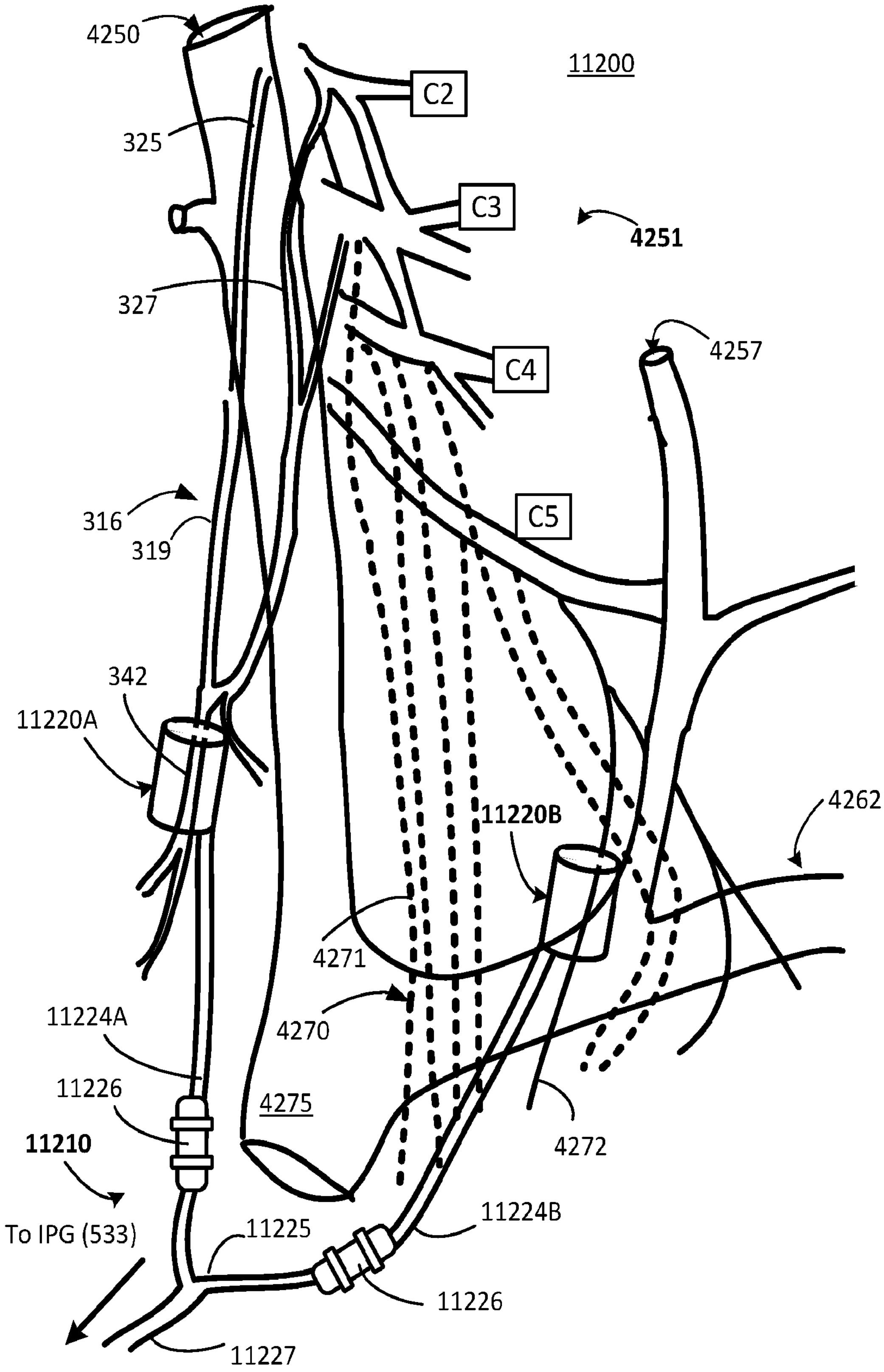

FIG. 57 is a diagram including patient anatomy 4251 like FIGS. 55-56 while schematically representing an example arrangement 11200 including a stimulating device 11210 including cuff electrodes 11220A, 11220B supported on respective distal lead portions 11224A, 11224B bifurcated, via junction 11225, from main lead portion 11227. In some examples, the stimulation device 11210 may comprise one or more anchor elements 11226 which may be provided at each distal lead portion 11124A, 11224B as shown in FIG. 57 and/or at main lead portion 11226 for robustly securing the at respective lead portions 11124A, 11124B, cuff electrodes 11220A, 11220B, etc. relative to non-nerve surrounding tissues to maintain the cuff electrodes 11220A, 11220B in stimulating relation to the target nerves.

As further shown in FIG. 57, in some examples one cuff electrode 11220A may be chronically implanted relative to a portion, such as but not limited to portion 342, of the ansa cervicalis-related nerve 316 while one cuff electrode 11220B may be chronically implanted relative to one of the phrenic nerve portions generally represented via the dashed lines 4271. In FIG. 57, one of the phrenic nerve portions is shown as a solid line 4272 to highlight its being engaged via cuff electrode 11220B.

The cuff electrode 11220A, 11220B may comprise a wide variety of cuff designs. In some such examples, the cuff electrodes may comprise at least some of substantially the same features as described for cuff electrodes shown in at least FIGS. 18-20.

In some examples, the cuff electrodes 11220A, 11220B (and associated lead portions) may be delivered via at least some of the paths, access incision, tools, etc. or analogous paths, access incisions, tools, etc. as described in the various examples of the present disclosure, such as but not limited to FIGS. 1-32D.

Figure 58:
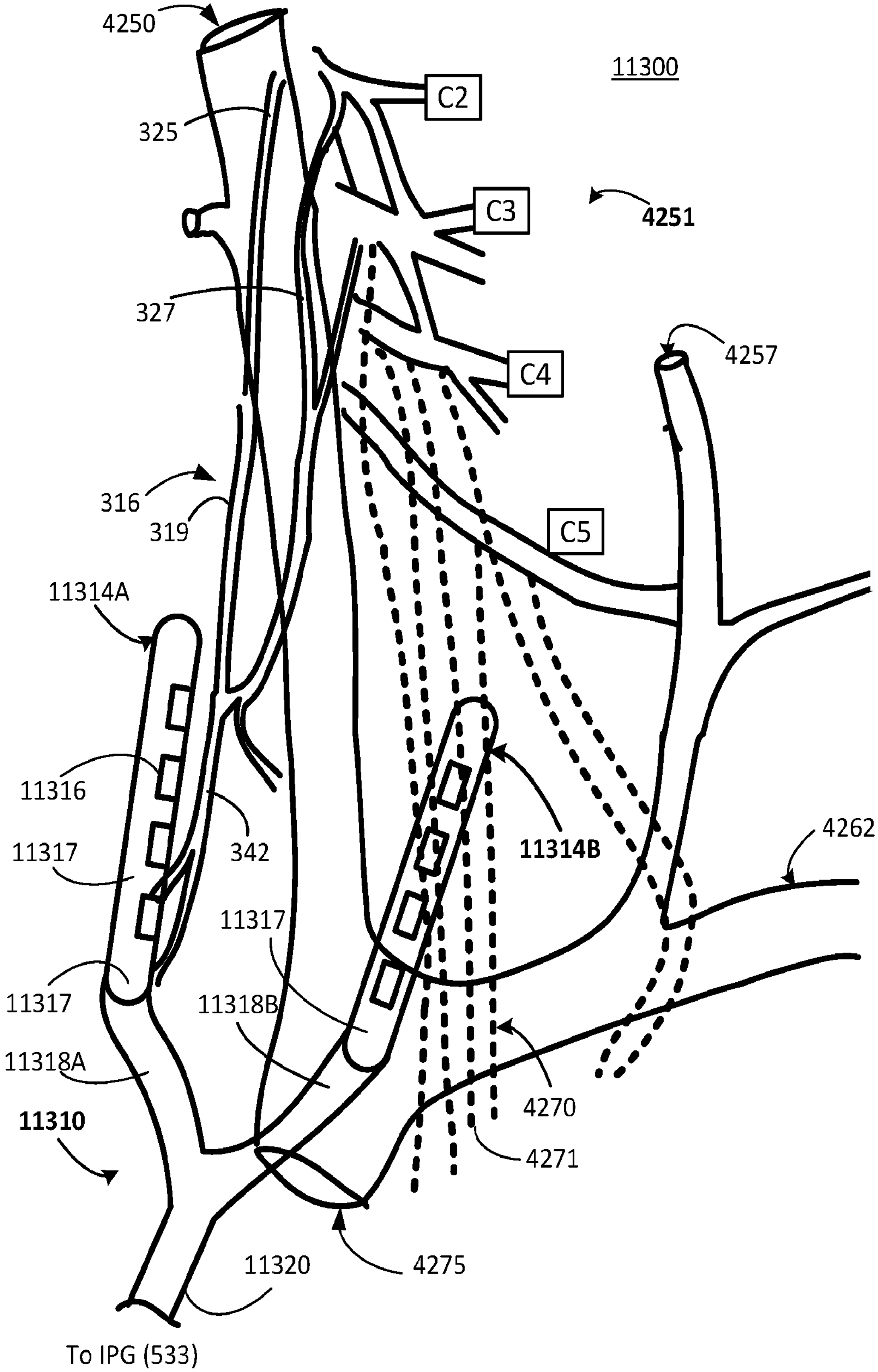

FIG. 58 is a diagram including patient anatomy 4251 like FIGS. 55-56 while schematically representing an example arrangement 11300 including a stimulation device 11310 including stimulation portions 11220A, 11220B (in an axial lead configuration) supported on respective distal lead portions 11318A, 11318B bifurcated from main lead portion 11320.

As further shown in FIG. 58, in some examples one stimulation portion 11314A may be chronically subcutaneously implanted relative to a portion, such as but not limited to portion 342, of the ansa cervicalis-related nerve 316 while one stimulation portion 11314B may be chronically subcutaneously implanted relative to one of the phrenic nerve portions generally represented via the dashed lines 4271. The stimulation portions 11314A, 11314B may comprise a wide variety of electrode arrangements in which an array of spaced apart electrode contacts 11316 are positioned on a carrier 11317 to position the multiple electrode contacts in close proximity to the target stimulation locations of a nerve, as shown in FIG. 58. In a manner similar to other axial-style stimulation portions (e.g. linear array of spaced apart electrode contacts) described throughout examples of the present disclosure, different combinations of the multiple electrode contacts 11316 of one or both stimulation portions 11314A, 11314B may be used to stimulate the respective ansa cervicalis-related nerve 316 and phrenic nerve portions 4271. The different combinations of electrode contacts on each respective stimulation portion may be used to optimize nerve capture during or after final positioning of the respective stimulation portions relative to the respective nerves, or may be used to implement selective stimulation as desired.

In some such examples, the stimulation portions 11314A, 11314B may comprise at least some of substantially the same features as described for the various example axial-style (e.g. linear electrode array) stimulation portions and lead, including anchoring, delivery, etc. in association with at least FIGS. 1-32D. In some examples, the stimulation portions 11314AA, 11314B (and associated lead portions) may be delivered via at least some of the paths, access incision, tools, etc. or analogous paths, access incisions, tools, etc. as described in the various examples of the present disclosure, such as but not limited to FIGS. 1-32D. Among the various types of securing elements, some example implementations may comprise sutures, tines, barbs, holes to induce tissue growth, and the like.

Figure 59A:
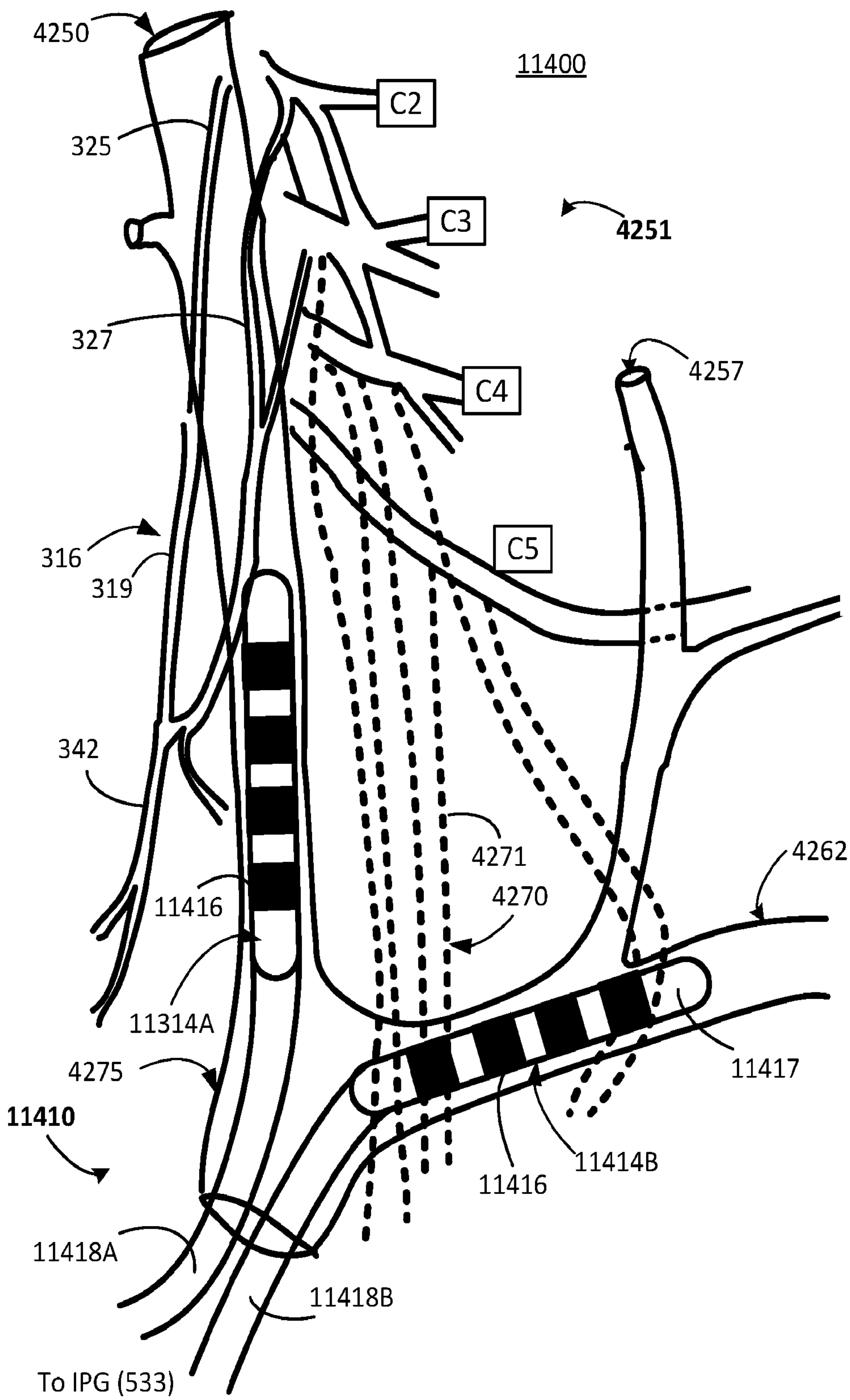
FIGS. 59C-59E are diagrams including a side view schematically representing example stimulation elements incorporating anchor structures, with FIG. 59F including a sectional view of FIG. 59E.

FIG. 59A is a diagram including patient anatomy 4251 like FIGS. 55-56 while schematically representing an example arrangement 11400 including a stimulation device 11410 including stimulation portions 11414A, 11414B (in an axial lead configuration) supported on respective leads 11418A, 11418B. While FIG. 58 illustrates separate leads 11418A, 11418B, it will be understood that in some examples, these leads may comprise bifurcated lead portions extending from a common, main lead portion in a manner similar to other such bifurcated leads disclosed in various examples of the present disclosure.

As shown in FIG. 59A, each respective stimulation portion 11414A, 11414B is chronically implanted via intravascular delivery. In some examples, the stimulation portion 11414A is advanced within and through the vasculature to extend within and through the internal jugular vein 4250 to be in transvenous stimulating relation to portions of the ansa cervicalis-related nerve 316, while the stimulation portion 11414B is advanced within and through the vasculature to extend within and through the subclavian vein 4262 to be in transvenous stimulating relation to at least some phrenic nerve portions 4271.

It will be understood that in some examples, stimulation portion 11414B may be advanced further to extend within and through a portion of the external jugular vein 4257 to place the stimulation portion 11414B in transvenous stimulating relation to phrenic nerve portions 4271 (shown in dashed lines) within proximity of the external jugular vein 4257.

The stimulation portions 11414A, 11414B in FIG. 59A may comprise at least some of substantially the same features as the subcutaneously delivered, stimulation portions 11314A, 11314B in FIG. 58, except being delivered intravascularly for transvenous stimulation.

In some such examples, the stimulation portions 11414A, 11414B may comprise at least some of substantially the same features as described for the various example transvenously delivered, axial-style (e.g. linear electrode array) stimulation portions and lead, including anchoring, delivery, etc. in association with at least FIGS. 1-32D. In some examples, the stimulation portions 11414AA, 11414B (and associated lead portions) may be delivered via at least some of the paths, access incision, tools, etc. or analogous paths, access incisions, tools, etc. as described in the various examples of the present disclosure, such as but not limited to FIGS. 1-32D.

However, in some examples such as at least the examples in FIGS. 59C-59F, the stimulation portion (e.g. array of electrodes) may comprise a more flexible, resilient structure, which functions in part, as a retention element for robustly securing the stimulation portions within the vasculature. In some such examples, the body of the lead and/or carrier (in the region supporting the electrodes of the stimulation portion) may be pre-formed in a shape, size, and/or orientation adapted to promote anchoring or fixation of the stimulation relative to the pertinent anatomical features in which the stimulation portion is to become secured. In some examples, the pre-formed shape may be implemented via a shape memory material. Via such arrangements, because of its flexible resilience, such a stimulation portion may be manipulated from its original shape in order to introduce and advance the stimulation portion and lead within the vasculature (or within a subcutaneous access, delivery path), with the stimulation portion being biased to return as close as possible to its original shape, which in turn helps to secure the stimulation portion in a desired location. In some examples, these above-noted size, shape, and/or orientation features may be implemented in the example arrangement of 11600 of FIG. 59B.

Figure 59B:
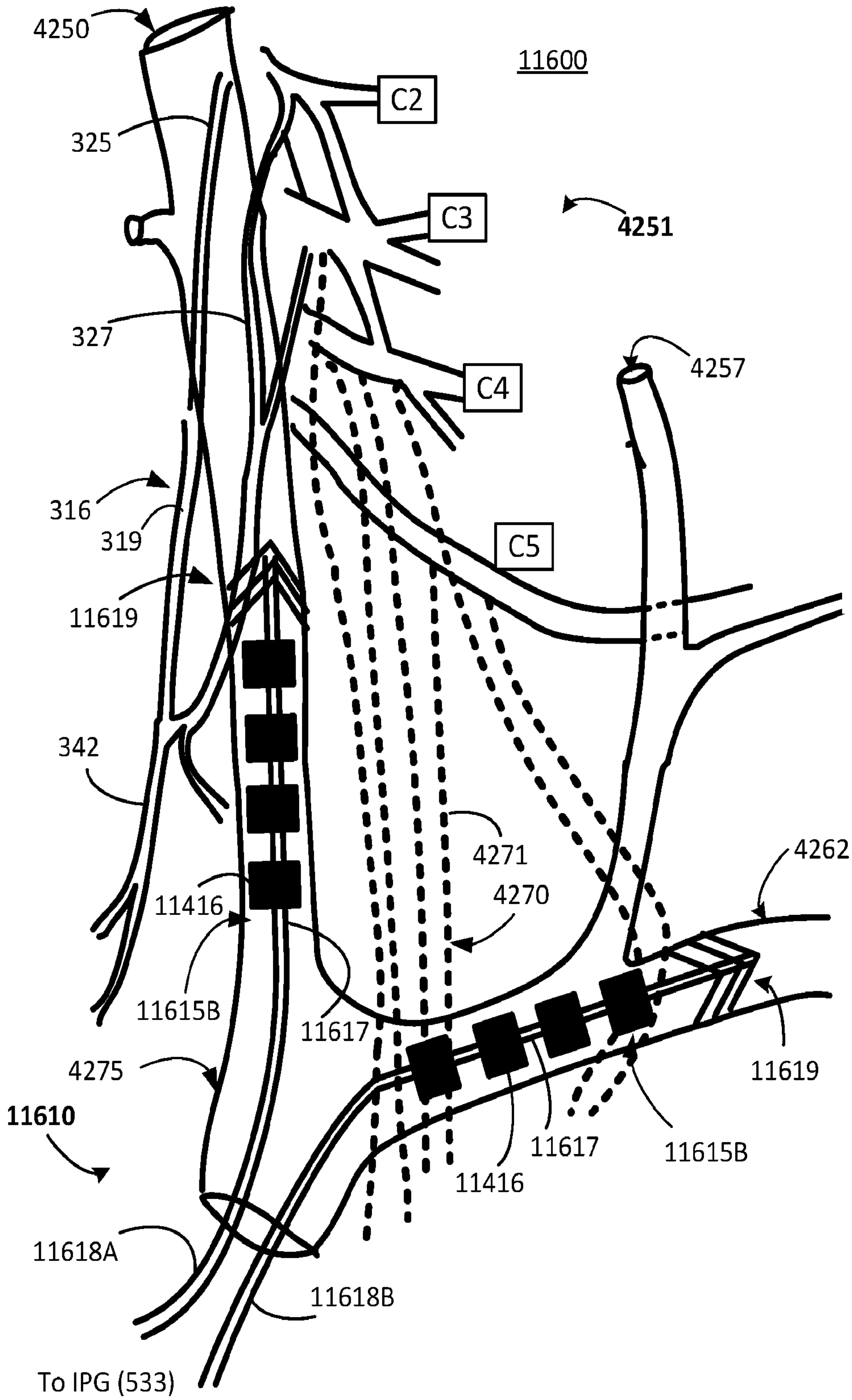

FIG. 59B is a diagram including patient anatomy 4251 like FIGS. 55-56 while schematically representing an example arrangement 11600 including a stimulation device 11610 including stimulation portions 11615A, 11615B supported on respective lead portions 11618A, 11618B. In some examples, the lead portions 11618A, 11618B may be completely independent physically, while in some examples the respective lead portions 11618A, 11618B may be bifurcated at some point proximally of the stimulation portions 11615A, 11615B. Each stimulation portion 11615A, 11615B comprises a distal lead portion 11617 (extending from main lead portion 11618A, 11618B) on which an array of spaced apart electrodes 11416 is supported. In a manner similar to the example arrangement in FIG. 59A, the respective stimulation portions 11615A, 11615B (and associated supporting leads) are advanced within and through the vasculature to position the stimulation portions 11615A, 11615B in transvenous stimulating relation to the respective nerves, such as portions of the ansa cervicalis-related nerve 316 and phrenic nerve portions 4271. In these positions, the stimulation portions 11615A, 11615B may comprise at least some of substantially the same features and attributes for positioning, delivering stimulation therapy, etc. as the stimulation portions in FIG. 59A, except for the differences noted below.

While the main lead portion 11618A, 11618B (for respective stimulation portions 11615A, 11615B in FIG. 59B) may be formed of a flexible, resilient material to implement expected functions of an implantable medical lead, the distal lead portions 11617 carrying the electrodes 11416 may have a higher degree of flexibility and/or degree of configurability, while still retaining their resilience (e.g. biased to maintain and/or return to shape), in order to permit the electrodes 11416 and distal lead portion 11417 to be manipulated into a position and shape within the vasculature to help secure the stimulation portion 11615A, 11615B as desired. In some examples, the stimulation device(s) 11610 may comprise an anchor structure 11619 mounted or formed at an utmost distal end of the stimulation portion 11615A, 11615B. It will be understood that, in some examples, at least some features of the anchor structure 11619 may be implemented at locations along the lead 11618A, 11618B other than the utmost distal end.

In some examples, the anchor structure 11619 may comprise an array of anchor elements (e.g. tines, barbed elements, etc.) which are flexible and resilient, with such elements sized, shaped, oriented, and/or positioned to frictionally engage non-nerve tissues, such as a sidewall of the vasculature through which the stimulation portion is being advanced and positioned. As shown in FIG. 59B, the anchor elements of structure 11619 are oriented to permit forward movement (advancing) the stimulation portion 11615A, 11615B within and through the vasculature while preventing or hindering movement of the stimulation portion in the opposite direction. In some examples, the anchor structure 11619 may comprise at least some of substantially the same features and attributes as described in association with at least FIGS. 30A-31G and/or other applicable examples of the present disclosure. Among those features, in some examples, some anchor elements can extend in an opposite direction from other anchor elements to prevent ratcheting, other undesired migration, etc.

It will be understood that the at least some of the features and attributes of the retention-style stimulation portions shown and described in FIGS. 59B-59F may be implemented in other various examples of the present disclosure for transvenous stimulation (via intravascular access/delivery) of nerve targets other than the phrenic nerve and/or ansa cervicalis-related nerve 316, and/or may be implemented in non-transvenous (e.g. subcutaneous, other) stimulation examples, forms of access, delivery, etc. Moreover, as applicable for at least some of the examples of the present disclosure, the features and attributes for transvenous delivery and retention of FIGS. 59A-59F (or non-transvenous) may be applied and implemented for nerve targets (e.g. pelvic, pudendal, cardiac etc.) other than those for treating sleep disordered breathing, and therefore may be applied in regions of the body (e.g. pelvic, other) other than the head-and-neck region and/or pectoral region.

Figure 59C:
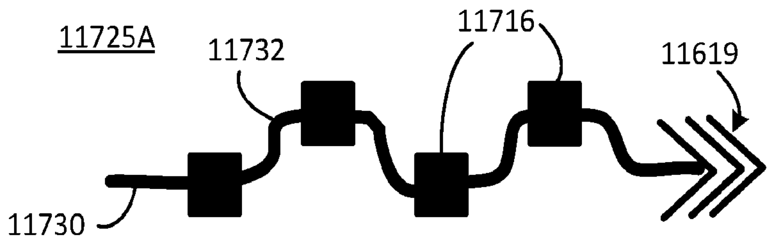

FIG. 59C is a diagram schematically representing an example stimulation portion 11725A comprising at least some of substantially the same features and attributes as the stimulation portions 11615A, 11615B in FIG. 59B, except comprising more particular retention features as further described below. Stimulation portion 11725A of FIG. 59C may comprise one example implementation of the stimulation portions 11615A, 11615B of FIG. 59B. As shown in FIG. 59C, the stimulation portion 11725A comprises a main lead portion 11730 and distal lead portion 11732 supporting an array of spaced apart electrodes 11716, and anchor structure 11619. The distal lead portion 11732 is made of a flexible, resilient material, which is pre-formed in a generally sinusoidal or sigmoid shape, which may act to help retain or anchor the stimulation portion 11725A when manipulated to fit within in a desired intravascular location in close proximity to a transvenous target stimulation location. In addition, this configuration also may provide strain relief for the electrodes, lead, etc. In some examples, the distal lead portion 11732 may comprise shape patterns other than sigmoid or sinusoidal while providing a variable length or variable shape feature.

Figure 59D:
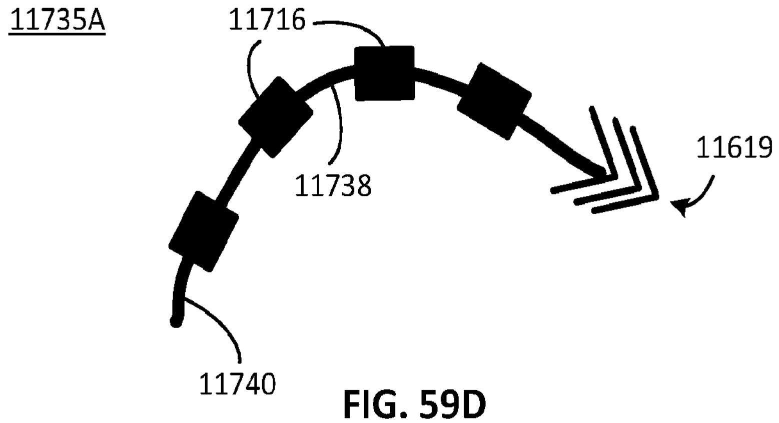

FIG. 59D is a diagram schematically representing an example stimulation portion 11735A comprising at least some of substantially the same features and attributes as the stimulation portions 11615A, 11615B in FIG. 59B, except comprising more particular retention features as further described below. Stimulation portion 11735A of FIG. 59D may comprise one example implementation of the stimulation portions 11615A, 11615B of FIG. 59B. As shown in FIG. 59D, the stimulation portion 11735A comprises a main lead portion 11740 and distal lead portion 11738 supporting an array of spaced apart electrodes 11716, and anchor structure 11619. The distal lead portion 11738 is made of a flexible, resilient material, which is pre-formed in a generally arcuate shape of a single curvature (e.g. J-shape), which may act to help retain or anchor the stimulation portion 11735A when manipulated to fit within in a desired intravascular location in close proximity to a transvenous target stimulation location. In some such examples, the particular single curvature shape may be formed to correspond to the anatomical shape (e.g. an arch) in which it will implanted or formed to be slightly incongruent to the anatomical shape (e.g. an arch) in which it will implanted so as to accentuate it retention ability.

Figure 59E:
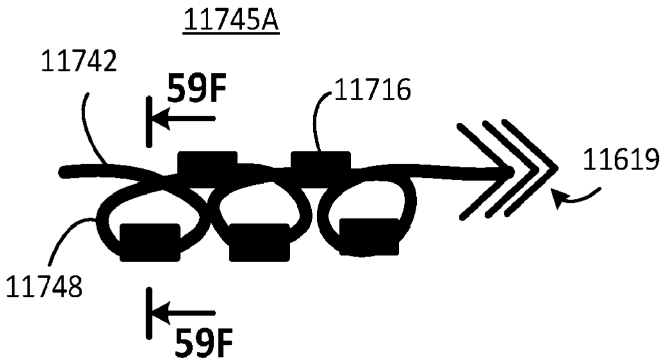
Figure 59F:
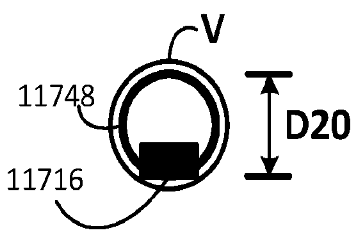

FIG. 59E is a diagram schematically representing an example stimulation portion 11745A comprising at least some of substantially the same features and attributes as the stimulation portions 11615A, 11615B in FIG. 59B, except comprising more particular retention features as further described below. Stimulation portion 11745A of FIG. 59E may comprise one example implementation of the stimulation portions 11615A, 11615B of FIG. 59B. As shown in FIG. 59E, the stimulation portion 11745A comprises a main lead portion 11742 and distal lead portion 11748 supporting an array of spaced apart electrodes 11716, and anchor structure 11619. It will be understood that the shape of the electrodes 11716 shown in FIGS. 59E-59F is provided for illustrative purposes/simplicity, and that in some examples electrodes 11716 may comprise a more rounded shape than shown in FIGS. 59E-59F.

With further reference to FIG. 59E, the distal lead portion 11748 is made of a flexible, resilient material, which is pre-formed in a generally helical or spiral shape, which may act to help retain or anchor the stimulation portion 11745A when manipulated to fit within in a desired intravascular location in close proximity to a transvenous target stimulation location. In some such examples, the particular tightness (or looseness) of the helical pattern may be formed to complement the anatomical shape in which it will implanted or formed to be slightly incongruent relative to the anatomical shape in which it will implanted so as to accentuate it retention ability. In some examples, a diameter (D20) of the helical pattern may generally correspond to a diameter (or greatest cross-sectional dimension) of the vasculature (V) in which the stimulation portion 11745A will be implanted, as further shown in the sectional view of FIG. 59F taken along lines 59F-59F in FIG. 59E. In some examples, the diameter of the helical shaped stimulation portion 11745A prior to implantation may be larger or smaller than the diameter of the vasculature (V) depending on the particular strategic goals for implantation and retention.

Figure 60:
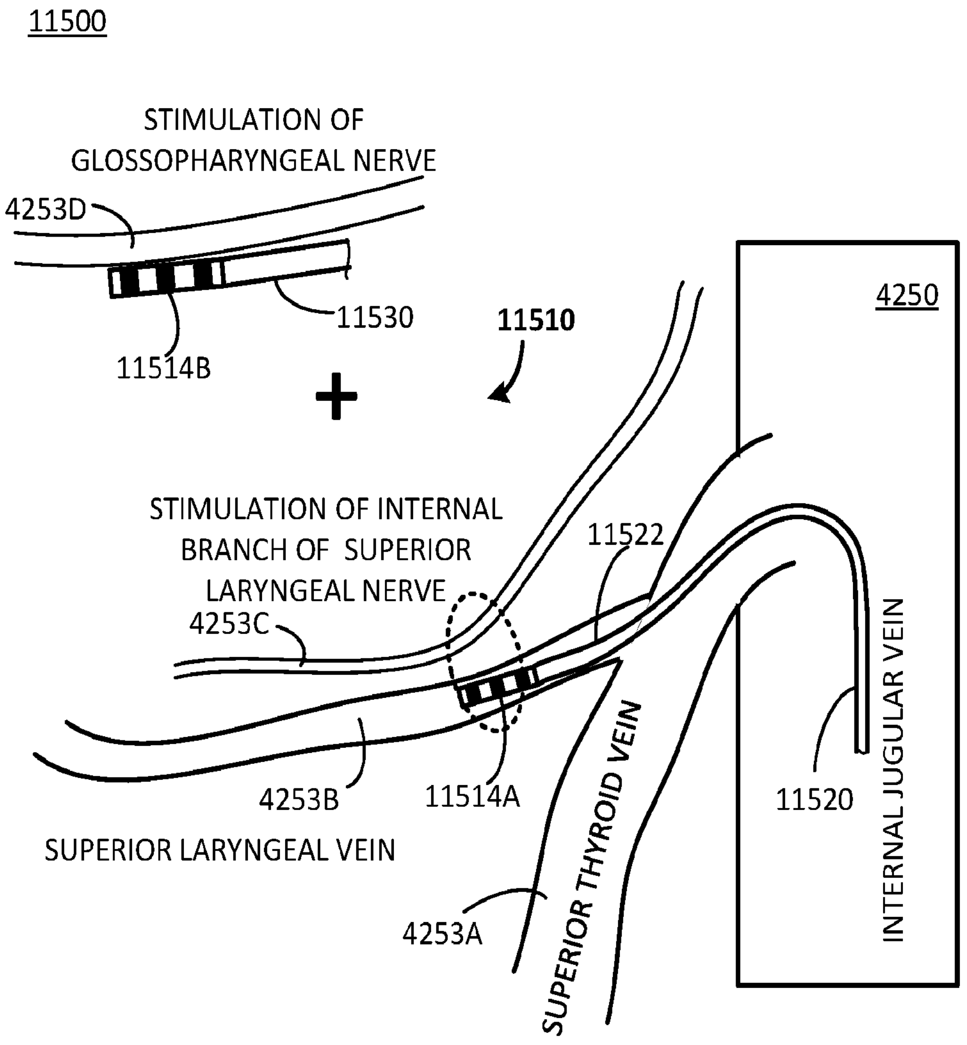
FIG. 60 is a diagram schematically representing patient anatomy and an example device and/or example method for transvenous stimulation of target nerve locations relating to upper airway patency.

FIG. 60 is a diagram schematically representing an example arrangement (e.g. example method and/or example device) providing (e.g. via implanting stimulation elements within the patient's body) for the combination of stimulating the glossopharyngeal nerve and of stimulating the internal branch of the superior laryngeal nerve, such as via intravascular access by the superior laryngeal vein, i.e. the internal branch of the superior thyroid vein. In some examples, the example arrangement 11500 in FIG. 60 may comprise one example implementation of the at least some aspects of the method 8284 described in association with at least FIG. 41B and/or at least the example arrangement in FIGS. 32A-32B to deliver stimulation therapy for treating sleep disordered breathing. It will be understood that the example arrangement 11500 is FIG. 60 is also illustrative for, and may be applicable, to examples of the present disclosure which identify target nerves other than the hypoglossal nerve and/or ansa cervicalis-related nerve.

As shown in FIG. 60, in one aspect the example arrangement may comprise a stimulation device 11510 including a stimulation portion 11514A supported on a distal lead portion 11522 and more proximal lead portion 11520. In some examples, the stimulation portion 11514A may comprise at least some of substantially the same features as stimulation portion 11414A (or 11414B) in FIG. 59A, which may comprise at least some of substantially the same features and attributes as the axial-style stimulation portions (and associated leads) described throughout various examples of the present disclosure. As shown in FIG. 60, the stimulation portion 11514A may be advanced within and through the vasculature, such as within and through the internal jugular vein 4250, within and through a portion of the superior thyroid vein 4253A, and then within and through the superior laryngeal vein 4253B to place the stimulation portion 11514A into transvenous stimulating relation to an internal branch 4253C of a superior laryngeal nerve. It will be understood that in some examples, this method of implantation and stimulation of the internal branch 4253C of the superior laryngeal nerve may be performed, regardless of whether a stimulation portion is provided for stimulating the glossopharyngeal nerve 4253D. Conversely, in some examples, a stimulation portion 11514B is provided solely for the glossopharyngeal nerve 4253D without providing one for the internal branch 4253C of the superior laryngeal nerve.

As further shown in FIG. 60, in some examples the example arrangement 11500 may comprise chronically implanting a stimulation portion 11514B in stimulating relation to the glossopharyngeal nerve 4253D. In some examples, the stimulation portion 11514B may be delivered intravascularly for transvenous stimulation of the glossopharyngeal nerve 4253D or may be delivered via other means (e.g. subcutaneously).

Instead of placing a stimulation portion 11514A with a lead portion (e.g. 11522, 11520) intravascularly as shown in FIG. 60, in some examples a microstimulator may be placed intravascularly (whether supported on a lead or independent) or subcutaneously in a method like that previously described in association with at least the example arrangement in FIGS. 32A-32B. Similarly, stimulation portion 11514B (for stimulating the glossopharyngeal nerve 4253D) also may be implemented as a microstimulator, whether delivered intravascularly for transvenous stimulation or delivered subcutaneously or other means.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The following examples may comprise at least some of substantially the same features and attributes as, and/or example implementations of, the previously described examples of the present disclosure. The following examples may be implemented alone or together, which may comprise any various complementary combinations.

Example A1. A method of therapy for sleep disordered breathing, comprising: stimulating, via at least one stimulation element, at least one upper airway patency-related tissue.

Example A2. The method of example A1, wherein the upper airway patency-related tissue comprises a hypoglossal nerve.

Example A3. The method of example A1, comprising positioning the at least one stimulation element at the hypoglossal nerve on a first side of the patient's body.

Example A4. The method of example A1, wherein the upper-airway patency-related tissue comprises solely the hypoglossal nerve.

Example A5. The method of example A1, wherein the upper airway patency-related tissue comprises an ansa cervicalis-related nerve.

Example A6. The method of example A5, wherein the ansa cervicalis-related nerves comprises at least one of a superior root of the ansa cervicalis-related nerve and branches extending from the superior root of the ansa cervicalis-related nerve.

Example A7. The method of example A1, wherein the upper-airway patency-related tissue comprises solely an ansa cervicalis-related nerve.

Example A8. The method of example A1, comprising positioning the at least one stimulation element at an ansa cervicalis-related nerve on a first side of the patient's body.

Example A9. The method of example A8, wherein the ansa cervicalis-related nerves comprises multiple separate portions of the ansa cervicalis-related nerve, and the at least one stimulation element comprises multiple stimulation elements with a respective different stimulation element in stimulating relation to a respective different portion of the ansa cervicalis-related nerve.

Example A10. The method of example A8, comprising: locating the stimulation at the ansa cervicalis-related nerve to cause stimulation of at least one of: an omohyoid muscle; a sternothyroid muscle; and a sternohyoid muscle.

Example A11. The method of example A8, comprising: locating the stimulation at the ansa cervicalis-related nerve to cause stimulation of at least one of: a sternothyroid muscle; and a sternohyoid muscle.

Example A12. The method of example A8, wherein the ansa cervicalis-related nerve comprises a first ansa cervicalis-related nerve on a first side of the body and a second ansa cervicalis-related nerve on an opposite second side of the body, and wherein the stimulating comprises stimulating both the respective first and second ansa cervicalis nerves.

Example A13. The method of example A12, wherein the stimulating both the respective first and second ansa cervicalis-related nerve comprises simultaneously stimulating the respective first and second ansa cervicalis-related nerves.

Example A14. The method of example A12, the stimulating both the respective first and second ansa cervicalis-related nerves comprises alternately stimulating the respective first and second ansa cervicalis-related nerves.

Example A15. The method of example A1, wherein the upper airway patency-related tissue comprises a hypoglossal nerve, wherein the at least one stimulation element comprises a first stimulation element, and comprising: implanting the first stimulation element to be in stimulating relation to the hypoglossal nerve.

Example A16. The method of example A15, wherein the at least one upper airway patency-related tissue comprises an ansa cervicalis-related nerve, wherein the at least one stimulation element further comprises a second stimulation element, and implanting the second stimulation element at the ansa cervicalis-related nerve in a separate implant procedure after a time period following the implantation of the first stimulation element.

Example A17. The method of example A16, comprising: performing the implanting of the second stimulation element upon a determination of a patient exhibiting symptomatic residual AHI despite treatment via the first stimulation element of the hypoglossal nerve.

Example 18. The method of example A16, wherein the implanting of the second stimulation element comprises: implanting a second stimulation lead, on which the second stimulation element is supported, in a position extending between an implanted pulse generator and the position of the second stimulation element at the ansa cervicalis-related nerve.

Example A19. The method of example A18, comprising the second stimulation element being positioned on a distal portion of the first stimulation lead.

Example A20. The method of example A19, comprising: implanting the second stimulation lead between the location of the second stimulation element at the ansa cervicalis-related nerve and the pulse generator, and connecting a proximal portion of the second stimulation lead to the pulse generator.

Example A21. The method of example A19, comprising: implanting and extending the second stimulation lead from the location of the second stimulation element at the ansa cervicalis-related nerve toward a port interface along an intermediate portion of the implanted first stimulation lead; and connecting a proximal portion of the second stimulation lead to the port interface of the first stimulation lead to establish electrical communication between the second stimulation lead and the pulse generator.

Example A22. The method of example A18, wherein the second stimulation element comprises a first microstimulator, and the first microstimulator is to be in wireless communication with at least one of the first stimulation element and the pulse generator.

Example A23. The method of example A15, wherein the first stimulation element comprises a first microstimulator, wherein the at least one upper airway patency-related tissue further comprises an ansa cervicalis-related nerve, wherein the at least one stimulation element further comprises a second stimulation element, and implanting the second stimulation element at the ansa cervicalis-related nerve in a separate implant procedure after a time period following the implantation of the first stimulation element.

Example A24. The method of example A23, wherein the second stimulation element comprises a second microstimulator.

Example A25. The method of example A24, comprising: coordinating stimulation among the respective first and second stimulation elements via the second microstimulator being in communication with the first microstimulator.

Example A26. The method of example A23, comprising the second stimulation element being on a distal portion of a second stimulation lead.

Example A27. The method of example A26, comprising implanting the second stimulation lead between the location of the second stimulation element at the ansa cervicalis-related nerve and an implanted pulse generator; and connecting a proximal portion of the second stimulation lead to the pulse generator.

Example A28. The method of example A1, wherein the upper airway patency-related tissue comprises an ansa cervicalis-related nerves, wherein the at least one stimulation element comprises a first stimulation element, and comprising: implanting the first stimulation element to be in stimulating relation to the ansa cervicalis-related nerves.

Example A29. The method of example A28, wherein the at least one upper airway patency-related tissue comprises a hypoglossal nerve, and wherein the at least one stimulation element comprises a second stimulation element, and implanting the second stimulation element in a separate implant procedure after a time period following the implantation of the first stimulation element.

Example A30. The method of example A29, comprising: performing the implanting of the second stimulation element upon a determination of a patient exhibiting symptomatic residual AHI despite treatment via the first stimulation element of the ansa cervicalis-related nerve.

Example A31. The method of example A15, wherein the at least one upper airway patency-related tissue comprises an ansa cervicalis-related nerve, and the at least one stimulation element further comprises a second stimulation element, and wherein implanting the second stimulation element comprises: performing a single implant procedure including implanting the first stimulation element relative to the hypoglossal nerve and implanting the second stimulation element relative to the ansa cervicalis-related nerve.

Example A32. The method of example A31, wherein performing the single implant procedure comprises a single stimulation lead supporting the first stimulation element and the second stimulation element.

Example A33. The method of example A32, wherein the single stimulation lead comprises a proximal portion and a bifurcated distal portion including a first stimulation portion including the first stimulation element and a second stimulation portion including the second stimulation element.

Example A34. The method of example A31, comprising: implanting a first stimulation lead, comprising the first stimulation element, to stimulate the ansa cervicalis-related nerve; and implanting a second stimulation lead, comprising the second stimulation element, to stimulate the hypoglossal nerve.

Example A35. The method of example A34, comprising: forming a single access-incision; inserting both the first and second respective stimulation leads into, and through, the single access-incision; and implanting the first stimulation element on the first stimulation lead at the ansa cervicalis-related nerve and implanting the second stimulation element on the second stimulation lead at the hypoglossal nerve.

Example A36. The method of example A35, comprising: forming at least one tunnel from the implant locations of the respective first and second stimulation elements to a second implant location; and implanting a pulse generator at the second implant location and connecting the first and second stimulation leads to the pulse generator.

Example A37. The method of example A36, comprising implementing the connecting via at least one of: a direction connection to a plurality of ports on the pulse generator; and an indirect connection to a port interface connected to the pulse generator.

Example A38. The method of example A37, comprising: implanting a single pulse generator; forming a first access-incision and a second access-incision; inserting a first portion of a tunneling tool into the first access-incision and a second portion of the tunneling tool into the second access-incision; and advancing the respective first and second portions of the tunneling tool to form first and second tunnels from the respective first and second access-incisions to the implanted pulse generator.

Example A39. The method of example A38, comprising: implanting the first stimulation lead into the first access-incision and advancing the first stimulation lead through the first tunnel to position a portion of the first stimulation lead for connection to the implanted pulse generator; and implanting the second stimulation lead into the second access-incision and advancing the second stimulation lead through the second tunnel to position a portion of the second stimulation lead for connection to the implanted pulse generator.

Example A40. The method of example A1, wherein the at least one stimulation element comprises a first stimulation element and a second stimulation element, and comprising at least one of: positioning the first stimulation element on a first side of the patient's body and positioning the second stimulation element on an opposite second side of the patient's body; and positioning the first stimulation element on a first side of the patient's body and positioning the second stimulation element on the same first side of the patient's body spaced apart from the first stimulation element.

Example A41. The method of example A1, the at least one stimulation element comprising a first stimulation element and a second stimulation element, wherein stimulation via the respective first and second stimulation elements are coordinated with each other.

Example A44. The method of example A41, comprising: applying the stimulation synchronized with sensed respiratory phase information.

Example A45. The method of example A41, comprising: applying the stimulation without synchronization to respiratory information.

Example A46. The method of example A41, comprising: positioning the first stimulation element at a first hypoglossal nerve on the first side of the patient's body and positioning the second stimulation element at a second hypoglossal nerve on the second side of the patient's body.

Example A47. The method of example A41, comprising: positioning the first stimulation element at a first ansa cervicalis-related nerve on the first side of the patient's body and the second stimulation element at second ansa cervicalis-related nerve on the second side of the patient's body.

Example 48. The method of example A41, comprising: positioning the first stimulation element at a first hypoglossal nerve on a first side of the patient's body; and positioning the second stimulation element at a first ansa cervicalis-related nerve at an opposite second side of the patient's body.

Example A49. The method of example A41, comprising at least one of: positioning, on the first side of the patient's body, the first stimulation element at the first hypoglossal nerve and the second stimulation element at the first ansa cervicalis-related nerve; or positioning, on the second side of the patient's body, the first stimulation element at the second hypoglossal nerve and the second stimulation element at the second ansa cervicalis-related nerve.

Example A50. The method of example A1, wherein the at least one stimulation element comprises at least one first stimulation element and at least one second stimulation element, the method comprising at least one of: positioning the at least one first stimulation element at at least one of a first hypoglossal nerve on a first side of the patient's body and a second hypoglossal nerve on an opposite second side of the patient's body; and positioning the at least one second stimulation element at at least one of a first ansa cervicalis-related nerve on the first side of the patient's body and a second ansa cervicalis-related nerve on the second side of the patient's body.

Example A51. The method of example A1, wherein at least one upper airway patency-related tissue comprises a hypoglossal nerve and an ansa cervicalis-related nerve, and wherein the at least one stimulation element comprises a first stimulation element, and comprising: positioning, on a first side of the patient's body, a first stimulation element at both of the hypoglossal nerve and the ansa cervicalis-related nerve.

Example 52. The method of example A51, wherein the first stimulation element comprises a cuff electrode to at least partially enclose a portion of the first hypoglossal nerve and a portion of the first ansa cervicalis-related nerve.

Example A53. The method of example A51, wherein the first stimulation element comprises at least one of a paddle electrode and an axial electrode array to be co-extensive with a portion of the first hypoglossal nerve and a portion of the first ansa cervicalis-related nerve.

Example A54. The method of example A51, wherein the first stimulation element comprises a first cuff electrode to at least partially enclose a portion of the first hypoglossal nerve and as a second cuff electrode to at least partially enclose a portion of the ansa cervicalis-related nerve.

Example A55. The method of example A1, wherein the at least one upper airway patency-related tissue comprises an ansa cervicalis-related nerve and the at least one stimulation element comprises a first stimulation element, and comprising: the at least one stimulation element comprising a second stimulation element; and stimulating, via the second stimulation element, a phrenic nerve, wherein the stimulation of the respective first and second stimulation elements are coordinated to treat multiple-type sleep apneas.

Example A56. The method of example A55, comprising: applying the stimulation, via at least one of the first and second stimulation elements, on both a left and right side of the patient's body.

Example 57. The method of example A55, comprising: applying the stimulation, via at least one of the first and second stimulation elements, on just one of a left side and an opposite right side of the patient's body.

Example A58. The method of example A55, wherein the at least one stimulation element comprises a third stimulation element, and comprising: stimulating, via the third stimulation element, a hypoglossal nerve, wherein the stimulation of the respective first, second, and third stimulation elements are coordinated to treat multiple-type sleep apneas.

Example A59. The method of example A55, comprising: delivering, via vascular access, at least the second stimulation element to a position adjacent a phrenic nerve.

Example A60. The method of example A55, comprising: positioning, a single electrode array interface including the respective first and second stimulation elements, to be in close proximity to both the ansa cervicalis-related nerve and the phrenic nerve.

Example A61. The method of example A1, comprising: delivering, via the vasculature, the at least one stimulation element to a position within the vasculature to be in stimulating relation to the upper airway patency-related tissue.

Example A62. The method of example A61, wherein the at least one stimulation element comprises a microstimulator.

Example A63. The method of example A61, wherein the upper airway patency-related tissue comprises a hypoglossal nerve.

Example A64. The method of example A61, wherein the upper airway patency-related tissue comprises an ansa cervicalis-related nerve.

Example A65. The method of example A64, wherein the vasculature comprises an anterior jugular vein.

Example A66. The method of example A64, wherein the vasculature comprises at least one of an inferior thyroid vein, a middle thyroid vein, and a superior thyroid vein.

Example A67. The method of example A64, wherein the vasculature comprises an external anterior jugular vein.

Example A68. The method of example A61, wherein the upper airway patency-related tissue comprises at least one of: a glossopharyngeal nerve; a superior laryngeal nerve; a superior cervical ganglion; a chemoreceptor; an ansa cervicalis-related nerve; and a hypoglossal nerve.

Example A69. The method of example A68, comprising: anchoring the at least one stimulation element via at least one of: an omohyoid tendon; a digastric tendon; a trachea; a sternum; a hyoid bone; a clavicle; and a thyroid-related tissue.

Example A70. The method of example A1, wherein the upper airway patency-related tissue comprises an upper airway patency-related muscle.

Example A71. The method of example A70, wherein the upper airway patency-related muscle comprises a genioglossus muscle.

Example A72. The method of example A70, comprising: delivering, via the vasculature, the at least one stimulation element to a position within the vasculature to be in stimulating relation to the upper airway patency-related muscle.

Example A73. The method of example A72, wherein the at least one stimulation element comprises a microstimulator.

Example A74. The method of example A72, wherein the upper airway patency-related muscle comprises an infrahyoid strap muscle.

Example A75. The method of example A74, wherein the infrahyoid strap muscle comprises at least one of a sternothyroid muscle and a sternohyoid muscle.

Example A76. The method of example A74, wherein the infrahyoid strap muscle comprises a sternothyroid muscle.

Example A77. The method of example A1, wherein the at least one upper airway patency-related tissue comprises an ansa cervicalis-related nerve, and comprising: anchoring the at least one stimulation element via at least one of: an omohyoid tendon; a digastric tendon; a trachea; a sternum; a hyoid bone; a clavicle; and a thyroid-related tissue.

Example A78. The method of example A77, comprising implementing the anchoring via at least one of: suture; tether; tines; and anchor element with wings.

Example A79. The method of example A77, comprising: implanting, via an implant access-incision, the at least one stimulation element at a location adjacent to, and superior to, a sternum.

Example A80. The method of example A1, wherein the upper airway patency-related tissue comprises an upper airway patency-related muscle, the method comprising: percutaneously delivering the at least one stimulation element to a position to be in stimulating relation to the upper airway patency-related muscle.

Example A81. The method of example A80, wherein the upper airway patency-related muscle comprises a sternothyroid muscle.

Example A82. The method of example A80, comprising: forming a percutaneous access point located intermediate between a hyoid bone and a sternum and lateral to a midline.

Example A83. The method of example A80, comprising monitoring nerves during the percutaneous delivery.

Example A84. The method of example A83, comprising performing the monitoring via a nerve integrity monitor (NIM).

Example A85. The method of example A1, wherein the at least one upper airway patency-related tissue comprises a first upper airway patency-related tissue and a second upper airway patency-related tissue, and comprising at least one of: the at least one stimulation element comprising a first microstimulator to stimulate the first upper airway patency-related tissue; and the at least one stimulation element comprising a second microstimulator to stimulate the second upper airway patency-related tissue.

Example A86. The method of example A85, wherein the first upper airway patency-related tissue comprises a hypoglossal nerve and the second upper airway patency-related tissue comprise a non-hypoglossal nerve.

Example A87. The method of example A86, wherein the non-hypoglossal nerve comprises a first portion of an ansa cervicalis-related nerve.

Example A88. The method of example A86, wherein the non-hypoglossal nerve comprises at least one of: a superior laryngeal nerve; and a glossopharyngeal nerve.

Example A89. The method of example A86, wherein the non-hypoglossal nerve comprises a superior laryngeal nerve and a glossopharyngeal nerve.

Example A90. The method of example A86, wherein the non-hypoglossal nerve comprises at least one of: a chemoreceptor; and a superior cervical ganglion nerve.

Example A91. The method of example A85, wherein the first upper airway patency-related tissue comprises an ansa cervicalis-related nerve and the second upper airway patency-related tissue comprises a superior cervical ganglion.

Example A92. The method of example A85, wherein the first upper airway patency-related tissue comprises an ansa cervicalis-related nerve and the second upper airway patency-related tissue comprises a hypoglossal nerve.

Example A93. The method of example A1, wherein the at least one upper airway patency-related tissue comprises a hypoglossal nerve and a non-hypoglossal nerve, and wherein the at least one stimulation element comprises a first stimulation element to stimulate the hypoglossal nerve and a second stimulation element to stimulate the non-hypoglossal nerve.

Example A94. The method of example A93, wherein the non-hypoglossal nerve comprises at least one of: an ansa cervicalis-related nerve; a glossopharyngeal nerve; a superior laryngeal nerve; a superior cervical ganglion; and a chemoreceptor.

Example A95. The method of example A93, wherein each of the respective first and second stimulation elements on separate stimulation lead portions.

Example A96. The method of example A95, wherein each of the respective first and second stimulation elements comprise at least one of: a unipolar electrode configuration; and a bipolar electrode configuration.

Example A97. The method of example A95, wherein the first stimulation element comprises a multiple electrode configuration.

Example A98. The method of example A97, wherein the non-hypoglossal nerve comprises an ansa cervicalis-related nerve.

Example A99. The method of example A98, wherein the second stimulation element comprises at least one of: a unipolar electrode configuration; and a guarded bipolar configuration.

Example A100. The method of example A1, wherein the upper airway patency-related tissue comprises an ansa cervicalis-related nerve, and comprising: selectively stimulating an ansa cervicalis-related nerve to selectively activate at least some muscle groups innervated by the ansa cervicalis-related nerve.

Example A101. The method of example A100, comprising implementing the selective stimulation via steering.

Example A102. The method of example A100, comprising: implementing the selective stimulation via locating the at least one stimulation element adjacent in stimulating relation to the ansa cervicalis-related nerve innervating a target muscle group to be stimulated, wherein the target muscle group comprises at least one of: a sternothyroid muscle group; a sternohyoid muscle group; and an omohyoid muscle group.

Example A103. The method of example A100, comprising performing the selective stimulation via excluding at least one muscle group innervated by the ansa cervicalis-related nerve from the stimulation.

Example A104. The method of example A103, comprising excluding the omohyoid muscle group.

Example A105. The method of example A1, wherein the upper airway patency-related tissue comprises at least one of: a first cervical (C1) spinal nerve; a second cervical (C2) spinal nerve; and a third cervical (C3) spinal nerve.

Example A106. The method of example A1, wherein the upper airway patency-related tissue comprises a first cervical (C1) spinal nerve and a second cervical (C2) spinal nerve, which together form a superior root of an ansa cervicalis-related nerve.

Example A107. The method of example A1, wherein the upper airway patency-related tissue comprises a second cervical (C2) spinal nerve and a third cervical (C3) spinal nerve, which together form an inferior root of an ansa cervicalis-related nerve.

Example A108. The method of example A1, wherein the upper airway patency-related tissue comprises an ansa cervicalis-related nerve, and comprising: implementing the stimulation according to a nerve fiber activation direction on the ansa cervicalis-related nerve.

Example A109. The method of example A1, wherein the upper airway patency-related tissue comprises an ansa cervicalis-related nerve, and comprising: implementing the stimulation according to at least one of a plurality of different target stimulation locations of the ansa cervicalis-related nerve, wherein each different target stimulation location is to cause contraction of a plurality of different muscle groups, which comprise a sternothyroid muscle, a sternohyoid muscle.

Example A110. The method of example A109, wherein the plurality of different muscle groups comprise an omohyoid muscle.

Example A111. The method of example A1, wherein the at least one upper airway patency-related tissue comprises at least one of: a superior cervical ganglion; a glossopharyngeal nerve; a superior laryngeal nerve; and a chemoreceptor.

Example A112. The method of example A1, wherein the at least one upper airway patency-related tissue comprises a glossopharyngeal nerve and a superior laryngeal nerve.

Example A113. The method of example A112, comprising: implementing the stimulation to stimulate solely the glossopharyngeal nerve and the superior laryngeal nerve.

Example A114. The method of example A112, wherein the at least one upper airway patency-related tissue further comprises a hypoglossal nerve and an ansa cervicalis-related nerve, and comprising implementing the stimulation of the glossopharyngeal nerve and the superior laryngeal nerve in addition to stimulation of at least one of the hypoglossal nerve and the ansa cervicalis-related nerve.

Example A115. The method of example A1, comprising forming a single implant-access incision in proximity to the ansa cervicalis-related nerve.

Example A116. The method of example A115, comprising implanting directly, via the single implant-access incision, a cuff electrode in stimulating relation to the ansa cervicalis-related nerve.

Example A117. The method of example A116, comprising: forming, via the single implant-access incision, a tunnel to a location in proximity to a hypoglossal nerve; and introducing and advancing a stimulation lead, via the single implant-access incision and via the tunnel, to place an axial electrode array in stimulating relation to the hypoglossal nerve.

Example 118. The method of example A117, comprising implanting, via the single implant-access incision, at least one of a microstimulator and an IPG.

Example A119. The method of example A115, wherein the single implant-access incision comprises the sole implant-access incision in the patient's body to implant the cuff electrode, the axial electrode array, and one of the microstimulator and the IPG.

Example A120. The method of example A1, comprising sensing, via at least one sensing element, at least one sleep disordered breathing-related parameter.

Example A121. The method of example A120, wherein the at least one sleep-disordered-breathing-related parameter comprises at least one of a respiratory phase parameter, an apnea-hypopnea index, a patient comfort parameter, an arousal index, and an upper airway collapse pattern, and wherein the stimulating comprises modulating the stimulation based on at least one of the respiratory phase parameter, an apnea-hypopnea index, a patient comfort parameter, a patient sleeping position, and an upper airway collapse pattern.

Example A122. The method of example A121, comprising synchronizing the stimulation relative to the sensed respiratory phase parameter.

Example A123. The method of example A121, comprising automatically titrating a stimulation parameter based on sensing at least one of the respiratory phase parameter, the AHI parameter, the patient comfort parameter, the patient sleeping position, and the upper airway collapse pattern.

Example A124. The method of example A123, wherein sensing the upper airway collapse pattern comprises: determining the upper airway collapse pattern via sensing a bioimpedance in relation to the neck region of the patient's body.

Example A125. The method of example A124, wherein determining the upper airway collapse pattern comprises identifying a type of the upper airway collapse pattern via identifying at least one of a value of, a change in value of, and a location of the sensed bioimpedance along the upper airway; and implementing the automatically titration of the stimulation parameter based on the identified value, identified change in value or identified location.

Example A126. The method of example A125, wherein the type of upper airway collapse pattern may comprise at least one of: concentric; lateral; anterior-posterior; and composite.

Example A127. The method of example A124, comprising implementing the sensing via an implantable, removably insertable array of spaced apart electrodes.

Example A128. The method of example A124, comprising implementing the sensing via an externally, releasably mountable array of spaced apart electrodes conformable to an exterior portion of the neck.

Example A129. The method of example A123, comprising: implementing the automatic titration of the stimulation parameter based on the sensed respiratory phase parameter information and as at least one of: at least one of a change in an amplitude, frequency, pulse width, duty cycle of stimulation; and selection of at least one stimulation target among a plurality of stimulation targets, which includes the hypoglossal nerve and the ansa cervicalis-related nerve.

Example A130. The method of example A129, wherein the plurality of stimulation targets comprises a glossopharyngeal nerve, a superior laryngeal nerve, a superior cervical ganglion nerve, and a chemoreceptor.

Example A131. The method of example A129, comprising: receiving a patient adjustment, as a single input, to a stimulation parameter; and implementing the patient adjustment by automatically adjusting a stimulation energy among a plurality of stimulation sites including at least one of a hypoglossal nerve site, an ansa cervicalis nerve site, and a second non-hypoglossal nerve site.

Example A132. The method of example A131, comprising automatically balancing the stimulation among the different stimulation sites.

Example A133. The method of example A132, wherein the automatically balancing comprises: initiating and maintaining the stimulation via stimulation of a first one of the respective stimulation sites; and adding, at a later 1618.216.1.11 point in time, stimulation of at least one respective second stimulation sites of the plurality of stimulation sites.

Example A134. The method of example A132, comprising implementing the automatic balancing based on sensing at least one of a respiratory phase parameter, AHI, a patient comfort parameter, a patient sleeping position, and an upper airway collapse pattern.

Example A135. The method of example A133, wherein the first one of the respective stimulation site comprises a hypoglossal nerve and the second respective stimulation site comprises an ansa cervicalis-related nerve.

Example A136. The method of example A133, wherein the first one of the respective stimulation site comprises an ansa cervicalis-related nerve and the second respective stimulation site comprises a hypoglossal nerve.

Example A137. The method of example A121, wherein the patient comfort parameter comprises an arousal index.

Example A138. The method of example A121, comprising: receiving a patient adjustment to a stimulation parameter upon a change in the patient comfort parameter, the stimulation parameter comprising an overall stimulation energy; and implementing the patient adjustment by redistributing the overall stimulation energy among an increased number of stimulation sites.

Example A139. The method of example A138, while maintaining same overall energy as before the patient adjustment.

Example A140. The method of example A138, wherein the patient adjustment comprises a single input parameter.

Example A141. The method of example A139, wherein patient adjustment comprises a decrease request in stimulation.

Example A142. The method of example A121, comprising: automatically adjusting, upon sensing a change in the AHI parameter, at least one of a stimulation parameter and a target stimulation location at the upper airway patency-related tissue, wherein the target stimulation location comprises at least one of a hypoglossal nerve and an ansa cervicalis-related nerve.

Example A143. The method of example A142, wherein implementing the sensing of the increase in the AHI parameter.

Example A144. The method of example A142, comprising: upon determining that the sensed change in the AHI parameter is associated with a change in patient sleeping position, adjusting the stimulation parameter relating to the ansa cervicalis-related nerve.

Example A145. The method of example A144, wherein the adjusting of the change in the stimulation parameter comprises increasing the stimulation parameter when the sensed change in the AHI parameter comprises a sensed increase in the AHI parameter.

Example A146. The method of example A120, wherein the at least one sensing element comprises a first sensing element and a second sensing element.

Example A147. The method of example A146, comprising at least one of: positioning the first sensing element on a first side of the patient's body and positioning the second sensing element on an opposite second side of the patient's body; and positioning the first sensing element on a first side of the patient's body and positioning the second sensing element on the same first side of the patient's body spaced apart from the first sensing element.

Example A148. The method of example A147, wherein the sensing comprises sensing an impedance between the respective first and second sensing elements.

Example A149. The method of example A148, wherein the sleep-disordered-breathing-related parameter comprises at least one of respiration and a sleep-disordered-breathing event.

Example A150. The method of example A148, wherein the respective first and second sensing elements comprise a first stimulation element and a second stimulation element, respectively.

Example A151. The method of example A150, comprising locating the first stimulation element at a first hypoglossal nerve on the first side of the patient's body and the second stimulation element at a second hypoglossal nerve on the second side of the patient's body.

Example A152. The method of example A150, comprising locating the first stimulation element at a first ansa cervicalis-related nerve on the first side of the patient's body and the second stimulation element at second ansa cervicalis-related nerve on the second side of the patient's body.

Example A153. The method of example A150, comprising: locating the first stimulation element, on the first side of the patient's body, at at least one of the first hypoglossal nerve and a first ansa cervicalis-related nerve; and locating the second stimulation element, on the second side of the patient's body, at at least one of the second hypoglossal nerve and a second ansa cervicalis-related nerve.

Example A154. The method of example A150, comprising at least one of: locating the first stimulation element, on the first side of the patient's body, at the first hypoglossal nerve and locating the second stimulation element on the first side of the patient's body at the first ansa cervicalis-related nerve; or locating the second stimulation element, on the second side of the patient's body, at the second hypoglossal nerve and locating the second stimulation element on the second side of the patient's body at the second ansa cervicalis-related nerve.

Example A155. The method of example A148, wherein the first sensing element comprises a first stimulation element and the second sensing element comprises an electrode on a housing of a pulse generator.

Example A156. The method of example A155, comprising positioning the first stimulation element at at least one of: at least one of a first hypoglossal nerve on a first side of the patient's body and a second hypoglossal nerve on an opposite second side of the patient's body; and at least one of a first ansa cervicalis nerve-related on the first side of the patient's body and a second ansa cervicalis-related nerve on the second side of the patient's body.

Example A156. The method of example A120, wherein the at least one sensing element comprises a first sensing element and a second sensing element, and comprising: measuring a bioimpedance between the first sensing element implanted relative to the at least one upper airway patency-related tissue and the second sensing element implanted relative to at least one of a phrenic nerve and a diaphragm.

Example A157. The method of example A156, wherein the first sensing element comprises a first stimulation element and the second sensing element comprises a second stimulation element.

Example A158. The method of example A120, wherein the at least one upper airway patency-related tissue comprises an upper airway patency-related muscle, and wherein the sensing comprises sensing at least one of a motion of the upper airway patency-related muscle and an EMG of the upper airway patency-related muscle.

Example A159. The method of example A158, comprising performing, via at least one of the sensed motion and the sensed EMG, at least one of: titration of an amplitude of a stimulation signal to be applied via the at least one stimulation element; and determination of a sufficiency of capture of the upper airway patency-related tissue to be stimulated via the stimulation element.

Example A160. The method of example A120, comprising determining the at least one sleep-disordered-breathing-related parameter as a respiratory parameter, by sensing via the at least one sensing element at least one of: a motion of an upper airway patency-related muscle of the at least one upper airway patency-related tissue; and a sound of respiration associated with the at least one upper airway patency-related tissue.

Example A161. The method of example A1, comprising forming a single implant-access incision in proximity to a hypoglossal nerve.

Example A162. The method of example A161, comprising implanting directly, via the single implant-access incision, a cuff electrode in stimulating relation to the hypoglossal nerve.

Example A163. The method of example A162, comprising: forming, via the single implant-access incision, a tunnel to a location in proximity to an ansa cervicalis-related nerve; and introducing and advancing a stimulation lead, via the single implant-access incision and via the tunnel, to place an axial electrode array in stimulating relation to the ansa cervicalis-related nerve.

Example A164. The method of example A163, comprising implanting, via the single implant-access incision, at least one of a microstimulator and an IPG.

Example A165. The method of example A115, wherein the single implant-access incision comprises the sole implant-access incision in the patient's body to implant the cuff electrode, the axial electrode array, and one of the microstimulator and the IPG.

Example A166. The method of example A1, wherein the upper airway patency-related tissue comprises an ansa cervicalis-related nerve.

Example A167. The method of example A166, wherein the upper airway patency-related tissue further comprises a superior cervical ganglion.

Example A168. The method of example A166, wherein the at least one upper airway patency-related tissue further comprises a hypoglossal nerve.

Example A169. The method of example A168, comprising applying a first duty cycle of stimulation to the hypoglossal nerve to be different from a second duty cycle of stimulation for application to the ansa cervicalis-related nerve.

Example A170. The method of example A169, comprising implementing the stimulation of the ansa cervicalis-related nerve to stimulate at least at least one of a sternothyroid muscle and a sternohyoid muscle.

Example A171. The method of example A169, wherein the first duty cycle is faster than the second duty cycle.

Example A172. The method of example A169, wherein the first duty cycle is slower than the second duty cycle.

Example A173. The method of example A169, comprising: applying the stimulation to the hypoglossal nerve as a phasic stimulation; and applying the stimulation to the ansa cervicalis-related nerve as a tonic stimulation.

Example A174. The method of example A173, wherein the tonic stimulation comprises a stimulation cycle comprising a stimulation period greater than a non-stimulation period.

Example A175. The method of example A1, wherein the at least one upper airway patency-related tissue comprises a hypoglossal nerve and comprises a second upper airway patency-related tissue comprising at least one of: an ansa cervicalis-related nerve; and an infrahyoid strap muscle.

Example A176. The method of example A175, comprising simultaneously stimulating the hypoglossal nerve and the second upper airway patency-related tissue.

Example A177. The method of example A176, comprising implementing the stimulation via interleaving a first stimulation signal to stimulate the hypoglossal nerve and a second stimulation signal to stimulate the second upper airway patency-related tissue.

Example A178. The method of example A176, comprising implementing both of the respective first and second stimulation signals via a single pulse generator.

Example A179. The method of example A176, comprising implementing the interleaving via applying the stimulation via a first frequency for the hypoglossal nerve and a different second frequency for the second upper airway patency-related tissue.

Example A180. The method of example A176, comprising implementing the simultaneous stimulation via time-shifting.

Example A181. The method of example 176, comprising implementing the simultaneous stimulation synchronously.

Example A182. The method of example A175, comprising implementing the stimulation via stimulating the hypoglossal nerve followed by stimulating the second upper airway patency-related tissue.

Example A183. The method of example A182, comprising maintaining the stimulation of the hypoglossal nerve during stimulation of the second upper airway patency-related tissue.

Example A184. The method of example A183, wherein the ansa cervicalis-related nerve comprises a portion of the nerve innervating at least the sternothyroid muscle group.

Example A185. The method of example A1, comprising implementing the stimulation as at least one of: a continuous stimulation at a low frequency; and a non-continuous stimulation including an on period and an off period, the non-continuous stimulation to cause muscular contraction.

Example A186. The method of example A175, comprising: implementing the stimulation, via selecting a stimulation target from among the hypoglossal nerve and the different muscle groups associated with the second upper airway patency-related tissue, based on determination of a first parameter, the first parameter comprising at least one of: a respiratory parameter including respiratory phase information; a patient comfort parameter; a posture parameter; an effectiveness of therapy parameter; a device usage parameter; a sleep stage parameter; an upper airway collapse pattern parameter; and an apnea-hypopnea index (AHI) parameter.

Example A187. The method of example A186, comprising implementing, via an accelerometer, the determination of at least one of: the respiratory parameter including respiratory phase information; the posture; the effectiveness of therapy parameter; the apnea-hypopnea index (AHI) parameter; and the sleep stage parameter.

Example A188. The method of example A187, comprising implementing determination of sleep stage via sensing via at least one of modalities of: acceleration; bioimpedance; pressure; pneumotach; and thermistor.

Example A189. The method of example A188, comprising implementing the sensing via employing at least some of the modalities to sense at least one of: respiration; posture; body position; body activity; and cardiac information.

Example A190. The method of example A186, comprising implementing a determination of patient comfort via at least one of patient feedback and clinician feedback.

Example A191. The method of example A186, comprising implementing the selectivity of a stimulation target, from among the hypoglossal nerve and the different muscle groups associated with the ansa cervicalis-related nerve loop, according to the first parameter via clinician titration.

Example A192. The method of example A186, comprising via application of a data model and according to the first parameter, implementing the selecting of at least one stimulation target from among the hypoglossal nerve and the different muscle groups associated with the ansa cervicalis-related nerve.

Example A193. The method of example A192, comprising at a first time period prior to the implementing the selecting of at least one stimulation target, constructing the data model via known inputs corresponding to all of the stimulation targets relative to known outputs corresponding to the first parameter.

Example A194. The method of example A192, wherein the constructed data model comprises a trained data model, which optionally comprises a trained machine learning model.

Example A195. The method of example A194, wherein the trained machine learning model comprises at least one of an artificial neural network, deep learning model, and a support vector machine.

Example A196. The method of example A192, wherein the first time period comprises a non-treatment period of the patient.

Example A197. The method of example A175, wherein the at least one upper airway patency-related tissue comprises a plurality of stimulation targets including: a hypoglossal nerve; an ansa cervicalis-related nerve; and an infrahyoid strap muscle.

Example A198. The method of example A197, comprising applying the stimulation, via an increased ramped stimulation signal, to each respective stimulation target to determine among the respective stimulation targets a relative degree of upper airway patency.

Example A199. The method of example A198, comprising applying the stimulation simultaneously to at least two of the respective stimulation targets.

Example A200. The method of example A197, comprising selecting which of the respective stimulation targets to stimulate based on an upper airway collapse pattern.

Example A201. The method of example A200, comprising classifying a type and a severity of the upper airway collapse pattern based on at least one of: snoring; a plurality of polysomnongraphy (PSG) parameters; a body position; a head-and-neck position; and a sleep stage.

Example A202. The method of example A200, comprising implementing the selection of stimulation targets based on the type and the severity of the upper airway collapse pattern.

Example A203. The method of example A202, comprising at least one of: selecting the stimulation target as a first portion of the ansa cervicalis-related nerve upon the upper airway collapse pattern being predominantly a lateral wall collapse pattern; selecting the stimulation target as a hypoglossal nerve upon the upper airway collapse pattern being predominantly a genioglossal collapse pattern; and selecting the stimulation target of an ansa cervicalis-related nerve as a first stimulation target prior to other stimulation targets upon the upper airway collapse pattern being predominantly a palate collapse pattern.

Example A204. The method of example A202, comprising titrating at least one stimulation parameter of the stimulation for at least one of: each different collapse pattern; and each sleeping position.

Example A205. The method of example A204, wherein the at least one stimulation parameter comprises at least one of: an amplitude; a pulse width; a frequency; a duty cycle; and a number, a type, and a location of stimulation elements.

Example A206. The method of example A175, wherein the at least one upper airway patency-related tissue comprises a plurality of muscle stimulation targets including a genioglossus muscle, a sternohyoid muscle, a sternothyroid muscle, and an omohyoid muscle.

Example A207. The method of example A206, the method further comprising implementing the stimulation via distributing an energy of a stimulation signal among a selectable multiple number of the stimulation targets as the energy of the stimulation signal is increased.

Example A208. The method of example A207, comprising implementing the stimulation of the muscle targets via directly stimulating the respective muscle stimulation target.

Example A209. The method of example A207, comprising stimulating a nerve by which the respective muscle stimulation targets are innervated.

Example A210. A method comprising prior to completion of chronic implantation of a sleep-disordered-breathing therapy system: stimulating, via a first stimulation element, at least one test stimulation location indicative of a response of an upper airway patency-related tissue to the stimulation.

Example B211. The method of example B210, wherein prior to completion comprises at least one of pre-operatively and intra-operatively.

Example A212. The method of example B210, the first stimulation element comprises a test stimulation element.

Example B213. The method of example B210, the first stimulation element comprises a chronically implantable stimulation element.

Example B214. The method of example B210, wherein the test stimulation location corresponds to a target stimulation location for implantation of a chronically implantable stimulation element.

Example B215. The method of example B214, comprising implementing the stimulation, via the first stimulation element, with the at least one test stimulation location comprising at least one of a hypoglossal nerve and a non-hypoglossal nerve comprising at least an ansa cervicalis-related nerve.

Example B216. The method of example B215, comprising: stimulating the hypoglossal nerve and determining a first response of upper airway patency to the stimulation; and after the determination of the first response, stimulating the non-hypoglossal nerve and determining a second response of upper airway patency to the stimulation.

Example B217. The method of example B216, comprising maintaining the stimulation of the hypoglossal nerve during stimulation of the non-hypoglossal nerve.

Example B218. The method of example B215, stimulating the ansa cervicalis nerve and determining a third response of upper airway patency to the stimulation; and after the determination of the third response, stimulating the hypoglossal nerve and determining a fourth response of upper airway patency to the stimulation.

Example B219. The method of example B218, comprising maintaining the stimulation of the ansa cervicalis-related nerve during stimulation of the hypoglossal nerve.

Example B220. The method of example B210, wherein the test stimulation location corresponds to a first location not intended for implantation of a chronically implantable stimulation element.

Example B221. The method of example B220, wherein the first location corresponds to an external location under the tongue.

Example B222. The method of example B210, comprising determining the response of the upper airway patency-related tissue to the stimulation.

Example B223. The method of example B222, comprising implementing the determining via observing the response.

Example B224. The method of example B223, wherein observing the response comprises: imaging at least one of a patency of the upper airway and a response of the upper airway patency-related muscle; and evaluating the relative patency and/or the response of the upper airway patency-related muscle.

Example B225. The method of example B210, wherein the first stimulation element comprises a test needle and wherein implementing the stimulation comprises percutaneously inserting the test needle into the ansa cervicalis-related nerve, and determining an upper airway response based on the stimulation.

Example B226. The method of example B225, wherein determining the response comprises identifying inferior movement of the larynx and implementing the identifying, during the stimulation, via at least one of measuring an EMG response of the larynx and imaging of the larynx.

Example C227. A method comprising identifying an upper airway collapse pattern via: placing an array of electrodes, including at least two spaced apart electrodes, in sensing relation to the upper airway; and measuring a bioimpedance, between the at least two spaced apart electrodes, which is indicative of a size of the upper airway patency.

Example C228. The method of example C227, comprising positioning at least some of the electrodes of the array in sensing relation to upper airway muscles innervated by at least one of an ansa cervicalis-related nerve and a hypoglossal nerve.

Example C229. The method of example C228, wherein the positioning comprises removably inserting the array of electrodes within the upper airway of the patient's body.

Example C230. The method of example C228, wherein the positioning comprises positioning the electrodes of the array externally on the patient's body in proximity to the upper airway.

Example C231. The method of example C227, comprising implementing the identification of the upper airway collapse pattern at a time prior to completing implantation of a chronically implantable stimulation element in stimulating relation to an upper airway patency-related tissue.

Example C232. The method of example C231, wherein the upper airway patency-related tissue comprises at least one of a hypoglossal nerve and a non-hypoglossal nerve, which comprises the ansa cervicalis-related nerve.

The invention claimed is:

1. A method of treating sleep disordered breathing comprising:

sensing, via at least one sensing element, respiratory cycles wherein each respiratory cycle includes an inspiratory phase and an expiratory phase; and applying electrical stimulation, based on the sensed respiratory cycles and via a first stimulation element, to an infrahyoid muscle-innervating nerve according to a first stimulation protocol including stimulation cycles of alternating stimulation periods and non-stimulation periods, wherein a first stimulation period coincides with the inspiratory phase of a respective one of the sensed respiratory cycles and, based on an upper airway patency hysteresis effect parameter, the stimulation protocol skips at least one respiratory cycle before applying a second stimulation period which coincides with the inspiratory phase of a later respective one of the respiratory cycles.

2. The method of claim 1, wherein the infrahyoid muscle-innervating nerve comprises a superior root portion of an ansa cervicalis nerve loop.

3. The method of claim 2, wherein the superior root portion innervates at least one of a sternothyroid muscle, a sternohyoid muscle, and an omohyoid muscle.

4. The method of claim 2, wherein the infrahyoid muscle-innervating nerve comprises at least one nerve portion extending distally from the superior root portion and innervating at least one of the sternothyroid muscle, the sternohyoid muscle, and the omohyoid muscle.

5. The method of claim 1, wherein the upper airway patency hysteresis effect parameter represents a degree and a duration of upper airway patency following at least one stimulation period of the at least one stimulation protocol.

6. The method of claim 1, wherein the upper airway patency hysteresis effect parameter comprises an upper airway patency hysteresis effect reference, which is based on at least one of:

a historical patient-specific average patency hysteresis effect; and a multiple patent average patency hysteresis effect.

7. The method of claim 1, wherein applying the stimulation via the first stimulation protocol comprises:

performing the stimulation of the infrahyoid muscle-innervating nerve via the first stimulation element without stimulating genioglossus-based patency tissue.

8. The method of claim 7, wherein the genioglossus-based patency tissue comprises at least one of a hypoglossal nerve and a genioglossus muscle innervated by the hypoglossal nerve.

9. The method of claim 1, comprising:

applying stimulation, via a second stimulation element, to a hypoglossal nerve according to a second stimulation protocol including alternating stimulation periods and non-stimulation periods, including implementing both the first and second stimulation protocols during the same sleep treatment period.

10. The method of claim 9, wherein the applying the stimulation of the hypoglossal nerve via the second stimulation protocol comprises applying the stimulation in a closed loop mode in which the stimulation of the hypoglossal nerve is timed to coincide with the inspiratory phase of each respiratory cycle.

11. The method of claim 9, wherein the applying the stimulation of the hypoglossal nerve via the second stimulation protocol comprises applying the stimulation in an open loop mode in which the stimulation of the hypoglossal nerve is not timed to be synchronous with the sensed inspiratory phase of the respective respiratory cycles.

* * * * *